United States Patent
Vu et al.

(10) Patent No.: US 10,138,219 B2
(45) Date of Patent: Nov. 27, 2018

(54) METHODS AND COMPOUNDS FOR RESTORING MUTANT P53 FUNCTION

(71) Applicant: PMV Pharmaceuticals, Inc., Cranbury, NJ (US)

(72) Inventors: Binh Vu, North Caldwell, NJ (US); Romyr Dominique, East Brunswick, NJ (US); Hongju Li, Edison, NJ (US)

(73) Assignee: PMV PHARMACEUTICALS, Cranbury, NJ (US)

( * ) Notice: Subject to any disclaimer, the term of this patent is extended or adjusted under 35 U.S.C. 154(b) by 0 days.

(21) Appl. No.: 15/436,333

(22) Filed: Feb. 17, 2017

(65) Prior Publication Data

US 2017/0240525 A1 Aug. 24, 2017

Related U.S. Application Data

(60) Provisional application No. 62/297,450, filed on Feb. 19, 2016.

(51) Int. Cl.

| | |
|---|---|
| *C07D 209/14* | (2006.01) |
| *C07D 401/12* | (2006.01) |
| *C07D 401/14* | (2006.01) |
| *C07D 405/12* | (2006.01) |
| *C07D 405/14* | (2006.01) |
| *C07D 409/12* | (2006.01) |
| *C07D 409/14* | (2006.01) |
| *C07D 471/04* | (2006.01) |
| *C07D 491/107* | (2006.01) |

(52) U.S. Cl.
CPC ......... *C07D 401/12* (2013.01); *C07D 209/14* (2013.01); *C07D 401/14* (2013.01); *C07D 405/12* (2013.01); *C07D 405/14* (2013.01); *C07D 409/12* (2013.01); *C07D 409/14* (2013.01); *C07D 471/04* (2013.01); *C07D 491/107* (2013.01)

(58) Field of Classification Search
CPC .. C07D 401/12; C07D 209/14; C07D 401/14; C07D 405/12; C07D 405/14; C07D 409/12; C07D 409/14; C07D 471/04; C07D 491/107
See application file for complete search history.

(56) References Cited

U.S. PATENT DOCUMENTS

| | | |
|---|---|---|
| 7,601,714 B2 | 10/2009 | Barbosa, Jr. et al. |
| 8,822,689 B2 | 9/2014 | Soll et al. |
| 8,859,780 B2 | 10/2014 | Ehring et al. |
| 8,865,715 B2 | 10/2014 | Dorsch et al. |
| 8,933,113 B2 | 1/2015 | Crespo et al. |
| 2012/0258920 A1 | 10/2012 | Sal et al. |

FOREIGN PATENT DOCUMENTS

| | | |
|---|---|---|
| WO | WO-0032175 A2 | 6/2000 |
| WO | WO-2006136823 A1 | 12/2006 |
| WO | WO-2009136175 A1 | 11/2009 |
| WO | WO-2012175962 A1 | 12/2012 |
| WO | WO-2013036208 A1 | 3/2013 |
| WO | WO-2016004513 A1 | 1/2016 |

OTHER PUBLICATIONS

Kubinyi (3D QSAR in Drug Design: Ligand-Protein Interactions and Molecular Similarity, vol. 2-3, Springer, 1998, 800 pages), p. 243-44 provided.*
Wermuth, The Practice of Medicinal Chemsitry, 2d ed. (2003), 768 pages. Chs. 9-10 provided.*
Coburn et al. (CAPLUS Abstract of WO 2010111483 (Sep. 30, 2010)).*
International Search Report and written opinion dated Jun. 21, 2017 for International Application No. PCT/US2017/018511.
Joerger, et al., Structure—function—rescue: the diverse nature of common p53 cancer mutants. Oncogene (2007) 26, 2226-2242.
Leblanc, et al., Homogeneous time-resolved fluorescence assay for identifying p53 interactions with its protein partners, directly in a cellular extract. Analytical Biochemistry 308 (2002) 247-254.
Liu, et al., Small molecule induced reactivation of mutant p53 in cancer cells. Nucleic Acids Research, 2013, vol. 41, No. 12. 6034-6044.
Ribeiro, et al., Chemical Variations on the p53 reactivation theme. Pharmaceuticals, May 2016; 9(25):1-33.
Selivanova, et al., Reactivation of mutant p53: molecular mechanisms and therapeutic potential, Oncogene, Apr. 2, 2007; vol. 26: p. 2243-2254.
Wilcken, et al., Halogen-Enriched Fragment Libraries as Leads for Drug Rescue of Mutant p53.Journal of the american chemicel society. 2012; 134:6810-6818.
Ansel, H.C. et al., Pharmaceutical dosage forms and drug delivery systems. 7th edition. 1999. 4 Pages.
Gennaro, A.R., Remington: The science and practice of pharmacy. 19th edition. 1995. 12 Pages.
Hoover, J. et al., Remington's Pharmaceutical science. 1970.
Liberman, H.A., Pharmaceutical Dosage Forms: Parenteral Medications. 1992. vol. 1. 4 pages.

* cited by examiner

*Primary Examiner* — Robert H Havlin
(74) *Attorney, Agent, or Firm* — Wilson Sonsini Goodrich & Rosati

(57) ABSTRACT

Mutations in oncogenes and tumor suppressors contribute to the development and progression of cancer. The present disclosure describes compounds and methods to recover wild-type function to p53 mutants. The compounds of the present invention can bind to mutant p53 and restore the ability of the p53 mutant to bind DNA and activate downstream effectors involved in tumor suppression. The disclosed compounds can be used to reduce the progression of cancers that contain a p53 mutation.

46 Claims, 2 Drawing Sheets
Specification includes a Sequence Listing.

SEQUENCE LISTING

```
<160> NUMBER OF SEQ ID NOS: 2

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
        35                  40                  45

Pro Val Gln Leu Trp Val Asp Ser Thr Pro Pro Gly Thr Arg Val
    50                  55                  60

Arg Ala Met Ala Ile Tyr Lys Gln Ser Gln His Met Thr Glu Val Val
65                  70                  75                  80

Arg Arg Cys Pro His His Glu Arg Cys Ser Asp Ser Asp Gly Leu Ala
                85                  90                  95

Pro Pro Gln His Leu Ile Arg Val Glu Gly Asn Leu Arg Val Glu Tyr
            100                 105                 110

Leu Asp Asp Arg Asn Thr Phe Arg His Ser Val Val Val Pro Cys Glu
        115                 120                 125

Pro Pro Glu Val Gly Ser Asp Cys Thr Thr Ile His Tyr Asn Tyr Met
    130                 135                 140

Cys Asn Ser Ser Cys Met Gly Gly Met Asn Arg Arg Pro Ile Leu Thr
145                 150                 155                 160

Ile Ile Thr Leu Glu Asp Ser Ser Gly Asn Leu Leu Gly Arg Asn Ser
                165                 170                 175

Phe Glu Val His Val Cys Ala Cys Pro Gly Arg Asp Arg Arg Thr Glu
            180                 185                 190
```

-continued

```
Glu Glu Asn Leu Arg Lys Lys Gly Glu Pro His His Glu Leu Pro Pro
            195                 200                 205
Gly Ser Thr Lys Arg Ala Leu Ser Asn Asn Thr
    210                 215

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
attaggcatg tctaggcatg tctagg                                        26
```

METHODS AND COMPOUNDS FOR RESTORING MUTANT P53 FUNCTION

CROSS REFERENCE

This application claims the benefit of U.S. Provisional Patent Application No. 62/297,450, filed on Feb. 19, 2016, the content of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Feb. 17, 2017, is named 44727702201_1.txt and is 2,540 bytes in size.

BACKGROUND

Cancer, an uncontrolled proliferation of cells, is a multi-factorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a compound of the formula:

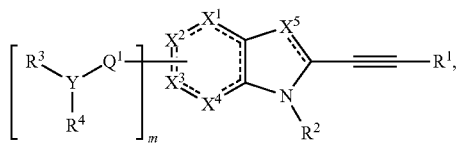

wherein:
each ══ is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^8$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, the invention provides a method of increasing p53 mutant activity in a cell, the method comprising contacting the cell with a therapeutically effective amount of a compound that binds the p53 mutant, wherein the compound increases the ability of the p53 mutant to bind DNA.

In some embodiments, the invention provides a method of inducing apoptosis in a cell, the method comprising contacting the cell with a therapeutically-effective amount of a compound that binds a p53 mutant, wherein the compound increases the ability of the p53 mutant to bind DNA, wherein the cell expresses the p53 mutant.

In some embodiments, the invention provides a method of treating a condition, the method comprising administering to a subject in need thereof a therapeutically-effective amount of a compound that binds a p53 mutant in the subject, wherein the binding of the compound to the p53 mutant increases the ability of the p53 mutant to bind DNA as compared to the ability of the p53 mutant to bind DNA in absence of the compound.

In some embodiments, the invention provides a method of determining an ability of a compound to activate mutant p53 binding to DNA, the method comprising:
a) contacting the compound with a tagged mutant p53 moiety and an antibody conjugated to a fluorescence energy acceptor against a tag of the tagged mutant p53 moiety in a test chamber;
b) contacting the tagged mutant p53 moiety with a biotin-labeled DNA and streptavidin conjugated to a fluorescence energy donor in the test chamber;

c) irradiating the test chamber with light that promotes fluorescence resonance energy transfer;
d) detecting the fluorescence resonance energy transfer;
e) determining an $SC_{150}$ value of the compound based on the fluorescence resonance energy transfer;
f) comparing the $SC_{150}$ value of the compound with that of a control sample, wherein the control sample comprises the tagged mutant p53 moiety, the antibody conjugated to the fluorescence energy acceptor against the tag of the tagged mutant p53 moiety, the biotin-labeled DNA, and the streptavidin conjugated to the fluorescence energy donor, wherein the control sample does not comprise the compound; and
g) determining based on the comparing a level of activation of protein-DNA binding in the presence of the compound.

In some embodiments, the invention provides a method of increasing p53 mutant activity in a cell, the method comprising contacting the cell with a therapeutically effective amount of a compound that binds the p53 mutant, wherein the compound increases the ability of the p53 mutant to bind DNA by at least about 50% in an assay, wherein the assay comprises:
a) contacting the compound with a tagged mutant p53 moiety and an antibody conjugated to a fluorescence energy acceptor against a tag of the tagged mutant p53 moiety in a test chamber;
b) contacting the tagged mutant p53 moiety with a biotin-labeled DNA and streptavidin conjugated to a fluorescence energy donor in the test chamber;
c) irradiating the test chamber with light that promotes fluorescence resonance energy transfer;
d) detecting the fluorescence resonance energy transfer;
e) determining an $SC_{150}$ value of the compound based on the fluorescence resonance energy transfer;
f) comparing the $SC_{150}$ value of the compound with that of a control sample, wherein the control sample comprises the tagged mutant p53 moiety, the antibody conjugated to the fluorescence energy acceptor against the tag of the tagged mutant p53 moiety, the biotin-labeled DNA, and the streptavidin conjugated to the fluorescence energy donor, wherein the control sample does not comprise the compound; and
g) determining based on the comparing a level of activation of protein-DNA binding in the presence of the compound.

In some embodiments, the invention provides a method of inducing apoptosis in a cell, the method comprising contacting the cell with a therapeutically-effective amount of a compound that binds a p53 mutant, wherein the cell expresses the p53 mutant, wherein the compound increases the ability of the p53 mutant to bind DNA by at least about 50% in an assay, wherein the assay comprises:
a) contacting the compound with a tagged mutant p53 moiety and an antibody conjugated to a fluorescence energy acceptor against a tag of the tagged mutant p53 moiety in a test chamber;
b) contacting the tagged mutant p53 moiety with a biotin-labeled DNA and streptavidin conjugated to a fluorescence energy donor in the test chamber;
c) irradiating the test chamber with light that promotes fluorescence resonance energy transfer;
d) detecting the fluorescence resonance energy transfer;
e) determining an $SC_{150}$ value of the compound based on the fluorescence resonance energy transfer;
f) comparing the $SC_{150}$ value of the compound with that of a control sample, wherein the control sample comprises the tagged mutant p53 moiety, the antibody conjugated to the fluorescence energy acceptor against the tag of the tagged mutant p53 moiety, the biotin-labeled DNA, and the streptavidin conjugated to the fluorescence energy donor, wherein the control sample does not comprise the compound; and
g) determining based on the comparing a level of activation of protein-DNA binding in the presence of the compound.

In some embodiments, the invention provides a method of treating a condition, the method comprising administering to a subject in need thereof a therapeutically-effective amount of a compound that binds a p53 mutant in the subject, wherein the binding of the compound to the p53 mutant increases the ability of the p53 mutant to bind DNA by at least about 50% as compared to the ability of the p53 mutant to bind DNA in absence of the compound as determined by an assay, wherein the assay comprises:
a) contacting the compound with a tagged mutant p53 moiety and an antibody conjugated to a fluorescence energy acceptor against a tag of the tagged mutant p53 moiety in a test chamber;
b) contacting the tagged mutant p53 moiety with a biotin-labeled DNA and streptavidin conjugated to a fluorescence energy donor in the test chamber;
c) irradiating the test chamber with light that promotes fluorescence resonance energy transfer;
d) detecting the fluorescence resonance energy transfer;
e) determining an $SC_{150}$ value of the compound based on the fluorescence resonance energy transfer;
f) comparing the $SC_{150}$ value of the compound with that of a control sample, wherein the control sample comprises the tagged mutant p53 moiety, the antibody conjugated to the fluorescence energy acceptor against the tag of the tagged mutant p53 moiety, the biotin-labeled DNA, and the streptavidin conjugated to the fluorescence energy donor, wherein the control sample does not comprise the compound; and
g) determining based on the comparing a level of activation of protein-DNA binding in the presence of the compound.

DETAILED DESCRIPTION

Figure 1:
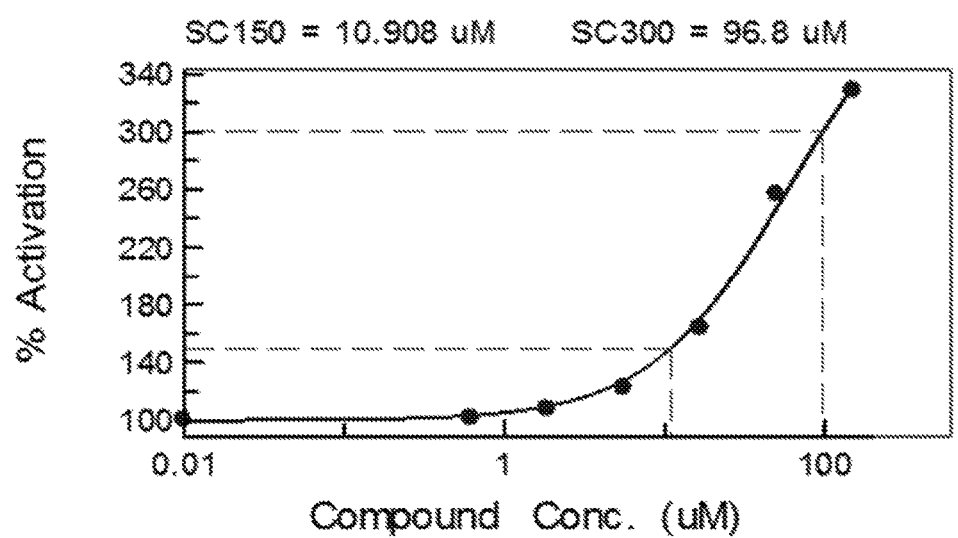
FIG. 1 shows a protein DNA binding assay of mutant p53 in the presence of compound of the invention.

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon;

sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Invention.

The compounds of the present invention can selectively bind to a p53 mutant and can recover wild-type activity of the p53 mutant including, for example, DNA binding function and activation of downstream targets involved in tumor suppression. In some embodiments, a compound of the invention selectively binds to the p53 Y220C mutant. The Y220C mutant is a temperature sensitive mutant, which binds to DNA at lower temperature and is denatured at body temperature. A compound of the invention can stabilize the Y220C mutant to reduce the likelihood of denaturation of the protein at body temperature.

Located in the periphery of the p53 β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the invention can bind to and occupy this surface crevice to stabilize the β-sandwich, thereby restoring wild-type p53 DNA-binding activity.

To determine the ability of a compound of the invention to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as β-galactosidase staining.

A p53 mutant that can be used to determine the effectiveness of a compound of the invention to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

```
                                              (SEQ ID NO. 1)
    SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP

ILTIITLEDS SGNLLGRNSF EVHVCACPGR DRRTEEENLR

KKGEPHHELP PGSTKRALSN NT
```

A compound of the invention can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the invention.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the invention can be used, for example, to induce apoptosis, cell cycle arrest, or senescence in a cell. In some embodiments, the cell is a cancer cell. In some embodiments, the cell carries a mutation in p53.

Compounds of the Invention.

Non-limiting examples of compounds of the invention include compounds of any of the following formulae:

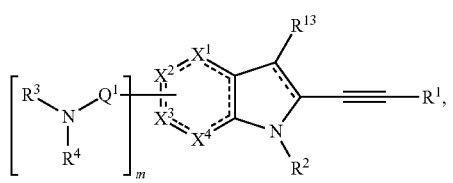

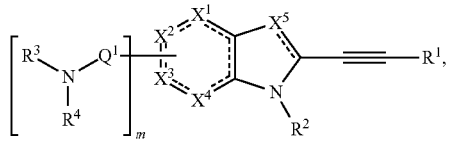

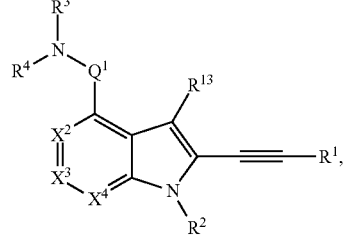

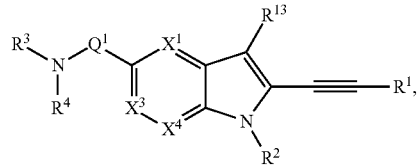

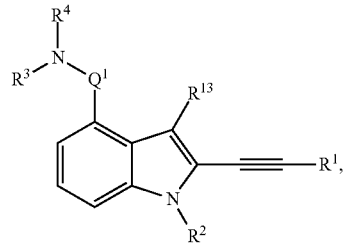

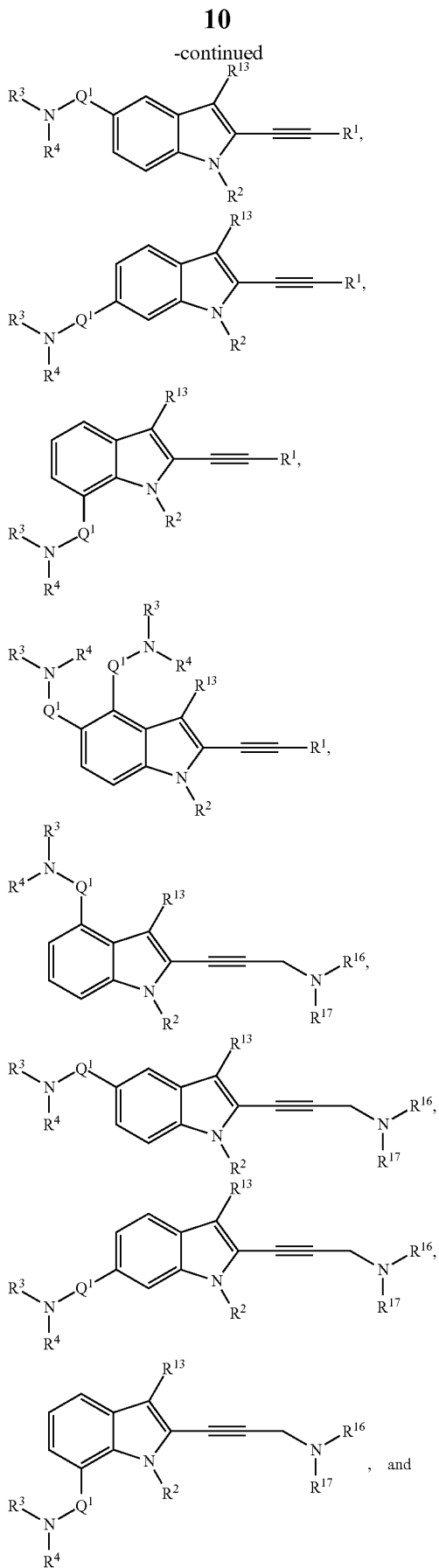

-continued

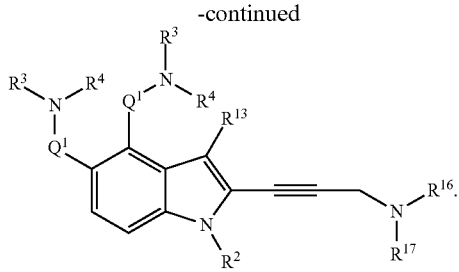

In some embodiments, a compound of the invention is a compound of the formula

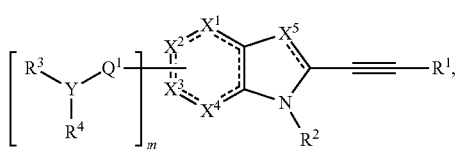

wherein each ═══ is independently a single bond or a double bond; $X^1$ is $CR^5$, $CR^5R^6$, N, $NR^5$, O, S, C═O, C═S, or a carbon atom connected to $Q^1$; $X^2$ is $CR^7$, $CR^7R^8$, N, $NR^7$, O, S, C═O, C═S, or a carbon atom connected to $Q^1$; $X^3$ is $CR^9$, $CR^9R^{10}$, N, $NR^9$, O, S, C═O, C═S, or a carbon atom connected to $Q^1$; $X^4$ is $CR^{11}$, $CR^{11}R^{12}$, N, $NR^{11}$, O, S, C═O, C═S, or a carbon atom connected to $Q^1$; $X^5$ is $CR^{13}$, N, or $NR^{13}$; wherein at least one of $X^1$, $X^2$, $X^3$, and $X^4$ is a carbon atom connected to $Q^1$; $Q^1$ is C═O, C═S, C═$CR^{14}R^{15}$, C═$NR^{14}$, alkylene, alkenylene, or alkynylene, each of which is independently substituted or unsubstituted, or a bond; m is 1, 2, 3, or 4; Y is N, O, or absent; $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, aryl, heteroaryl, or heterocyclyl, each of which is independently substituted or unsubstituted, or hydrogen; each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent; each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen; each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen; each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the pattern of dashed bonds is chosen to provide an aromatic system, for example, an indole, an indolene, a pyrrolopyridine, a pyrrolopyrimidine, or a pyrrolopyrazine.

In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, the compound is of the formula:

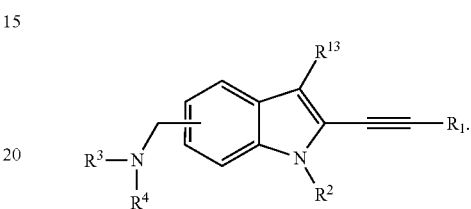

In some embodiments, the compound is of the formula:

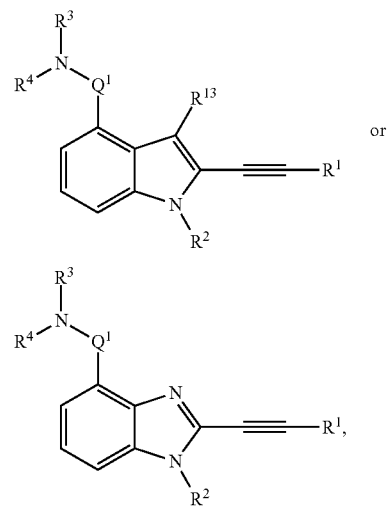

wherein R is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, Si$R^{16}R^{17}R^{18}$, alkyl, alkenyl, alkynyl, aryl, heteroaryl, or heterocyclyl, each of which is independently substituted or unsubstituted, or hydrogen.

In some embodiments, m is 1, 2, 3, or 4. In some embodiments, m is 1. In some embodiments, $X^3$ is carbon atom connected to $Q^1$, and m is 1. In some embodiments, the compound is of the formula:

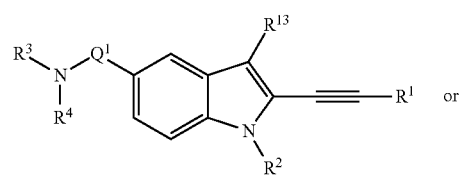

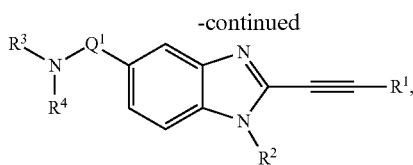

wherein $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, SiR$^{16}$R$^{17}$R$^{18}$, alkyl, alkenyl, alkynyl, aryl, heteroaryl, or heterocyclyl, each of which is independently substituted or unsubstituted, or hydrogen.

In some embodiments, R is alkyl, alkenyl, —C(O)R$^{16}$, —C(O)OR$^{16}$, or —C(O)NR$^{16}$R$^{17}$. In some embodiments, $R^1$ is a substituted alkyl. $R^1$ can be substituted by one or more substituents selected from hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, cyclic alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups. In some embodiments, $R^1$ is alkyl substituted with an amine group. In some embodiments, $R^1$ is alkyl substituted with NR$^{16}$R$^{17}$.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each R$^{16}$ and R$^{17}$ is independently alkyl, alkenyl, aryl, heteroaryl, heterocyclyl, or hydrogen. In some embodiments, $Q^1$ is $C_1$-alkylene, R$^{16}$ is aryl, and R$^{17}$ is alkyl. In some embodiments, $Q^1$ is $C_1$-alkylene, R$^{16}$ is aryl, and R$^{17}$ is hydrogen. In some embodiments, $Q^1$ is $C_1$-alkylene, R$^{16}$ is heteroaryl, and R$^{17}$ is alkyl. In some embodiments, $Q^1$ is $C_1$-alkylene, R$^{16}$ is heteroaryl, and R$^{17}$ is hydrogen. In some embodiments, $Q^1$ is $C_1$-alkylene, R$^{16}$ is substituted heteroaryl, and R$^{17}$ is hydrogen. In some embodiments, $Q^1$ is $C_1$-alkylene, R$^{16}$ is substituted alkyl, and R$^{17}$ is hydrogen. In some embodiments, R$^{17}$ is aryl, heteroaryl, or heterocyclyl, each of which is independently substituted or unsubstituted with halogen, alkyl, or hydroxyl. In some embodiments, R$^{16}$ is hydrogen, and R$^{17}$ is aryl or heteroaryl, substituted or unsubstituted with halogen or alkyl. In some embodiments, R$^{16}$ is alkyl, and R$^{17}$ is heteroaryl substituted with halogen or alkyl. In some embodiments, R$^{17}$ is aryl, heteroaryl, or heterocyclyl, each of which is independently substituted or unsubstituted with alkyl. In some embodiments, R$^{17}$ is aryl or heteroaryl, each of which is independently substituted with alkyl, wherein the alkyl is optionally substituted with fluorine, chlorine, bromine, iodine, or cyano.

In some embodiments, $R^2$ is hydrogen or alkyl. In some embodiments, R$^{13}$ is alkyl, alkenyl, hydrogen, or halogen. In some embodiments, $R^2$ is alkyl, and R$^{13}$ is alkyl. In some embodiments, $R^2$ is hydrogen, and R$^{13}$ is alkyl. In some embodiments, $R^2$ is methyl, ethyl, propyl, iso-propyl, butyl, or tert-butyl. In some embodiments, R$^{13}$ is methyl, ethyl, propyl, iso-propyl, butyl or tert-butyl. In some embodiments, $R^2$ is hydrogen, and R$^{13}$ is hydrogen.

In some embodiments, $R^3$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen, and $R^4$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen. In some embodiments, $R^3$ is hydrogen and $R^4$ is substituted alkyl. In some embodiments, $R^3$ is hydrogen and $R^4$ is alkyl substituted with aryl. In some embodiments, $R^3$ is alkyl and $R^4$ is alkyl. In some embodiments, $R^3$ is alkyl and $R^4$ is aryl.

In some embodiments, $R^3$ is hydrogen, and $R^4$ is heterocyclyl. In some embodiments, the compound is of the formula:

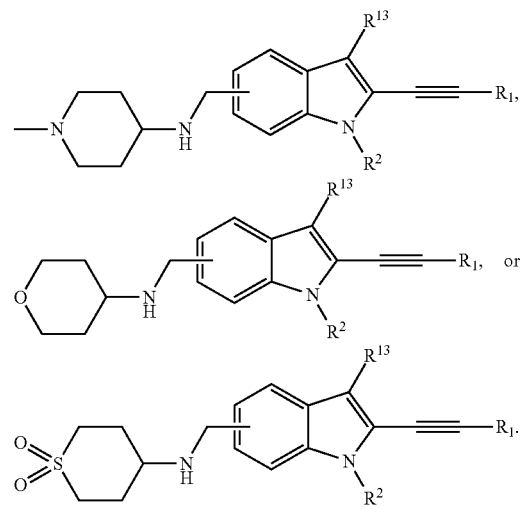

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, $R^3$ and $R^4$ together with the nitrogen atom to which $R^3$ and $R^4$ are bound form a ring of a following formula:

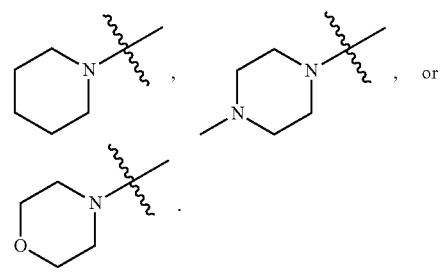

In some embodiments, R$^{16}$ is alkyl, alkenyl, aryl, heteroaryl, heterocyclyl, or hydrogen, and R$^{17}$ is aryl, heteroaryl, or heterocyclyl. In some embodiments, R$^{17}$ is phenyl, indolyl, piperidinyl, imidazolyl, thiazolyl, morpholinyl, pyrrolyl, or pyridinyl.

In some embodiments, the compound is of the formula:

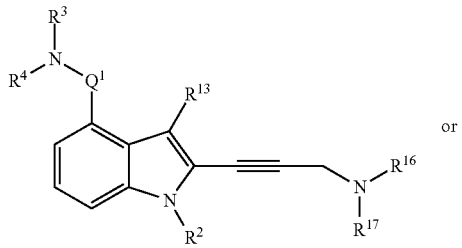

or

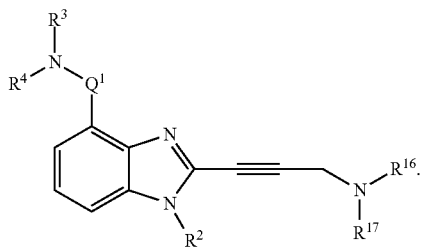

In some embodiments, the compound is of the formula:

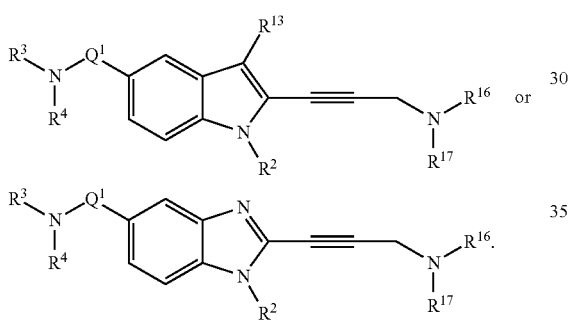

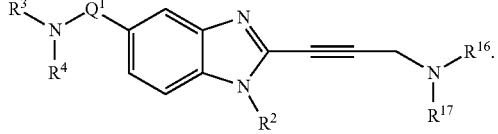

In some embodiments, the compound is of the formula:

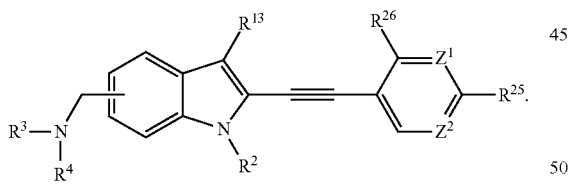

wherein each $Z^1$ and $Z^2$ is independently $CR^x$ or N; each $R^x$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, hydrogen, or halogen; each $R^{25}$ and $R^{26}$ is independently —C(O)$R^{21}$, —C(O)O$R^{21}$, —C(O)N$R^{21}R^{22}$, —O$R^{21}$, —S$R^{21}$, —SO$_2R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen.

In some embodiments, $Z^1$ is N. In some embodiments, $Z^1$ and $Z^2$ are N. In some embodiments, each $R^{25}$ and $R^{26}$ is independently a halogen. In some embodiments, $R^{25}$ is

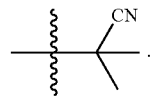 [SMILES: *C(C)(C)C#N]

In some embodiments, $R_{25}$ is SO$_2R^{21}$. In some embodiments, $R^{25}$ is SO$_2R^{21}$, wherein $R^{21}$ is alkyl. In some embodiments, $R^{25}$ is SO$_2R^{21}$, wherein $R^{21}$ is methyl.

Non-limiting examples of compounds of the current disclosure include the following:

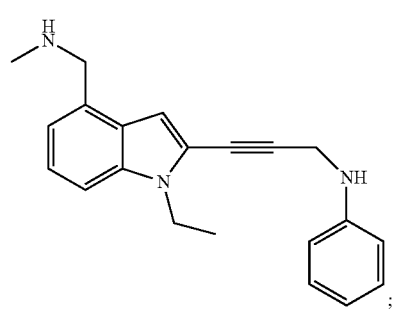

;

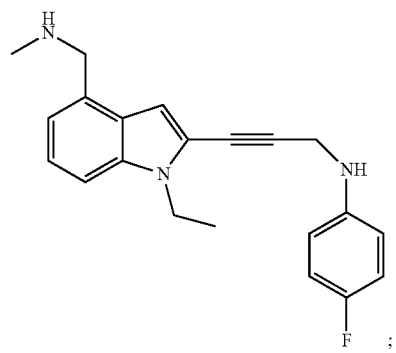

;

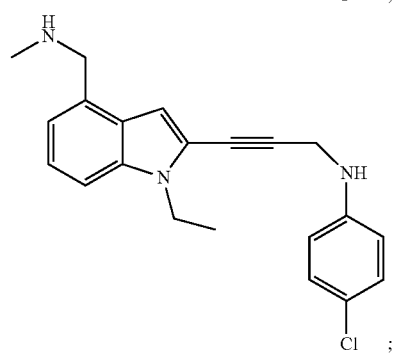

;

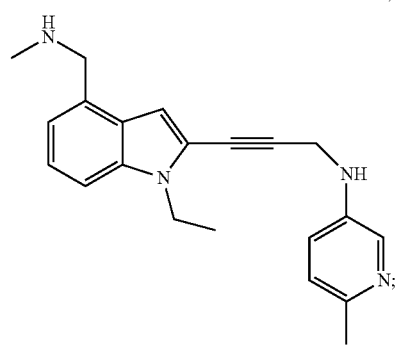

;

17
-continued
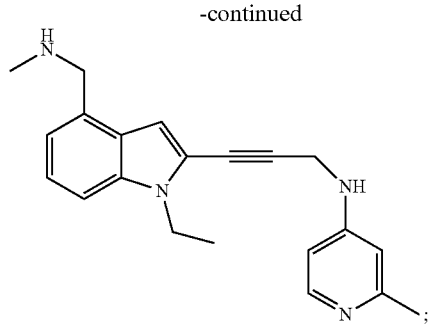
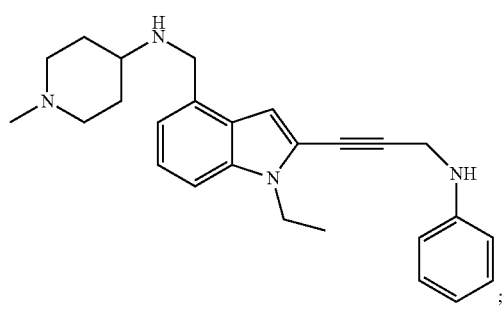
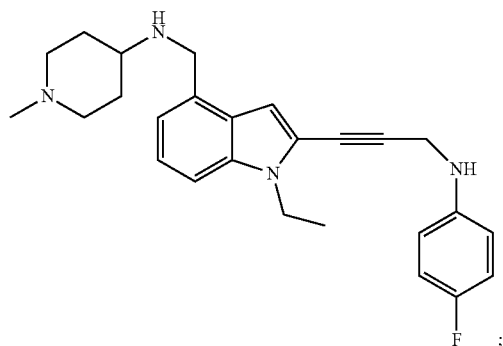
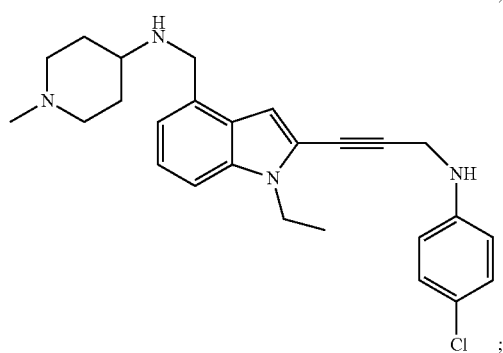
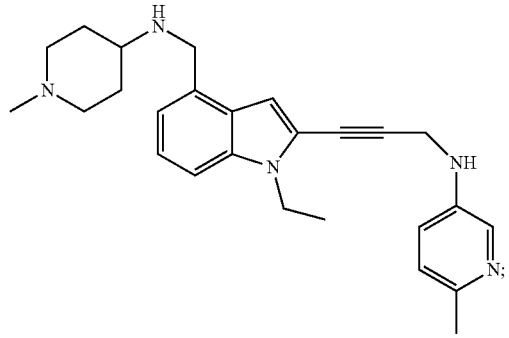
18
-continued
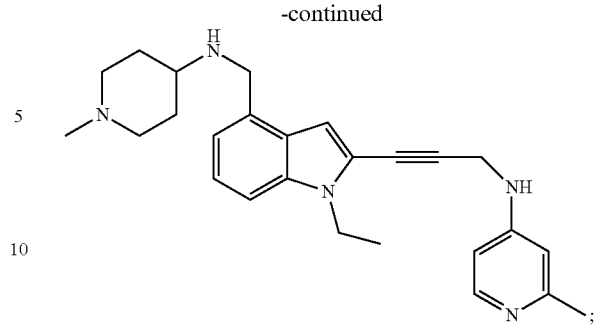
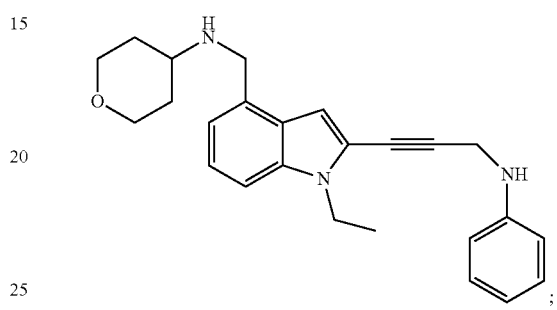
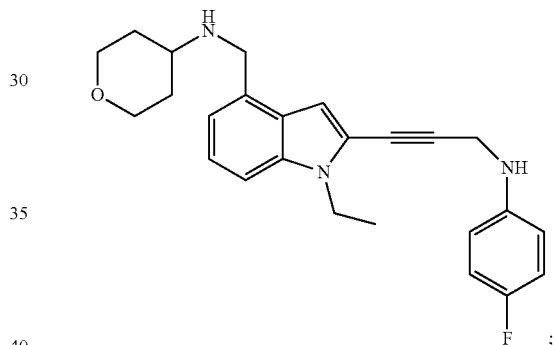
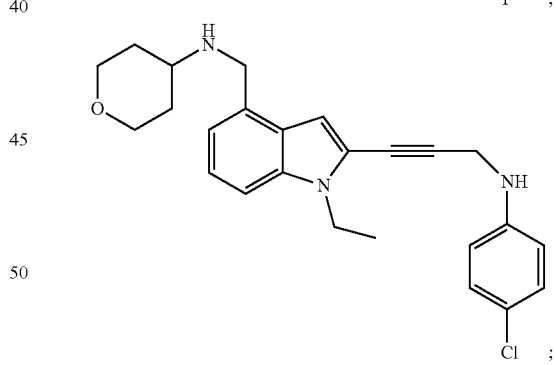
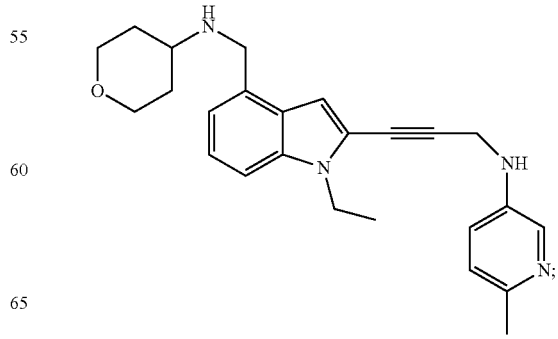

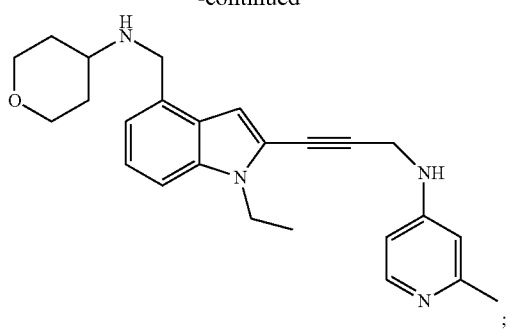
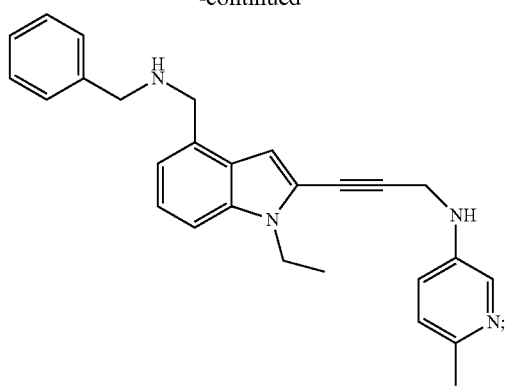
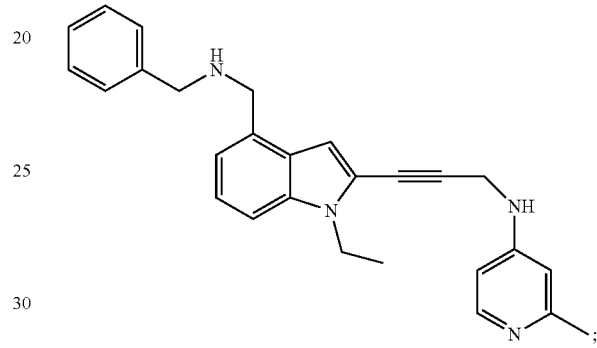
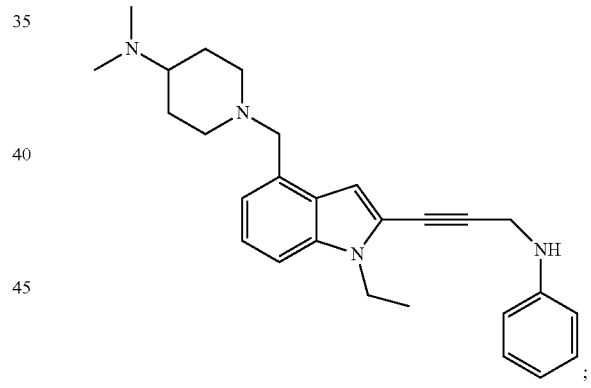
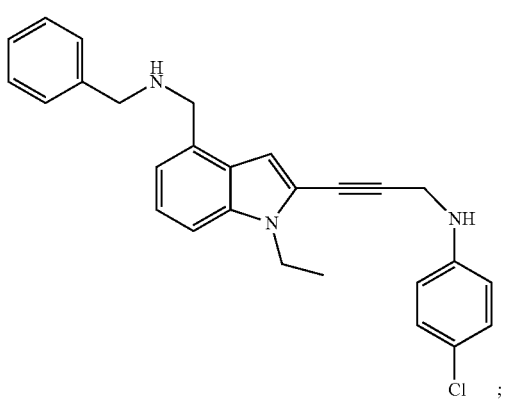
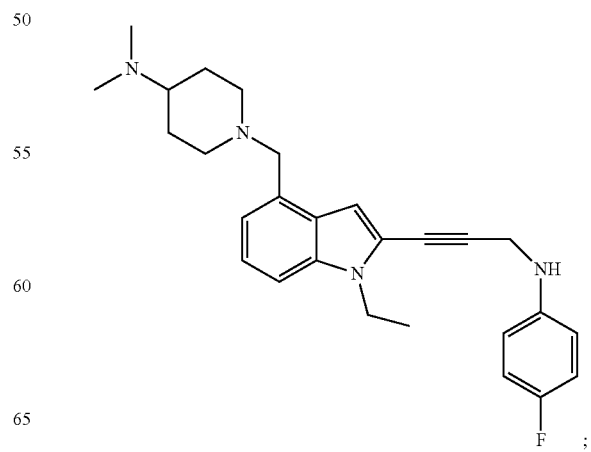

21
-continued
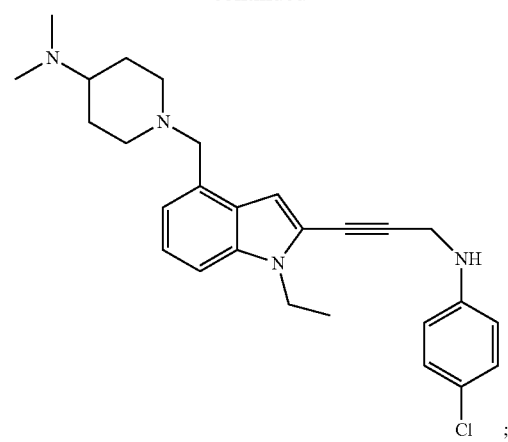
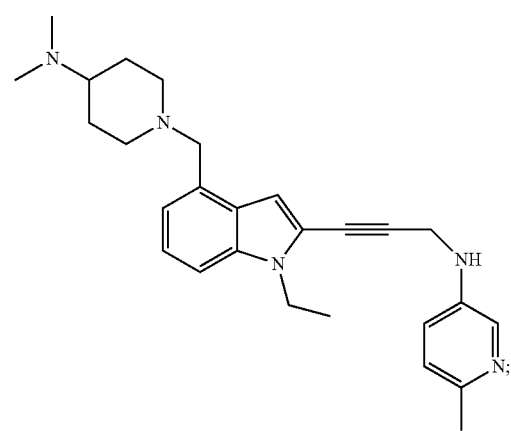
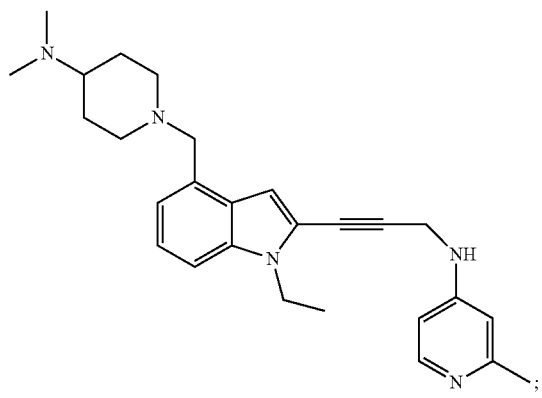
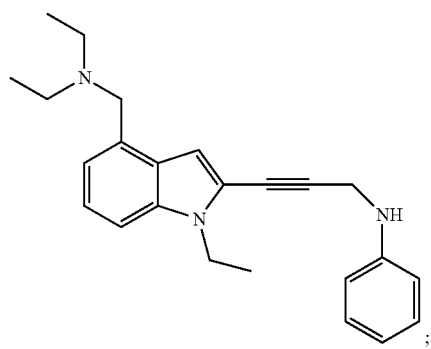
22
-continued
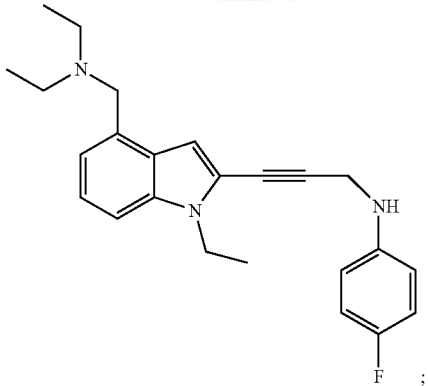
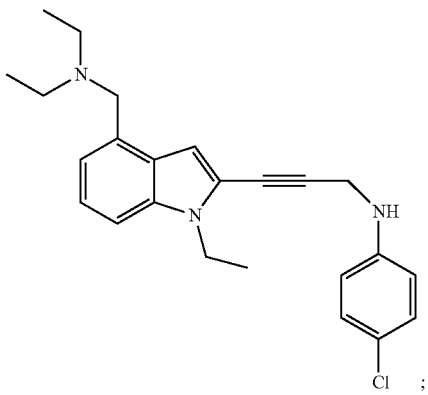
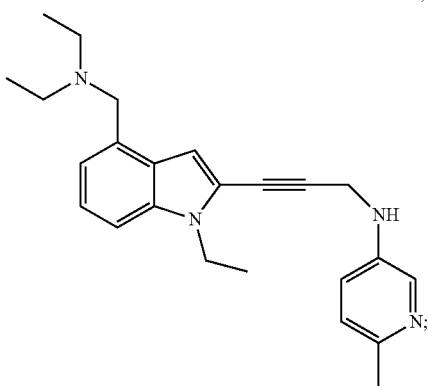
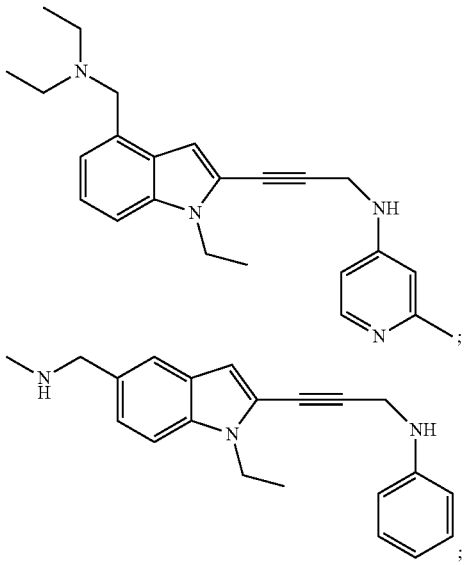

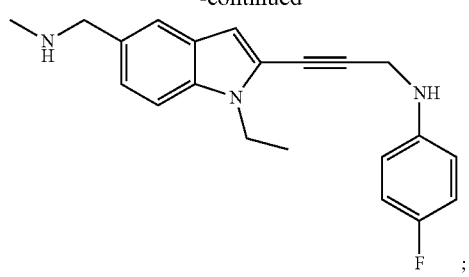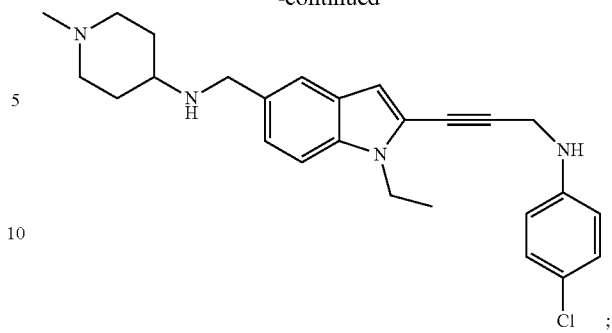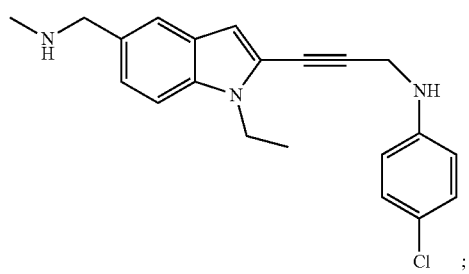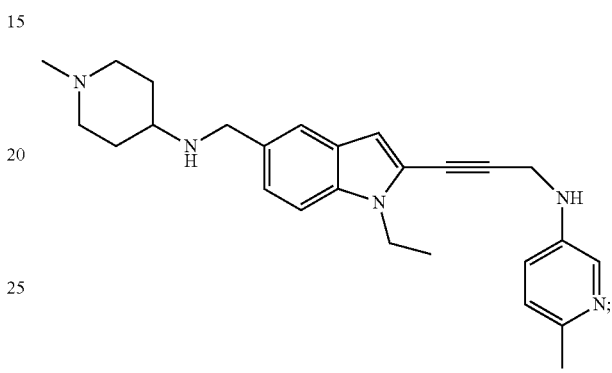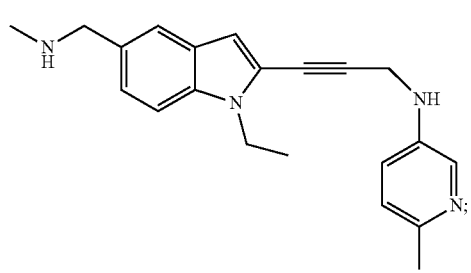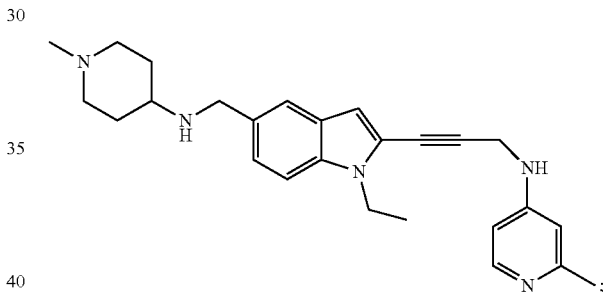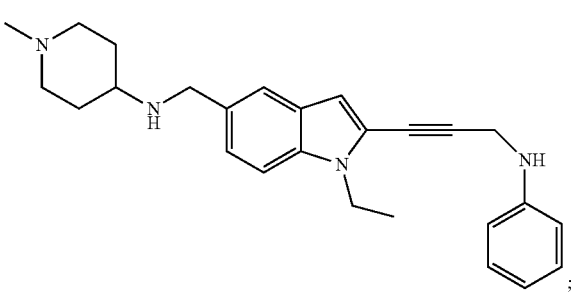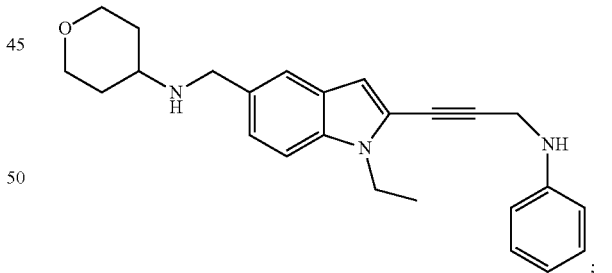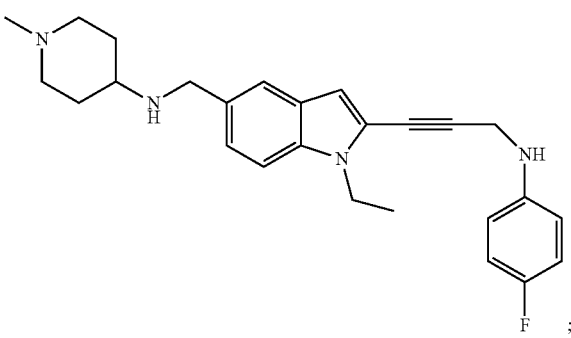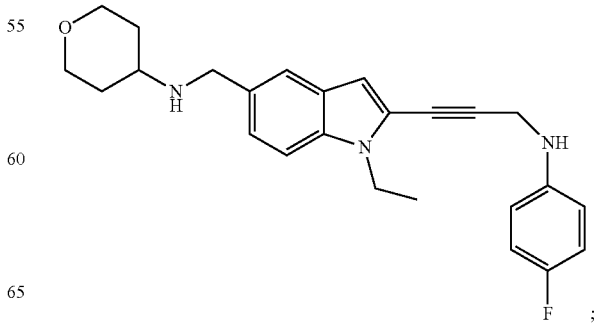

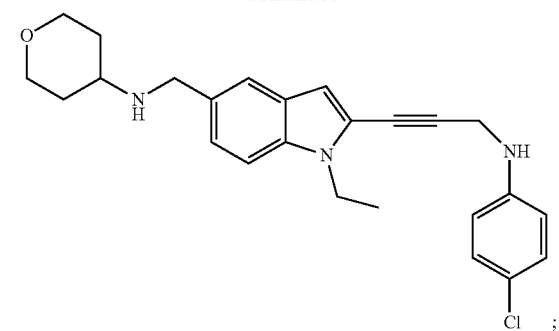
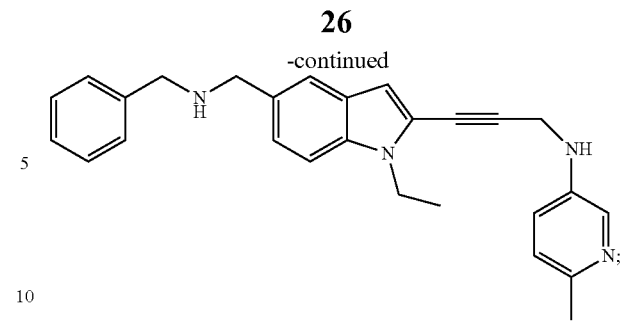
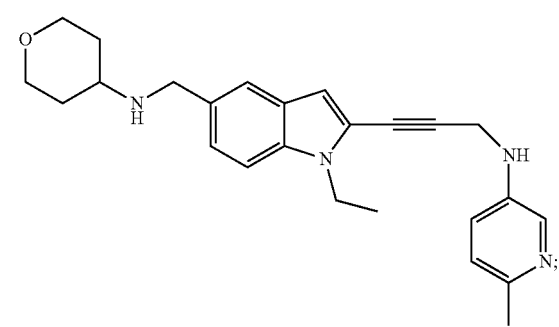
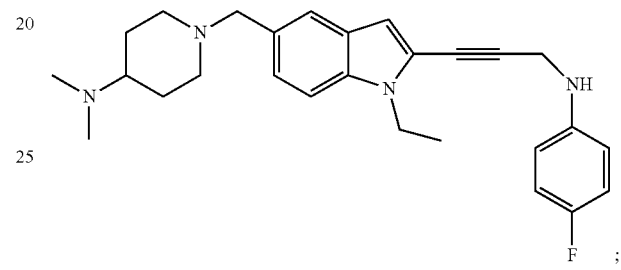
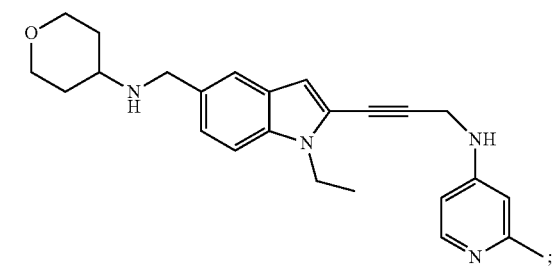
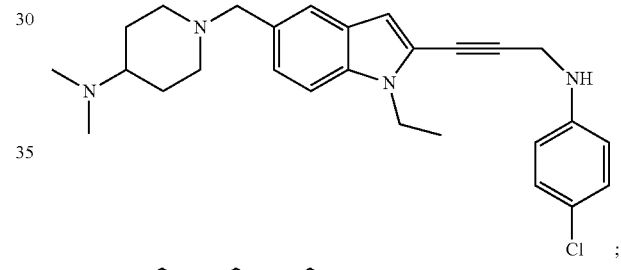
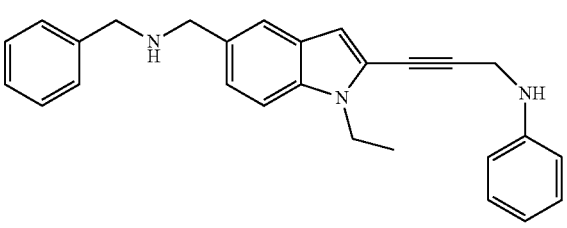
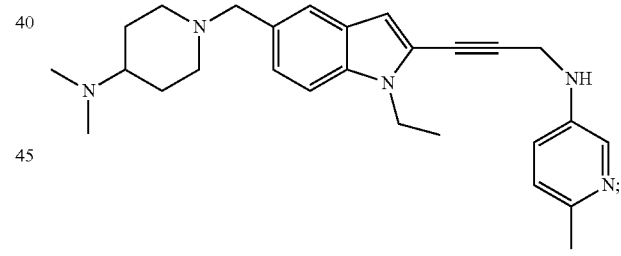
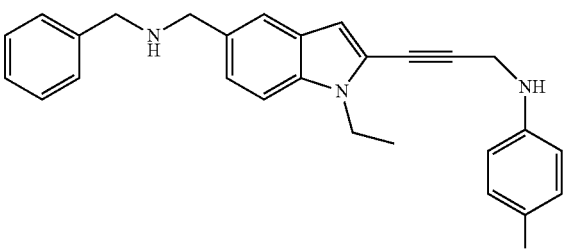
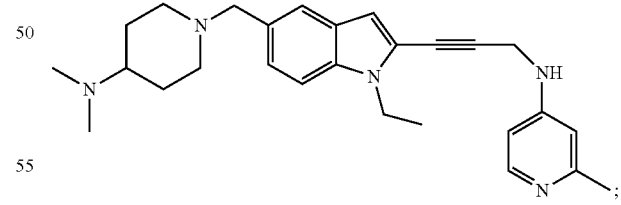
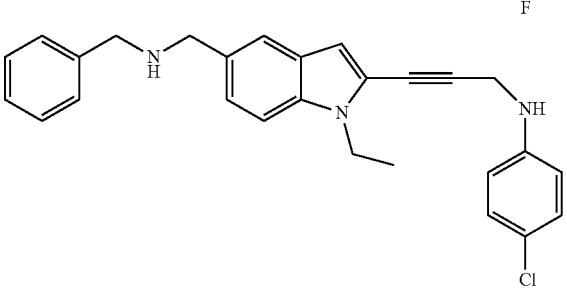
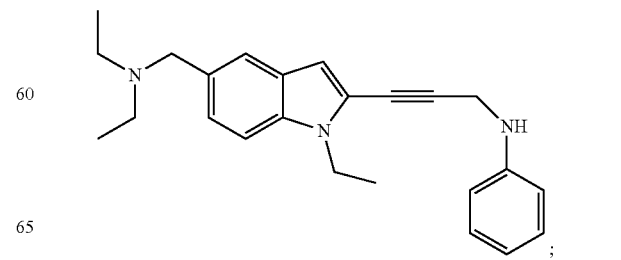

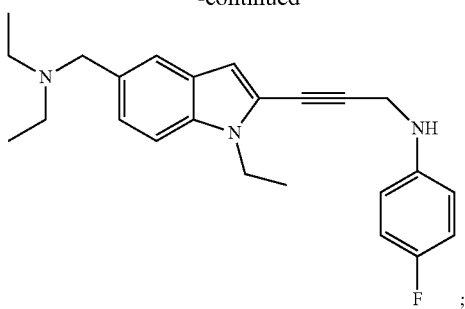
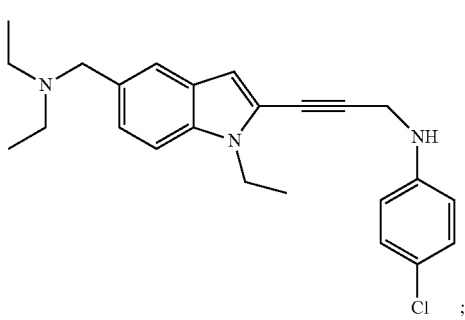
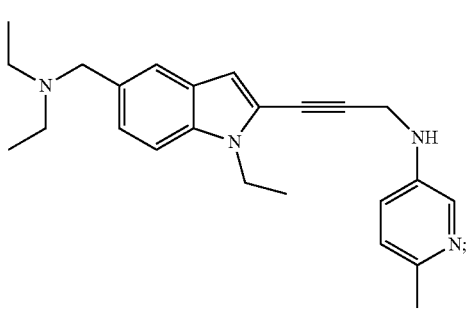
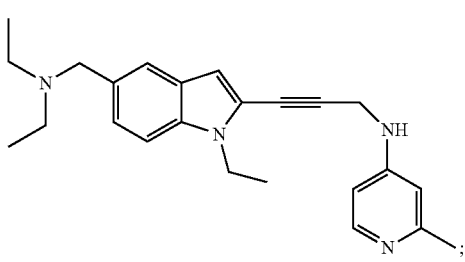
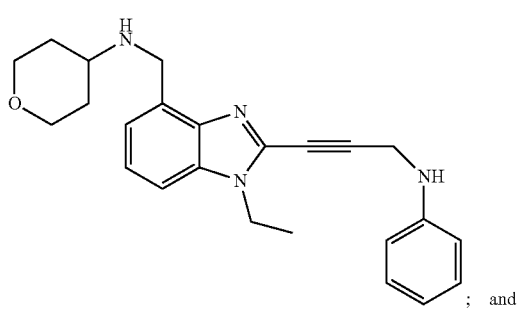
; and
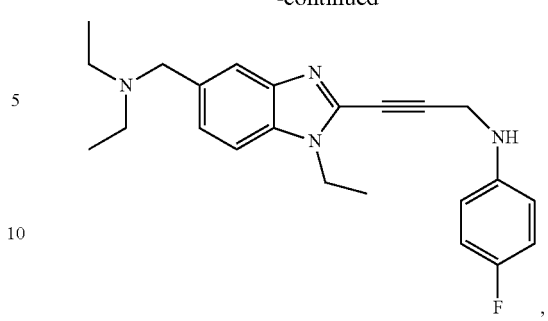
or a pharmaceutically-acceptable salt of any of the foregoing.
Non-limiting examples of compounds of the current disclosure include the following:
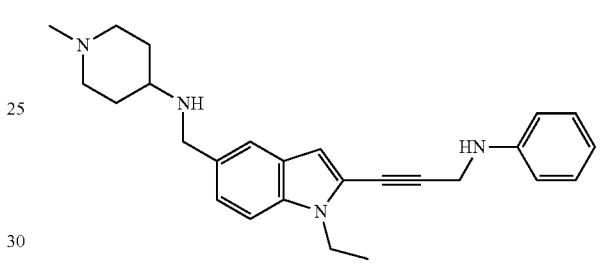
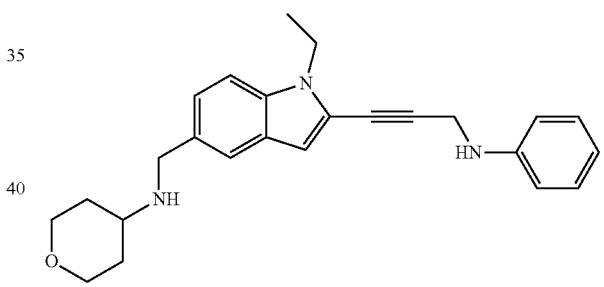
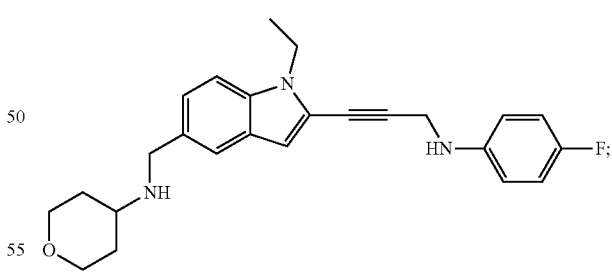

-continued
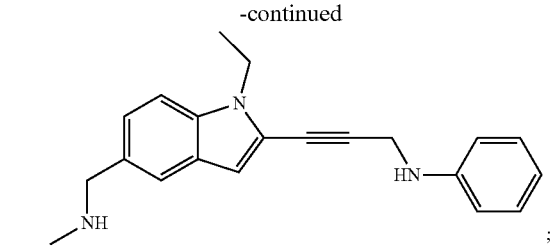
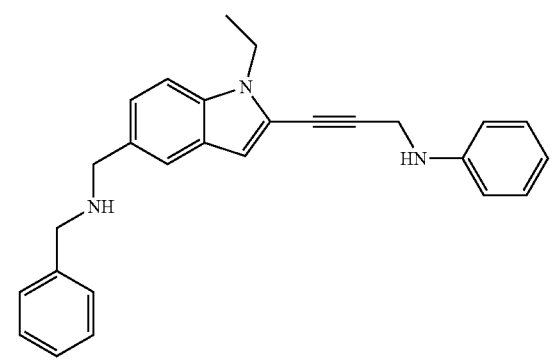
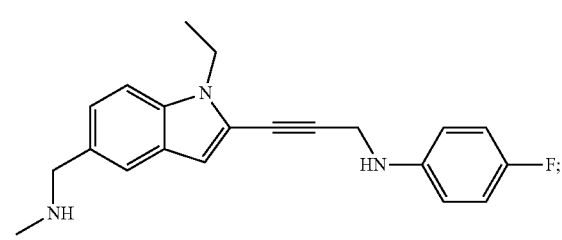
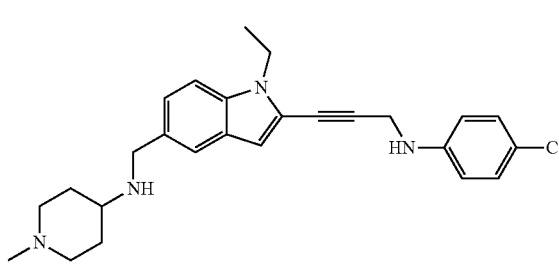
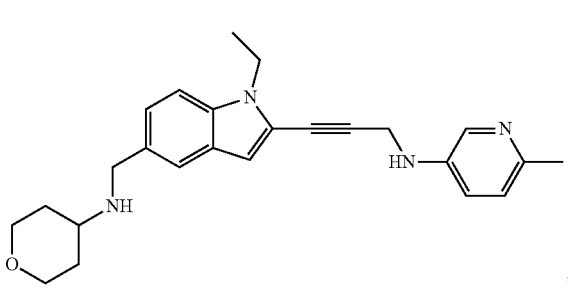
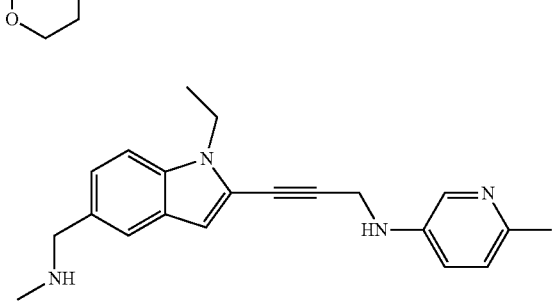
-continued
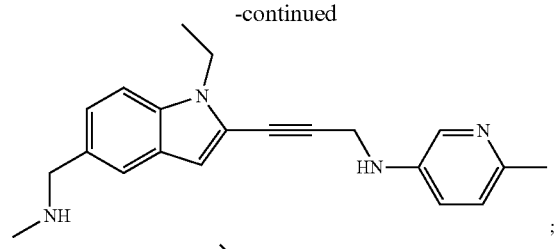
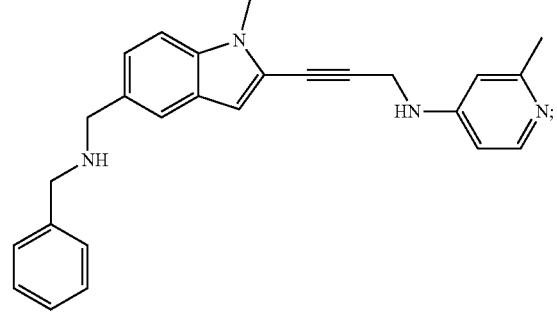
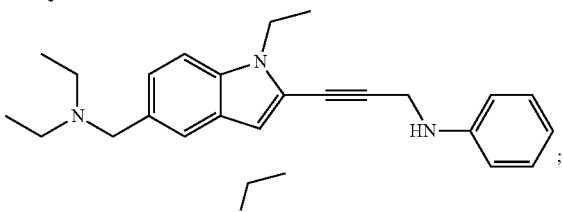
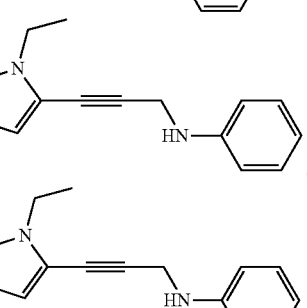

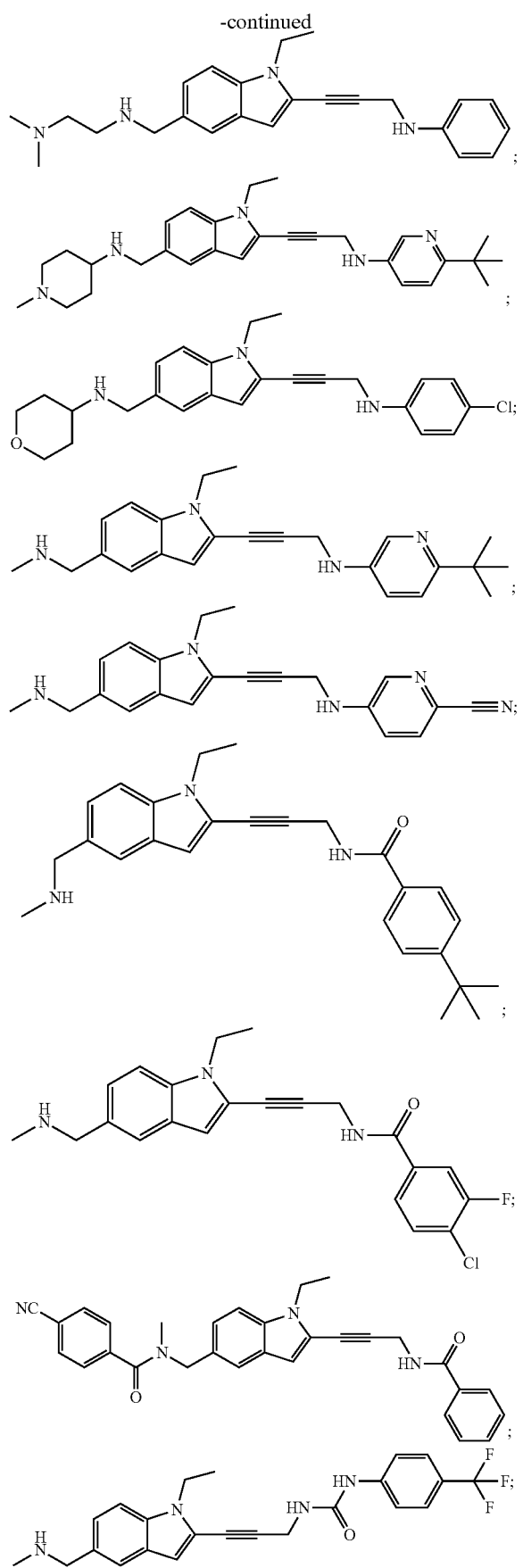
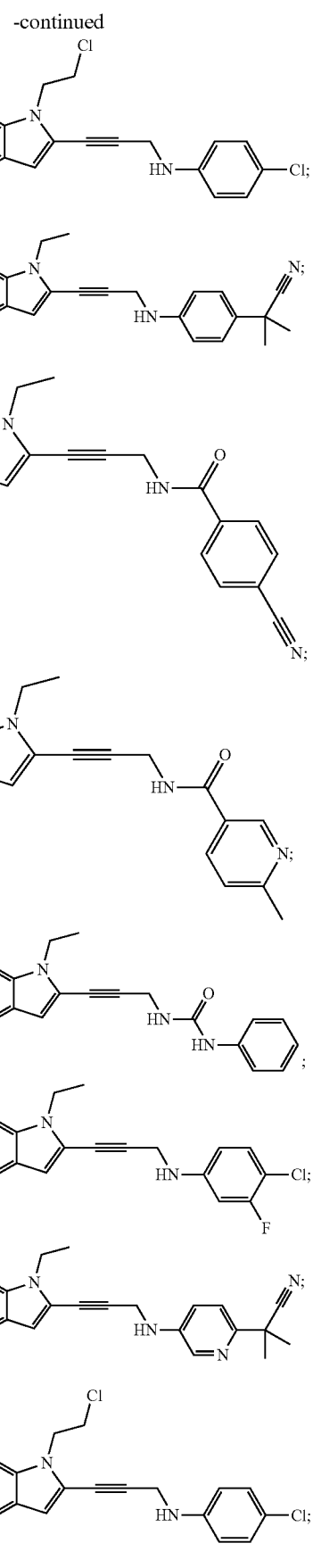

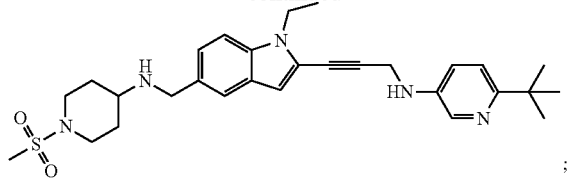
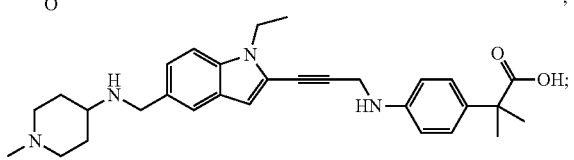
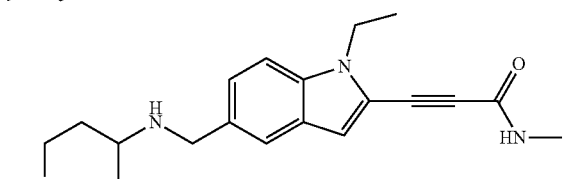
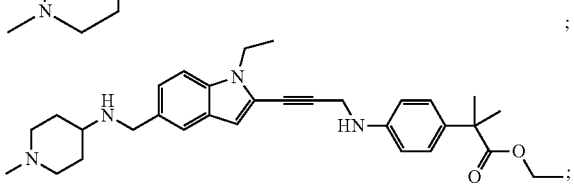
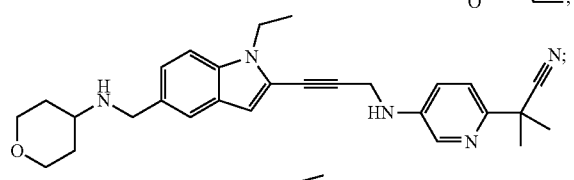
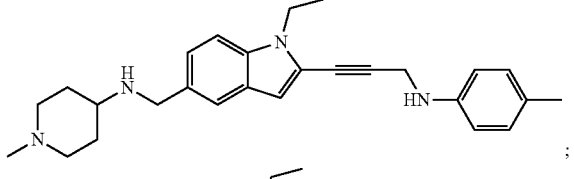
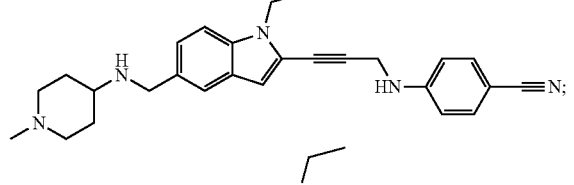
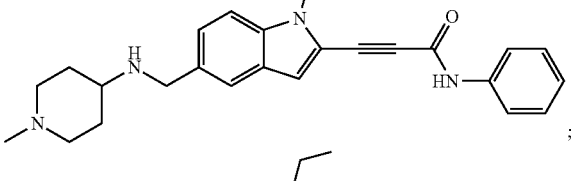
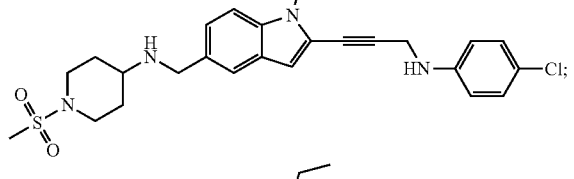
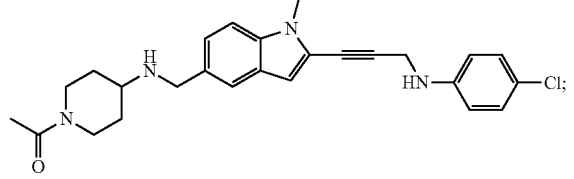
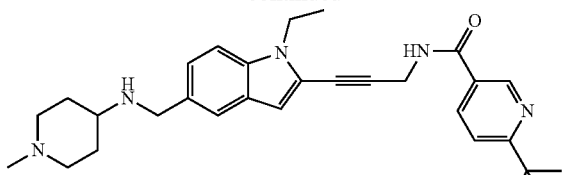
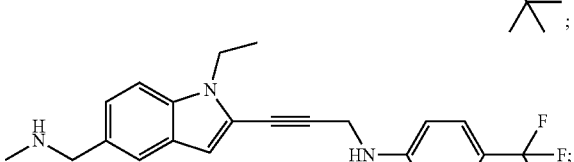
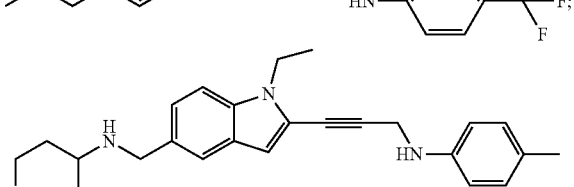
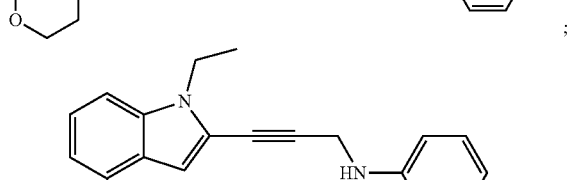
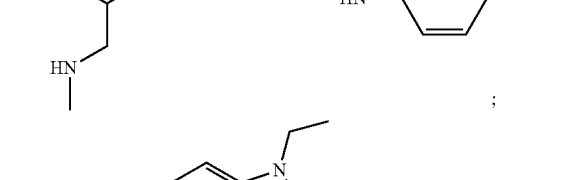
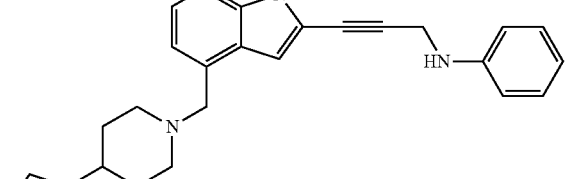
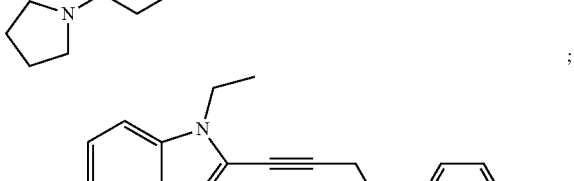
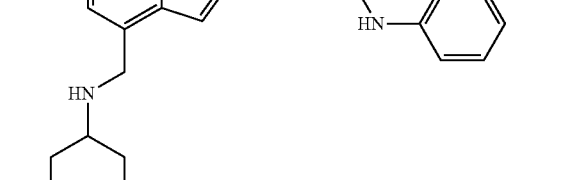
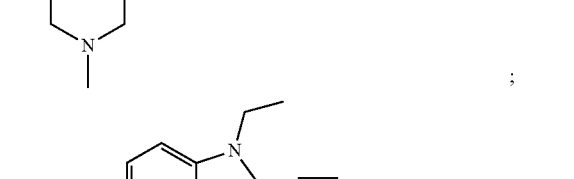
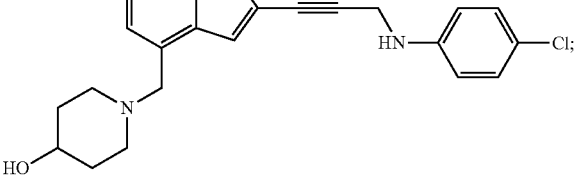

35
-continued
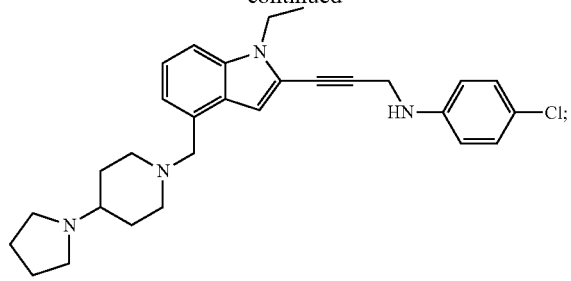
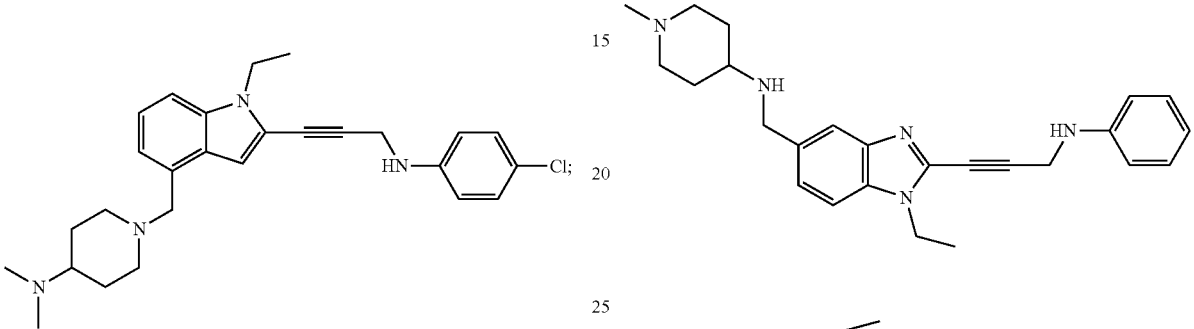
36
-continued
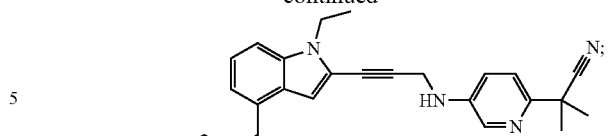
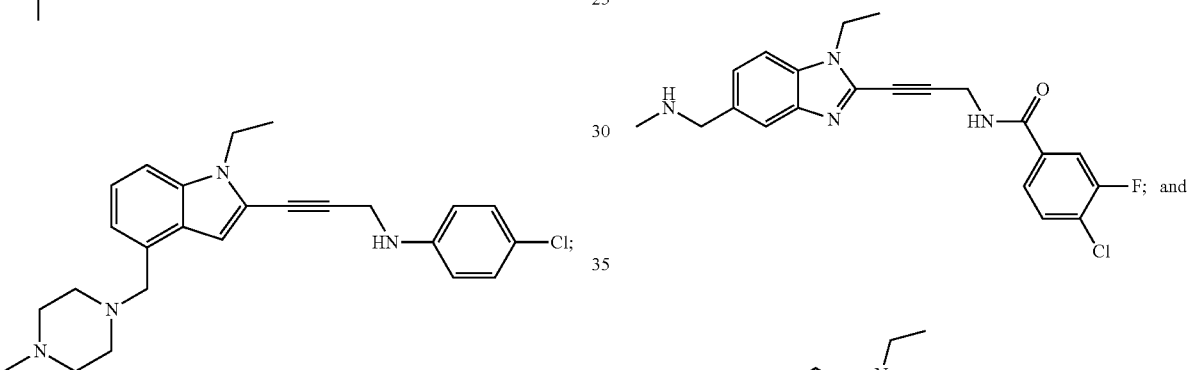
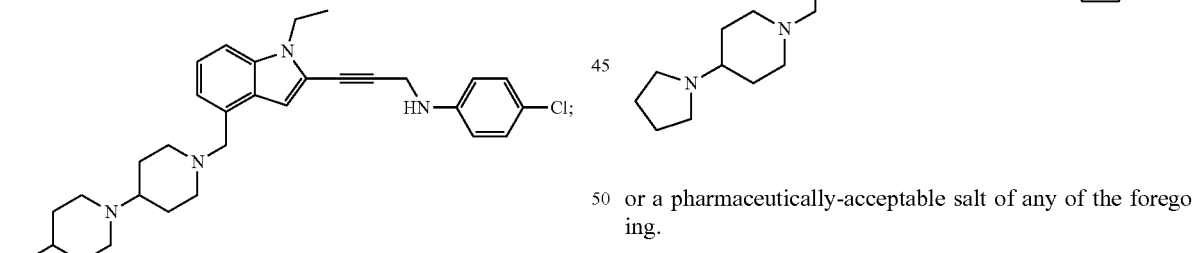
or a pharmaceutically-acceptable salt of any of the foregoing.
Non-limiting examples of compounds of the current disclosure include the following:
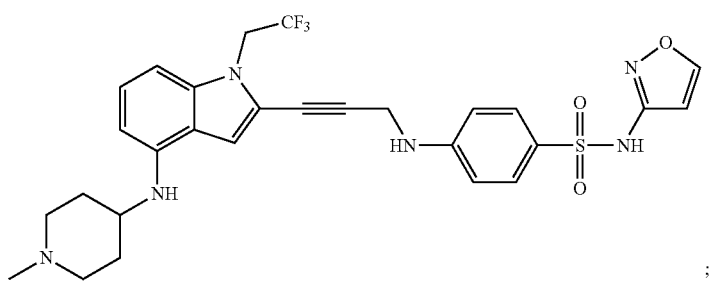

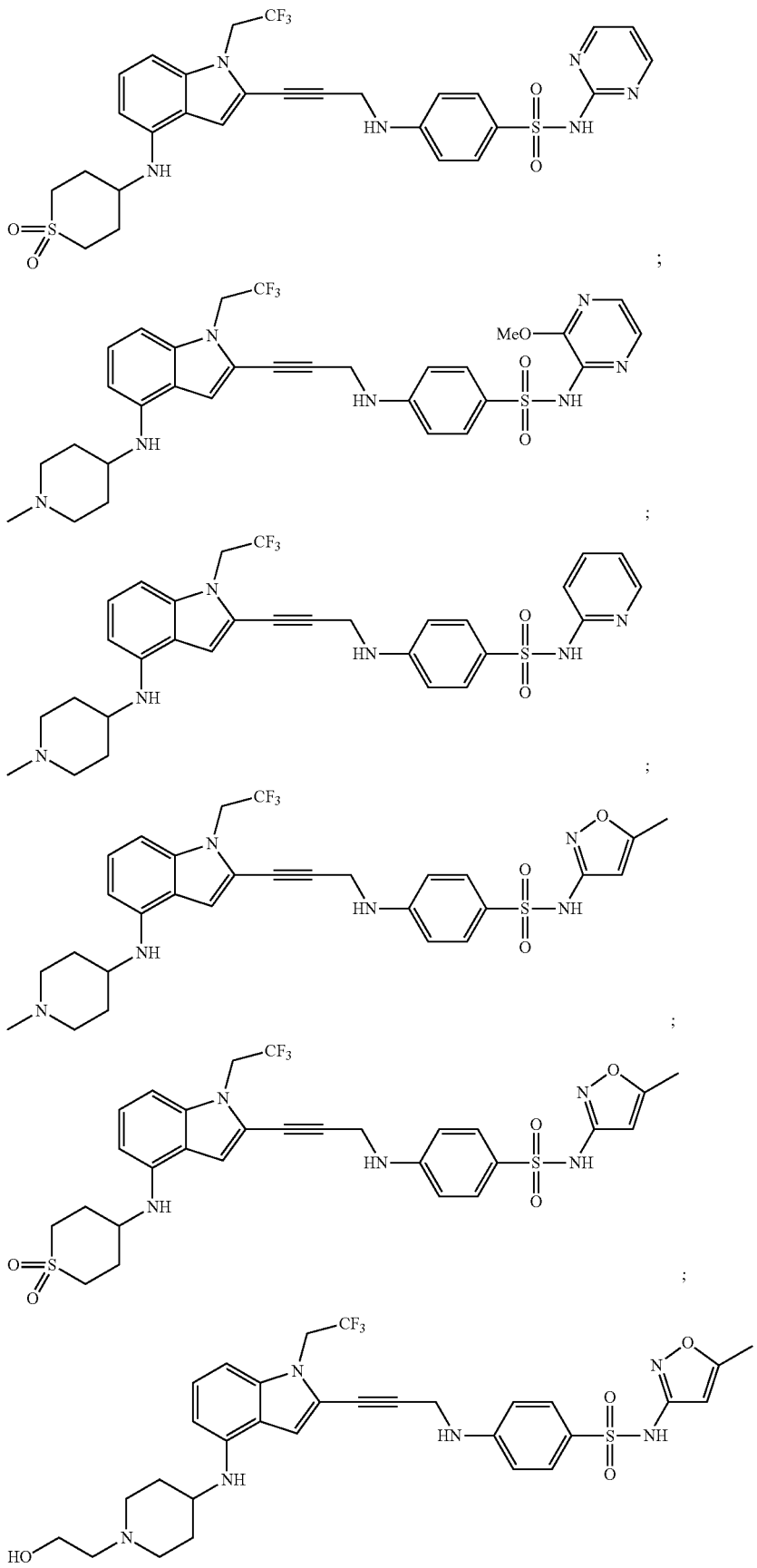

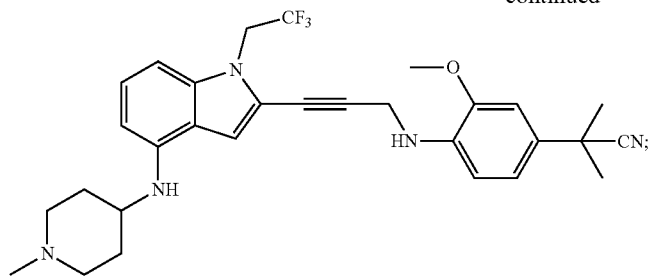
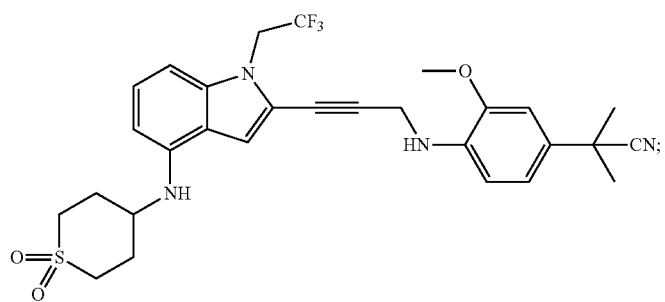
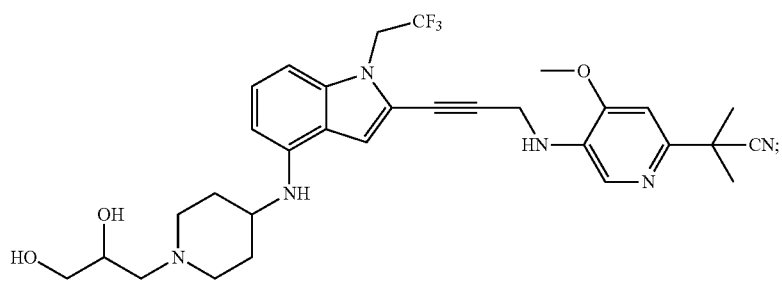
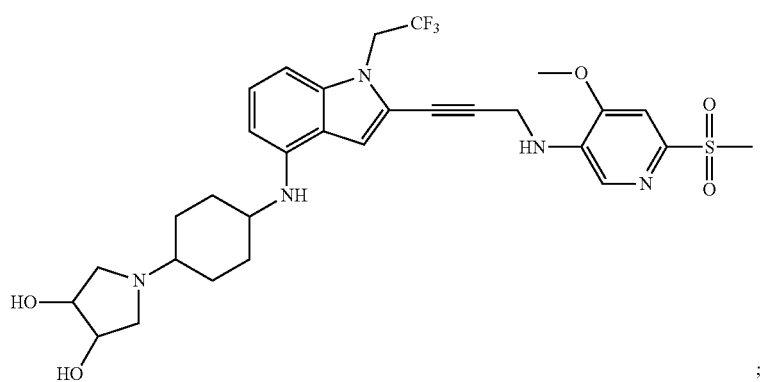
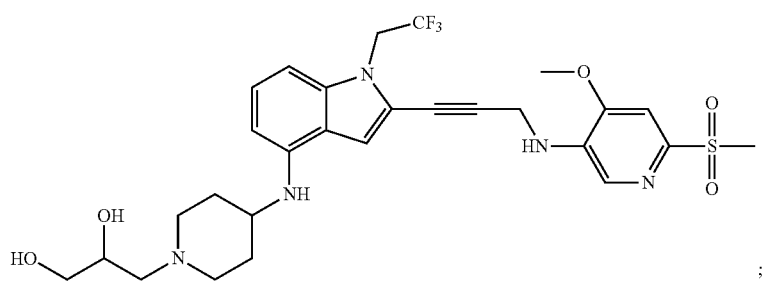

-continued
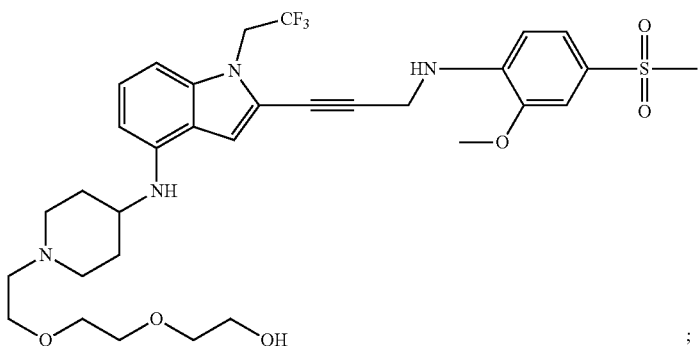
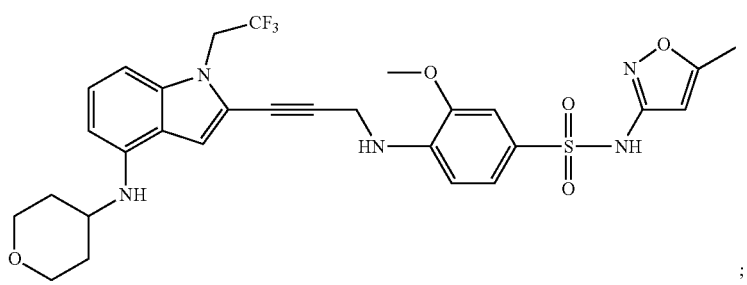
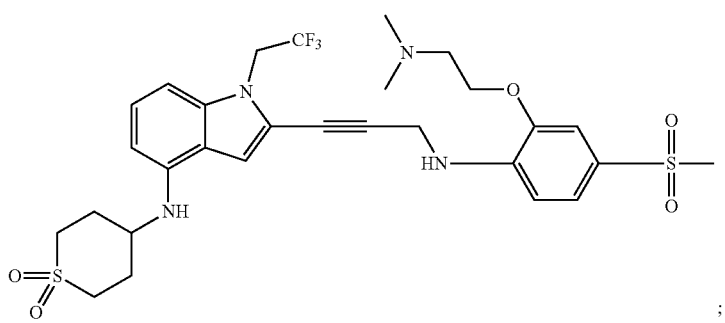
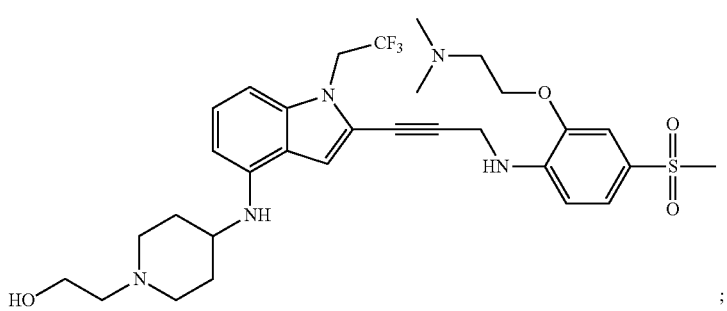
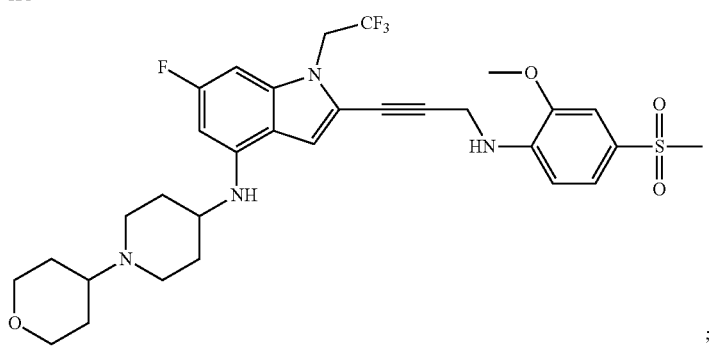

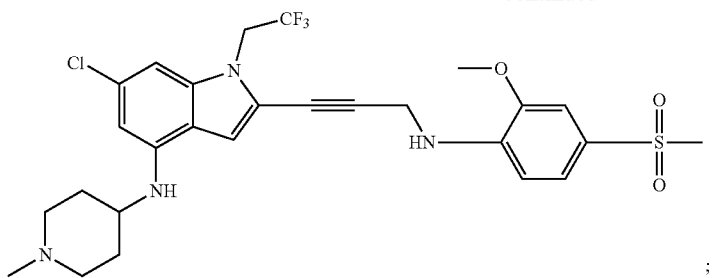
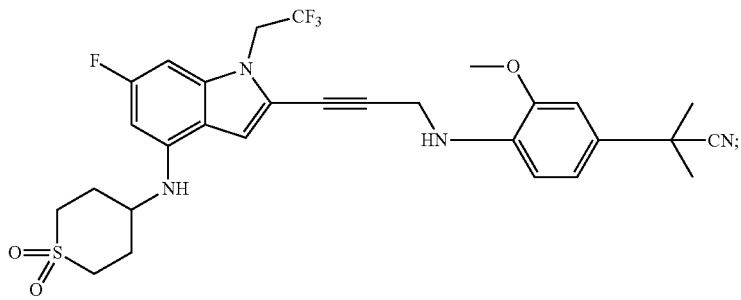
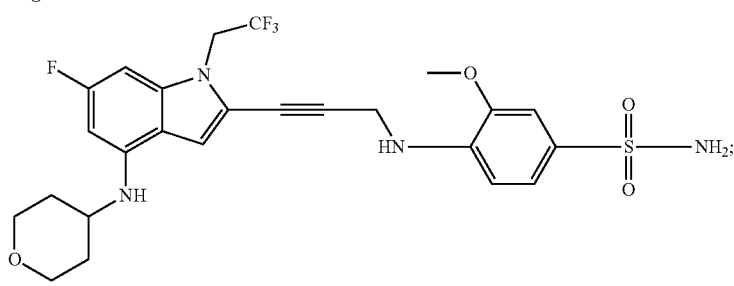
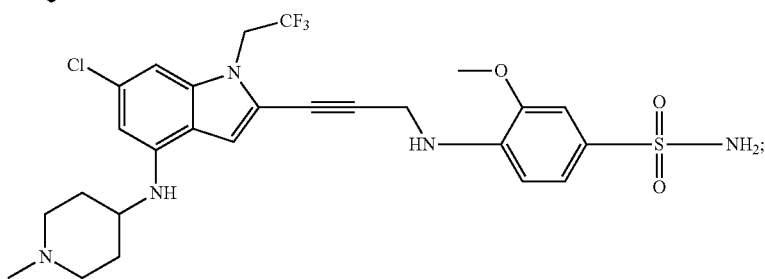
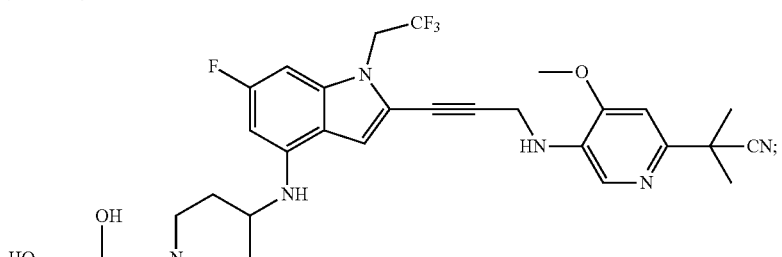
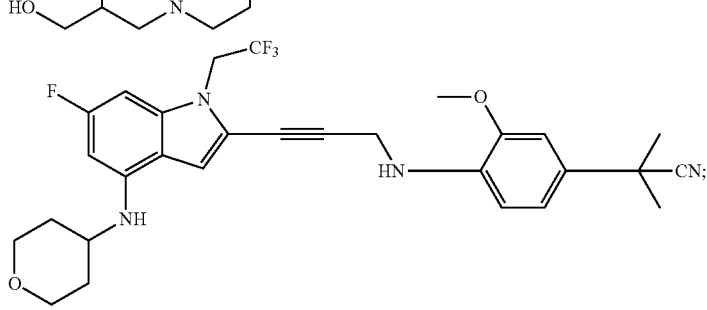

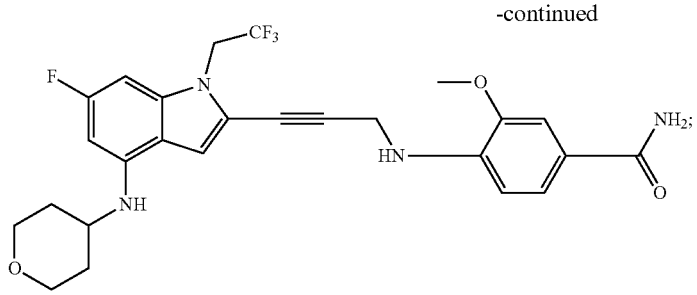
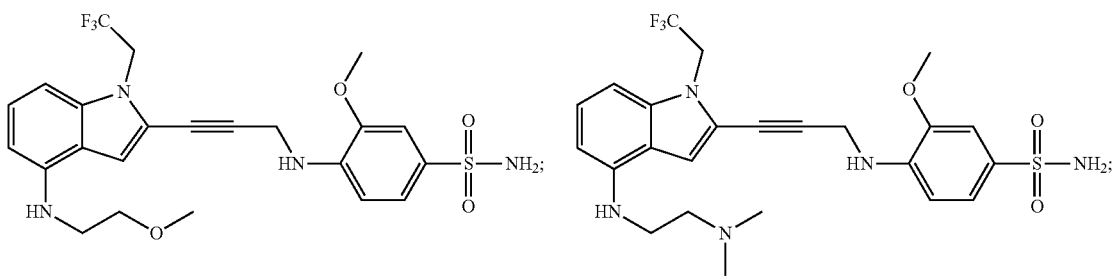
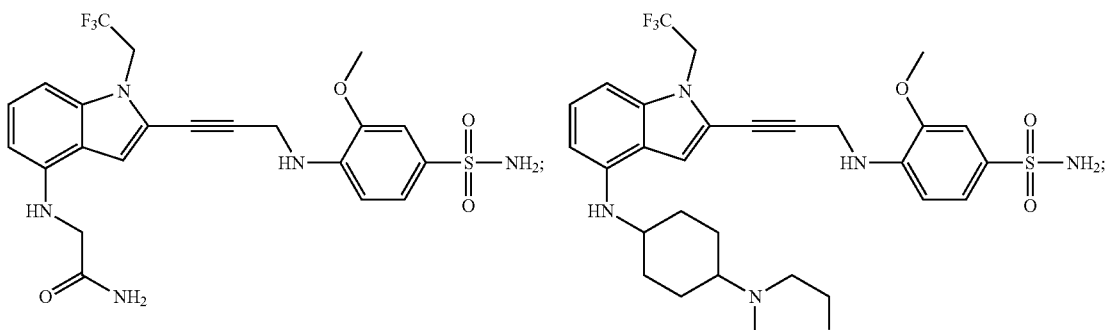
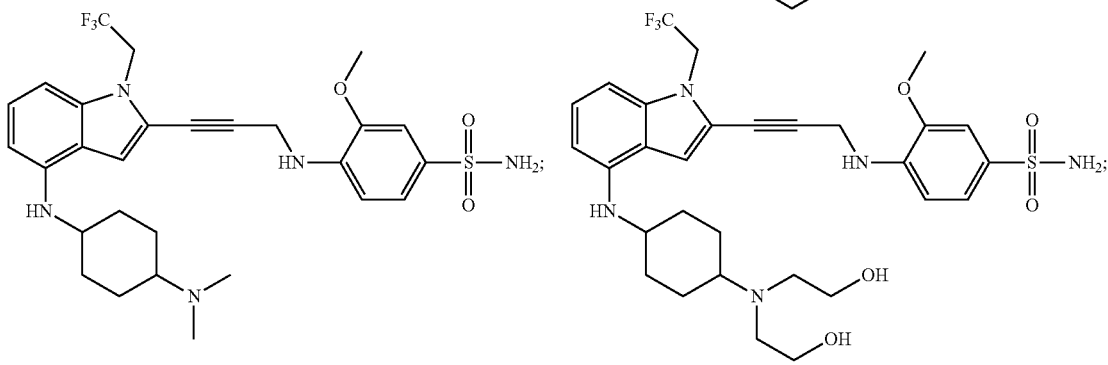
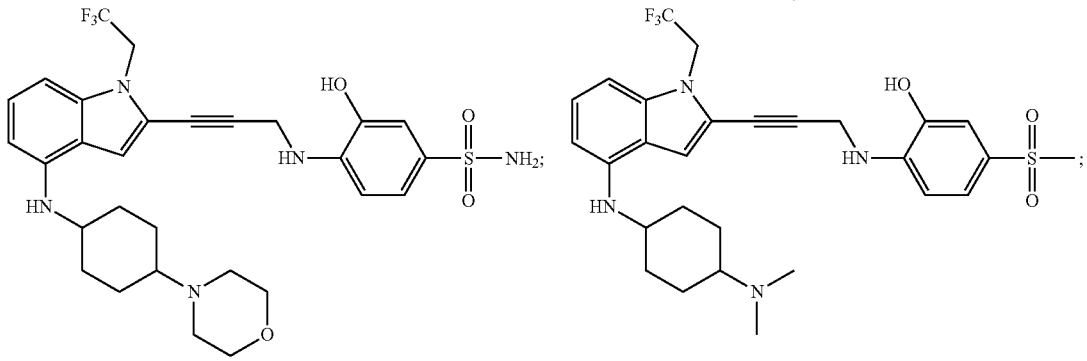

-continued
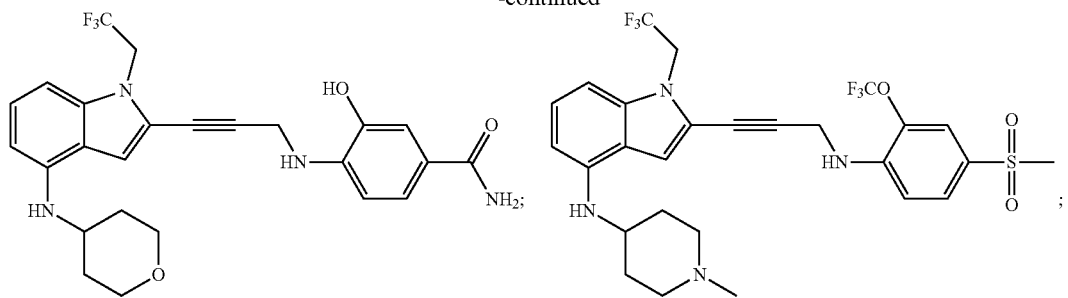
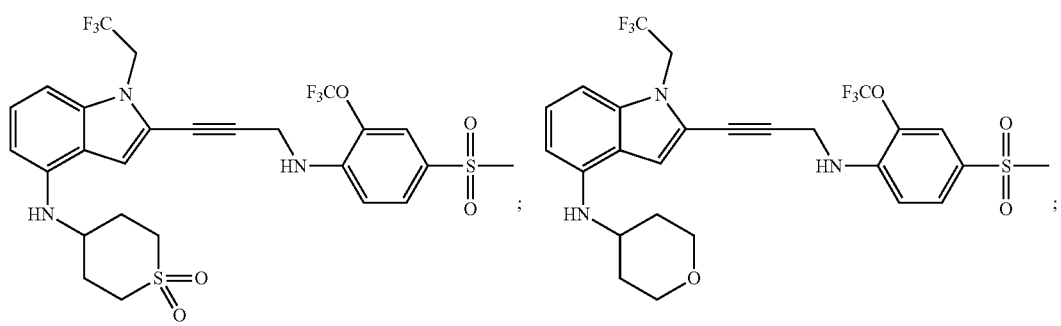
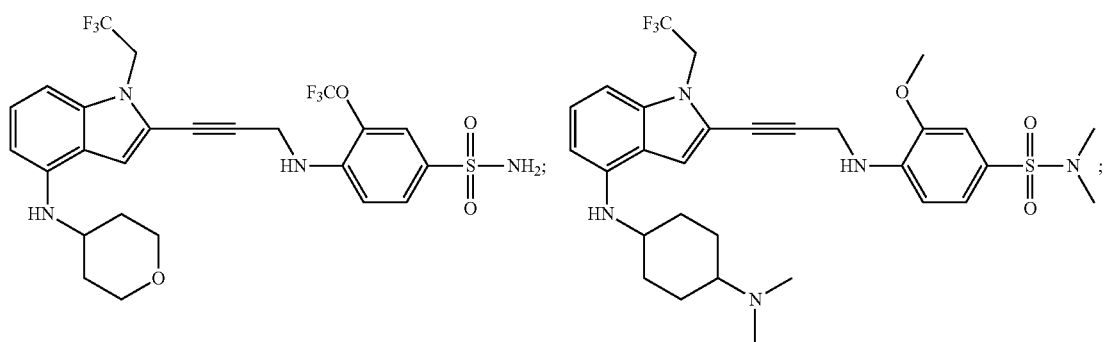
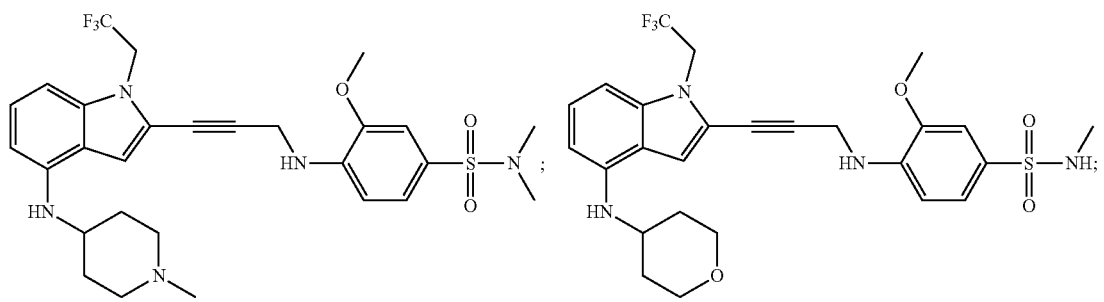
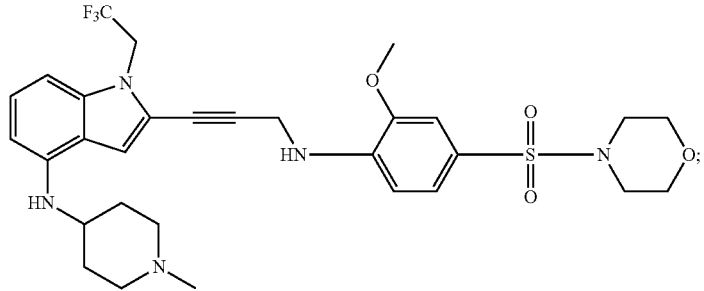

-continued
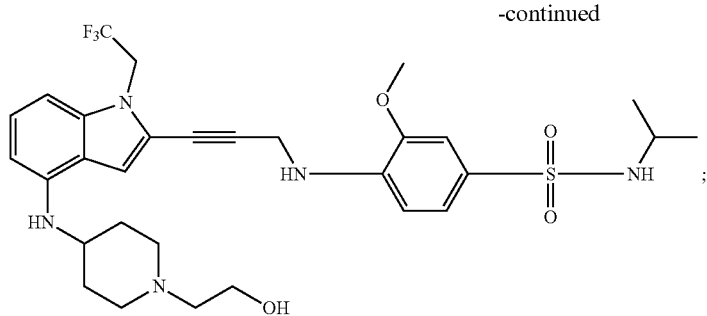
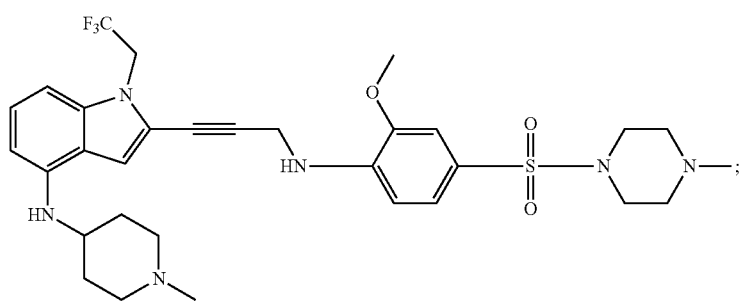
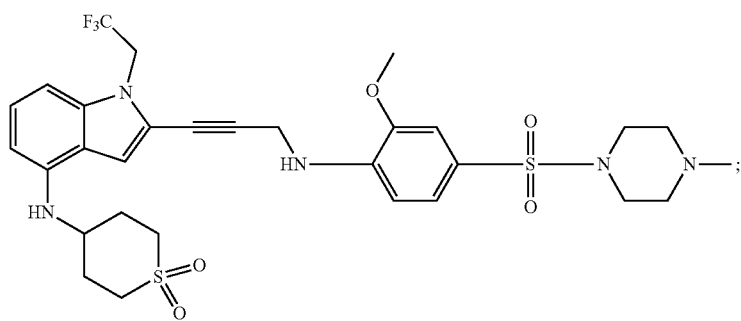
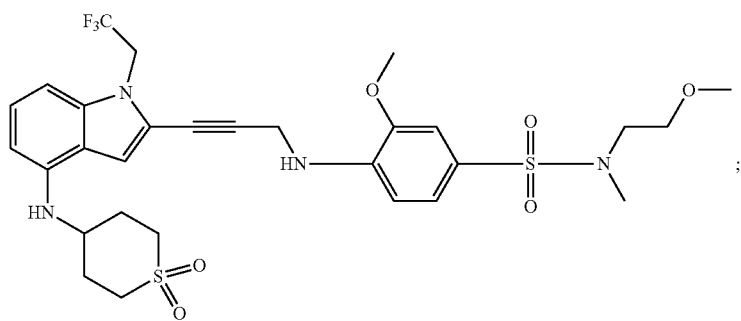
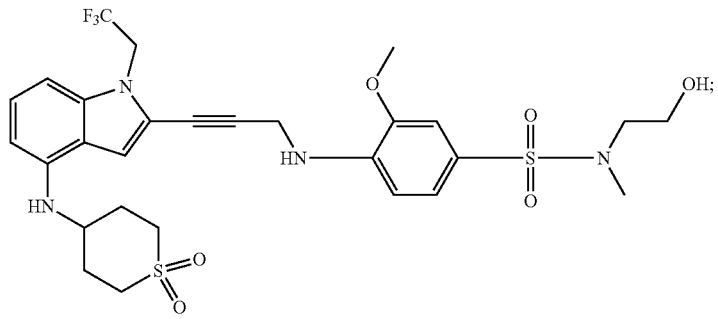

-continued

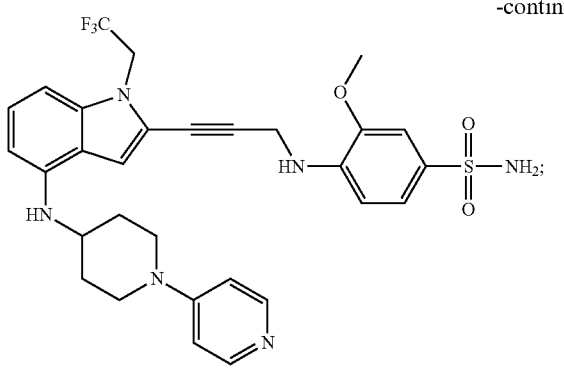
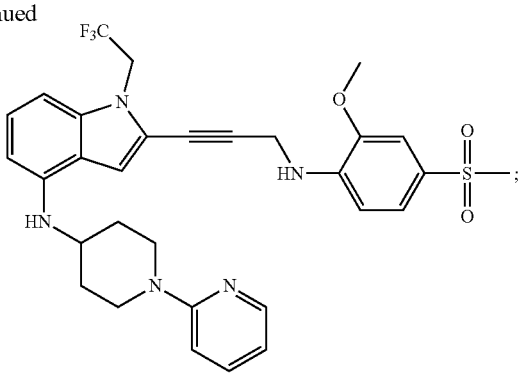
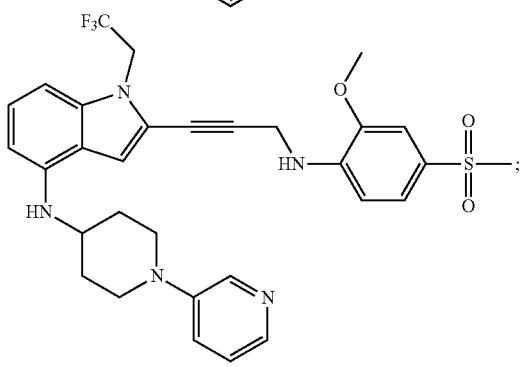
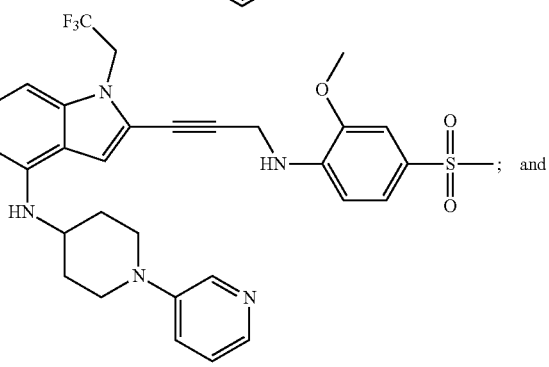

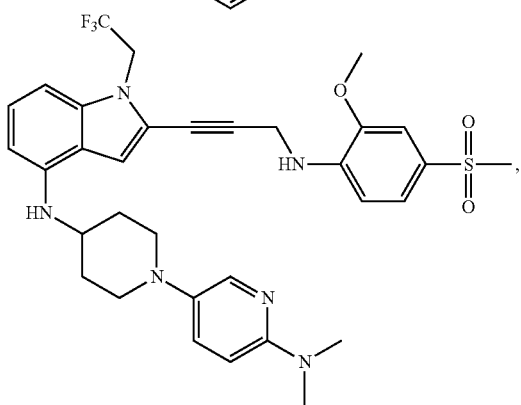

or a pharmaceutically-acceptable salt of any of the forgoing.
In some embodiments, the compound is of the formula

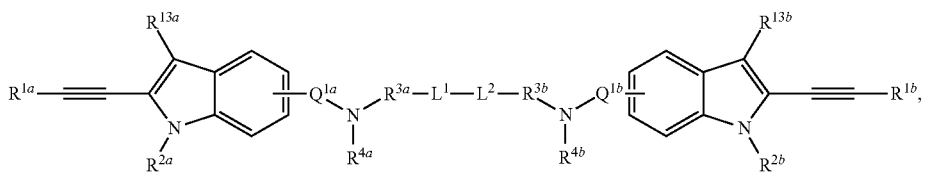

wherein each $Q^{1a}$ and $Q^{1b}$ is independently C=O, C=S, C=CR$^{14'}$R$^{15'}$, C=NR$^{14'}$, alkylene, alkenylene, or alkynylene, each of which is independently substituted or unsubstituted, or a bond; each R$^{1a}$ and R$^{1b}$ is independently —C(O)R$^{16'}$, —C(O)OR$^{16'}$, —C(O)NR$^{16'}$R$^{7'}$, —OR$^{16'}$, —SR$^{16'}$, —NR$^{16'}$R$^{17'}$, —NR$^{16'}$C(O)R$^{16'}$, —OC(O)R$^{16'}$, —SiR$^{16'}$R$^{17'}$R$^{8'}$, alkyl, alkenyl, alkynyl, aryl, heteroaryl, or heterocyclyl, each of which is independently substituted or unsubstituted, or hydrogen; each R$^{3a}$ and R$^{3b}$ is independently alkylene, alkenylene, alkynylene, arylene, heteroarylene, or heterocyclylene, each of which is independently substituted or unsubstituted, or hydrogen; each R$^{4a}$ and R$^{4b}$ is independently absent, —C(O)R$^{19'}$, —C(O)OR$^{19'}$, —C(O)NR$^{19'}$R$^{20'}$, —SOR$^{19'}$, —SO$_2$R$^{19'}$, alkyl, alkenyl, alkynyl, aryl, heteroaryl, or heterocyclyl, each of which is independently substituted or unsubstituted, or hydrogen; each R$^{2a}$, R$^{2b}$, R$^{13a}$, and R$^{13b}$ is independently —C(O)R$^{21'}$, —C(O)OR$^{21'}$, —C(O)NR$^{21'}$R$^{22'}$, —OR$^{21'}$, —SR$^{21'}$, —NR$^{21'}$R$^{22'}$, —NR$^{21'}$C(O)R$^{22'}$, —OC(O)R$^{21'}$, alkyl, alkenyl, alkynyl, aryl, heteroaryl, or heterocyclyl, each of which is independently substituted or unsubstituted, or hydrogen or halogen; each R$^{19'}$ and R$^{20'}$ is independently —C(O)R$^{23'}$, —C(O)OR$^{23'}$, —C(O)NR$^{23'}$R$^{24'}$, —OR$^{23'}$, —SR$^{23'}$, —NR$^{23'}$R$^{24'}$, —NR$^{23'}$C(O)R$^{24'}$, —OC(O)R$^{23'}$, alkyl, alkenyl, alkynyl, aryl, heteroaryl, or heterocyclyl, each of which is independently substituted or unsubstituted, or hydrogen or halogen; each R$^{21'}$ and R$^{22'}$ is independently alkyl, alkenyl, alkynyl, aryl, heteroaryl, or heterocyclyl, each of which is independently substituted or unsubstituted, or hydrogen; each R$^{23'}$ and R$^{24'}$ is independently alkyl, alkenyl, alkynyl, aryl, heteroaryl, or heterocyclyl, each of which is independently substituted or unsubstituted, or hydrogen; L$^1$ is a linker moiety; and L$^2$ is a linker moiety, or a pharmaceutically acceptable salt thereof.

In some embodiments, each L$^1$ and L$^2$ is independently an ester, ether, thioether, polyethyleneglycol (PEG), alkylene, alkenylene, alkynylene, heteroalkylene, cycloalkylene, heterocyclylene, arylene, heteroarylene, or heterocycloalkylene group, any of which is substituted or unsubstituted. In some embodiments, each L$^1$ and L$^2$ is independently alkylene, alkenylene, alkynylene, heteroalkylene, cycloalkylene, heterocycloalkylene, cycloarylene, or heterocycloalkylene.

In some embodiments, L$^1$ is alkylene and L$^2$ is an ester.

Compounds herein can include all stereoisomers, enantiomers, diastereomers, mixtures, racemates, atropisomers, and tautomers thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5- trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the compounds of the invention show non-lethal toxicity.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the invention can be applied topically to the skin, or a body cavity, for example, oral, vaginal, bladder, cranial, spinal, thoracic, or pelvic cavity of a subject. The compounds of the invention can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

EXAMPLES

Example 1: Preparation of 1-Anilino-3-{1-ethyl-5-[(1-methyl-4-piperidylamino)methyl]-1H-indol-2-yl}-2-propyne

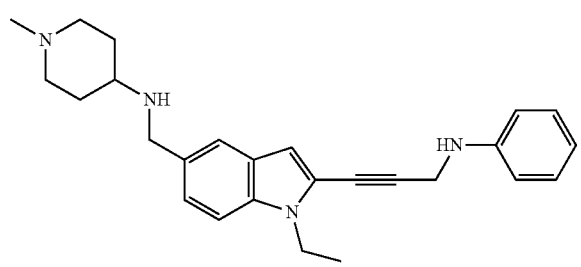 [SMILES: CCn1c(C#CCNc2ccccc2)cc2cc(CNC3CCN(C)CC3)ccc21]

Preparation of
5-bromo-1-(phenylsulfonyl)-1H-indole

To a solution of 5-bromo-indole (60 g, 309 mmol) in tetrahydrofuran (600 mL) was added NaH (18.5 g, 464 mmol, 60% in mineral oil) at 0° C. The mixture was stirred at 0° C. for 1 h. Then $PhSO_2Cl$ (65 g, 370 mmol) in tetrahydrofuran (600 mL) was added dropwise at 0° C. The reaction mixture was stirred at 0° C. for 1 h and allowed to warm to 25° C. for 17 h. The residue was poured into a mixture of ice and saturated solution of ammonium chloride (2000 mL, w/w=1/1) and stirred for 20 min. The aqueous phase was extracted with ethyl acetate (3×800 mL). The combined organic phases were washed with brine (3×800 mL), dried over anhydrous sodium sulphate, filtered, and concentrated in vacuo. The residue was purified by flash column chromatography (silica gel, column height: 500 mm, diameter: 100 mm, 100-200 mesh silica gel, eluting with a gradient of petroleum ether/ethyl acetate 20/1 to 10/1) to give 5-bromo-1-(phenylsulfonyl)-1H-indole (74 g, 72% yield) as yellow solid.

Preparation of
5-bromo-2-iodo-1-(phenylsulfonyl)-1H-indole

To a stirred solution of 5-bromo-1-(phenylsulfonyl)-1H-indole (28 g, 83.28 mmol) in anhydrous tetrahydrofuran (500 mL) at −70 OC was added dropwise a solution of LDA (2 M, 62.46 mL). After the mixture was stirred at 0° C. for 2 h, the progress of anion formation was checked by addition of $D_2O$ to an aliquot. The solution was then cooled to −70° C., and a solution of $I_2$ (23.25 g, 91.61 mmol) in tetrahydrofuran (500 mL) was added. The reaction mixture was stirred at 0° C. for 0.5 h and allowed for warm to 17° C. for 15 h. The residue was poured into saturated ammonium chloride solution (1000 mL) and stirred for 3 min. The aqueous phase was extracted with ethyl acetate (3×500 mL). The combined organic phases were washed with brine (2×500 mL), dried over anhydrous sodium sulphate filtered and concentrated in vacuo. The residue was purified by flash column chromatography (silica gel, eluting with a gradient of petroleum ether/ethyl acetate, 10/1 to 5/1) to give 5-bromo-2-iodo-1-(phenylsulfonyl)-1H-indole (20.00 g, 70% yield) as yellow solid.

Preparation of 5-bromo-2-iodo-1H-indole

A mixture of 5-bromo-2-iodo-1-(phenylsulfonyl)-1H-indole (30.00 g, 61.67 mmol) and potassium carbonate (2 M, 100 mL) in methanol (300 mL) was stirred at 90° C. for 2 h. After the reaction was completed as confirmed by thin layer chromatography (petroleum ether/ethyl acetate 5/1), 80% of the solvent was removed, and the reaction mixture was filtered to give crude 5-bromo-2-iodo-1H-indole (13 g, yellow solid). The crude product was used in the next reaction without further purification.

Preparation of 5-bromo-1-ethyl-2-iodo-1H-indole

To a mixture of 5-bromo-2-iodo-1H-indole (14.62 g, 36.34 mmol) and ethyl iodide (8.50 g, 54.51 mmol) in tetrahydrofuran (200 mL) was added NaH (2.91 g, 72.68 mmol, 60% in mineral oil) in one portion at 0° C. under nitrogen. The mixture was stirred at 0° C. for 30 min, then warmed to 25° C. and stirred for 11.5 h. Thin layer chromatography (petroleum ether/ethyl acetate, 5/1) showed that the reaction was complete. The reaction mixture was poured into aqueous ammonium chloride (500 mL) and stirred for 5 min. The aqueous phase was extracted with ethyl acetate (2×200 mL). The combined organic phases were washed with brine (2×200 mL), dried over anhydrous sodium sulphate, filtered, and concentrated in vacuo to give crude 5-bromo-1-ethyl-2-iodo-1H-indole (10 g, yellow solid). The crude product was used directly without further purification.

$^1$H NMR (400 MHz MeOD): δ 7.60-7.65 (dd, J=1.92 Hz, 1H), 7.17-7.59 (m, 2H), 6.69 (s, 1H), 4.17-4.26 (m, 2H), 1.26-1.29 (t, 3H)

Preparation of [3-(5-bromo-1-ethyl-1H-indol-2-yl)-2-propynyl]aniline

A flask was charged with copper(I) iodide (544.2 mg, 2.86 mmol) and triethylamine (3.62 g, 35.73 mmol), and a solution of crude 5-bromo-1-ethyl-2-iodo-1H-indole (5.00 g, 14.29 mmol) and N-2-propynylaniline (2.25 g, 17.15 mmol) in tetrahydrofuran (50 mL) was added under nitrogen, followed by the addition of tetrakis(triphenylphosphine)palladium(0) (825.4 mg, 714.50 μmol). The reaction mixture was stirred at 25° C. for 1 h. Thin layer chromatography (petroleum ether/ethyl acetate 5/1) showed that the reaction was complete. The reaction was diluted with 50 mL ethyl acetate and 100 mL 2M EDTA, and the biphasic mixture was stirred at 25° C. for 3 h. The reaction mixture was extracted with ethyl acetate (3×40 mL), and the combined organic extracts were washed with 150 mL of saturated brine, dried over sodium sulphate, and concentrated in vacuo. The crude residue was purified by flash column chromatography (silica gel, column height: 20 mm, diameter: 10 mm, 100-200 mesh silica gel, eluting with a gradient of petroleum ether/ethyl acetate, 30/1 to 20/1) to give [3-(5-bromo-1-ethyl-1H-indol-2-yl)-2-propynyl]aniline (3.10 g, 49.13% yield) as yellow solid.

$^1$H NMR (400 MHz, MeOD) δ 7.68 (s, 1H), 7.24-7.30 (m, 4H), 7.11-7.13 (d, J=4.0 Hz, 1H), 6.78-6.83 (m, 3H), 6.62 (s, 1H), 4.27 (s, 1H), 4.08-4.13 (m, 2H), 4.02 (s, 1H), 1.21-1.24 (t, 3H).

Preparation of 2-(3-anilino-1-propynyl)-1-ethyl-1H-indole-5-carbaldehyde

To a solution of [3-(5-bromo-1-ethyl-1H-indol-2-yl)-2-propynyl]aniline (500 mg, 1.42 mmol) in tetrahydrofuran (10.00 mL) cooled to −78° C. under nitrogen was added n-butyllithium (2.5 M, 3.41 mL) in one portion. The mixture was stirred at −78° C. for 30 min, then 4-morpholinecarbaldehyde (1.63 g, 14.20 mmol) was added in one portion at −78° C. The mixture was stirred for 1.5 h, and thin layer chromatography (petroleum ether/ethyl acetate, 5/1) showed that the reaction was complete. The residue was poured into aqueous ammonium chloride ice-water (20 mL, w/w=1/1) and stirred for 3 min. The aqueous phase was extracted with ethyl acetate (2×10 mL). The combined organic phases were washed with brine (2×10 mL), dried over anhydrous sodium sulphate, filtered, and concentrated in vacuo to give crude 2-(3-anilino-1-propynyl)-1-ethyl-1H-indole-5-carbaldehyde (600 mg) as yellow oil. The product was used directly in the next step without further purification.

Preparation of 1-anilino-3-{1-ethyl-5-[(1-methyl-4-piperidylamino)methyl]-1H-indol-2-yl}-2-propyne To a mixture of 2-(3-anilino-1-propynyl)-1-ethyl-1H-indole-5-carbaldehyde (200 mg, 529.15 μmol, 1 eq.) and 1-methylpiperidin-4-amine (53.5 mg, 529.15 μmol, 1 eq.) in methylene chloride (10 mL) was added anhydrous magnesium sulphate (318.5 mg, 2.65 mmol, 5 eq.) in one portion at 25° C. under nitrogen. The mixture was stirred at 25° C. for 60 min, then NaBH(OAc)$_3$ (336.5 mg, 1.59 mmol, 3 eq.) was added, and the reaction mixture was stirred for 5 h. LCMS showed that the reaction was complete. The residue was poured into ice-water (10 mL, w/w=1/1) and stirred for 3 min. The aqueous phase was extracted with methylene chloride (3×5 mL). The combined organic phases were washed with brine (3×5 mL), dried over anhydrous sodium sulfate, filtered, and concentrated in vacuo. The crude residue was purified by preparative HPLC (Gilson 281 semi-preparative HPLC system; column: Waters Xbridge 150×25, 5u; flowrate: 20 mL/min; eluting with a gradient of acetonitrile in water, 0.04% HCl) to give 1-anilino-3-{1-ethyl-5-[(1-methyl-4-piperidylamino)methyl]-1H-indol-2-yl}-2-propyne. LC-MS (ES$^+$, m/z): 401.3 [(M+H)$^+$]

Example 2: Preparation of 1-Anilino-3-{1-ethyl-5-[(methylamino)methyl]-1H-indol-2-yl}-2-propyne

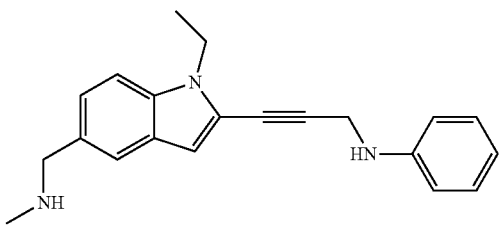 [SMILES: CCn1c(C#CCNc2ccccc2)cc2cc(CNC)ccc21]

In a manner similar to the method described in Example 1, 2-(3-anilino-1-propynyl)-1-ethyl-1H-indole-5-carbaldehyde was reacted with methylamine to give 1-anilino-3-{1-ethyl-5-[(methylamino)methyl]-1H-indol-2-yl}-2-propyne. LC-MS (ES$^+$, m/z): 287.2 [(M-NHMe)$^+$]

Example 3: Preparation of 1-Anilino-3-{1-ethyl-5-[(tetrahydro-2H-pyran-4-ylamino)methyl]-1H-indol-2-yl}-2-propyne

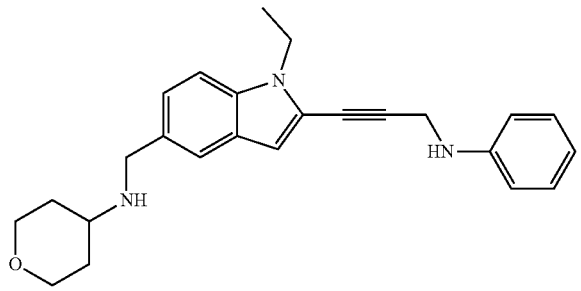 [SMILES: CCn1c(C#CCNc2ccccc2)cc2cc(CNC3CCOCC3)ccc21]

In a manner similar to the method described in Example 1, 2-(3-anilino-1-propynyl)-1-ethyl-1H-indole-5-carbaldehyde was reacted with 4-aminotetrahydropyran to give 1-anilino-3-{1-ethyl-5-[(tetrahydro-2H-pyran-4-ylamino)methyl]-1H-indol-2-yl}-2-propyne. LC-MS (ES$^+$, m/z): 388.3 [(M+H)$^+$]

Example 4: Preparation of 1-Anilino-3-[5-(benzylaminomethyl)-1-ethyl-1H-indol-2-yl]-2-propyne

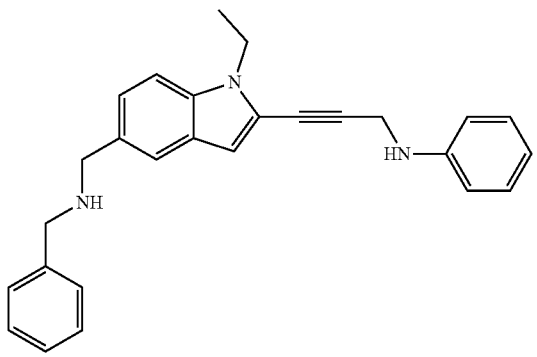 [SMILES: CCn1c(C#CCNc2ccccc2)cc2cc(CNCc3ccccc3)ccc21]

In a manner similar to the method described in Example 1, 2-(3-anilino-1-propynyl)-1-ethyl-1H-indole-5-carbaldehyde was reacted with benzylamine to give 1-anilino-3-[5-(benzylaminomethyl)-1-ethyl-1H-indol-2-yl]-2-propyne. LC-MS (ES$^+$, m/z): 394.3 [(M+H)$^+$]

Example 5: Preparation of 3-{1-Ethyl-5-[(methylamino)methyl]-1H-indol-2-yl}-1-(p-fluorophenylamino)-2-propyne

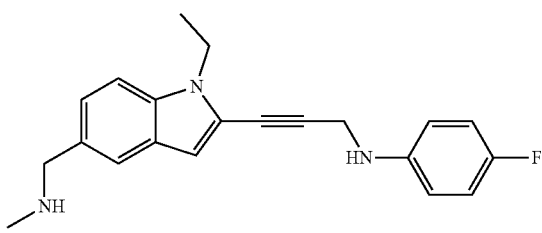 [SMILES: CCn1c(C#CCNc2ccc(F)cc2)cc2cc(CNC)ccc21]

Preparation of [3-(5-bromo-1-ethyl-1H-indol-2-yl)-2-propynyl](p-fluorophenyl)amine To a solution 5-bromo-1-ethyl-2-iodo-indole (800 mg, 2.29 mmol, 1 eq.) in tetrahydrofuran (5 mL) was added 4-fluoro-N-prop-2-ynyl-aniline (341 mg, 2.29 mmol, 1 eq.), triethylamine (694 mg, 6.86 mmol, 951 μL, 3 eq.), copper(I) iodide (44 mg, 228.58 μmol, 0.1 eq.) and tetrakis(triphenylphosphine)palladium(0) (264 mg, 228.58 μmol, 0.1 eq.) at 25° C. The mixture was stirred for 2 h, then poured into EDTA solution (2M, 20 mL) and stirred for another 2 h. The mixture was extracted with ethyl acetate (2×20 mL), and the combined organic phases were washed with water (20 mL) and brine (20 mL), dried over anhydrous sodium sulfate. The solids were filtered off, and the solvent was removed in vacuo. The crude residue was purified by flash column chromatography (silica gel, eluting with petroleum ether/ethyl acetate, 10/1) to give N-[3-(5-bromo-1-ethyl-indol-2-yl)prop-2-ynyl]-4-fluoro-aniline (750 mg, 88.2% yield) as a yellow solid.

Preparation of 1-ethyl-2-[3-(4-fluoroanilino)prop-1-ynyl]indole-5-carbaldehyde To a solution N-[3-(5-bromo-1-ethyl-indol-2-yl)prop-2-ynyl]-4-fluoro-aniline (700 mg, 1.89 mmol, 1 eq.) in tetrahydrofuran (5.00 mL) cooled to −78° C. was added n-butyllithium (2.5 M, 3.02 mL, 4 eq.). After the mixture was stirred at −78° C. for 0.5 h, morpholine-4-carbaldehyde (1.09 g, 9.43 mmol, 944 μL, 5 eq.) was added. At 2 h after the addition, thin layer chromatography showed that the reaction was complete. The reaction mixture was poured into aqueous ammonium chloride (5 mL), extracted with ethyl acetate (5 mL). The combined organic phases were washed by water (5 mL) and brine (5 mL), dried over anhydrous sodium sulfate. The solids were filtered off, and the filtrate was concentrated in vacuo. The crude residue was purified by flash column chromatography (silica gel, eluting with petroleum ether/ethyl acetate, 1/1) to give 1-ethyl-2-[3-(4-fluoroanilino)prop-1-ynyl]indole-5-carbaldehyde (300 mg, 49.6% yield) as a yellow solid.

In a manner similar to the method described in Example 1, 1-ethyl-2-[3-(4-fluoroanilino)prop-1-ynyl]indole-5-carbaldehyde was reacted with methylamine to give 3-{1-ethyl-5-[(methylamino)methyl]-1H-indol-2-yl}-1-(p-fluorophenylamino)-2-propyne. LC-MS (ES$^+$, m/z): 305.2 [(M-NHMe)$^+$]

Example 6: Preparation of 3-{1-Ethyl-5-[(tetrahydro-2H-pyran-4-ylamino)methyl]-1H-indol-2-yl}-1-(p-fluorophenylamino)-2-propyne

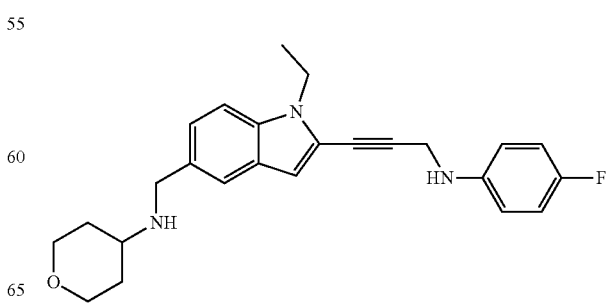

In a manner similar to the method described in Example 1, 1-ethyl-2-[3-(4-fluoroanilino)prop-1-ynyl]indole-5-carbaldehyde was reacted with 4-aminotetrahydropyran to give 3-{1-ethyl-5-[(tetrahydro-2H-pyran-4-ylamino)methyl]-1H-indol-2-yl}-1-(p-fluorophenylamino)-2-propyne.

LC-MS (ES+, m/z): 406.3 [(M+H)+]

Example 7: Preparation of 1-(p-Chlorophenylamino)-3-{1-ethyl-5-[(1-methyl-4-piperidylamino)methyl]-1H-indol-2-yl}-2-propyne

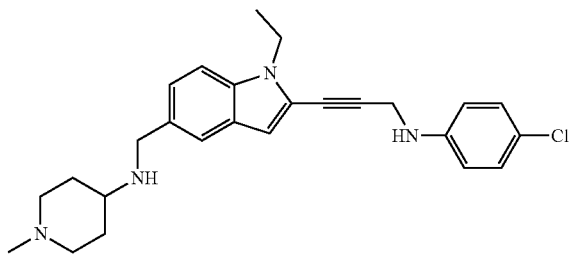 [SMILES: CCn1c(C#CCNc2ccc(Cl)cc2)cc2cc(CNC3CCN(C)CC3)ccc21]

1-Ethyl-2-[3-(4-chloroanilino)prop-1-ynyl]indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 1-ethyl-2-[3-(4-chloroanilino)prop-1-ynyl]indole-5-carbaldehyde was reacted with 1-methylpiperidin-4-amine to give 1-(4-chlorophenylamino)-3-{1-ethyl-5-[(1-methyl-4-piperidylamino)methyl]-1H-indol-2-yl}-2-propyne.

LC-MS (ES+, m/z): 435.3 [(M+H)+]

Example 8: Preparation of 3-{1-Ethyl-5-[(tetrahydro-2H-pyran-4-ylamino)methyl]-1H-indol-2-yl}-1-(6-methyl-3-pyridylamino)-2-propyne

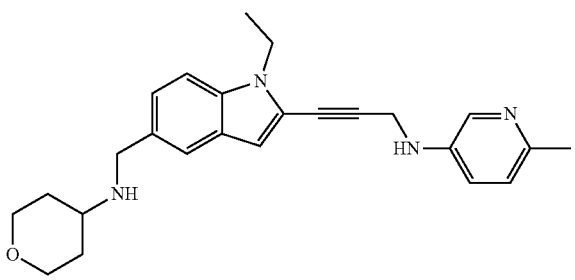 [SMILES: CCn1c(C#CCNc2ccc(C)nc2)cc2cc(CNC3CCOCC3)ccc21]

1-Ethyl-2-{3-[(6-methylpyridin-3-yl)amino]prop-1-yn-1-yl}-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 1-ethyl-2-{3-[(6-methylpyridin-3-yl)amino]prop-1-yn-1-yl}-1H-indole-5-carbaldehyde was reacted with 4-aminotetrahydropyran to give 3-{1-ethyl-5-[(tetrahydro-2H-pyran-4-ylamino)methyl]-1H-indol-2-yl}-1-(6-methyl-3-pyridylamino)-2-propyne.

LC-MS (ES+, m/z): 403.3 [(M+H)+]

Example 9: Preparation of 3-{1-Ethyl-5-[(methylamino)methyl]-1H-indol-2-yl}-1-(6-methyl-3-pyridylamino)-2-propyne

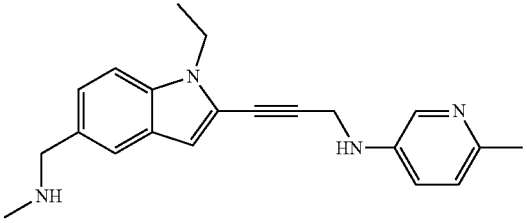

1-Ethyl-2-{3-[(6-methylpyridin-3-yl)amino]prop-1-yn-1-yl}-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 1-ethyl-2-{3-[(6-methylpyridin-3-yl)amino]prop-1-yn-1-yl}-1H-indole-5-carbaldehyde was reacted with methylamine to give 3-{1-ethyl-5-[(methylamino)methyl]-1H-indol-2-yl}-1-(6-methyl-3-pyridylamino)-2-propyne.

LC-MS (ES+, m/z): 302.2 [(M-NHMe)+]

Example 10: Preparation of 3-{1-Ethyl-5-[(1-methyl-4-piperidylamino)methyl]-1H-indol-2-yl}-1-(2-methyl-4-pyridylamino)-2-propyne

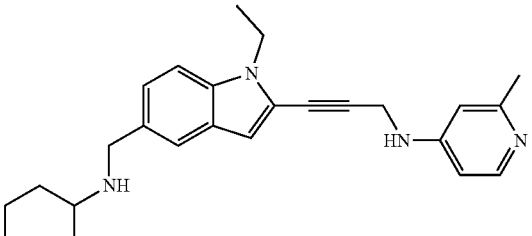

1-Ethyl-2-{3-[(2-methylpyridin-4-yl)amino]prop-1-yn-1-yl}-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 1-ethyl-2-{3-[(2-methylpyridin-4-yl)amino]prop-1-yn-1-yl}-1H-indole-5-carbaldehyde was reacted with 1-methylpiperidin-4-amine to give 3-{1-ethyl-5-[(1-methyl-4-piperidylamino)methyl]-1H-indol-2-yl}-1-(2-methyl-4-pyridylamino)-2-propyne.

LC-MS (ES+, m/z): 416.3 [(M+H)+]

Example 11: Preparation of 3-[5-(Benzylaminomethyl)-1-ethyl-1H-indol-2-yl]-1-(2-methyl-4-pyridylamino)-2-propyne

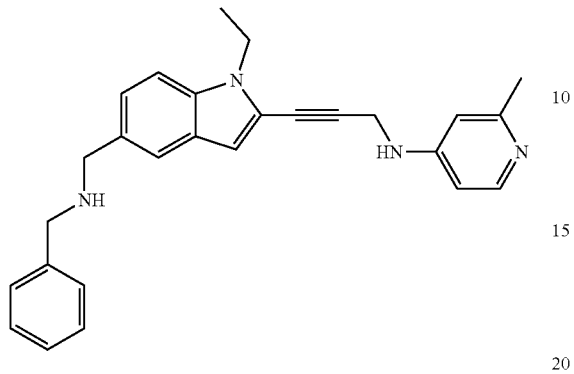

1-Ethyl-2-{3-[(2-methylpyridin-4-yl)amino]prop-1-yn-1-yl}-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 1-ethyl-2-{3-[(2-methylpyridin-4-yl)amino]prop-1-yn-1-yl}-1H-indole-5-carbaldehyde was reacted with benzylamine to give 3-[5-(benzylaminomethyl)-1-ethyl-1H-indol-2-yl]-1-(2-methyl-4-pyridylamino)-2-propyne.

LC-MS (ES+, m/z): 409.1 [(M+H)+]

Example 12: Preparation of N-(3-{5-[(Diethylamino)methyl]-1-ethyl-1H-indol-2-yl}prop-2-yn-1-yl)aniline

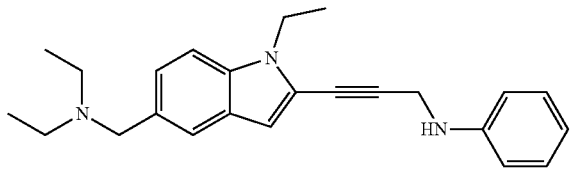 [SMILES: CCN(CC)Cc1ccc2c(c1)cc(C#CCNc1ccccc1)n2CC]

In a manner similar to the method described in Example 1, 2-(3-anilino-1-propynyl)-1-ethyl-1H-indole-5-carbaldehyde was reacted with diethylamine to give N-(3-{5-[(diethylamino)methyl]-1-ethyl-1H-indol-2-yl}prop-2-yn-1-yl)aniline.

LC-MS (ES+, m/z): 360.3 [(M+H)+]

Example 13: Preparation of 4-Chloro-N-(3-{5-[(diethylamino)methyl]-1-ethyl-1H-indol-2-yl}prop-2-yn-1-yl)aniline

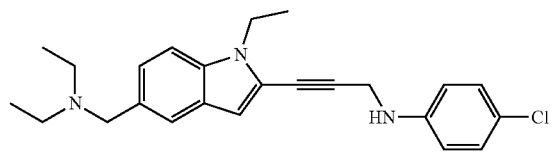 [SMILES: CCN(CC)Cc1ccc2c(c1)cc(C#CCNc1ccc(Cl)cc1)n2CC]

In a manner similar to the method described in Example 1, 1-ethyl-2-[3-(4-chloroanilino)prop-1-ynyl]indole-5-carbaldehyde was reacted with diethylamine to give 4-chloro-N-(3-{5-[(diethylamino)methyl]-1-ethyl-1H-indol-2-yl}prop-2-yn-1-yl) aniline. LC-MS (ES+, m/z): 394.3 [(M+H)+]

Example 14: Preparation of N-({1-Ethyl-2-[3-(phenylamino)prop-1-yn-1-yl]-1H-indol-5-yl}methyl) oxetan-3-amine

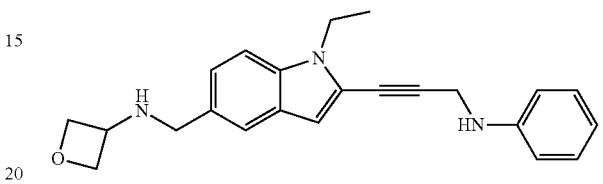

In a manner similar to the method described in Example 1, 2-(3-anilino-1-propynyl)-1-ethyl-1H-indole-5-carbaldehyde was reacted with oxetan-3-amine to give N-({1-Ethyl-2-[3-(phenylamino)prop-1-yn-1-yl]-1H-indol-5-yl}methyl) oxetan-3-amine.

LC-MS (ES+, m/z): 360.2 [(M+H)+]

Example 15: Preparation of N-[3-(1-Ethyl-5-{[(2-methylpropyl)amino]methyl}-1H-indol-2-yl) prop-2-yn-1-yl]aniline

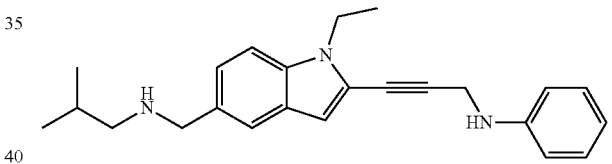

In a manner similar to the method described in Example 1, 2-(3-anilino-1-propynyl)-1-ethyl-1H-indole-5-carbaldehyde was reacted with 2-methylpropylamine to give N-[3-(1-ethyl-5-{[(2-methylpropyl)amino]methyl}-1H-indol-2-yl)prop-2-yn-1-yl]aniline.

LC-MS (ES+, m/z): 360.3 [(M+H)+]

Example 16: Preparation of N-[3-(1-Ethyl-5-{[(2-methoxyethyl)amino]methyl}-1H-indol-2-yl) prop-2-yn-1-yl]aniline

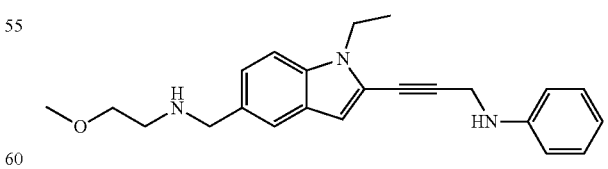

In a manner similar to the method described in Example 1, 2-(3-anilino-1-propynyl)-1-ethyl-1H-indole-5-carbaldehyde was reacted with 2-methoxyethylamine to give N-[3-(1-ethyl-5-{[(2-methoxyethyl)amino]methyl}-1H-indol-2-yl)prop-2-yn-1-yl]aniline.

LC-MS (ES+, m/z): 362.2 [(M+H)+]

Example 17: Preparation of N-({1-ethyl-2-[3-(phenylamino)prop-1-yn-1-yl]-1H-indol-5-yl}methyl)-1-methanesulfonylpiperidin-4-amine

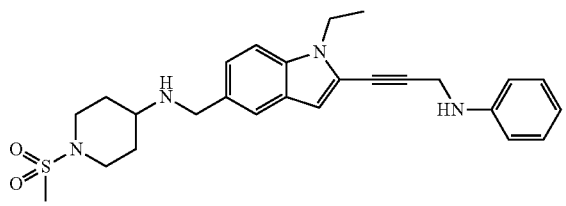 [SMILES: CCn1c(C#CCNc2ccccc2)cc2cc(CNC3CCN(S(C)(=O)=O)CC3)ccc21]

In a manner similar to the method described in Example 1, 2-(3-anilino-1-propynyl)-1-ethyl-1H-indole-5-carbaldehyde was reacted with 1-methanesulfonylpiperidin-4-amine to give N-({1-ethyl-2-[3-(phenylamino)prop-1-yn-1-yl]-1H-indol-5-yl}methyl)-1-methanesulfonylpiperidin-4-amine.

LC-MS (ES+, m/z): 465.2 [(M+H)+]

Example 18: Preparation of N-(3-{1-Ethyl-5-[(ethylamino)methyl]-1H-indol-2-yl}prop-2-yn-1-yl)aniline

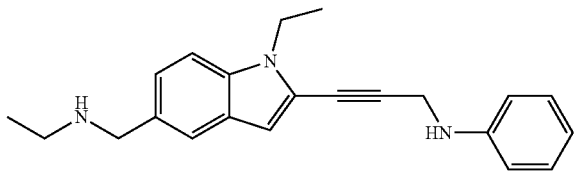 [SMILES: CCNCc1ccc2c(c1)cc(C#CCNc1ccccc1)n2CC]

In a manner similar to the method described in Example 1, 2-(3-anilino-1-propynyl)-1-ethyl-1H-indole-5-carbaldehyde was reacted with ethylamine to give N-(3-{1-ethyl-5-[(ethylamino)methyl]-1H-indol-2-yl}prop-2-yn-1-yl)aniline.

LC-MS (ES+, m/z): 332.2 [(M+H)+]

Example 19: Preparation of N-{3-[5-({[2-(Dimethylamino)ethyl]amino}methyl)-1-ethyl-1H-indol-2-yl]prop-2-yn-1-yl}aniline

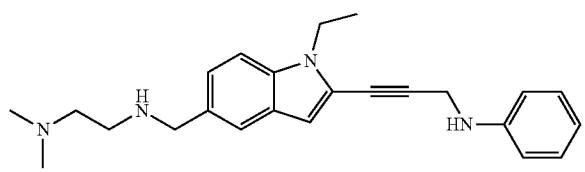 [SMILES: CCn1c(C#CCNc2ccccc2)cc2cc(CNCCN(C)C)ccc21]

In a manner similar to the method described in Example 1, 2-(3-anilino-1-propynyl)-1-ethyl-1H-indole-5-carbaldehyde was reacted with 2-dimethylaminoethylamine to give N-{3-[5-({[2-(dimethylamino)ethyl]amino}methyl)-1-ethyl-1H-indol-2-yl]prop-2-yn-1-yl}aniline.

LC-MS (ES+, m/z): 375.3 [(M+H)+]

Example 20: Preparation of 6-tert-Butyl-N-[3-(1-ethyl-5-{[(1-methylpiperidin-4-yl)amino]methyl}-1H-indol-2-yl)prop-2-yn-1-yl]pyridin-3-amine

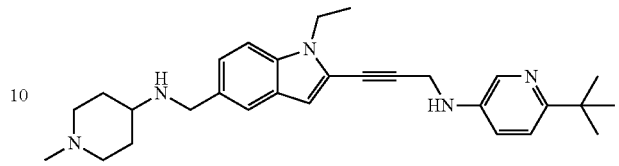

2-{3-[(6-tert-Butylpyridin-3-yl)amino]prop-1-yn-1-yl}-1-ethyl-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 2-{3-[(6-tert-butylpyridin-3-yl)amino]prop-1-yn-1-yl}-1-ethyl-1H-indole-5-carbaldehyde was reacted with 1-methylpiperidin-4-amine to give 6-tert-butyl-N-[3-(1-ethyl-5-{[(1-methylpiperidin-4-yl)amino]methyl}-1H-indol-2-yl)prop-2-yn-1-yl]pyridin-3-amine.

LC-MS (ES+, m/z): 458.6 [(M+H)+]

Example 21: Preparation of N-[(2-{3-[(4-Chlorophenyl)amino]prop-1-yn-1-yl}-1-ethyl-1H-indol-5-yl)methyl]oxan-4-amine

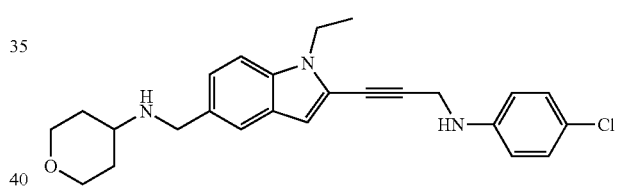

In a manner similar to the method described in Example 1, 1-ethyl-2-[3-(4-chloroanilino)prop-1-ynyl]indole-5-carbaldehyde was reacted with 4-aminotetrahydropyran to give N-[(2-{3-[(4-chlorophenyl)amino]prop-1-yn-1-yl}-1-ethyl-1H-indol-5-yl)methyl]oxan-4-amine.

LC-MS (ES+, m/z): 422.2 [(M+H)+]

Example 22: Preparation of 6-tert-Butyl-N-(3-{1-ethyl-5-[(methylamino)methyl]-1H-indol-2-yl}prop-2-yn-1-yl)pyridin-3-amine

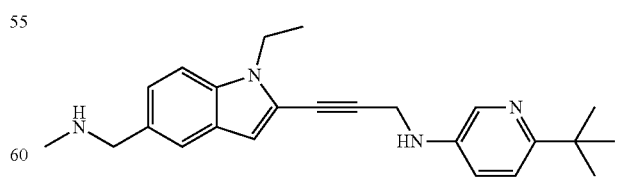

2-{3-[(6-tert-Butylpyridin-3-yl)amino]prop-1-yn-1-yl}-1-ethyl-1H-indole-5-carbaldehyde was prepared in a manner similar to that described in Example 6 for the preparation of 1-ethyl-2-[3-(4-fluoroanilino)prop-1-ynyl]indole-5-carbaldehyde.

In a manner similar to the method described in Example 1, 2-{3-[(6-tert-butylpyridin-3-yl)amino]prop-1-yn-1-yl}-1-ethyl-1H-indole-5-carbaldehyde was reacted with methylamine to give 6-tert-butyl-N-(3-{1-ethyl-5-[(methylamino)methyl]-1H-indol-2-yl}prop-2-yn-1-yl)pyridin-3-amine.

LC-MS (ES+, m/z): 375.3 [(M+H)+]

Example 23: Preparation of 4-[(3-{1-Ethyl-5-[(methylamino)methyl]-1H-indol-2-yl}prop-2-yn-1-yl)amino]benzonitrile

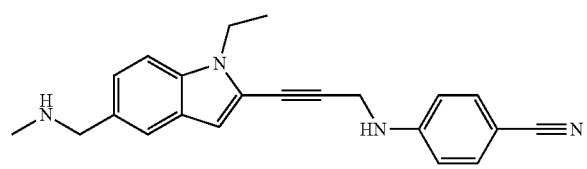 [SMILES: CCn1c(C#CCNc2ccc(C#N)cc2)cc2cc(CNC)ccc21]

To a solution of N-methyl[(1-ethyl-2-iodo-1H-indol-5-yl)methyl]amino 2,2-dimethylpropionate (1 eq.) in dimethylsulfoxide (5.0 mL) was added p-(2-propynylamino)benzonitrile (1 eq.), copper(I) iodide (0.47 eq.), diisopropylamine (3 eq.) and tetrakis(triphenylphosphine)palladium(0) (0.1 eq.) at 25° C., then the mixture was stirred for 2 h under nitrogen atmosphere. After LCMS showed that the reaction was complete, the reaction mixture was poured into a solution of EDTA (20 mL) and stirred for 2 h. The mixture was extracted with ethyl acetate (20 mL), and the organic phase was washed by water (50 mL), and brine (50 mL), and dried over anhydrous sodium sulfate. The solids were filtered off, and the filtrate was concentrated in vacuo to give the crude product as black brown oil. Purification of the crude product by flash column chromatography (silica gel, eluting with 2/1 petroleum ether/ethyl acetate) gave N-methyl({2-[3-(p-cyanophenylamino)-1-propynyl]-1-ethyl-1H-indol-5-yl}methyl)amino 2,2-dimethylpropionate as yellow oil.

To a solution of N-methyl({2-[3-(p-cyanophenylamino)-1-propynyl]-1-ethyl-1H-indol-5-yl}methyl)amino 2,2-dimethylpropionate (1 eq.) in acetonitrile (2 mL) was added BiCl3 (4 eq.) at 50° C., then the mixture was stirred under nitrogen atmosphere for 1 h. LCMS showed that the reaction was complete. The reaction mixture was poured into a solution of EDTA (20 mL) and stirred for 2 h. The mixture was extracted with ethyl acetate (20 mL), and the organic phase was washed by water (50 mL), and brine (50 mL), and dried over anhydrous sodium sulfate. The solids were filtered off, and the filtrate was concentrated in vacuo to give the crude product as yellow oil. Purification of the crude product by flash column chromatography (silica gel, eluting with 10/1 methylene chloride/methanol) gave p-(3-{1-ethyl-5-[(methylamino)methyl]-1H-indol-2-yl}-2-propynylamino)benzonitrile as white solids.

LC-MS (ES+, m/z): 343.1 [(M+H)+]

Example 24: Preparation of 4-tert-Butyl-N-(3-{1-ethyl-5-[(methylamino)methyl]-1H-indol-2-yl}prop-2-yn-1-yl)benzamide

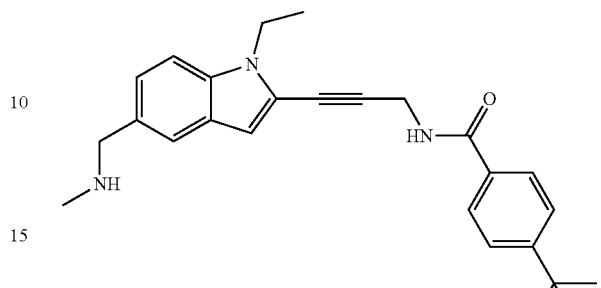

In a manner similar to the method described in Example 23, (2-propynylamino)[p-(tert-butyl)phenyl]formaldehyde was used to prepare 4-tert-butyl-N-(3-{1-ethyl-5-[(methylamino)methyl]-1H-indol-2-yl}prop-2-yn-1-yl)benzamide.

LC-MS (ES+, m/z): 371.1 [(M-NHMe)+]

Example 25: Preparation of 4-Chloro-N-(3-{1-ethyl-5-[(methylamino)methyl]-1H-indol-2-yl}prop-2-yn-1-yl)-3-fluorobenzamide

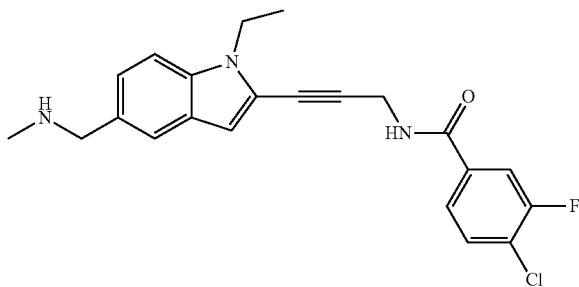 [SMILES: CCn1c(C#CCNC(=O)c2ccc(Cl)c(F)c2)cc2cc(CNC)ccc21]

In a manner similar to the method described in Example 23, (4-chloro-3-fluorophenyl)(2-propynylamino)formaldehyde was used to prepare 4-chloro-N-(3-{1-ethyl-5-[(methylamino)methyl]-1H-indol-2-yl}prop-2-yn-1-yl)-3-fluorobenzamide.

LC-MS (ES+, m/z): 367.1 [(M-NHMe)+]

Example 26: Preparation of 4-Cyano-N-({1-ethyl-2-[3-(phenylformamido)prop-1-yn-1-yl]-1H-indol-5-yl}methyl)-N-methylbenzamide

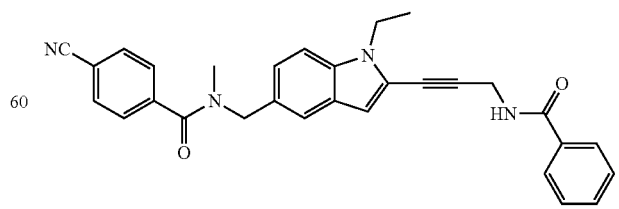

In a manner similar to the method described in Example 23, phenyl(2-propynylamino)formaldehydeformaldehyde was used to prepared (3-{1-ethyl-5-[(methylamino)methyl]-1H-indol-2-yl}-2-propynylamino)phenylformaldehyde.

To a solution of (3-{1-ethyl-5-[(methylamino)methyl]-1H-indol-2-yl}-2-propynylamino)phenylformaldehyde (1 eq.) and triethylamine (3 eq.) in methylene chloride (5 mL) was added 4-cyanobenzoyl chloride (1 eq.) at 25° C., then the mixture was stirred for 5 h under nitrogen atmosphere. LCMS showed that the reaction was complete. The reaction mixture was poured into a saturated solution of sodium bicarbonate (20 mL) and stirred 5 min. The mixture was extracted with ethyl acetate (20 mL), and the organic phase was washed by water (50 mL) and brine (50 mL), and dried over anhydrous sodium sulfate. The solids were filtered off, and the filtrate was concentrated in vacuo to give the crude product as black brown oil. Purification of the crude product by flash column chromatography (silica gel, eluting with 10/1 methylene chloride/methanol) gave 4-cyano-N-({1-ethyl-2-[3-(phenylformamido)prop-1-yn-1-yl]-1H-indol-5-yl}methyl)-N-methylbenzamide as white solids.

LC-MS (ES$^+$, m/z): 475.2 [(M+H)$^+$]

Example 27: Preparation of 3-(3-{1-Ethyl-5-[(methylamino)methyl]-1H-indol-2-yl}prop-2-yn-1-yl)-1-[4-(trifluoromethyl)phenyl]urea

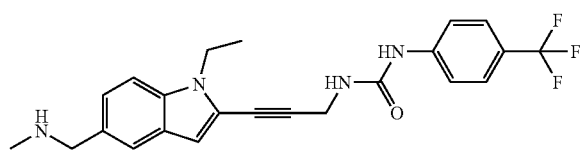 [SMILES: CCn1c(C#CCNC(=O)Nc2ccc(C(F)(F)F)cc2)cc2cc(CNC)ccc21]

In a manner similar to the method described in Example 23, 3-(2-propynyl)-1-[p-(trifluoromethyl)phenyl]urea was used to prepare 3-(3-{1-ethyl-5-[(methylamino)methyl]-1H-indol-2-yl}prop-2-yn-1-yl)-1-[4-(trifluoromethyl)phenyl]urea.

LC-MS (ES$^+$, m/z): 398.1 [(M-NHMe)$^+$]

Example 28: Preparation of N-{[1-(2-Chloroethyl)-2-{3-[(4-chlorophenyl)amino]prop-1-yn-1-yl}-1H-indol-5-yl]methyl}oxan-4-amine

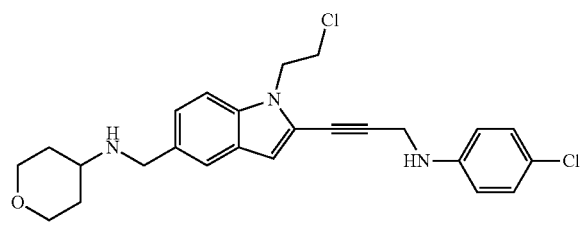 [SMILES: ClCCn1c(C#CCNc2ccc(Cl)cc2)cc2cc(CNC3CCOCC3)ccc21]

To a solution of 1H-indole-5-carbaldehyde (85 g, 585.56 mmol, 1 eq.) in methylene chloride (100 mL) was added potassium hydroxide (65.38 g, 1.17 mol, 2 eq.) and n-Bu$_4$NSO$_4$ (198.82 g, 585.56 mmol, 1 eq.). The mixture was stirred at 25° C. for 30 min, then PhSO$_2$Cl (155.13 g, 878.34 mmol, 112.41 mL, 1.5 eq.) was added. The mixture was stirred at 25° C. for 1 h, and thin layer chromatography showed that the reaction was complete. The reaction mixture was poured into aqueous ammonium chloride (200 mL) and extracted with methylene chloride (3×200 mL). The combined organic layers were washed with brine (2×100 mL) and dried over anhydrous sodium sulphate. The solids were filtered off, and the filtrate was concentrated in vacuo. The crude residue was purified by flash column chromatography (silica gel, eluting with petroleum ether/methylene chloride: 15/1) to give 1-(benzenesulfonyl)indole-5-carbaldehyde as a white solid (124 g, 71% yield).

To the solution of 1-(benzenesulfonyl)indole-5-carbaldehyde (4 g, 14.02 mmol, 1 eq.) and tetrahydro-2H-pyran-4-ylamine (2.84 g, 28.04 mmol, 2 eq.) in methylene chloride (80 mL) was added NaBH(OAc)$_3$ (5.94 g, 28.04 mmol, 2 eq.) and anhydrous magnesium sulphate (16.9 g, 140.2 mmol, 10 eq.). The reaction mixture was stirred at 25° C. for 12 h, and thin layer chromatography showed that the reaction was complete. The mixture was poured into aqueous sodium bicarbonate solution (100 mL) and extracted with methylene chloride (3×50 mL). The combined organic layers were washed with aqueous sodium bicarbonate solution (3×50 mL) and brine (50 mL), and dried over anhydrous sodium sulphate. The solids were filtered off, and the filtrate was concentrated in vacuo to give N-[[1-(benzenesulfonyl)indol-5-yl]methyl]-tetrahydropyran-4-amine as an off-white gum (4.6 g). The crude product was used directly without further purification.

To the solution of N-[[1-(benzenesulfonyl)indol-5-yl]methyl]tetrahydropyran-4-amine (4.6 g, 12.42 mmol, 1 eq.) in dioxane (60 mL) was added (Boc)$_2$O (4.61 g, 21.11 mmol, 4.85 mL, 1.70 eq.), and the reaction mixture was stirred at 90° C. for 1 h. Thin layer chromatography showed that the reaction was complete. The reaction mixture was concentrated in vacuo, and the crude was purified by flash column chromatography (silica gel, eluting with petroleum ether/ethyl acetate: 4/1) to give tert-butyl N-[[1-(benzenesulfonyl)indol-5-yl]methyl]-N-tetrahydropyran-4-yl-carbamate as a white solid (4 g, 68% yield).

To the solution of tert-butyl N-[[1-(benzenesulfonyl)indol-5-yl]methyl]-N-tetrahydropyran-4-yl-carbamate (500 mg, 1.05 mmol, 1 eq.) in tetrahydrofuran (6 mL) was added LDA (2 M, 1.31 mL, 2.5 eq.) in several small portions, and the reaction mixture was stirred at −78° C. for 1 h. A solution of iodine (293.2 mg, 1.16 mmol, 1.1 eq.) in 1 mL of tetrahydrofuran was added, and the reaction mixture was stirred at −78° C. for another 1 h. LCMS showed that the conversion was about 20%. The reaction mixture was poured into aqueous ammonium chloride (100 mL) and extracted with methylene chloride (3×30 mL). The combined organic layers were washed with water (3×30 mL) and brine (10 mL), and dried over anhydrous sodium sulphate. The solids were filtered off, and the filtrate was concentrated in vacuo to give tert-butyl N-[[1-(benzenesulfonyl)-2-iodo-indol-5-yl]methyl]-N-tetrahydropyran-4-yl-carbamate as a yellow oil (2.5 g, 4.19 mmol). The crude product was used directly without further purification.

To the solution of tert-butyl N-[[1-(benzenesulfonyl)-2-iodo-indol-5-yl]methyl]-N-tetrahydropyran-4-yl-carbamate (2.5 g, 4.19 mmol, 1 eq.) in methanol (50 mL) was added potassium carbonate (2.9 g, 20.95 mmol, 5 eq.), and the reaction mixture was stirred at 80° C. for 5 h. Thin layer chromatography showed that the reaction was complete. The reaction mixture was poured into 100 mL ice water, and acidified with 37% HCl to pH=4. The mixture was extracted with methylene chloride (3×30 mL), and the combined organic layers were washed with water (2×30 mL) and brine (2×30 mL), and dried over anhydrous sodium sulphate. The solids were filtered off, and the filtrate was concentrated in vacuo. The crude residue was purified by flash column chromatography (silica gel, eluting with petroleum ether/ ethyl acetate: 8/1) to give tert-butyl N-[(2-iodo-1H-indol-5-yl)methyl]-N-tetrahydropyran-4-yl-carbamate as a white solid (900 mg, 43% yield).

To a solution of tert-butyl N-[(2-iodo-1H-indol-5-yl)methyl]-N-tetrahydropyran-4-yl-carbamate (300 mg, 90% purity, 591.69 µmol, 1 eq.) in dichloroethane (58.6 mg, 591.69 µmol, 1 eq.) was added KOH (199.2 mg, 3.55 mmol, 6 eq.), potassium carbonate (204.4 mg, 1.48 mmol, 2.5 eq.), and TBAI (218.6 mg, 591.69 µmol, 1 eq.). The reaction mixture was stirred at 25° C. for 6 h. Thin layer chromatography showed that the reaction was complete. The reaction mixture was filtered, and the filtrate was concentrated in vacuo. The crude residue was purified by preparative thin layer chromatography (silica gel, eluting with petroleum ether/ethyl acetate: 4/1) to give tert-butyl N-[[1-(2-chloroethyl)-2-iodo-indol-5-yl]methyl]-N-tetrahydropyran-4-yl-carbamate as light yellow oil (260 mg, 83% yield).

To a solution of 4-chloro-N-prop-2-ynyl-aniline (122 mg, 736.68 µmol, 1.5 eq.) in dimethylsulfoxide (5 mL) was added N-isopropylpropan-2-amine (149.09 mg, 1.47 mmol, 207.07 µL, 3.00 eq.) and copper(I) iodide (28.06 mg, 147.34 µmol, 0.3 eq.), followed by addition of tert-butyl N-[[1-(2-chloroethyl)-2-iodo-indol-5-yl]methyl]-N-tetrahydropyran-4-yl-carbamate (260 mg, 491.12 µmol, 1 eq.) and tetrakis(triphenylphosphine)palladium(0) (56.8 mg, 49.11 mol, 0.1 eq.). After the reaction mixture was stirred at 25° C. for 1 h, thin layer chromatography showed that the reaction was complete. Aqueous EDTA solution (20 mL) was added, and the mixture was stirred for 2 h. The mixture was extracted with methylene chloride (3×10 mL). The combined organic layers were washed with water (3×10 mL) and brine (10 mL), and dried over anhydrous sodium sulphate. The solids were filtered off, and the filtrate was concentrated in vacuo. The crude residue was purified by preparative thin layer chromatography (silica gel, eluting with petroleum ether/ethyl acetate: 3/1) to give tert-butyl N-[[2-[3-(4-chloroanilino)prop-1-ynyl]-1-(2-chloroethyl)indol-5-yl]methyl]-N-tetrahydropyran-4-yl-carbamate as light yellow solids (200 mg, 71% yield).

To the solution of tert-butyl N-[[2-[3-(4-chloroanilino)prop-1-ynyl]-1-(2-chloroethyl)indol-5-yl]methyl]-N-tetrahydropyran-4-yl-carbamate (100 mg, 161.72 µmol, 1 eq.) in acetonitrile (2 mL) was added trichlorobismuthane (204 mg, 646.88 µmol, 42.94 µL, 4 eq.), and the reaction mixture was stirred at 50° C. for 2 h. LCMS showed that the reaction was complete. Aqueous EDTA solution (20 mL) was added, and the mixture was stirred for 2 h. The mixture was extracted with methylene chloride (3×10 mL). The combined organic layers were washed with water (3×10 mL) and brine (10 mL), and dried over anhydrous sodium sulphate. The solids were filtered off, and the filtrate was concentrated in vacuo. The crude residue was first purified by preparative thin layer chromatography (silica gel, eluting with methylene chloride/methanol: 5/1) and again by preparative HPLC (C18 silica gel, eluting with acetonitrile and water) to give N-[[2-[3-(4-chloroanilino)prop-1-ynyl]-1-(2-chloroethyl)indol-5-yl]methyl]tetrahydropyran-4-amine as a yellow solid (14.9 mg, 19% yield).

LC-MS (ES$^+$, m/z): 456.2 [(M+H)$^+$]

Example 29: Preparation of 2-(4-{[3-(1-Ethyl-5-{[(1-methylpiperidin-4-yl)amino]methyl}-1H-indol-2-yl)prop-2-yn-1-yl]amino}phenyl)-2-methylpropanenitrile

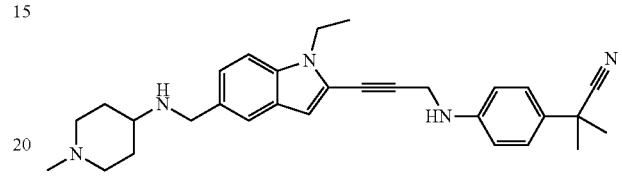

To a solution of 2-methyl-2-[p-(2-propynylamino)phenyl]propiononitrile (2 eq.) and [(1-ethyl-2-iodo-1H-indol-5-yl)methyl](1-methyl-4-piperidyl)amino 2,2-dimethylpropionate (100 mg, 1 eq.) in dimethylsulfoxide (2 mL) was added N-isopropylpropan-2-amine (3 eq.) and copper(I) iodide (0.2 eq.), followed by the addition of tetrakis(triphenylphosphine)palladium(0) (0.1 eq.). After the reaction mixture was stirred at 25° C. for 1 h, the mixture was poured into aqueous solution of EDTA (10 mL) and stirred at 25° C. for 1 h. The reaction mixture was extracted with ethyl acetate (2×20 mL), and the combined organic extracts were washed by water (10 mL), and brine (10 mL), and dried over anhydrous sodium sulfate. The solids were filtered off, and the filtrate was concentrated in vacuo to give the crude residue. Purification of the crude residue by flash column chromatography (silica gel, eluting with 15/1 methylene chloride/methanol) gave ({1-ethyl-2-[3-(3-phenylureido)-1-propynyl]-1H-indol-5-yl}methyl)(1-methyl-4-piperidyl)amino 2,2-dimethylpropionate.

To a solution of ({1-ethyl-2-[3-(3-phenylureido)-1-propynyl]-1H-indol-5-yl}methyl)(1-methyl-4-piperidyl)amino 2,2-dimethylpropionate (60 mg, 108.48 µmol, 1 eq.) in acetonitrile (2 mL) at 50° C. was added trichlorobismuthane (4 eq.). The reaction mixture was stirred at 50° C. for 30 min then poured into aqueous EDTA solution (15 mL). The biphasic mixture was stirred at 25° C. for 2 h and separated. The mixture was extracted with ethyl acetate (2×40 mL), and the organic phase was washed by water (10 mL), and brine (10 mL), and dried over anhydrous sodium sulfate. The solids were filtered off, and the filtrate was concentrated in vacuo. Purification of the crude residue by reversed phase HPLC (C18, eluting with acetonitrile and water) gave 2-(4-{[3-(1-ethyl-5-{[(1-methylpiperidin-4-yl)amino]methyl}-1H-indol-2-yl)prop-2-yn-1-yl]amino}phenyl)-2-methylpropanenitrile.

LC-MS (ES$^+$, m/z): 468.2 [(M+H)$^+$]

Example 30: Preparation of 4-Cyano-N-(3-{1-ethyl-5-[(methylamino)methyl]-1H-indol-2-yl}prop-2-yn-1-yl)benzamide

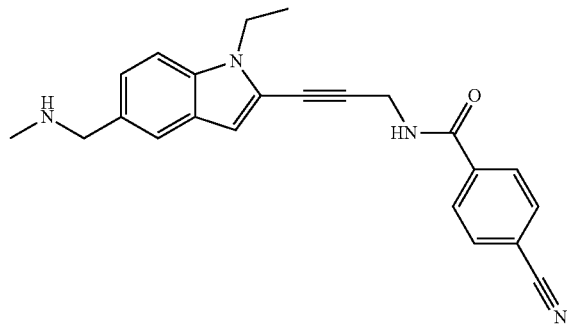 [SMILES: CCn1c(C#CCNC(=O)c2ccc(C#N)cc2)cc2cc(CNC)ccc21]

In a manner similar to the method described in Example 23, p-[(2-propynylamino)carbonyl]benzonitrile was used to prepare 4-cyano-N-(3-{1-ethyl-5-[(methylamino)methyl]-1H-indol-2-yl}prop-2-yn-1-yl)benzamide.
LC-MS (ES$^+$, m/z): 330.2 [(M-NHMe)$^+$]

Example 31: Preparation of N-(3-{1-Ethyl-5-[(methylamino)methyl]-1H-indol-2-yl}prop-2-yn-1-yl)-6-methylpyridine-3-carboxamide

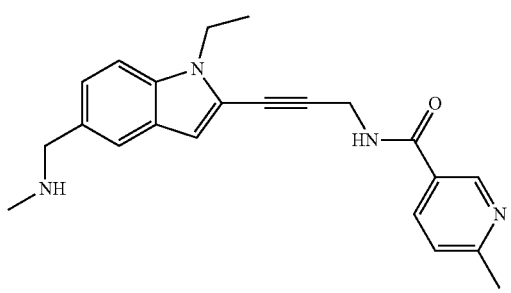

In a manner similar to the method described in Example 23, (6-methyl-3-pyridyl)(2-propynylamino)formaldehyde was used to prepare N-(3-{1-ethyl-5-[(methylamino)methyl]-1H-indol-2-yl}prop-2-yn-1-yl)-6-methylpyridine-3-carboxamide.
LC-MS (ES$^+$, m/z): 330.2 [(M-NHMe)$^+$]

Example 32: Preparation of 3-[3-(1-Ethyl-5-{[(1-methylpiperidin-4-yl)amino]methyl}-1H-indol-2-yl)prop-2-yn-1-yl]-1-phenylurea

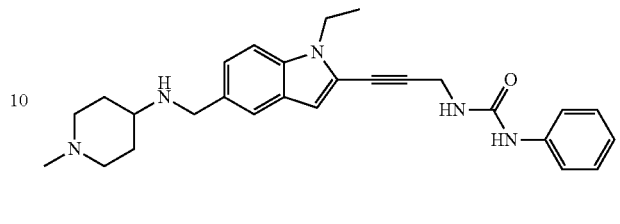

In a manner similar to the method described in Example 29, 3-phenyl-1-(2-propynyl)urea was used to prepare 3-[3-(1-ethyl-5-{[(1-methylpiperidin-4-yl)amino]methyl}-1H-indol-2-yl)prop-2-yn-1-yl]-1-phenylurea.
LC-MS (ES$^+$, m/z): 444.3 [(M+H)$^+$]

Example 33: Preparation of N-[(2-{3-[(4-Chloro-3-fluorophenyl)amino]prop-1-yn-1-yl}-1-ethyl-1H-indol-5-yl)methyl]-1-methylpiperidin-4-amine

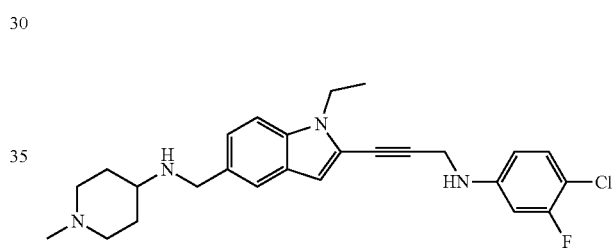

In a manner similar to the method described in Example 29, N-2-propynyl(4-chloro-3-fluorophenyl)amine was used to prepare N-[(2-{3-[(4-chloro-3-fluorophenyl)amino]prop-1-yn-1-yl}-1-ethyl-1H-indol-5-yl)methyl]-1-methylpiperidin-4-amine.
LC-MS (ES$^+$, m/z): 453.3 [(M+H)$^+$]

Example 34: Preparation of 2-(5-{[3-(1-Ethyl-5-{[(1-methylpiperidin-4-yl)amino]methyl}-1H-indol-2-yl)prop-2-yn-1-yl]amino}pyridin-2-yl)-2-methylpropanenitrile

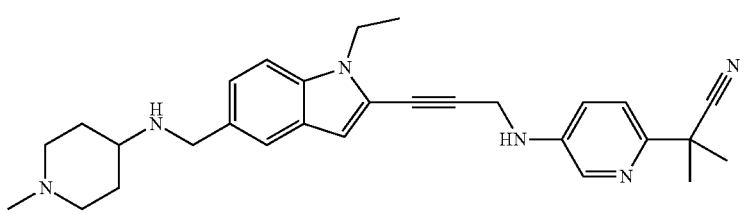 [SMILES: CCn1c(C#CCNc2ccc(C(C)(C)C#N)nc2)cc2cc(CNC3CCN(C)CC3)ccc21]

To a solution of 2-methyl-2-[5-(2-propynylamino)-2-pyridyl]propiononitrile (2.5 eq.) in dimethylsulfoxide (2 mL) was added N-isopropylpropan-2-amine (3 eq.) and copper(I) iodide (0.3 eq.), followed by the addition of 1-ethyl-2-iodo-1H-indole-5-carbaldehyde (100 mg, 1 eq.) and tetrakis(triphenylphosphine)palladium(0) (0.1 eq.). After the reaction mixture was stirred at 25° C. under nitrogen atmosphere for 1 h, the mixture was poured into aqueous EDTA solution (15 mL). The biphasic the mixture was stirred at 25° C. for 2 h, diluted with water (10 mL), and extracted with ethyl acetate (2×40 mL). The organic phase was washed with brine (15 mL) and dried over anhydrous sodium sulfate. The solids were filtered off, and the filtrate was concentrated in vacuo to give the crude residue. Purification of the crude product by preparative thin layer chromatography (silica gel, eluting with 2/1 petroleum ether/ethyl acetate) gave 2-{5-[3-(1-ethyl-5-formyl-1H-indol-2-yl)-2-propynylamino]-2-pyridyl}-2-methylpropiononitrile.

To a solution of 2-{5-[3-(1-ethyl-5-formyl-1H-indol-2-yl)-2-propynylamino]-2-pyridyl}-2-methylpropiononitrile (1 eq.) in methylene chloride/methanol (4 mL, 1/1 mixture) was added 1-methyl-4-piperidylamine (4 eq.) and anhydrous magnesium sulfate (15 eq.), respectively. The mixture was stirred at 25° C. for 12 h, then sodium bicarbonate (1 eq.) and NaBH₃CN (4 eq.) was added at 0° C. The reaction mixture was stirred at 0° C. for 2 h then quenched by saturated solution of sodium bicarbonate (10 mL). The mixture was extracted with ethyl acetate (2×30 mL), and the combined organic phases were washed by water (30 mL), and brine (30 mL), and dried over anhydrous sodium sulfate. The solids were filtered off, and the filtrate was concentrated in vacuo to give a crude residue. Purification of the crude residue by preparative HPLC (C18 silica gel, eluting with acetonitrile and water) gave 2-(4-{[3-(1-ethyl-5-{[(1-methylpiperidin-4-yl)amino]methyl}-1H-indol-2-yl)prop-2-yn-1-yl]amino}phenyl)-2-methylpropanenitrile.

LC-MS (ES$^+$, m/z): 469.4 [(M+H)$^+$]

Example 35: Preparation of N-{[1-(2-Chloroethyl)-2-{3-[(4-chlorophenyl)amino]prop-1-yn-1-yl}-1H-indol-5-yl]methyl}-1-methylpiperidin-4-amine

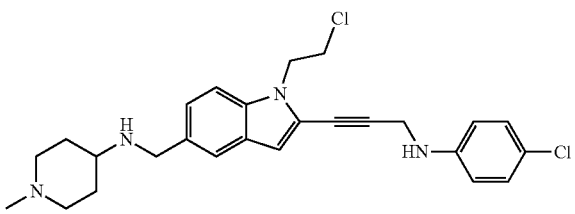 [SMILES: CN1CCC(NCc2ccc3c(c2)cc(C#CCNc2ccc(Cl)cc2)n3CCCl)CC1]

In a manner similar to the method described in Example 28, 1-methylpiperidin-4-amine was used to prepare N-{[1-(2-chloroethyl)-2-{3-[(4-chlorophenyl)amino]prop-1-yn-1-yl}-1H-indol-5-yl]methyl}-1-methylpiperidin-4-amine.

LC-MS (ES$^+$, m/z): 469.1 [(M+H)$^+$]

Example 36: Preparation of 6-tert-Butyl-N-[3-(1-ethyl-5-{[(1-methanesulfonylpiperidin-4-yl)amino]methyl}-1H-indol-2-yl)prop-2-yn-1-yl]pyridin-3-amine

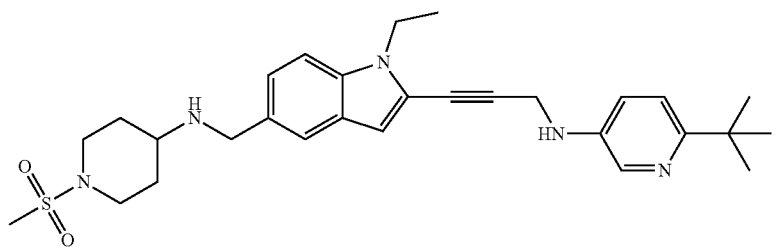 [SMILES: CCn1c(C#CCNc2ccc(C(C)(C)C)nc2)cc2cc(CNC3CCN(S(C)(=O)=O)CC3)ccc21]

In a manner similar to the method described in Example 34, N-2-propynyl[6-(tert-butyl)-3-pyridyl]amine was used to prepare 6-tert-butyl-N-[3-(1-ethyl-5-{[(1-methanesulfonylpiperidin-4-yl)amino]methyl}-1H-indol-2-yl)prop-2-yn-1-yl]pyridin-3-amine.

LC-MS (ES$^+$, m/z): 522.4 [(M+H)$^+$]

Example 37: Preparation of 2-(4-{[3-(1-Ethyl-5-{[(1-methylpiperidin-4-yl)amino]methyl}-1H-indol-2-yl)prop-2-yn-1-yl]amino}phenyl)-2-methylpropanoic acid

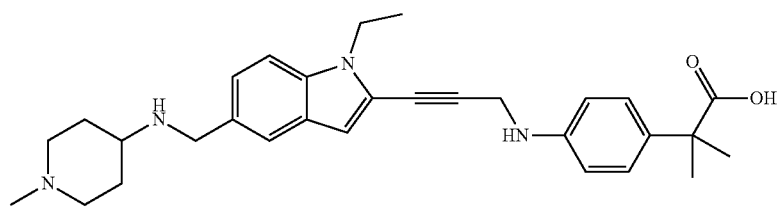 [SMILES: CCn1c(C#CCNc2ccc(C(C)(C)C(=O)O)cc2)cc2cc(CNC3CCN(C)CC3)ccc21]

In a manner similar to the method described in Example 34, ethyl 2-methyl-2-[p-(2-propynylamino)phenyl]propionate was used to prepare ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate. The ester was then saponified by sodium hydroxide in methanol and water to give 2-(4-{[3-(1-ethyl-5-{[(1-methylpiperidin-4-yl)

amino]methyl}-1H-indol-2-yl)prop-2-yn-1-yl]amino}phenyl)-2-methylpropanoic acid.

LC-MS (ES+, m/z): 487.4 [(M+H)+]

Example 38: Preparation of 3-(1-Ethyl-5-{[(1-methylpiperidin-4-yl)amino]methyl}-1H-indol-2-yl)-N-methylprop-2-ynamide

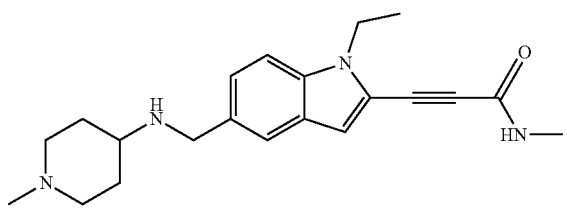

To the solution of methylamine (1.23 g, 11.89 mmol, 30% in water, 1 eq.) in methanol (20 mL) was added methyl prop-2-ynoate (1 g, 11.89 mmol, 990 µL, 1 eq.) dropwise at −50° C. for 30 min, and the reaction mixture was stirred at −50° C. for 1.5 h. LCMS showed that the reaction was complete. The reaction mixture was concentrated at 25° C. to give the crude product which was washed with petroleum ether (2×10 mL) to give N-methylprop-2-ynamide (460 mg, 4.98 mmol, 41.9% yield, 90% purity) as a white solid.

To a solution of 1-(methylamino)-2-propyn-1-one (3 eq.) in dimethylsulfoxide (4 mL) was added N-isopropylpropan-2-amine (3 eq.) and copper(I) iodide (0.2 eq.), followed by the addition of 1-ethyl-2-iodo-1H-indole-5-carbaldehyde (100 mg, 1 eq.) and tetrakis(triphenylphosphine)palladium (0) (0.1 eq.). After the reaction mixture was stirred at 20° C. under nitrogen atmosphere for 12 h, the mixture was poured into aqueous EDTA solution (10 mL). The biphasic the mixture was stirred at 25° C. for 2 h and continued to stand for 4 h, then was extracted with ethyl acetate (20 mL). The organic phase was washed with water (20 mL) and brine (20 mL), and dried over anhydrous sodium sulfate. The solids were filtered off, and the filtrate was concentrated in vacuo to give the crude residue. Purification of the crude product by flash column chromatography (silica gel, eluting with a 10/1 to 5/1 gradient of petroleum ether/ethyl acetate) to give a yellow oil. The oil was further purified by preparative HPLC (C18 silica gel, eluting with acetonitrile and water) to give 1-ethyl-2-[3-(methylamino)-3-oxo-1-propynyl]-1H-indole-5-carbaldehyde as a yellow solid (50 mg, 16.3% yield).

To a solution of 1-ethyl-2-[3-(methylamino)-3-oxo-1-propynyl]-1H-indole-5-carbaldehyde (1 eq.) in methylene chloride (4 mL) was added 1-methyl-4-piperidylamine (7 eq.) and anhydrous magnesium sulfate (15 eq.), respectively. The mixture was stirred at 25° C. for 12 h, then NaBH3CN (2 eq.) was added at 0° C. The reaction mixture was stirred at 25° C. for 1 h then quenched by saturated solution of sodium bicarbonate (10 mL). The mixture was concentrated in ethyl acetate (20 mL), and the organic phase were washed by water (50 mL) and brine (50 mL), and dried over anhydrous sodium sulfate. The solids were filtered off, and the filtrate was concentrated in vacuo to give a crude residue. Purification of the crude residue by preparative HPLC (C18 silica gel, eluting with acetonitrile and water) gave 3-(1-ethyl-5-{[(1-methylpiperidin-4-yl)amino]methyl}-1H-indol-2-yl)-N-methylprop-2-ynamide.

LC-MS (ES+, m/z): 353.3 [(M+H)+]

Example 39: Preparation of Ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate

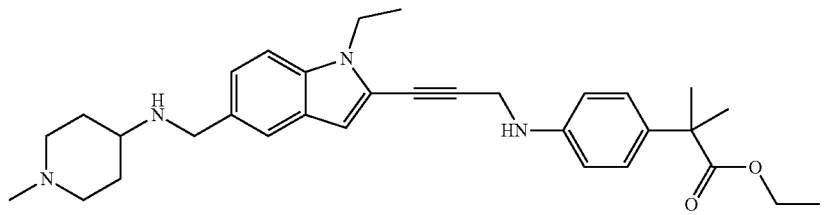 [SMILES: CCOC(=O)C(C)(C)c1ccc(NCC#Cc2cc3cc(CNC4CCN(C)CC4)ccc3n2CC)cc1]

In a manner similar to the method described in Example 34, ethyl 2-methyl-2-[p-(2-propynylamino)phenyl]propionate was used to prepare ethyl 2-(4-{[3-(1-ethyl-5-{[(1-methylpiperidin-4-yl)amino]methyl}-1H-indol-2-yl)prop-2-yn-1-yl]amino}phenyl)-2-methylpropanoate.

LC-MS (ES+, m/z): 515.4 [(M+H)+]

Example 40: Preparation of 2-(5-{[3-(1-Ethyl-5-{[(oxan-4-yl)amino]methyl}-1H-indol-2-yl)prop-2-yn-1-yl]amino}pyridin-2-yl)-2-methylpropanenitrile

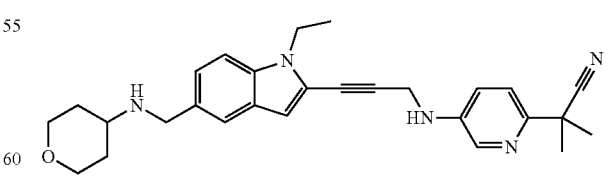

To a solution of 2-methyl-2-[5-(2-propynylamino)-2-pyridyl]propiononitrile (1 eq.) in dimethylsulfoxide (2 mL) was added N-isopropylpropan-2-amine (3 eq.) and copper(I) iodide (0.47 eq.), followed by the addition of 1-ethyl-2-iodo- 1H-indole-5-carbaldehyde (100 mg, 1 eq.) and tetrakis(triphenylphosphine)palladium(0) (0.1 eq.). After the reaction mixture was stirred at 40° C. under nitrogen atmosphere for 2 h, the mixture was poured into aqueous EDTA solution (20 mL). The biphasic mixture was stirred at 25° C. for 2 h, then extracted with ethyl acetate (20 mL). The organic phase was washed with water (50 mL) and brine (50 mL), and dried over anhydrous sodium sulfate. The solids were filtered off, and the filtrate was concentrated in vacuo to give the crude residue. Purification of the crude product by flash column chromatography (silica gel, eluting with 2/1 petroleum ether/ethyl acetate) gave 2-{5-[3-(1-ethyl-5-formyl-1H-indol-2-yl)-2-propynylamino]-2-pyridyl}-2-methylpropiononitrile.

To a solution of 2-{5-[3-(1-ethyl-5-formyl-1H-indol-2-yl)-2-propynylamino]-2-pyridyl}-2-methylpropiononitrile (1 eq.) in methylene chloride (2 mL) was added tetrahydro-2H-pyran-4-ylamine (8 eq.) and anhydrous magnesium sulfate (10 eq.), respectively. The mixture was stirred at 25° C. for 2 h, then NaBH$_3$CN (10 eq.) was added. The reaction mixture was stirred at 25° C. for 1 h then quenched by saturated solution of sodium bicarbonate (10 mL). The mixture was extracted with ethyl acetate (20 mL), and the organic phase was washed by water (50 mL) and brine (50 mL), and dried over anhydrous sodium sulfate. The solids were filtered off, and the filtrate was concentrated in vacuo to give a crude residue as yellow oil. Purification of the crude residue by preparative HPLC (C18 silica gel, eluting with acetonitrile and water) gave 2-(5-{[3-(1-ethyl-5-{[(oxan-4-yl)amino]methyl}-1H-indol-2-yl)prop-2-yn-1-yl]amino}pyridin-2-yl)-2-methylpropanenitrile.

LC-MS (ES$^+$, m/z): 456.3 [(M+H)$^+$]

Example 41: Preparation of N-[(1-Ethyl-2-{3-[(4-methylphenyl)amino]prop-1-yn-1-yl}-1H-indol-5-yl)methyl]-1-methylpiperidin-4-amine

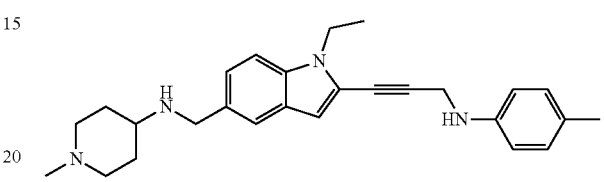

In a manner similar to the method described in Example 34, N-2-propynyl(p-tolyl)amine was used to prepare N-[(1-ethyl-2-{3-[(4-methylphenyl)amino]prop-1-yn-1-yl}-1H-indol-5-yl)methyl]-1-methylpiperidin-4-amine.

LC-MS (ES$^+$, m/z): 415.3 [(M+H)$^+$]

Example 42: Preparation of 4-{[3-(1-Ethyl-5-{[(1-methylpiperidin-4-yl)amino]methyl}-1H-indol-2-yl)prop-2-yn-1-yl]amino}benzonitrile

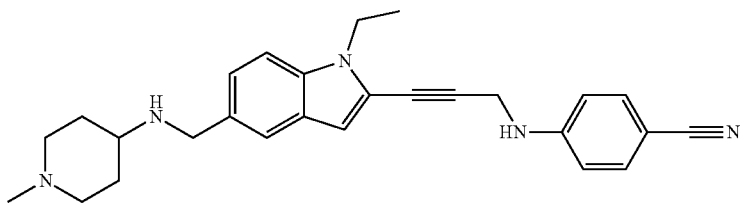 [SMILES: CCn1c(C#CCNc2ccc(C#N)cc2)cc2cc(CNC3CCN(C)CC3)ccc21]

In a manner similar to the method described in Example 34, p-(2-propynylamino)benzonitrile was used to prepare 4-{[3-(1-ethyl-5-{[(1-methylpiperidin-4-yl)amino]methyl}-1H-indol-2-yl)prop-2-yn-1-yl]amino}benzonitrile.

LC-MS (ES$^+$, m/z): 426.3 [(M+H)$^+$]

Example 43: Preparation of 3-(1-Ethyl-5-{[(1-methylpiperidin-4-yl)amino]methyl}-1H-indol-2-yl)-N-phenylprop-2-ynamide

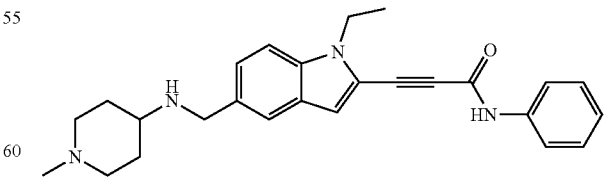

In a manner similar to the method described in Example 38, 3-(1-ethyl-5-{[(1-methylpiperidin-4-yl)amino]methyl}-1H-indol-2-yl)-N-phenylprop-2-ynamide was prepared.

LC-MS (ES$^+$, m/z): 415.3 [(M+H)$^+$]

Example 44: Preparation of N-[(2-{3-[(4-Chlorophenyl)amino]prop-1-yn-1-yl}-1-ethyl-1H-indol-5-yl)methyl]-1-methanesulfonylpiperidin-4-amine

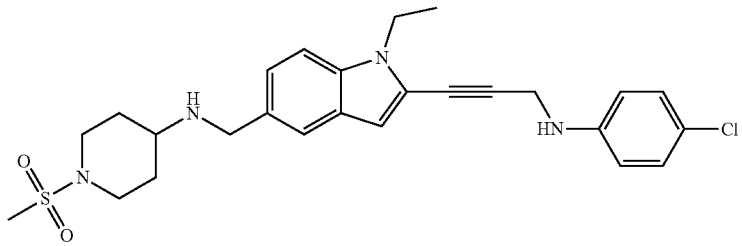 [SMILES: CCn1c(C#CCNc2ccc(Cl)cc2)cc2cc(CNC3CCN(S(C)(=O)=O)CC3)ccc21]

A flask was charged with copper(I) iodide (0.3 eq.) and triethylamine (2.5 eq.) a solution of N-2-propynyl(p-chlorophenyl)amine (2 eq.) and 5-bromo-1-ethyl-2-iodo-1H-indole (1 eq.) in tetrahydrofuran (10 mL) was added under nitrogen, followed by the addition of tetrakis(triphenylphosphine)palladium(0) (0.05 eq.). The reaction mixture was stirred at 25° C. for 1 h. Thin layer chromatography (petroleum ether/ethyl acetate: 5/1) showed that the reaction was complete. The reaction was diluted with 50 mL ethyl acetate and 100 mL 2M EDTA, and the biphasic mixture was stirred at 25° C. for 3 h. The phases were separated, and the aqueous layer was extracted with ethyl acetate (3×40 mL). The combined organic phases were washed with saturated brine (150 mL) and dried over anhydrous sodium sulphate. The solids were filtered off, and the filtrate was concentrated under reduced pressure. The crude residue was purified by flash column chromatography (silica gel, eluting with 30/1 to 20/1 gradient of petroleum ether/ethyl acetate) to give [3-(5-bromo-1-ethyl-1H-indol-2-yl)-2-propynyl](p-chlorophenyl)amine as a yellow solid.

To a mixture of [3-(5-bromo-1-ethyl-1H-indol-2-yl)-2-propynyl](p-chlorophenyl)amine (1 eq.) in tetrahydrofuran (10 mL) was added n-butyllithium (2.5 M, 6 eq.) in one portion at −78° C. under nitrogen. The mixture was stirred at −78° C. for 30 min, then 4-morpholinecarbaldehyde (10 eq.) was added in one portion. The reaction mixture was then stirred at −78° C. for 1.5 h. Thin layer chromatography (petroleum ether/ethyl acetate: 5/1) showed that the reaction was complete. The reaction mixture was poured into saturated ammonium chloride solution/ice mixture (20 mL, w/w=1/1) and stirred for 3 min. The aqueous phase was extracted with ethyl acetate (2×10 mL). The combined organic phases were washed with brine (2×10 mL) and dried over anhydrous sodium sulphate. The solids were filtered off, and the filtrate was concentrated in vacuo to give crude 2-[3-(p-chlorophenylamino)-1-propynyl]-1-ethyl-1H-indole-5-carbaldehyde as yellow oil.

To a mixture of 2-[3-(p-chlorophenylamino)-1-propynyl]-1-ethyl-1H-indole-5-carbaldehyde (1 eq.) and 1-(methylsulfonyl)-4-piperidylamine (2 eq.) in methylene chloride (10 mL) was added anhydrous magnesium sulphate (5 eq.) in one portion at 25° C. under nitrogen. The mixture was stirred at 25° C. for 60 min, then NaBH(OAc)₃ (3 eq.) was added. The reaction mixture was stirred for 5 h, and LCMS showed that the reaction was complete. The reaction mixture was poured into ice-water (10 mL, w/w=1/1), and the biphasic mixture was stirred for 3 min, then separated. The aqueous phase was extracted with methylene chloride (3×5 mL). The combined organic phases were washed with brine (3×5 mL) and dried over anhydrous sodium sulphate. The solids were filtered off, and the filtrate was concentrated in vacuo. The crude residue was purified by preparative HPLC (C18 silica gel, eluting with acetonitrile and water) to give N-[(2-{3-[(4-chlorophenyl)amino]prop-1-yn-1-yl}-1-ethyl-1H-indol-5-yl)methyl]-1-methanesulfonylpiperidin-4-amine.

LC-MS (ES⁺, m/z): 499.2 [(M+H)⁺]

Example 45: Preparation of 1-(4-{[(2-{3-[(4-Chlorophenyl)amino]prop-1-yn-1-yl}-1-ethyl-1H-indol-5-yl)methyl]amino}piperidin-1-yl)ethan-1-one

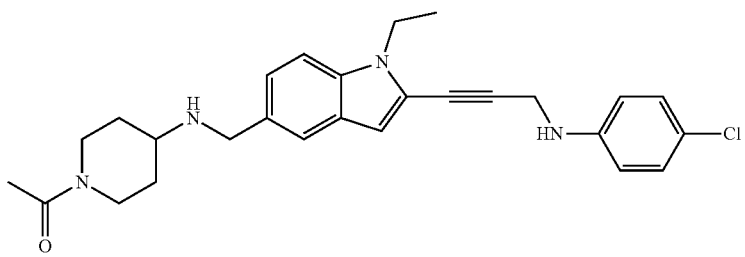 [SMILES: CCn1c(C#CCNc2ccc(Cl)cc2)cc2cc(CNC3CCN(C(C)=O)CC3)ccc21]

In a manner similar to the method described in Example 44, 2-[3-(p-chlorophenylamino)-1-propynyl]-1-ethyl-1H-indole-5-carbaldehyde was reacted with 1-(4-amino-1-piperidyl)-1-ethanone to give 1-(4-{[(2-{3-[(4-chlorophenyl)amino]prop-1-yn-1-yl}-1-ethyl-1H-indol-5-yl)methyl]amino}piperidin-1-yl)ethan-1-one.

LC-MS (ES⁺, m/z): 463.3 [(M+H)⁺]

Example 46: Preparation of 6-tert-Butyl-N-[3-(1-ethyl-5-{[(1-methylpiperidin-4-yl)amino]methyl}-1H-indol-2-yl)prop-2-yn-1-yl]pyridine-3-carboxamide

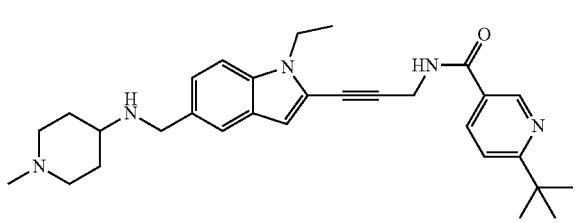 [SMILES: CCn1c(C#CCNC(=O)c2ccc(C(C)(C)C)nc2)cc2cc(CNC3CCN(C)CC3)ccc21]

In a manner similar to the method described in Example 29, (2-propynylamino)[6-(tert-butyl)-3-pyridyl]formaldehyde was used to prepare 6-tert-butyl-N-[3-(1-ethyl-5-{[(1-methylpiperidin-4-yl)amino]methyl}-1H-indol-2-yl)prop-2-yn-1-yl]pyridine-3-carboxamide.

LC-MS (ES$^+$, m/z): 486.4 [(M+H)$^+$]

Example 47: Preparation of N-(3-{1-Ethyl-5-[(methylamino)methyl]-1H-indol-2-yl}prop-2-yn-1-yl)-4-(trifluoromethyl)aniline

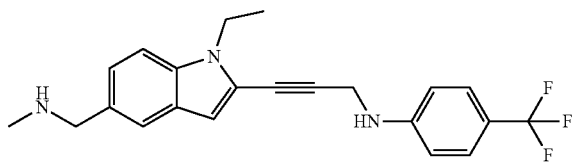 [SMILES: CCn1c(C#CCNc2ccc(C(F)(F)F)cc2)cc2cc(CNC)ccc21]

In a manner similar to the method described in Example 23, N-2-propynyl[p-(trifluoromethyl)phenyl]amine was used to prepare N-(3-{1-ethyl-5-[(methylamino)methyl]-1H-indol-2-yl}prop-2-yn-1-yl)-4-(trifluoromethyl)aniline.

LC-MS (ES$^+$, m/z): 355.2 [(M-NHMe)$^+$]

Example 48: Preparation of N-[(1-Ethyl-2-{3-[(4-methylphenyl)amino]prop-1-yn-1-yl}-1H-indol-5-yl)methyl]oxan-4-amine

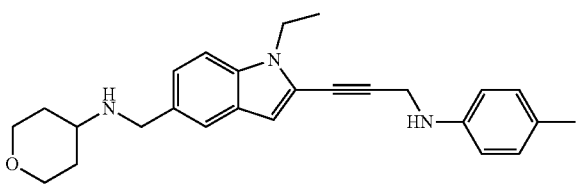 [SMILES: CCn1c(C#CCNc2ccc(C)cc2)cc2cc(CNC3CCOCC3)ccc21]

In a manner similar to the method described in Example 40, N-2-propynyl(p-tolyl)amine was used to prepare N-[(1-ethyl-2-{3-[(4-methylphenyl)amino]prop-1-yn-1-yl}-1H-indol-5-yl)methyl]oxan-4-amine.

LC-MS (ES$^+$, m/z): 402.3 [(M+H)$^+$]

Example 49: Preparation of N-(3-{1-ethyl-4-[(methylamino)methyl]-1H-indol-2-yl}prop-2-yn-1-yl)aniline

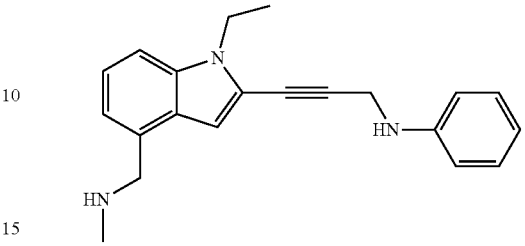

A flask was charged with copper(I) iodide (~60 mg, 0.3 eq.) and triethylamine (~100 mg, 2.5 eq.), and a solution of N-(prop-2-yn-1-yl)aniline (~200 mg, 2.0 eq.) and 4-bromo-1-ethyl-2-iodo-1H-indole (~100 mg, 1.0 eq., prepared from 4-bromo-1H-indole in analogous manner as described in Example 1) in tetrahydrofuran (10 mL) was added under nitrogen, followed by the addition of tetrakis(triphenylphosphine)palladium(0) (~20 mg, 0.05 eq.). The reaction mixture was stirred at 25° C. for 1 h. TLC (petroleum ether:ethyl acetate=5:1) showed that the reaction was complete. The reaction was diluted with ethyl acetate (50 mL) and EDTA (2M, 100 mL), and the biphasic mixture was stirred at 25° C. for 3 h. The reaction mixture was extracted with ethyl acetate (3×40 mL). The organic extracts were washed with saturated brine (150 mL) and dried over anhydrous sodium sulphate. The solids were filtered off, and the filtrate was concentrated in vacuo. The crude residue was purified by flash column chromatography (silica gel, eluting with petroleum ether/ethyl acetate, gradient 30/1 to 20/1) to give N-[3-(4-bromo-1-ethyl-1H-indol-2-yl)prop-2-yn-1-yl]aniline as yellow solid.

LC-MS (ES$^+$, m/z): 353.1 [(M+H)$^+$]

To a mixture of N-[3-(4-bromo-1-ethyl-1H-indol-2-yl)prop-2-yn-1-yl]aniline (1 eq.) in tetrahydrofuran (10 mL) was added n-butyllithium (2.5 M, 6 eq.) in one portion at −78° C. under nitrogen. The mixture was stirred at −78° C. for 30 min, 4-morpholinecarbaldehyde (10 eq.) was added in one portion at −78° C. The reaction mixture was stirred at −78° C. for 1.5 h. TLC (petroleum ether:ethyl acetate=5:1) showed that the reaction was complete. The residue was poured into aqueous ammonium chloride ice-water (20 mL, w/w=1/1) and stirred for 3 min. The aqueous phase was extracted with ethyl acetate (2×10 mL). The combined organic phases were washed with brine (2×10 mL), dried over anhydrous sodium sulphate, filtered, and concentrated in vacuo to give crude 1-ethyl-2-[3-(phenylamino)prop-1-yn-1-yl]-1H-indole-4-carbaldehyde as yellow oil. The product was used directly in the next step without further purification.

LC-MS (ES$^+$, m/z): 275.1 [(M-CHO)$^+$]

To a mixture of 1-ethyl-2-[3-(phenylamino)prop-1-yn-1-yl]-1H-indole-4-carbaldehyde (1 eq.) and methylamine (1 eq.) in methylene chloride (10 mL) was added anhydrous magnesium sulphate (5 eq.) in one portion at 25° C. under nitrogen. The mixture was stirred at 25° C. for 60 min, then NaBH(OAc)$_3$ (3 eq.) was added, and the reaction mixture was stirred for 5 h. The residue was poured into ice-water (10 mL, w/w=1/1) and stirred for 3 min. The aqueous phase was extracted with methylene chloride (3×5 mL). The combined organic phases were washed with brine (3×5 mL), dried over anhydrous sodium sulphate, filtered, and concentrated in vacuo. The crude residue was purified by preparative HPLC to give N-(3-{1-ethyl-4-[(methylamino)methyl]-1H-indol-2-yl}prop-2-yn-1-yl)aniline LC-MS (ES⁺, m/z): 318.2 [(M+H)⁺]

Example 50: Preparation of N-[3-(1-ethyl-4-{[4-(pyrrolidin-1-yl)piperidin-1-yl]methyl}-1H-indol-2-yl)prop-2-yn-1-yl]aniline

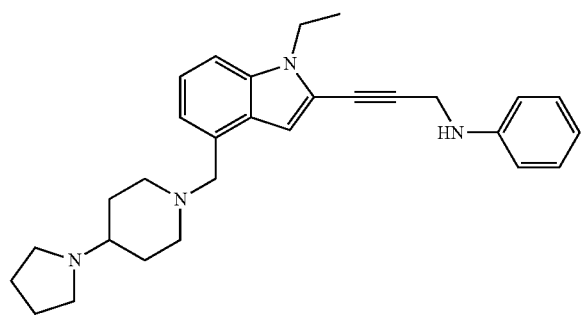 [SMILES: CCn1c(C#CCNc2ccccc2)cc2c(CN3CCC(N4CCCC4)CC3)cccc21]

In a manner similar to the method described in Example 49, 4-(pyrrolidin-1-yl)piperidine was used to prepare N-[3-(1-ethyl-4-{[4-(pyrrolidin-1-yl)piperidin-1-yl]methyl}-1H-indol-2-yl)prop-2-yn-1-yl]aniline.

LC-MS (ES⁺, m/z): 441.3 [(M+H)⁺]

Example 51: Preparation of N-({1-ethyl-2-[3-(phenylamino)prop-1-yn-1-yl]-1H-indol-4-yl}methyl)-1-methylpiperidin-4-amine

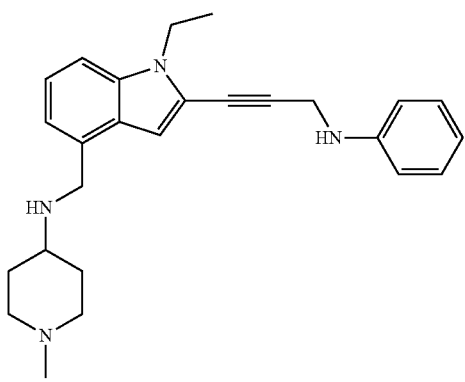 [SMILES: CCn1c(C#CCNc2ccccc2)cc2c(CNC3CCN(C)CC3)cccc21]

In a manner similar to the method described in Example 49, 1-methylpiperidin-4-amine was used to prepare N-({1-ethyl-2-[3-(phenylamino)prop-1-yn-1-yl]-1H-indol-4-yl}methyl)-1-methylpiperidin-4-amine.

LC-MS (ES⁺, m/z): 401.3 [(M+H)⁺]

Example 52: Preparation of 1-[(2-{3-[(4-chlorophenyl)amino]prop-1-yn-1-yl}-1-ethyl-1H-indol-4-yl)methyl]piperidin-4-ol

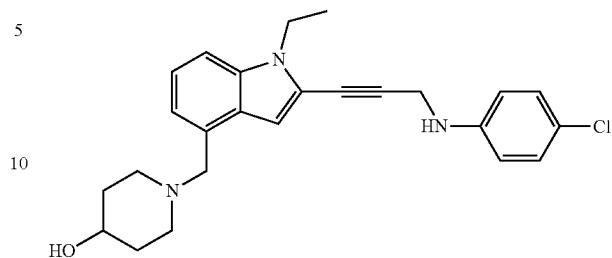

In a manner similar to the method described in Example 49, 4-hydroxypiperidine and 4-chloro-N-(prop-2-yn-1-yl)aniline were used to prepare 1-[(2-{3-[(4-chlorophenyl)amino]prop-1-yn-1-yl}-1-ethyl-1H-indol-4-yl)methyl]piperidin-4-ol.

LC-MS (ES⁺, m/z): 422.1 [(M+H)⁺]

Example 53: Preparation of 4-Chloro-N-[3-(1-ethyl-4-{[4-(pyrrolidin-1-yl)piperidin-1-yl]methyl}-1H-indol-2-yl)prop-2-yn-1-yl]aniline

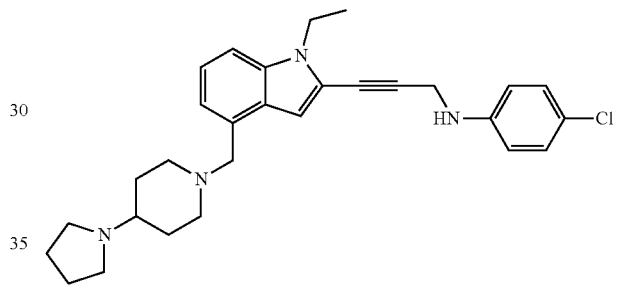

In a manner similar to the method described in Example 49, 4-(pyrrolidin-1-yl)piperidine and 4-chloro-N-(prop-2-yn-1-yl)aniline were used to prepare 4-chloro-N-[3-(1-ethyl-4-{[4-(pyrrolidin-1-yl)piperidin-1-yl]methyl}-1H-indol-2-yl)prop-2-yn-1-yl]aniline.

LC-MS (ES⁺, m/z): 475.3 [(M+H)⁺]

Example 54: Preparation of 1-[(2-{3-[(4-chlorophenyl)amino]prop-1-yn-1-yl}-1-ethyl-1H-indol-4-yl)methyl]-N,N-dimethylpiperidin-4-amine

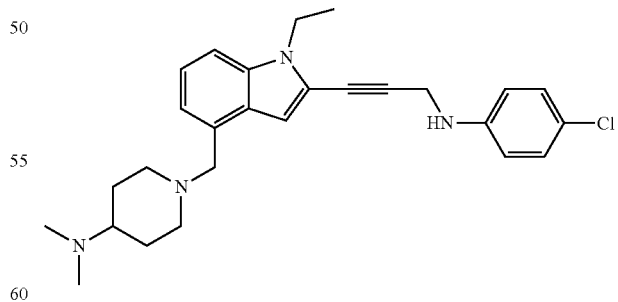

In a manner similar to the method described in Example 49, N,N-dimethylpiperidin-4-amine and 4-chloro-N-(prop-2-yn-1-yl)aniline were used to prepare 1-[(2-{3-[(4-chlorophenyl)amino]prop-1-yn-1-yl}-1-ethyl-1H-indol-4-yl)methyl]-N,N-dimethylpiperidin-4-amine.

LC-MS (ES⁺, m/z): 449.2 [(M+H)⁺]

Example 55: Preparation of 4-Chloro-N-(3-{1-ethyl-4-[(4-methylpiperazin-1-yl)methyl]-1H-indol-2-yl}prop-2-yn-1-yl)aniline

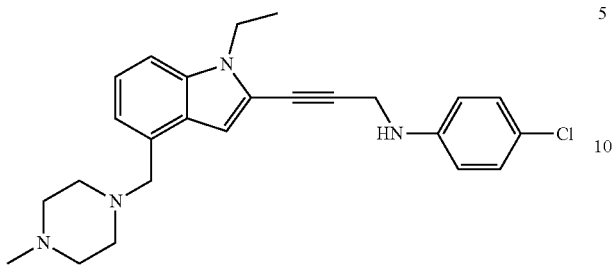

In a manner similar to the method described in Example 49, 1-methylpiperazine and 4-chloro-N-(prop-2-yn-1-yl)aniline were used to prepare 4-chloro-N-(3-{1-ethyl-4-[(4-methylpiperazin-1-yl)methyl]-1H-indol-2-yl}prop-2-yn-1-yl)aniline.
LC-MS (ES$^+$, m/z): 421.3 [(M+H)$^+$]

Example 56: Preparation of 1-{1-[(2-{3-[(4-Chlorophenyl)amino]prop-1-yn-1-yl}-1-ethyl-1H-indol-4-yl)methyl]piperidin-4-yl}piperidin-4-ol

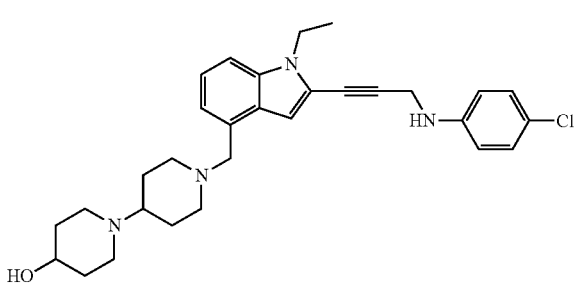 [SMILES: CCn1c(C#CCNc2ccc(Cl)cc2)cc2c(CN3CCC(N4CCC(O)CC4)CC3)cccc21]

In a manner similar to the method described in Example 49, 1,4'-bipiperidin-4-ol and 4-chloro-N-(prop-2-yn-1-yl)aniline were used to prepare 1-{1-[(2-{3-[(4-chlorophenyl)amino]prop-1-yn-1-yl}-1-ethyl-1H-indol-4-yl)methyl]piperidin-4-yl}piperidin-4-ol.
LC-MS (ES$^+$, m/z): 505.1 [(M+H)$^+$]

Example 57: Preparation of 2-(5-{[3-(4-{[4-(4-Aminopiperidin-1-yl)piperidin-1-yl]methyl}-1-ethyl-1H-indol-2-yl)prop-2-yn-1-yl]amino}pyridin-2-yl)-2-methylpropanenitrile

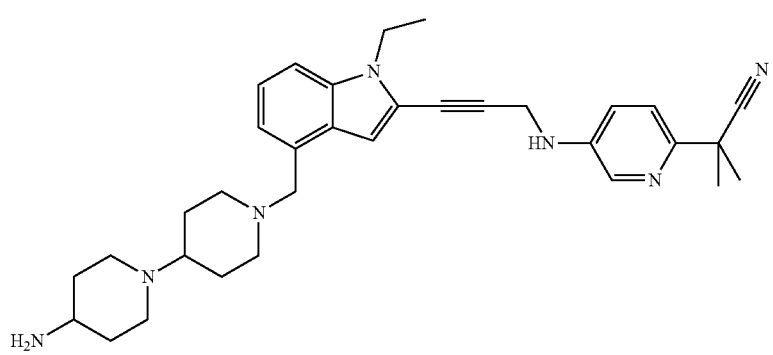 [SMILES: CCn1c(C#CCNc2ccc(C(C)(C)C#N)nc2)cc2c(CN3CCC(N4CCC(N)CC4)CC3)cccc21]

In a manner similar to the method described in Example 49, 1,4'-bipiperidin-4-amine and 2-methyl-2-[5-(prop-2-yn-1-ylamino)pyridin-2-yl]propanenitrile were used to prepare 2-(5-{[3-(4-{[4-(4-aminopiperidin-1-yl)piperidin-1-yl]methyl}-1-ethyl-1H-indol-2-yl)prop-2-yn-1-yl]amino}pyridin-2-yl)-2-methylpropanenitrile.
LC-MS (ES$^+$, m/z): 538.3 [(M+H)$^+$]

Example 58: Preparation of 1-[(1-ethyl-2-{3-[(4-fluorophenyl)amino]prop-1-yn-1-yl}-1H-indol-5-yl)methyl]-N,N-dimethylpiperidin-4-amine

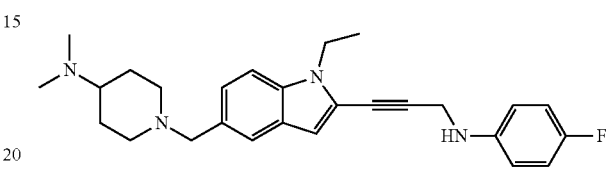

In a manner similar to the method described in Example 1, 1-[(1-ethyl-2-{3-[(4-fluorophenyl)amino]prop-1-yn-1-yl}-1H-indol-5-yl)methyl]-N,N-dimethylpiperidin-4-amine was prepared.
LC-MS (ES$^+$, m/z): 433.3 [(M+H)$^+$]

Example 59: Preparation of 4-N-({1-ethyl-2-[3-(phenylamino)prop-1-yn-1-yl]-1H-indol-5-yl}methyl)-1-N,1-N-dimethylcyclohexane-1,4-diamine

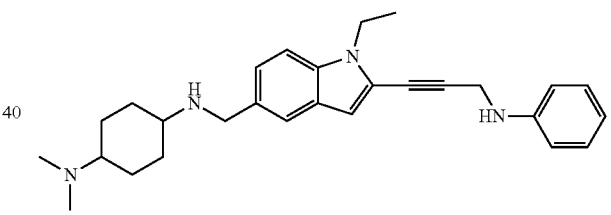

In a manner similar to the method described in Example 1, 4-N-({1-ethyl-2-[3-(phenylamino)prop-1-yn-1-yl]-1H-indol-5-yl}methyl)-1-N, 1-N-dimethylcyclohexane-1,4-diamine was prepared.
LC-MS (ES$^+$, m/z): 429.3 [(M+H)$^+$]

Example 60: Preparation of 4-chloro-N-(3-{1-ethyl-5-[(methylamino)methyl]-1H-indol-2-yl}prop-2-yn-1-yl)-3-fluoroaniline

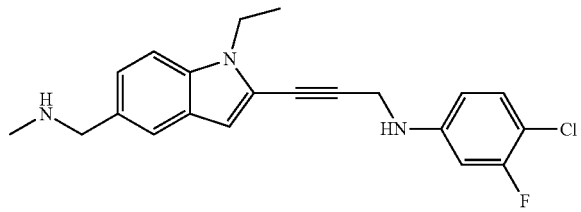 [SMILES: CCn1c(C#CCNc2ccc(Cl)c(F)c2)cc2cc(CNC)ccc21]

In a manner similar to the method described in Example 1, 4-chloro-N-(3-{1-ethyl-5-[(methylamino)methyl]-1H-indol-2-yl}prop-2-yn-1-yl)-3-fluoroaniline was prepared.
LC-MS (ES$^+$, m/z): 339.0 [(M-NHMe)$^+$] and 370.0 [(M+H)$^+$]

Example 61: Preparation of 6-tert-butyl-N-(3-{1-ethyl-5-[(methylamino)methyl]-1H-indol-2-yl}prop-2-yn-1-yl)pyridine-3-carboxamide

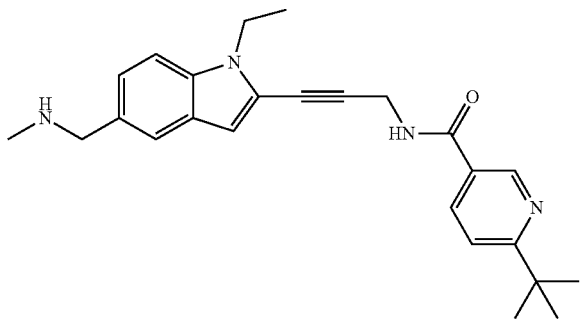 [SMILES: CCn1c(C#CCNC(=O)c2ccc(C(C)(C)C)nc2)cc2cc(CNC)ccc21]

In a manner similar to the method described in Example 1, 6-tert-butyl-N-(3-{1-ethyl-5-[(methylamino)methyl]-1H-indol-2-yl}prop-2-yn-1-yl)pyridine-3-carboxamide was prepared.
LC-MS (ES$^+$, m/z): 372.2 [(M-NHMe)$^+$]

Example 62: Preparation of N-(3-{1-ethyl-5-[(methylamino)methyl]-1H-indol-2-yl}prop-2-yn-1-yl)benzamide

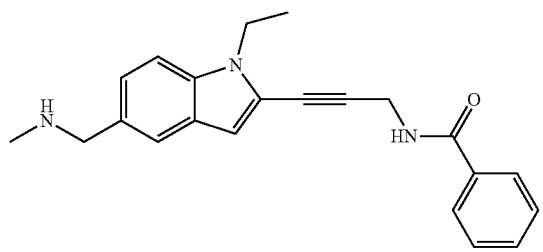 [SMILES: CCn1c(C#CCNC(=O)c2ccccc2)cc2cc(CNC)ccc21]

In a manner similar to the method described in Example 1, N-(3-{1-ethyl-5-[(methylamino)methyl]-1H-indol-2-yl}prop-2-yn-1-yl)benzamide was prepared.
LC-MS (ES$^+$, m/z): 315.1 [(M-NHMe)$^+$]

Example 63: Preparation of 3-(3-{1-ethyl-5-[(methylamino)methyl]-1H-indol-2-yl}prop-2-yn-1-yl)-1-(4-methylphenyl)urea

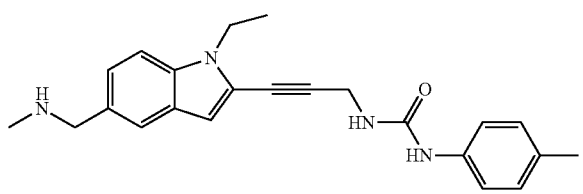

In a manner similar to the method described in Example 1, 3-(3-{1-ethyl-5-[(methylamino)methyl]-1H-indol-2-yl}prop-2-yn-1-yl)-1-(4-methylphenyl)urea was prepared.
LC-MS (ES$^+$, m/z): 344.1 [(M-NHMe)$^+$]

Example 64: Preparation of 4-chloro-N-(3-{1-ethyl-5-[(methylamino)methyl]-1H-indol-2-yl}prop-2-yn-1-yl)aniline

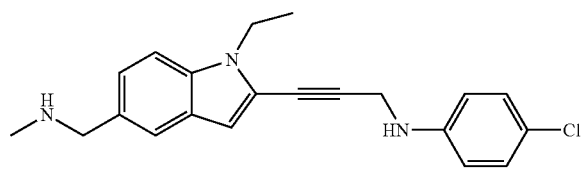 [SMILES: CCn1c(C#CCNc2ccc(Cl)cc2)cc2cc(CNC)ccc21]

In a manner similar to the method described in Example 1, 4-chloro-N-(3-{1-ethyl-5-[(methylamino)methyl]-1H-indol-2-yl}prop-2-yn-1-yl)aniline was prepared.
LC-MS (ES$^+$, m/z): 321.0 [(M-NHMe)$^+$]

Example 65: Preparation of 4-{[3-(1-ethyl-5-{[(oxan-4-yl)amino]methyl}-1H-indol-2-yl)prop-2-yn-1-yl]amino}benzonitrile

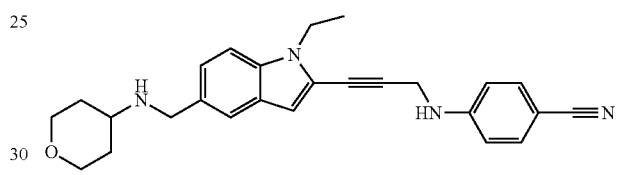

In a manner similar to the method described in Example 28, 4-{[3-(1-ethyl-5-{[(oxan-4-yl)amino]methyl}-1H-indol-2-yl)prop-2-yn-1-yl]amino}benzonitrile was prepared.
LC-MS (ES$^+$, m/z): 413.2 [(M+H)$^+$]

Example 66: Preparation of N-[(2-{3-[(4-chloro-3-fluorophenyl)amino]prop-1-yn-1-yl}-1-ethyl-1H-indol-5-yl)methyl]oxan-4-amine

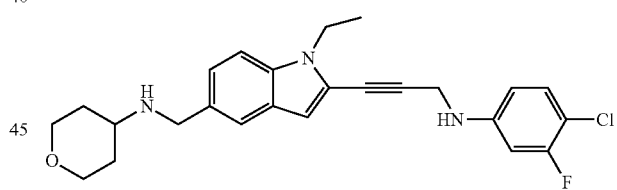

In a manner similar to the method described in Example 28, N-[(2-{3-[(4-chloro-3-fluorophenyl)amino]prop-1-yn-1-yl}-1-ethyl-1H-indol-5-yl)methyl]oxan-4-amine was prepared.
LC-MS (ES$^+$, m/z): 440.1 [(M+H)$^+$]

Example 67: Preparation of 3-[3-(1-ethyl-5-{[(oxan-4-yl)amino]methyl}-1H-indol-2-yl)prop-2-yn-1-yl]-1-phenylurea

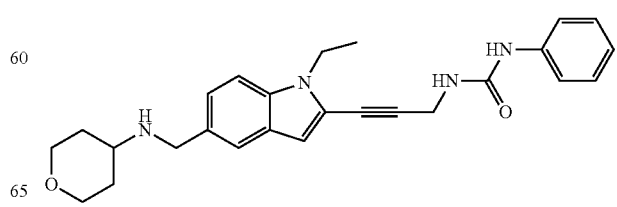

In a manner similar to the method described in Example 28, 3-[3-(1-ethyl-5-{[(oxan-4-yl)amino]methyl}-1H-indol-2-yl)prop-2-yn-1-yl]-1-phenylurea was prepared.
LC-MS (ES+, m/z): 431.1 [(M+H)+]

Example 68: Preparation of 6-tert-butyl-N-[3-(1-ethyl-5-{[(oxan-4-yl)amino]methyl}-1H-indol-2-yl)prop-2-yn-1-yl]pyridin-3-amine

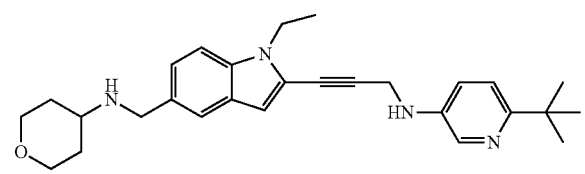 [SMILES: CCn1c(C#CCNc2ccc(C(C)(C)C)nc2)cc2cc(CNC3CCOCC3)ccc21]

In a manner similar to the method described in Example 28, 6-tert-butyl-N-[3-(1-ethyl-5-{[(oxan-4-yl)amino]methyl}-1H-indol-2-yl)prop-2-yn-1-yl]pyridin-3-amine was prepared.
LC-MS (ES+, m/z): 445.3 [(M+H)+]

Example 69: Preparation of 4-{[(2-{3-[(4-chlorophenyl)amino]prop-1-yn-1-yl}-1-ethyl-1H-indol-5-yl)methyl]amino}-1λ6-thiane-1,1-dione

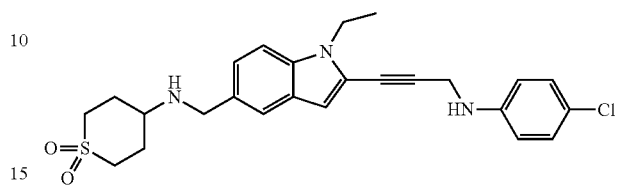

In a manner similar to the method described in Example 28, 4-{[(2-{3-[(4-chlorophenyl)amino]prop-1-yn-1-yl}-1-ethyl-1H-indol-5-yl)methyl]amino}-1λ6-thiane-1,1-dione was prepared.
LC-MS (ES+, m/z): 492.2 [(M+Na)+]

Example 70: Preparation of N-[(2-{3-[(4-chlorophenyl)amino]prop-1-yn-1-yl}-1-ethyl-1H-indol-5-yl)methyl]-1-(2-methanesulfonylethyl)piperidin-4-amine

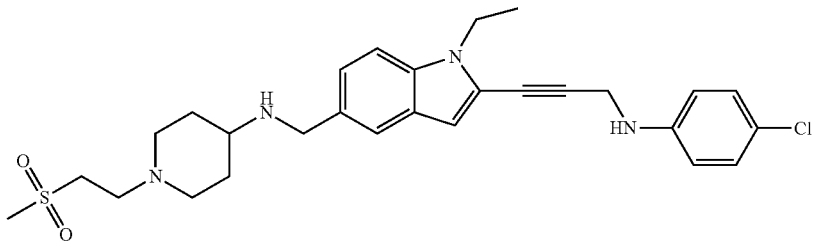 [SMILES: CCn1c(C#CCNc2ccc(Cl)cc2)cc2cc(CNC3CCN(CCS(C)(=O)=O)CC3)ccc21]

In a manner similar to the method described in Example 28, N-[(2-{3-[(4-chlorophenyl)amino]prop-1-yn-1-yl}-1-ethyl-1H-indol-5-yl)methyl]-1-(2-methanesulfonylethyl)piperidin-4-amine was prepared.
LC-MS (ES+, m/z): 527.3 [(M+H)+]

Example 71: Preparation of 1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one

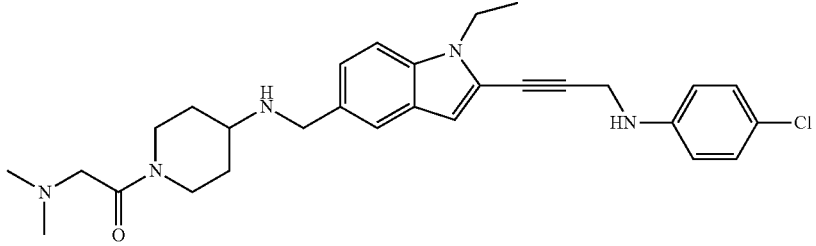 [SMILES: CCn1c(C#CCNc2ccc(Cl)cc2)cc2cc(CNC3CCN(C(=O)CN(C)C)CC3)ccc21]

In a manner similar to the method described in Example 28, 1-(4-{[(2-{3-[(4-chlorophenyl)amino]prop-1-yn-1-yl}-1-ethyl-1H-indol-5-yl)methyl]amino}piperidin-1-yl)-2-(dimethylamino)ethan-1-one was prepared.
LC-MS (ES+, m/z): 506.3 [(M+H)+]

Example 72: Preparation of 2-(4-{[(2-{3-[(4-chloro-phenyl)amino]prop-1-yn-1-yl}-1-ethyl-1H-indol-5-yl)methyl]amino}piperidin-1-yl)-N,N-dimethylacetamide

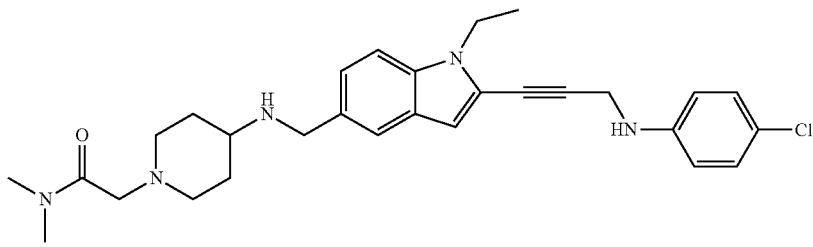 [SMILES: CCn1c(C#CCNc2ccc(Cl)cc2)cc2cc(CNC3CCN(CC(=O)N(C)C)CC3)ccc21]

In a manner similar to the method described in Example 28, 2-(4-{[(2-{3-[(4-chlorophenyl)amino]prop-1-yn-1-yl}-1-ethyl-1H-indol-5-yl)methyl]amino}piperidin-1-yl)-N,N-dimethylacetamide was prepared.

LC-MS (ES$^+$, m/z): 506.2 [(M+H)$^+$]

Example 73: Preparation of 2-tert-butyl-N-[3-(1-ethyl-5-{[(1-methylpiperidin-4-yl)amino]methyl}-1H-indol-2-yl)prop-2-yn-1-yl]pyrimidin-5-amine

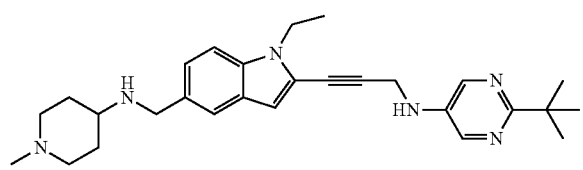 [SMILES: CCn1c(C#CCNc2cnc(C(C)(C)C)nc2)cc2cc(CNC3CCN(C)CC3)ccc21]

In a manner similar to the method described in Example 28, 2-tert-butyl-N-[3-(1-ethyl-5-{[(1-methylpiperidin-4-yl)amino]methyl}-1H-indol-2-yl)prop-2-yn-1-yl]pyrimidin-5-amine was prepared.

LC-MS (ES$^+$, m/z): 459.4 [(M+H)$^+$]

Example 74: Preparation of 2-methyl-2-(5-{[3-(5-{[(oxan-4-yl)amino]methyl}-1-(2,2,2-trifluoroethyl)-1H-indol-2-yl)prop-2-yn-1-yl]amino}pyridin-2-yl)propanenitrile

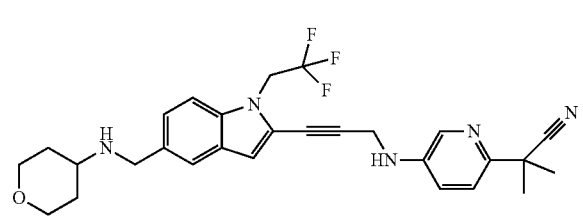 [SMILES: CC(C)(C#N)c1ccc(NCC#Cc2cc3cc(CNC4CCOCC4)ccc3n2CC(F)(F)F)cn1]

In a manner similar to the method described in Example 28, 2-methyl-2-(5-{[3-(5-{[(oxan-4-yl)amino]methyl}-1-(2,2,2-trifluoroethyl)-1H-indol-2-yl)prop-2-yn-1-yl]amino}pyridin-2-yl)propanenitrile was prepared.

LC-MS (ES$^+$, m/z): 510.2 [(M+H)$^+$]

Example 75: Preparation of 2-[5-({3-[1-(2-fluoro-ethyl)-5-{[(oxan-4-yl)amino]methyl}-1H-indol-2-yl]prop-2-yn-1-yl}amino)pyridin-2-yl]-2-methylpropanenitrile

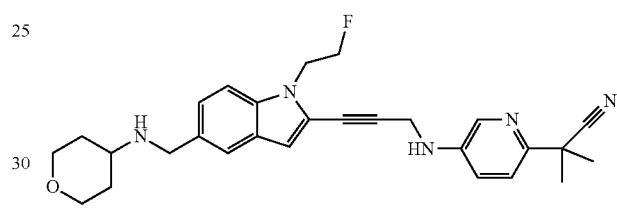

In a manner similar to the method described in Example 28, 2-[5-({3-[1-(2-fluoroethyl)-5-{[(oxan-4-yl)amino]methyl}-1H-indol-2-yl]prop-2-yn-1-yl}amino)pyridin-2-yl]-2-methylpropanenitrile was prepared.

LC-MS (ES$^+$, m/z): 474.2 [(M+H)$^+$]

Example 76: Preparation of 3-(1-ethyl-5-{[(1-methylpiperidin-4-yl)amino]methyl}-1H-indol-2-yl)prop-2-yn-1-ol

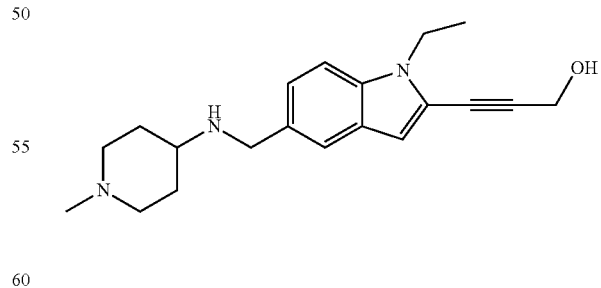

In a manner similar to the method described in Example 28, 3-(1-ethyl-5-{[(1-methylpiperidin-4-yl)amino]methyl}-1H-indol-2-yl)prop-2-yn-1-ol was prepared.

LC-MS (ES$^+$, m/z): 326.2 [(M+H)$^+$]

Example 77: Preparation of 2-[5-({3-[1-(2-chloro-ethyl)-5-{[(oxan-4-yl)amino]methyl}-1H-indol-2-yl]prop-2-yn-1-yl}amino)pyridin-2-yl]-2-methylpropanenitrile

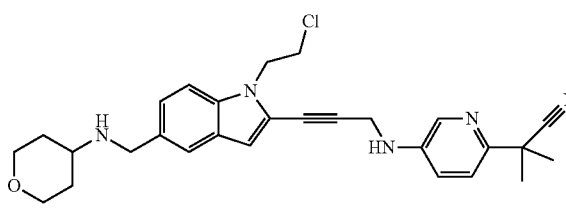

In a manner similar to the method described in Example 28, 2-[5-({3-[1-(2-chloroethyl)-5-{[(oxan-4-yl)amino]methyl}-1H-indol-2-yl]prop-2-yn-1-yl}amino)pyridin-2-yl]-2-methylpropanenitrile was prepared.

LC-MS (ES+, m/z): 490.2 [(M+H)+]

Example 78: Preparation of 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile

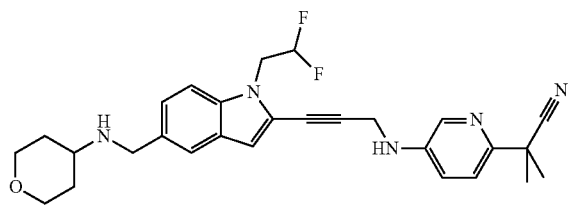 [SMILES: CC(C)(C#N)c1ccc(NCC#Cc2cc3cc(CNC4CCOCC4)ccc3n2CC(F)F)cn1]

In a manner similar to the method described in Example 28, 2-[5-({3-[1-(2,2-difluoroethyl)-5-{[(oxan-4-yl)amino]methyl}-1H-indol-2-yl]prop-2-yn-1-yl}amino)pyridin-2-yl]-2-methylpropanenitrile was prepared.

LC-MS (ES+, m/z): 492.3 [(M+H)+]

Example 79: Preparation of 6-chloro-N-[3-(1-ethyl-5-{[(1-methylpiperidin-4-yl)amino]methyl}-1H-indol-2-yl)prop-2-yn-1-yl]pyridin-3-amine

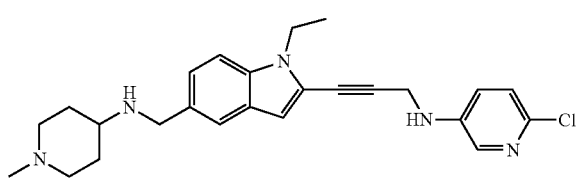 [SMILES: CCn1c(C#CCNc2ccc(Cl)nc2)cc2cc(CNC3CCN(C)CC3)ccc21]

In a manner similar to the method described in Example 28, 6-chloro-N-[3-(1-ethyl-5-{[(1-methylpiperidin-4-yl)amino]methyl}-1H-indol-2-yl)prop-2-yn-1-yl]pyridin-3-amine was prepared.

LC-MS (ES+, m/z): 436.1 [(M+H)+]

Example 80: Preparation of tert-butyl N-({3-ethyl-2-[3-(phenylamino)prop-1-yn-1-yl]-1H-indol-6-yl}methyl)-N-(oxan-4-yl)carbamate

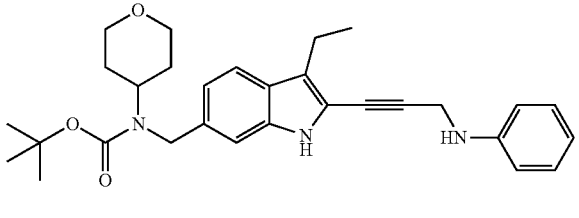 [SMILES: CCc1c(C#CCNc2ccccc2)[nH]c2cc(CN(C(=O)OC(C)(C)C)C3CCOCC3)ccc12]

Synthetic Scheme:

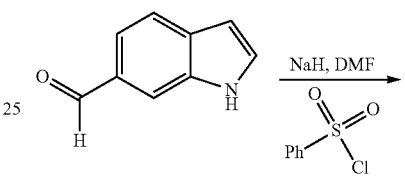

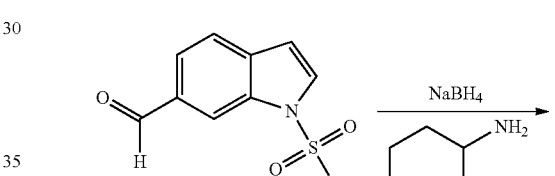

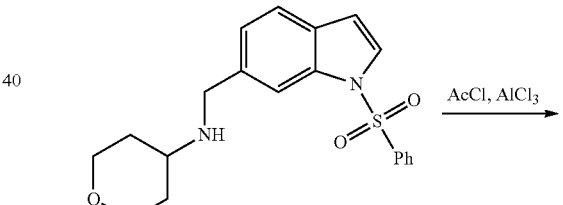

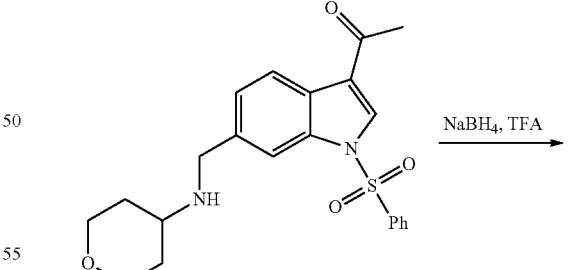

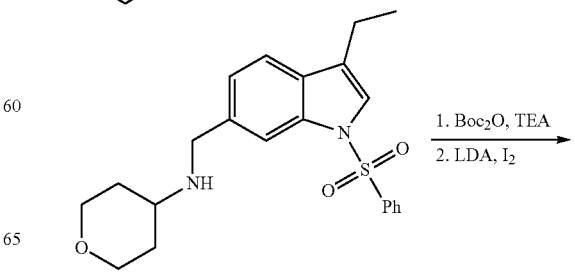

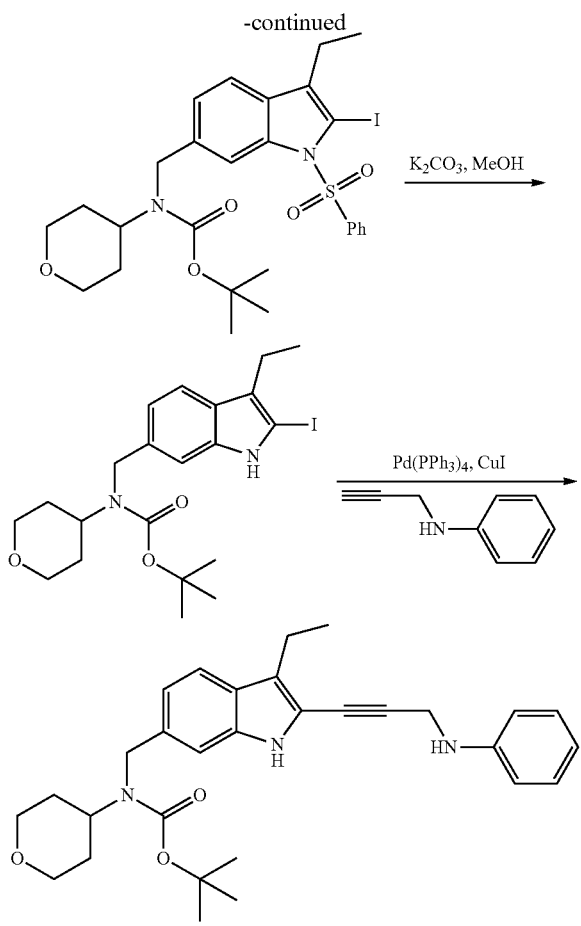

To a solution of 1H-indole-6-carbaldehyde (1.5 g, 10.34 mmol) in dimethylformamide (30 mL) at 0° C. was added sodium hydride (455 mg, 11.3 mmol). The mixture was stirred at 25° C. for 30 min, then cooled to 0° C. before benzenesulfonyl chloride (1.39 mL, 1.92 g, 11.3 mmol) was added. The mixture was stirred at 25° C. overnight. The reaction was monitored by thin layer chromatography. After the reaction was completed, the mixture was poured into ice/water (300 mL) with stirring for 1 h. The solids were filtered and washed with water (100 mL) and hexane (50 mL), and dried overnight to give 1-(phenylsulfonyl)-1H-indole-5-carbaldehyde as a yellow solid (2.90 g, 96% yield).

To the suspension of 1-(phenylsulfonyl)-1H-indole-5-carbaldehyde (1.7 g, 5.96 mmol) in methanol (30 mL) was added 4-amino-tetrahydropyran (0.74 mL, 0.72 g, 7.16 mmol) dropwise. The reaction mixture was stirred at 25° C. for 12 h, then cooled to 0° C., whereupon sodium borohydride was added in small portions. The mixture was stirred at 0° C. for 10 min, then was allowed to warm up to 25° C. with stirring for another 10 min. 1N Sodium hydroxide solution (20 mL) was added slowly with stirring for 30 min, and then the mixture was concentrated in vacuo. The residue was diluted with brine (50 mL) and water (50 mL), and extracted with ethyl acetate (3×50 mL). The combined organic layers were washed with brine (50 mL) and water (3×50 mL), and dried over anhydrous sodium sulfate. The solids were filtered off, and the filtrate was concentrated in vacuo to give {[1-(phenylsulfonyl)-1H-indol-5-yl]methyl}-tetrahydro-2H-pyran-4-ylamine as a yellow gum (2.15 g, 96% crude yield). The crude product was used directly without further purification.

A dried flask (250 mL) was charged with methylene chloride (60 mL) and aluminum trichloride (2.27 g, 17.01 mmol) under nitrogen at 0° C. {[1-(Phenylsulfonyl)-1H-indol-5-yl]methyl}-tetrahydro-2H-pyran-4-ylamine (2.0 g, 4.86 mmol) in methylene chloride (15 mL) was added dropwise, and the mixture was stirred for 10 min after addition. Acetyl chloride in methylene (0.36 mL, 0.39 g, 5.10 mmol) in methylene chloride (15 mL) was then added dropwise, and the resultant mixture was stirred for 10 min at 0° C. The mixture was then allowed to warm up to 25° C., and stirring continued for 3 h. The reaction mixture was decanted and the residue was treated with ice/water (30 mL), followed by the addition of 1N sodium hydroxide solution (30 mL). The mixture was stirred for 30 min and extracted with ethyl acetate (3×50 mL). The combined organic layers were washed with brine (50 mL) and water (3×50 mL), and dried over anhydrous sodium sulfate. The solids were filtered off, and the filtrate was concentrated in vacuo to give 1-{1-(phenylsulfonyl)-5-[(tetrahydro-2H-pyran-4-ylamino)methyl]-1H-indol-3-yl}-1-ethanone as a white foaming solid (1.92 g, 87% crude yield).

A dried flask (250 mL) was charged with trifluoroacetic acid (30 mL) under nitrogen at 0° C., and sodium borohydride (2.60 g, 69.01 mmol) was added in portions with vigorous stirring. 1-{1-(phenylsulfonyl)-5-[(tetrahydro-2H-pyran-4-ylamino)methyl]-1H-indol-3-yl}-1-ethanone (1.90 g, 4.60 mmol) in methylene chloride (30 mL) was added dropwise at 0° C., and the resultant mixture was allowed to warm to 25° C. Stirring was continued for 5 h. The reaction mixture was quenched with ice/water (20 mL) and basicified with 1N sodium hydroxide (450 mL) with stirring over 30 min. The mixture was then extracted with methylene chloride (3×30 mL), and the organic layers were washed with water (50 mL), dried over anhydrous sodium sulfate, filtered, and concentrated in vacuo to give {[3-ethyl-1-(phenylsulfonyl)-1H-indol-5-yl]methyl}-tetrahydro-2H-pyran-4-ylamine as a light brown foaming solid (1.60 g, 86% crude yield).

To {[3-ethyl-1-(phenylsulfonyl)-1H-indol-5-yl]methyl}-tetrahydro-2H-pyran-4-ylamine (0.96 g, 4.02 mmol) in methylene chloride (50 mL) was added Boc-anhydride (0.96 g, 4.42 mmol) dropwise followed by dropwise addition of trimethylamine (0.83 mL, 6.03 mmol) at 25° C. The reaction mixture was stirred at 25° C. for 3 h. The mixture was diluted with water (100 mL) and extracted with methylene chloride (3×40 mL). The combined organic layers were washed with water (50 mL), dried over anhydrous sodium sulfate, filtered, and concentrated in vacuo. The crude product was purified by flash column chromatography (silica gel, eluting with hexane/ethyl acetate 4/1) to give tert-butyl (3-ethyl-1-(phenylsulfonyl)-1H-indol-6-yl)methyl(tetrahydro-2H-pyran-4-yl)carbamate as a white solid (550 mg).

To a solution of tert-butyl (3-ethyl-1-(phenylsulfonyl)-1H-indol-6-yl)methyl(tetrahydro-2H-pyran-4-yl)carbamate (196 mg, 0.40 mmol) in tetrahydrofuran (10 mL) at −78° C. under nitrogen was added lithium diisopropylamide (1 M, 1.18 mL, 3 eq.) dropwise with stirring at −78° C. for 1 h. A solution of iodine (105 mg, 0.413 mmol, 1.05 eq.) in 1 mL of tetrahydrofuran was added dropwise, and the reaction mixture was stirred at −78° C. for another 5 min after addition. The reaction mixture was poured into aqueous ammonium chloride (5 mL), and extracted with ethyl acetate (3×30 mL). The combined organic layers were washed with water (3×30 mL) and brine (10 mL), and dried over anhydrous sodium sulfate. The solids were filtered off, and the filtrate was concentrated in vacuo to give (tert-butyl (3-ethyl-2-iodo-1-(phenylsulfonyl)-1H-indol-6-yl)methyl (tetrahydro-2H-pyran-4-yl)carbamate as a yellow oil (270 mg). The crude product was used directly without further purification.

To a solution of (tert-butyl (3-ethyl-2-iodo-1-(phenylsulfonyl)-1H-indol-6-yl)methyl(tetrahydro-2H-pyran-4-yl)carbamate (248 mg, 0.4 mmol, 1 eq.) in methanol (6.8 mL) was added 2M potassium carbonate solution (3.7 mL, 6.4 mmol), and the reaction mixture was stirred at 80° C. for 16 h. The reaction mixture was concentrated in vacuo, diluted with water (10 mL), and extracted with ethyl acetate (3×30 mL). The combined organic layers were washed with water (2×30 mL) and brine (2×30 mL), and dried over anhydrous magnesium sulfate. The solids were filtered off, and the filtrate was concentrated in vacuo to give crude tert-butyl (3-ethyl-2-iodo-1H-indol-6-yl)methyl(tetrahydro-2H-pyran-4-yl) carbamate as an orange oil (200 mg). The crude product was used directly without further purification.

To a solution of N-prop-2-yn-1-yl-aniline (20 mg, 150 µmol) in DMSO (1 mL) was added N-isopropylpropan-2-amine (53 al, 375 µmol) and copper(I) iodide (5 mg, 25 µmol) at room temperature under nitrogen, with stirring for 5 min. A solution of tert-butyl (3-ethyl-2-iodo-1H-indol-6-yl)methyl(tetrahydro-2H-pyran-4-yl)carbamate (60 mg, 125 µmol, 1 eq.) in DMSO (0.5 mL) and tetrakis(triphenylphosphine)palladium(0) (15 mg, 12.5 µmol, 0.1 eq.) were then added, and the reaction mixture was stirred at 25° C. for 1 h. The reaction was quenched with ice/water (10 mL). Ethyl acetate (30 mL) and aqueous EDTA solution (20 mL) was added, and the mixture was stirred for 2 h. The mixture was extracted with ethyl acetate (3×30 mL), and the combined organic layers were washed with water (3×10 mL) and brine (10 mL), and dried over anhydrous magnesium sulfate. The solids were filtered off, and the filtrate was concentrated in vacuo. The crude residue was purified by preparative HPLC to give tert-butyl N-({3-ethyl-2-[3-(phenylamino)prop-1-yn-1-yl]-1H-indol-6-yl}methyl)-N-(oxan-4-yl)carbamate as a light yellow solid (40 mg).

LC-MS (ES$^+$, m/z): 532.3 [(M+HCO$_2$H)$^+$]

Example 81: Preparation of 6-Chloro-N-[3-(1-ethyl-4-{[4-(pyrrolidin-1-yl)piperidin-1-yl]methyl}-1H-indol-2-yl)prop-2-yn-1-yl]pyridin-3-amine

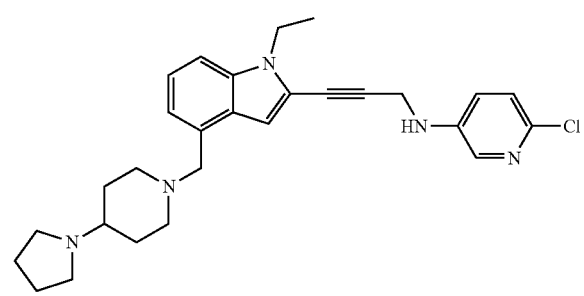

In a manner similar to the method described in Example 28, 6-chloro-N-[3-(1-ethyl-4-{[4-(pyrrolidin-1-yl)piperidin-1-yl]methyl}-1H-indol-2-yl)prop-2-yn-1-yl]pyridin-3-amine was prepared.

LC-MS (ES$^+$, m/z): 476.2 [(M+H)$^+$]

Example 82: Preparation of 3-(1-ethyl-5-{[(1-methylpiperidin-4-yl)amino]methyl}-1H-indol-2-yl)prop-2-yn-1-yl benzoate

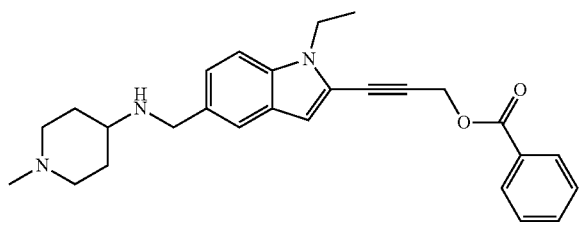 [SMILES: CCn1c(C#CCOC(=O)c2ccccc2)cc2cc(CNC3CCN(C)CC3)ccc21]

In a manner similar to the method described in Example 28, 3-(1-ethyl-5-{[(1-methylpiperidin-4-yl)amino]methyl}-1H-indol-2-yl)prop-2-yn-1-yl benzoate was prepared.

LC-MS (ES$^+$, m/z): 430.3 [(M+H)$^+$]

Example 83: Preparation of 2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile

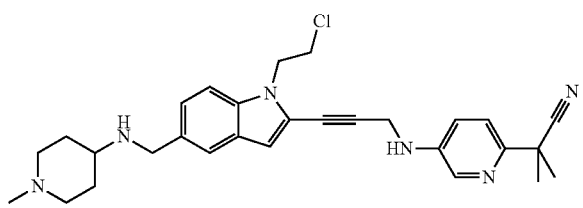 [SMILES: CN1CCC(NCc2ccc3c(c2)cc(C#CCNc2ccc(C(C)(C)C#N)nc2)n3CCCl)CC1]

In a manner similar to the method described in Example 28, 2-[5-({3-[1-(2-chloroethyl)-5-{[(1-methylpiperidin-4-yl)amino]methyl}-1H-indol-2-yl]prop-2-yn-1-yl}amino)pyridin-2-yl]-2-methylpropanenitrile was prepared.

LC-MS (ES$^+$, m/z): 503.2 [(M+H)$^+$]

Example 84: Preparation of N-(6-chloropyridin-3-yl)-3-(1-ethyl-5-{[(1-methylpiperidin-4-yl)amino]methyl}-1H-indol-2-yl)prop-2-ynamide

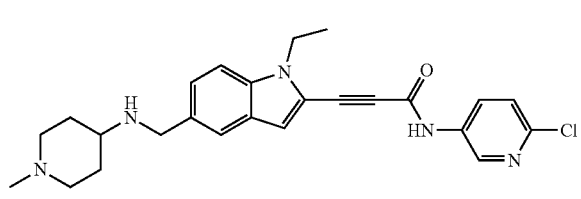 [SMILES: CCn1c(C#CC(=O)Nc2ccc(Cl)nc2)cc2cc(CNC3CCN(C)CC3)ccc21]

In a manner similar to the method described in Example 28, N-(6-chloropyridin-3-yl)-3-(1-ethyl-5-{[(1-methylpiperidin-4-yl)amino]methyl}-1H-indol-2-yl)prop-2-ynamide was prepared.

LC-MS (ES$^+$, m/z): 450.2 [(M+H)$^+$]

Example 85: Preparation of N-[6-(1-cyano-1-methylethyl)pyridin-3-yl]-3-(1-ethyl-5-{[(1-methylpiperidin-4-yl)amino]methyl}-1H-indol-2-yl)prop-2-ynamide

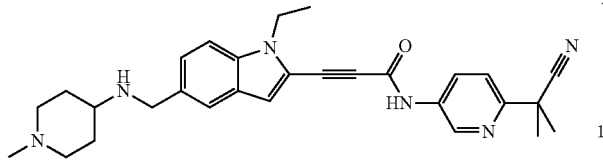

In a manner similar to the method described in Example 28, N-[6-(1-cyano-1-methylethyl)pyridin-3-yl]-3-(1-ethyl-5-{[(1-methylpiperidin-4-yl)amino]methyl}-1H-indol-2-yl)prop-2-ynamide was prepared.

LC-MS (ES+, m/z): 483.3 [(M+H)+]

Example 86: Preparation of N-({3-ethyl-2-[3-(phenylamino)prop-1-yn-1-yl]-1H-indol-6-yl}methyl)oxan-4-amine

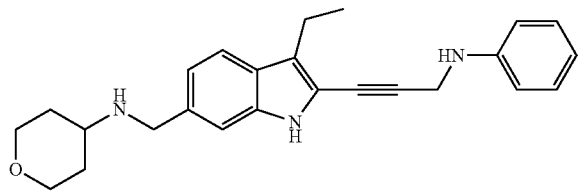 [SMILES: CCc1c(C#CCNc2ccccc2)[nH]c2cc(CNC3CCOCC3)ccc12]

To the solution of tert-butyl N-({3-ethyl-2-[3-(phenylamino)prop-1-yn-1-yl]-1H-indol-6-yl}methyl)-N-(oxan-4-yl)carbamate (11 mg, 22.5 µmol, prepared as described in Example 80) in acetonitrile (1 mL) was added trichlorobismuthane (50 mg, 158.7 µmol, 42.94 µL), and the reaction mixture was stirred at 50° C. for 25 min. Aqueous EDTA solution (20 mL) and ethyl acetate (5 mL) were added, and the mixture was stirred for 2 h. The reaction mixture was extracted with ethyl acetate (3×10 mL), the combined organic layers were washed with water (3×10 mL) and brine (10 mL), and dried over anhydrous magnesium sulphate. The solids were filtered off, and the filtrate was concentrated in vacuo. The crude residue was purified immediately by preparative HPLC (C18 silica gel, eluting with acetonitrile and water) to give N-({3-ethyl-2-[3-(phenylamino)prop-1-yn-1-yl]-1H-indol-6-yl}methyl)oxan-4-amine as a yellow solid (5 mg, 57% yield).

LC-MS (ES+, m/z): 388.2 [(M+H)+]

Example 87: Preparation of 2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile

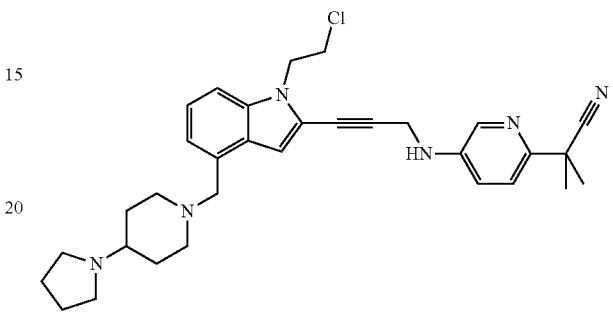

In a manner similar to the method described in Example 1 using 4-bromo-indole instead of 5-bromo-indole, 2-[5-({3-[1-(2-chloroethyl)-4-{[4-(pyrrolidin-1-yl)piperidin-1-yl]methyl}-1H-indol-2-yl]prop-2-yn-1-yl}amino)pyridin-2-yl]-2-methylpropanenitrile was prepared.

LC-MS (ES+, m/z): 543.3 [(M+H)+]

Example 88: Preparation of 2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile

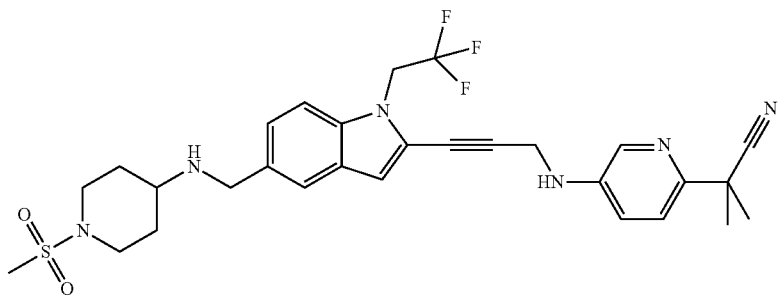 [SMILES: CC(C)(C#N)c1ccc(NCC#Cc2cc3cc(CNC4CCN(S(C)(=O)=O)CC4)ccc3n2CC(F)(F)F)cn1]

In a manner similar to the method described in Example 28, 2-(5-{[3-(5-{[(1-methanesulfonylpiperidin-4-yl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES+, m/z): 587.3 [(M+H)+]

Example 89: Preparation of 2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile

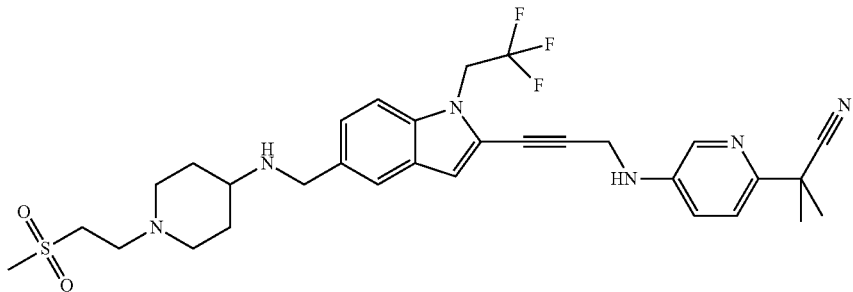 [SMILES: CC(C)(C#N)c1ccc(NCC#Cc2cc3cc(CNC4CCN(CCS(C)(=O)=O)CC4)ccc3n2CC(F)(F)F)cn1]

In a manner similar to the method described in Example 28, 2-[5-({3-[5-({[1-(2-methanesulfonylethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile was prepared.

LC-MS (ES$^+$, m/z): 615.3 [(M+H)$^+$]

Example 90: Preparation of 2-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile

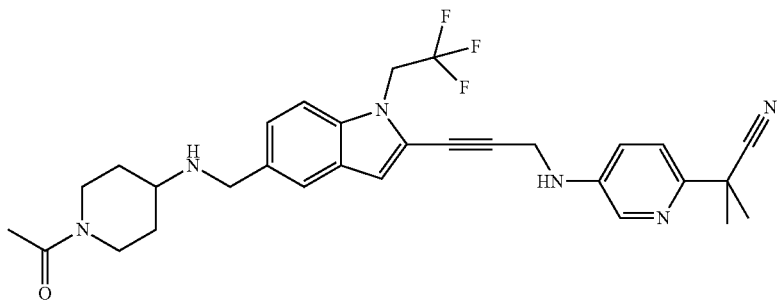 [SMILES: CC(=O)N1CCC(NCc2ccc3c(c2)cc(C#CCNc2ccc(C(C)(C)C#N)nc2)n3CC(F)(F)F)CC1]

In a manner similar to the method described in Example 28, 2-(5-{[3-(5-{[(1-acetylpiperidin-4-yl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES$^+$, m/z): 551.3 [(M+H)$^+$]

Example 91: Preparation of 2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile

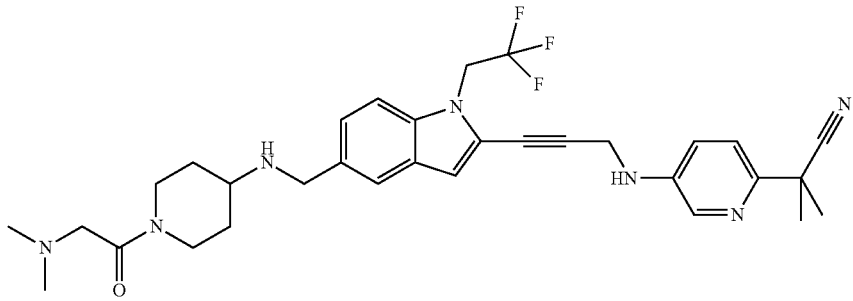 [SMILES: CN(C)CC(=O)N1CCC(NCc2ccc3c(c2)cc(C#CCNc2ccc(C(C)(C)C#N)nc2)n3CC(F)(F)F)CC1]

In a manner similar to the method described in Example 28, 2-{5-[(3-{5-[({1-[2-(dimethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile was prepared.
LC-MS (ES+, m/z): 594.4 [(M+H)+]

Example 92: Preparation of 2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile

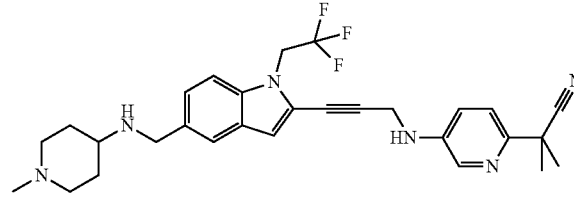

In a manner similar to the method described in Example 28, 2-methyl-2-(5-{[3-(5-{[(1-methylpiperidin-4-yl)amino]methyl}-1-(2,2,2-trifluoroethyl)-1H-indol-2-yl)prop-2-yn-1-yl]amino}pyridin-2-yl)propanenitrile was prepared.
LC-MS (ES+, m/z): 523.3 [(M+H)+]

Example 93: Preparation of 2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile

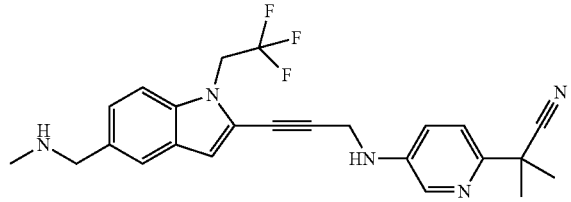 [SMILES: CNCc1ccc2c(c1)cc(C#CCNc1ccc(C(C)(C)C#N)nc1)n2CC(F)(F)F]

In a manner similar to the method described in Example 28, 2-methyl-2-{5-[(3-{5-[(methylamino)methyl]-1-(2,2,2-trifluoroethyl)-1H-indol-2-yl}prop-2-yn-1-yl)amino]pyridin-2-yl}propanenitrile was prepared.
LC-MS (ES+, m/z): 440.3 [(M+H)+]

Example 94: Preparation of 6-Chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine

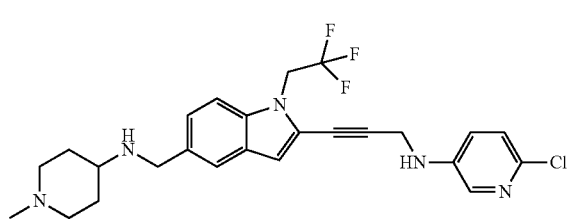 [SMILES: CN1CCC(NCc2ccc3c(c2)cc(C#CCNc2ccc(Cl)nc2)n3CC(F)(F)F)CC1]

In a manner similar to the method described in Example 28, 6-chloro-N-[3-(5-{[(1-methylpiperidin-4-yl)amino]methyl}-1-(2,2,2-trifluoroethyl)-1H-indol-2-yl)prop-2-yn-1-yl]pyridin-3-amine was prepared.
LC-MS (ES+, m/z): 490.1 [(M+H)+]

Example 95: Preparation of 6-chloro-N-[3-(5-{[(oxan-4-yl)amino]methyl}-1-(2,2,2-trifluoroethyl)-1H-indol-2-yl)prop-2-yn-1-yl]pyridin-3-amine

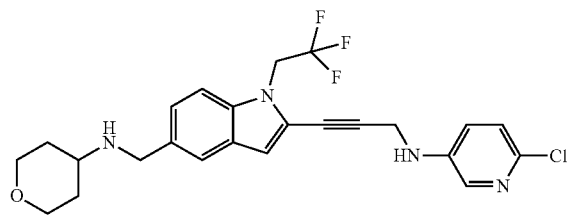 [SMILES: FC(F)(F)Cn1c(C#CCNc2ccc(Cl)nc2)cc2cc(CNC3CCOCC3)ccc21]

In a manner similar to the method described in Example 28, 6-chloro-N-[3-(5-{[(oxan-4-yl)amino]methyl}-1-(2,2,2-trifluoroethyl)-1H-indol-2-yl)prop-2-yn-1-yl]pyridin-3-amine was prepared.
LC-MS (ES+, m/z): 477.1 [(M+H)+]

Example 96: Preparation of 2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile

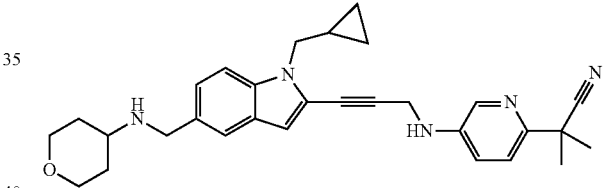

In a manner similar to the method described in Example 28, 2-[5-({3-[1-(cyclopropylmethyl)-5-{[(oxan-4-yl)amino]methyl}-1H-indol-2-yl]prop-2-yn-1-yl}amino)pyridin-2-yl]-2-methylpropanenitrile was prepared.
LC-MS (ES+, m/z): 482.3 [(M+H)+]

Example 97: Preparation of 2-(5-{[3-(4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile

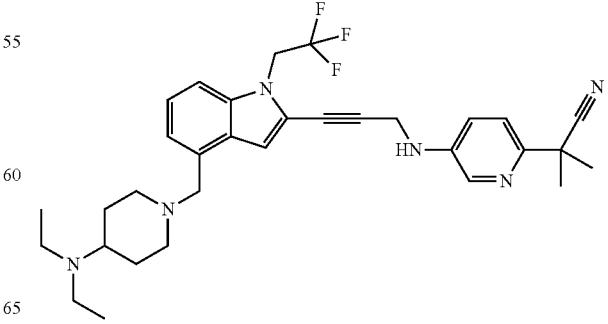

In a manner similar to the method described in Example 1 using 4-bromo-indole, 2-(5-{[3-(4-{[4-(diethylamino)piperidin-1-yl]methyl}1-(2,2,2-trifluoroethyl)-1H-indol-2-yl)prop-2-yn-1-yl]amino}pyridin-2-yl)-2-methylpropanenitrile was prepared.
LC-MS (ES+, m/z): 565.2 [(M+H)+]

Example 98: Preparation of 2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile

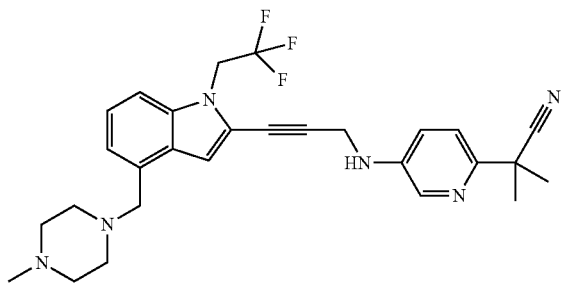 [SMILES: CN1CCN(Cc2cccc3c2cc(C#CCNc2ccc(C(C)(C)C#N)nc2)n3CC(F)(F)F)CC1]

In a manner similar to the method described in Example 1 using 4-bromo-indole, 2-methyl-2-{5-[(3-{4-[(4-methylpiperazin-1-yl)methyl]-1-(2,2,2-trifluoroethyl)-1H-indol-2-yl}prop-2-yn-1-yl)amino]pyridin-2-yl}propanenitrile was prepared.
LC-MS (ES+, m/z): 509.1 [(M+H)+]

Example 99: Preparation of 2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile

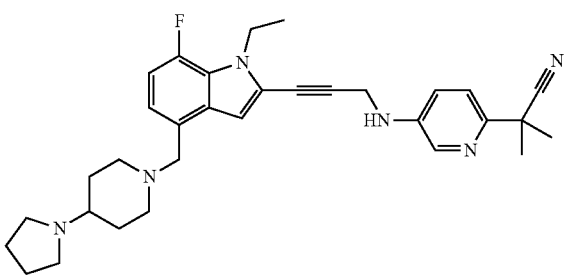 [SMILES: CCn1c(C#CCNc2ccc(C(C)(C)C#N)nc2)cc2c(CN3CCC(N4CCCC4)CC3)ccc(F)c21]

In a manner similar to the method described in Example 1 using 4-bromo-7-fluoro-indole, 2-(5-{[3-(1-ethyl-7-fluoro-4-{[4-(pyrrolidin-1-yl)piperidin-1-yl]methyl}-1H-indol-2-yl)prop-2-yn-1-yl]amino}pyridin-2-yl)-2-methylpropanenitrile was prepared.
LC-MS (ES+, m/z): 527.2 [(M+H)+]

Example 100: Preparation of 2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile

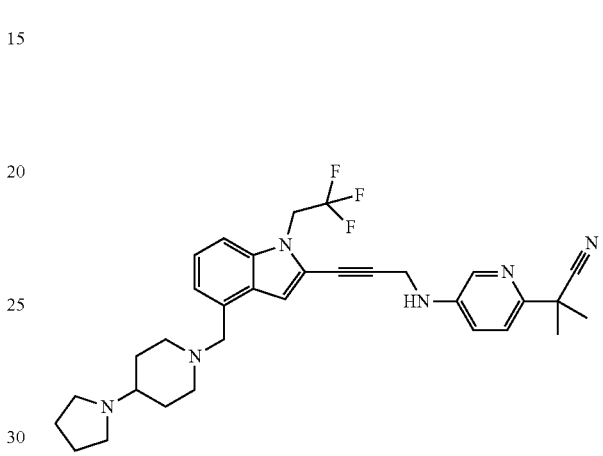

In a manner similar to the method described in Example 1 using 4-bromo-indole, 2-methyl-2-(5-{[3-(4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)propanenitrile was prepared.
LC-MS (ES+, m/z): 563.3 [(M+H)+]

Example 101: Preparation of 2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile

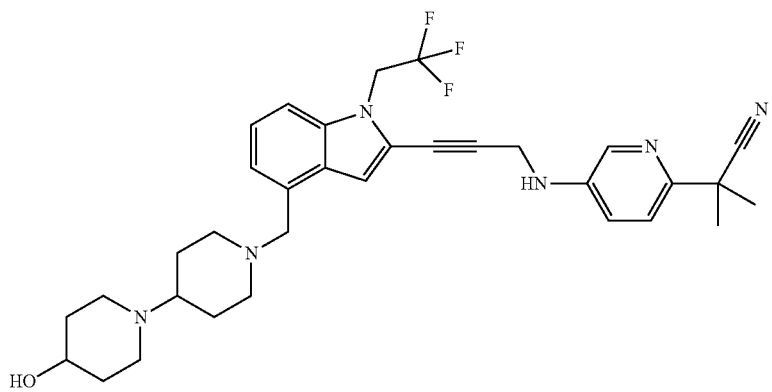 [SMILES: CC(C)(C#N)c1ccc(NCC#Cc2cc3c(CN4CCC(N5CCC(O)CC5)CC4)cccc3n2CC(F)(F)F)cn1]

In a manner similar to the method described in Example 1 using 4-bromo-indole, 2-(5-{[3-(4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile was prepared.

LC-MS (ES⁺, m/z): 593.2 [(M+H)⁺]

Example 102: Preparation of N-(6-cyanopyridin-3-yl)-3-(1-ethyl-5-{[(1-methylpiperidin-4-yl)amino]methyl}-1H-indol-2-yl)prop-2-ynamide

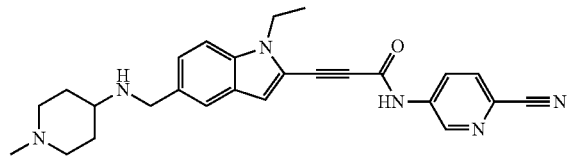 [SMILES: CCn1c(C#CC(=O)Nc2ccc(C#N)nc2)cc2cc(CNC3CCN(C)CC3)ccc21]

In a manner similar to the method described in Example 28, N-(6-cyanopyridin-3-yl)-3-(1-ethyl-5-{[(1-methylpiperidin-4-yl)amino]methyl}-1H-indol-2-yl)prop-2-ynamide was prepared.

LC-MS (ES⁺, m/z): 441.3 [(M+H)⁺]

Example 103: Preparation of N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide

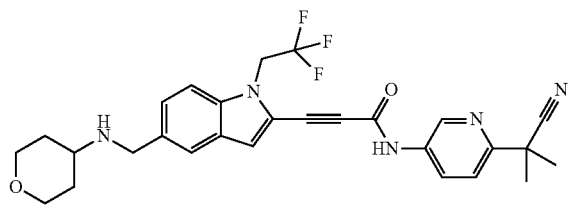 [SMILES: CC(C)(C#N)c1ccc(NC(=O)C#Cc2cc3cc(CNC4CCOCC4)ccc3n2CC(F)(F)F)cn1]

In a manner similar to the method described in Example 28, N-[6-(1-cyano-1-methylethyl)pyridin-3-yl]-3-(5-{[(oxan-4-yl)amino]methyl}-1-(2,2,2-trifluoroethyl)-1H-indol-2-yl)prop-2-ynamide was prepared.

LC-MS (ES⁺, m/z): 524.2 [(M+H)⁺]

Example 104: Preparation of N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide

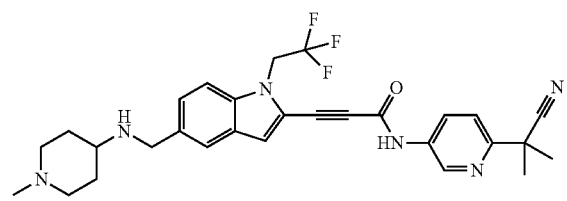 [SMILES: CN1CCC(NCc2ccc3c(c2)cc(C#CC(=O)Nc2ccc(C(C)(C)C#N)nc2)n3CC(F)(F)F)CC1]

In a manner similar to the method described in Example 28, N-[6-(1-cyano-1-methylethyl)pyridin-3-yl]-3-(5-{[(1-methylpiperidin-4-yl)amino]methyl}-1-(2,2,2-trifluoroethyl)-1H-indol-2-yl)prop-2-ynamide was prepared.

LC-MS (ES⁺, m/z): 537.2 [(M+H)⁺]

Example 105: Preparation of 2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile

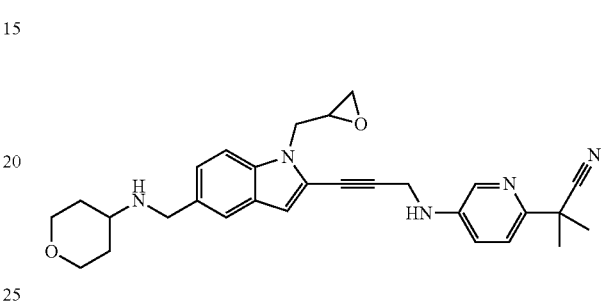

In a manner similar to the method described in Example 28, 2-methyl-2-(5-{[3-(5-{[(oxan-4-yl)amino]methyl}-1-(oxiran-2-ylmethyl)-1H-indol-2-yl)prop-2-yn-1-yl]amino}pyridin-2-yl)propanenitrile was prepared.

LC-MS (ES⁺, m/z): 484.4 [(M+H)⁺]

Example 106: Preparation of 2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile

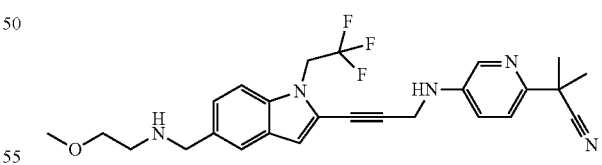

In a manner similar to the method described in Example 28, 2-(5-{[3-(5-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES⁺, m/z): 484.3 [(M+H)⁺]

Example 107: Preparation of 2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile

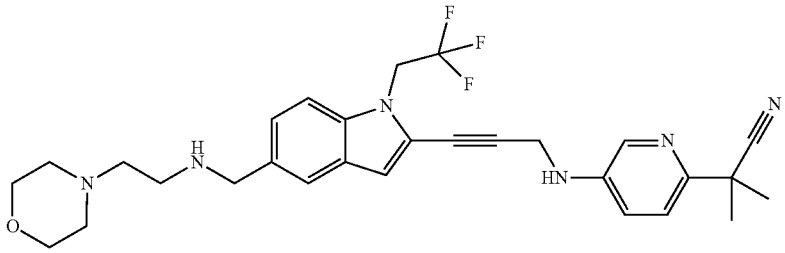 [SMILES: CC(C)(C#N)c1ccc(NCC#Cc2cc3cc(CNCCN4CCOCC4)ccc3n2CC(F)(F)F)cn1]

In a manner similar to the method described in Example 28, 2-methyl-2-[5-({3-[5-({[2-(morpholin-4-yl)ethyl]amino}methyl)-1-(2,2,2-trifluoroethyl)-1H-indol-2-yl]prop-2-yn-1-yl}amino)pyridin-2-yl]propanenitrile was prepared.

LC-MS (ES+, m/z): 539.3 [(M+H)+]

Example 108: Preparation of 2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile

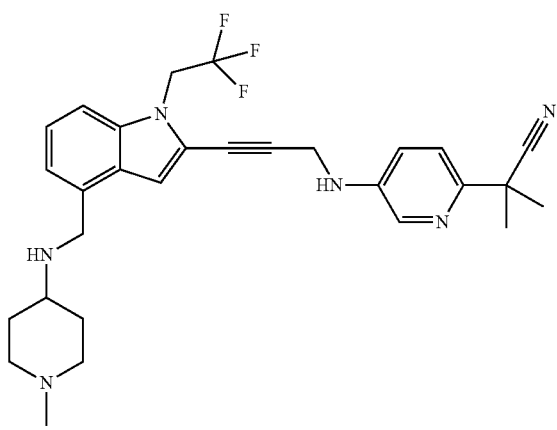 [SMILES: CN1CCC(NCc2cccc3c2cc(C#CCNc2ccc(C(C)(C)C#N)nc2)n3CC(F)(F)F)CC1]

In a manner similar to the method described in Example 1 using 4-bromo-indole, 2-methyl-2-(5-{[3-(4-{[(1-methylpiperidin-4-yl)amino]methyl}-1-(2,2,2-trifluoroethyl)-1H-indol-2-yl)prop-2-yn-1-yl]amino}pyridin-2-yl)propanenitrile was prepared.

LC-MS (ES+, m/z): 523.4 [(M+H)+]

Example 109: Preparation of 2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile

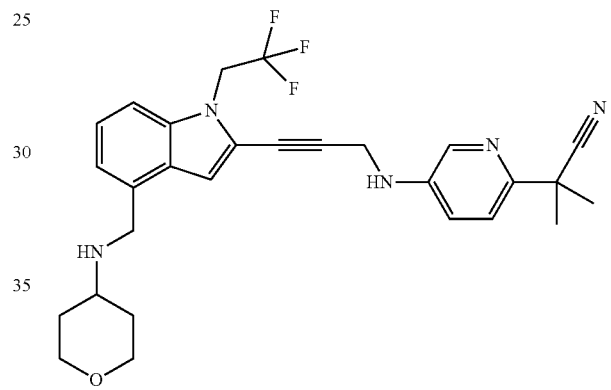

In a manner similar to the method described in Example 1 using 4-bromo-indole, 2-methyl-2-(5-{[3-(4-{[(oxan-4-yl)amino]methyl}-1-(2,2,2-trifluoroethyl)-1H-indol-2-yl)prop-2-yn-1-yl]amino}pyridin-2-yl)propanenitrile was prepared.

LC-MS (ES+, m/z): 510.3 [(M+H)+]

Example 110: Preparation of 2-[5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile

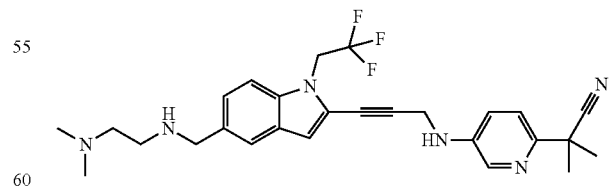

In a manner similar to the method described in Example 28, 2-[5-({3-[5-({[2-(dimethylamino)ethyl]amino}methyl)-1-(2,2,2-trifluoroethyl)-1H-indol-2-yl]prop-2-yn-1-yl}amino)pyridin-2-yl]-2-methylpropanenitrile was prepared.

LC-MS (ES+, m/z): 497.4 [(M+H)+]

Example 111: Preparation of 2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile

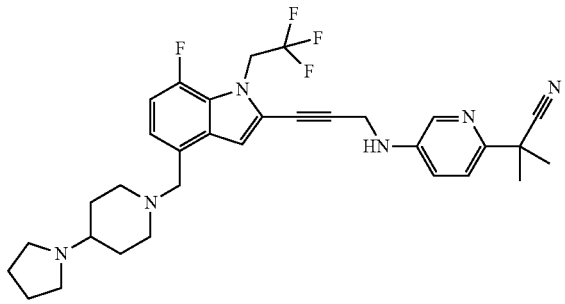 [SMILES: CC(C)(C#N)c1ccc(NCC#Cc2cc3c(CN4CCC(N5CCCC5)CC4)ccc(F)c3n2CC(F)(F)F)cn1]

In a manner similar to the method described in Example 1 using 4-bromo-7-fluoro-indole, 2-(5-{[3-(7-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile was prepared.
LC-MS (ES+, m/z): 581.4 [(M+H)+]

Example 112: Preparation of 2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile

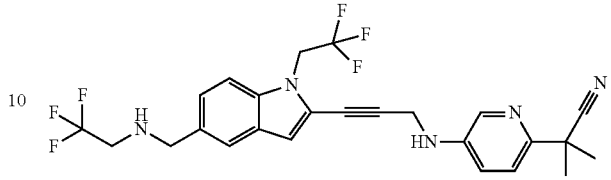

In a manner similar to the method described in Example 28, 2-methyl-2-[5-({3-[1-(2,2,2-trifluoroethyl)-5-{[(2,2,2-trifluoroethyl)amino]methyl}-1H-indol-2-yl]prop-2-yn-1-yl}amino)pyridin-2-yl]propanenitrile was prepared.
LC-MS (ES+, m/z): 508.2 [(M+H)+]

Example 113: Preparation of 2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile

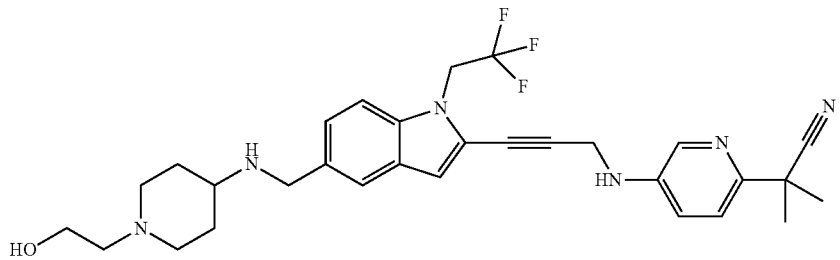 [SMILES: CC(C)(C#N)c1ccc(NCC#Cc2cc3cc(CNC4CCN(CCO)CC4)ccc3n2CC(F)(F)F)cn1]

In a manner similar to the method described in Example 28, 2-[5-({3-[5-({[1-(2-hydroxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile was prepared.
LC-MS (ES+, m/z): 553.4 [(M+H)+]

Example 114: Preparation of 2-[5-({3-[5-({[1-(2-methoxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile

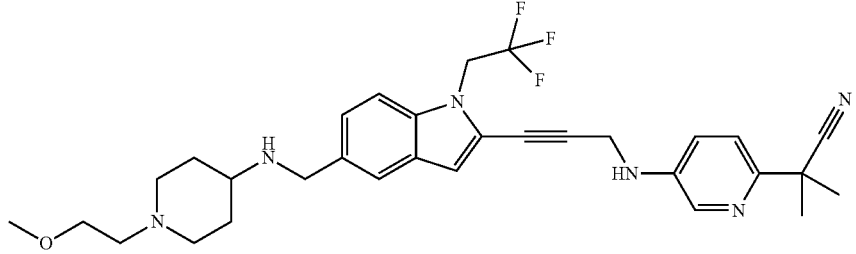 [SMILES: COCCN1CCC(NCc2ccc3c(c2)cc(C#CCNc2ccc(C(C)(C)C#N)nc2)n3CC(F)(F)F)CC1]

In a manner similar to the method described in Example 28, 2-[5-({3-[5-({[1-(2-methoxyethyl)piperidin-4-yl]amino}methyl)-1-(2,2,2-trifluoroethyl)-1H-indol-2-yl]prop-2-yn-1-yl}amino)pyridin-2-yl]-2-methylpropanenitrile was prepared.
LC-MS (ES+, m/z): 567.4 [(M+H)+]

Example 115: Preparation of 2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile

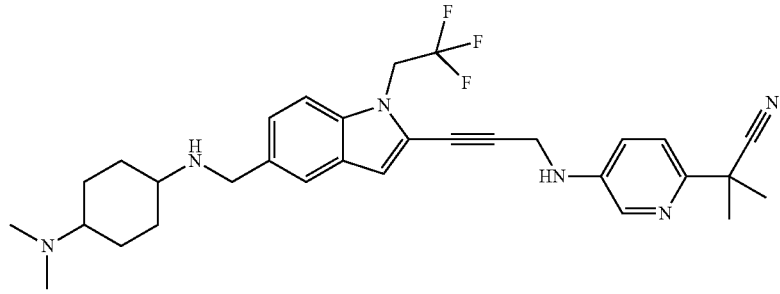 [SMILES: CN(C)C1CCC(NCc2ccc3c(c2)cc(C#CCNc2ccc(C(C)(C)C#N)nc2)n3CC(F)(F)F)CC1]

In a manner similar to the method described in Example 28, 2-[5-({3-[5-({[4-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile was prepared.
LC-MS (ES+, m/z): 551.6 [(M+H)+]

Example 116: Preparation of 2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile

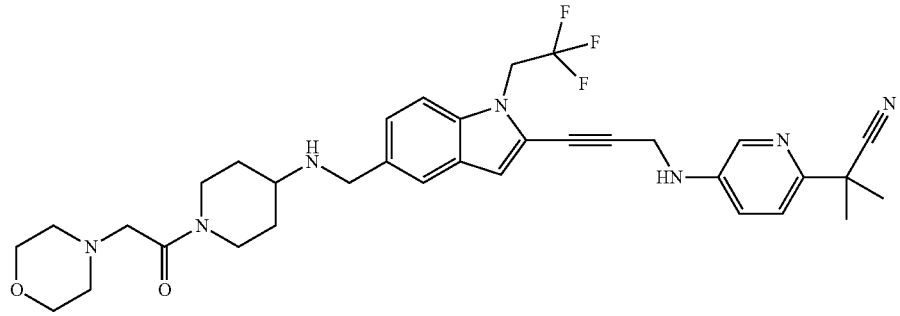 [SMILES: CC(C)(C#N)c1ccc(NCC#Cc2cc3cc(CNC4CCN(C(=O)CN5CCOCC5)CC4)ccc3n2CC(F)(F)F)cn1]

In a manner similar to the method described in Example 28, 2-methyl-2-{5-[(3-{5-[({1-[2-(morpholin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile was prepared.
LC-MS (ES+, m/z): 636.4 [(M+H)+]

Example 117: Preparation of 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile

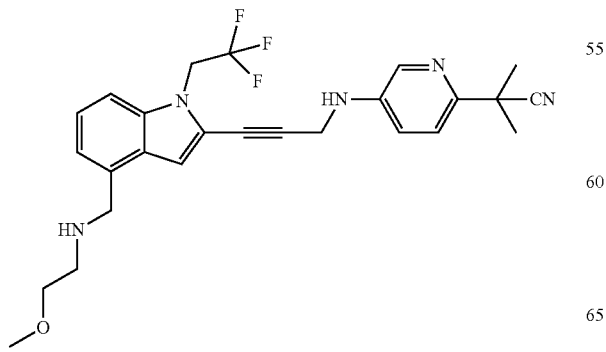

In a manner similar to the method described in Example 1 using 4-bromo-indole, 2-(5-{[3-(4-{[(2-methoxyethyl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES$^+$, m/z): 484.3 [(M+H)$^+$]

Example 118: Preparation of 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile

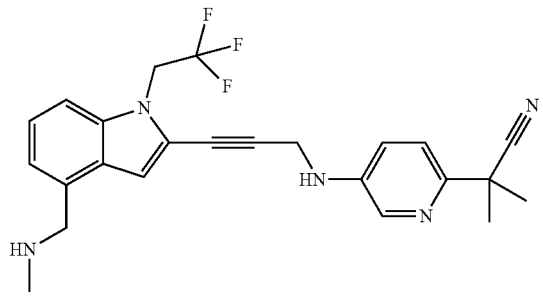 [SMILES: CNCc1cccc2c1cc(C#CCNc1ccc(C(C)(C)C#N)nc1)n2CC(F)(F)F]

In a manner similar to the method described in Example 1 using 4-bromo-indole, 2-methyl-2-{5-[(3-{4-[(methylamino)methyl]-1-(2,2,2-trifluoroethyl)-1H-indol-2-yl}prop-2-yn-1-yl)amino]pyridin-2-yl}propanenitrile was prepared.

LC-MS (ES$^+$, m/z): 440.3 [(M+H)$^+$]

Example 119: Preparation of 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile

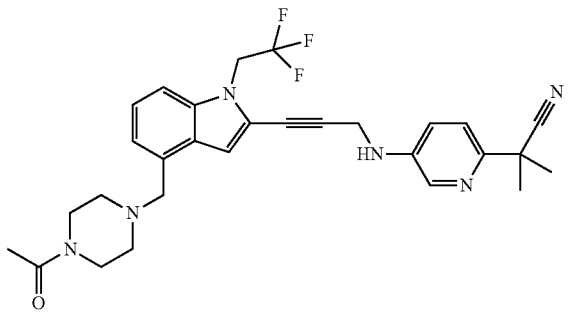 [SMILES: CC(=O)N1CCN(Cc2cccc3c2cc(C#CCNc2ccc(C(C)(C)C#N)nc2)n3CC(F)(F)F)CC1]

In a manner similar to the method described in Example 1 using 4-bromo-indole, 2-{5-[(3-{4-[(4-acetylpiperazin-1-yl)methyl]-1-(2,2,2-trifluoroethyl)-1H-indol-2-yl}prop-2-yn-1-yl)amino]pyridin-2-yl}-2-methylpropanenitrile was prepared.

LC-MS (ES$^+$, m/z): 537.3 [(M+H)$^+$]

Example 120: Preparation of 2-methyl-2-[5-({3-[4-(morpholin-4-ylmethyl)-1-(2,2,2-trifluoroethyl)-1H-indol-2-yl]prop-2-yn-1-yl}amino)pyridin-2-yl]propanenitrile

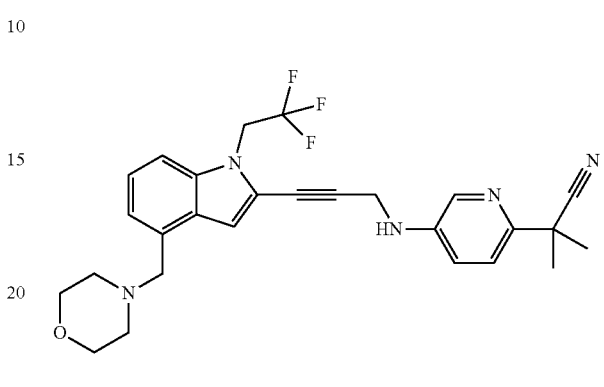

In a manner similar to the method described in Example 1 using 4-bromo-indole, 2-methyl-2-[5-({3-[4-(morpholin-4-ylmethyl)-1-(2,2,2-trifluoroethyl)-1H-indol-2-yl]prop-2-yn-1-yl}amino)pyridin-2-yl]propanenitrile was prepared.

LC-MS (ES$^+$, m/z): 496.2 [(M+H)$^+$]

Example 121: Preparation of 2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile

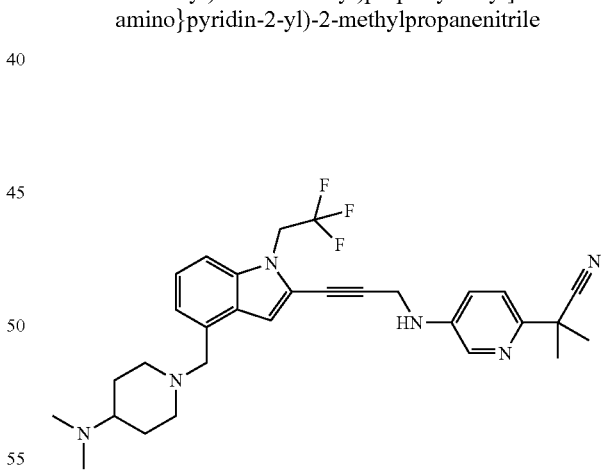

In a manner similar to the method described in Example 1 using 4-bromo-indole, 2-(5-{[3-(4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile was prepared.

LC-MS (ES$^+$, m/z): 537.3 [(M+H)$^+$]

Example 122: Preparation of 2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile

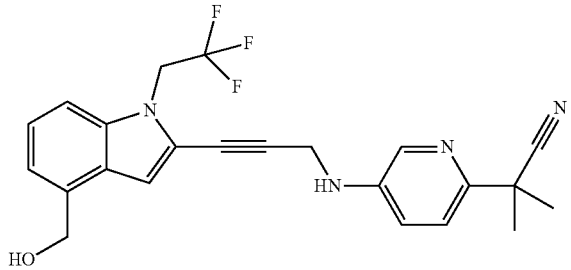 [SMILES: CC(C)(C#N)c1ccc(NCC#Cc2cc3c(CO)cccc3n2CC(F)(F)F)cn1]

In a manner similar to the method described in Example 1 using 4-bromo-indole, 2-[5-({3-[4-(hydroxymethyl)-1-(2,2,2-trifluoroethyl)-1H-indol-2-yl]prop-2-yn-1-yl}amino)pyridin-2-yl]-2-methylpropanenitrile was prepared.
LC-MS (ES+, m/z): 409.0 [(M-OH)+]

Example 123: Preparation of 2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile

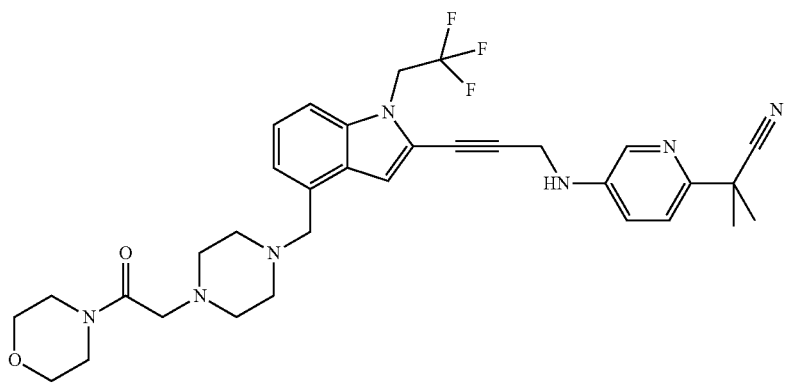 [SMILES: CC(C)(C#N)c1ccc(NCC#Cc2cc3c(CN4CCN(CC(=O)N5CCOCC5)CC4)cccc3n2CC(F)(F)F)cn1]

In a manner similar to the method described in Example 1 using 4-bromo-indole, 2-methyl-2-[5-({3-[4-({4-[2-(morpholin-4-yl)-2-oxoethyl]piperazin-1-yl}methyl)-1-(2,2,2-trifluoroethyl)-1H-indol-2-yl]prop-2-yn-1-yl}amino)pyridin-2-yl]propanenitrile was prepared.
LC-MS (ES+, m/z): 622.4 [(M+H)+]

Example 124: Preparation of 2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile

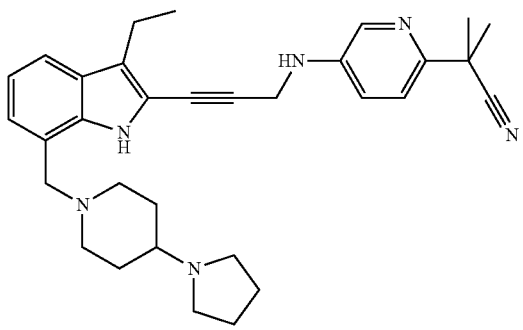 [SMILES: CCc1c(C#CCNc2ccc(C(C)(C)C#N)nc2)[nH]c2c(CN3CCC(N4CCCC4)CC3)cccc12]

In a manner similar to the method described in Example 81 and Example 86, 2-(5-{[3-(3-ethyl-7-{[4-(pyrrolidin-1-yl)piperidin-1-yl]methyl}-1H-indol-2-yl)prop-2-yn-1-yl]amino}pyridin-2-yl)-2-methylpropanenitrile was prepared.
LC-MS (ES+, m/z): 509.4 [(M+H)+]

Example 125: Preparation of methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate

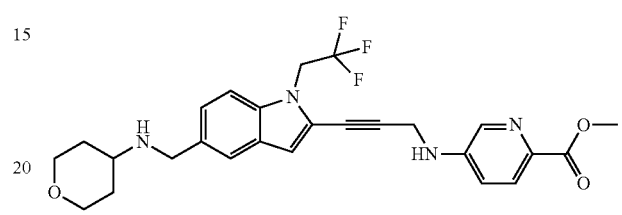

In a manner similar to the method described in Example 28, methyl 5-{[3-(5-{[(oxan-4-yl)amino]methyl}-1-(2,2,2-trifluoroethyl)-1H-indol-2-yl)prop-2-yn-1-yl]amino}pyridine-2-carboxylate was prepared.
LC-MS (ES+, m/z): 501.4 [(M+H)+]

Example 126: Preparation of N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide

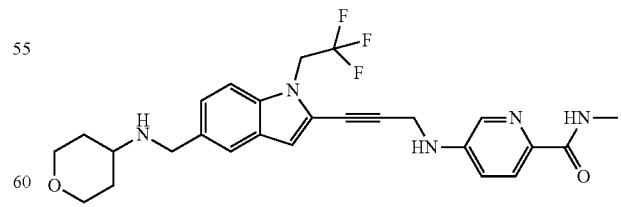

In a manner similar to the method described in Example 28, N-methyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.
LC-MS (ES+, m/z): 530.3 [(M+H)+]

Example 127: Preparation of N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide

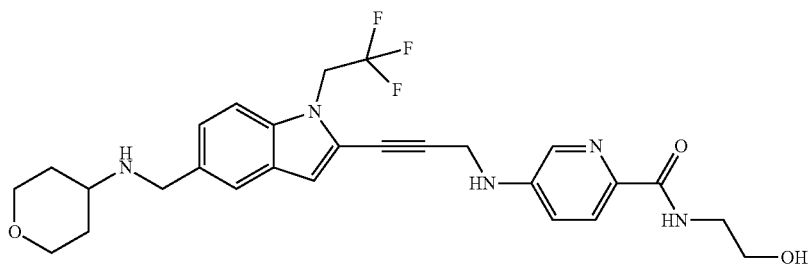 [SMILES: O=C(NCCO)c1ccc(NCC#Cc2cc3cc(CNC4CCOCC4)ccc3n2CC(F)(F)F)cn1]

In a manner similar to the method described in Example 28, N-(2-hydroxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.
LC-MS (ES$^+$, m/z): 530.3 [(M+H)$^+$]

Example 128: Preparation of N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide

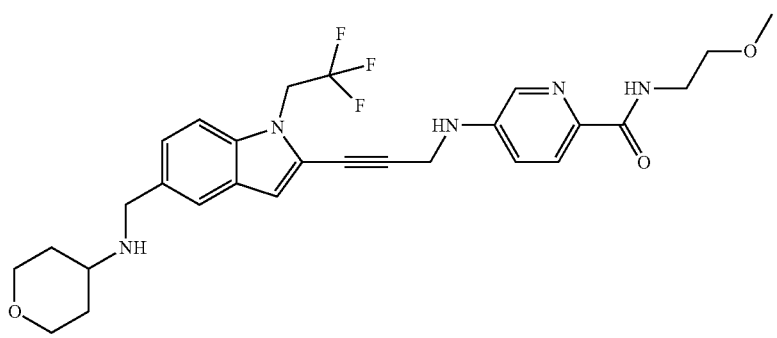 [SMILES: COCCNC(=O)c1ccc(NCC#Cc2cc3cc(CNC4CCOCC4)ccc3n2CC(F)(F)F)cn1]

In a manner similar to the method described in Example 28, N-(2-methoxyethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.
LC-MS (ES$^+$, m/z): 544.4 [(M+H)$^+$]

Example 129: Preparation of 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid

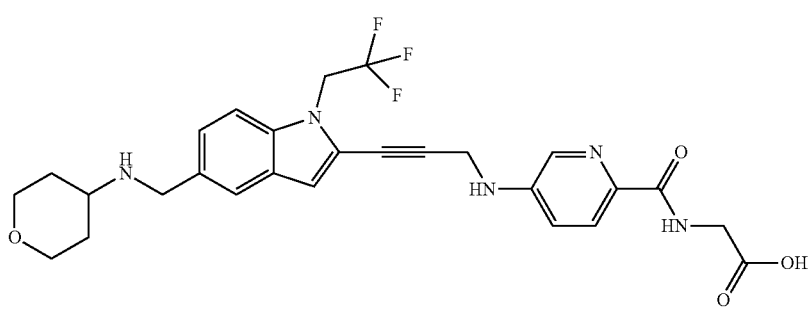 [SMILES: O=C(O)CNC(=O)c1ccc(NCC#Cc2cc3cc(CNC4CCOCC4)ccc3n2CC(F)(F)F)cn1]

In a manner similar to the method described in Example 28, 2-[(5-{[3-(5-{[(oxan-4-yl)amino]methyl}-1-(2,2,2-trifluoroethyl)-1H-indol-2-yl)prop-2-yn-1-yl]amino}pyridin-2-yl)formamido]acetic acid was prepared.

LC-MS (ES⁺, m/z): 544.3 [(M+H)⁺]

Example 130: Preparation of 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid

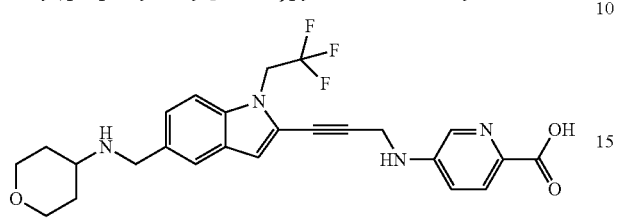

In a manner similar to the method described in Example 28, 5-{[3-(5-{[(oxan-4-yl)amino]methyl}-1-(2,2,2-trifluoroethyl)-1H-indol-2-yl)prop-2-yn-1-yl]amino}pyridine-2-carboxylic acid was prepared.

LC-MS (ES⁺, m/z): 487.4 [(M+H)⁺]

Example 131: Preparation of N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide

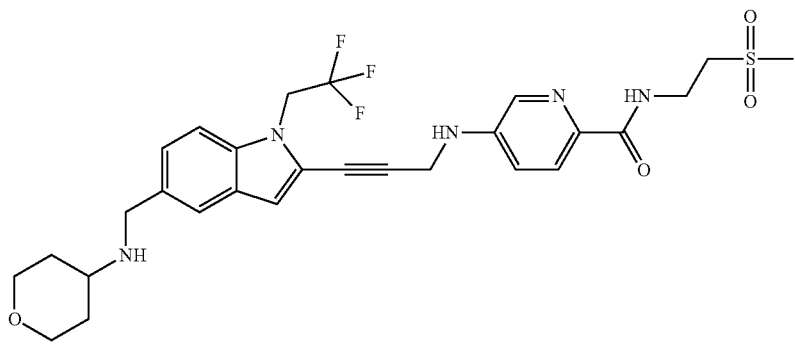 [SMILES: CS(=O)(=O)CCNC(=O)c1ccc(NCC#Cc2cc3cc(CNC4CCOCC4)ccc3n2CC(F)(F)F)cn1]

In a manner similar to the method described in Example 28, N-(2-methanesulfonylethyl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.

LC-MS (ES⁺, m/z): 592.3 [(M+H)⁺]

Example 132: Preparation of 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile

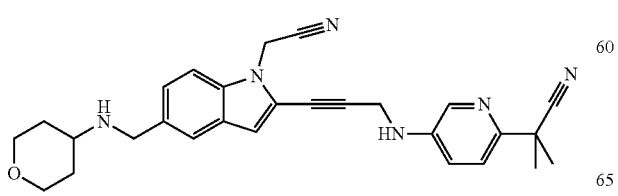

In a manner similar to the method described in Example 28, 2-[5-({3-[1-(cyanomethyl)-5-{[(oxan-4-yl)amino]methyl}-1H-indol-2-yl]prop-2-yn-1-yl}amino)pyridin-2-yl]-2-methylpropanenitrile was prepared.

LC-MS (ES⁺, m/z): 467.3 [(M+H)⁺]

Example 133: Preparation of 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile

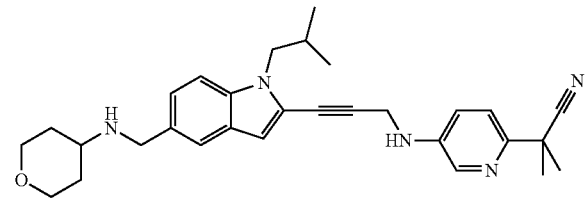 [SMILES: CC(C)Cn1c(C#CCNc2ccc(C(C)(C)C#N)nc2)cc2cc(CNC3CCOCC3)ccc21]

In a manner similar to the method described in Example 28, 2-methyl-2-[5-({3-[1-(2-methylpropyl)-5-{[(oxan-4-yl)amino]methyl}-1H-indol-2-yl]prop-2-yn-1-yl}amino)pyridin-2-yl]propanenitrile was prepared.

LC-MS (ES⁺, m/z): 484.2 [(M+H)⁺]

Example 134: Preparation of 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile

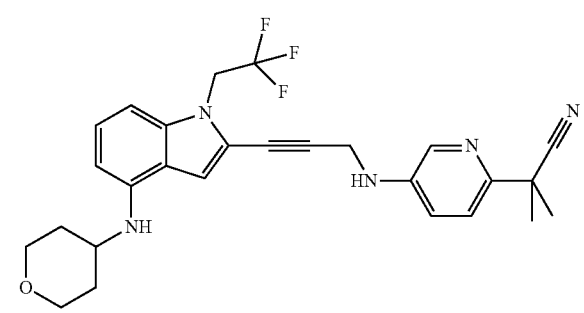 [SMILES: CC(C)(C#N)c1ccc(NCC#Cc2cc3c(NC4CCOCC4)cccc3n2CC(F)(F)F)cn1]

In a manner similar to the method described in Example 1 using 4-bromo-indole, 2-methyl-2-{5-[(3-{4-[(oxan-4-yl)amino]-1-(2,2,2-trifluoroethyl)-1H-indol-2-yl}prop-2-yn-1-yl)amino]pyridin-2-yl}propanenitrile was prepared.
LC-MS (ES+, m/z): 496.3 [(M+H)+]

Example 135: Preparation of 5-{[3-(5-{[(oxan-4-yl)amino]methyl}-1-(2,2,2-trifluoroethyl)-1H-indol-2-yl)prop-2-yn-1-yl]amino}pyridine-2-carbonitrile

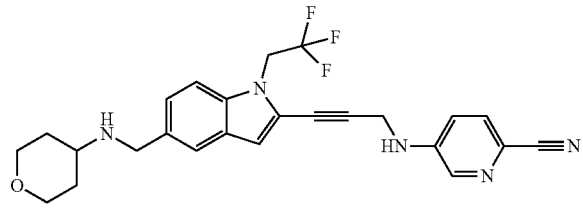 [SMILES: N#Cc1ccc(NCC#Cc2cc3cc(CNC4CCOCC4)ccc3n2CC(F)(F)F)cn1]

In a manner similar to the method described in Example 28, 5-{[3-(5-{[(oxan-4-yl)amino]methyl}-1-(2,2,2-trifluoroethyl)-1H-indol-2-yl)prop-2-yn-1-yl]amino}pyridine-2-carbonitrile was prepared.
LC-MS (ES+, m/z): 468.3 [(M+H)+]

Example 136: Preparation of N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide

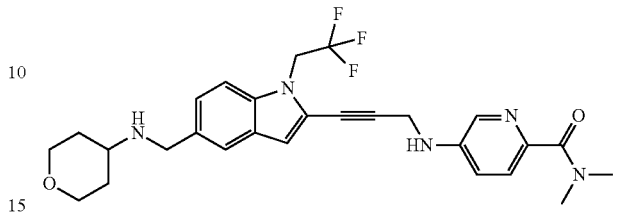

In a manner similar to the method described in Example 28, N,N-dimethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.
LC-MS (ES+, m/z): 514.3 [(M+H)+]

Example 137: Preparation of N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide

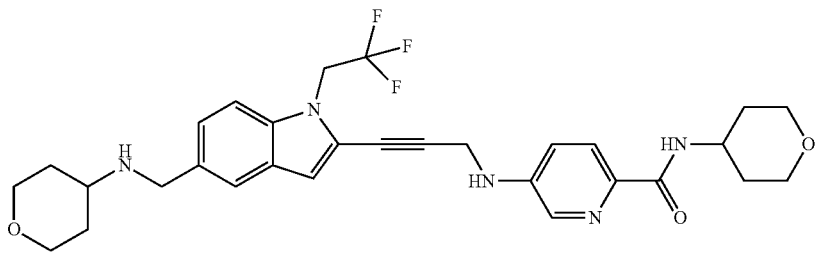 [SMILES: O=C(NC1CCOCC1)c1ccc(NCC#Cc2cc3cc(CNC4CCOCC4)ccc3n2CC(F)(F)F)cn1]

In a manner similar to the method described in Example 28, N-(oxan-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.
LC-MS (ES+, m/z): 570.3 [(M+H)+]

Example 138: Preparation of 2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine

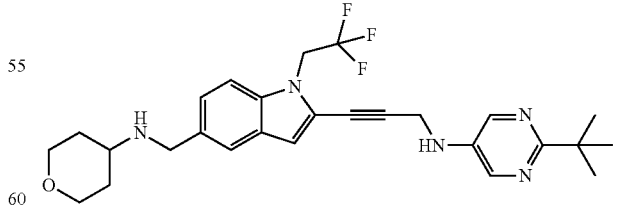

In a manner similar to the method described in Example 28, 2-tert-butyl-N-[3-(5-{[(oxan-4-yl)amino]methyl}-1-(2,2,2-trifluoroethyl)-1H-indol-2-yl)prop-2-yn-1-yl]pyrimidin-5-amine was prepared.
LC-MS (ES+, m/z): 500.3 [(M+H)+]

Example 139: Preparation of N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide

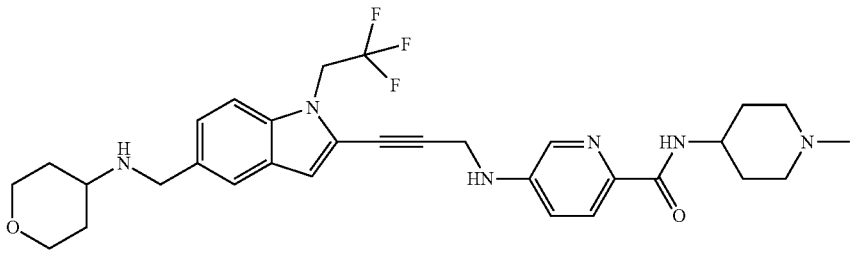 [SMILES: CN1CCC(NC(=O)c2ccc(NCC#Cc3cc4cc(CNC5CCOCC5)ccc4n3CC(F)(F)F)cn2)CC1]

In a manner similar to the method described in Example 28, N-(1-methylpiperidin-4-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide was prepared.

LC-MS (ES+, m/z): 583.5 [(M+H)+]

Example 140: Preparation of N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide

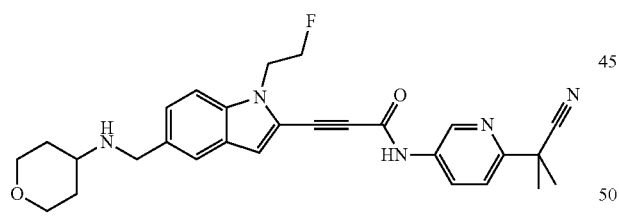

In a manner similar to the method described in Example 28, N-[6-(1-cyano-1-methylethyl)pyridin-3-yl]-3-[1-(2-fluoroethyl)-5-{[(oxan-4-yl)amino]methyl}-1H-indol-2-yl]prop-2-ynamide was prepared.

LC-MS (ES+, m/z): 488.3 [(M+H)+]

Example 141: Preparation of 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile

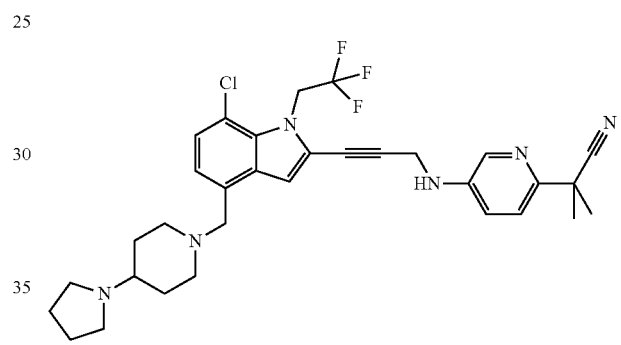

In a manner similar to the method described in Example 1 using 4-bromo-6-chloro-indole, 2-(5-{[3-(7-chloro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile was prepared.

LC-MS (ES+, m/z): 597.5 [(M+H)+]

Example 142: Preparation of 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile

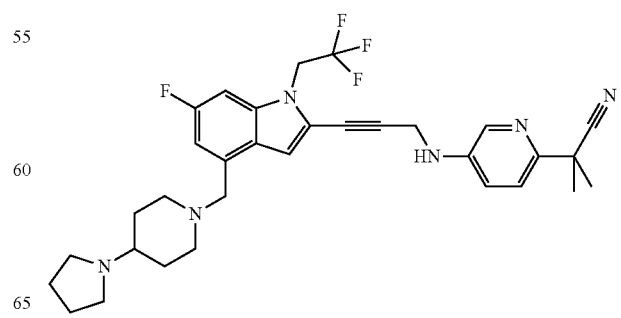

Synthetic Scheme:

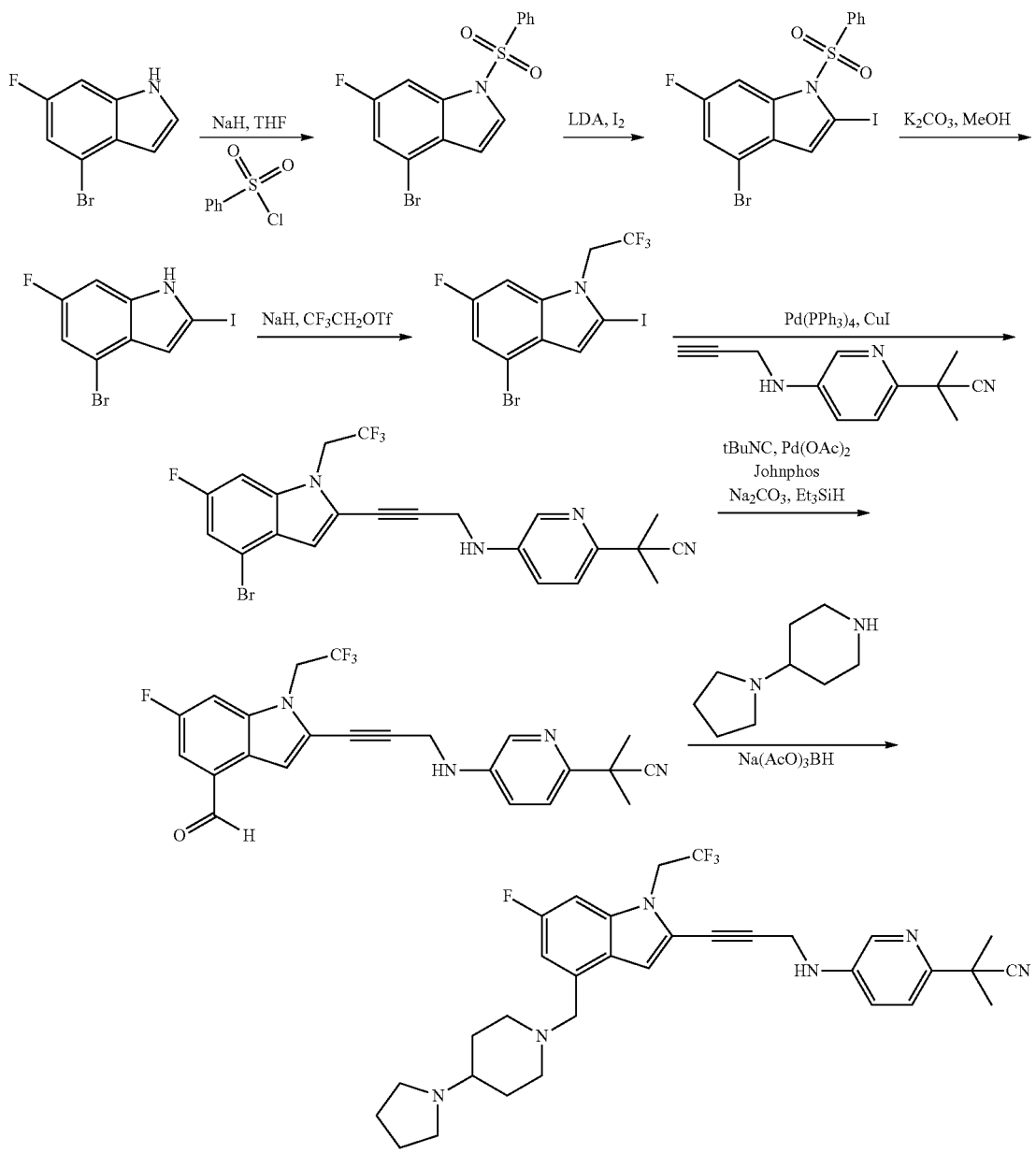

To a solution of 4-bromo-6-fluoro-indole (2 g, 9.38 mmol) in anhydrous tetrahydrofuran (30 mL) cooled in an ice bath was added sodium hydride (0.452 g, 11.3 mmol, 60% in mineral oil). The reaction mixture was stirred under nitrogen for 10 min before benzenesulfonyl chloride (1.44 mL, 11.3 mmol) was added. The black solution was allowed to warm to room temperature over 4 h. TLC and LCMS indicated completion of the reaction. Saturated aqueous ammonium chloride solution was added slowly, and the resulting solution was extracted with ethyl acetate (2×). The combined organic phases were washed with brine, dried over anhydrous sodium sulfate, filtered, and concentrated in vacuo. The crude solid was triturated with ethanol. The resulting beige solid was collected by filtration to give 4-bromo-6-fluoro-1-(phenylsulfonyl)-1H-indole (2.6 g, 79% yield).

To a solution of 4-bromo-6-fluoro-1-(phenylsulfonyl)-1H-indole (0.6 g, 1.7 mmol) in anhydrous tetrahydrofuran (10 mL) cooled at −78° C. under a nitrogen atmosphere was added 1M lithium diisopropylamide solution in tetrahydrofuran/hexanes (2.7 mL, 2.7 mmol). The reaction mixture was maintained at −78° C. for 90 min. Then a solution of iodine (0.427 mg, 1.7 mmol) in tetrahydrofuran (10 mL) was added slowly (over 2 min). The reaction mixture was allowed to warm to room temperature over 14 h. LCMS indicated completion of the reaction. Saturated aqueous ammonium chloride solution was added slowly, and the resulting solution was extracted with ethyl acetate (2×). The combined organic phases were washed with brine, dried over anhydrous sodium sulfate, filtered, and concentrated to give 4-bromo-7-fluoro-2-iodo-1-(phenylsulfonyl)-1H-indole. The crude solid was used in the next step without further purification.

To a suspension of the crude 4-bromo-7-fluoro-2-iodo-1-(phenylsulfonyl)-1H-indole (1.7 mmol) in methanol (30 mL) was added a 2M K$_2$CO$_3$ aqueous solution (10 mL, 20 mmol). The reaction mixture was heated at 60° C. for 18 h. Methanol was removed under vacuum. The residual aqueous phase was diluted with saturated aqueous ammonium chloride and extracted with ethyl acetate (2×). The combined organic phases were washed with brine, dried over anhydrous sodium sulfate, filtered, and concentrated. The crude residue was purified by flash column chromatography (ISCO 24 g, eluting with a gradient of ethyl acetate and hexanes). The desired product was eluted with 20% ethyl acetate in hexanes. The fractions were combined to give 4-bromo-6-fluoro-2-iodo-1H-indole as an oil (310 mg, 54% yield).

To a solution of 4-bromo-6-fluoro-2-iodo-1H-indole (200 mg, 0.59 mmol) in anhydrous tetrahydrofuran (4 mL) was added sodium hydride (48 mg, 1.2 mmol, 60% in mineral oil). The reaction mixture was stirred under a nitrogen atmosphere for 10 min. Then, 2,2,2-trifluoroethyltrifluoromethanesulfonate (0.170 mL, 1.2 mmol) was added. The reaction mixture was stirred at room temperature for 14 h. A saturated aqueous ammonium chloride solution was added slowly, and the resulting solution was extracted with ethyl acetate (2×). The combined organic phases were washed with brine, dried over anhydrous sodium sulfate, filtered, and concentrated. The crude solid was dried under vacuum to give 4-bromo-7-fluoro-2-iodo-1-(2,2,2-trifluoroethyl)-1H-indole. The crude product was used in the next step without further purification.

To a scintillation vial containing crude 4-bromo-7-fluoro-2-iodo-1-(2,2,2-trifluoroethyl)-1H-indole (0.59 mmol) was added 2-methyl-2-[5-(2-propynylamino)-2-pyridyl]propiononitrile (207 mg, 0.89 mmol), CuI (22 mg, 0.12 mmol), Pd (PPh$_3$)$_4$ (65 mg, 0.006 mmol). Anhydrous tetrahydrofuran (5 mL) followed by TEA (0.206 mL, 1.5 mmol) were added, and the reaction mixture was heated at 40 C for 1 h under a nitrogen atmosphere. The reaction mixture was cooled to room temperature, and diluted with 0.5 M EDTA (5 mL) and ethyl acetate (5 mL). The reaction mixture was stirred at room temperature for 30 min. The organic phases were extracted with ethyl acetate (2×). The combined organic phases were washed with brine, dried over anhydrous sodium sulfate, filtered, and concentrated. The crude material was purified by flash column chromatography (ISCO 20 g, eluting with a gradient of ethyl acetate and hexanes). The desired fractions were eluted with 50% ethyl acetate in hexanes. The fractions were combined to give 2-(5-{3-[4-bromo-7-fluoro-1-(2,2,2-trifluoroethyl)-1H-indol-2-yl]-2-propynylamino}-2-pyridyl)-2-methylpropiononitrile (120 mg, 41% yield).

To a solution of 2-(5-{3-[4-bromo-7-fluoro-1-(2,2,2-trifluoroethyl)-1H-indol-2-yl]-2-propynylamino}-2-pyridyl)-2-methylpropiononitrile (120 mg, 0.24 mmol) in anhydrous dimethylformamide (2 mL) in a scintillation vial was added Johnphos (4 mg, 0.012 mmol), sodium carbonate (25 mg, 0.24 mmol), palladium acetate (3 mg, 0.012 mmol), triethylsilane (0.114 mL, 0.72 mmol) and tert-butyl isonitrile (0.055 mL, 0.49 mmol). The reaction mixture was heated at 65° C. under a nitrogen atmosphere for 10 h. 0.5 M EDTA (4 mL) and ethyl acetate (10 mL) were added to the reaction mixture, which was stirred at room temperature for 1 h. The organic phases were extracted with ethyl acetate (2×). The combined organic phases were washed with brine (3×), dried over anhydrous sodium sulfate, then concentrated. The crude material was purified by flash column chromatography (ISCO 12 g, eluting with a gradient of ethyl acetate and hexanes) to give the recovered starting material (60 mg) and the desired 2-(5-{3-[7-fluoro-4-formyl-1-(2,2,2-trifluoroethyl)-1H-indol-2-yl]-2-propynylamino}-2-pyridyl)-2-methylpropiononitrile (40 mg, 75% yield based on starting material recovery), as the more polar compound.

To a solution of 2-(5-{3-[7-fluoro-4-formyl-1-(2,2,2-trifluoroethyl)-1H-indol-2-yl]-2-propynylamino}-2-pyridyl)-2-methylpropiononitrile (20 mg, 0.045 mmol) in dichloromethane (1 mL) was added 4-pyrrolidine-1-yl-piperidine (14 mg, 0.09 mmol) and sodium triacetoxyborohydride (28 mg, 0.14 mmol). The reaction mixture was stirred at room temperature for 3 h. The reaction mixture was diluted with ethyl acetate and washed with an aqueous sodium bicarbonate solution. The organic phases were extracted with ethyl acetate (2×). The combined organic phases were washed with brine (3×), dried over anhydrous sodium sulfate, filtered, then concentrated. The crude material was purified by prep HPLC (Combiflash TM EZ-prep system, eluting with a gradient of water (formic acid 0.1%) and acetonitrile (formic acid 0.1%) to give 2-(5-{[3-(6-fluoro-4-{[4-(pyrrolidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile (5 mg, 19% yield).

LC-MS (ES$^+$, m/z): 581.1 [(M+H)$^+$]

Example 143: Preparation of 2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile

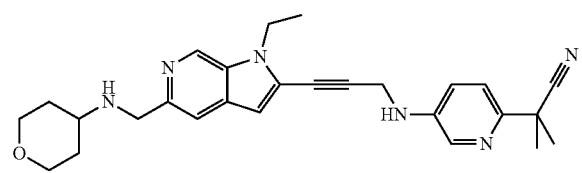 [SMILES: CCn1c(C#CCNc2ccc(C(C)(C)C#N)nc2)cc2cc(CNC3CCOCC3)ncc21]

In a manner similar to the method described in Example 28 using 1,6-diaza-1H-indene-5-carbaldehyde as starting material, 2-(5-{[3-(1-ethyl-5-{[(oxan-4-yl)amino]methyl}-1H-pyrrolo[2,3-c]pyridin-2-yl)prop-2-yn-1-yl]amino}pyridin-2-yl)-2-methylpropanenitrile was prepared.

LC-MS (ES$^+$, m/z): 511.1 [(M+H)$^+$]

Example 144: Preparation of 2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile

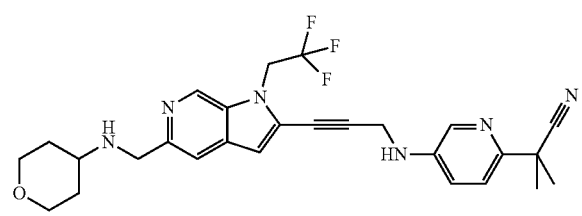

In a manner similar to the method described in Example 28 using 1,6-diaza-1H-indene-5-carbaldehyde as starting material, 2-methyl-2-(5-{[3-(5-{[(oxan-4-yl)amino]methyl}-1-(2,2,2-trifluoroethyl)-1H-pyrrolo[2,3-c]pyridin-2-yl)prop-2-yn-1-yl]amino}pyridin-2-yl)propanenitrile was prepared.

LC-MS (ES+, m/z): 457.3 [(M+H)+]

Example 145: Preparation of 2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile

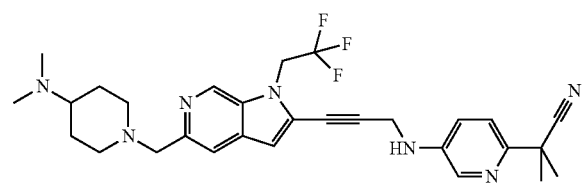 [SMILES: CN(C)C1CCN(Cc2cc3cc(C#CCNc4ccc(C(C)(C)C#N)nc4)n(CC(F)(F)F)c3cn2)CC1]

In a manner similar to the method described in Example 28 using 1,6-diaza-1H-indene-5-carbaldehyde as starting material, 2-(5-{[3-(5-{[4-(dimethylamino)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile was prepared.

LC-MS (ES+, m/z): 538.1 [(M+H)+]

Example 146: Preparation of 2-(5-{[3-(7-chloro-4-{[4-(pyrrolidin-1-yl)piperidin-1-yl]methyl}-1-(2,2,2-trifluoroethyl)-1H-pyrrolo[2,3-c]pyridin-2-yl)prop-2-yn-1-yl]amino}pyridin-2-yl)-2-methylpropanenitrile

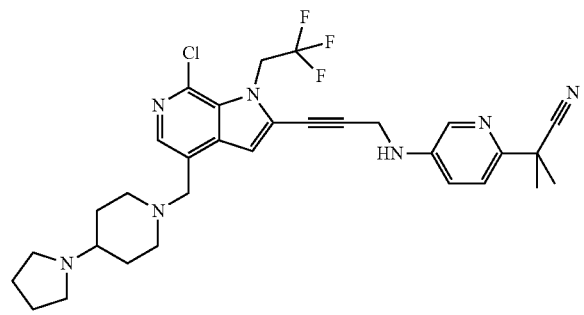

Synthetic Scheme:

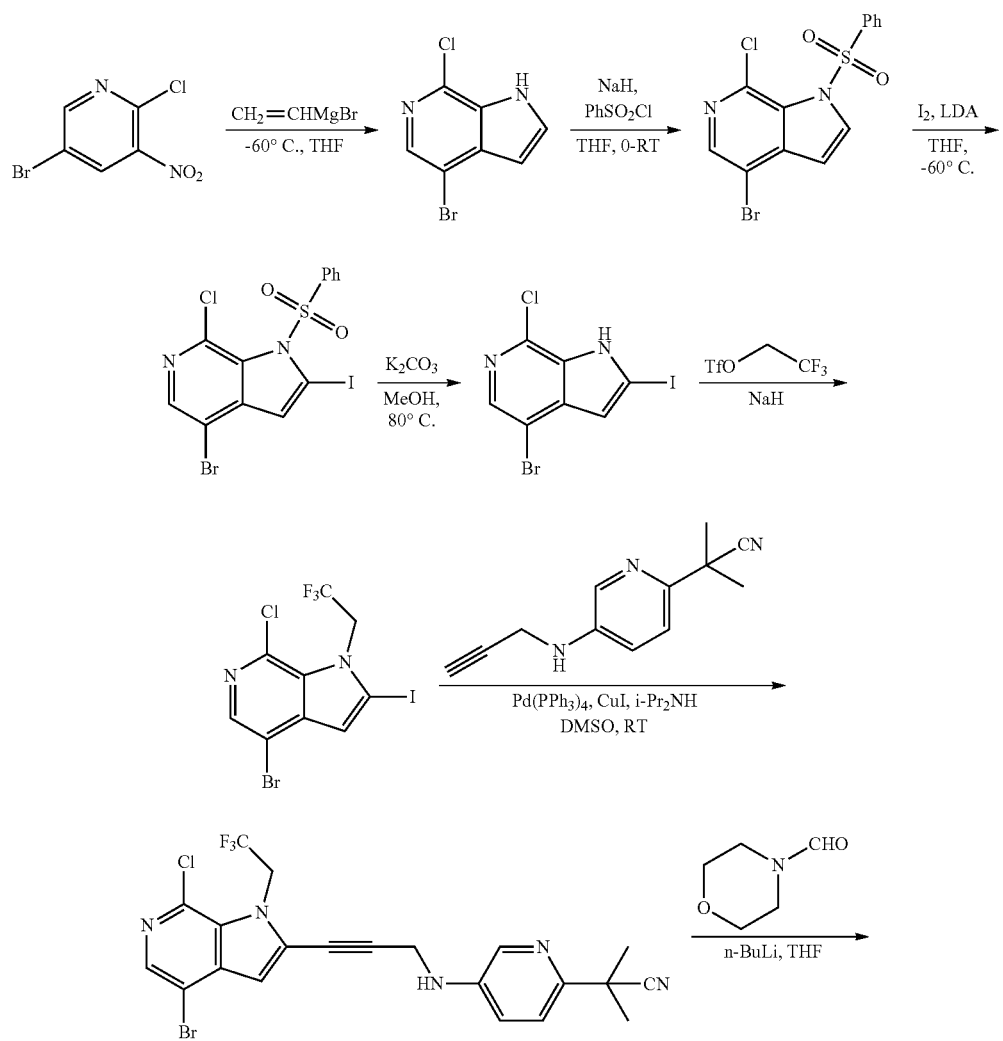

-continued

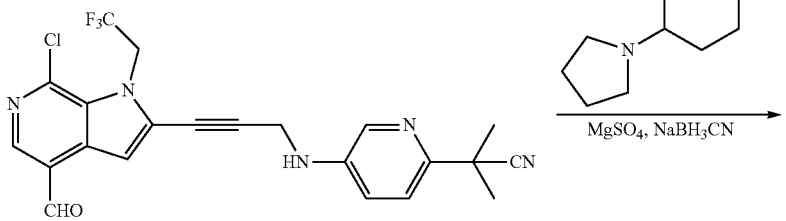

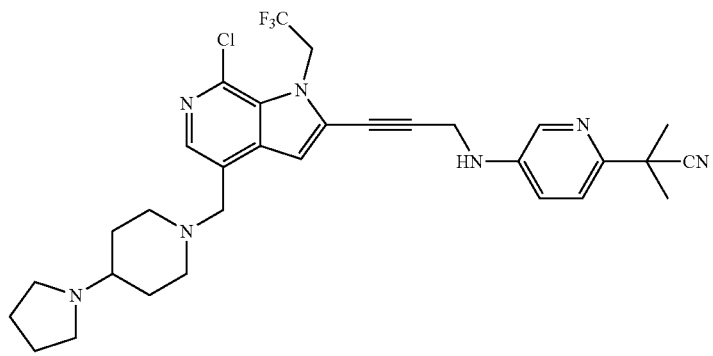

5-Bromo-2-chloro-3-nitro-pyridine (20.2 g, 85.07 mmol, 1 equiv.) was dissolved in dry tetrahydrofuran (100 mL) under nitrogen atmosphere, and the solution was cooled to −78° C. Bromo(vinyl)magnesium (1 M, 340 mL, 4 equiv.) was added to the solution, and the reaction mixture was stirred at −78° C. for 4 h. LCMS analysis showed that the reaction was completed. The reaction was quenched with saturated ammonium chloride (150 mL). The aqueous phase was extracted with ethyl acetate (3×150 mL), and the combined organic layers were dried over magnesium sulfate, filtered and concentrated. The crude product was purified by flash column chromatography (silica gel, eluting with a 1/1 mixture of ethyl acetate and petroleum ether) to afford 4-bromo-7-chloro-1H-pyrrolo[2,3-c]pyridine as a yellow solid (4.12 g, 21% yield).

To a mixture of sodium hydride (1.16 g, 28.98 mmol, 60% purity, 3.15 equiv.) stirred in tetrahydrofuran (20 mL) was added 4-bromo-7-chloro-H-pyrrolo[2,3-c]pyridine (2.13 g, 9.20 mmol, 1 equiv.) dissolved in tetrahydrofuran (10 mL) dropwise at 0° C. After the addition, the mixture was stirred at 0° C. for 1 h, and benzenesulfonyl chloride (2.06 g, 11.68 mmol, 1.5 mL, 1.27 equiv.) dissolved in tetrahydrofuran (10 mL) was added dropwise at 0° C. The resulting mixture was stirred at 0° C. for 2 h, and quenched by adding saturated ammonium chloride (50 mL) at 0° C.

The resulting reaction mixture was extracted with ethyl acetate (3×50 mL). The combined organic layers were washed with water (50 mL), dried over anhydrous sodium sulfate, filtered and concentrated in vacuo. The crude product was purified by flash column chromatography (silica gel, eluting with methylene chloride/petroleum ether: 1/1) to give 1-(benzenesulfonyl)-4-bromo-7-chloro-pyrrolo[2,3-c] pyridine as a light yellow solid (2.03 g, 59% yield).

Lithium diisopropylamide (2 M, 1.62 mL) was added dropwise to a solution of 1-(benzenesulfonyl)-4-bromo-7-chloro-pyrrolo[2,3-c]pyridine (400 mg, 1.08 mmol) in tetrahydrofuran cooled to −78° C. (20 mL). After the addition, the mixture was stirred at −78° C. temperature for 1 h, and then iodine (312 mg, 1.23 mmol) in tetrahydrofuran (12 mL) was added dropwise at −78° C. The resulting mixture was stirred at −78° C. for 1 h before being partitioned between saturated ammonium chloride (40 mL) and ethyl acetate (40 mL). The reaction mixture was then extracted with ethyl acetate (3×50 mL). The combined organic layers were washed with water (50 mL), dried over anhydrous sodium sulfate, filtered and concentrated in vacuo. The crude product was purified by flash column chromatography (silica gel, eluting with methylene chloride/petroleum ether: 1/1) to give 1-(benzenesulfonyl)-4-bromo-7-chloro-2-iodo-pyrrolo [2,3-c]pyridine as a light yellow solid (240 mg, 45% yield).

A mixture of 1-(benzenesulfonyl)-4-bromo-7-chloro-2-iodo-pyrrolo[2,3-c]pyridine (600 mg, 1.21 mmol) and potassium carbonate (500 mg, 3.62 mmol) dissolved in methanol (20 mL) was stirred at 80° C. for 4 h under nitrogen atmosphere. The solution was concentrated under reduced pressure to afford the crude product. The crude product was purified by preparative thin layer chromatography (methylene chloride:petroleum ether 1:1) to give 4-bromo-7-chloro-2-iodo-1H-pyrrolo[2,3-c]pyridine as a white solid (350 mg, 81% yield).

4-Bromo-7-chloro-2-iodo-1H-pyrrolo[2,3-c]pyridine was used in the methods described in Examples 1 and 49 to prepare 2-(5-{[3-(7-chloro-4-{[4-(pyrrolidin-1-yl)piperidin-1-yl]methyl}-1-(2,2,2-trifluoroethyl)-1H-pyrrolo[2,3-c] pyridin-2-yl)prop-2-yn-1-yl]amino}pyridin-2-yl)-2-methyl-propanenitrile.

LC-MS (ES+, m/z): 598.2[(M+H)+]

In a manner similar to the method described in Example 142, the following compounds were prepared:

| Ex | Structure | Name | LC-MS (ES+, m/z) |
|---|---|---|---|
| 147 | 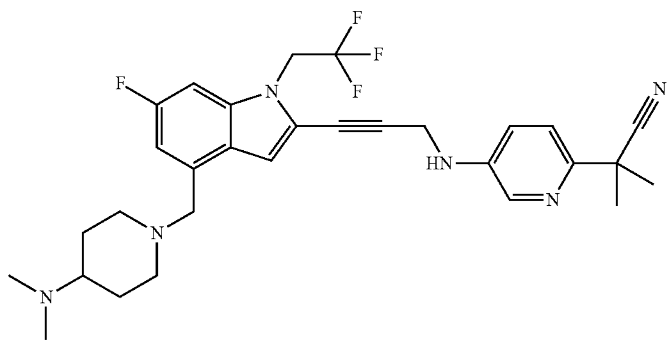 [SMILES: CN(C)C1CCN(Cc2cc(F)cc3c2cc(C#CCNc2ccc(C(C)(C)C#N)nc2)n3CC(F)(F)F)CC1] | 2-(5-{[3-(4-{[4-(dimethylamino)-piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile | 555.2 [(M + H)+] |
| 148 | 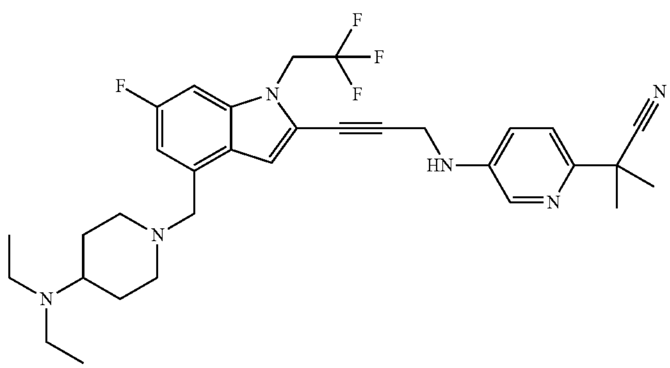 | 2-(5-{[3-(4-{[4-(diethylamino)piperidin-1-yl]methyl}-6-fluoro-1-(2,2,2-trifluoroethyl)-1H-indol-2-yl)prop-2-yn-1-yl]amino}pyridin-2-yl)-2-methylpropanenitrile | 583.3 [(M + H)+] |
| 149 | 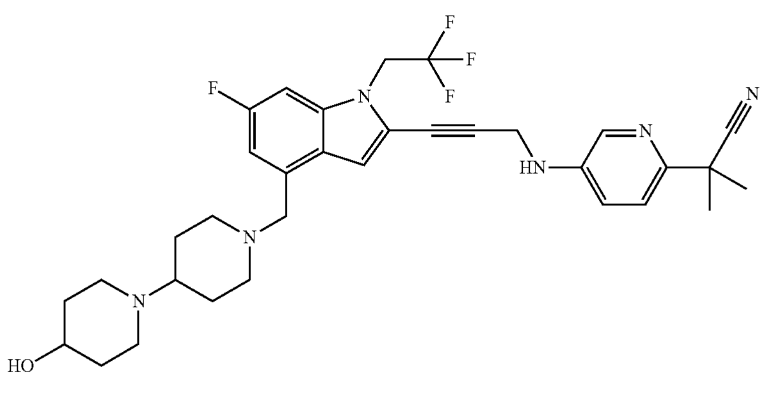 | 2-(5-{[3-(6-fluoro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile | 611.4 [(M + H)+] |
| 150 | 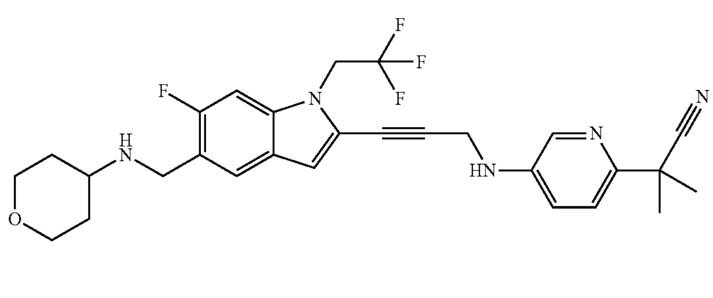 [SMILES: CC(C)(C#N)c1ccc(NCC#Cc2cc3cc(CNC4CCOCC4)c(F)cc3n2CC(F)(F)F)cn1] | 2-(5-{[3-(6-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile | 528.3 [(M + H)+] |

| Ex | Structure | Name | LC-MS (ES+, m/z) |
|---|---|---|---|
| 151 | 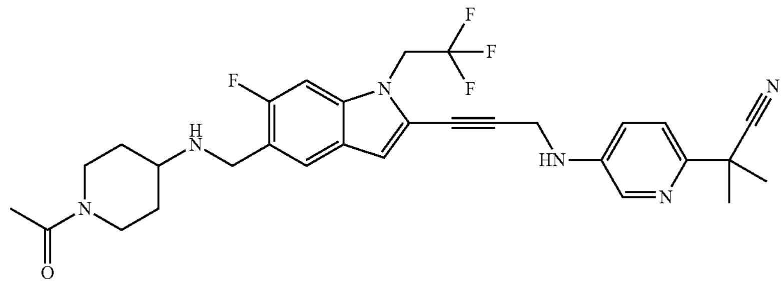 [SMILES: CC(=O)N1CCC(NCc2cc3cc(C#CCNc4ccc(C(C)(C)C#N)nc4)n(CC(F)(F)F)c3cc2F)CC1] | 2-(5-{[3-(5-{[(1-acetylpiperidin-4-yl)amino]methyl}-6-fluoro-1-(2,2,2-trifluoroethyl)-1H-indol-2-yl)prop-2-yn-1-yl]amino}pyridin-2-yl)-2-methylpropanenitrile | 569.3 [(M + H)+] |
| 152 | 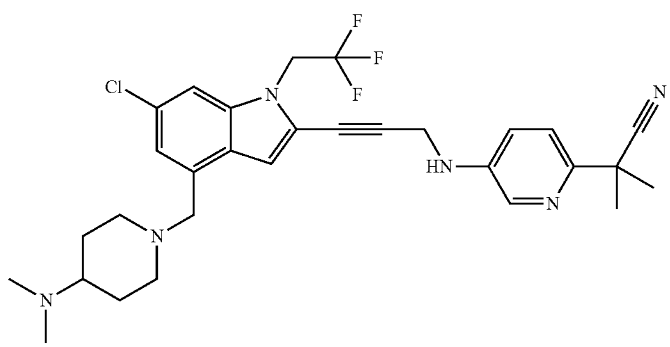 | 2-(5-{[3-(6-chloro-4-{[4-(dimethylamino)piperidin-1-yl]methyl}-1-(2,2,2-trifluoroethyl)-1H-indol-2-yl)prop-2-yn-1-yl]amino}pyridin-2-yl)-2-methylpropanenitrile | 571.3 [(M + H)+] |
| 153 | 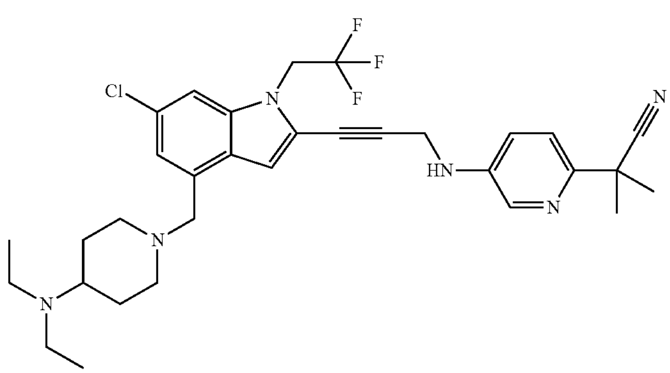 [SMILES: CCN(CC)C1CCN(Cc2cc(Cl)cc3c2cc(C#CCNc2ccc(C(C)(C)C#N)nc2)n3CC(F)(F)F)CC1] | 2-(5-{[3-(6-chloro-4-{[4-(diethylamino)piperidin-1-yl]methyl}-1-(2,2,2-trifluoroethyl)-1H-indol-2-yl)prop-2-yn-1-yl]amino}pyridin-2-yl)-2-methylpropanenitrile | 599.2 [(M + H)+] |
| 154 | 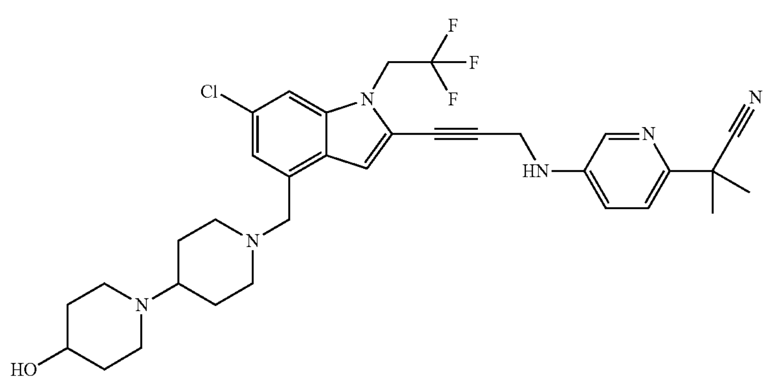 [SMILES: CC(C)(C#N)c1ccc(NCC#Cc2cc3c(CN4CCC(N5CCC(O)CC5)CC4)cc(Cl)cc3n2CC(F)(F)F)cn1] | 2-(5-{[3-(6-chloro-4-{[4-(4-hydroxypiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile | 627.3 [(M + H)+] |

Starting from 2-iodo-1H-indole-4-carbaldehyde (prepared from methyl 1H-indole-4-carboxylate) and using similar methods as described in Examples 1 and 49, the following compounds were prepared:

| Ex | Structure | Name | LC-MS (ES+, m/z) |
|---|---|---|---|
| 155 | 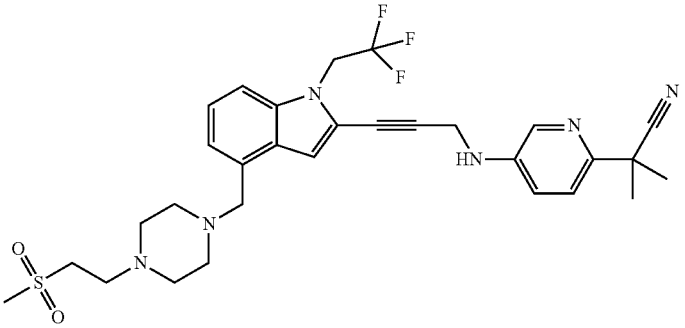 [SMILES: CC(C)(C#N)c1ccc(NCC#Cc2cc3c(CN4CCN(CCS(C)(=O)=O)CC4)cccc3n2CC(F)(F)F)cn1] | 2-(5-{[3-(4-{[4-(2-methanesulfonyl-ethyl)piperazin-1-yl]methyl}-1-(2,2,2-trifluoroethyl)-1H-indol-2-yl)prop-2-yn-1-yl]amino}pyridin-2-yl)-2-methylpropanenitrile | 601.3 [(M + H)+] |
| 156 | 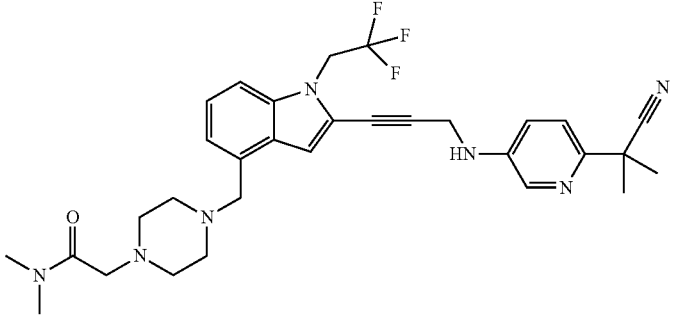 | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)-N,N-dimethylacetamide | 580.4 [(M + H)+] |
| 157 | 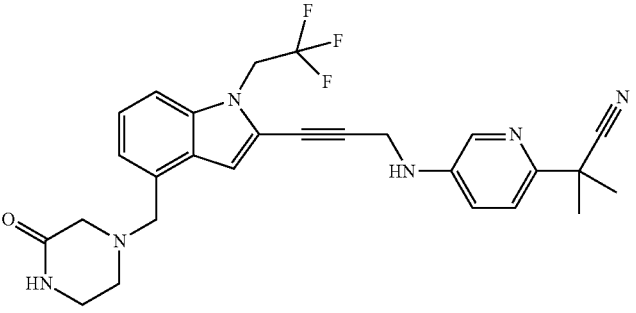 [SMILES: CC(C)(C#N)c1ccc(NCC#Cc2cc3c(CN4CCNC(=O)C4)cccc3n2CC(F)(F)F)cn1] | 2-methyl-2-{5-[(3-{4-[(3-oxopiperazin-1-yl)methyl]-1-(2,2,2-trifluoroethyl)-1H-indol-2-yl}prop-2-yn-1-yl)amino]pyridin-2-yl}propanenitrile | 509.3 [(M + H)+] |
| 158 | 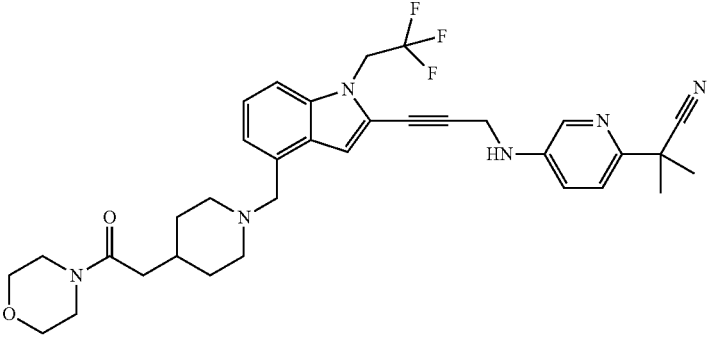 [SMILES: CC(C)(C#N)c1ccc(NCC#Cc2cc3c(CN4CCC(CC(=O)N5CCOCC5)CC4)cccc3n2CC(F)(F)F)cn1] | 2-methyl-2-[5-({3-[4-({4-[2-(morpholin-4-yl)-2-oxoethyl]piperidin-1-yl}methyl)-1-(2,2,2-trifluoroethyl)-1H-indol-2-yl]prop-2-yn-1-yl}amino)pyridin-2-yl]propanenitrile | 621.4 [(M + H)+] |

-continued

| Ex | Structure | Name | LC-MS (ES+, m/z) |
|---|---|---|---|
| 159 | 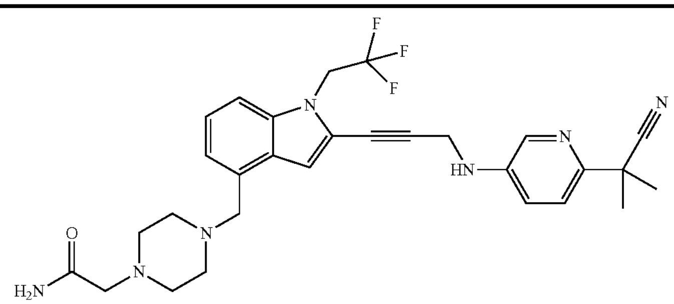 | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-1-yl)acetamide | 552.3 [(M + H)+] |
| 160 | 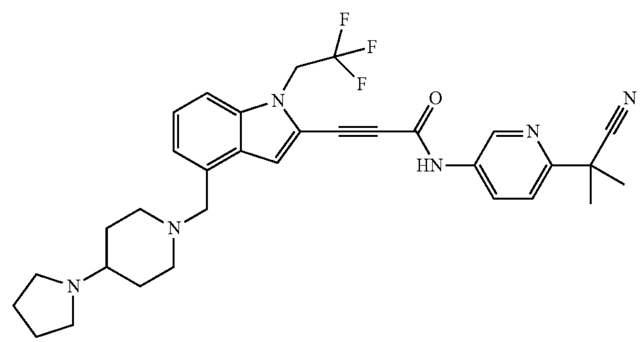 [SMILES: CC(C)(C#N)c1ccc(NC(=O)C#Cc2cc3c(CN4CCC(N5CCCC5)CC4)cccc3n2CC(F)(F)F)cn1] | N-[6-(1-cyano-1-methylethyl)pyridin-3-yl]-3-(4-{[4-(pyrrolidin-1-yl)piperidin-1-yl]methyl}-1-(2,2,2-trifluoroethyl)-1H-indol-2-yl)prop-2-ynamide | 577.3 [(M + H)+] |
| 161 | 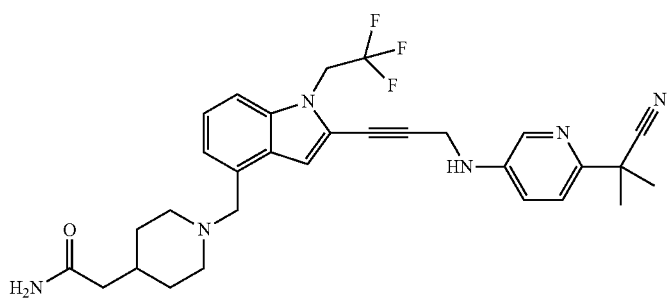 [SMILES: CC(C)(C#N)c1ccc(NCC#Cc2cc3c(CN4CCC(CC(N)=O)CC4)cccc3n2CC(F)(F)F)cn1] | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperidin-4-yl)acetamide | 551.3 [(M + H)+] |
| 162 | 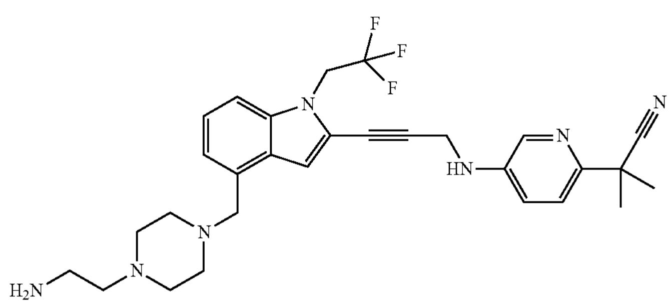 [SMILES: CC(C)(C#N)c1ccc(NCC#Cc2cc3c(CN4CCN(CCN)CC4)cccc3n2CC(F)(F)F)cn1] | 2-(5-{[3-(4-{[4-(2-aminoethyl)-piperazin-1-yl]methyl}-1-(2,2,2-trifluoroethyl)-1H-indol-2-yl)prop-2-yn-1-yl]amino}pyridin-2-yl)-2-methylpropanenitrile | 538.3 [(M + H)+] |
| 163 | 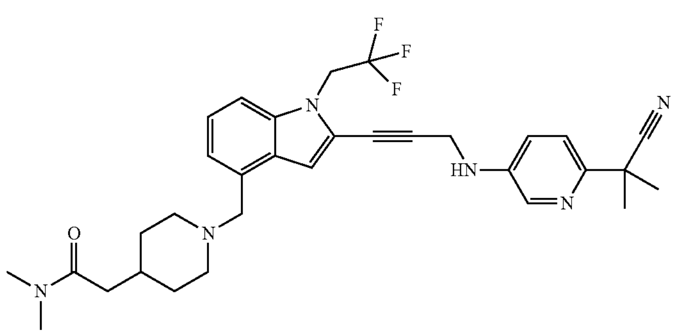 [SMILES: CN(C)C(=O)CC1CCN(Cc2cccc3c2cc(C#CCNc2ccc(C(C)(C)C#N)nc2)n3CC(F)(F)F)CC1] | 2-(1-{[2-(3-{[6-(1-cyano-1-methylethyl)pyridin-3-yl]amino}prop-1-yn-1-yl)-1-(2,2,2-trifluoroethyl)-1H-indol-4-yl]methyl}piperazin-4-yl)-N,N-dimethylacetamide | 579.4 [(M + H)+] |

| Ex | Structure | Name | LC-MS (ES+, m/z) |
|---|---|---|---|
| 164 | 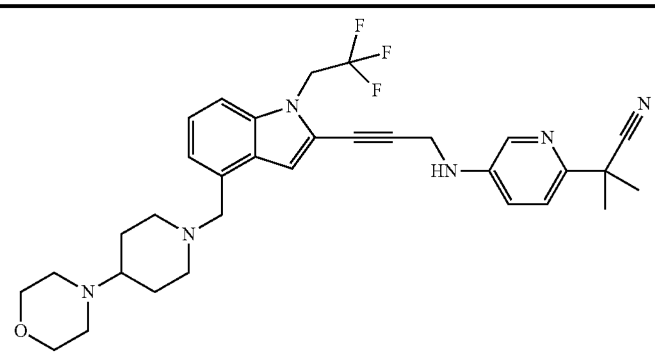 | 2-methyl-2-(5-{[3-(4-{[4-(morpholin-4-yl)piperidin-1-yl]methyl}-1-(2,2,2-trifluoroethyl)-1H-indol-2-yl)prop-2-yn-1-yl]amino}pyridin-2-yl)propanenitrile | 579.4 [(M + H)+] |
| 165 | 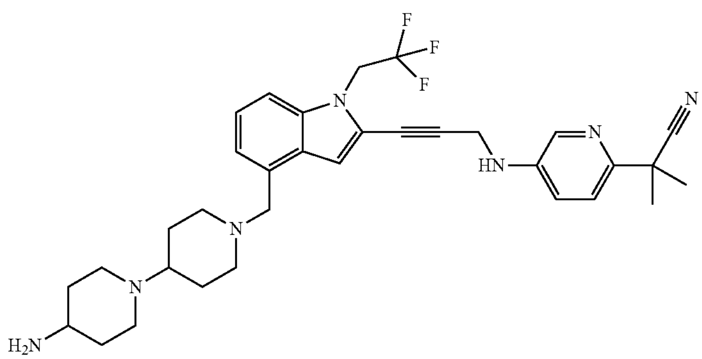 [SMILES: CC(C)(C#N)c1ccc(NCC#Cc2cc3c(CN4CCC(N5CCC(N)CC5)CC4)cccc3n2CC(F)(F)F)cn1] | 2-(5-{[3-(4-{[4-(4-aminopiperidin-1-yl)piperidin-1-yl]methyl}-1-(2,2,2-trifluoroethyl)-1H-indol-2-yl)prop-2-yn-1-yl]amino}pyridin-2-yl)-2-methylpropanenitrile | 592.4 [(M + H)+] |

Example 166: Preparation of 2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile

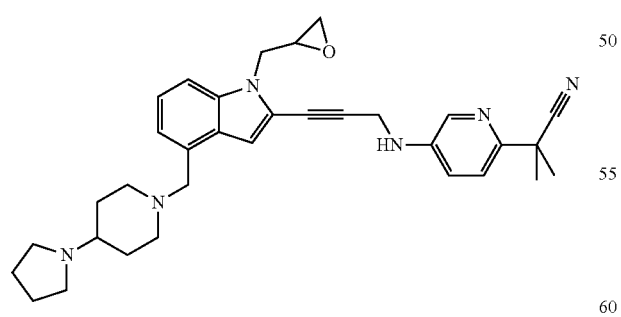

In a manner similar to the method described in Examples 1 and 49, 2-iodo-1H-indole-4-carbaldehyde was reacted with 2-(bromomethyl)oxirane, and subsequently coupled with 2-methyl-2-{5-[(prop-2-yn-1-yl)amino]pyridin-2-yl}propanenitrile. The resulting intermediate was subjected to reductive amination with 4-(pyrrolidin-1-yl)piperidine to give 2-methyl-2-[5-({3-[1-(oxiran-2-ylmethyl)-4-{[4-(pyrrolidin-1-yl)piperidin-1-yl]methyl}-1H-indol-2-yl]prop-2-yn-1-yl}amino)pyridin-2-yl]propanenitrile.

LC-MS (ES+, m/z): 537.4 [(M+H)+]

Example 167: Preparation of 2-(5-{[3-(3-ethyl-6-{[(oxan-4-yl)amino]methyl}-1H-indol-2-yl)prop-2-yn-1-yl]amino}pyridin-2-yl)-2-methylpropanenitrile

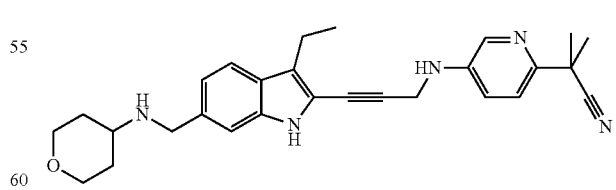

In a manner similar to the methods described in Examples 80 and 86, 2-(5-{[3-(3-ethyl-6-{[(oxan-4-yl)amino]methyl}-1H-indol-2-yl)prop-2-yn-1-yl]amino}pyridin-2-yl)-2-methylpropanenitrile was prepared.

LC-MS (ES+, m/z): 456.2[(M+H)+]

Example 168: Preparation of 2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile

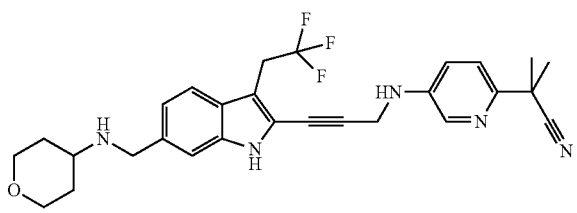 [SMILES: CC(C)(C#N)c1ccc(NCC#Cc2[nH]c3cc(CNC4CCOCC4)ccc3c2CC(F)(F)F)cn1]

In a manner similar to the methods described in Examples 80 and 86, 2-methyl-2-(5-{[3-(6-{[(oxan-4-yl)amino]methyl}-3-(2,2,2-trifluoroethyl)-1H-indol-2-yl)prop-2-yn-1-yl]amino}pyridin-2-yl)propanenitrile was prepared.

LC-MS (ES+, m/z): 510.3[(M+H)+]

Example 169: Preparation of 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile

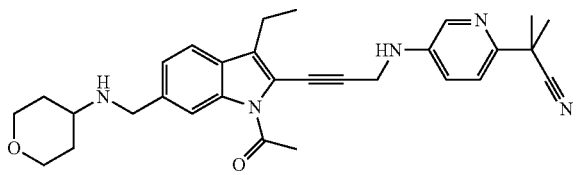 [SMILES: CCc1c(C#CCNc2ccc(C(C)(C)C#N)nc2)n(C(C)=O)c2cc(CNC3CCOCC3)ccc12]

In a manner similar to the method described in Examples 80 and 86, 2-(5-{[3-(1-acetyl-3-ethyl-6-{[(oxan-4-yl)amino]methyl}-1H-indol-2-yl)prop-2-yn-1-yl]amino}pyridin-2-yl)-2-methylpropanenitrile was prepared.

LC-MS (ES+, m/z): 498.3 [(M+H)+]

Example 170: Preparation of 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile

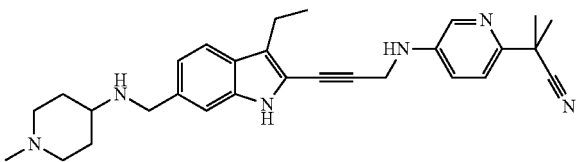 [SMILES: CCc1c(C#CCNc2ccc(C(C)(C)C#N)nc2)[nH]c2cc(CNC3CCN(C)CC3)ccc12]

In a manner similar to the method described in Examples 80 and 86, 2-(5-{[3-(3-ethyl-6-{[(1-methylpiperidin-4-yl)amino]methyl}-1H-indol-2-yl)prop-2-yn-1-yl]amino}pyridin-2-yl)-2-methylpropanenitrile was prepared.

LC-MS (ES+, m/z): 469.3 [(M+H)+]

Example 171: Preparation of 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile

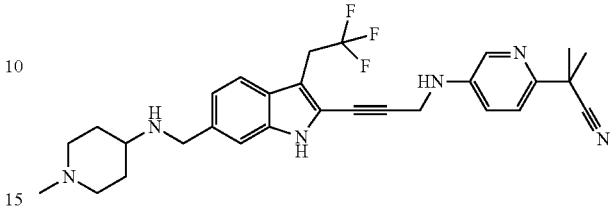

In a manner similar to the method described in Examples 80 and 86, 2-methyl-2-(5-{[3-(6-{[(1-methylpiperidin-4-yl)amino]methyl}-3-(2,2,2-trifluoroethyl)-1H-indol-2-yl)prop-2-yn-1-yl]amino}pyridin-2-yl)propanenitrile was prepared.

LC-MS (ES+, m/z): 523.4 [(M+H)+]

Example 172: Preparation of 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile

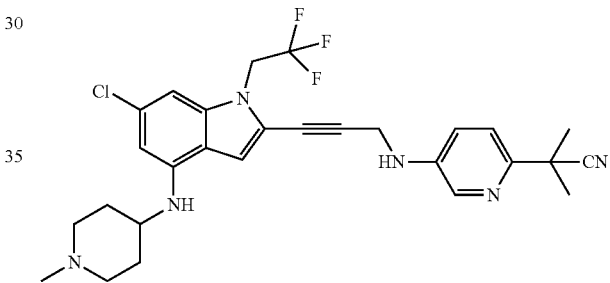

Synthetic Scheme:

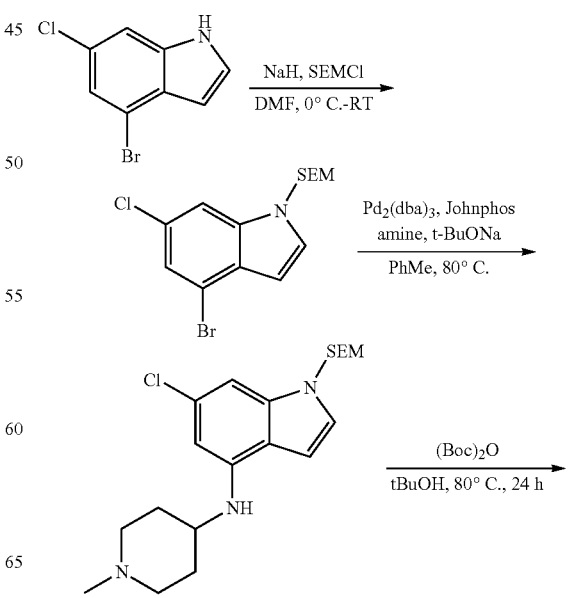

-continued

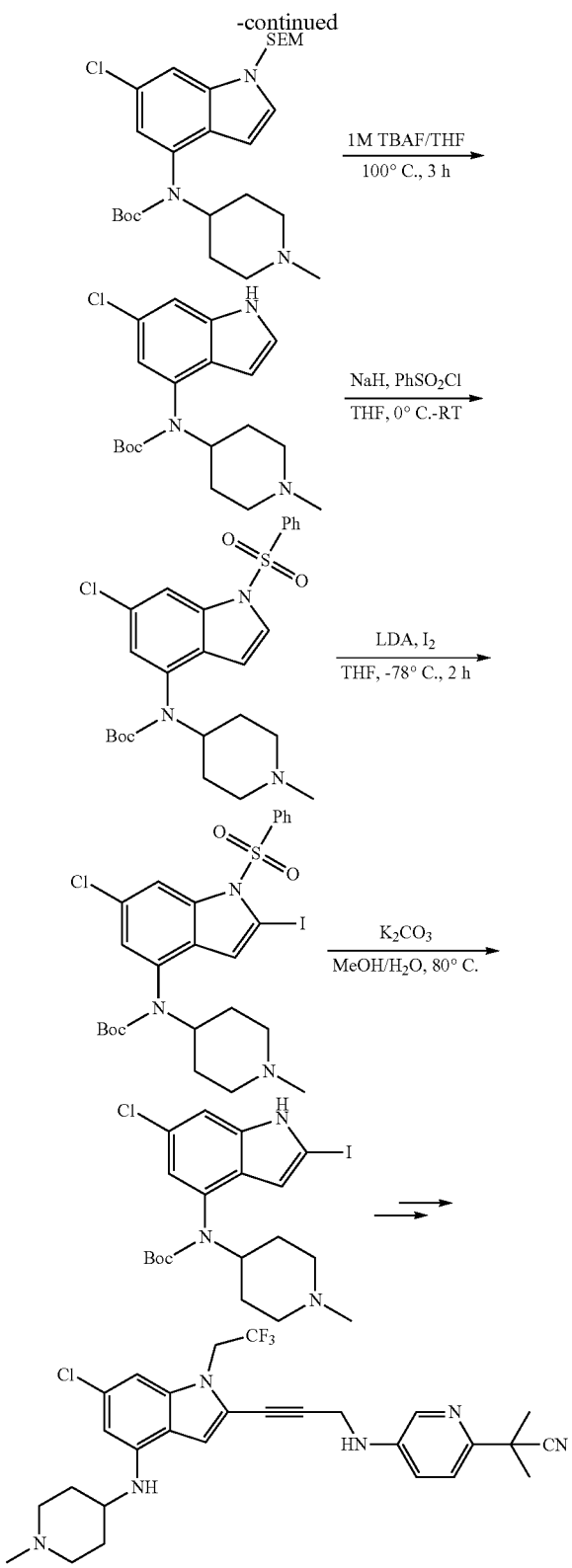

Sodium hydride (1.39 g, 34.70 mmol, 60% in mineral oil) was added to a solution of 4-bromo-6-chloro-indole (4 g, 17.35 mmol) in dimethylformamide (60 mL) at 0° C. The reaction was stirred at 0° C. for 1 h, and 2-(trimethylsilyl) ethoxymethyl chloride (SEMCl, 4.34 g, 26.03 mmol) was added to the reaction mixture. The reaction was stirred at 20° C. for 1 h, and a saturated solution of ammonium chloride (50.0 mL) was added. The reaction mixture was extracted with methylene chloride (3×100 mL). The combined organic layers were washed with water (3×100 mL), brine (50 mL), dried over anhydrous sodium sulfate, filtered, and concentrated in vacuo. The crude product was purified by flash column chromatography (silica gel, eluting with petroleum ether/ethyl acetate: 300/1 to 150/1) to give 4-bromo-6-chloro-1-{[2-(trimethylsilyl)ethoxy]methyl}-1H-indole as yellow oil (90% purity).

To a solution of 4-bromo-6-chloro-1-{[2-(trimethylsilyl) ethoxy]methyl}-1H-indole (1.50 g, 3.74 mmol, 90% purity) and 1-methylpiperidin-4-amine (1.5 g, 13.13 mmol) dissolved in toluene (30 mL) was added t-BuONa (720 mg, 7.48 mmol), JohnPhos (302 mg, 1.01 mmol), and $Pd_2(dba)_3$ (308 mg, 336.60 µmol). The reaction was then stirred at 80° C. for 12 h in a sealed tube. The reaction mixture was treated with water (10 mL) and extracted with ethyl acetate (3×50 mL). The combined organic layers were washed with brine (20 mL), dried over anhydrous sodium sulfate, filtered and concentrated in vacuo. The crude product was purified by flash column chromatography (silica gel, eluting with methylene chloride/methanol: 50/1) to give 6-chloro-N-(1-methylpiperidin-4-yl)-1-{[2-(trimethylsilyl)ethoxy]methyl}-1H-indol-4-amine as yellow oil (1.6 g, 33% yield, 90% purity).

To a solution of 6-chloro-N-(1-methylpiperidin-4-yl)-1-{[2-(trimethylsilyl)-ethoxy]methyl}-1H-indol-4-amine (1.55 g, 3.55 mmol, 90% purity) in t-BuOH (21 mL) was added di-tert-butyl dicarbonate (19 g, 87.06 mmol). The reaction was stirred at 80° C. for 24 h, cooled to room temperature, and concentrated. The crude product was purified by flash column chromatography (silica gel, eluting with methylene chloride/methanol: 100/1) to give tert-butyl-N-(6-chloro-1-{[2-(trimethylsilyl)ethoxy]methyl}-1H-indol-4-yl)-N-(1-methylpiperidin-4-yl)carbamate as yellow oil (1.20 g, 2.31 mmol, 65% yield, 95% purity).

A solution of tert-butyl-N-(6-chloro-1-{[2-(trimethylsilyl)ethoxy]methyl}-1H-indol-4-yl)-N-(1-methylpiperidin-4-yl)carbamate (470 mg, 665.80 µmol) dissolved in TBAF (1 M in tetrahydrofuran, 8 mL) was stirred at 100° C. for 3 h, cooled to room temperature, and concentrated. The crude residue was dissolved in methylene chloride (60 mL) and washed with water (20 mL), brine (20 mL), dried over anhydrous sodium sulfate, filtered and concentrated to give 470 mg of the crude tert-butyl-N-(6-chloro-1H-indol-4-yl)-N-(1-methylpiperidin-4-yl)carbamate, which was used without further purification.

Sodium hydride (113 mg, 2.82 mmol, 60% in mineral oil) was added to a solution of crude tert-butyl-N-(6-chloro-1H-indol-4-yl)-N-(1-methylpiperidin-4-yl)carbamate (470 mg, 1.29 mmol) in tetrahydrofuran (10 mL) at 0° C. The resulting mixture was stirred at 0° C. for 30 min. Benzenesulfonyl chloride (345 mg, 1.95 mmol) was added to the reaction mixture. The ice bath was removed, the reaction mixture was allowed to warm up to room temperature, and the reaction mixture was stirred for 30 min at room temperature. The reaction was cooled to 0° C. and quenched with water (10 mL). The mixture was extracted with ethyl acetate (2×20 mL). The combined organic layers were washed with brine (10 mL), dried over anhydrous sodium sulfate, filtered and concentrated in vacuo. The crude product was purified by flash column chromatography (silica gel, eluting with methylene chloride/methanol: 50/1) to give tert-butyl N-[1-(benzenesulfonyl)-6-chloro-1H-indol-4-yl]-N-(1-methylpiperidin-4-yl)-carbamate as yellow oil (800 mg, 88% yield, 72% purity).

Lithium diisopropylamide (2M in tetrahydrofuran, 520 μL) was added to a solution of tert-butyl N-[1-(benzenesulfonyl)-6-chloro-1H-indol-4-yl]-N-(1-methylpiperidin-4-yl)-carbamate (260 mg, 371.40 μmol, 72% purity) in tetrahydrofuran (6 mL) at −65° C. The reaction was stirred at −65° C. for 1.5 h, and an iodine solution (144 mg, 567.35 μmol in 1.5 mL tetrahydrofuran) was added dropwise to the reaction. The reaction was stirred at −65° C. for 0.5 h, and a saturated solution of ammonium chloride (1.0 mL) was added. The reaction mixture was warmed to 20° C. and extracted with ethyl acetate (3×20 mL). The combined organic layers were washed with brine (20 mL), dried over anhydrous sodium sulfate, filtered, and concentrated to give crude tert-butyl N-[1-(benzenesulfonyl)-6-chloro-2-iodo-1H-indol-4-yl]-N-(1-methylpiperidin-4-yl)-carbamate as yellow solid (700 mg). The crude product was used directly in the next step without further purification.

To a solution of tert-butyl N-[1-(benzenesulfonyl)-6-chloro-2-iodo-1H-indol-4-yl]-N-(1-methylpiperidin-4-yl)-carbamate (900 mg) in methanol (15 mL) was added aqueous potassium carbonate (0.5 mL, 2M). The reaction was then stirred at 80° C. for 30 min, cooled to room temperature, and concentrated. The residue was extracted with ethyl acetate (3×10 mL). The combined organic layers were washed with brine (10 mL), dried over anhydrous sodium sulfate, filtered, and concentrated in vacuo. The crude product was purified by preparative thin layer chromatography (silica gel, eluting with methylene chloride/methanol: 10/1 with 0.1% triethylamine) to give tert-butyl N-(6-chloro-2-iodo-1H-indol-4-yl)-N-(1-methylpiperidin-4-yl)-carbamate as yellow solid (250 mg, 41% yield, 80% purity).

In a similar manner to the method described in Example 28, tert-butyl N-(6-chloro-2-iodo-1H-indol-4-yl)-N-(1-methylpiperidin-4-yl)carbamate was used to prepare 2-{5-[(3-{6-chloro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile.

LC-MS (ES$^+$, m/z): 543.3 [(M+H)$^+$]

Example 173: Preparation of 2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide

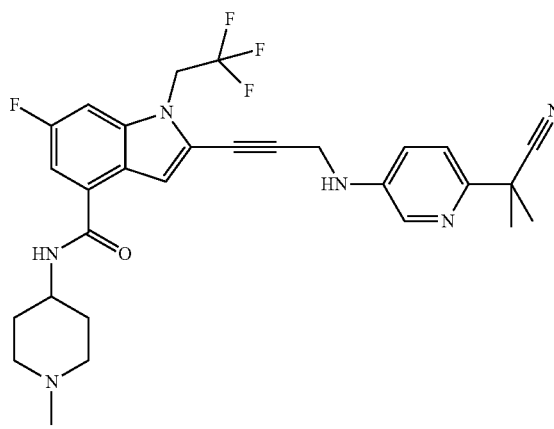 [SMILES: CN1CCC(NC(=O)c2cc(F)cc3c2cc(C#CCNc2ccc(C(C)(C)C#N)nc2)n3CC(F)(F)F)CC1]

To a solution of 2-[5-({3-[6-fluoro-4-formyl-1-(2,2,2-trifluoroethyl)-1H-indol-2-yl]prop-2-yn-1-yl}amino)pyridin-2-yl]-2-methylpropanenitrile (250 mg, 553.78 μmol, Example 142) in tetrahydrofuran (4 mL) and water (1 mL) was added 2-methylbut-2-ene (388 mg, 5.54 mmol), NaH$_2$PO$_4$ (133 mg, 1.11 mmol), and NaClO$_2$ (400 mg, 4.43 mmol, added in several small portions). The resulting reaction mixture was stirred at 25° C. for 1 h, poured into 30 mL aqueous ammonium chloride, and extracted with ethyl acetate (3×10 mL). The combined organic layers were washed with water (3×10 mL), brine (10 mL), and dried over anhydrous sodium sulfate, and concentrated. The residue was washed with 2 mL of a 1:1 methylene chloride and petroleum ether solution to afford 2-(3-{[6-(1-cyano-1-methylethyl)pyridin-3-yl]amino}prop-1-yn-1-yl)-6-fluoro-1-(2,2,2-trifluoroethyl)-1H-indole-4-carboxylic acid as a yellow solid (120 mg, 38% yield, 80% purity).

To a solution of 2-(3-{[6-(1-cyano-1-methylethyl)pyridin-3-yl]amino}prop-1-yn-1-yl)-6-fluoro-1-(2,2,2-trifluoroethyl)-1H-indole-4-carboxylic acid (50 mg, 87.26 μmol, 80% purity) in methylene chloride (3 mL) was added diisopropylethylamine (56 mg, 436.29 μmol) and HATU (50 mg, 130.89 μmol). Subsequently, 1-methylpiperidin-4-amine (20 mg, 174.52 μmol) was added to the reaction mixture. The resulting reaction mixture was stirred at 25° C. for 30 min, poured into 30 mL of aqueous ammonium chloride, and extracted with ethyl acetate (3×10 mL). The combined organic layers were washed with water (3×10 mL), brine (10 mL), dried over anhydrous sodium sulfate, and concentrated. The crude residue was purified by reversed phase preparative high performance liquid chromatography (HPLC) to give 2-(3-{[6-(1-cyano-1-methylethyl)pyridin-3-yl]amino}prop-1-yn-1-yl)-6-fluoro-N-(1-methylpiperidin-4-yl)-1-(2,2,2-trifluoroethyl)-1H-indole-4-carboxamide as a white solid (13.7 mg, 26% yield).

LC-MS (ES$^+$, m/z): 555.2 [(M+H)$^+$]

Example 174: Preparation of 2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile

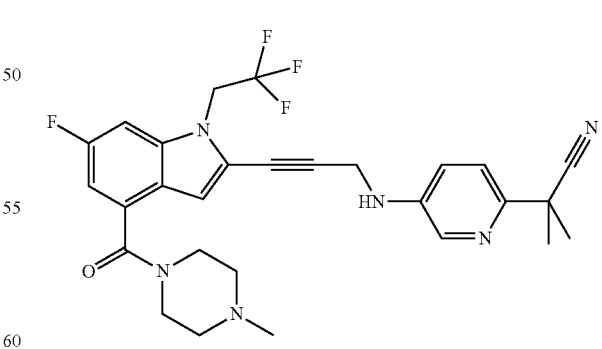

In a manner similar to the method described in Example 173, 2-[5-({3-[6-fluoro-4-(4-methylpiperazine-1-carbonyl)-1-(2,2,2-trifluoroethyl)-1H-indol-2-yl]prop-2-yn-1-yl}amino)pyridin-2-yl]-2-methylpropanenitrile was prepared.

LC-MS (ES$^+$, m/z): 541.2[(M+H)$^+$]

Example 175: Preparation of 6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine

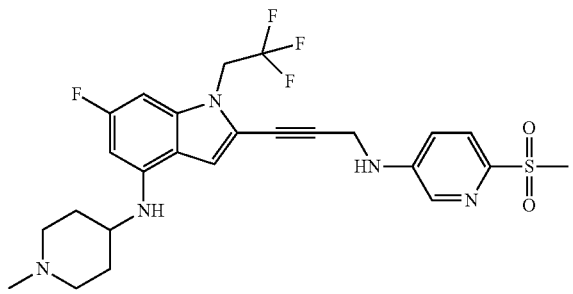

Using 4-bromo-6-fluoro-indole in a manner similar to the method described in Example 172, 6-fluoro-2-{3-[(6-methanesulfonylpyridin-3-yl)amino]prop-1-yn-1-yl}-N-(1-methylpiperidin-4-yl)-1-(2,2,2-trifluoroethyl)-1H-indol-4-amine was prepared.

LC-MS (ES+, m/z): 538.2 [(M+H)+]

Example 176: Preparation of 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile

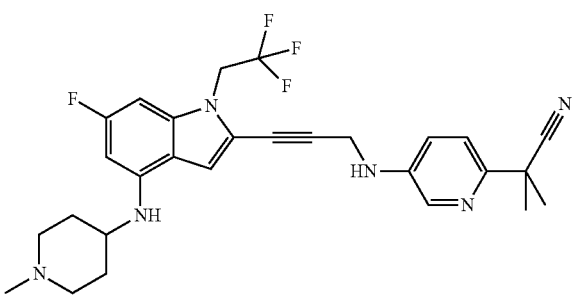 [SMILES: CN1CCC(Nc2cc(F)cc3c2cc(C#CCNc2ccc(C(C)(C)C#N)nc2)n3CC(F)(F)F)CC1]

Using 4-bromo-6-fluoro-indole in a manner similar to the method described in Example 172, 2-{5-[(3-{6-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile was prepared.

LC-MS (ES+, m/z): 527.2[(M+H)+]

Example 177: Preparation of 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide

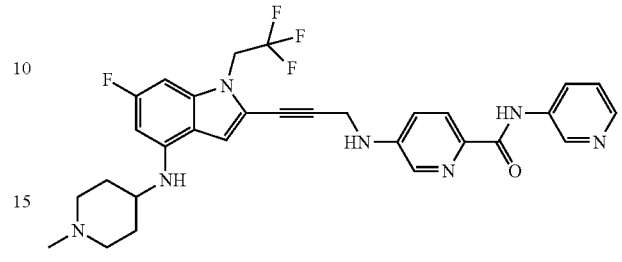

Using 4-bromo-6-fluoro-indole in a manner similar to the method described in Example 172, 5-[(3-{6-fluoro-4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide was prepared.

LC-MS (ES+, m/z): 580.3 [(M+H)+]

Example 178: Preparation of 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile

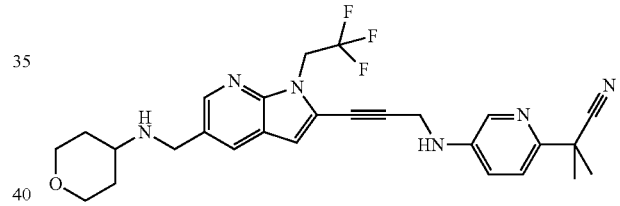

In a manner similar to the method described in Example 142, 2-methyl-2-(5-{[3-(5-{[(oxan-4-yl)amino]methyl}-1-(2,2,2-trifluoroethyl)-1H-pyrrolo[2,3-b]pyridin-2-yl)prop-2-yn-1-yl]amino}pyridin-2-yl)propanenitrile was prepared.

LC-MS (ES+, m/z): 511[(M+H)+]

Example 179: Preparation of 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile

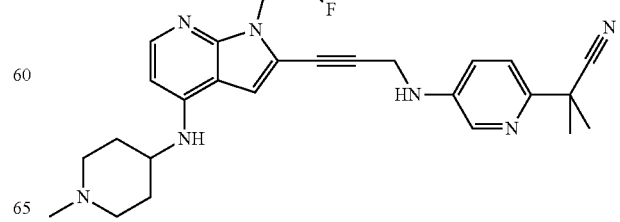

Synthetic Scheme:

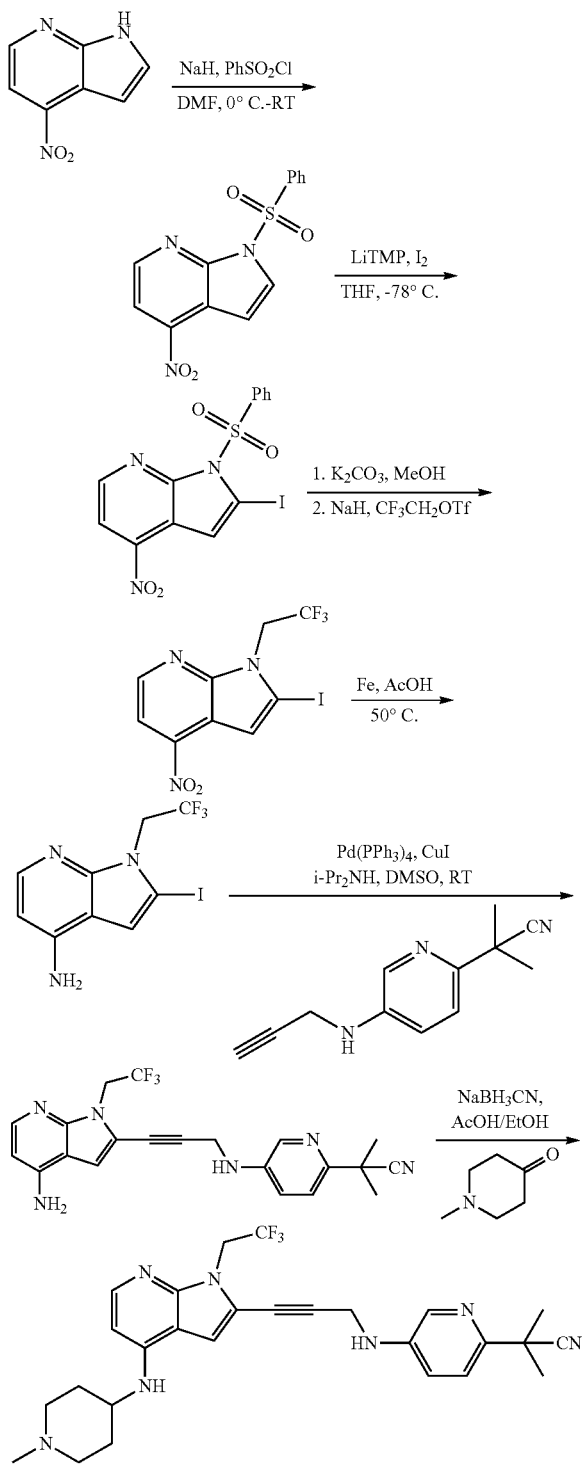

To a mixture of sodium hydride (4.41 g, 110.34 mmol, 60% in mineral oil) in tetrahydrofuran (20 mL) at 0° C. was added a solution of 4-nitro-1H-pyrrolo[2,3-b]pyridine (6 g, 36.78 mmol) in tetrahydrofuran (5 mL). The mixture was stirred 1 h at 0° C., then benzenesulfonyl chloride (9.74 g, 55.17 mmol, 7.06 mL) was added. The mixture was stirred at 0° C. for 1 h, and then quenched by adding saturated aqueous ammonium chloride. The reaction mixture was extracted with ethyl acetate (3×20 mL). The combined organic layers were washed with brine (5 mL), dried over anhydrous sodium sulfate, filtered, and concentrated in vacuo. The crude product was purified by flash column chromatography (silica gel, eluting with petroleum ether/ethyl acetate: 30/1 to 5:1) to give 1-(benzenesulfonyl)-4-nitro-1H-pyrrolo[2,3-b]pyridine as yellow solid (4.90 g, 44% yield).

A solution of 1-(benzenesulfonyl)-4-nitro-pyrrolo[2,3-b]pyridine (1 g, 3.30 mmol) in tetrahydrofuran (10 mL) was added to a solution of lithium 2,2,6,6-tetramethylpiperidide (1.70 g, 11.55 mmol) in tetrahydrofuran (27 mL) at −78° C. The mixture was stirred at −78° C. for 1 h, then an iodine solution was added (1.84 g, 7.26 mmol, dissolved in 1.46 mL tetrahydrofuran). After stirring at −78° C. for 1 h, the reaction mixture was quenched by adding saturated aqueous ammonium chloride. The resulting mixture was extracted with ethyl acetate (3×20 mL). The combined organic layers were washed with brine (5 mL), dried over anhydrous sodium sulfate, filtered, and concentrated in vacuo to give the crude 1-(benzenesulfonyl)-2-iodo-4-nitro-1H-pyrrolo[2,3-b]pyridine, which was used without further purification (600 mg).

To a solution of 1-(benzenesulfonyl)-2-iodo-4-nitro-1H-pyrrolo[2,3-b]pyridine (2 g, 4.66 mmol) in methanol (20 mL) was added potassium carbonate (2.58 g, 18.64 mmol), and the resulting reaction mixture was stirred at 80° C. for 1 h. The solids were filtered off, and the resulting filtrate was concentrated. The crude product was purified by flash column chromatography (silica gel, eluting with petroleum ether/ethyl acetate: 1/1) to give product 2-iodo-4-nitro-1H-pyrrolo[2,3-b]pyridine as yellow solid (435 mg, 1.51 mmol, 32% yield).

To a mixture of sodium hydride (187 mg, 4.68 mmol, 60% in mineral oil) in tetrahydrofuran (20 mL) at 0° C. was added 2,2,2-trifluoroethyl trifluoromethanesulfonate (1.81 g, 7.80 mmol). The resulting reaction mixture was stirred at 0° C. for 1 h, and 2-iodo-4-nitro-1H-pyrrolo[2,3-b]pyridine (451 mg, 1.56 mmol) was added to the reaction mixture. The mixture was stirred at 0° C. for 1 h, and was quenched by adding saturated aqueous ammonium chloride. The resulting mixture was extracted with ethyl acetate (3×20 mL). The combined organic layers were washed with brine (5 mL), dried over anhydrous sodium sulfate, filtered, and concentrated in vacuo. The crude product was purified by flash column chromatography (silica gel, eluting with petroleum ether/ethyl acetate: 30/1 to 5/1) to give 2-iodo-4-nitro-1-(2,2,2-trifluoroethyl)-1H-pyrrolo[2,3-b]pyridine as yellow oil (260 mg, 45%).

To a solution of 2-iodo-4-nitro-1-(2,2,2-trifluoroethyl)-1H-pyrrolo[2,3-b]pyridine (235 mg, 633.34 μmol) in acetic acid (5 mL) was added Fe (142 mg, 2.53 mmol), and the mixture was stirred at 50° C. for 2 h. The reaction mixture was then poured into water and extracted with ethyl acetate (3×20 mL). The combined organic layers were washed with brine (5 mL), dried over anhydrous sodium sulfate, filtered, and concentrated in vacuo. The crude product was purified by flash column chromatography (silica gel, eluting with petroleum ether/ethyl acetate: 30/1 to 5/1) to give 2-iodo-1-(2,2,2-trifluoroethyl)-1H-pyrrolo[2,3-b]pyridin-4-amine as yellow oil (100 mg, 46% yield).

To the solution of 2-methyl-2-{5-[(prop-2-yn-1-yl)amino]pyridin-2-yl}propanenitrile (180 mg, 762.30 μmol) in dimethyl sulfoxide (2 mL) was added N-isopropylpropan-2-amine (536 μL, 3.81 mmol). Then, 2-iodo-1-(2,2,2-trifluoroethyl)pyrrolo[2,3-b]pyridin-4-amine (130 mg, 381.15 μmol), CuI (7 mg, 38.11 μmol), and tetrakis(triphenylphosphine)palladium(0) (44 mg, 38.11 μmol) were added to the reaction mixture. The reaction was stirred at 25°

C. for 2 h under a nitrogen atmosphere, and poured into water (5 mL). The reaction mixture was extracted with ethyl acetate (3×20 mL), and the combined organic layers were stirred with saturated ethylenediamine-tetraacetic acid (EDTA) solution (~20 mL) for 1 h. The combined organic layer was washed with brine (5 mL), dried over anhydrous sodium sulfate, filtered, and concentrated in vacuo. The crude product was purified by preparative thin layer chromatography (silica gel, eluting with petroleum ether/ethyl acetate: 1/2) to give 2-[5-[3-[4-amino-1-(2,2,2-trifluoroethyl)pyrrolo[2,3-b]pyridin-2-yl]prop-2-ynylamino]-2-pyridyl]-2-methyl-propanenitrile as yellow solid (130 mg, 83% yield).

To a solution of 1-methylpiperidin-4-one (11 mg, 97 µmol, 11 µL) in ethanol (2 mL) and acetic acid (7.3 mg, 121.25 µmol, 7 µL) was added 2-[5-[3-[4-amino-1-(2,2,2-trifluoroethyl)pyrrolo[2,3-b]pyridin-2-yl]prop-2-ynylamino]-2-pyridyl]-2-methyl-propanenitrile (10 mg, 24.25 µmol) and 4 Å molecular sieves (30 mg). The mixture was stirred for 12 h at 50° C., and sodium cyanoborohydride (15 mg, 242.50 µmol) was added. The resulting reaction mixture was stirred at 50° C. for 2 h, and then diluted with water (~10 mL). The reaction mixture was extracted with ethyl acetate (3×10 mL), and the combined organic layers were washed with brine (5 mL), dried over anhydrous sodium sulfate, filtered, and concentrated in vacuo. The crude product was purified by preparative HPLC to give 2-methyl-2-{5-[(3-{4-[(1-methylpiperidin-4-yl)amino]-1-(2,2,2-trifluoroethyl)-1H-pyrrolo[2,3-b]pyridin-2-yl}prop-2-yn-1-yl)amino]pyridin-2-yl}propanenitrile (3 mg, 22% yield).

LC-MS (ES$^+$, m/z): 510.3 [(M+H)$^+$]

Example 180: Preparation of 2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile

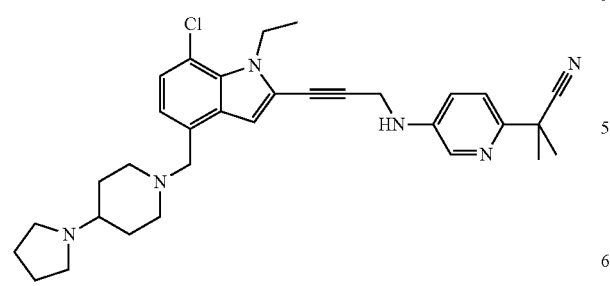

In a manner similar to the method described in Example 141, 2-(5-{[3-(7-chloro-1-ethyl-4-{[4-(pyrrolidin-1-yl)piperidin-1-yl]methyl}-1H-indol-2-yl)prop-2-yn-1-yl]amino}pyridin-2-yl)-2-methylpropanenitrile was prepared.

LC-MS (ES$^+$, m/z): 543.4[(M+H)$^+$]

Example 181: Preparation of 2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile

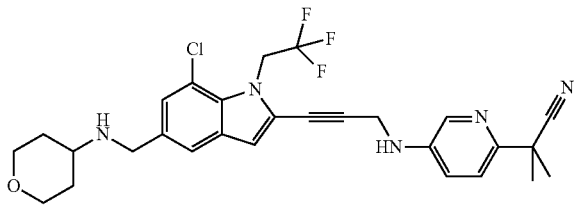

Starting with 5-bromo-7-chloro-1H-indole, using a similar method as described in Example 1, 2-(5-{[3-(7-chloro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES$^+$, m/z): 544.3 [(M+H)$^+$]

Example 182: Preparation of 2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile

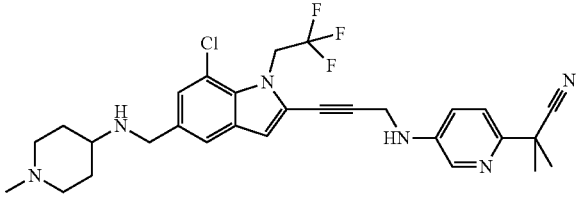 [SMILES: CN1CCC(NCc2cc(Cl)c3c(c2)cc(C#CCNc2ccc(C(C)(C)C#N)nc2)n3CC(F)(F)F)CC1]

Starting with 5-bromo-7-chloro-1H-indole, using a similar method as described in Example 1, 2-(5-{[3-(7-chloro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile was prepared.

LC-MS (ES$^+$, m/z): 557.3 [(M+H)$^+$]

Example 183: Preparation of 2-{5-[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile

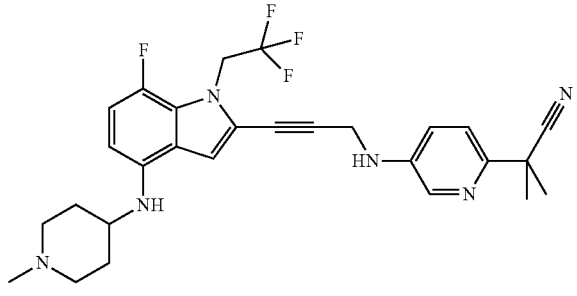 [SMILES: CN1CCC(Nc2ccc(F)c3c2cc(C#CCNc2ccc(C(C)(C)C#N)nc2)n3CC(F)(F)F)CC1]

Starting with 4-bromo-7-fluoro-1H-indole and in a manner similar to the method described in Example 172, 2-{5-

[(3-{7-fluoro-4-[(1-methylpiperidin-4-yl)amino]-1-(2,2,2-trifluoroethyl)-1H-indol-2-yl}prop-2-yn-1-yl)amino]pyridin-2-yl}-2-methylpropanenitrile was prepared.
LC-MS (ES+, m/z): 527.3 [(M+H)+]

Example 184: Preparation of 2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile

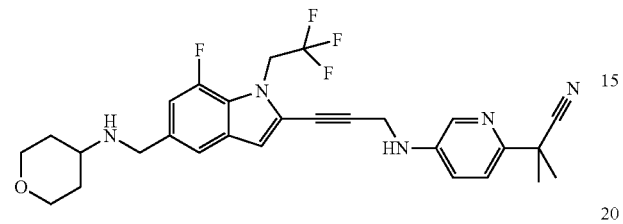

Starting with 5-bromo-7-fluoro-1H-indole and using a similar method as described in Example 1, 2-(5-{[3-(7-fluoro-5-{[(oxan-4-yl)amino]methyl}-1-(2,2,2-trifluoroethyl)-1H-indol-2-yl)prop-2-yn-1-yl]amino}pyridin-2-yl)-2-methylpropanenitrile was prepared.
LC-MS (ES+, m/z): 528.3 [(M+H)+]

Example 185: Preparation of 2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile

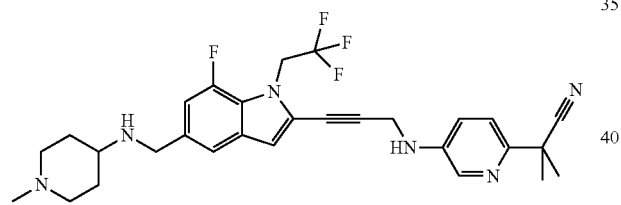

Starting with 5-bromo-7-fluoro-1H-indole and using a similar method as described in Example 1, 2-(5-{[3-(7-fluoro-5-{[(1-methylpiperidin-4-yl)amino]methyl}-1-(2,2,2-trifluoroethyl)-1H-indol-2-yl)prop-2-yn-1-yl]amino}pyridin-2-yl)-2-methylpropanenitrile was prepared.
LC-MS (ES+, m/z): 541.3 [(M+H)+]

Example 186: Preparation of 2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile

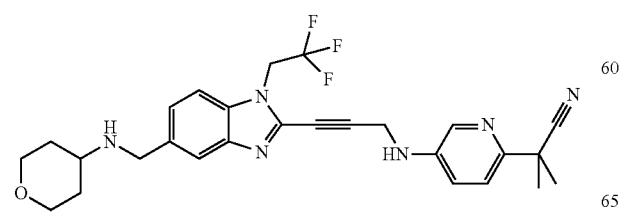

Synthetic Scheme

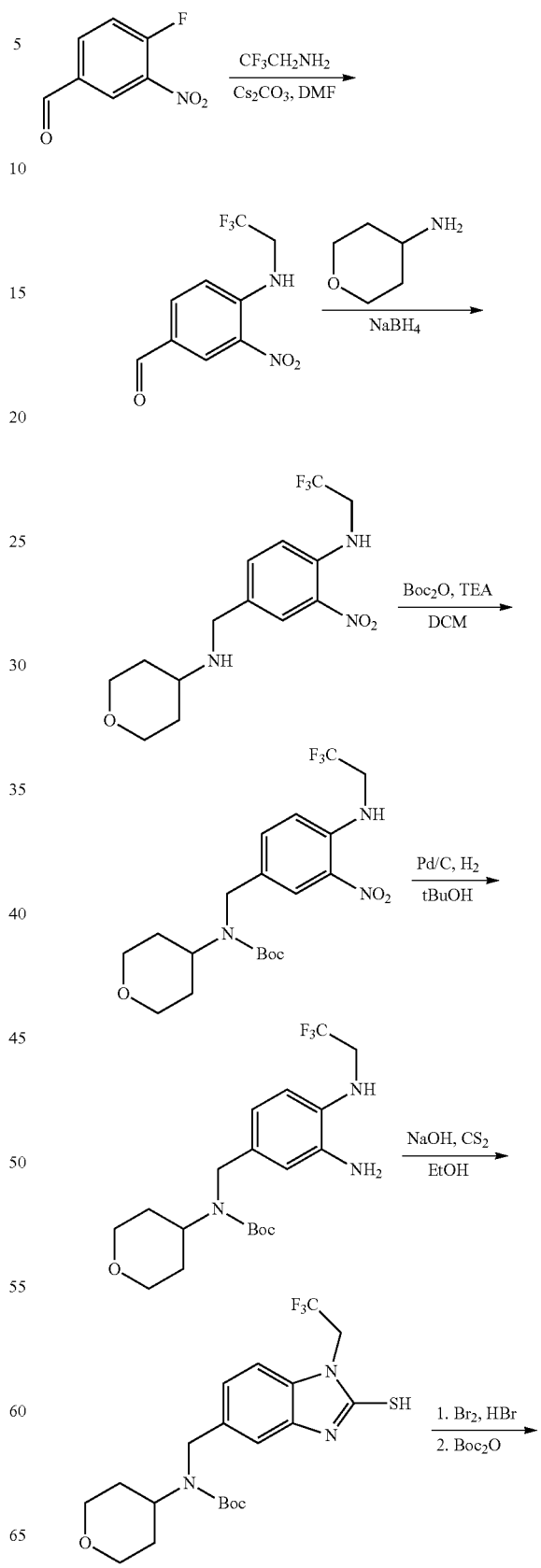

-continued

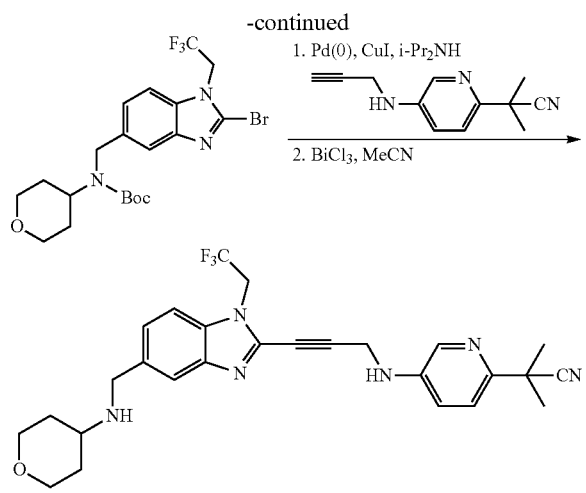

To a solution of 4-fluoro-3-nitro-benzaldehyde (6 g, 35.48 mmol) in dimethylformamide (10 mL) was added $Cs_2CO_3$ (23.12 g, 70.96 mmol). Then, 2,2,2-trifluoroethanamine (3.87 g, 39.03 mmol, 3.07 mL) was added to the reaction mixture. The reaction mixture was stirred at 100° C. for 1 h, cooled to room temperature, and concentrated. Water (500 mL) was added to the mixture, and the resulting mixture was extracted with ethyl acetate (3×500 mL). The combined organic layers were washed with water (3×300 mL), brine (300 mL) dried over anhydrous sodium sulfate, filtered, and concentrated in vacuo. The crude product was purified by flash column chromatography (silica gel, eluting with petroleum ether/tetrahydrofuran: 100/1). The yellow solid obtained was further washed with petroleum ether/methylene chloride/methanol: 30/10/2 mL and filtered to give 3-nitro-4-[(2,2,2-trifluoroethyl)amino]benzaldehyde (2.50 g, 80% purity).

A solution of 3-nitro-4-[(2,2,2-trifluoroethyl)amino]benzaldehyde (2.80 g, 9.03 mmol, 80% purity) and 4-aminopyran (2.74 g, 27.09 mmol) in tetrahydrofuran (30 mL) and methanol (30 mL) was stirred at 20° C. for 2 h. $NaBH_4$ (1.02 g, 27.09 mmol) was then added to the solution. The reaction mixture was stirred at 20° C. for 1 h, poured into water (20 mL), and concentrated. The residue was extracted with methylene chloride/methanol (5×40 mL). The combined organic layers were washed with brine (20 mL), dried over anhydrous sodium sulfate, filtered, and concentrated. The crude compound was purified by flash column chromatography (silica gel, eluting with methylene chloride/methanol: 150/1 to 50/1) to give N-({3-nitro-4-[(2,2,2-trifluoroethyl) amino]phenyl}methyl)oxan-4-amine as yellow solid (3.01 g, 94% yield).

To a solution of N-({3-nitro-4-[(2,2,2-trifluoroethyl) amino]phenyl}methyl)oxan-4-amine (3 g, 8.46 mmol) in methylene chloride (70 mL) was added triethylamine (3.52 mL, 25.38 mmol and di-tert-butyl dicarbonate (2.03 g, 9.31 mmol). The reaction mixture was stirred at 20° C. for 24 h, water (20 mL) was added to the reaction mixture, and the resulting mixture was extracted with methylene chloride (3×50 mL). The combined organic layers were washed with brine (20 mL), dried over anhydrous sodium sulfate, filtered, and concentrated in vacuo. The crude product was purified by flash column chromatography (silica gel, eluting with methylene chloride/methanol: 200/1) to give tert-butyl N-({3-nitro-4-[(2,2,2-trifluoroethyl)amino]phenyl}methyl)-N-(oxan-4-yl)carbamate as yellow solid (3.90 g, 96% yield).

To a solution of tert-butyl N-({3-nitro-4-[(2,2,2-trifluoroethyl)amino]phenyl}methyl)-N-(oxan-4-yl)carbamate (3.50 g, 7.27 mmol) in t-BuOH (80 mL) and tetrahydrofuran (18 mL) was added 10% Pd on carbon (500 mg, 7.27 mmol). The mixture was stirred at 20° C. for 30 min under a hydrogen atmosphere (15 psi). The reaction was filtered, and the filtrate was concentrated to give tert-butyl N-({3-amino-4-[(2,2,2-trifluoroethyl)amino]phenyl}methyl)-N-(oxan-4-yl)carbamate as a white solid (3 g). The crude product was used in the next step without further purification.

To a solution of tert-butyl N-({3-amino-4-[(2,2,2-trifluoroethyl)amino]phenyl}methyl)-N-(oxan-4-yl)carbamate (1 g, 2.23 mmol) in ethanol (30 mL) was added potassium hydroxide (626 mg, 11.15 mmol). Carbon disulfite (6.30 g, 82.74 mmol, 5 mL) was then added to the reaction, and the reaction mixture was stirred at 80° C. for 1 h. After being concentrated, the pH of the crude mixture was adjusted to 9 with 12M HCl. The reaction mixture was extracted with methylene chloride (3×50 mL). The combined organic layers were washed with brine (30 mL), dried over anhydrous sodium sulfate, filtered, and concentrated in vacuo. The crude product was purified by flash column chromatography (silica gel, eluting with methylene chloride) to give tert-butyl N-(oxan-4-yl)-N-{[2-sulfanyl-1-(2,2,2-trifluoroethyl)-1H-1,3-benzodiazol-5-yl]methyl}carbamate (1 g, 99% yield).

Bromine (1.32 mmol, 68 µL) in acetic acid (0.5 mL) was added dropwise to a solution of tert-butyl N-(oxan-4-yl)-N-{[2-sulfanyl-1-(2,2,2-trifluoroethyl)-1H-1,3-benzodiazol-5-yl]methyl}carbamate (150 mg, 329.97 µmol) in acetic acid (1.70 mL) and HBr (69 µL, 442.16 µmol, 35% solution in acetic acid) at 20° C. HBr (154 µL, 35% in acetic acid) in acetic acid (1 mL) was then added to the reaction, and the reaction mixture was stirred at 50° C. for 2 h. After the pH was adjusted to 10 with 20% sodium hydroxide (10 mL), the mixture was extracted with methylene chloride (3×20 mL). The combined organic layers were washed with water (10 mL), dried over anhydrous sodium sulfate, filtered, and concentrated in vacuo. The crude product was purified by preparative thin layer chromatography (silica gel, eluting with methylene chloride/methanol: 10/1) to give N-{[2-bromo-1-(2,2,2-trifluoroethyl)-1H-1,3-benzodiazol-5-yl]methyl}oxan-4-amine (25 mg, 9% yield).

A solution of N-{[2-bromo-1-(2,2,2-trifluoroethyl)-1H-1,3-benzodiazol-5-yl]methyl}oxan-4-amine (30 mg, 68.84 µmol) and di-tert-butyl dicarbonate (35 mg, 158.33 µmol) in dioxane (3 mL) was stirred at 70° C. for 2 h. After the reaction mixture was cooled to room temperature and concentrated, the residue was purified by preparative thin layer chromatography (eluting with methylene chloride/methanol: 10/1) to give tert-butyl N-{[2-bromo-1-(2,2,2-trifluoroethyl)-1H-1,3-benzodiazol-5-yl]methyl}-N-(oxan-4-yl)carbamate as white solids (30 mg, 80% yield).

To a solution of 2-methyl-2-[5-(prop-2-ynylamino)-2-pyridyl]propanenitrile (50 mg, 212.41 µmol), diisopropylamine (1.42 mmol, 200 µL) and CuI (1.2 mg, 6.40 µmol) in dimethyl sulfoxide (2.5 mL) was added tert-butyl N-{[2-bromo-1-(2,2,2-trifluoroethyl)-1H-1,3-benzodiazol-5-yl]methyl}-N-(oxan-4-yl)carbamate (35 mg, 63.98 µmol) and tetrakis(triphenylphosphine)palladium(0) (7 mg, 6.40 µmol, 0.10 equiv.). The reaction mixture was stirred at 80° C. for 1 h under a nitrogen atmosphere, and then treated with a saturated EDTA solution (5 mL). The biphasic mixture was stirred at 20° C. for 1 h, and then extracted with methylene chloride (3×10 mL). The combined organic layers were washed with water (50 mL), dried over anhydrous sodium sulfate, filtered, and concentrated in vacuo. The crude product was purified twice by preparative thin layer chromatography (silica gel, eluting with methylene chloride/methanol: 10/1, ethyl acetate/methanol: 30/3, respectively) to give tert-butyl N-{[2-(3-{[6-(1-cyano-1-methylethyl)pyridin-3-yl]amino}prop-1-yn-1-yl)-1-(2,2,2-trifluoroethyl)-1H-1,3-benzodiazol-5-yl]methyl}-N-(oxan-4-yl)carbamate as black solids (41 mg, 84% yield, 80% purity).

To a solution of tert-butyl N-{[2-(3-{[6-(1-cyano-1-methylethyl)pyridin-3-yl]amino}prop-1-yn-1-yl)-1-(2,2,2-trifluoroethyl)-1H-1,3-benzodiazol-5-yl]methyl}-N-(oxan-4-yl)carbamate (35 mg, 45.85 µmol) in acetonitrile (3 mL) was added bismuth trichloride (443.83 µmol, 30 µL). The reaction mixture was stirred at 60° C. for 1 h, and treated with a saturated EDTA solution (10 mL). The biphasic mixture was stirred at 20° C. for 1 h, and extracted with ethyl acetate (3×20 mL). The combined organic layers were washed with brine (2×10 mL), dried over anhydrous sodium sulfate, filtered, and concentrated in vacuo. The crude product was purified by preparative HPLC to give 2-methyl-2-(5-{[3-(5-{[(oxan-4-yl)amino]methyl}-1-(2,2,2-trifluoroethyl)-1H-1,3-benzodiazol-2-yl)prop-2-yn-1-yl]amino}pyridin-2-yl)propanenitrile as white solids (6.5 mg, 25% yield, 98% purity).

LC-MS (ES⁺, m/z): 511.3 [(M+H)⁺]

Example 187: Preparation of N-{[2-(2-phenylethynyl)-1-(2,2,2-trifluoroethyl)-1H-1,3-benzodiazol-5-yl]methyl}oxan-4-amine

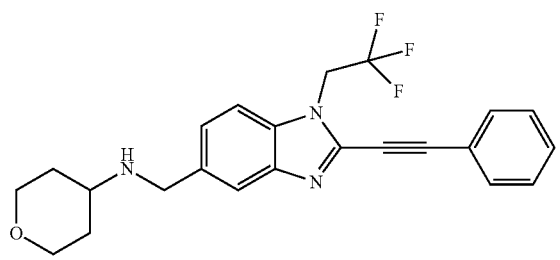 [SMILES: FC(F)(F)Cn1c(C#Cc2ccccc2)nc2cc(CNC3CCOCC3)ccc21]

To a solution of tert-butyl N-({3-amino-4-[(2,2,2-trifluoroethyl)amino]phenyl}methyl)-N-(oxan-4-yl)carbamate (200 mg, 446.16 µmol) in dimethylformamide (5 mL) was added 3-phenylprop-2-ynal (174 mg, 1.34 mmol, 163 µL). Oxone (274 mg, 446.16 µmol) was then added, and the reaction mixture was stirred at 20° C. for 2 h. The reaction mixture was then treated with a saturated sodium bicarbonate solution (5 mL) and a saturated Na₂SO₃ solution (5 mL), and the mixture was stirred at 20° C. for 1 h. The mixture was then extracted with ethyl acetate (3×10 mL). The combined organic layers were washed with water (3×10 mL), brine (10 mL), dried over anhydrous sodium sulfate, filtered, and concentrated in vacuo. The crude product was purified by preparative thin layer chromatography (silica gel, eluting with ethyl acetate/petroleum ether: 1/1) to give tert-butyl N-(oxan-4-yl)-N-{[2-(2-phenylethynyl)-1-(2,2,2-trifluoroethyl)-1H-1,3-benzodiazol-5-yl]methyl}carbamate as yellow oil (80 mg, 31% yield).

Tert-butyl N-(oxan-4-yl)-N-{[2-(2-phenylethynyl)-1-(2,2,2-trifluoroethyl)-1H-1,3-benzodiazol-5-yl]methyl}carbamate (60 mg, 105.2 mmol) was deprotected using bismuth trichloride using the method described in Example 186 to give N-{[2-(2-phenylethynyl)-1-(2,2,2-trifluoroethyl)-1H-1,3-benzodiazol-5-yl]methyl}oxan-4-amine (35 mg, light yellow solid).

LC-MS (ES⁺, m/z): 414.3 [(M+H)⁺]

Example 188: Preparation of 2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile

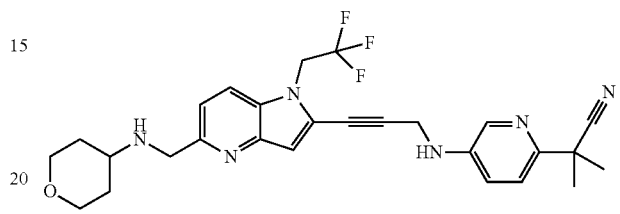

To a solution of methyl 1H-pyrrolo[3,2-b]pyridine-5-carboxylate (3.01 g, 17.05 mmol) in dimethylformamide (30 mL) at 0° C. was added sodium hydride (890 mg, 22.17 mmol, 60% in mineral oil). The mixture was stirred at 0° C. for 30 min, and PhSO₂Cl (2.2 mL, 17.05 mmol) was added. The ice bath was then removed, and the mixture was allowed to warm up to room temperature and was stirred overnight at room temperature. The reaction mixture was poured into ice/water (300 mL) and stirred for 1 h. The solids were filtered, washed with water (100 mL) and hexane (50 mL), and the resulting solution was dried overnight to give methyl 1-(benzenesulfonyl)-1H-pyrrolo[3,2-b]pyridine-5-carboxylate as an off-white solid (3.50 g, 66% yield).

Methyl 1-(benzenesulfonyl)-1H-pyrrolo[3,2-b]pyridine-5-carboxylate (500 mg, 1.58 mmol) was dissolved in dry tetrahydrofuran (50 mL) and cooled to −78° C. under a nitrogen atmosphere. A DIBAL solution (1.8 M, 5.3 mL, 9.48 mmol) was added dropwise, and the reaction mixture was stirred at −78° C. for 20 min. The mixture was then poured into a mixture of water (20 mL), 1N sodium hydroxide (20 mL), and brine (20 mL), and was stirred for 10 min. The mixture was then extracted with ethyl acetate (3×30 mL). The combined organic layers were washed with water, dried over anhydrous magnesium sulfate, filtered, and concentrated in vacuo. The crude product was purified by flash column chromatography (silica gel, eluting with methylene chloride/ethyl acetate: 4/1) to give 1-(benzenesulfonyl)-1H-pyrrolo[3,2-b]pyridine-5-carbaldehyde as white solid (320 mg, 70% yield).

In a manner similar to the methods described in Examples 1 and 49, 1-(benzenesulfonyl)-1H-pyrrolo[3,2-b]pyridine-5-carbaldehyde and 2-methyl-2-{5-[(prop-2-yn-1-yl)amino]pyridin-2-yl}propanenitrile were used to prepare 2-methyl-2-(5-{[3-(5-{[(oxan-4-yl)amino]methyl}-1-(2,2,2-trifluoroethyl)-1H-pyrrolo[3,2-b]pyridin-2-yl)prop-2-yn-1-yl]amino}pyridin-2-yl)propanenitrile.

LC-MS (ES⁺, m/z): 511.1 [(M+H)⁺]

Example 189: Preparation of 2-{3-[(4-methanesulfonylphenyl)amino]prop-1-yn-1-yl}-5-methyl-N-(1-methylpiperidin-4-yl)-1-(2,2,2-trifluoroethyl)-1H-indol-4-amine

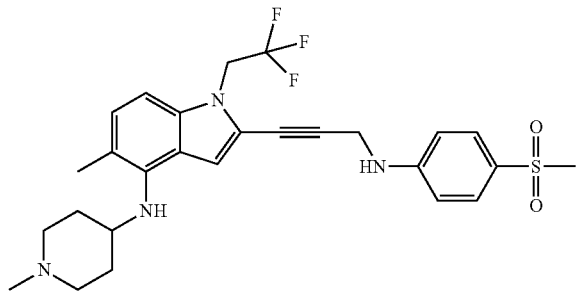

In a manner similar to the method described in Example 179, 5-methyl-4-nitro-1H-indole and 4-methanesulfonyl-N-(prop-2-yn-1-yl)aniline were used to prepare 2-{3-[(4-methanesulfonylphenyl)-amino]prop-1-yn-1-yl}-5-methyl-N-(1-methylpiperidin-4-yl)-1-(2,2,2-trifluoroethyl)-1H-indol-4-amine.

LC-MS (ES$^+$, m/z): 533.1 [(M+H)$^+$]

Example 190: Preparation of 4-[(2-{3-[(4-methanesulfonylphenyl)amino]prop-1-yn-1-yl}-5-methyl-1-(2,2,2-trifluoroethyl)-1H-indol-4-yl)amino]-1λ$^6$-thiane-1,1-dione

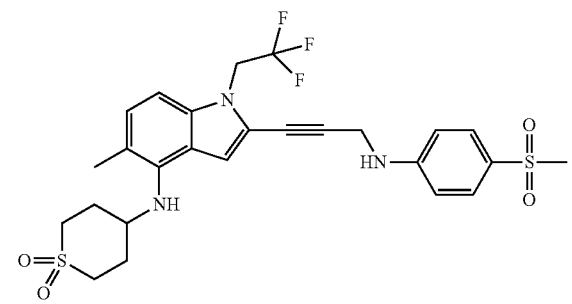 [SMILES: Cc1ccc2c(cc(C#CCNc3ccc(S(C)(=O)=O)cc3)n2CC(F)(F)F)c1NC1CCS(=O)(=O)CC1]

In a manner similar to the method described in Example 179, 5-methyl-4-nitro-1H-indole and 4-methanesulfonyl-N-(prop-2-yn-1-yl)aniline were used to prepare 4-[(2-{3-[(4-methanesulfonylphenyl)-amino]prop-1-yn-1-yl}-5-methyl-1-(2,2,2-trifluoroethyl)-1H-indol-4-yl)amino]-1λ$^6$-thiane-1,1-dione.

LC-MS (ES$^+$, m/z): 568.2 [(M+H)$^+$]

Example 191: Preparation of 2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile

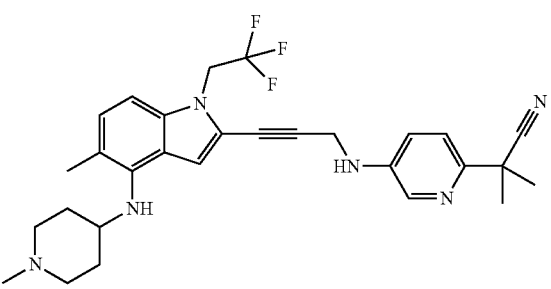 [SMILES: Cc1ccc2c(cc(C#CCNc3ccc(C(C)(C)C#N)nc3)n2CC(F)(F)F)c1NC1CCN(C)CC1]

In a manner similar to the method described in Example 179, 5-methyl-4-nitro-1H-indole and 2-methyl-2-{5-[(prop-2-yn-1-yl)amino]pyridin-2-yl}propanenitrile were used to prepare 2-methyl-2-{5-[(3-{5-methyl-4-[(1-methylpiperidin-4-yl)amino]-1-(2,2,2-trifluoroethyl)-1H-indol-2-yl}prop-2-yn-1-yl)amino]pyridin-2-yl}propanenitrile.

LC-MS (ES$^+$, m/z): 523.0 [(M+H)$^+$]

Example 192: Preparation of N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine

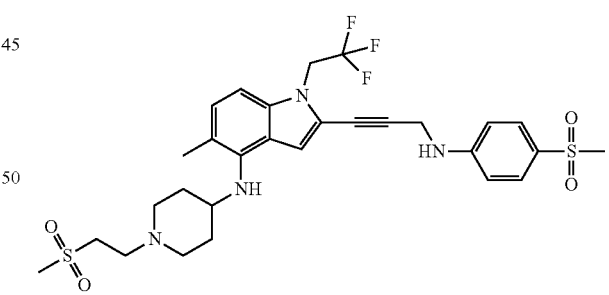

In a manner similar to the method described in Example 179, 5-methyl-4-nitro-1H-indole and 4-methanesulfonyl-N-(prop-2-yn-1-yl)aniline were used to prepare N-[1-(2-methanesulfonylethyl)piperidin-4-yl]-2-{3-[(4-methanesulfonylphenyl)amino]prop-1-yn-1-yl}-5-methyl-1-(2,2,2-trifluoroethyl)-1H-indol-4-amine.

LC-MS (ES$^+$, m/z): 625.3 [(M+H)$^+$]

Example 193: Preparation of 4-[(3-{5-methyl-4-[(piperidin-4-yl)amino]-1-(2,2,2-trifluoroethyl)-1H-indol-2-yl}prop-2-yn-1-yl)amino]benzene-1-sulfonamide

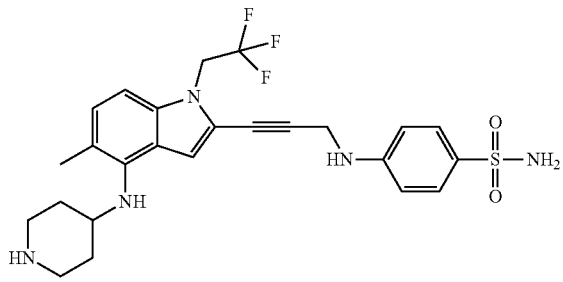 [SMILES: Cc1ccc2c(cc(C#CCNc3ccc(S(N)(=O)=O)cc3)n2CC(F)(F)F)c1NC1CCNCC1]

In a manner similar to the method described in Example 179, 5-methyl-4-nitro-1H-indole and 4-[(prop-2-yn-1-yl)amino]benzene-1-sulfonamide were used to prepare 4-[(3-{5-methyl-4-[(piperidin-4-yl)amino]-1-(2,2,2-trifluoroethyl)-1H-indol-2-yl}prop-2-yn-1-yl)amino]benzene-1-sulfonamide.

LC-MS (ES$^+$, m/z): 519.9 [(M+H)$^+$]

Example 194: Preparation of 2-{3-[(4-methanesulfonylphenyl)amino]prop-1-yn-1-yl}-5-methyl-N-[1-(oxan-4-yl)piperidin-4-yl]-1-(2,2,2-trifluoroethyl)-1H-indol-4-amine

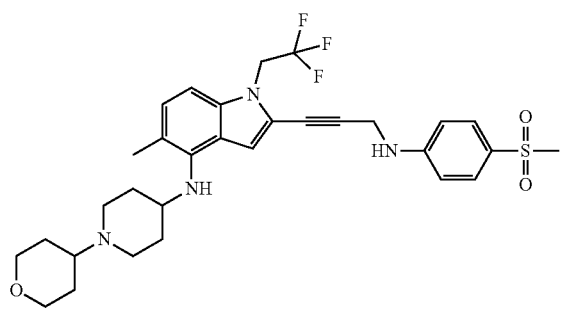 [SMILES: Cc1ccc2c(cc(C#CCNc3ccc(S(C)(=O)=O)cc3)n2CC(F)(F)F)c1NC1CCN(C2CCOCC2)CC1]

In a manner similar to the method described in Example 179, 5-methyl-4-nitro-1H-indole and 4-methanesulfonyl-N-(prop-2-yn-1-yl)aniline were used to prepare 2-{3-[(4-methanesulfonylphenyl)-amino]prop-1-yn-1-yl}-5-methyl-N-[1-(oxan-4-yl)piperidin-4-yl]-1-(2,2,2-trifluoroethyl)-1H-indol-4-amine.

LC-MS (ES$^+$, m/z): 603.3 [(M+H)$^+$]

Example 195: Preparation of 2-{4-[(2-{3-[(4-methanesulfonylphenyl)amino]prop-1-yn-1-yl}-5-methyl-1-(2,2,2-trifluoroethyl)-1H-indol-4-yl)amino]piperidin-1-yl}ethan-1-ol

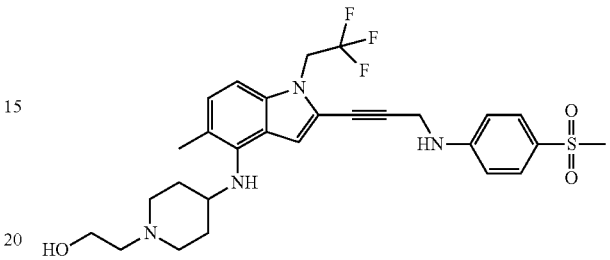

In a manner similar to the method described in Example 179, 5-methyl-4-nitro-1H-indole and 4-methanesulfonyl-N-(prop-2-yn-1-yl)aniline were used to prepare 2-{4-[(2-{3-[(4-methanesulfonyl-phenyl)-amino]prop-1-yn-1-yl}-5-methyl-1-(2,2,2-trifluoroethyl)-1H-indol-4-yl)amino] piperidin-1-yl}ethan-1-ol.

LC-MS (ES$^+$, m/z): 563.3 [(M+H)$^+$]

Example 196: Preparation of 2-[5-({3-[4-(methoxymethyl)-1-(2,2,2-trifluoroethyl)-1H-indol-2-yl]prop-2-yn-1-yl}amino)pyridin-2-yl]-2-methylpropanenitrile

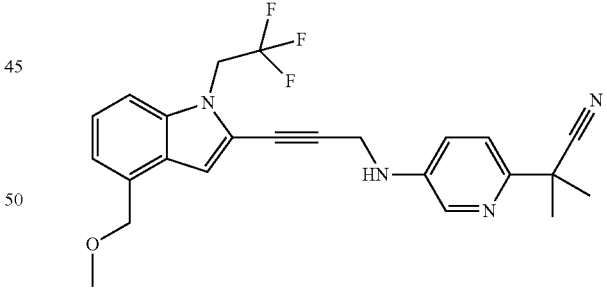

In a manner similar to the methods described in Examples 1 and 49, 2-iodo-1H-indole-4-carbaldehyde (prepared from methyl 1H-indole-4-carboxylate) and 2-methyl-2-{5-[(prop-2-yn-1-yl)amino]pyridin-2-yl}propanenitrile were used to prepare 2-[5-({3-[4-(methoxymethyl)-1-(2,2,2-trifluoroethyl)-1H-indol-2-yl]prop-2-yn-1-yl}amino)pyridin-2-yl]-2-methylpropanenitrile.

LC-MS (ES$^+$, m/z): 441.2 [(M+H)$^+$]

Example 197: Preparation of 2-[5-({3-[4-(cyanomethyl)-1-(2,2,2-trifluoroethyl)-1H-indol-2-yl]prop-2-yn-1-yl}amino)pyridin-2-yl]-2-methylpropanenitrile

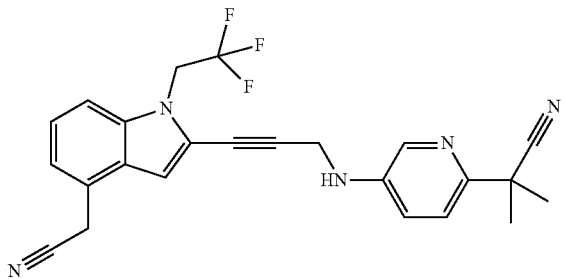 [SMILES: CC(C)(C#N)c1ccc(NCC#Cc2cc3c(CC#N)cccc3n2CC(F)(F)F)cn1]

In a manner similar to the methods described in Examples 1 and 49, 2-iodo-1H-indole-4-carbaldehyde (prepared from methyl 1H-indole-4-carboxylate) and 2-methyl-2-{5-[(prop-2-yn-1-yl)amino]pyridin-2-yl}propanenitrile were used to prepare 2-[5-({3-[4-(cyanomethyl)-1-(2,2,2-trifluoroethyl)-1H-indol-2-yl]prop-2-yn-1-yl}amino)pyridin-2-yl]-2-methylpropanenitrile.
LC-MS (ES+, m/z): 436.2 [(M+H)+]

Example 198: Preparation of 2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile

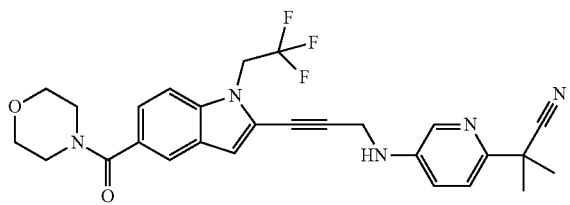 [SMILES: CC(C)(C#N)c1ccc(NCC#Cc2cc3cc(C(=O)N4CCOCC4)ccc3n2CC(F)(F)F)cn1]

To a solution of methyl 2-[3-[[6-(1-cyano-1-methyl-ethyl)-3-pyridyl]amino]prop-1-ynyl]1-(2,2,2-trifluoroethyl)indole-5-carboxylate (300 mg, 594.14 μmol) in methanol (4.5 mL) was added sodium hydroxide (5 M, 810 μL), and the resulting reaction mixture was stirred at 25° C. for 1 h. The reaction mixture was then poured to aqueous ammonium chloride (10 mL), and the pH was adjusted to 3 using 1N HCl. The reaction mixture was then extracted with ethyl acetate (3×10 mL). The combined organic layers were washed with water (2×10 mL), brine (2×10 mL), dried over anhydrous sodium sulfate, filtered, and concentrated in vacuo to give crude 2-[3-[[6-(1-cyano-1-methyl-ethyl)-3-pyridyl]amino]prop-1-ynyl]-1-(2,2,2-trifluoroethyl)indole-5-carboxylic acid (brown solid), which was used without further purification.

2-[3-[[6-(1-Cyano-1-methyl-ethyl)-3-pyridyl]amino]prop-1-ynyl]-1-(2,2,2-trifluoroethyl)indole-5-carboxylic acid (1 equiv.) coupled with morpholine (2 equiv.) using HATU (2 equiv.) and diisopropylethylamine (3 equiv.) in methylene chloride at 25° C. for 1 h to give 2-methyl-2-[5-({3-[5-(morpholine-4-carbonyl)-1-(2,2,2-trifluoroethyl)-1H-indol-2-yl]prop-2-yn-1-yl}amino)pyridin-2-yl]propanenitrile after purification by preparative HPLC.
LC-MS (ES+, m/z): 510.3 [(M+H)+]

Example 199: Preparation of 2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile

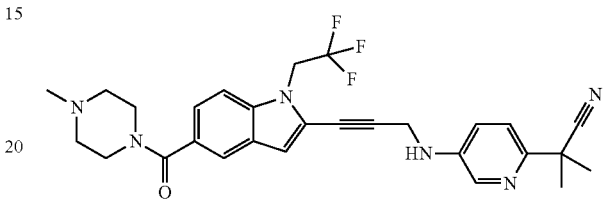

In a manner similar to the method described in Example 198, 2-methyl-2-[5-({3-[5-(4-methylpiperazine-1-carbonyl)-1-(2,2,2-trifluoroethyl)-1H-indol-2-yl]prop-2-yn-1-yl}amino)pyridin-2-yl]propanenitrile was prepared.
LC-MS (ES+, m/z): 523.3 [(M+H)+]

Example 200: Preparation of 2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile

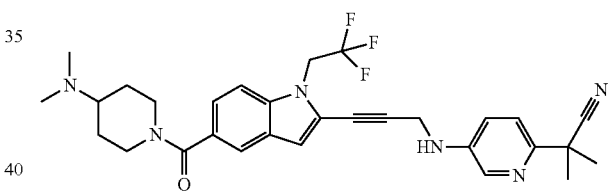

In a manner similar to the method described in Example 198, 2-{5-[(3-{5-[4-(dimethylamino)piperidine-1-carbonyl]-1-(2,2,2-trifluoroethyl)-1H-indol-2-yl}prop-2-yn-1-yl)amino]pyridin-2-yl}-2-methylpropanenitrile was prepared.
LC-MS (ES+, m/z): 551.4 [(M+H)+]

Example 201: Preparation of 2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide

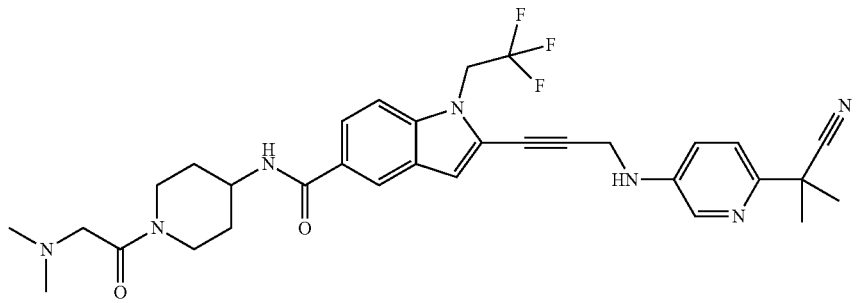 [SMILES: CN(C)CC(=O)N1CCC(NC(=O)c2ccc3c(c2)cc(C#CCNc2ccc(C(C)(C)C#N)nc2)n3CC(F)(F)F)CC1]

In a manner similar to the method described in Example 198, 2-(3-{[6-(1-cyano-1-methylethyl)pyridin-3-yl]amino}prop-1-yn-1-yl)-N-{1-[2-(dimethylamino)acetyl]piperidin-4-yl}-1-(2,2,2-trifluoroethyl)-1H-indole-5-carboxamide was prepared.

LC-MS (ES+, m/z): 608.4 [(M+H)+]

Example 202: Preparation of 2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide

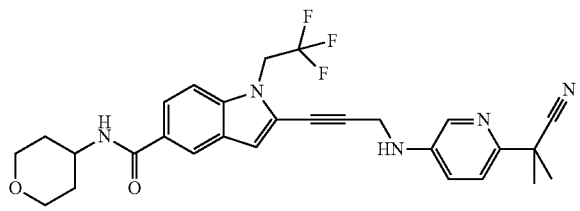 [SMILES: CC(C)(C#N)c1ccc(NCC#Cc2cc3cc(C(=O)NC4CCOCC4)ccc3n2CC(F)(F)F)cn1]

In a manner similar to the method described in Example 198, 2-(3-{[6-(1-cyano-1-methylethyl)pyridin-3-yl]amino}prop-1-yn-1-yl)-N-(oxan-4-yl)-1-(2,2,2-trifluoroethyl)-1H-indole-5-carboxamide was prepared.

LC-MS (ES+, m/z): 524.3 [(M+H)+]

Example 203: Preparation of 2-methyl-2-(5-{[3-(5-{1-[(oxan-4-yl)amino]ethyl}-1-(2,2,2-trifluoroethyl)-1H-indol-2-yl)prop-2-yn-1-yl]amino}pyridin-2-yl)propanenitrile

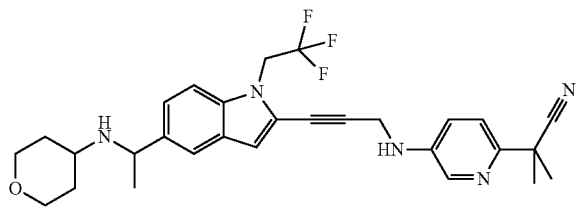 [SMILES: CC(NC1CCOCC1)c1ccc2c(c1)cc(C#CCNc1ccc(C(C)(C)C#N)nc1)n2CC(F)(F)F]

In a manner similar to the methods described in Example 1 and 49, 1-(1H-indol-5-yl)ethan-1-one and 2-methyl-2-{5-[(prop-2-yn-1-yl)amino]pyridin-2-yl}propanenitrile were used to prepare 2-methyl-2-(5-{[3-(5-{1-[(oxan-4-yl)amino]ethyl}-1-(2,2,2-trifluoroethyl)-1H-indol-2-yl)prop-2-yn-1-yl]amino}-pyridin-2-yl)propanenitrile.

LC-MS (ES+, m/z): 524.4 [(M+H)+]

Example 204: Preparation of 2-methyl-2-{5-[(3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile

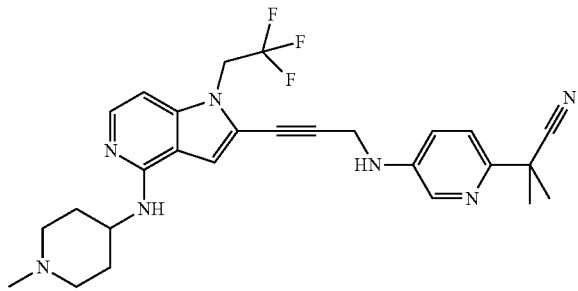 [SMILES: CN1CCC(Nc2nccc3c2cc(C#CCNc2ccc(C(C)(C)C#N)nc2)n3CC(F)(F)F)CC1]

To a solution of 2-(5-aminopyridin-2-yl)-2-methylpropanenitrile (4.0 g, 24.81 mmol) in dioxane (100 mL) was added di-tert-butyl dicarbonate (10.83 g, 49.62 mmol), and the reaction mixture was stirred at 100° C. for 6 h. The reaction mixture was then concentrated to give the crude product, which was washed with petroleum ether (2×6 mL) and filtered to give tert-butyl N-[6-(1-cyano-1-methylethyl)-pyridin-3-yl]carbamate as a white solid (5.80 g, 89% yield).

To a solution of tert-butyl N-[6-(1-cyano-1-methylethyl)-pyridin-3-yl]carbamate (5.80 g, 21.97 mmol) in dimethylformamide (100 mL) was added sodium hydride (2.64 g, 65.91 mmol, 60% in mineral oil). The reaction mixture was stirred at 0° C. for 30 min, and propargyl bromide (7.5 mL, 87.44 mmol) was added to the reaction mixture. The resulting reaction mixture was stirred at 25° C. for another 30 min, poured into ice water (100 mL), and extracted with ethyl acetate (3×30 mL). The combined organic layers were washed with water (50 mL), dried over anhydrous sodium sulfate, filtered, and concentrated in vacuo. The crude product was purified by flash column chromatography (silica gel, eluting with petroleum ether/ethyl acetate: 6/1) to give tert-butyl N-[6-(1-cyano-1-methylethyl)pyridin-3-yl]-N-(prop-2-yn-1-yl)carbamate as colorless oil (6.5 g, 98% yield).

A solution of tert-butyl N-[6-(1-cyano-1-methylethyl)pyridin-3-yl]-N-(prop-2-yn-1-yl)carbamate (2 g, 6.65 mmol) in HCl/ethyl acetate (4 M, 10 mL) was stirred at 25° C. for 3 h, and then quenched with aqueous sodium bicarbonate. The resulting mixture was concentrated, and the residue was washed with petroleum ether (2×5 mL) to give 2-methyl-2-{5-[(prop-2-yn-1-yl)amino]pyridin-2-yl}propanenitrile as an off-white solid (1.50 g, 94% yield, hydrochloride salt).

In a manner similar to the method described in Example 172, 4-chloro-1H-pyrrolo[3,2-c]pyridine and 2-methyl-2-{5-[(prop-2-yn-1-yl)amino]pyridin-2-yl}propanenitrile were used to prepare 2-methyl-2-{5-[(3-{4-[(1-methylpiperidin-4-yl)amino]-1-(2,2,2-trifluoroethyl)-1H-pyrrolo[3,2-c]pyridin-2-yl}prop-2-yn-1-yl)amino]pyridin-2-yl}propanenitrile.

LC-MS (ES+, m/z): 510.3 [(M+H)+]

Example 205: Preparation of 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile

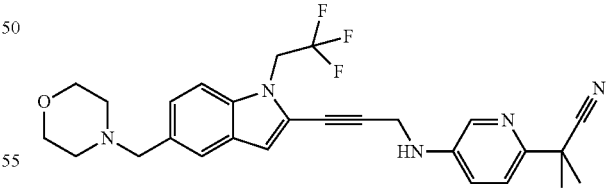

Synthetic Scheme:

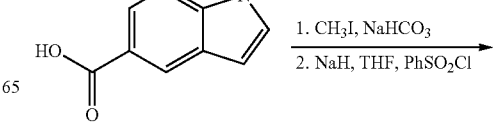

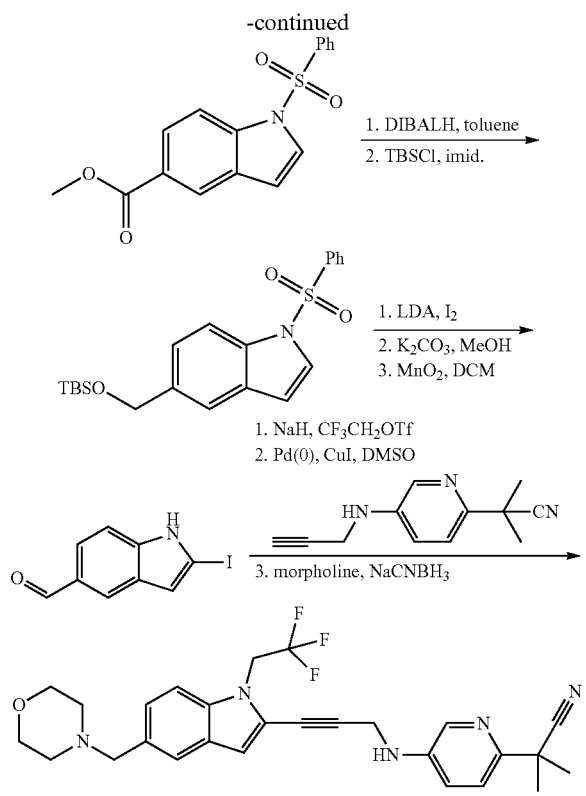

To a solution of 1H-indole-5-carboxylic acid (150 g, 930.75 mmol) in dimethylformamide (1.50 L) was added sodium bicarbonate (312.77 g, 3.72 mol) and iodomethane (528.44 g, 3.72 mol, 232 mL). The mixture was stirred at 30° C. for 2 h, quenched by the addition of water (3000 mL) at 30° C., and extracted with ethyl acetate (3×500 mL). The combined organic layers were washed with brine (500 mL), dried over anhydrous sodium sulfate, filtered, and concentrated to give methyl 1H-indole-5-carboxylate (300 g, crude) was obtained as a yellow solid.

To a solution of methyl 1H-indole-5-carboxylate (80 g, 456.67 mmol) in tetrahydrofuran (800 mL) was added sodium hydride (27.4 g, 685.01 mmol, 60% in mineral oil) and benzenesulfonyl chloride (80.66 g, 456.67 mmol, 58.5 mL). The mixture was stirred at 0° C. for 2 h, quenched by the addition of saturated ammonium chloride (1000 mL) at 0° C., and extracted with ethyl acetate (3×1000 mL). The combined organic layers were washed with brine (1000 mL), dried over anhydrous sodium sulfate, filtered, and concentrated to give crude methyl 1-(benzenesulfonyl)-1H-indole-5-carboxylate as yellow solid (400 g).

To a stirred solution of methyl 1-(benzenesulfonyl)-1H-indole-5-carboxylate (70 g, 221.98 mmol) in toluene (1 L) at −78° C. was added a solution of DIBAL-H (1 M, 888 mL). The mixture was stirred at −78° C. for 50 min, quenched by the addition of saturated ammonium chloride (1000 mL) at 0° C., and extracted with ethyl acetate (3×1000 mL). The combined organic layers were washed with brine (2000 mL), dried over anhydrous sodium sulfate, filtered, and concentrated in vacuo. The crude product was purified by flash column chromatography (silica gel, eluting with petroleum ether/ethyl acetate: 30/1 to 5/1) to give [1-(benzenesulfonyl)-1H-indol-5-yl]methanol as yellow solid (180 g, 94% yield).

To a solution of [1-(benzenesulfonyl)-1H-indol-5-yl]methanol (34 g, 118.33 mmol) in methylene chloride (500 mL) was added imidazole (24.17 g, 354.99 mmol) and TBSCl (26.75 g, 177.50 mmol). The mixture was stirred at 30° C. for 1 h, quenched by the addition of water (500 mL), and extracted with ethyl acetate (3×500 mL). The combined organic layers were washed with brine (300 mL), dried over anhydrous sodium sulfate, filtered, and concentrated to give crude 1-(benzenesulfonyl)-5-[(tert-butyldimethylsilyl)oxy]-1H-indole (150 g).

To a stirred solution of 1-(benzenesulfonyl)-5-[(tert-butyldimethylsilyl)oxy]-1H-indole (30 g, 74.70 mmol) in anhydrous tetrahydrofuran (18 mL) at −78° C. was added a solution of lithium diisopropylamide (2 M, 112 mL). The mixture was stirred at −78° C. for 10 min, then iodine solution (56.88 g, 224.11 mmol, in 45 mL of tetrahydrofuran) was added. The mixture was stirred at −78° C. for 50 min, quenched with saturated ammonium chloride (1000 mL) and extracted with ethyl acetate (3×1000 mL). The organic layers were washed with aq. Na$_2$S$_2$O$_3$ (1000 mL), and brine (1000 mL), dried over anhydrous sodium sulfate and concentrated to give crude 1-(benzenesulfonyl)-5-[(tert-butyldimethylsilyl)oxy]-2-iodo-1H-indole as a yellow solid (200 g).

To a solution of 1-(benzenesulfonyl)-5-[(tert-butyldimethylsilyl)oxy]-2-iodo-1H-indole (20.0 g, 37.92 mmol) in methanol/water (2.40 L) was added potassium carbonate (5.24 g, 37.92 mmol) in methanol/water (2.40 L). The mixture was stirred at 120° C. for 5 h under a nitrogen atmosphere. The solids were filtered off and washed with methylene chloride. The filtrate was washed with water (2.4 L), brine (2.4 L), dried over anhydrous sodium sulfate, filtered, and concentrated in vacuo. The crude product was purified by flash column chromatography (silica gel, eluting with petroleum ether/ethyl acetate: 1/1) to give (2-iodo-1H-indol-5-yl)methanol as a yellow solid (19 g, 28% yield, 60% purity).

A mixture of (2-iodo-1H-indol-5-yl)methanol (15.83 g, 34.79 mmol) and MnO$_2$ (24.20 g, 278.32 mmol) in methylene chloride (150 mL) was stirred at 30° C. for 5 h under a nitrogen atmosphere. The reaction mixture was filtered using diatomaceous earth and washed with methylene chloride (2×150 mL). The filtrate was washed with brine, dried over anhydrous sodium sulfate, filtered, and concentrated in vacuo. The crude product was purified by flash column chromatography (silica gel, eluting with petroleum ether/ ethyl acetate: 10/1) to give 2-iodo-1H-indole-5-carbaldehyde as a yellow solid (8 g, 66.17% yield, 78% purity). The crude product was used without further purification.

To a solution of 2-iodo-1H-indole-5-carbaldehyde (3 g, 8.63 mmol) in tetrahydrofuran (40 mL) cooled to 0° C. was added sodium hydride (1.04 g, 25.90 mmol, 60% in mineral oil). The mixture was stirred at 0° C. for 30 min under a nitrogen atmosphere, and 2,2,2-trifluoroethyl trifluoromethanesulfonate (5.01 g, 21.58 mmol) was added dropwise to the reaction mixture. The ice bath was then removed, the reaction mixture was stirred for 1 h under a nitrogen atmosphere, quenched with saturated ammonium chloride (100 mL), and extracted with ethyl acetate (2×150 mL). The combined organic layers were washed with brine, dried over anhydrous sodium sulfate, filtered, and concentrated in vacuo. The crude product was purified by flash column chromatography (silica gel, eluting with petroleum ether/ ethyl acetate: 10/1) to give 2-iodo-1-(2,2,2-trifluoroethyl)-1H-indole-5-carbaldehyde as red solid (3 g, 98% yield).

To a solution of 2-methyl-2-[5-(prop-2-ynylamino)-2-pyridyl]propanenitrile (2.40 g, 9.18 mmol) in dimethyl sulfoxide (18 mL) was added N-isopropylpropan-2-amine (3.10 g, 30.60 mmol, 4.3 mL) and CuI (291 mg, 1.53 mmol).

Then, 2-iodo-1-(2,2,2-trifluoroethyl)-1H-indole-5-carbaldehyde (1.80 g, 5.10 mmol) and tetrakis(triphenylphosphine)palladium(0) (589 mg, 510 μmol) were added to the reaction mixture. The mixture was stirred at room temperature for 2 h under a nitrogen atmosphere. The reaction mixture was quenched by EDTA (50 mL) and extracted with ethyl acetate (2×25 mL). The combined organic layers were washed with brine, dried over anhydrous sodium sulfate, filtered, and concentrated in vacuo. The crude product was purified by preparative thin layer chromatography (silica gel, eluting with ethyl acetate/petroleum ether: 1/2) to give 2-[5-({3-[5-formyl-1-(2,2,2-trifluoroethyl)-1H-indol-2-yl]prop-2-yn-1-yl}amino)pyridin-2-yl]-2-methylpropanenitrile as yellow oil (2 g, 92.40% yield).

To a solution of 2-[5-({3-[5-formyl-1-(2,2,2-trifluoroethyl)-1H-indol-2-yl]prop-2-yn-1-yl}amino)pyridin-2-yl]-2-methylpropanenitrile (1 equiv.) and morpholine (1 equiv.) in methylene chloride (2 mL) and methanol (2 mL) was added magnesium sulfate (15 equiv.). After stirring the mixture at room temperature for 12 h, sodium bicarbonate (1 equiv.) and sodium cyanoborohydride (5 equiv.) were added to the reaction mixture. The reaction was stirred at room temperature for 1 h, and the mixture was then quenched by adding saturated sodium bicarbonate (10 mL). The mixture was extracted with ethyl acetate (2×30 mL). The combined organic layers were washed with brine (20 mL), dried over anhydrous sodium sulfate, filtered, and concentrated in vacuo. The crude product was purified by preparative HPLC to give 2-methyl-2-[5-({3-[5-(morpholin-4-ylmethyl)-1-(2,2,2-trifluoroethyl)-1H-indol-2-yl]prop-2-yn-1-yl}amino)pyridin-2-yl]propanenitrile.

LC-MS (ES$^+$, m/z): 496.3 [(M+H)$^+$]

In a manner similar to the method described in Example 205, the following compounds were prepared:

| Ex | Structure | Name | LC-MS (ES$^+$, m/z) |
|---|---|---|---|
| 206 | 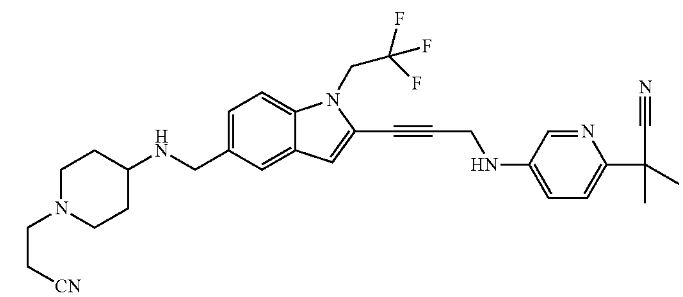 [SMILES: CC(C)(C#N)c1ccc(NCC#Cc2cc3cc(CNC4CCN(CCC#N)CC4)ccc3n2CC(F)(F)F)cn1] | 2-[5-({3-[5-({[1-(2-cyanoethyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile | 562.3 [(M + H)$^+$] |
| 207 | 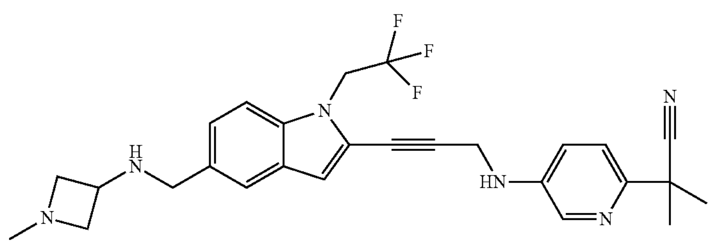 [SMILES: CN1CC(NCc2ccc3c(c2)cc(C#CCNc2ccc(C(C)(C)C#N)nc2)n3CC(F)(F)F)C1] | 2-methyl-2-(5-{[3-(5-{[(1-methylazetidin-3-yl)amino]methyl}-1-(2,2,2-trifluoroethyl)-1H-indol-2-yl)prop-2-yn-1-yl]amino}pyridin-2-yl)propanenitrile | 495.3 [(M + H)$^+$] |
| 208 | 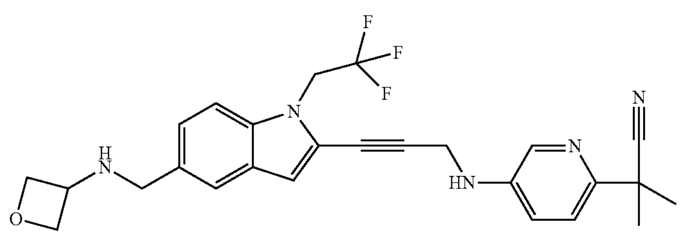 [SMILES: CC(C)(C#N)c1ccc(NCC#Cc2cc3cc(CNC4COC4)ccc3n2CC(F)(F)F)cn1] | 2-methyl-2-(5-{[3-(5-{[(oxetan-3-yl)amino]methyl}-1-(2,2,2-trifluoroethyl)-1H-indol-2-yl)prop-2-yn-1-yl]amino}pyridin-2-yl)propanenitrile | 482.3 [(M + H)$^+$] |
| 209 | 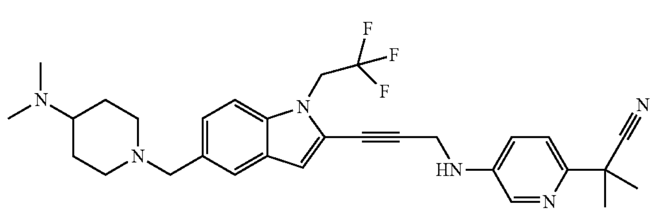 [SMILES: CN(C)C1CCN(Cc2ccc3c(c2)cc(C#CCNc2ccc(C(C)(C)C#N)nc2)n3CC(F)(F)F)CC1] | 2-(5-{[3-(5-{[4-(dimethylamino)-piperidin-1-yl]methyl}-1-(2,2,2-trifluoroethyl)-1H-indol-2-yl)prop-2-yn-1-yl]amino}pyridin-2-yl)-2-methylpropanenitrile | 537.3 [(M + H)$^+$] |

-continued

| Ex | Structure | Name | LC-MS (ES+, m/z) |
|---|---|---|---|
| 210 | 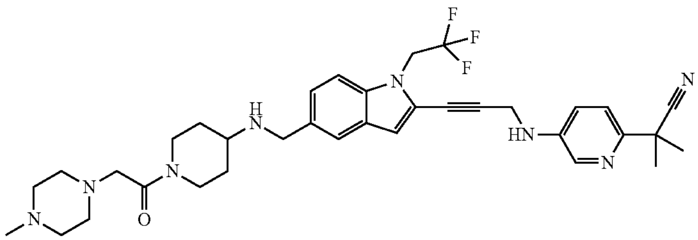 [SMILES: CN1CCN(CC(=O)N2CCC(NCc3ccc4c(c3)cc(C#CCNc3ccc(C(C)(C)C#N)nc3)n4CC(F)(F)F)CC2)CC1] | 2-methyl-2-{5-[(3-{5-[({1-[2-(4-methylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile | 649.4 [(M + H)+] |
| 211 | 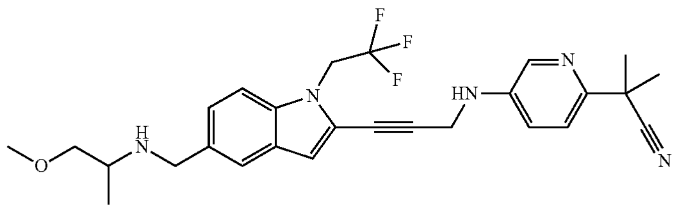 [SMILES: COCC(C)NCc1ccc2c(c1)cc(C#CCNc1ccc(C(C)(C)C#N)nc1)n2CC(F)(F)F] | 2-(5-{[3-(5-{[(1-methoxypropan-2-yl)amino]methyl}-1-(2,2,2-trifluoroethyl)-1H-indol-2-yl)prop-2-yn-1-yl]amino}pyridin-2-yl)-2-methylpropanenitrile | 498.3 [(M + H)+] |
| 212 | 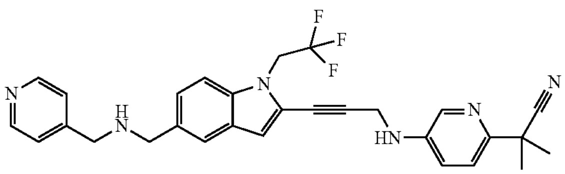 [SMILES: CC(C)(C#N)c1ccc(NCC#Cc2cc3cc(CNCc4ccncc4)ccc3n2CC(F)(F)F)cn1] | 2-methyl-2-(5-{[3-(5-{[(pyridin-4-ylmethyl)amino]methyl}-1-(2,2,2-trifluoroethyl)-1H-indol-2-yl)prop-2-yn-1-yl]amino}pyridin-2-yl)propanenitrile | 517.3 [(M + H)+] |
| 213 | 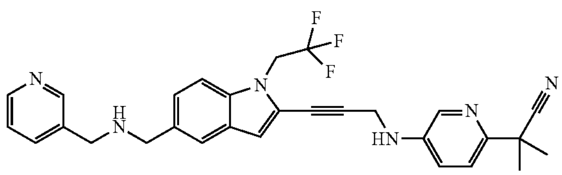 [SMILES: CC(C)(C#N)c1ccc(NCC#Cc2cc3cc(CNCc4cccnc4)ccc3n2CC(F)(F)F)cn1] | 2-methyl-2-(5-{[3-(5-{[(pyridin-3-ylmethyl)amino]methyl}-1-(2,2,2-trifluoroethyl)-1H-indol-2-yl)prop-2-yn-1-yl]amino}pyridin-2-yl)propanenitrile | 517.3 [(M + H)+] |
| 214 | 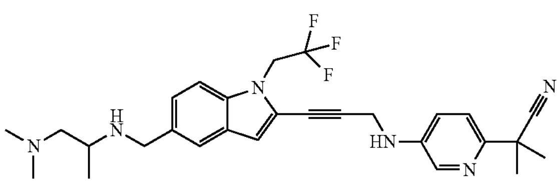 [SMILES: CC(CN(C)C)NCc1ccc2c(c1)cc(C#CCNc1ccc(C(C)(C)C#N)nc1)n2CC(F)(F)F] | 2-[5-({3-[5-({[1-(dimethylamino)-propan-2-yl]amino}methyl)-1-(2,2,2-trifluoroethyl)-1H-indol-2-yl]prop-2-yn-1-yl}amino)pyridin-2-yl]-2-methylpropanenitrile | 511.3 [(M + H)+] |
| 215 | 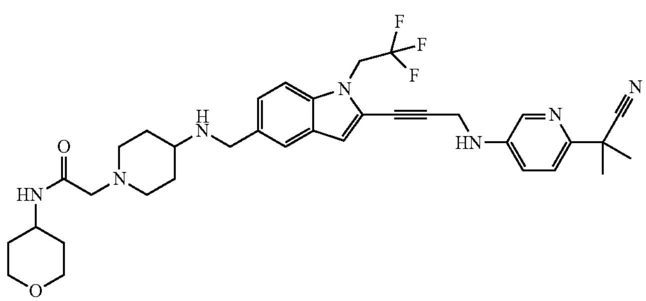 [SMILES: CC(C)(C#N)c1ccc(NCC#Cc2cc3cc(CNC4CCN(CC(=O)NC5CCOCC5)CC4)ccc3n2CC(F)(F)F)cn1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(oxan-4-yl)acetamide | 650.4 [(M + H)+] |
| 216 | 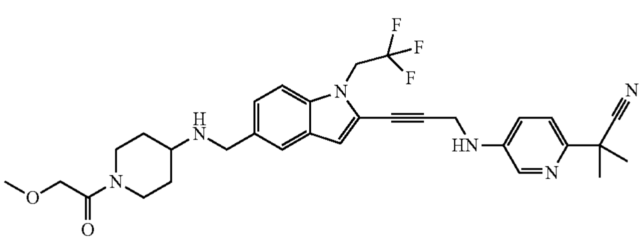 [SMILES: COCC(=O)N1CCC(NCc2ccc3c(c2)cc(C#CCNc2ccc(C(C)(C)C#N)nc2)n3CC(F)(F)F)CC1] | 2-[5-({3-[5-({[1-(2-methoxyacetyl)-piperidin-4-yl]amino}methyl)-1-(2,2,2-trifluoroethyl)-1H-indol-2-yl]prop-2-yn-1-yl}amino)pyridin-2-yl]-2-methylpropanenitrile | 581.4 [(M + H)+] |

-continued

| Ex | Structure | Name | LC-MS (ES+, m/z) |
|---|---|---|---|
| 217 | 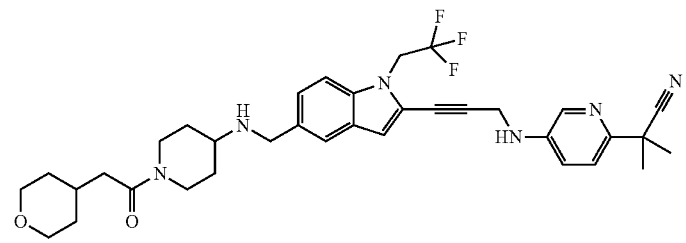 | 2-methyl-2-{5-[(3-{5-[({1-[2-(oxan-4-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile | 635.4 [(M + H)+] |
| 218 | 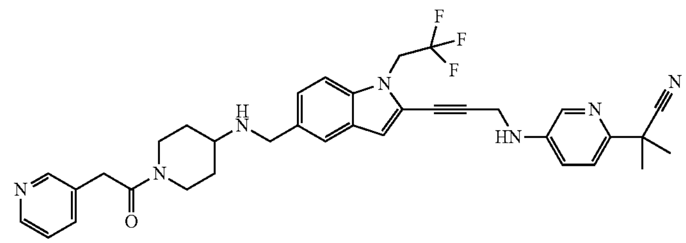 [SMILES: CC(C)(C#N)c1ccc(NCC#Cc2cc3cc(CNC4CCN(C(=O)Cc5cccnc5)CC4)ccc3n2CC(F)(F)F)cn1] | 2-methyl-2-{5-[(3-{5-[({1-[2-(pyridin-3-yl)acetyl]piperidin-4-yl}amino)-methyl]-1-(2,2,2-trifluoroethyl)-1H-indol-2-yl}prop-2-yn-1-yl)amino]-pyridin-2-yl}propanenitrile | 628.4 [(M + H)+] |
| 219 | 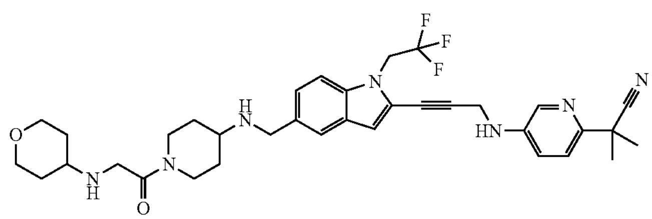 [SMILES: CC(C)(C#N)c1ccc(NCC#Cc2cc3cc(CNC4CCN(C(=O)CNC5CCOCC5)CC4)ccc3n2CC(F)(F)F)cn1] | 2-methyl-2-(5-{[3-(5-{[(1-{2-[(oxan-4-yl)amino]acetyl}piperidin-4-yl)amino]methyl}-1-(2,2,2-trifluoroethyl)-1H-indol-2-yl)prop-2-yn-1-yl]amino}pyridin-2-yl)-propanenitrile | 650.4 [(M + H)+] |
| 220 | 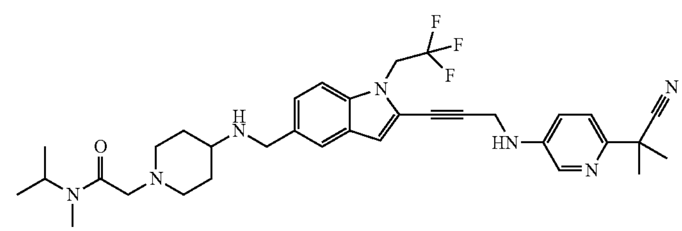 [SMILES: CC(C)N(C)C(=O)CN1CCC(NCc2ccc3c(c2)cc(C#CCNc2ccc(C(C)(C)C#N)nc2)n3CC(F)(F)F)CC1] | 2-[4-({[2-(3-{[6-(1-cyano-1-methylethyl)pyridin-3-yl]amino}prop-1-yn-1-yl)-1-(2,2,2-trifluoroethyl)-1H-indol-5-ylmethyl]amino)piperidin-1-yl]-N-methyl-N-(propan-2-yl)acetamide | 622.4 [(M + H)+] |
| 221 | 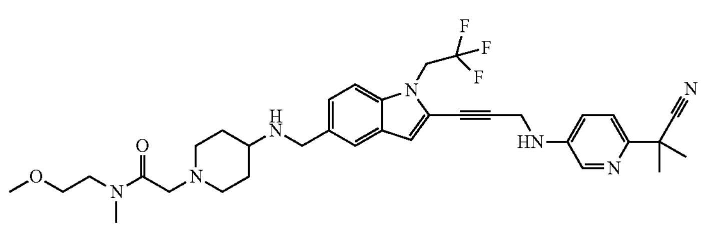 [SMILES: COCCN(C)C(=O)CN1CCC(NCc2ccc3c(c2)cc(C#CCNc2ccc(C(C)(C)C#N)nc2)n3CC(F)(F)F)CC1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(2-methoxyethyl)-N-methylacetamide | 638.4 [(M + H)+] |
| 222 | 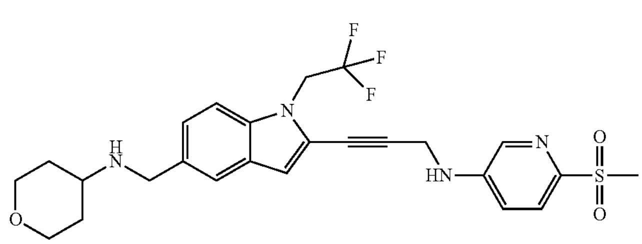 [SMILES: CS(=O)(=O)c1ccc(NCC#Cc2cc3cc(CNC4CCOCC4)ccc3n2CC(F)(F)F)cn1] | 6-methanesulfonyl-N-[3-(5-{[(oxan-4-yl)amino]methyl}-1-(2,2,2-trifluoroethyl)-1H-indol-2-yl)prop-2-yn-1-yl]pyridin-3-amine | 521.3 [(M + H)+] |

-continued

| Ex | Structure | Name | LC-MS (ES+, m/z) |
|---|---|---|---|
| 223 | 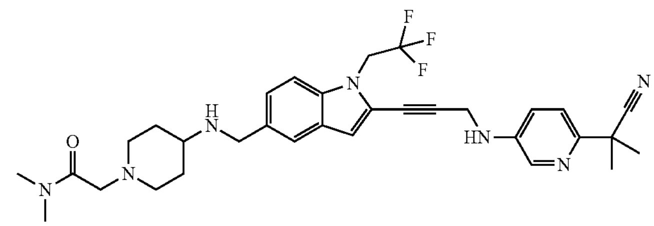 [SMILES: CN(C)C(=O)CN1CCC(NCc2ccc3c(c2)cc(C#CCNc2ccc(C(C)(C)C#N)nc2)n3CC(F)(F)F)CC1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N,N-dimethylacetamide | 594.4 [(M + H)+] |
| 224 | 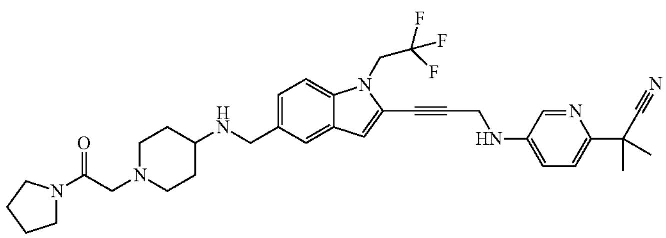 [SMILES: CC(C)(C#N)c1ccc(NCC#Cc2cc3cc(CNC4CCN(CC(=O)N5CCCC5)CC4)ccc3n2CC(F)(F)F)cn1] | 2-methyl-2-{5-[(3-{5-[({1-[2-oxo-2-(pyrrolidin-1-yl)ethyl]piperidin-4-yl}amino)methyl]-1-(2,2,2-trifluoroethyl)-1H-indol-2-yl}prop-2-yn-1-yl)amino]pyridin-2-yl}propanenitrile | 620.4 [(M + H)+] |
| 225 | 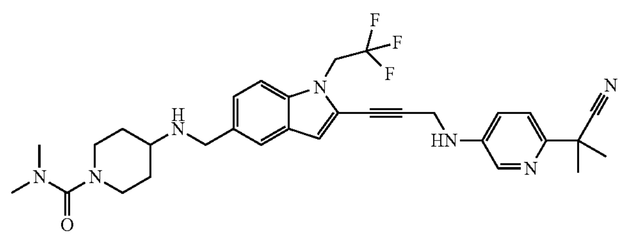 [SMILES: CN(C)C(=O)N1CCC(NCc2ccc3c(c2)cc(C#CCNc2ccc(C(C)(C)C#N)nc2)n3CC(F)(F)F)CC1] | 4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-N,N-dimethylpiperidine-1-carboxamide | 580.4 [(M + H)+] |
| 226 | 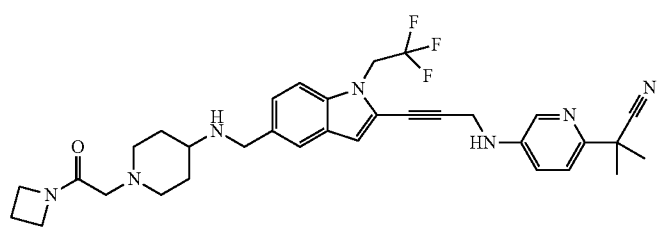 [SMILES: CC(C)(C#N)c1ccc(NCC#Cc2cc3cc(CNC4CCN(CC(=O)N5CCC5)CC4)ccc3n2CC(F)(F)F)cn1] | 2-{5-[(3-{5-[({1-[2-(azetidin-1-yl)-2-oxoethyl]piperidin-4-yl}amino)-methyl]-1-(2,2,2-trifluoroethyl)-1H-indol-2-yl}prop-2-yn-1-yl)amino]-pyridin-2-yl}-2-methylpropanenitrile | 606.4 [(M + H)+] |
| 227 | 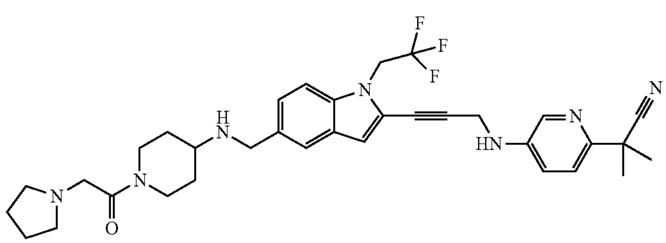 [SMILES: CC(C)(C#N)c1ccc(NCC#Cc2cc3cc(CNC4CCN(C(=O)CN5CCCC5)CC4)ccc3n2CC(F)(F)F)cn1] | 2-methyl-2-{5-[(3-{5-[({1-[2-(pyrrolidin-1-yl)acetyl]piperidin-4-yl}amino)methyl]-1-(2,2,2-trifluoroethyl)-1H-indol-2-yl}prop-2-yn-1-yl)amino]pyridin-2-yl}-propanenitrile | 620.4 [(M + H)+] |
| 228 | 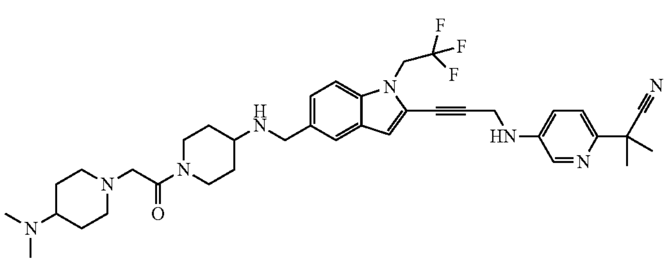 [SMILES: CN(C)C1CCN(CC(=O)N2CCC(NCc3ccc4c(c3)cc(C#CCNc3ccc(C(C)(C)C#N)nc3)n4CC(F)(F)F)CC2)CC1] | 2-(5-{[3-(5-{[(1-{2-[4-(dimethylamino)piperidin-1-yl]acetyl}piperidin-4-yl)amino]-methyl}-1-(2,2,2-trifluoroethyl)-1H-indol-2-yl)prop-2-yn-1-yl]amino}pyridin-2-yl)-2-methylpropanenitrile | 677.5 [(M + H)+] |

-continued

| Ex | Structure | Name | LC-MS (ES+, m/z) |
|---|---|---|---|
| 229 | 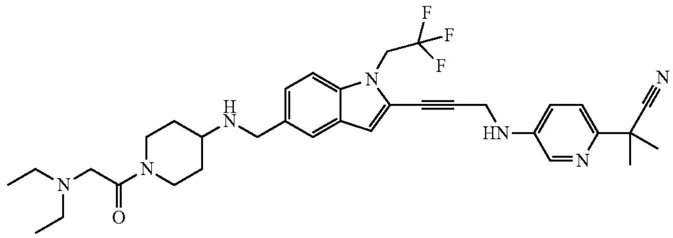 [SMILES: CCN(CC)CC(=O)N1CCC(NCc2ccc3c(c2)cc(C#CCNc2ccc(C(C)(C)C#N)nc2)n3CC(F)(F)F)CC1] | 2-{5-[(3-{5-[({1-[2-(diethylamino)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile | 622.4 [(M + H)+] |
| 230 | 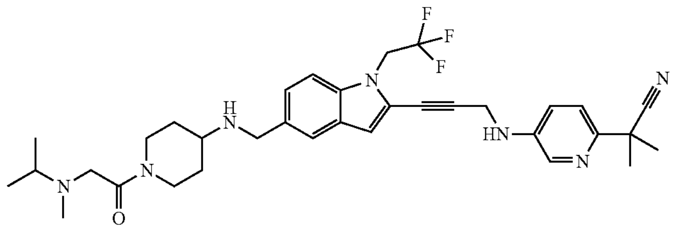 [SMILES: CC(C)N(C)CC(=O)N1CCC(NCc2ccc3c(c2)cc(C#CCNc2ccc(C(C)(C)C#N)nc2)n3CC(F)(F)F)CC1] | 2-methyl-2-(5-{[3-(5-{[(1-{2-[methyl(propan-2-yl)amino]acetyl}piperidin-4-yl)amino]methyl]-1-(2,2,2-trifluoroethyl)-1H-indol-2-yl)prop-2-yn-1-yl]amino}pyridin-2-yl)propanenitrile | 622.4 [(M + H)+] |
| 231 | 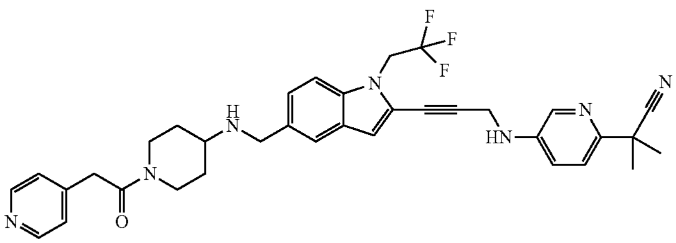 | 2-methyl-2-{5-[(3-{5-[({1-[2-(pyridin-4-yl)acetyl]piperidin-4-yl}amino)methyl]-1-(2,2,2-trifluoroethyl)-1H-indol-2-yl}prop-2-yn-1-yl)amino]pyridin-2-yl}propanenitrile | 628.4 [(M + H)+] |
| 232 | 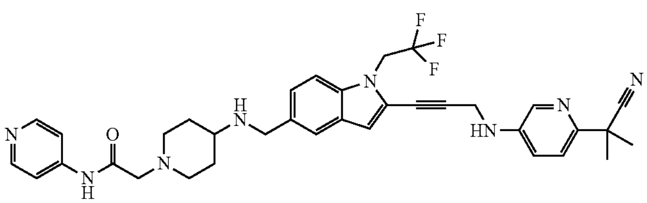 [SMILES: CC(C)(C#N)c1ccc(NCC#Cc2cc3cc(CNC4CCN(CC(=O)Nc5ccncc5)CC4)ccc3n2CC(F)(F)F)cn1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-4-yl)acetamide | 643.4 [(M + H)+] |
| 233 | 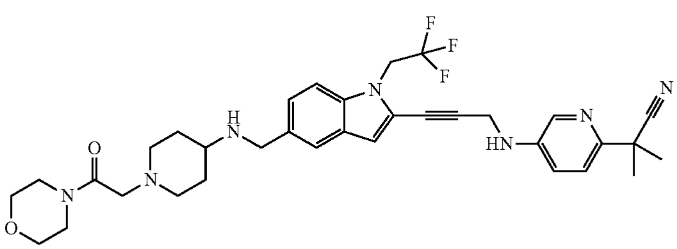 [SMILES: CC(C)(C#N)c1ccc(NCC#Cc2cc3cc(CNC4CCN(CC(=O)N5CCOCC5)CC4)ccc3n2CC(F)(F)F)cn1] | 2-methyl-2-{5-[(3-{5-[({1-[2-(mopholin-4-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile | 636.4 [(M + H)+] |
| 234 | 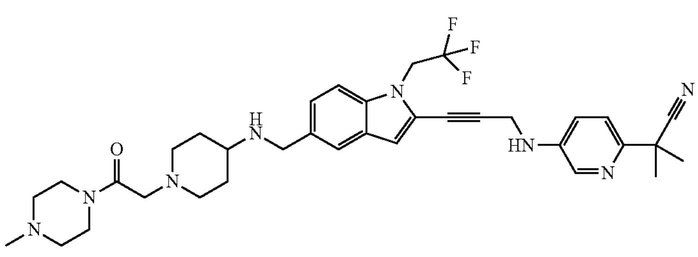 [SMILES: CN1CCN(C(=O)CN2CCC(NCc3ccc4c(c3)cc(C#CCNc3ccc(C(C)(C)C#N)nc3)n4CC(F)(F)F)CC2)CC1] | 2-methyl-2-{5-[(3-{5-[({1-[2-(4-methylpiperazin-1-yl)-2-oxoethyl]piperidin-4-yl}amino)methyl]-1-(2,2,2-trifluoroethyl)-1H-indol-2-yl}prop-2-yn-1-yl)amino]pyridin-2-yl}propanenitrile | 649.4 [(M + H)+] |

-continued

| Ex | Structure | Name | LC-MS (ES+, m/z) |
|---|---|---|---|
| 235 | 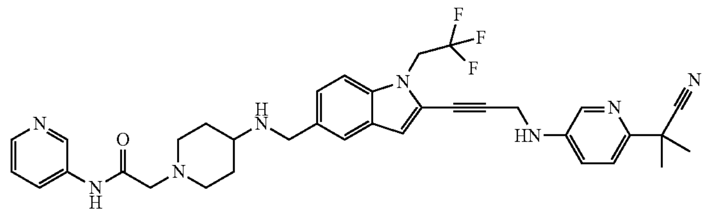 [SMILES: CC(C)(C#N)c1ccc(NCC#Cc2cc3cc(CNC4CCN(CC(=O)Nc5cccnc5)CC4)ccc3n2CC(F)(F)F)cn1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(pyridin-3-yl)acetamide | 643.4 [(M + H)+] |
| 236 | 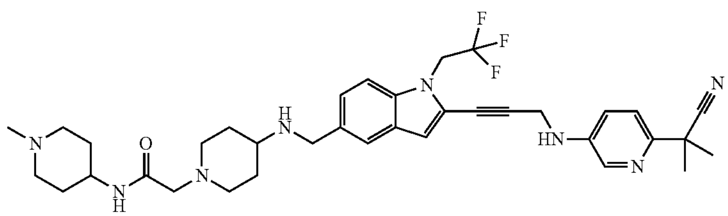 [SMILES: CN1CCC(NC(=O)CN2CCC(NCc3ccc4c(c3)cc(C#CCNc3ccc(C(C)(C)C#N)nc3)n4CC(F)(F)F)CC2)CC1] | 2-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)piperidin-1-yl]-N-(1-methylpiperidin-4-yl)acetamide | 663.5 [(M + H)+] |
| 237 | 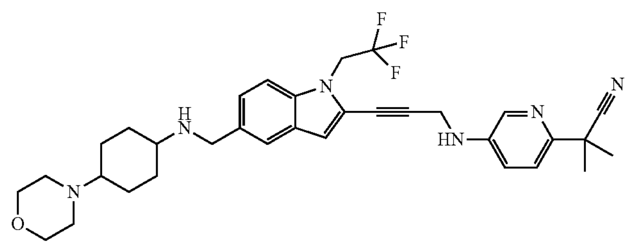 [SMILES: CC(C)(C#N)c1ccc(NCC#Cc2cc3cc(CNC4CCC(N5CCOCC5)CC4)ccc3n2CC(F)(F)F)cn1] | 2-methyl-2-[5-({3-[5-({[4-(morpholin-4-yl)cyclohexyl]amino}methyl)-1-(2,2,2-trifluoroethyl)-1H-indol-2-yl]prop-2-yn-1-yl}amino)pyridin-2-yl]propanenitrile | 593.4 [(M + H)+] |
| 238 | 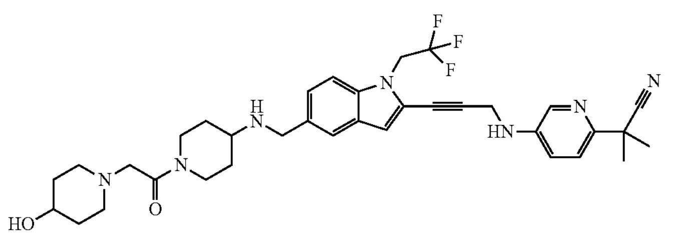 [SMILES: CC(C)(C#N)c1ccc(NCC#Cc2cc3cc(CNC4CCN(C(=O)CN5CCC(O)CC5)CC4)ccc3n2CC(F)(F)F)cn1] | 2-{5-[(3-{5-[({1-[2-(4-hydroxypiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile | 650.4 [(M + H)+] |
| 239 | 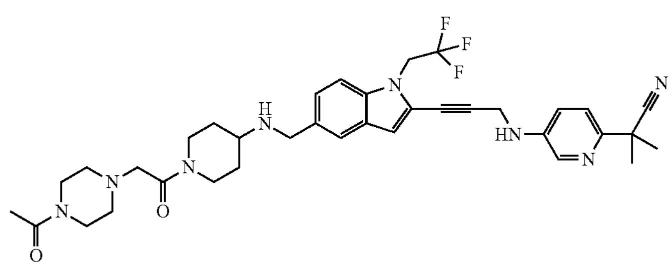 [SMILES: CC(=O)N1CCN(CC(=O)N2CCC(NCc3ccc4c(c3)cc(C#CCNc3ccc(C(C)(C)C#N)nc3)n4CC(F)(F)F)CC2)CC1] | 2-{5-[(3-{5-[({1-[2-(4-acetylpiperazin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile | 677.4 [(M + H)+] |
| 240 | 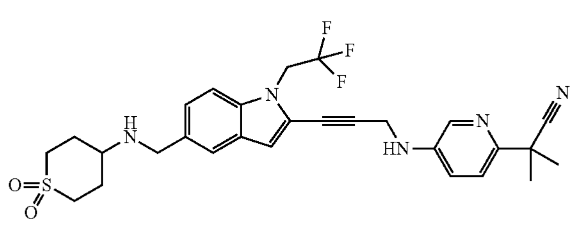 [SMILES: CC(C)(C#N)c1ccc(NCC#Cc2cc3cc(CNC4CCS(=O)(=O)CC4)ccc3n2CC(F)(F)F)cn1] | 2-(5-{[3-(5-{[(1,1-dioxo-1λ⁶-thian-4-yl)amino]methyl}-1-(2,2,2-trifluoroethyl)-1H-indol-2-yl)prop-2-yn-1-yl]amino}pyridin-2-yl)-2-methylpropanenitrile | 558.3 [(M + H)+] |

-continued

| Ex | Name | LC-MS (ES+, m/z) |
|---|---|---|
| 241 | 2-{5-[(3-{5-[({1-[2-(1,1-dioxo-1λ,4-thiomorpholin-4-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile | 684.3 [(M + H)+] |
| 242 | 2-[5-({3-[5-({[1-(4-acetylpiperazine-1-carbonyl)piperidin-4-yl]amino}methyl]-1-(2,2,2-trifluoroethyl)-1H-indol-2-yl}prop-2-yn-1-yl)amino]pyridin-2-yl]-2-methylpropanenitrile | 663.4 [(M + H)+] |
| 243 | 2-(5-{[3-(5-{[(1-{2-[bis(2-hydroxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 654.5 [(M + H)+] |
| 244 | 2-methyl-2-{5-[(3-{5-[({1-[2-(3-oxopiperazin-1-yl)acetyl]piperidin-4-yl}amino)methyl]-1-(2,2,2-trifluoroethyl)-1H-indol-2-yl}prop-2-yn-1-yl)amino]pyridin-2-yl}propanenitrile | 649.5 [(M + H)+] |
| 245 | 2-methyl-2-[5-({3-[5-({[1-(morpholine-4-carbonyl)piperidin-4-yl]amino}-methyl]-1-(2,2,2-trifluoroethyl)-1H-indol-2-yl]prop-2-yn-1-yl}amino)pyridin-2-yl]propanenitrile | 622.4 [(M + H)+] |
| 246 | 2-methyl-2-(5-{[3-(5-{[(1-methylpiperidin-3-yl)amino]methyl}-1-(2,2,2-trifluoroethyl)-1H-indol-2-yl)prop-2-yn-1-yl]amino}pyridin-2-yl)propanenitrile | 523.4 [(M + H)+] |

-continued

| Ex | Structure | Name | LC-MS (ES+, m/z) |
|---|---|---|---|
| 247 | 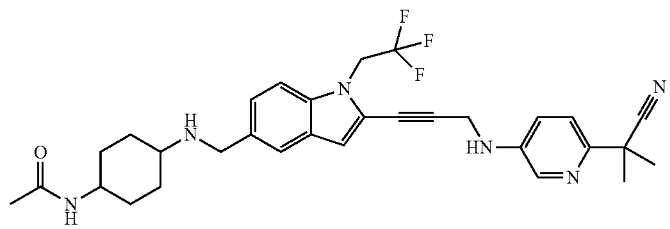 [SMILES: CC(=O)NC1CCC(NCc2ccc3c(c2)cc(C#CCNc2ccc(C(C)(C)C#N)nc2)n3CC(F)(F)F)CC1] | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]acetamide | 565.4 [(M + H)+] |
| 248 | 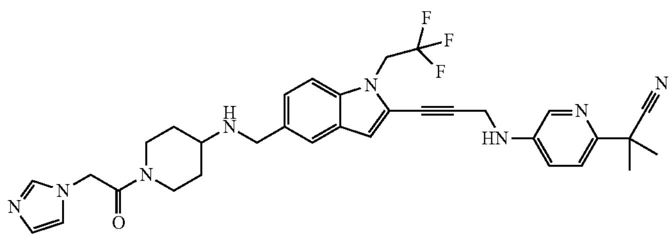 [SMILES: CC(C)(C#N)c1ccc(NCC#Cc2cc3cc(CNC4CCN(C(=O)Cn5ccnc5)CC4)ccc3n2CC(F)(F)F)cn1] | 2-{5-[(3-{5-[({1-[2-(1H-imidazol-1-yl)acetyl]piperidin-4-yl}amino)-methyl]-1-(2,2,2-trifluoroethyl)-1H-indol-2-yl}prop-2-yn-1-yl)amino]pyridin-2-yl}-2-methylpropanenitrile | 617.3 [(M + H)+] |
| 249 | 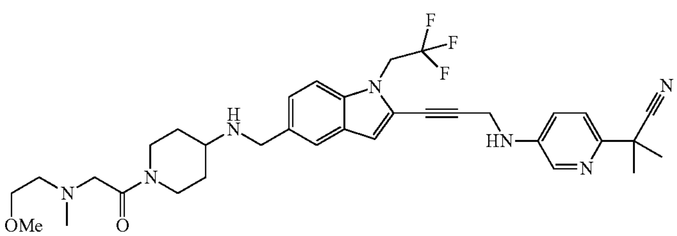 [SMILES: COCCN(C)CC(=O)N1CCC(NCc2ccc3c(c2)cc(C#CCNc2ccc(C(C)(C)C#N)nc2)n3CC(F)(F)F)CC1] | 2-(5-{[3-(5-{[(1-{2-[(2-methoxyethyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 638.4 [(M + H)+] |
| 250 | 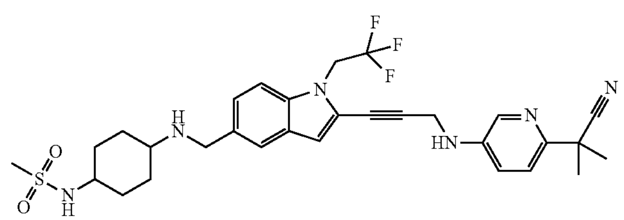 [SMILES: CC(C)(C#N)c1ccc(NCC#Cc2cc3cc(CNC4CCC(NS(C)(=O)=O)CC4)ccc3n2CC(F)(F)F)cn1] | N-[4-({[2-(3-{[6-(1-cyano-1-methylethyl)pyridin-3-yl]amino}prop-1-yn-1-yl)-1-(2,2,2-trifluoroethyl)-1H-indol-5-yl]methyl}amino)-cyclohexyl]methanesulfonamide | 601.4 [(M + H)+] |
| 251 | 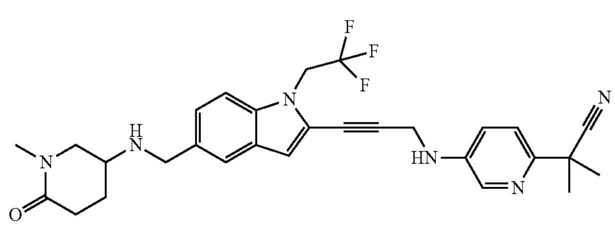 [SMILES: CN1CC(NCc2ccc3c(c2)cc(C#CCNc2ccc(C(C)(C)C#N)nc2)n3CC(F)(F)F)CCC1=O] | 2-methyl-2-(5-{[3-(5-{[(1-methyl-6-oxopiperidin-3-yl)amino]methyl}-1-(2,2,2-trifluoroethyl)-1H-indol-2-yl)prop-2-yn-1-yl]amino}pyridin-2-yl)propanenitrile | 537.3 [(M + H)+] |
| 252 | 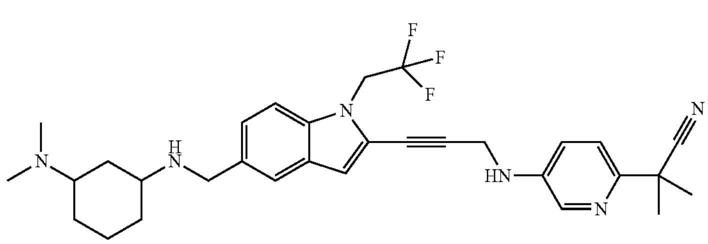 [SMILES: CN(C)C1CCCC(NCc2ccc3c(c2)cc(C#CCNc2ccc(C(C)(C)C#N)nc2)n3CC(F)(F)F)C1] | 2-[5-({3-[5-({[3-(dimethylamino)cyclohexyl]amino}methyl)-1-(2,2,2-trifluoroethyl)-1H-indol-2-yl]prop-2-yn-1-yl}amino)pyridin-2-yl]-2-methylpropanenitrile | 551.4 [(M + H)+] |

-continued

| Ex | Structure | Name | LC-MS (ES+, m/z) |
|---|---|---|---|
| 253 | 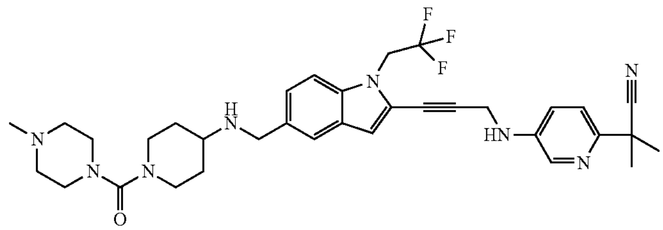 [SMILES: CN1CCN(C(=O)N2CCC(NCc3ccc4c(c3)cc(C#CCNc3ccc(C(C)(C)C#N)nc3)n4CC(F)(F)F)CC2)CC1] | 2-methyl-2-[5-({3-[5-({[1-(4-methylpiperazine-1-carbonyl)piperidin-4-yl]amino}methyl)-1-(2,2,2-trifluoroethyl)-1H-indol-2-yl]prop-2-yn-1-yl}amino)pyridin-2-yl]propanenitrile | 635.4 [(M + H)+] |
| 254 | 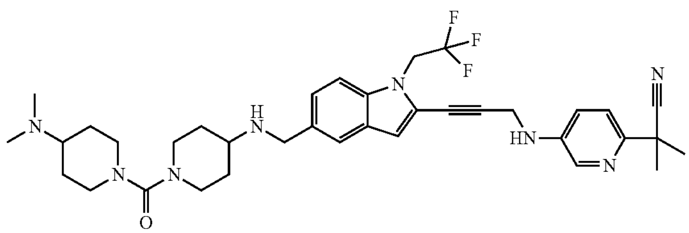 [SMILES: CN(C)C1CCN(C(=O)N2CCC(NCc3ccc4c(c3)cc(C#CCNc3ccc(C(C)(C)C#N)nc3)n4CC(F)(F)F)CC2)CC1] | 2-{5-[(3-{5-[({1-[4-(dimethylamino)piperidine-1-carbonyl]piperidin-4-yl}amino)-methyl]-1-(2,2,2-trifluoromethyl)-1H-indol-2-yl}prop-2-yn-1-yl)amino]pyridin-2-yl}-2-methylpropanenitrile | 663.4 [(M + H)+] |
| 255 | 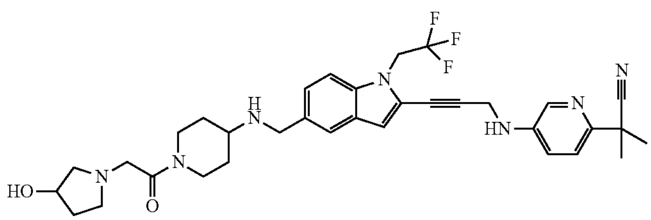 [SMILES: CC(C)(C#N)c1ccc(NCC#Cc2cc3cc(CNC4CCN(C(=O)CN5CCC(O)C5)CC4)ccc3n2CC(F)(F)F)cn1] | 2-{5-[(3-{5-[({1-[2-(3-hydroxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile | 636.4 [(M + H)+] |
| 256 | 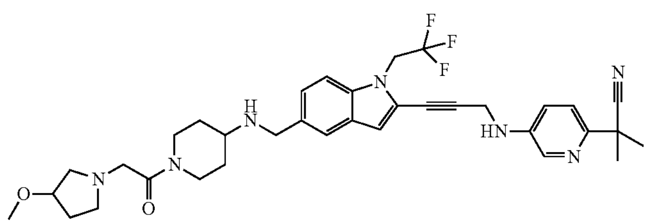 [SMILES: COC1CCN(CC(=O)N2CCC(NCc3ccc4c(c3)cc(C#CCNc3ccc(C(C)(C)C#N)nc3)n4CC(F)(F)F)CC2)C1] | 2-{5-[(3-{5-[({1-[2-(3-methoxypyrrolidin-1-yl)acetyl]-piperidin-4-yl}amino)methyl]-1-(2,2,2-trifluoroethyl)-1H-indol-2-yl}prop-2-yn-1-yl)amino]pyridin-2-yl}-2-methylpropanenitrile | 650.4 [(M + H)+] |
| 257 | 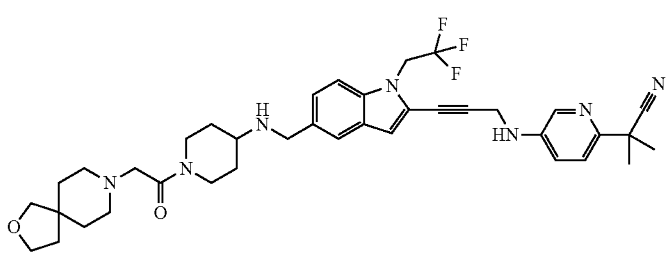 [SMILES: CC(C)(C#N)c1ccc(NCC#Cc2cc3cc(CNC4CCN(C(=O)CN5CCC6(CCOC6)CC5)CC4)ccc3n2CC(F)(F)F)cn1] | 2-methyl-2-[5-({3-[5-({[1-(2-{2-oxa-8-azaspiro[4.5]decan-8-yl}acetyl)-piperidin-4-yl]amino}methyl)-1-(2,2,2-trifluoroethyl)-1H-indol-2-yl]prop-2-yn-1-yl}amino)pyridin-2-yl]propanenitrile | 690.4 [(M + H)+] |
| 258 | 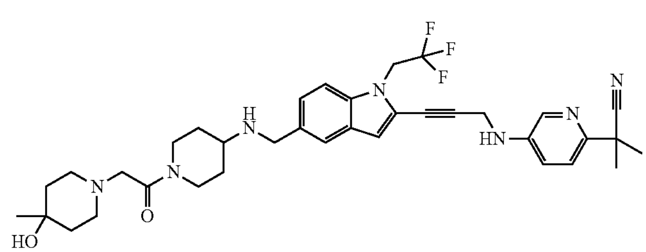 [SMILES: CC1(O)CCN(CC(=O)N2CCC(NCc3ccc4c(c3)cc(C#CCNc3ccc(C(C)(C)C#N)nc3)n4CC(F)(F)F)CC2)CC1] | 2-{5-[(3-{5-[({1-[2-(4-hydroxy-4-methylpiperidin-1-yl)acetyl]piperidin-4-yl}amino)methyl]-1-(2,2,2-trifluoroethyl)-1H-indol-2-yl}prop-2-yn-1-yl)amino]pyridin-2-yl}-2-methylpropanenitrile | 664.5 [(M + H)+] |

| Ex | Structure | Name | LC-MS (ES+, m/z) |
|---|---|---|---|
| 259 | 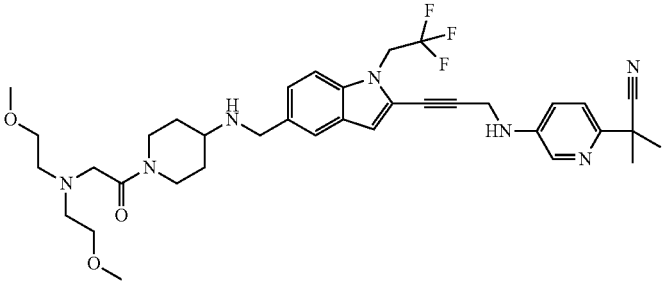 [SMILES: COCCN(CCOC)CC(=O)N1CCC(NCc2ccc3c(c2)cc(C#CCNc2ccc(C(C)(C)C#N)nc2)n3CC(F)(F)F)CC1] | 2-(5-{[3-(5-{[(1-{2-[bis(2-methoxyethyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 682.4 [(M + H)+] |
| 260 | 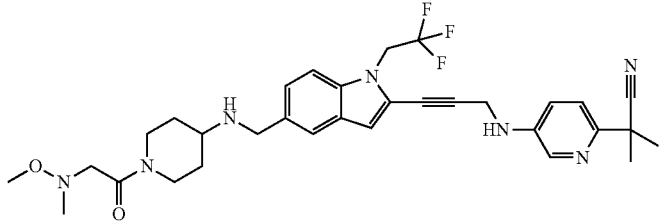 [SMILES: CON(C)CC(=O)N1CCC(NCc2ccc3c(c2)cc(C#CCNc2ccc(C(C)(C)C#N)nc2)n3CC(F)(F)F)CC1] | 2-(5-{[3-(5-{[(1-{2-[methoxy(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 610.3 [(M + H)+] |
| 261 | 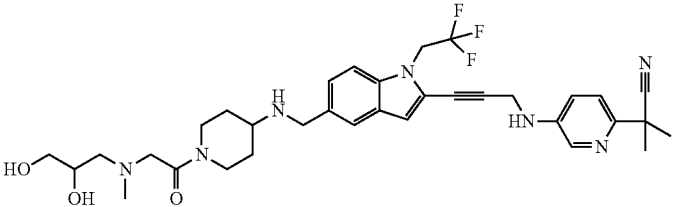 [SMILES: CN(CC(=O)N1CCC(NCc2ccc3c(c2)cc(C#CCNc2ccc(C(C)(C)C#N)nc2)n3CC(F)(F)F)CC1)CC(O)CO] | 2-(5-{[3-(5-{[(1-{2-[(2,3-dihydroxypropyl)(methyl)amino]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 654.4 [(M + H)+] |
| 262 | 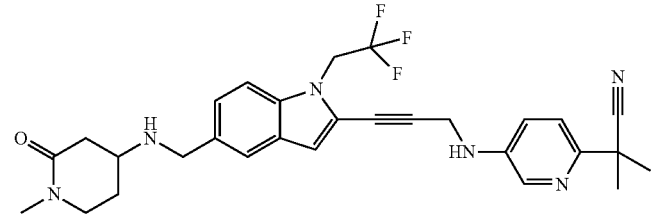 [SMILES: CN1CCC(NCc2ccc3c(c2)cc(C#CCNc2ccc(C(C)(C)C#N)nc2)n3CC(F)(F)F)CC1=O] | 2-methyl-2-(5-{[3-(5-{[(1-methyl-2-oxopiperidin-4-yl)amino]methyl}-1-(2,2,2-trifluoroethyl)-1H-indol-2-yl)prop-2-yn-1-yl]amino}pyridin-2-yl)propanenitrile | 537.3 [(M + H)+] |
| 263 | 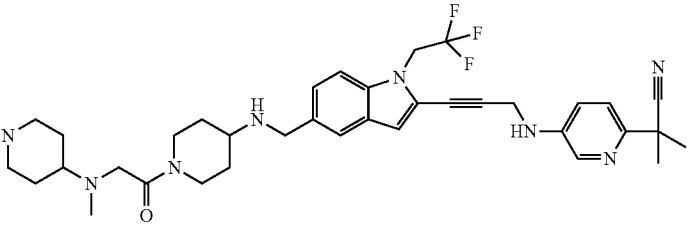 | 2-methyl-2-(5-{[3-(5-{[(1-{2-[methyl(1-methylpiperidin-4-yl)amino]acetyl}piperidin-4-yl)amino]methyl}-1-(2,2,2-trifluoroethyl)-1H-indol-2-yl)prop-2-yn-1-yl]amino}pyridin-2-yl)propanenitrile | 677.3 [(M + H)+] |
| 264 | 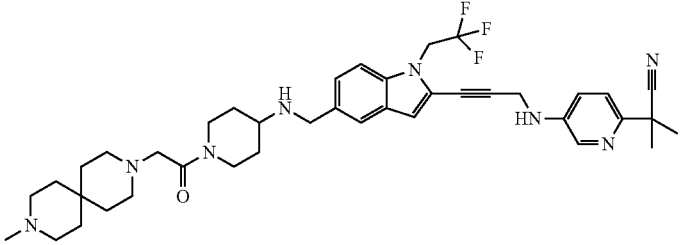 [SMILES: CN1CCC2(CC1)CCN(CC(=O)N1CCC(NCc3ccc4c(c3)cc(C#CCNc3ccc(C(C)(C)C#N)nc3)n4CC(F)(F)F)CC1)CC2] | 2-methyl-2-[5-({3-[5-({[1-(2-{9-methyl-3,9-diazaspiro[5.5]undecan-3-yl}acetyl)piperidin-4-yl]amino}methyl)-1-(2,2,2-trifluoroethyl)-1H-indol-2-yl]prop-2-yn-1-yl}amino)pyridin-2-yl]propanenitrile | 717.5 [(M + H)+] |

-continued

| Ex | Structure | Name | LC-MS (ES+, m/z) |
|---|---|---|---|
| 265 | 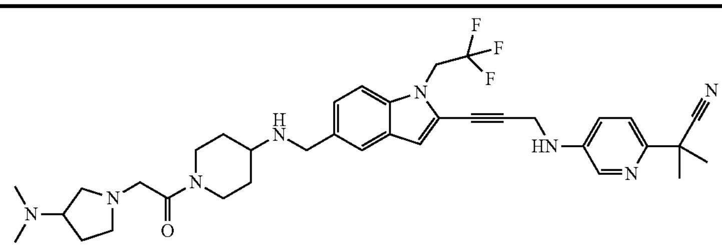 | 2-(5-{[3-(5-{[(1-{2-[3-(dimethyl-amino)pyrrolidin-1-yl]acetyl}piperidin-4-yl)amino]methyl}-1-(2,2,2-trifluoroethyl)-1H-indol-2-yl)prop-2-yn-1-yl]amino}pyridin-2-yl)-2-methylpropanenitrile | 663.5 [(M + H)+] |

Example 266: Preparation of N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine

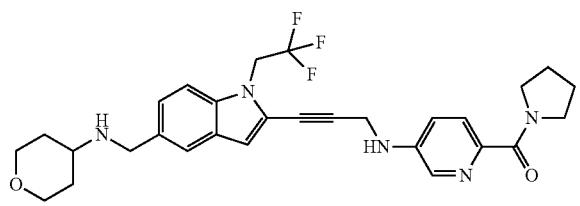 [SMILES: O=C(c1ccc(NCC#Cc2cc3cc(CNC4CCOCC4)ccc3n2CC(F)(F)F)cn1)N1CCCC1]

To a solution of 2-iodo-1-(2,2,2-trifluoroethyl)-1H-indole-5-carbaldehyde (1 equiv.) in methylene chloride (20 mL) was added tetrahydro-2H-pyran-4-amine (8 equiv.) and magnesium sulfate (10 equiv.). The reaction mixture was then stirred for 2 h at room temperature under a nitrogen atmosphere. Sodium cyanoborohydride (4 equiv.) was then added to the reaction, and the mixture was stirred for 1 h under a nitrogen atmosphere. The reaction mixture was poured into an aqueous sodium bicarbonate solution (50 mL) and extracted with methylene chloride (100 mL). The combined organic layers were washed with water (50 mL), brine (50 mL), dried over anhydrous sodium sulfate, filtered, and concentrated in vacuo. The crude residue was purified by flash column chromatography (silica gel, eluting with methylene chloride/methanol: 40/1~20/1) to give N-((2-iodo-1-(2,2,2-trifluoroethyl)-1H-indol-5-yl)methyl)tetrahydro-2H-pyran-4-amine as yellow solid.

To a solution of 5-((tert-butoxycarbonyl)(prop-2-yn-1-yl)amino)picolinic acid (1 equiv.) and pyrrolidine (1.2 equiv.) in methylene chloride (5 mL) were added triethylamine (2 equiv.) and HATU (1.20 equiv.). The reaction was stirred at 20° C. for 1 h, and water (20 mL) was added. The mixture was extracted with methylene chloride (3×20 mL). The combined organic layers were washed with brine (30 mL), dried over anhydrous sodium sulfate, filtered, and concentrated in vacuo. The crude product was purified by flash column chromatography (silica gel, eluting with petroleum ether/ethyl acetate: 4/1 to 2/1) to give tert-butyl prop-2-yn-1-yl(6-(pyrrolidine-1-carbonyl)pyridin-3-yl)carbamate as a light yellow oil. The crude product was used in the next step without further purification.

A solution of tert-butyl prop-2-yn-1-yl(6-(pyrrolidine-1-carbonyl)pyridin-3-yl)carbamate (1 equiv.) in HCl/ethyl acetate (5 mL) was stirred at room temperature for 2 h. The reaction mixture was then concentrated in vacuo to give crude (5-(prop-2-yn-1-ylamino)pyridin-2-yl)(pyrrolidin-1-yl)methanone as yellow solid. The crude product was used in the next step without further purification.

In a manner similar to the method described in Example 205, N-{[2-iodo-1-(2,2,2-trifluoroethyl)-1H-indol-5-yl]methyl}oxan-4-amine was coupled with (5-(prop-2-yn-1-ylamino)pyridin-2-yl)(pyrrolidin-1-yl)methanone to give N-[3-(5-{[(oxan-4-yl)amino]methyl}-1-(2,2,2-trifluoroethyl)-1H-indol-2-yl)prop-2-yn-1-yl]-6-(pyrrolidine-1-carbonyl)pyridin-3-amine.

LC-MS (ES+, m/z): 540.3 [(M+H)+]

Starting with 2-iodo-1-(2,2,2-trifluoroethyl)-1H-indole-5-carbaldehyde and using the procedure described in Example 266, the following compounds were prepared:

| Ex | Structure | Name | LC-MS (ES+, m/z) |
|---|---|---|---|
| 267 | 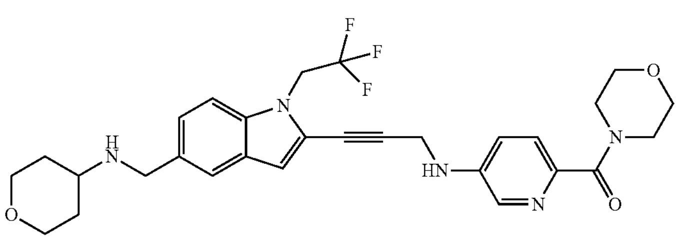 [SMILES: O=C(c1ccc(NCC#Cc2cc3cc(CNC4CCOCC4)ccc3n2CC(F)(F)F)cn1)N1CCOCC1] | 6-(morpholine-4-carbonyl)-N-[3-(5-{[(oxan-4-yl)amino]methyl}-1-(2,2,2-trifluoroethyl)-1H-indol-2-yl)prop-2-yn-1-yl]pyridin-3-amine | 556.3 [(M + H)+] |

-continued

| Ex | Structure | Name | LC-MS (ES+, m/z) |
|---|---|---|---|
| 268 | 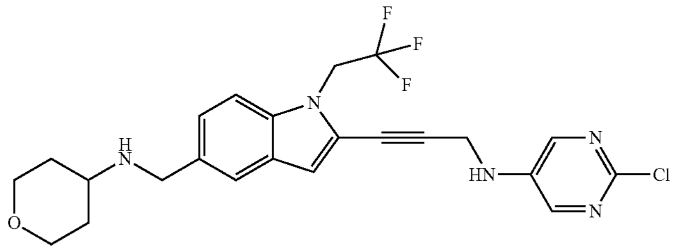 [SMILES: FC(F)(F)Cn1c(C#CCNc2cnc(Cl)nc2)cc2cc(CNC3CCOCC3)ccc21] | 2-chloro-N-[3-(5-{[(oxan-4-yl)amino]-methyl}-1-(2,2,2-trifluoroethyl)-1H-indol-2-yl)prop-2-yn-1-yl]pyrimidin-5-amine | 478.2 [(M + H)+] |
| 269 | 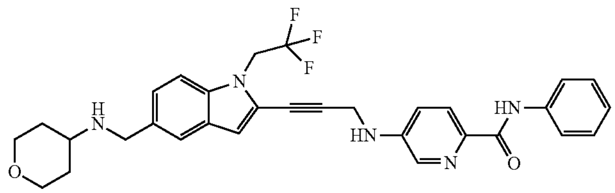 [SMILES: O=C(Nc1ccccc1)c1ccc(NCC#Cc2cc3cc(CNC4CCOCC4)ccc3n2CC(F)(F)F)cn1] | 5-{[3-(5-{[(oxan-4-yl)amino]methyl}-1-(2,2,2-trifluoroethyl)-1H-indol-2-yl)prop-2-yn-1-yl]amino}-N-phenylpyridine-2-carboxamide | 562.3 [(M + H)+] |
| 270 | 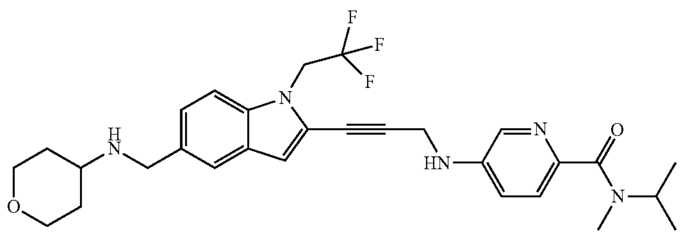 [SMILES: CC(C)N(C)C(=O)c1ccc(NCC#Cc2cc3cc(CNC4CCOCC4)ccc3n2CC(F)(F)F)cn1] | N-methyl-5-{[3-(5-{[(oxan-4-yl)amino]methyl}-1-(2,2,2-trifluoroethyl)-1H-indol-2-yl)prop-2-yn-1-yl]amino}-N-(propan-2-yl)pyridine-2-carboxamide | 542.4 [(M + H)+] |
| 271 | 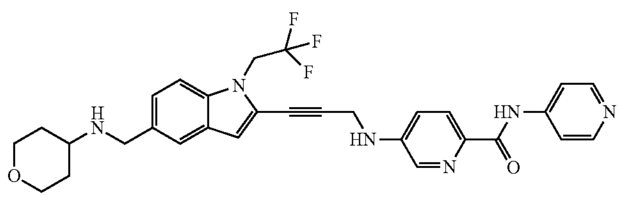 [SMILES: O=C(Nc1ccncc1)c1ccc(NCC#Cc2cc3cc(CNC4CCOCC4)ccc3n2CC(F)(F)F)cn1] | 5-{[3-(5-{[(oxan-4-yl)amino]methyl}-1-(2,2,2-trifluoroethyl)-1H-indol-2-yl)prop-2-yn-1-yl]amino}-N-(pyridin-4-yl)pyridine-2-carboxmamide | 563.3 [(M + H)+] |
| 272 | 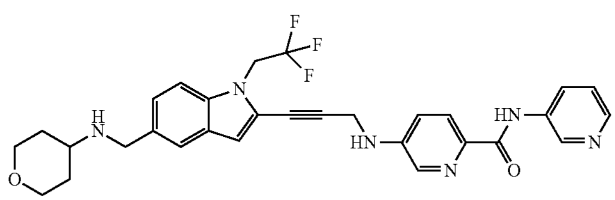 [SMILES: O=C(Nc1cccnc1)c1ccc(NCC#Cc2cc3cc(CNC4CCOCC4)ccc3n2CC(F)(F)F)cn1] | 5-{[3-(5-{[(oxan-4-yl)amino]methyl}-1-(2,2,2-trifluoroethyl)-1H-indol-2-yl)prop-2-yn-1-yl]amino}-N-(pyridin-3-yl)pyridine-2-carboxamide | 563.3 [(M + H)+] |
| 273 | 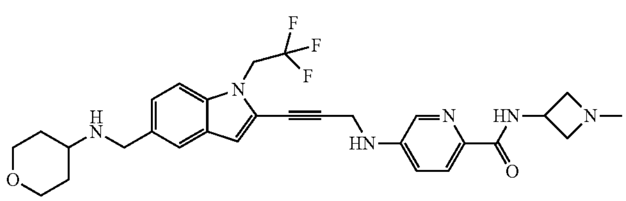 [SMILES: CN1CC(NC(=O)c2ccc(NCC#Cc3cc4cc(CNC5CCOCC5)ccc4n3CC(F)(F)F)cn2)C1] | N-(1-methylazetidin-3-yl)-5-{[3-(5-{[(oxan-4-yl)amino]methyl}-1-(2,2,2-trifluoroethyl)-1H-indol-2-yl)prop-2-yn-1-yl]amino}pyridine-2-carboxamide | 555.3 [(M + H)+] |
| 274 | 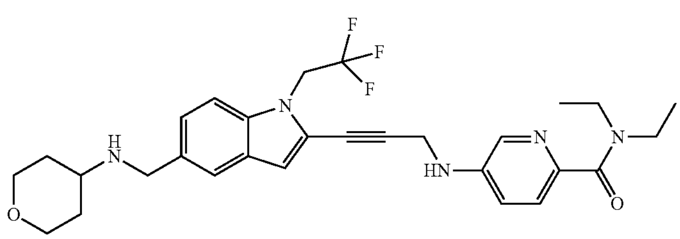 [SMILES: CCN(CC)C(=O)c1ccc(NCC#Cc2cc3cc(CNC4CCOCC4)ccc3n2CC(F)(F)F)cn1] | N,N-diethyl-5-{[3-(5-{[(oxan-4-yl)amino]methyl}-1-(2,2,2-trifluoroethyl)-1H-indol-2-yl)prop-2-yn-1-yl]amino}pyridine-2-carboxamide | 542.4 [(M + H)+] |

-continued

| Ex | Structure | Name | LC-MS (ES+, m/z) |
|---|---|---|---|
| 275 | 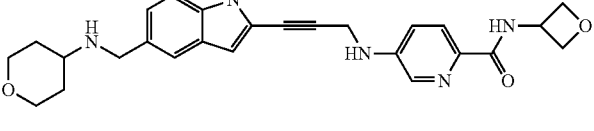 | 5-{[3-(5-{[(oxan-4-yl)amino]methyl}-1-(2,2,2-trifluoroethyl)-1H-indol-2-yl)prop-2-yn-1-yl]amino}-N-(oxetan-3-yl)pyridine-2-carboxamide | 542.3 [(M + H)+] |
| 276 | 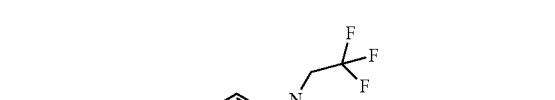 | 1-(4-{[(2-{3-[(2-tert-butylpyrimidin-5-yl)amino]prop-1-yn-1-yl}-1-(2,2,2-trifluoroethyl)-1H-indol-5-yl)methyl]amino}piperidin-1-yl)-2-(dimethylamino)ethan-1-one | 584.4 [(M + H)+] |
| 277 | 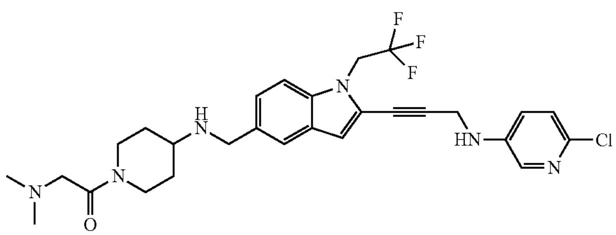 [SMILES: CN(C)CC(=O)N1CCC(NCc2ccc3c(c2)cc(C#CCNc2ccc(Cl)nc2)n3CC(F)(F)F)CC1] | 1-(4-{[(2-{3-[(6-chloropyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one | 561.3 [(M + H)+] |
| 278 | 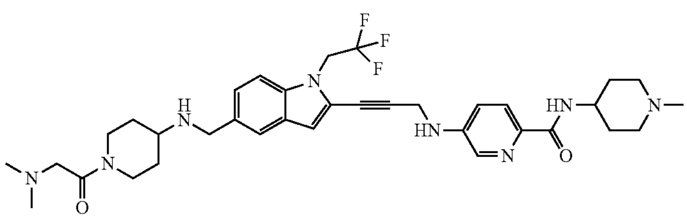 | 5-[(3-{5-[({1-[2-(dimethylamino)-acetyl]piperidin-4-yl}amino)methyl]-1-(2,2,2-trifluoroethyl)-1H-indol-2-yl}prop-2-yn-1-yl)amino]-N-(1-methylpiperidin-4-yl)pyridine-2-carboxamide | 667.5 [(M + H)+] |
| 279 | 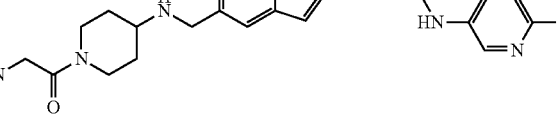 | 1-(4-{[(2-{3-[(4-chloro-3-fluorophenyl)amino]prop-1-yn-1-yl}-1-(2,2,2-trifluoroethyl)-1H-indol-5-yl)methyl]amino}piperidin-1-yl)-2-(dimethylamino)ethan-1-one | 578.3 [(M + H)+] |
| 280 | 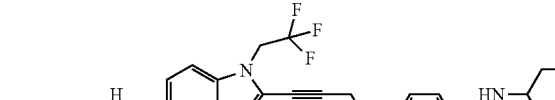 | 2-(dimethylamino)-1-(4-{[(2-{3-[(6-methylpyridin-3-yl)amino]prop-1-yn-1-yl}-1-(2,2,2-trifluoroethyl)-1H-indol-5-yl)methyl]amino}piperidin-1-yl)ethan-1-one | 541.3 [(M + H)+] |

-continued

| Ex | Structure | Name | LC-MS (ES+, m/z) |
|---|---|---|---|
| 281 | 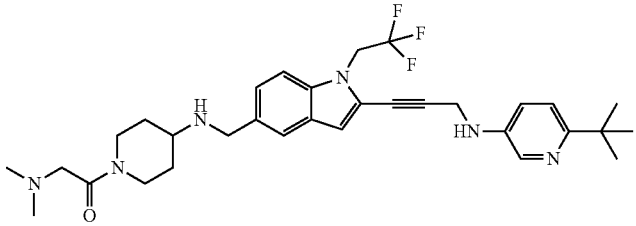 [SMILES: CN(C)CC(=O)N1CCC(NCc2ccc3c(c2)cc(C#CCNc2ccc(C(C)(C)C)nc2)n3CC(F)(F)F)CC1] | 1-(4-{[(2-{3-[(6-tert-butylpyridin-3-yl)amino]prop-1-yn-1-yl}-1-(2,2,2-trifluoroethyl)-1H-indol-5-yl)methyl]amino}piperidin-1-yl)-2-(dimethylamino)ethan-1-one | 583.4 [(M + H)+] |
| 282 | 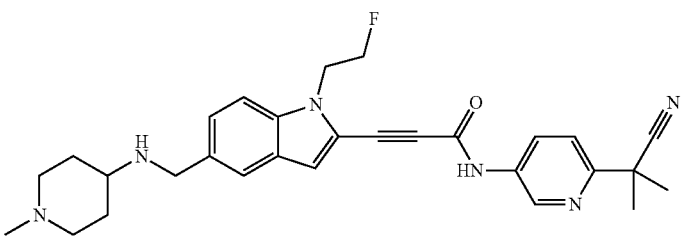 [SMILES: CN1CCC(NCc2ccc3c(c2)cc(C#CC(=O)Nc2ccc(C(C)(C)C#N)nc2)n3CCF)CC1] | N-[6-(1-cyano-1-methylethyl)pyridin-3-yl]-3-[1-(2-fluoroethyl)-5-{[(1-methylpiperidin-4-yl)amino]methyl}-1H-indol-2-yl]prop-2-ynamide | 501.3 [(M + H)+] |
| 283 | 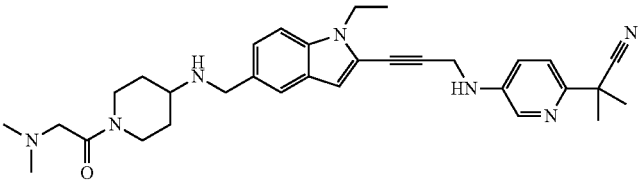 [SMILES: CCn1c(C#CCNc2ccc(C(C)(C)C#N)nc2)cc2cc(CNC3CCN(C(=O)CN(C)C)CC3)ccc21] | 2-{5-[(3-{5-[({1-[2-(dimethylamino)acetyl]piperidin-4-yl}amino)methyl]-1-ethyl-1H-indol-2-yl}prop-2-yn-1-yl)amino]pyridin-2-yl}-2-methylpropanenitrile | 540.4 [(M + H)+] |
| 284 | 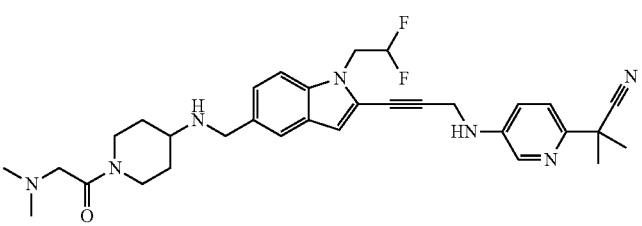 [SMILES: CN(C)CC(=O)N1CCC(NCc2ccc3c(c2)cc(C#CCNc2ccc(C(C)(C)C#N)nc2)n3CC(F)F)CC1] | 2-[5-({3-[1-(2,2-difluoroethyl)-5-[({1-[2-(dimethylamino)acetyl]piperidin-4-yl}amino)methyl]-1H-indol-2-yl]prop-2-yn-1-yl}amino)pyridin-2-yl]-2-methylpropanenitrile | 576.4 [(M + H)+] |
| 285 | 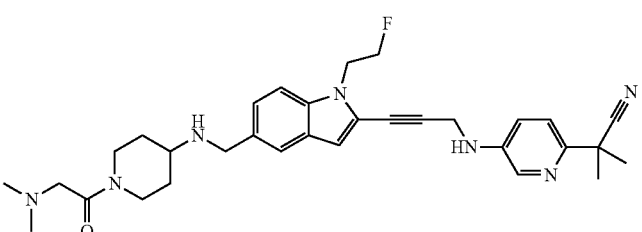 | 2-{5-[(3-{5-[({1-[2-(dimethylamino)acetyl]piperidin-4-yl}amino)methyl]-1-(2-fluoroethyl)-1H-indol-2-yl}prop-2-yn-1-yl)amino]pyridin-2-yl}-2-methylpropanenitrile | 558.4 [(M + H)+] |
| 286 | 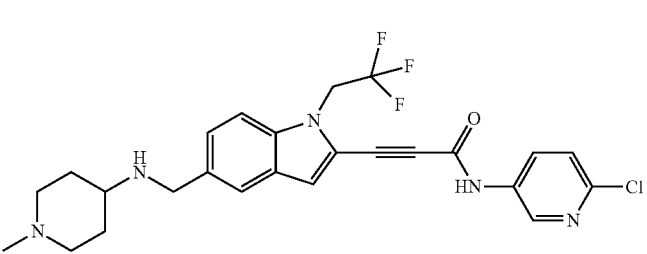 [SMILES: CN1CCC(NCc2ccc3c(c2)cc(C#CC(=O)Nc2ccc(Cl)nc2)n3CC(F)(F)F)CC1] | N-(6-chloropyridin-3-yl)-3-(5-{[(1-methylpiperidin-4-yl)amino]methyl}-1-(2,2,2-trifluoroethyl)-1H-indol-2-yl)prop-2-ynamide | 504.2 [(M + H)+] |

| Ex | Structure | Name | LC-MS (ES+, m/z) |
|---|---|---|---|
| 287 | 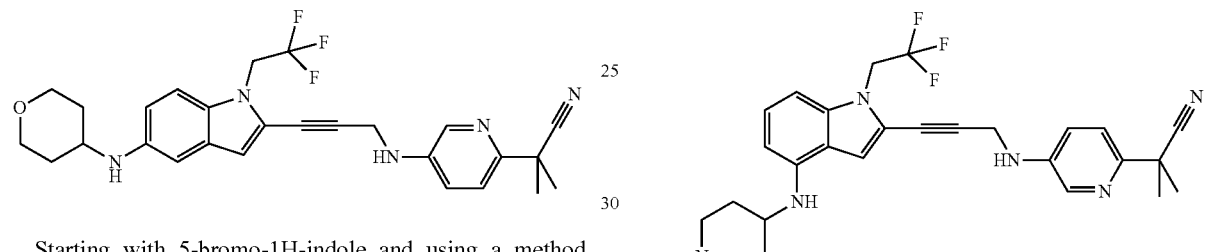 | 2-(5-{[3-(5-{[(1-acetylpiperidin-4-yl)amino]methyl}-1-(oxiran-2-ylmethyl)-1H-indol-2-yl)prop-2-yn-1-yl]amino}pyridin-2-yl)-2-methylpropanenitrile | 525.3 [(M + H)+] |

Example 288: Preparation of 2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile

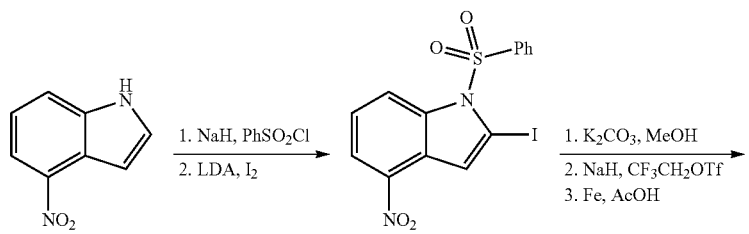

Starting with 5-bromo-1H-indole and using a method similar to that described in Example 1, 2-methyl-2-{5-[(3-{5-[(oxan-4-yl)amino]-1-(2,2,2-trifluoroethyl)-1H-indol-2-yl}prop-2-yn-1-yl)amino]pyridin-2-yl}propanenitrile was prepared.

LC-MS (ES+, m/z): 496.3 [(M+H)+]

Example 289: Preparation of 2-{5-[(3-{4-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile

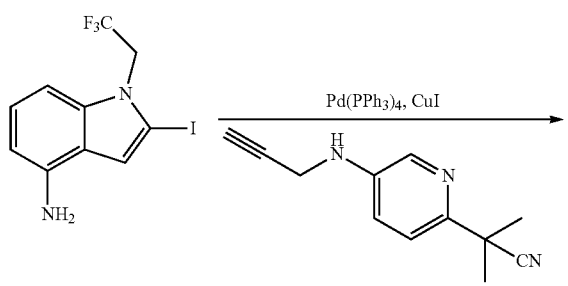

Synthetic Scheme

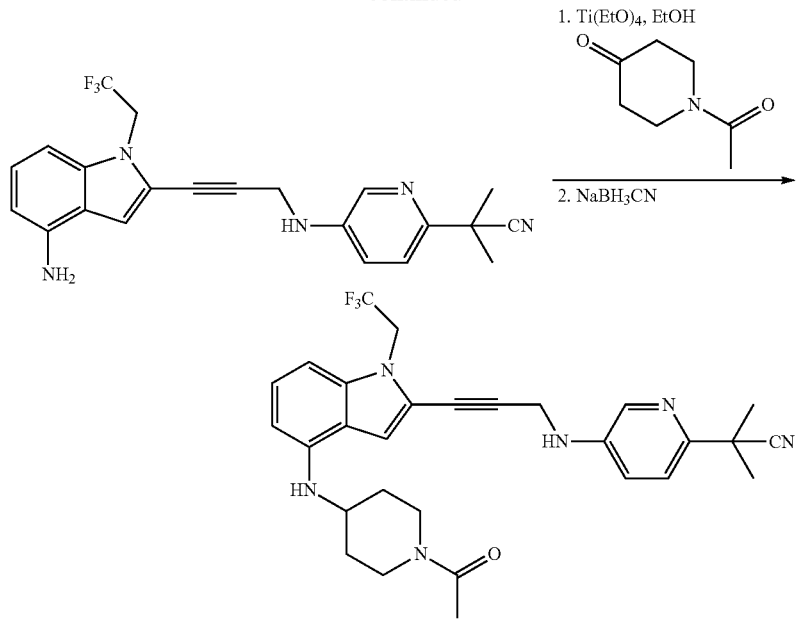

To a solution of 4-nitro-indole (1 equiv.) in dimethylformamide was added sodium hydride (1.50 equiv.) and benzenesulfonyl chloride (1.0 equiv.). The mixture was stirred at 0~30° C. for 2 h, and quenched with aqueous ammonium chloride at 0° C. The mixture was filtered, the solids were washed with water and petroleum ether, and the resulting solution was concentrated and dried in vacuo to give 4-nitro-1-(phenylsulfonyl)-1H-indole.

To a stirred solution of 4-nitro-1-(phenylsulfonyl)-1H-indole (1.0 equiv.) in anhydrous tetrahydrofuran at −78° C. was added a solution of lithium diisopropylamide (2 M, 3.0 equiv.). The resulting mixture was stirred at −78° C. for 60 min, and a solution of iodine (1.5 equiv.) in tetrahydrofuran was added dropwise. After stirring at −78° C. for 30 min, the mixture was quenched with saturated ammonium chloride and extracted with ethyl acetate. The combined organic layers were washed with aqueous $Na_2S_2O_3$ and brine, dried over anhydrous sodium sulfate, filtered, and concentrated in vacuo to give crude 2-iodo-4-nitro-1-(phenylsulfonyl)-1H-indole which was used without further purification.

In a similar method as described in Example 205, 2-iodo-4-nitro-1-(phenylsulfonyl)-1H-indole was treated with potassium carbonate in methanol to give 2-iodo-4-nitro-1H-indole.

To a solution of 2-iodo-4-nitro-1H-indole (1.0 equiv.) in tetrahydrofuran was added sodium hydride (5.0 equiv.) at 0° C. The mixture was stirred at 0~25° C. for 30 min, and $CF_3CH_2OTf$ (4.0 equiv.) was added to the reaction mixture. After stirring the reaction at room temperature for 2 h, the reaction was quenched by adding water at 0° C., and extracted with ethyl acetate. The combined organic layers were washed with brine, dried over anhydrous sodium sulfate, filtered, and concentrated in vacuo. The crude product was purified by recrystallization with a mixture of ethyl acetate and petroleum ether to give 2-iodo-4-nitro-1-(2,2,2-trifluoroethyl)-1H-indole as a yellow solid.

To a solution of 2-iodo-4-nitro-1-(2,2,2-trifluoroethyl)-1H-indole (1.0 equiv.) in acetic acid was added Fe (6.0 equiv.). The mixture was stirred at 50° C. for 2 h then poured into water 0° C. (using a magnet to remove Fe powder) and filtered to give a crude product. The crude product was taken up in ethyl acetate and washed with brine, dried over anhydrous sodium sulfate, filtered and concentrated. The concentrated solution was added dropwise to petroleum ether to precipitate out the product. 2-Iodo-1-(2,2,2-trifluoroethyl)-1H-indol-4-amine was obtained by filtration as a yellow solid.

To a solution of 2-methyl-2-(5-(prop-2-yn-1-ylamino)pyridin-2-yl)propanenitrile (693 mg, 2.94 mmol, prepared from 2-(5-aminopyridin-2-yl)-2-methylpropanenitrile and propargyl bromide) in dimethyl sulfoxide (5 mL) was added N-isopropylpropan-2-amine (892 mg, 8.82 mmol) and CuI (84 mg, 441 μmol). 2-Iodo-1-(2,2,2-trifluoroethyl)indol-4-amine (500 mg, 1.47 mmol) and tetrakis(triphenylphosphine)palladium(0) (170 mg, 147 μmol) were then added. The resulting reaction mixture was stirred at room temperature for 2 h under a nitrogen atmosphere, and the reaction was then quenched with an EDTA solution (5 mL). The reaction mixture was extracted with ethyl acetate (2×5 mL), and the combined organic layers were concentrated in vacuo. The residue was purified by preparative thin layer chromatography (silica gel, eluting with 1/1 mixture of ethyl acetate/petroleum ether) to give 2-(5-((3-(4-amino-1-(2,2,2-trifluoroethyl)-1H-indol-2-yl)prop-2-yn-1-yl)amino)pyridin-2-yl)-2-methylpropanenitrile as a black-brown solid (1.0 g, 73.25% yield, 88.6% purity).

To a solution of 2-(5-((3-(4-amino-1-(2,2,2-trifluoroethyl)-1H-indol-2-yl)prop-2-yn-1-yl)amino)pyridin-2-yl)-2-methylpropanenitrile (150 mg, 364.59 μmol) in ethanol (3 mL) was added 1-acetylpiperidin-4-one (5 equiv.) and tetraethoxytitanium (83 mg, 364.59 μmol). The mixture was stirred under 50° C. for 2 h, and sodium cyanoborohydride (115 mg, 1.82 mmol) was added. After stirring the reaction at 50° C. for 1 h, the reaction mixture was poured into a saturated solution of sodium bicarbonate (10 mL). The resulting mixture was then filtered, and the filtrate was extracted with ethyl acetate (2×20 mL). The combined organic layers were concentrated in vacuo, and the crude residue was purified by preparative HPLC to give 2-{5-[(3-{14-[(1-acetylpiperidin-4-yl)amino]-1-(2,2,2-trifluoroethyl)-1H-indol-2-yl}prop-2-yn-1-yl)amino]pyridin-2-yl}-2-methylpropanenitrile as a yellow solid.

LC-MS (ES$^+$, m/z): 537.1 [(M+H)$^+$]

Starting with 2-iodo-1-(2,2,2-trifluoroethyl)-1H-indol-4-amine and using a procedure similar to that described in Example 289, the following compounds were prepared:

| Ex | Structure | Name | LC-MS (ES$^+$, m/z) |
|---|---|---|---|
| 290 | 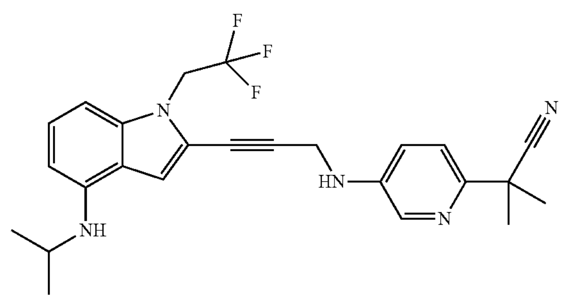 [SMILES: CC(C)Nc1cccc2c1cc(C#CCNc1ccc(C(C)(C)C#N)nc1)n2CC(F)(F)F] | 2-methyl-2-{5-[(3-{4-[(propan-2-yl)amino]-1-(2,2,2-trifluoroethyl)-1H-indol-2-yl}prop-2-yn-1-yl)amino]pyridin-2-yl}propanenitrile | 454.3 [(M + H)$^+$] |
| 291 | 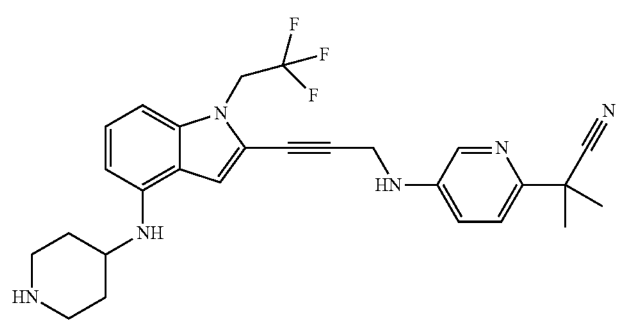 [SMILES: CC(C)(C#N)c1ccc(NCC#Cc2cc3c(NC4CCNCC4)cccc3n2CC(F)(F)F)cn1] | 2-methyl-2-{5-[(3-{4-[(piperidin-4-yl)amino]-1-(2,2,2-trifluoroethyl)-1H-indol-2-yl}prop-2-yn-1-yl)amino]pyridin-2-yl}propanenitrile | 495.3 [(M + H)$^+$] |
| 292 | 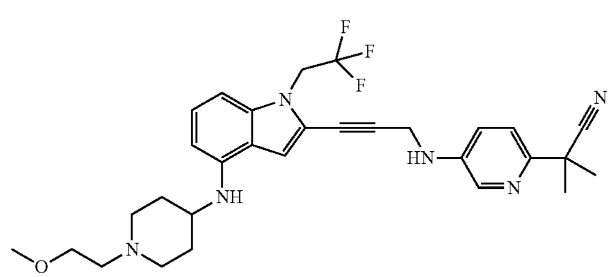 [SMILES: COCCN1CCC(Nc2cccc3c2cc(C#CCNc2ccc(C(C)(C)C#N)nc2)n3CC(F)(F)F)CC1] | 2-(5-{[3-(4-{[1-(2-methoxyethyl)-piperidin-4-yl]amino}-1-(2,2,2-trifluoroethyl)-1H-indol-2-yl)prop-2-yn-1-yl]amino}pyridin-2-yl)-2-methylpropanenitrile | 553.2 [(M + H)$^+$] |
| 293 | 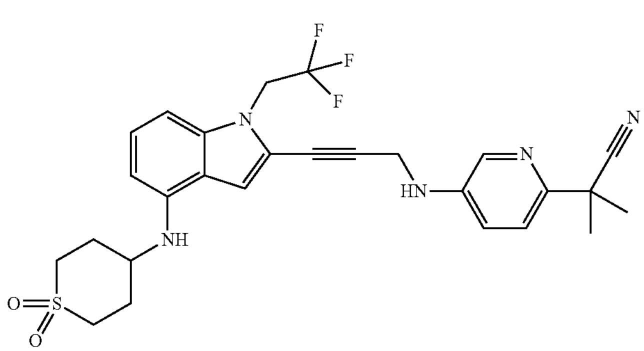 [SMILES: CC(C)(C#N)c1ccc(NCC#Cc2cc3c(NC4CCS(=O)(=O)CC4)cccc3n2CC(F)(F)F)cn1] | 2-{5-[(3-{4-[(1,1-dioxo-1$\lambda^6$-thian-4-yl)amino]-1-(2,2,2-trifluoroethyl)-1H-indol-2-yl}prop-2-yn-1-yl)amino]pyridin-2-yl}-2-methylpropanenitrile | 544.2 [(M + H)$^+$] |

-continued

| Ex | Structure | Name | LC-MS (ES+, m/z) |
|---|---|---|---|
| 294 | 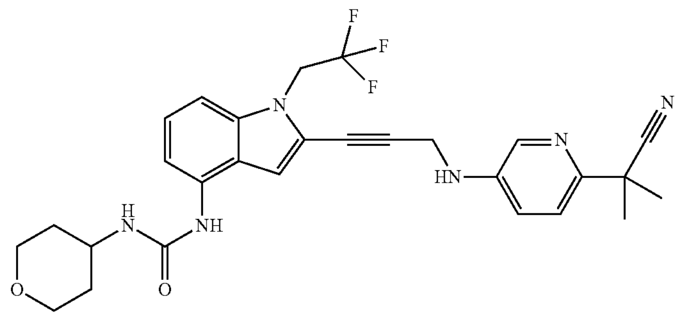 [SMILES: CC(C)(C#N)c1ccc(NCC#Cc2cc3c(NC(=O)NC4CCOCC4)cccc3n2CC(F)(F)F)cn1] | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(oxan-4-yl)urea | 539.3 [(M + H)+] |
| 295 | 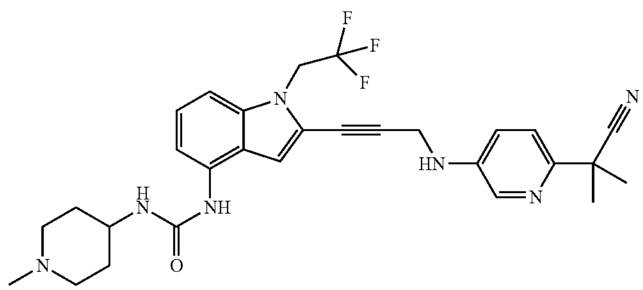 [SMILES: CN1CCC(NC(=O)Nc2cccc3c2cc(C#CCNc2ccc(C(C)(C)C#N)nc2)n3CC(F)(F)F)CC1] | 3-[2-(3-{[6-(1-cyano-1-methylethyl)-pyridin-3-yl]amino}prop-1-yn-1-yl)-1-(2,2,2-trifluoroethyl)-1H-indol-4-yl]-1-(1-methylpiperidin-4-yl)urea | 552.3 [(M + H)+] |
| 296 | 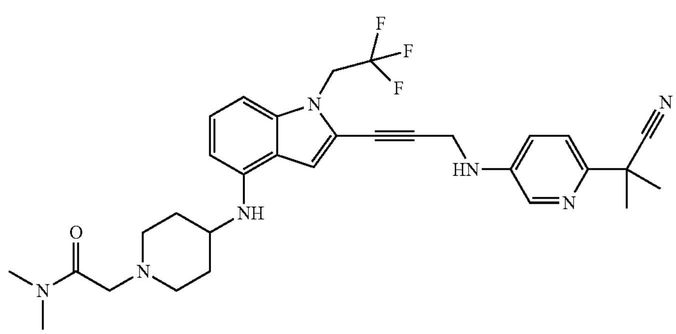 | 2-(4-{[2-(3-{[6-(1-cyano-1-methylethyl)-pyridin-3-yl]amino}prop-1-yn-1-yl)-1-(2,2,2-trifluoroethyl)-1H-indol-4-yl]amino}piperidin-1-yl)-N,N-dimethylacetamide | 580.4 [(M + H)+] |
| 297 | 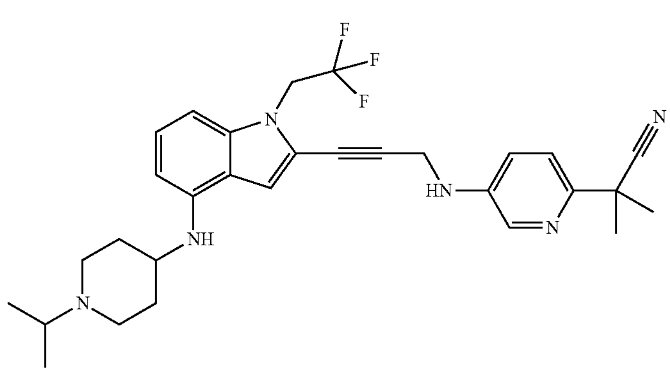 [SMILES: CC(C)N1CCC(Nc2cccc3c2cc(C#CCNc2ccc(C(C)(C)C#N)nc2)n3CC(F)(F)F)CC1] | 2-methyl-2-(5-{[3-(4-{[1-(propan-2-yl)piperidin-4-yl]amino}-1-(2,2,2-trifluoroethyl)-1H-indol-2-yl)prop-2-yn-1-yl]amino}pyridin-2-yl)propanenitrile | 537.2 [(M + H)+] |

-continued

| Ex | Structure | Name | LC-MS (ES+, m/z) |
|---|---|---|---|
| 298 | 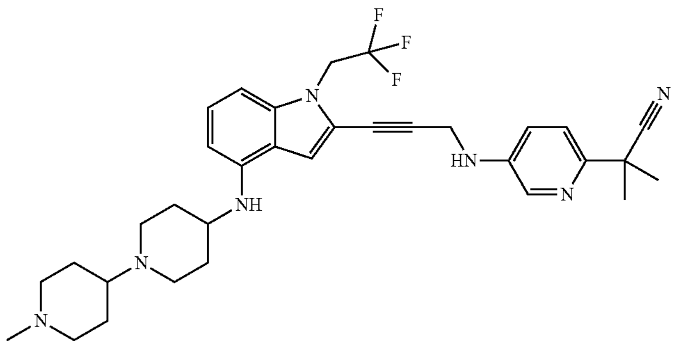 [SMILES: CN1CCC(N2CCC(Nc3cccc4c3cc(C#CCNc3ccc(C(C)(C)C#N)nc3)n4CC(F)(F)F)CC2)CC1] | 2-methyl-2-(5-{[3-(4-{[1-(1-methylpiperidin-4-yl)piperidin-4-yl]amino}-1-(2,2,2-trifluoroethyl)-1H-indol-2-yl)prop-2-yn-1-yl]amino}pyridin-2-yl)propanenitrile | 592.4 [(M + H)+] |
| 299 | 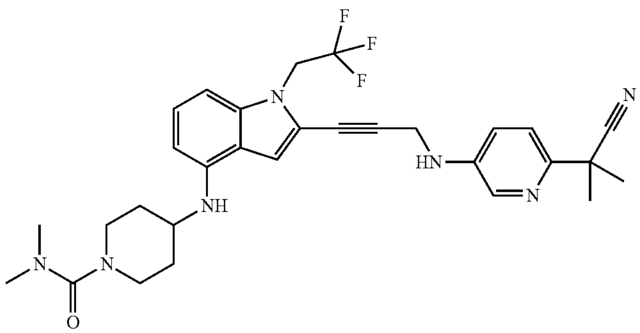 [SMILES: CN(C)C(=O)N1CCC(Nc2cccc3c2cc(C#CCNc2ccc(C(C)(C)C#N)nc2)n3CC(F)(F)F)CC1] | 4-{[2-(3-{[6-(1-cyano-1-methylethyl)-pyridin-3-yl]amino}prop-1-yn-1-yl)-1-(2,2,2-trifluoroethyl)-1H-indol-4-yl]amino}-N,N-dimethylpiperidine-1-carboxamide | 566.4 [(M + H)+] |
| 300 | 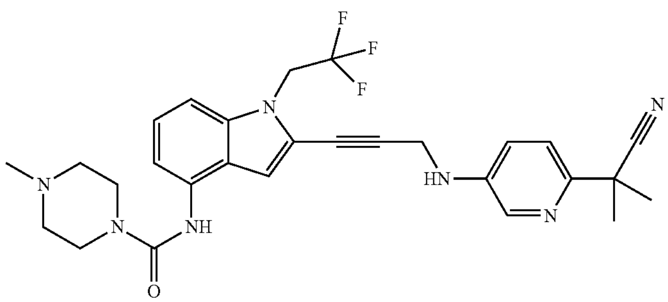 [SMILES: CN1CCN(C(=O)Nc2cccc3c2cc(C#CCNc2ccc(C(C)(C)C#N)nc2)n3CC(F)(F)F)CC1] | N-[2-(3-{[6-(1-cyano-1-methylethyl)-pyridin-3-yl]amino}prop-1-yn-1-yl)-1-(2,2,2-trifluoroethyl)-1H-indol-4-yl]-4-methylpiperazine-1-carboxamide | 538.3 [(M + H)]+ |
| 301 | 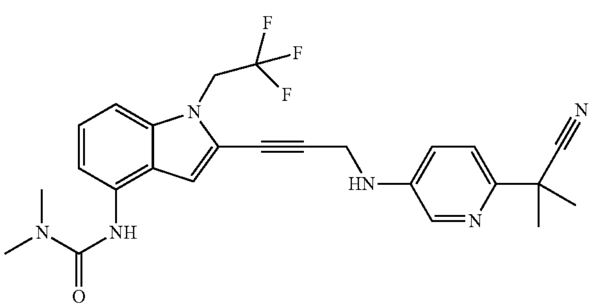 [SMILES: CN(C)C(=O)Nc1cccc2c1cc(C#CCNc1ccc(C(C)(C)C#N)nc1)n2CC(F)(F)F] | 1-[2-(3-{[6-(1-cyano-1-methylethyl)pyridin-3-yl]amino}prop-1-yn-1-yl)-1-(2,2,2-trifluoroethyl)-1H-indol-4-yl]-3,3-dimethylurea | 483.3 [(M + H)+] |
| 302 | 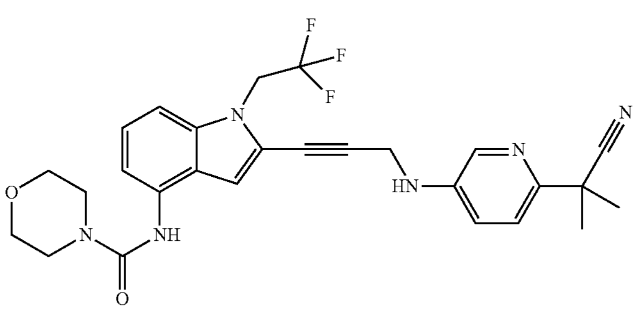 [SMILES: CC(C)(C#N)c1ccc(NCC#Cc2cc3c(NC(=O)N4CCOCC4)cccc3n2CC(F)(F)F)cn1] | N-[2-(3-{[6-(1-cyano-1-methylethyl)-pyridin-3-yl]amino}prop-1-yn-1-yl)-1-(2,2,2-trifluoroethyl)-1H-indol-4-yl]morpholine-4-carboxamide | 525.3 [(M + H)+] |

-continued

| Ex | Structure | Name | LC-MS (ES+, m/z) |
|---|---|---|---|
| 303 | 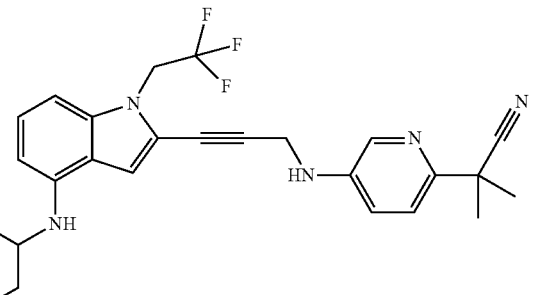 | 2-{5-[(3-{4-[(4-hydroxycyclohexyl)-amino]-1-(2,2,2-trifluoroethyl)-1H-indol-2-yl}prop-2-yn-1-yl)amino]pyridin-2-yl}-2-methylpropanenitrile | 510.3 [(M + H)+] |
| 304 | 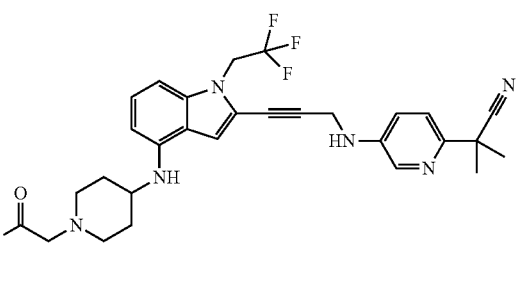 | 2-methyl-2-[5-({3-[4-({1-[2-(4-methylpiperazin-1-yl)-2-oxoethyl]-piperidin-4-yl}amino)-1-(2,2,2-trifluoroethyl)-1H-indol-2-yl]prop-2-yn-1-yl}amino)pyridin-2-yl]propanenitrile | 635.4 [(M + H)+] |
| 305 | 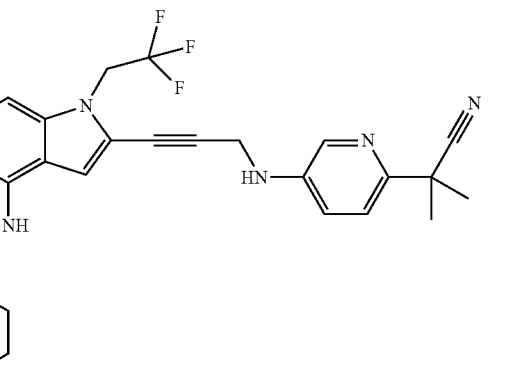 | 2-methyl-2-{5-[(3-{4-[(oxan-4-ylmethyl)amino]-1-(2,2,2-trifluoroethyl)-1H-indol-2-yl}prop-2-yn-1-yl)amino]pyridin-2-yl}propanenitrile | 510.1 [(M + H)+] |
| 306 | 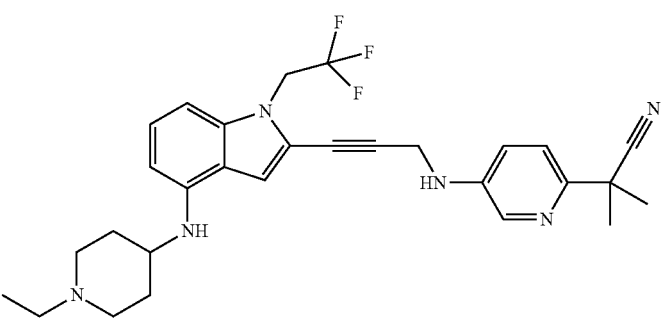 [SMILES: CCN1CCC(Nc2cccc3c2cc(C#CCNc2ccc(C(C)(C)C#N)nc2)n3CC(F)(F)F)CC1] | 2-{5-[(3-{4-[(1-ethylpiperidin-4-yl)amino]-1-(2,2,2-trifluoroethyl)-1H-indol-2-yl}prop-2-yn-1-yl)amino]pyridin-2-yl}-2-methylpropanenitrile | 523.4 [(M + H)+] |

-continued

| Ex | Structure | Name | LC-MS (ES+, m/z) |
|---|---|---|---|
| 307 | 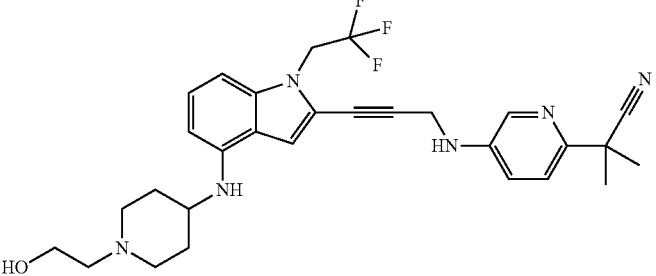 | 2-(5-{[3-(4-{[1-(2-hydroxyethyl)piperidin-4-yl]amino}-1-(2,2,2-trifluoroethyl)-1H-indol-2-yl)prop-2-yn-1-yl]amino}pyridin-2-yl)-2-methylpropanenitrile | 539.2 [(M + H)+] |
| 308 | 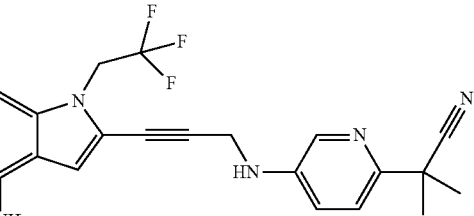 | 2-{5-[(3-{4-[(1-methanesulfonylpiperidin-4-yl)amino]-1-(2,2,2-trifluoroethyl)-1H-indol-2-yl}prop-2-yn-1-yl)amino]pyridin-2-yl}-2-methylpropanenitrile | 573.1 [(M + H)+] |
| 309 | 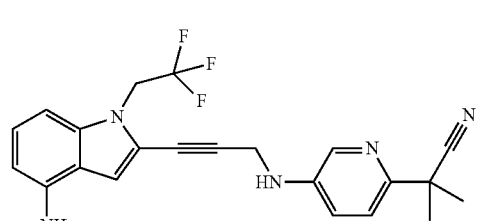 | 2-(5-{[3-(4-{[1-(2-methanesulfonyl-ethyl)piperidin-4-yl]amino}-1-(2,2,2-trifluoroethyl)-1H-indol-2-yl)prop-2-yn-1-yl]amino}pyridin-2-yl)-2-methylpropanenitrile | 601.2 [(M + H)+] |
| 310 | 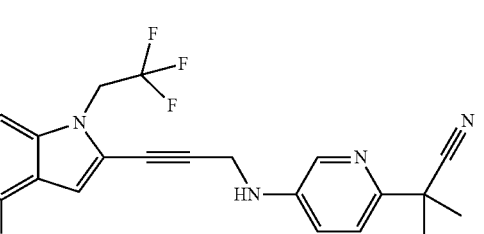 | 2-methyl-2-(5-{[3-(4-{[(1r,4r)-4-hydroxycyclohexyl]amino}-1-(2,2,2-trifluoroethyl)-1H-indol-2-yl)prop-2-yn-1-yl]amino}pyridin-2-yl)propanenitrile | 510.3 [(M + H)+] |

| Ex | Structure | Name | LC-MS (ES+, m/z) |
|---|---|---|---|
| 311 | 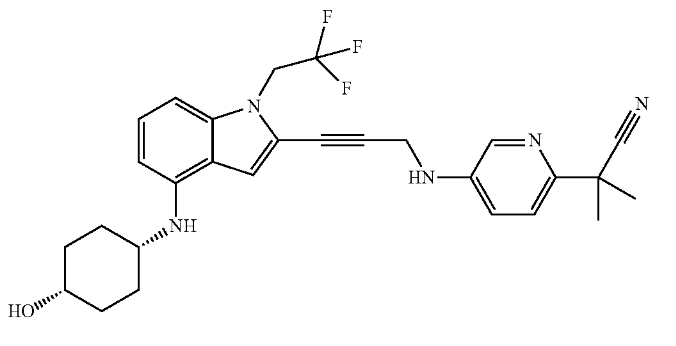 [SMILES: CC(C)(C#N)c1ccc(NCC#Cc2cc3c(N[C@H]4CC[C@@H](O)CC4)cccc3n2CC(F)(F)F)cn1] | 2-methyl-2-(5-{[3-(4-{[(1s,4s)-4-hydroxycyclohexyl]amino}-1-(2,2,2-trifluoroethyl)-1H-indol-2-yl)prop-2-yn-1-yl]amino}pyridin-2-yl)propanenitrile | 510.3 [(M + H)+] |
| 312 | 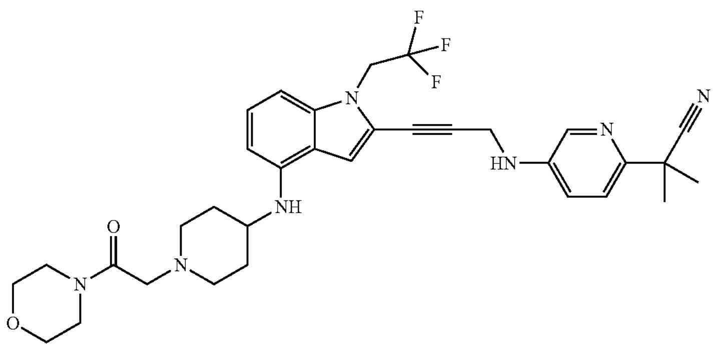 [SMILES: CC(C)(C#N)c1ccc(NCC#Cc2cc3c(NC4CCN(CC(=O)N5CCOCC5)CC4)cccc3n2CC(F)(F)F)cn1] | 2-methyl-2-[5-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)pyridin-2-yl]propanenitrile | 622.4 [(M + H)+] |
| 313 | 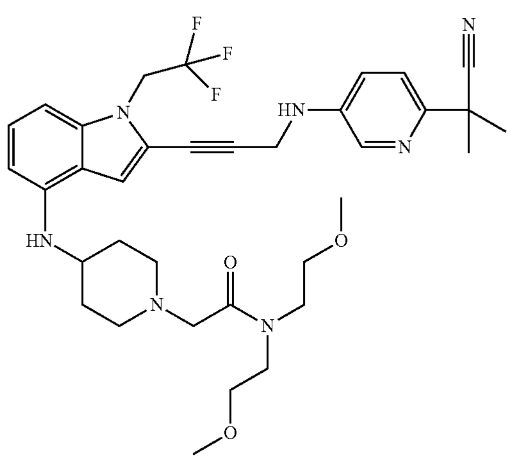 [SMILES: COCCN(CCOC)C(=O)CN1CCC(Nc2cccc3c2cc(C#CCNc2ccc(C(C)(C)C#N)nc2)n3CC(F)(F)F)CC1] | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N,N-bis(2-methoxyethyl)acetamide | 668.4 [(M + H)+] |
| 314 | 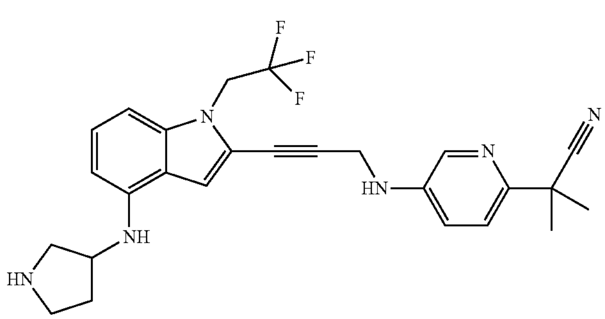 [SMILES: CC(C)(C#N)c1ccc(NCC#Cc2cc3c(NC4CCNC4)cccc3n2CC(F)(F)F)cn1] | 2-methyl-2-{5-[3-{4-[(pyrrolidin-3-yl)amino]-1-(2,2,2-trifluoroethyl)-1H-indol-2-yl}prop-2-yn-1-yl)amino]pyridin-2-yl}propanenitrile | 481.3 [(M + H)+] |

| Ex | Structure | Name | LC-MS (ES+, m/z) |
|---|---|---|---|
| 315 | 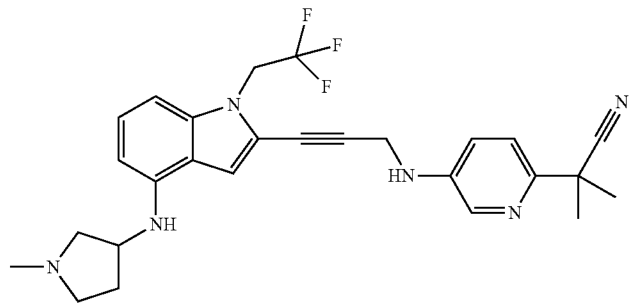 [SMILES: CN1CCC(Nc2cccc3c2cc(C#CCNc2ccc(C(C)(C)C#N)nc2)n3CC(F)(F)F)C1] | 2-methyl-2-{5-[(3-{4-[(1-methylpyrrolidin-3-yl)amino]-1-(2,2,2-trifluoroethyl)-1H-indol-2-yl}prop-2-yn-1-yl)amino]pyridin-2-yl}propanenitrile | 495.3 [(M + H)+] |
| 316 | 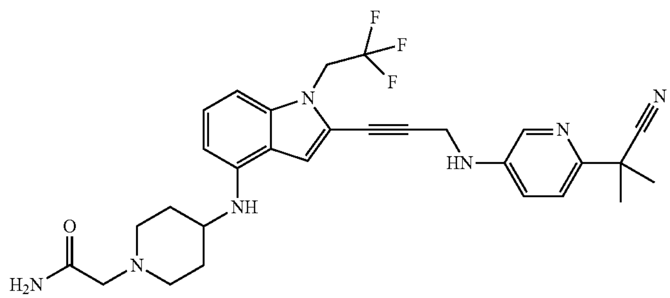 [SMILES: CC(C)(C#N)c1ccc(NCC#Cc2cc3c(NC4CCN(CC(N)=O)CC4)cccc3n2CC(F)(F)F)cn1] | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetamide | 552.4 [(M + H)+] |
| 317 | 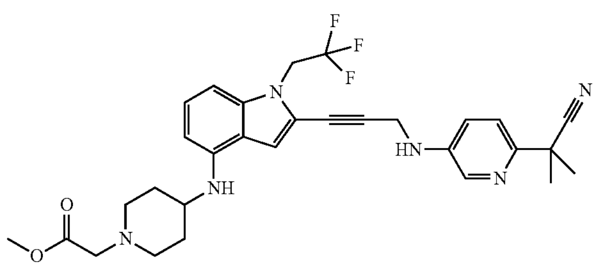 [SMILES: COC(=O)CN1CCC(Nc2cccc3c2cc(C#CCNc2ccc(C(C)(C)C#N)nc2)n3CC(F)(F)F)CC1] | methyl 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)acetate | 567.3 [(M + H)+] |
| 318 | 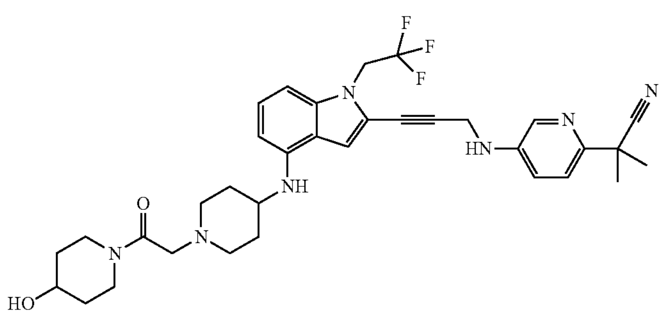 [SMILES: CC(C)(C#N)c1ccc(NCC#Cc2cc3c(NC4CCN(CC(=O)N5CCC(O)CC5)CC4)cccc3n2CC(F)(F)F)cn1] | 2-[5-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile | 636.4 [(M + H)+] |
| 319 | 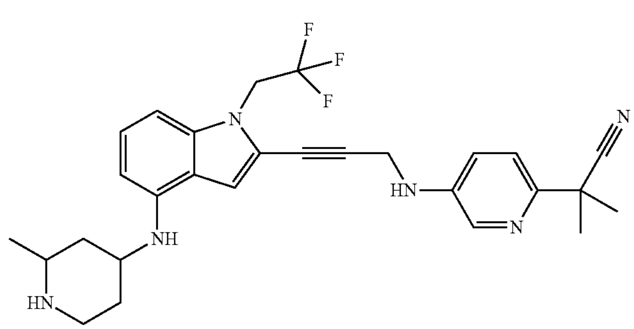 [SMILES: CC1CC(Nc2cccc3c2cc(C#CCNc2ccc(C(C)(C)C#N)nc2)n3CC(F)(F)F)CCN1] | 2-methyl-2-{5-[(3-{4-[(2-methylpiperidin-4-yl)amino]-1-(2,2,2-trifluoroethyl)-1H-indol-2-yl}prop-2-yn-1-yl)amino]pyridin-2-yl}propanenitrile | 509.3 [(M + H)+] |

-continued

| Ex | Structure | Name | LC-MS (ES+, m/z) |
|---|---|---|---|
| 320 | 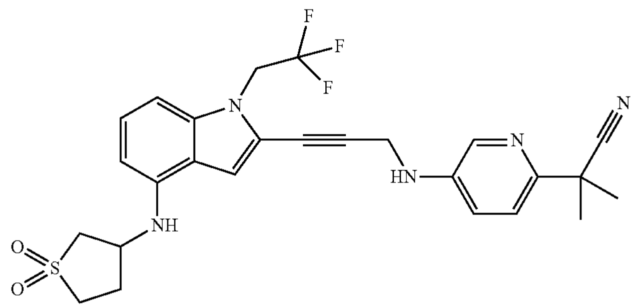 [SMILES: CC(C)(C#N)c1ccc(NCC#Cc2cc3c(NC4CCS(=O)(=O)C4)cccc3n2CC(F)(F)F)cn1] | 2-{5-[(3-{4-[(1,1,-dioxo-1λ⁶-thiolan-3-yl)amino]-1-(2,2,2-trifluoroethyl)-1H-indol-2-yl}prop-2-yn-1-yl)amino]pyridin-2-yl}-2-methylpropanenitrile | 530.3 [(M + H)⁺] |
| 321 | 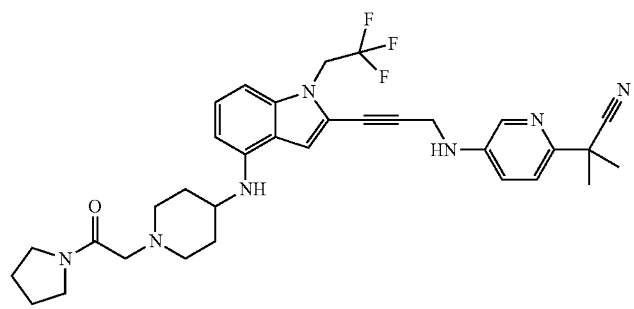 [SMILES: CC(C)(C#N)c1ccc(NCC#Cc2cc3c(NC4CCN(CC(=O)N5CCCC5)CC4)cccc3n2CC(F)(F)F)cn1] | 2-methyl-2-[5-({3-[4-({1-[2-oxo-2-(pyrrolidin-1-yl)ethyl]piperidin-4-yl}amino)-1-(2,2,2-trifluoroethyl)-1H-indol-2-yl]prop-2-yn-1-yl}amino)pyridin-2-yl]propanenitrile | 606.4 [(M + H)⁺] |
| 322 | 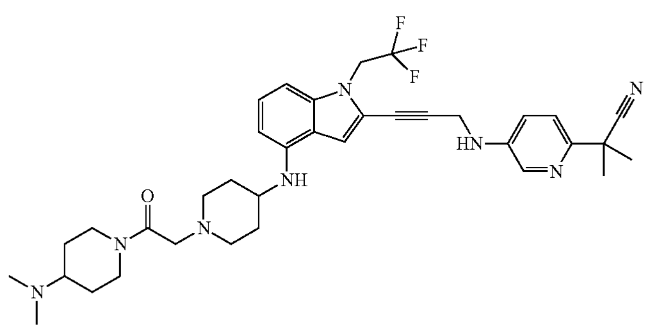 [SMILES: CN(C)C1CCN(C(=O)CN2CCC(Nc3cccc4c3cc(C#CCNc3ccc(C(C)(C)C#N)nc3)n4CC(F)(F)F)CC2)CC1] | 2-{5-[(3-{4-[(1-{2-[4-(dimethylamino)piperidin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile | 663.4 [(M + H)⁺] |
| 323 | 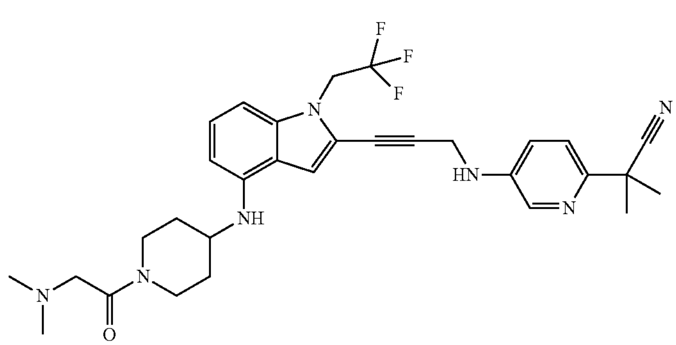 [SMILES: CN(C)CC(=O)N1CCC(Nc2cccc3c2cc(C#CCNc2ccc(C(C)(C)C#N)nc2)n3CC(F)(F)F)CC1] | 2-[5-({3-[4-({1-[2-(dimethylamino)acetyl]piperidin-4-yl}amino)-1-(2,2,2-trifluoroethyl)-1H-indol-2-yl]prop-2-yn-1-yl}amino)pyridin-2-yl]-2-methylpropanenitrile | 580.4 [(M + H)⁺] |

| Ex | Structure | Name | LC-MS (ES+, m/z) |
|---|---|---|---|
| 324 | 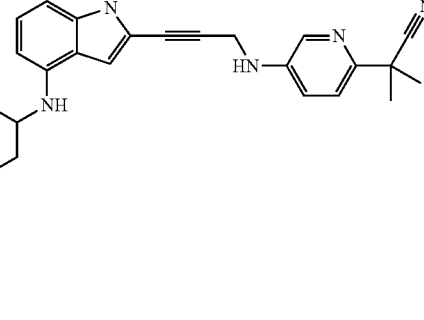 | 2-(5-{[3-(4-{[1-(1,1-dioxo-1λ⁶-thian-4-yl)piperidin-4-yl]amino}-1-(2,2,2-trifluoroethyl)-1H-indol-2-yl)prop-2-yn-1-yl]amino}pyridin-2-yl)-2-methylpropanenitrile | 627.3 [(M + H)⁺] |
| 325 | 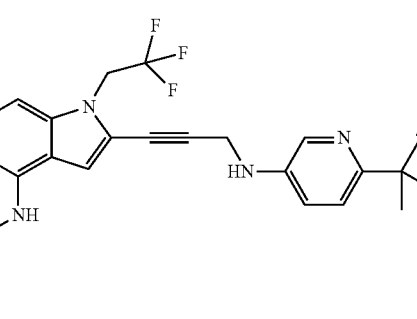 | 2-(5-{[3-(4-{[1-(cyanomethyl)piperidin-4-yl]amino}-1-(2,2,2-trifluoroethyl)-1H-indol-2-yl)prop-2-yn-1-yl]amino}pyridin-2-yl)-2-methylpropanenitrile | 534.3 [(M + H)⁺] |
| 326 | 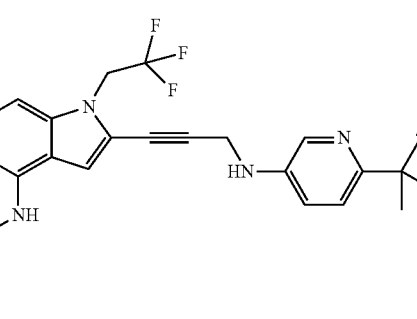 | 2-methyl-2-[5-({3-[1-(2,2,2-trifluoroethyl)-4-{[1-(2,2,2-trifluoroethyl)piperidin-4-yl]amino}-1H-indol-2-yl]prop-2-yn-1-yl}amino)pyridin-2-yl]propanenitrile | 577.3 [(M + H)⁺] |
| 327 | 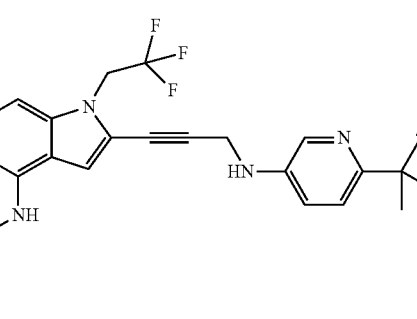 | 2-{5-[(3-{4-[(1-{2-[4-(2-methanesulfonylethyl)piperazin-1-yl]-2-oxoethyl}piperidin-4-yl)amino]-1-(2,2,2-trifluoroethyl)-1H-indol-2-yl}prop-2-yn-1-yl)amino]pyridin-2-yl}-2-methylpropanenitrile | 727.4 [(M + H)⁺] |

| Ex | Structure | Name | LC-MS (ES+, m/z) |
|---|---|---|---|
| 328 | 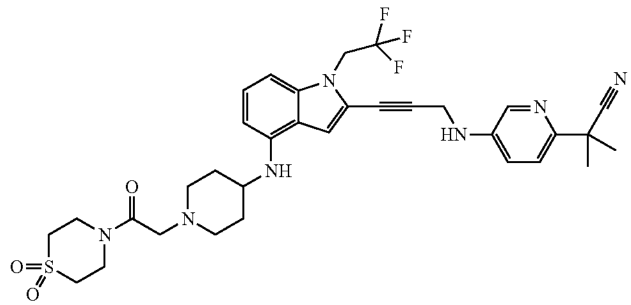 [SMILES: CC(C)(C#N)c1ccc(NCC#Cc2cc3c(NC4CCN(CC(=O)N5CCS(=O)(=O)CC5)CC4)cccc3n2CC(F)(F)F)cn1] | 2-[5-({3-[4-({1-[2-(1,1-dioxo-1λ☐,4-thiomorpholin-4-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile | 670.3 [(M + H)+] |
| 329 | 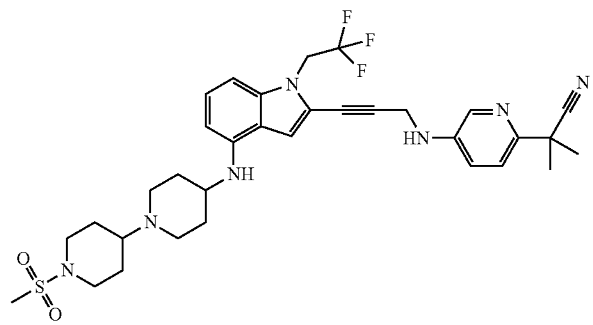 [SMILES: CC(C)(C#N)c1ccc(NCC#Cc2cc3c(NC4CCN(C5CCN(S(C)(=O)=O)CC5)CC4)cccc3n2CC(F)(F)F)cn1] | 2-(5-{[3-(4-{[1-(1-methanesulfonylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile | 656.4 [(M + H)+] |
| 330 | 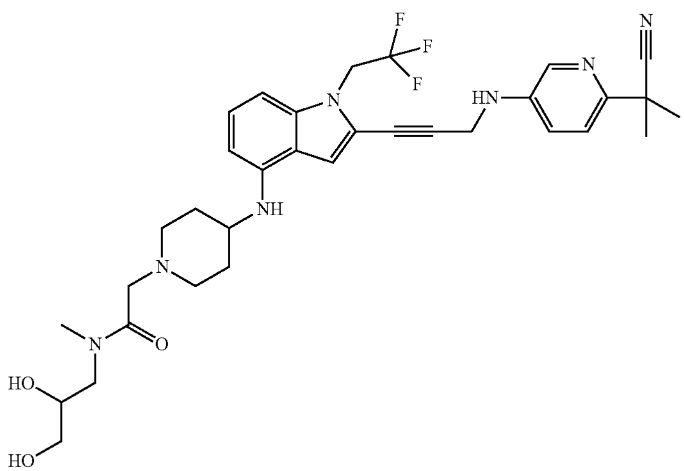 [SMILES: CN(CC(O)CO)C(=O)CN1CCC(Nc2cccc3c2cc(C#CCNc2ccc(C(C)(C)C#N)nc2)n3CC(F)(F)F)CC1] | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)-N-methylacetamide | 640.4 [(M + H)+] |
| 331 | 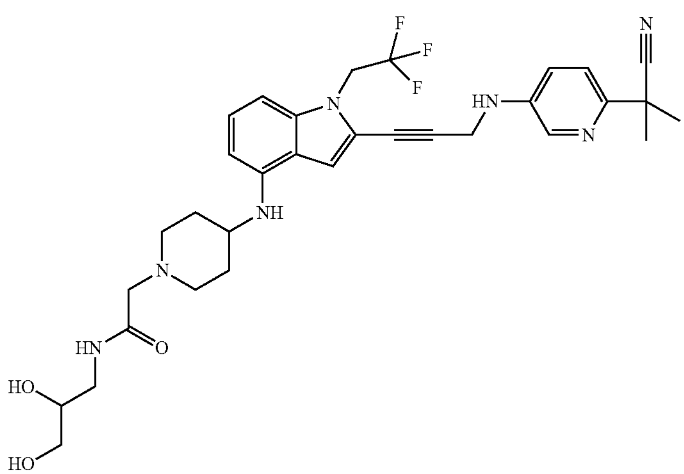 [SMILES: CC(C)(C#N)c1ccc(NCC#Cc2cc3c(NC4CCN(CC(=O)NCC(O)CO)CC4)cccc3n2CC(F)(F)F)cn1] | 2-(4-{[2-(3-{[6-(1-cyano-1-methylethyl)pyridin-3-yl]amino}prop-1-yn-1-yl)-1-(2,2,2-trifluoroethyl)-1H-indol-4-yl]amino}piperidin-1-yl)-N-(2,3-dihydroxypropyl)acetamide | 626.4 [(M + H)+] |

-continued

| Ex | Structure | Name | LC-MS (ES+, m/z) |
|---|---|---|---|
| 332 | 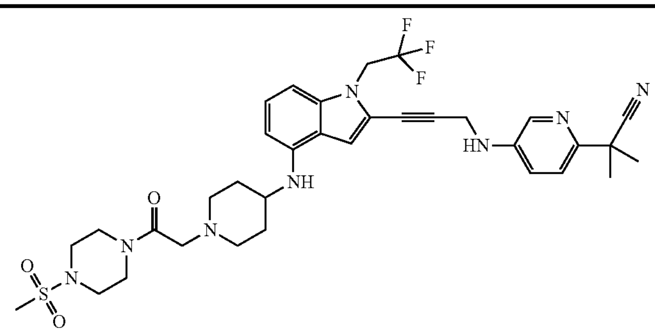 | 2-[5-({3-[4-({1-[2-(4-methanesulfonylpiperazin-1-yl)-2-oxoethyl]piperidin-4-yl}amino)-1-(2,2,2-trifluoroethyl)-1H-indol-2-yl]prop-2-yn-1-yl}amino)pyridin-2-yl]-2-methylpropanenitrile | 699.4 [(M + H)+] |
| 333 | 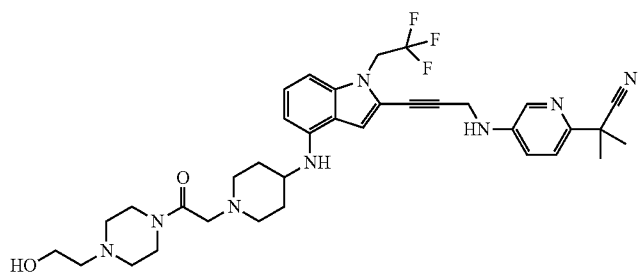 [SMILES: CC(C)(C#N)c1ccc(NCC#Cc2cc3c(NC4CCN(CC(=O)N5CCN(CCO)CC5)CC4)cccc3n2CC(F)(F)F)cn1] | 2-{5-[(3-{4-[(1-{2-[4-(2-hydroxyethyl)piperazin-1-yl]-2-oxoethyl}piperidin-4-yl]amino}-1-(2,2,2-trifluoroethyl)-1H-indol-2-yl)prop-2-yn-1-yl}amino)pyridin-2-yl]-2-methylpropanenitrile | 665.4 [(M + H)+] |
| 334 | 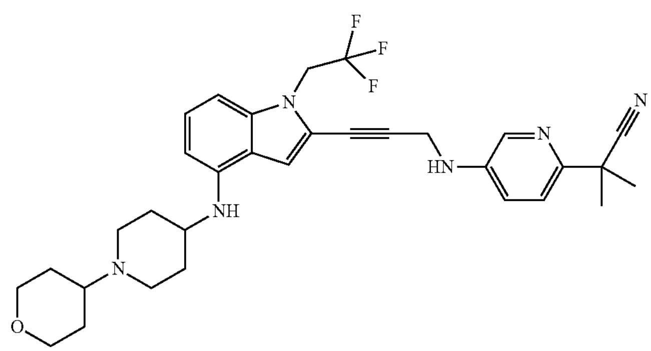 [SMILES: CC(C)(C#N)c1ccc(NCC#Cc2cc3c(NC4CCN(C5CCOCC5)CC4)cccc3n2CC(F)(F)F)cn1] | 2-methyl-2-(5-{[3-(4-{[1-(oxan-4-yl)piperidin-4-yl]amino}-1-(2,2,2-trifluoroethyl)-1H-indol-2-yl)prop-2-yn-1-yl]amino}pyridin-2-yl)propanenitrile | 579.4 [(M + H)+] |
| 335 | 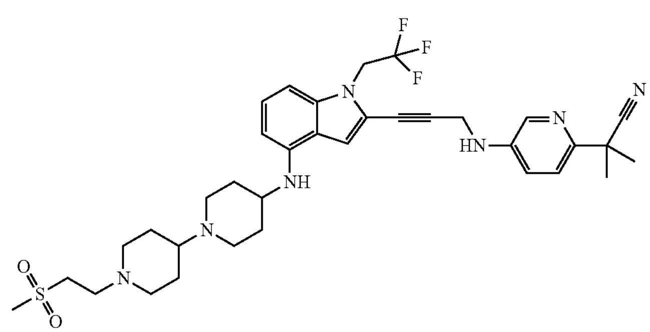 [SMILES: CC(C)(C#N)c1ccc(NCC#Cc2cc3c(NC4CCN(C5CCN(CCS(C)(=O)=O)CC5)CC4)cccc3n2CC(F)(F)F)cn1] | 2-[5-({3-[4-({1-[1-(2-methanesulfonylethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile | 684.2 [(M + H)+] |
| 336 | 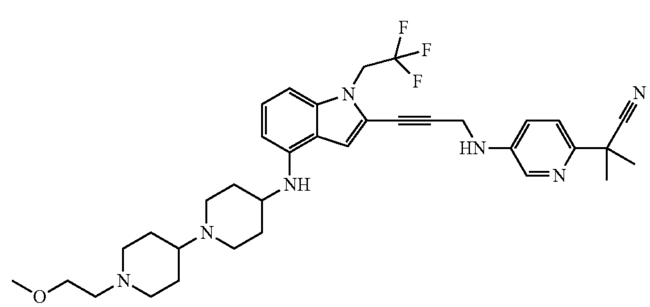 [SMILES: COCCN1CCC(N2CCC(Nc3cccc4c3cc(C#CCNc3ccc(C(C)(C)C#N)nc3)n4CC(F)(F)F)CC2)CC1] | 2-[5-({3-[4-({1-[1-(2-methanesulfonylethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile | 636.2 [(M + H)+] |

| Ex | Structure | Name | LC-MS (ES+, m/z) |
|---|---|---|---|
| 337 | 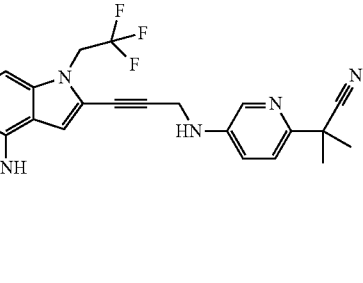 | 2-[5-({3-[4-({1-[1-(2-hydroxyethyl)piperidin-4-yl]piperidin-4-yl}amino)-1-(2,2,2-trifluoroethyl)-1H-indol-2-yl]prop-2-yn-1-yl}amino)pyridin-2-yl]-2-methylpropanenitrile | 622.2 [(M + H)+] |
| 338 | 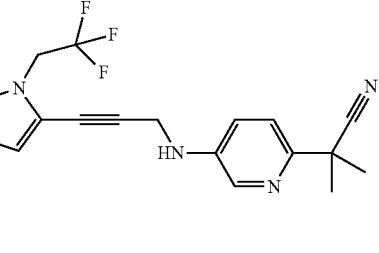 | 2-[5-({3-[4-({1-[2-(dimethylamino)ethyl]piperidin-4-yl}amino)-1-(2,2,2-trifluoroethyl)-1H-indol-2-yl]prop-2-yn-1-yl}amino)pyridin-2-yl]-2-methylpropanenitrile | 566.4 [(M + H)+] |
| 339 | 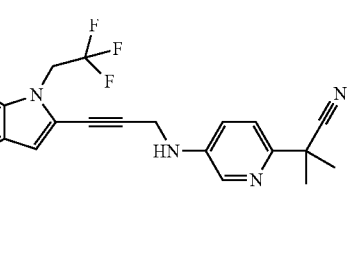 | 2-(5-{[3-(4-{[1-(1-acetylpiperidin-4-yl)piperidin-4-yl]amino}-1-(2,2,2-trifluoroethyl)-1H-indol-2-yl)prop-2-yn-1-yl]amino}pyridin-2-yl)-2-methylpropanenitrile | 620.4 [(M + H)+] |
| 340 | 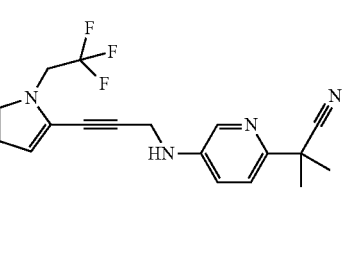 | 2-methyl-2-[5-({3-[4-({1-[(1r,4r)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile | 593.4 [(M + H)+] |

| Ex | Structure | Name | LC-MS (ES+, m/z) |
|---|---|---|---|
| 341 | 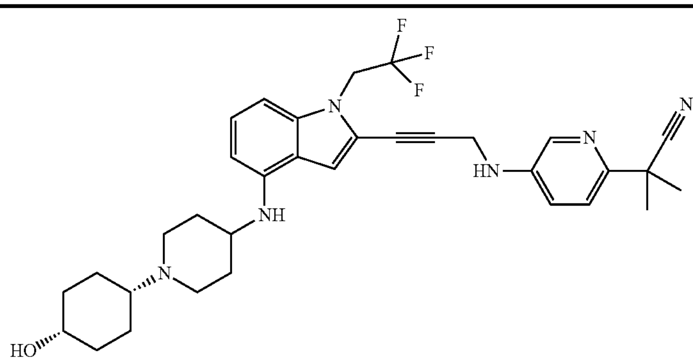 | 2-methyl-2-[5-({3-[4-({1-[(1s,4s)-4-hydroxycyclohexyl]piperidin-4-yl}amino)-1-(2,2,2-trifluoroethyl)-1H-indol-2-yl]prop-2-yn-1-yl}amino)pyridin-2-yl]propanenitrile | 593.4 [(M + H)+] |

Example 342: Preparation of N-(1-methylpiperidin-4-yl)-2-{3-[(6-methylpyridin-3-yl)amino]prop-1-yn-1-yl}-1-(2,2,2-trifluoroethyl)-1H-indol-4-amine

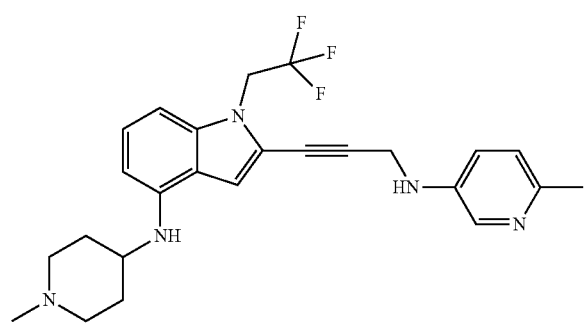

To a mixture of 2-iodo-1-(2,2,2-trifluoroethyl)-1H-indol-4-amine (8 g, 23.52 mmol) in ethanol (70 mL) at 25° C. were added 1-methylpiperidin-4-one (13.31 g, 117.60 mmol, 13.7 mL) and tetraethoxy titanium (26.83 g, 117.60 mmol, 24.39 mL). The reaction mixture was heated to 50° C. and stirred at 50° C. for 12 h, and sodium cyanoborohydride (7.39 g, 117.60 mmol) was added to the reaction at 25° C. After stirring at 25° C. for 2 h, the reaction was diluted with saturated aqueous sodium bicarbonate and extracted with ethyl acetate (3×50 mL). The combined organic layers were washed with brine (50 mL), dried over anhydrous sodium sulfate, filtered, and concentrated in vacuo. The crude product was purified by flash column chromatography (silica gel, eluting with methylene chloride/methanol: 40/1 to 10/1) to give 2-iodo-N-(1-methylpiperidin-4-yl)-1-(2,2,2-trifluoroethyl)-1H-indol-4-amine as a yellow solid (2.17 g, 19.64% yield, 93.1% purity).

2-Iodo-N-(1-methylpiperidin-4-yl)-1-(2,2,2-trifluoroethyl)-1H-indol-4-amine was reacted with 6-methyl-N-(prop-2-yn-1-yl)pyridin-3-amine (prepared from 6-methylpyridin-3-amine) under Sonogashira coupling conditions to give N-(1-methylpiperidin-4-yl)-2-{3-[(6-methylpyridin-3-yl)amino]prop-1-yn-1-yl}-1-(2,2,2-trifluoroethyl)-1H-indol-4-amine.

LC-MS (ES+, m/z): 456.2 [(M+H)+]

Starting with 2-iodo-1-(2,2,2-trifluoroethyl)-1H-indol-4-amine and using the similar method as described in Example 342, the following compounds were prepared:

| Ex | Structure | Name | LC-MS (ES+, m/z) |
|---|---|---|---|
| 343 | 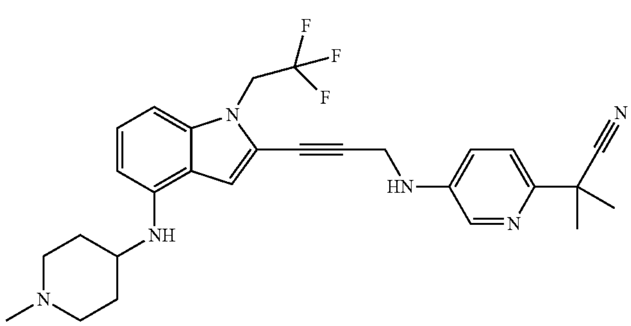 [SMILES: CN1CCC(Nc2cccc3c2cc(C#CCNc2ccc(C(C)(C)C#N)nc2)n3CC(F)(F)F)CC1] | 2-methyl-2-{5-[(3-{4-[(1-methylpiperidin-4-yl)amino]-1-(2,2,2-trifluoroethyl)-1H-indol-2-yl}prop-2-yn-1-yl)amino]pyridin-2-yl}propanenitrile | 509.3 [(M + H)+] |

-continued

| Ex | Structure | Name | LC-MS (ES+, m/z) |
|---|---|---|---|
| 344 | 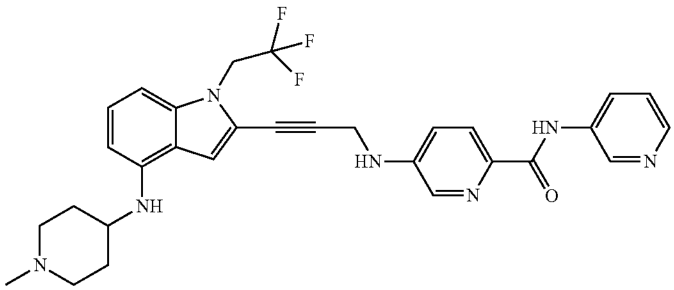 [SMILES: CN1CCC(Nc2cccc3c2cc(C#CCNc2ccc(C(=O)Nc4cccnc4)nc2)n3CC(F)(F)F)CC1] | 5-[(3-{4-[(1-methylpiperidin-4-yl)amino]-1-(2,2,2-trifluoroethyl)-1H-indol-2-yl}prop-2-yn-1-yl)amino]-N-(pyridin-3-yl)pyridine-2-carboxamide | 562.3 [(M + H)+] |
| 345 | 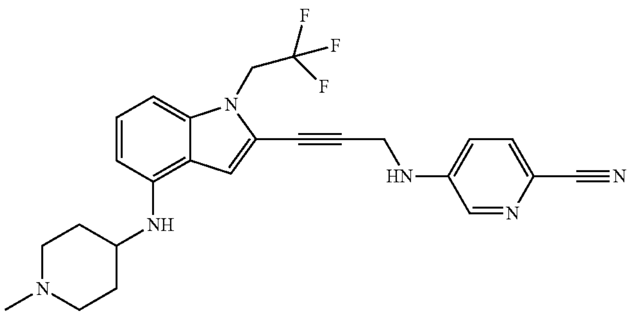 [SMILES: CN1CCC(Nc2cccc3c2cc(C#CCNc2ccc(C#N)nc2)n3CC(F)(F)F)CC1] | 5-[(3-{4-[(1-methylpiperidin-4-yl)amino]-1-(2,2,2-trifluoroethyl)-1H-indol-2-yl}prop-2-yn-1-yl)amino]pyridine-2-carbonitrile | 467.3 [(M + H)+] |
| 346 | 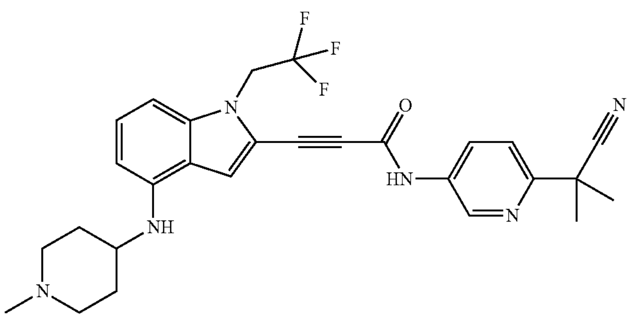 [SMILES: CN1CCC(Nc2cccc3c2cc(C#CC(=O)Nc2ccc(C(C)(C)C#N)nc2)n3CC(F)(F)F)CC1] | N-[6-(1-cyano-1-methylethyl)pyridin-3-yl]-3-{4-[(1-methylpiperidin-4-yl)amino]-1-(2,2,2-trifluoroethyl)-1H-indol-2-yl}prop-2-ynamide | 523.3 [(M + H)+] |
| 347 | 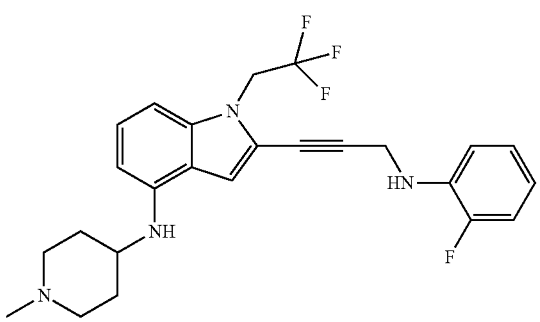 [SMILES: CN1CCC(Nc2cccc3c2cc(C#CCNc2ccccc2F)n3CC(F)(F)F)CC1] | 2-{3-[(2-fluorophenyl)amino]prop-1-yn-1-yl}-N-(1-methylpiperidin-4-yl)-1-(2,2,2-trifluoroethyl)-1H-indol-4-amine | 459.2 [(M + H)+] |
| 348 | 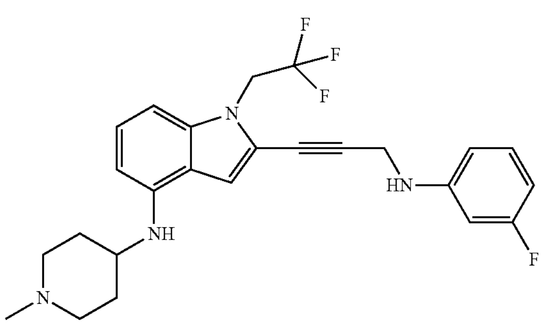 [SMILES: CN1CCC(Nc2cccc3c2cc(C#CCNc2cccc(F)c2)n3CC(F)(F)F)CC1] | 2-{3-[(3-fluorophenyl)amino]prop-1-yn-1-yl}-N-(1-methylpiperidin-4-yl)-1-(2,2,2-trifluoroethyl)-1H-indol-4-amine | 459.1 [(M + H)+] |

-continued

| Ex | Structure | Name | LC-MS (ES+, m/z) |
|---|---|---|---|
| 349 | 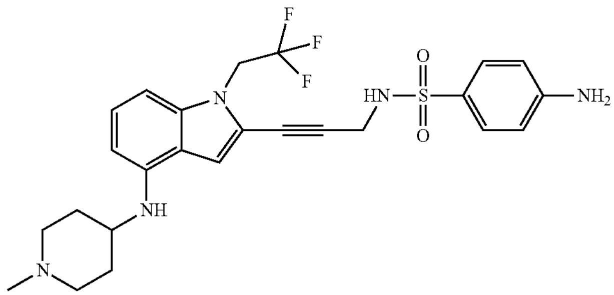 [SMILES: CN1CCC(Nc2cccc3c2cc(C#CCNS(=O)(=O)c2ccc(N)cc2)n3CC(F)(F)F)CC1] | 4-amino-N-(3-{4-[(1-methylpiperidin-4-yl)amino]-1-(2,2,2-trifluoroethyl)-1H-indol-2-yl}prop-2-yn-1-yl)benzene-1-sulfonamide | 520.3 [(M + H)+] |
| 350 | 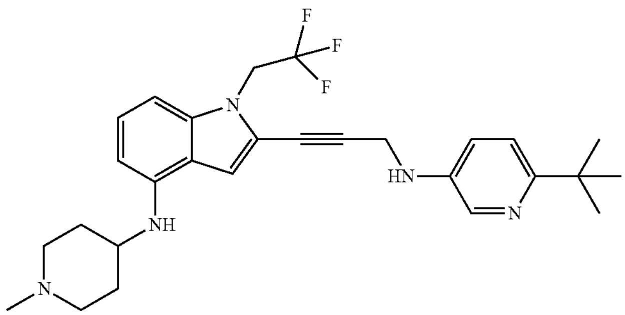 [SMILES: CN1CCC(Nc2cccc3c2cc(C#CCNc2ccc(C(C)(C)C)nc2)n3CC(F)(F)F)CC1] | 2-{3-[(6-tert-butylpyridin-3-yl)amino]prop-1-yn-1-yl}-N-(1-methylpiperidin-4-yl)-1-(2,2,2-trifluoroethyl)-1H-indol-4-amine | 498.4 [(M + H)+] |
| 351 | 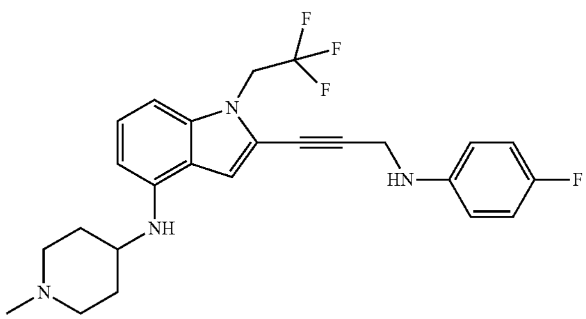 [SMILES: CN1CCC(Nc2cccc3c2cc(C#CCNc2ccc(F)cc2)n3CC(F)(F)F)CC1] | 2-{3-[(4-fluorophenyl)amino]prop-1-yn-1-yl}-N-(1-methylpiperidin-4-yl)-1-(2,2,2-trifluoroethyl)-1H-indol-4-amine | 459.3 [(M + H)+] |
| 352 | 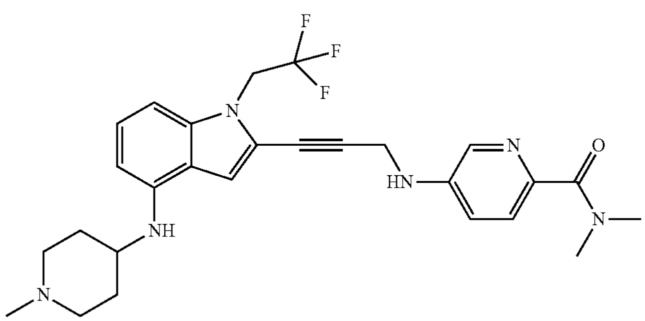 | N,N-dimethyl-5-[(3-{4-[(1-methylpiperidin-4-yl)amino]-1-(2,2,2-trifluoroethyl)-1H-indol-2-yl}prop-2-yn-1-yl)amino]pyridine-2-carboxamide | 513.3 [(M + H)+] |
| 353 | 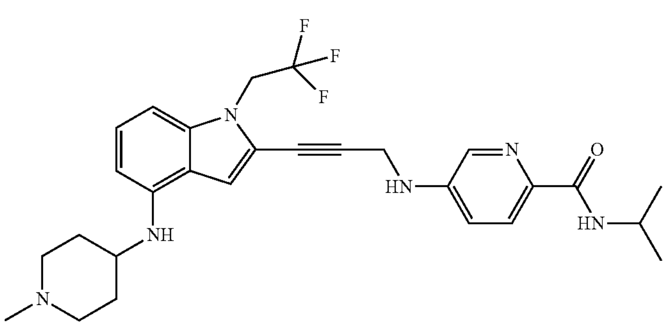 [SMILES: CC(C)NC(=O)c1ccc(NCC#Cc2cc3c(NC4CCN(C)CC4)cccc3n2CC(F)(F)F)cn1] | 5-[(3-{4-[(1-methylpiperidin-4-yl)amino]-1-(2,2,2-trifluoroethyl)-1H-indol-2-yl}prop-2-yn-1-yl)amino]-N-(propan-2-yl)pyridine-2-carboxamide | 527.3 [(M + H)+] |

-continued

| Ex | Structure | Name | LC-MS (ES+, m/z) |
|---|---|---|---|
| 354 | 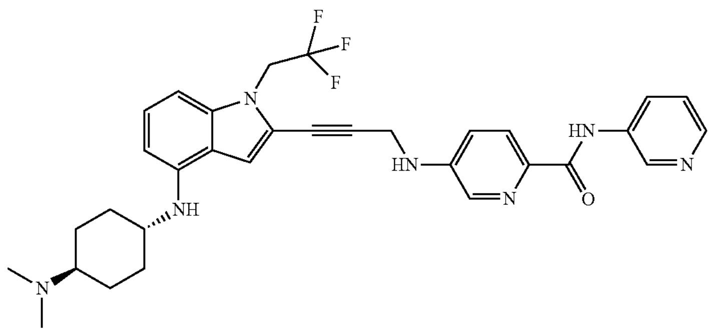 [SMILES: CN(C)[C@H]1CC[C@H](Nc2cccc3c2cc(C#CCNc2ccc(C(=O)Nc4cccnc4)nc2)n3CC(F)(F)F)CC1] | N-(pyridin-3-yl)-5-{[3-(4-{[(1r,4r)-4-(dimethylamino)cyclohexyl]amino}-1-(2,2,2-trifluoroethyl)-1H-indol-2-yl)prop-2-yn-1-yl]amino}pyridine-2-carboxamide | 590.3 [(M + H)+] |
| 355 | 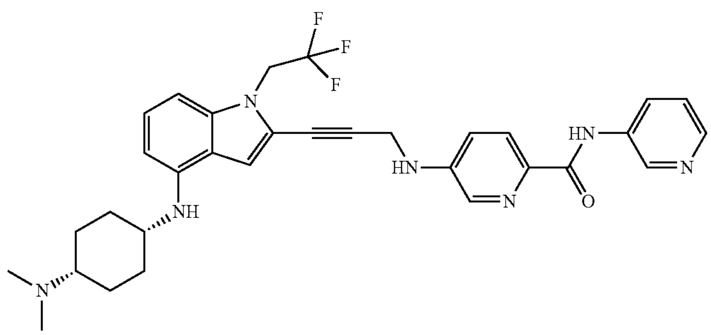 [SMILES: CN(C)[C@H]1CC[C@@H](Nc2cccc3c2cc(C#CCNc2ccc(C(=O)Nc4cccnc4)nc2)n3CC(F)(F)F)CC1] | N-(pyridin-3-yl)-5-{[3-(4-{[(1s,4s)-4-(dimethylamino)cyclohexyl]amino}-1-(2,2,2-trifluoroethyl)-1H-indol-2-yl)prop-2-yn-1-yl]amino}pyridine-2-carboxamide | 590.4 [(M + H)+] |
| 356 | 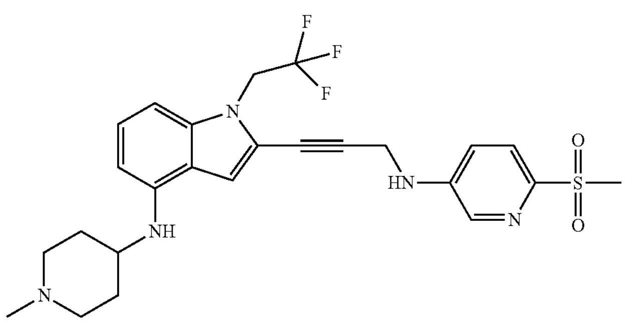 | 2-{3-[(6-methanesulfonylpyridin-3-yl)amino[prop-1-yn-1-yl]-N-(1-methylpiperidin-4-yl)-1-(2,2,2-trifluoroethyl)-1H-indol-4-amine | 520.3 [(M + H)+] |
| 357 | 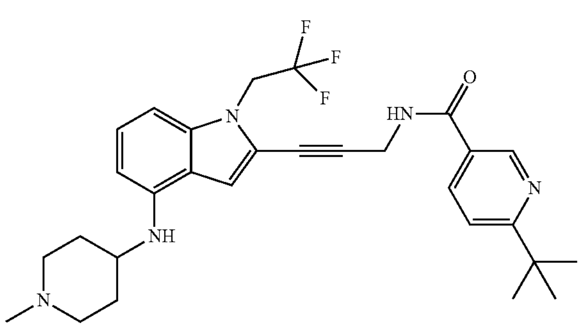 [SMILES: CN1CCC(Nc2cccc3c2cc(C#CCNC(=O)c2ccc(C(C)(C)C)nc2)n3CC(F)(F)F)CC1] | 6-tert-butyl-N-(3-{4-[(1-methylpiperidin-4-yl)amino]-1-(2,2,2-trifluoroethyl)-1H-indol-2-yl}prop-2-yn-1-yl)pyridine-3-carboxamide | 526.4 [(M + H)+] |

-continued

| Ex | Structure | Name | LC-MS (ES+, m/z) |
|---|---|---|---|
| 358 | 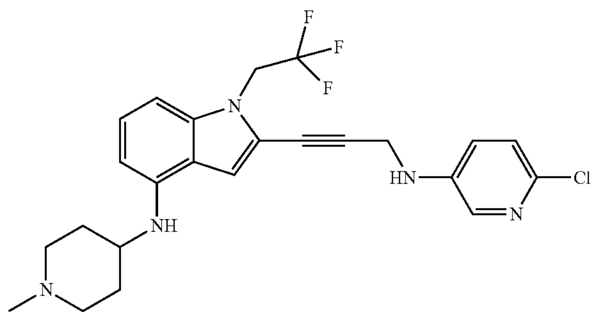 [SMILES: CN1CCC(Nc2cccc3c2cc(C#CCNc2ccc(Cl)nc2)n3CC(F)(F)F)CC1] | 2-{3-[(6-chloropyridin-3-yl)amino]prop-1-yn-1-yl}-N-(1-methylpiperidin-4-yl)-1-(2,2,2-trifluoroethyl)-1H-indol-4-amine | 476.3 [(M + H)+] |
| 359 | 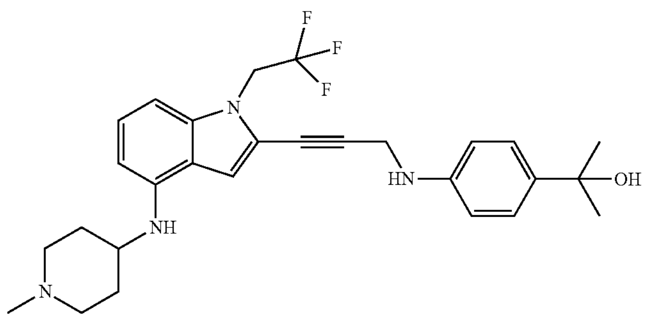 [SMILES: CN1CCC(Nc2cccc3c2cc(C#CCNc2ccc(C(C)(C)O)cc2)n3CC(F)(F)F)CC1] | 2-{4-[(3-{4-[(1-methylpiperidin-4-yl)amino]-1-(2,2,2-trifluoroethyl)-1H-indol-2-yl}prop-2-yn-1-yl)amino]phenyl}propan-2-ol | 499.3 [(M + H)+] |
| 360 | 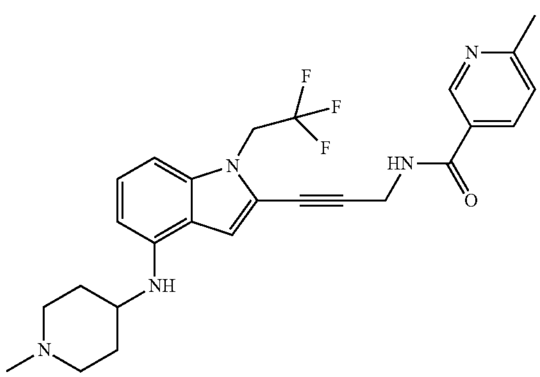 | 6-methyl-N-(3-{4-[(1-methylpiperidin-4-yl)amino]-1-(2,2,2-trifluoroethyl)-1H-indol-2-yl}prop-2-yn-1-yl)pyridine-3-carboxamide | 484.2 [(M + H)+] |
| 361 | 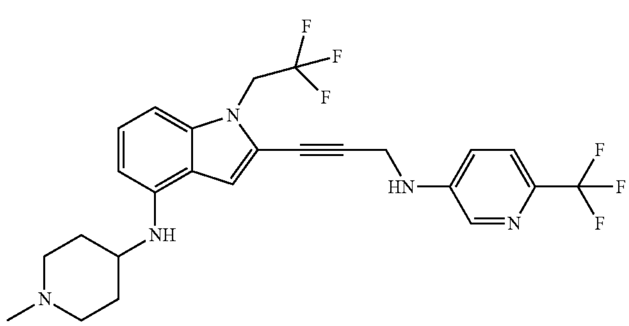 [SMILES: CN1CCC(Nc2cccc3c2cc(C#CCNc2ccc(C(F)(F)F)nc2)n3CC(F)(F)F)CC1] | N-(1-methylpiperidin-4-yl)-1-(2,2,2-trifluoroethyl)-2-(3-{[6-(trifluoromethyl)pyridin-3-yl]amino}prop-1-yn-1-yl)-1H-indol-4-amine | 510.3 [(M + H)+] |

-continued

| Ex | Structure | Name | LC-MS (ES+, m/z) |
|---|---|---|---|
| 362 | 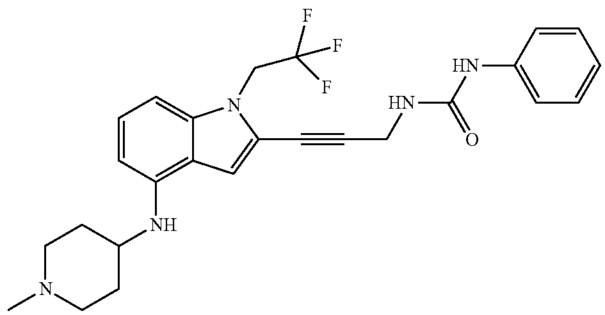 [SMILES: CN1CCC(Nc2cccc3c2cc(C#CCNC(=O)Nc2ccccc2)n3CC(F)(F)F)CC1] | 3-(3-{4-[(1-methylpiperidin-4-yl)amino]-1-(2,2,2-trifluoroethyl)-1H-indol-2-yl}prop-2-yn-1-yl)-1-phenylurea | 484.2 [(M + H)+] |
| 363 | 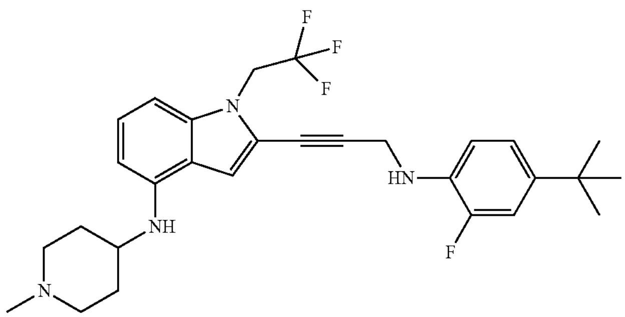 [SMILES: CN1CCC(Nc2cccc3c2cc(C#CCNc2ccc(C(C)(C)C)cc2F)n3CC(F)(F)F)CC1] | 2-{3-[(4-tert-butyl-2-fluorophenyl)-amino]prop-1-yn-1-yl}-N-(1-methylpiperidin-4-yl)-1-(2,2,2-trifluoroethyl)-1H-indol-4-amine | 515.3 [(M + H)+] |
| 364 | 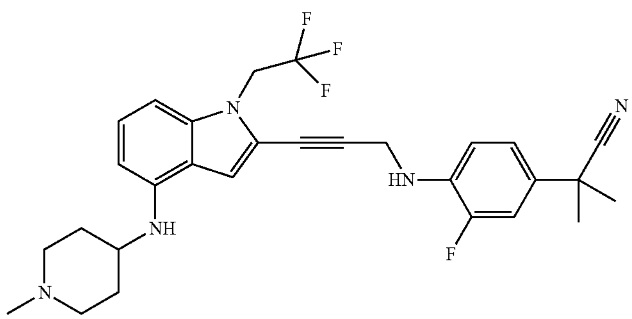 [SMILES: CN1CCC(Nc2cccc3c2cc(C#CCNc2ccc(C(C)(C)C#N)cc2F)n3CC(F)(F)F)CC1] | 2-{3-fluoro-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile | 526.2 [(M + H)+] |
| 365 | 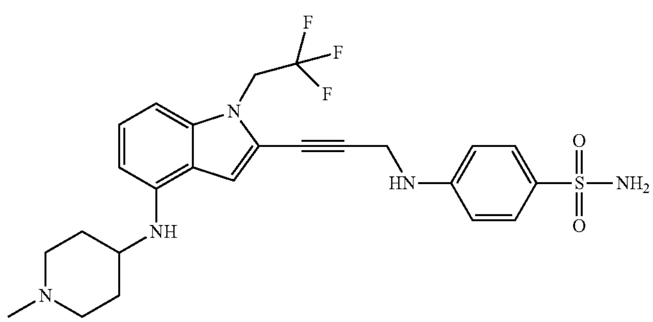 [SMILES: CN1CCC(Nc2cccc3c2cc(C#CCNc2ccc(S(N)(=O)=O)cc2)n3CC(F)(F)F)CC1] | 4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 520.3 [(M + H)+] |
| 366 | 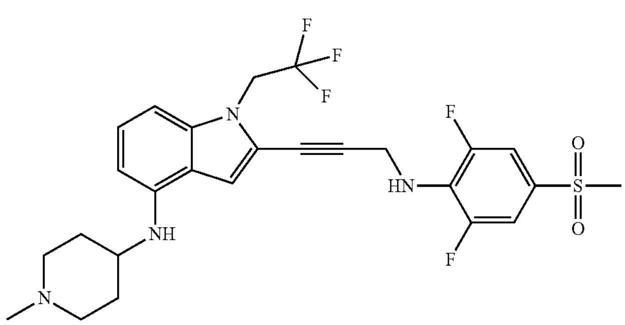 | 2-{3-[(2,6-difluoro-4-methane-sulfonylphenyl)amino]prop-1-yn-1-yl}-N-(1-methylpiperidin-4-yl)-1-(2,2,2-trifluoroethyl)-1H-indol-4-amine | 555.2 [(M + H)+] |

-continued

| Ex | Structure | Name | LC-MS (ES+, m/z) |
|---|---|---|---|
| 367 | 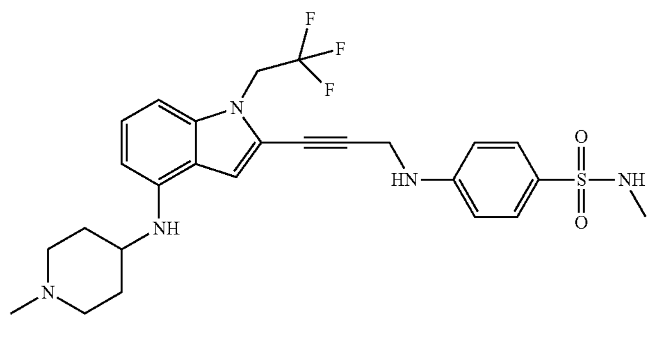 | N-methyl-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 534.3 [(M + H)+] |
| 368 | 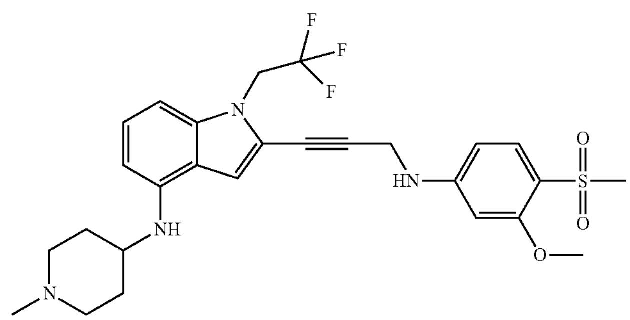 | 2-{3-[(4-methanesulfonyl-3-methoxyphenyl)amino]prop-1-yn-1-yl}-N-(1-methylpiperidin-4-yl)-1-(2,2,2-trifluoroethyl)-1H-indol-4-amine | 549.2 [(M + H)+] |
| 369 | 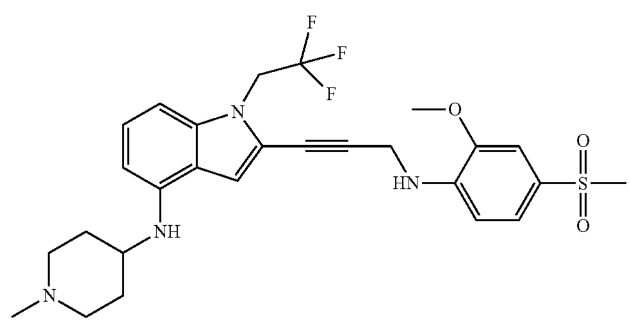 | 2-{3-[(4-methanesulfonyl-2-methoxyphenyl)amino]prop-1-yn-1-yl}-N-(1-methylpiperidin-4-yl)-1-(2,2,2-trifluoroethyl)-1H-indol-4-amine | 549.2 [(M + H)+] |
| 370 | 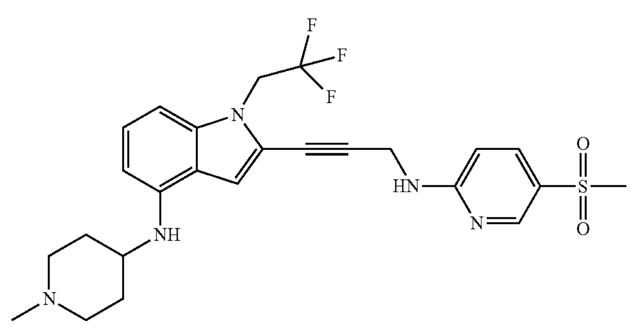 | 2-{3-[(5-methanesulfonylpyridin-2-yl)amino]prop-1-yn-1-yl}-N-(1-methylpiperidin-4-yl)-1-(2,2,2-trifluoroethyl)-1H-indol-4-amine | 520.2 [(M + H)+] |

-continued

| Ex | Structure | Name | LC-MS (ES+, m/z) |
|---|---|---|---|
| 371 | 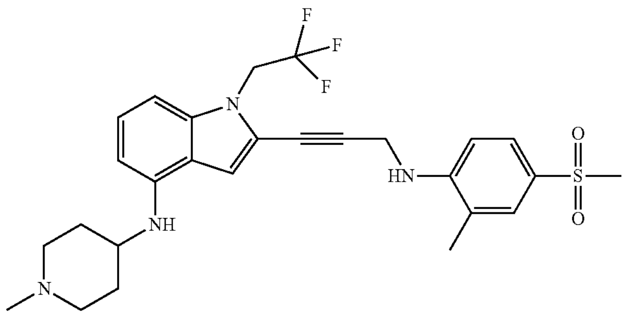 | 2-{3-[(4-methanesulfonyl-2-methylphenyl)amino]prop-1-yn-1-yl}-N-(1-methylpiperidin-4-yl)-1-(2,2,2-trifluoroethyl)-1H-indol-4-amine | 533.1 [(M + H)+] |
| 372 | 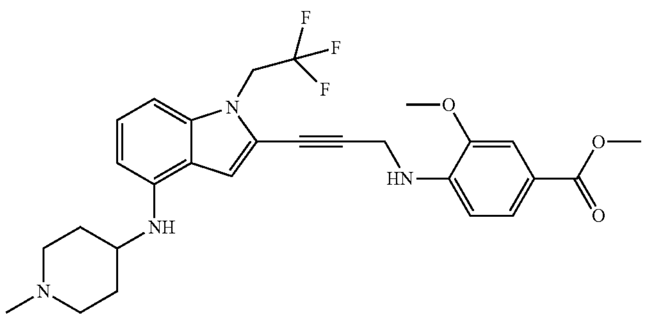 | methyl 3-methoxy-4-[(3-{4-[(1-methylpiperidin-4-yl)amino]-1-(2,2,2-trifluoroethyl)-1H-indol-2-yl}prop-2-yn-1-yl)amino]benzoate | 529.2 [(M + H)+] |
| 373 | 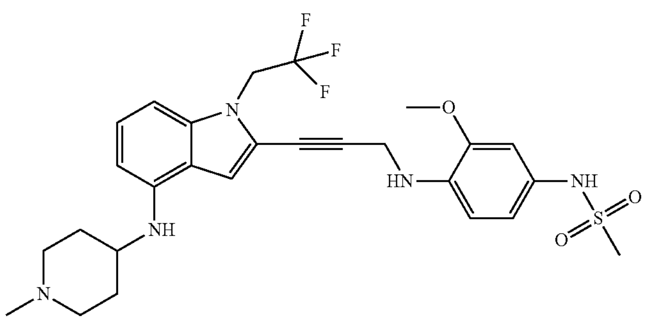 [SMILES: COc1cc(NS(C)(=O)=O)ccc1NCC#Cc1cc2c(NC3CCN(C)CC3)cccc2n1CC(F)(F)F] | N-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}methanesulfonamide | 564.3 [(M + H)+] |
| 374 | 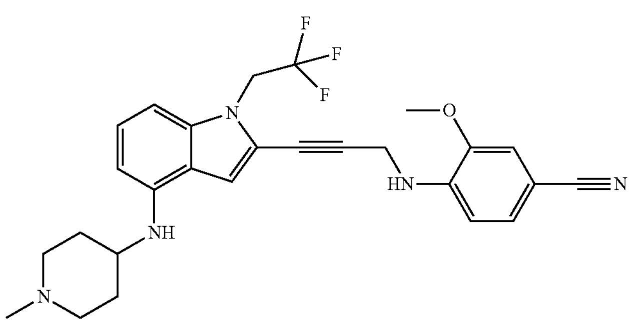 [SMILES: COc1cc(C#N)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]benzonitrile | 496.3 [(M + H)+] |
| 375 | 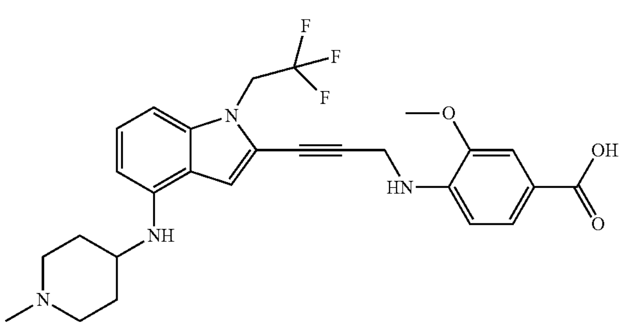 [SMILES: COc1cc(C(=O)O)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]benzoic acid | 515.2 [(M + H)+] |

-continued

| Ex | Structure | Name | LC-MS (ES+, m/z) |
|---|---|---|---|
| 376 | 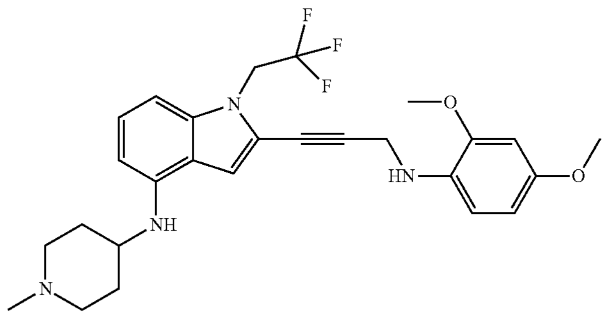 | 2-{3-[(2,4-dimethoxyphenyl)amino]prop-1-yn-1-yl}-N-(1-methylpiperidin-4-yl)-1-(2,2,2-trifluoroethyl)-1H-indol-4-amine | 501.2 [(M + H)+] |
| 377 | 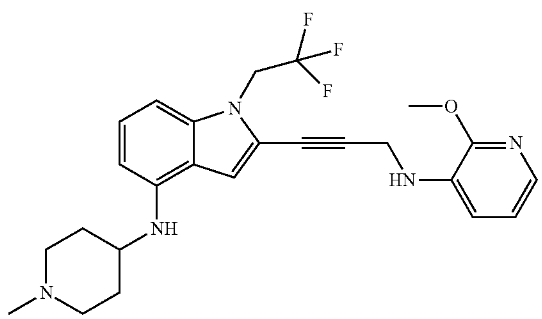 [SMILES: COc1ncccc1NCC#Cc1cc2c(NC3CCN(C)CC3)cccc2n1CC(F)(F)F] | 2-{3-[(2-methoxypyridin-3-yl)amino]prop-1-yn-1-yl}-N-(1-methylpiperidin-4-yl)-1-(2,2,2-trifluoroethyl)-1H-indol-4-amine | 472.4 [(M + H)+] |
| 378 | 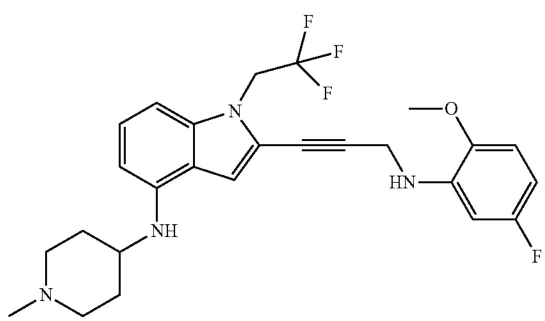 [SMILES: COc1ccc(F)cc1NCC#Cc1cc2c(NC3CCN(C)CC3)cccc2n1CC(F)(F)F] | 2-{3-[(5-fluoro-2-methoxyphenyl)-amino]prop-1-yn-1-yl}-N-(1-methylpiperidin-4-yl)-1-(2,2,2-trifluoroethyl)-1H-indol-4-amine | 489.4 [(M + H)+] |
| 379 | 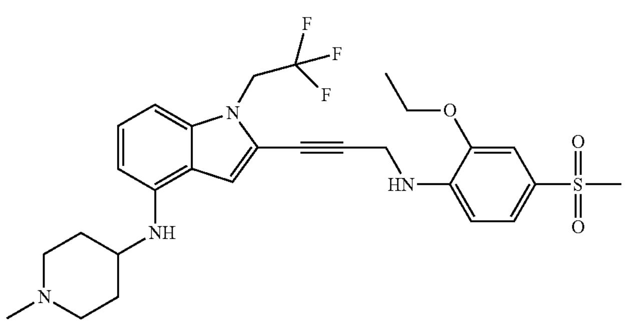 | 2-{3-[(2-ethoxy-4-methane-sulfonylphenyl)amino]prop-1-yn-1-yl}-N-(1-methylpiperidin-4-yl)-1-(2,2,2-trifluoroethyl)-1H-indol-4-amine | 563.2 [(M + H)+] |

-continued

| Ex | Structure | Name | LC-MS (ES+, m/z) |
|---|---|---|---|
| 380 | 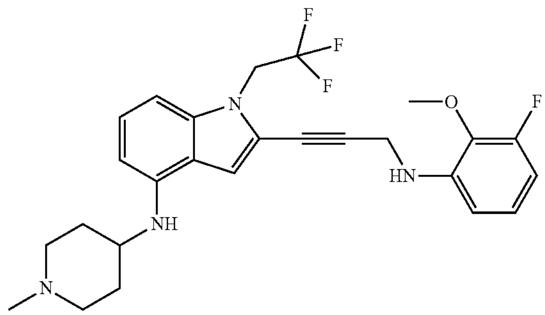 [SMILES: COc1c(F)cccc1NCC#Cc1cc2c(NC3CCN(C)CC3)cccc2n1CC(F)(F)F] | 2-{3-[(3-fluoro-2-methoxyphenyl)-amino]prop-1-yn-1-yl}-N-(1-methylpiperidin-4-yl)-1-(2,2,2-trifluoroethyl)-1H-indol-4-amine | 489.5 [(M + H)+] |
| 381 | 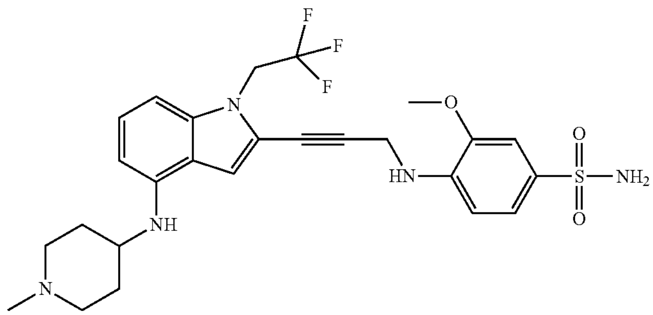 [SMILES: COc1cc(S(N)(=O)=O)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]benzene-1-sulfonamide | 550.1 [(M + H)+] |
| 382 | 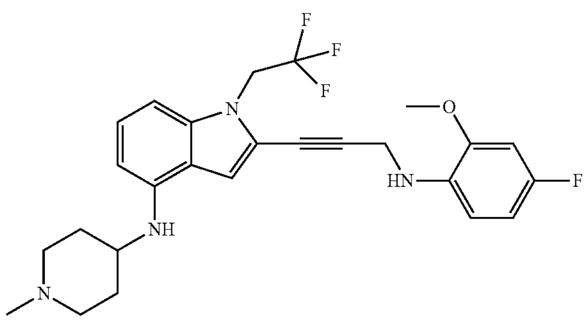 [SMILES: COc1cc(F)ccc1NCC#Cc1cc2c(NC3CCN(C)CC3)cccc2n1CC(F)(F)F] | 2-{3-[(4-fluoro-2-methoxyphenyl)-amino]prop-1-yn-1-yl}-N-(1-methylpiperidin-4-yl)-1-(2,2,2-trifluoroethyl)-1H-indol-4-amine | 489.2 [(M + H)+] |
| 383 | 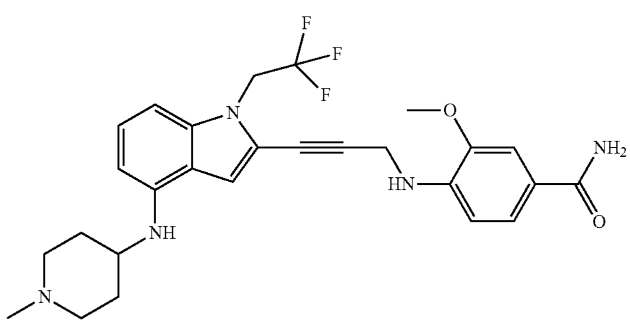 [SMILES: COc1cc(C(N)=O)ccc1NCC#Cc1cc2c(NC3CCN(C)CC3)cccc2n1CC(F)(F)F] | 3-methoxy-4-[(3-{4-[(1-methylpiperidin-4-yl)amino]-1-(2,2,2-trifluoroethyl)-1H-indol-2-yl}prop-2-yn-1-yl)amino]-benzamide | 514.2 [(M + H)+] |
| 384 | 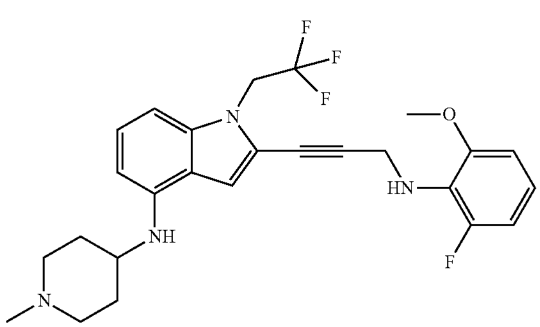 [SMILES: COc1cccc(F)c1NCC#Cc1cc2c(NC3CCN(C)CC3)cccc2n1CC(F)(F)F] | 2-{3-[(2-fluoro-6-methoxyphenyl)-amino]prop-1-yn-1-yl}-N-(1-methylpiperidin-4-yl)-1-(2,2,2-trifluoroethyl)-1H-indol-4-amine | 489.2 [(M + H)+] |

| Ex | Structure | Name | LC-MS (ES+, m/z) |
|---|---|---|---|
| 385 | 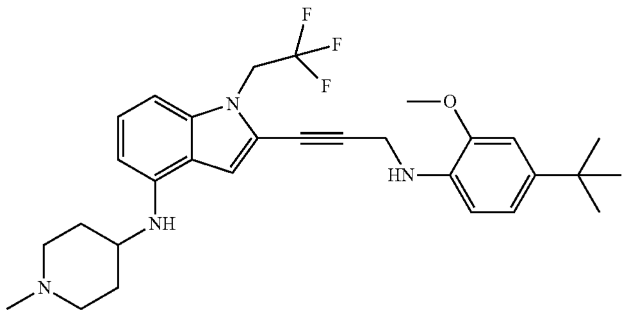 [SMILES: COc1cc(C(C)(C)C)ccc1NCC#Cc1cc2c(NC3CCN(C)CC3)cccc2n1CC(F)(F)F] | 2-{3-[(4-tert-butyl-2-methoxyphenyl)-amino]prop-1-yn-1-yl}-N-(1-methylpiperidin-4-yl)-1-(2,2,2-trifluoroethyl)-1H-indol-4-amine | 527.3 [(M + H)+] |
| 386 | 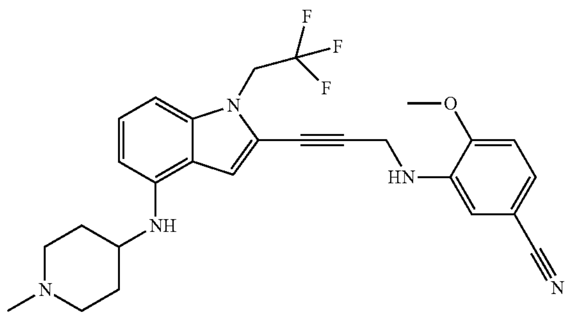 [SMILES: COc1ccc(C#N)cc1NCC#Cc1cc2c(NC3CCN(C)CC3)cccc2n1CC(F)(F)F] | 4-methoxy-3-[(3-{4-[(1-methylpiperidin-4-yl)amino]-1-(2,2,2-trifluoroethyl)-1H-indol-2-yl}prop-2-yn-1-yl)amino]-benzonitrile | 496.2 [(M + H)+] |
| 387 | 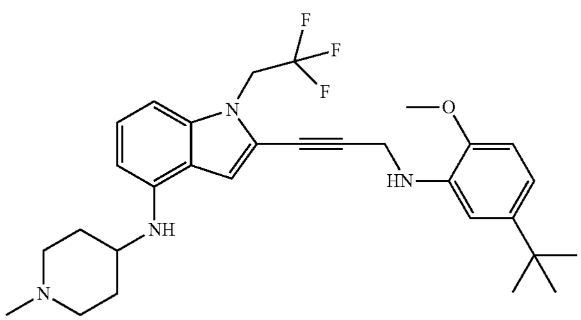 [SMILES: COc1ccc(C(C)(C)C)cc1NCC#Cc1cc2c(NC3CCN(C)CC3)cccc2n1CC(F)(F)F] | 2-{3-[(5-tert-butyl-2-methoxyphenyl)-amino]prop-1-yn-1-yl}-N-(1-methylpiperidin-4-yl)-1-(2,2,2-trifluoroethyl)-1H-indol-4-amine | 527.6 [(M + H)+] |
| 388 | 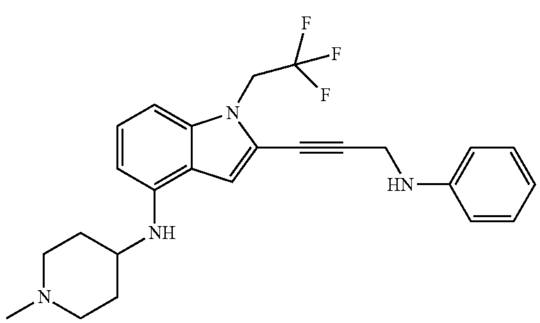 [SMILES: CN1CCC(Nc2cccc3c2cc(C#CCNc2ccccc2)n3CC(F)(F)F)CC1] | N-(1-methylpiperidin-4-yl)-2-[3-(phenylamino)prop-1-yn-1-yl]-1-(2,2,2-trifluoroethyl)-1H-indol-4-amine | 441.4 [(M + H)+] |

-continued

| Ex | Structure | Name | LC-MS (ES+, m/z) |
|---|---|---|---|
| 389 | 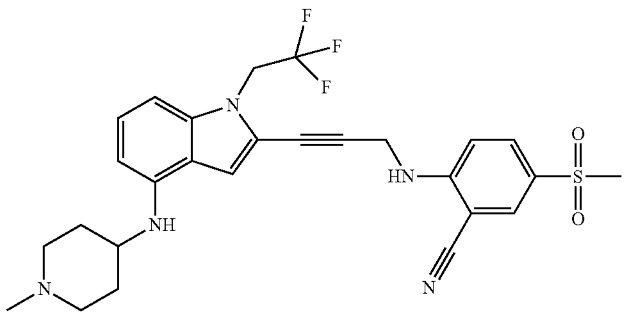 | 5-methanesulfonyl-2-[(3-{4-[(1-methylpiperidin-4-yl)amino]-1-(2,2,2-trifluoroethyl)-1H-indol-2-yl}prop-2-yn-1-yl)amino]benzonitrile | 544.2 [(M + H)+] |
| 390 | 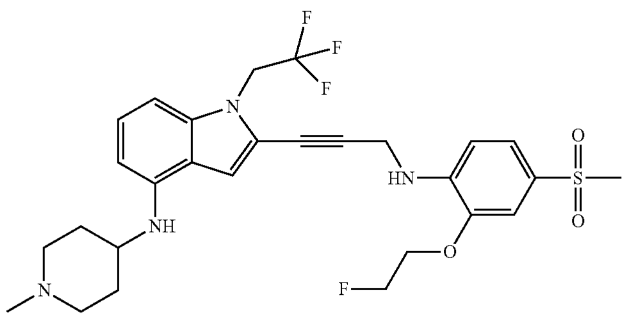 | 2-(3-{[2-(2-fluoroethoxy)-4-methanesulfonylphenyl]amino}prop-1-yn-1-yl)-N-(1-methylpiperidin-4-yl)-1-(2,2,2-trifluoroethyl)-1H-indol-4-amine | 581.2 [(M + H)+] |
| 391 | 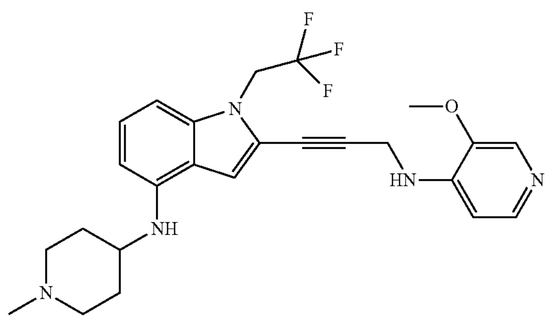 [SMILES: COc1cnccc1NCC#Cc1cc2c(NC3CCN(C)CC3)cccc2n1CC(F)(F)F] | 2-{3-[(3-methoxypyridin-4-yl)amino]prop-1-yn-1-yl}-N-(1-methylpiperidin-4-yl)-1-(2,2,2-trifluoroethyl)-1H-indol-4-amine | 472.2 [(M + H)+] |
| 392 | 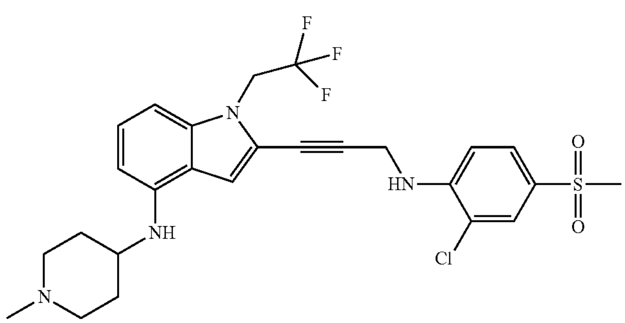 | 2-{3-[(2-chloro-4-methanesulfonyl-phenyl)amino]prop-1-yn-1-yl}-N-(1-methylpiperidin-4-yl)-1-(2,2,2-trifluoroethyl)-1H-indol-4-amine | 553.1 [(M + H)+] |
| 393 | 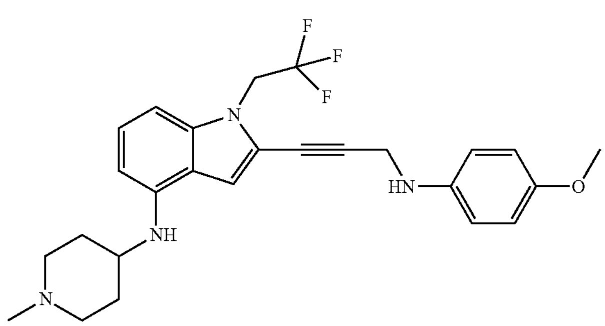 | 2-{3-[(4-methoxyphenyl)amino]prop-1-yn-1-yl}-N-(1-methylpiperidin-4-yl)-1-(2,2,2-trifluoroethyl)-1H-indol-4-amine | 471.2 [(M + H)+] |

| Ex | Structure | Name | LC-MS (ES+, m/z) |
|---|---|---|---|
| 394 | 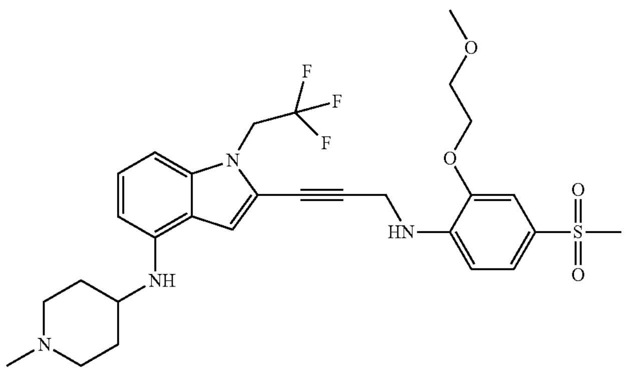 | 2-(3-{[4-methanesulfonyl-2-(2-methoxyethoxy)phenyl]amino}prop-1-yn-1-yl)-N-(1-methylpiperidin-4-yl)-1-(2,2,2-trifluoroethyl)-1H-indol-4-amine | 593.2 [(M + H)+] |

Example 395: Preparation of 5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carbonitrile

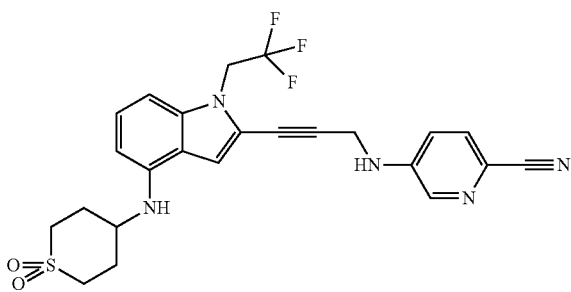 [SMILES: N#Cc1ccc(NCC#Cc2cc3c(NC4CCS(=O)(=O)CC4)cccc3n2CC(F)(F)F)cn1]

To a solution of 2-iodo-1-(2,2,2-trifluoroethyl)-1H-indol-4-amine (500 mg, 1.06 mmol) in ethanol (15 mL) were added 1,1-dioxothian-4-one (471 mg, 3.18 mmol) and tetraethoxytitanium (1.21 g, 5.29 mmol, 1.1 mL). The mixture was stirred at 50° C. for 12 h, and sodium cyanoborohydride (665 mg, 10.59 mmol) was added to the reaction. After stirring the reaction at 80° C. for 2 h, the reaction mixture was diluted with ethyl acetate (15 mL) and poured into a saturated solution of sodium bicarbonate (40 mL). The mixture was extracted with ethyl acetate (3×40 mL). The combined organic layers were washed with brine (3×120 mL), dried over anhydrous sodium sulfate, filtered, and concentrated in vacuo. The crude product was purified by flash column chromatography to give 4-((2-iodo-1-(2,2,2-trifluoroethyl)-1H-indol-4-yl)amino)tetrahydro-2H-thiopyran 1,1-dioxide as a light red solid (450 mg, 69% yield, 77% purity).

4-((2-Iodo-1-(2,2,2-trifluoroethyl)-1H-indol-4-yl)amino)tetrahydro-2H-thiopyran 1,1-dioxide was reacted with 5-(prop-2-yn-1-ylamino)picolinonitrile (prepared from 5-amino-picolinonitrile and propargyl bromide) under Sonogashira coupling conditions to give 5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carbonitrile.

LC-MS (ES+, m/z): 502.2 [(M+H)+]

Starting with 2-iodo-1-(2,2,2-trifluoroethyl)-1H-indol-4-amine and using a method similar to that described in Example 396, the following compounds were prepared:

| Ex | Structure | Name | LC-MS (ES+, m/z) |
|---|---|---|---|
| 396 | 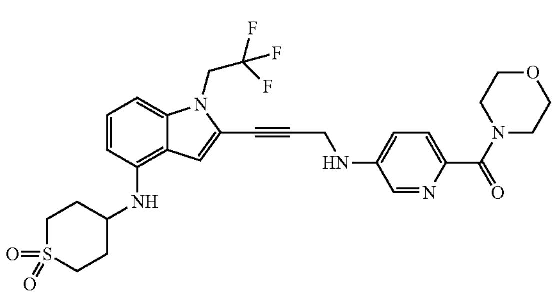 [SMILES: O=C(c1ccc(NCC#Cc2cc3c(NC4CCS(=O)(=O)CC4)cccc3n2CC(F)(F)F)cn1)N1CCOCC1] | 4-{[2-(3-{[6-(morpholine-4-carbonyl)pyridin-3-yl]amino}prop-1-yn-1-yl)-1-(2,2,2-trifluoroethyl)-1H-indol-4-yl]amino}-1λ⁶-thiane-1,1-dione | 590.2 [(M + H)+] |

| Ex | Structure | Name | LC-MS (ES+, m/z) |
|---|---|---|---|
| 397 | 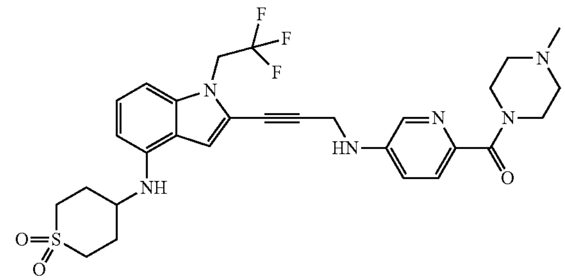 [SMILES: CN1CCN(C(=O)c2ccc(NCC#Cc3cc4c(NC5CCS(=O)(=O)CC5)cccc4n3CC(F)(F)F)cn2)CC1] | 4-{[2-(3-{[6-(4-methylpiperazine-1-carbonyl)pyridin-3-yl]amino}prop-1-yn-1-yl)-1-(2,2,2-trifluoroethyl)-1H-indol-4-yl]amino}-1λ6-thiane-1,1-dione | 603.2 [(M + H)+] |
| 398 | 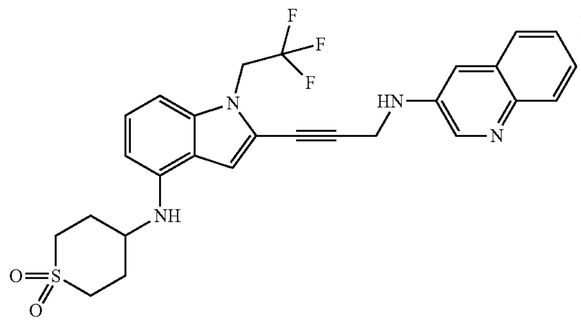 [SMILES: O=S1(=O)CCC(Nc2cccc3c2cc(C#CCNc2cnc4ccccc4c2)n3CC(F)(F)F)CC1] | 4-[(2-{3-[(quinolin-3-yl)amino]prop-1-yn-1-yl}-1-(2,2,2-trifluoroethyl)-1H-indol-4-yl)amino]-1λ6-thiane-1,1-dione | 527.2 [(M + H)+] |
| 399 | 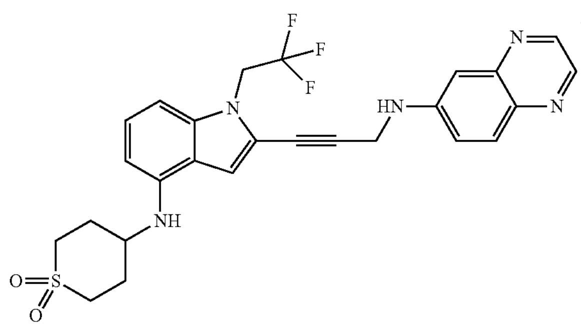 [SMILES: O=S1(=O)CCC(Nc2cccc3c2cc(C#CCNc2ccc4nccnc4c2)n3CC(F)(F)F)CC1] | 4-[(2-{3-[(quinoxalin-6-yl)amino]prop-1-yn-1-yl}-1-(2,2,2-trifluoroethyl)-1H-indol-4-yl)amino]-1λ6-thiane-1,1-dione | 528.3 [(M + H)+] |
| 400 | 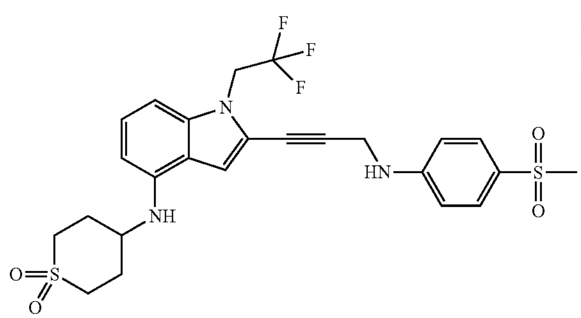 | 4-[(2-{3-[(4-methanesulfonylphenyl)-amino]prop-1-yn-1-yl}-1-(2,2,2-trifluoroethyl)-1H-indol-4-yl)amino]-1λ6-thiane-1,1-dione | 554.2 [(M + H)+] |
| 401 | 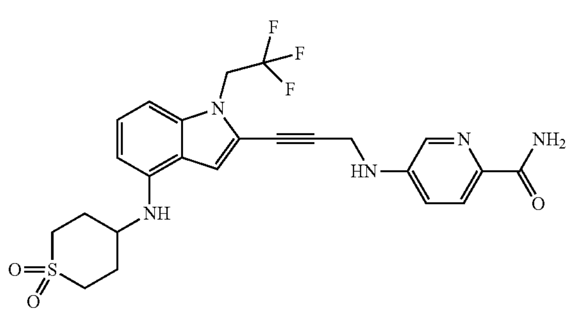 | 5-[(3-{4-[(1,1-dioxo-1λ6-thian-4-yl)amino]-1-(2,2,2-trifluoroethyl)-1H-indol-2-yl}prop-2-yn-1-yl)amino]pyridine-2-carboxamide | 520.2 [(M + H)+] |

| Ex | Structure | Name | LC-MS (ES+, m/z) |
|---|---|---|---|
| 402 | 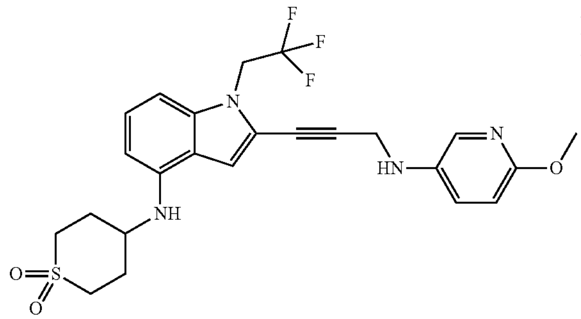 [SMILES: COc1ccc(NCC#Cc2cc3c(NC4CCS(=O)(=O)CC4)cccc3n2CC(F)(F)F)cn1] | 4-[(2-{3-[(6-methoxypyridin-3-yl)amino]prop-1-yn-1-yl}-1-(2,2,2-trifluoroethyl)-1H-indol-4-yl)amino]-1λ6-thiane-1,1-dione | 507.2 [(M + H)+] |
| 403 | 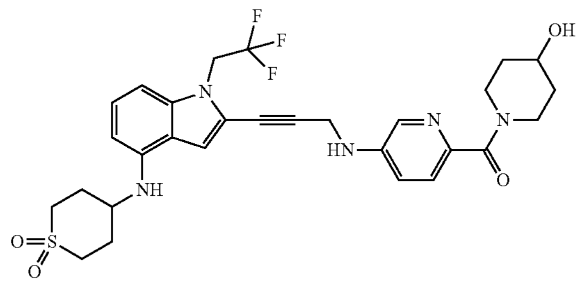 [SMILES: O=C(c1ccc(NCC#Cc2cc3c(NC4CCS(=O)(=O)CC4)cccc3n2CC(F)(F)F)cn1)N1CCC(O)CC1] | 4-{[2-(3-{[6-(4-hydroxypiperidine-1-carbonyl)pyridin-3-yl]amino}prop-1-yn-1-yl)-1-(2,2,2-trifluoroethyl)-1H-indol-4-yl]amino}-1λ6-thiane-1,1-dione | 604.3 [(M + H)+] |
| 404 | 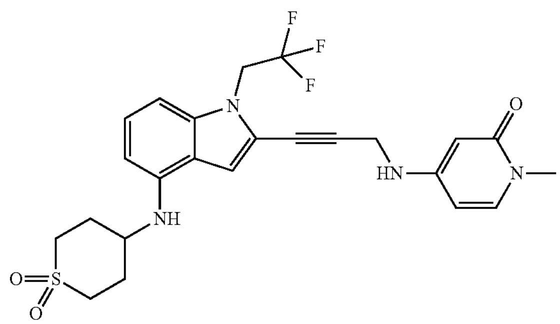 [SMILES: Cn1ccc(NCC#Cc2cc3c(NC4CCS(=O)(=O)CC4)cccc3n2CC(F)(F)F)cc1=O] | 4-[(2-{3-[(1-methyl-2-oxo-1,2-dihydropyridin-4-yl)amino]prop-1-yn-1-yl}-1-(2,2,2-trifluoroethyl)-1H-indol-4-yl)amino]-1λ6-thiane-1,1-dione | 507.2 [(M + H)+] |
| 405 | 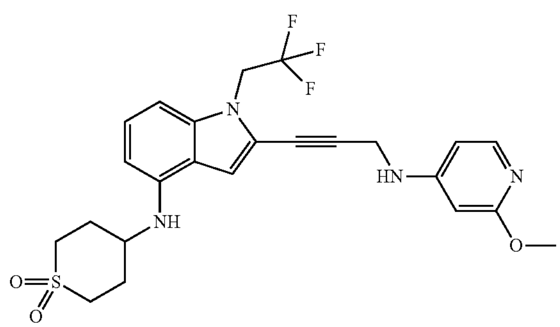 [SMILES: COc1cc(NCC#Cc2cc3c(NC4CCS(=O)(=O)CC4)cccc3n2CC(F)(F)F)ccn1] | 4-[(2-{3-[(2-methoxypyridin-4-yl)amino]prop-1-yn-1-yl}-1-(2,2,2-trifluoroethyl)-1H-indol-4-yl)amino]-1λ6-thiane-1,1-dione | 507.2 [(M + H)+] |
| 406 | 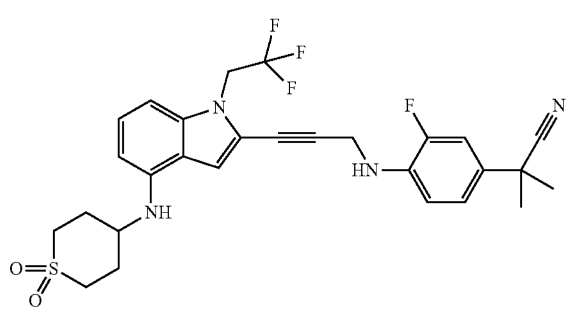 | 2-{4-[(3-{4-[(1,1-dioxo-1λ6-thian-4-yl)amino]-1-(2,2,2-trifluoroethyl)-1H-indol-2-yl}prop-2-yn-1-yl)amino]-3-fluorophenyl}-2-methylpropanenitrile | 561.1 [(M + H)+] |

-continued

| Ex | Structure | Name | LC-MS (ES+, m/z) |
|---|---|---|---|
| 407 | 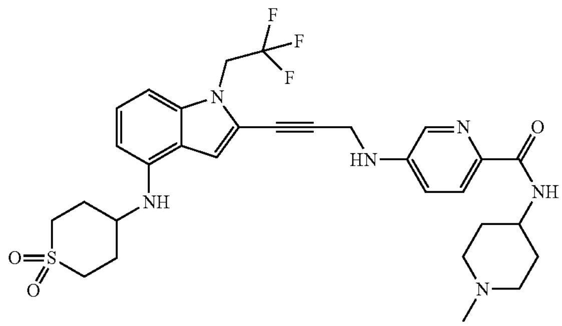 [SMILES: CN1CCC(NC(=O)c2ccc(NCC#Cc3cc4c(NC5CCS(=O)(=O)CC5)cccc4n3CC(F)(F)F)cn2)CC1] | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-(1-methylpiperidin-4-yl)pyridine-2-carboxamide | 617.3 [(M + H)+] |
| 408 | 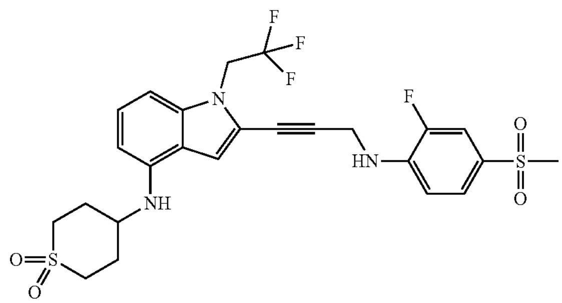 | 4-[(2-{3-[(2-fluoro-4-methanesulfonyl-phenyl)amino]prop-1-yn-1-yl}-1-(2,2,2-trifluoroethyl)-1H-indol-4-yl)amino]-1λ⁶-thiane-1,1-dione | 572.2 [(M + H)+] |
| 409 | 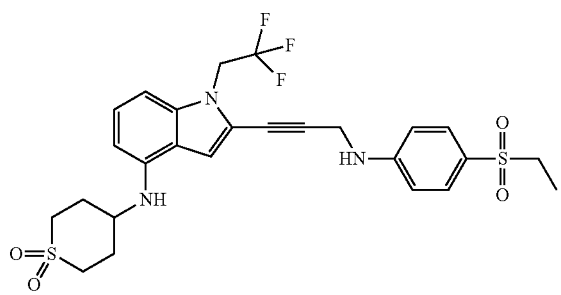 [SMILES: CCS(=O)(=O)c1ccc(NCC#Cc2cc3c(NC4CCS(=O)(=O)CC4)cccc3n2CC(F)(F)F)cc1] | 4-{[2-(3-{[4-(ethanesulfonyl)-phenyl]amino}prop-1-yn-1-yl)-1-(2,2,2-trifluoroethyl)-1H-indol-4-yl]amino}-1λ⁶-thiane-1,1-dione | 568.2 [(M + H)+] |
| 410 | 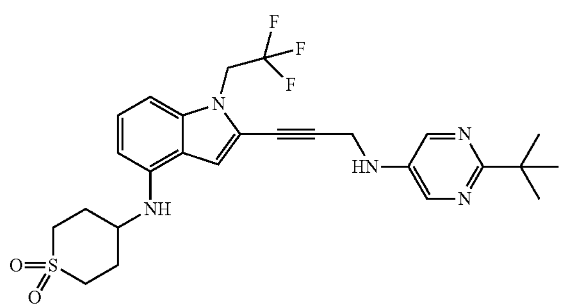 [SMILES: CC(C)(C)c1ncc(NCC#Cc2cc3c(NC4CCS(=O)(=O)CC4)cccc3n2CC(F)(F)F)cn1] | 4-[(2-{3-[(2-tert-butylpyrimidin-5-yl)amino]prop-1-yn-1-yl}-1-(2,2,2-trifluoroethyl)-1H-indol-4-yl)amino]-1λ⁶-thiane-1,1-dione | 534.2 [(M + H)+] |
| 411 | 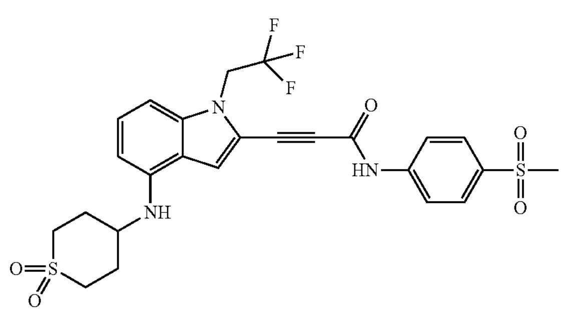 [SMILES: CS(=O)(=O)c1ccc(NC(=O)C#Cc2cc3c(NC4CCS(=O)(=O)CC4)cccc3n2CC(F)(F)F)cc1] | 3-{4-[(1,1-dioxo-1λ⁶-thian-4-yl)amino]-1-(2,2,2-trifluoroethyl)-1H-indol-2-yl}-N-(4-methanesulfonyl-phenyl)-prop-2-ynamide | 568.2 [(M + H)+] |

| Ex | Structure | Name | LC-MS (ES+, m/z) |
|---|---|---|---|
| 412 | 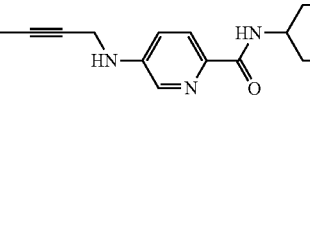 | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-(oxan-4-yl)pyridine-2-carboxamide | 604.3 [(M + H)⁺] |
| 413 | 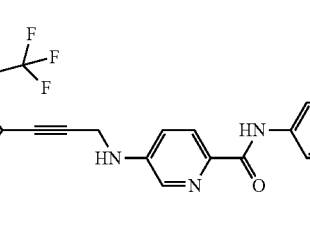 | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-(pyridin-3-yl)pyridine-2-carboxamide | 597.3 [(M + H)⁺] |
| 414 | 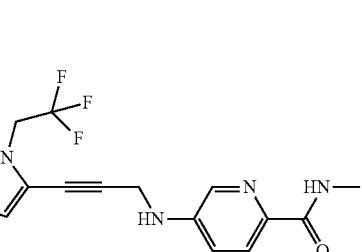 | 5-[(3-{4-[(1,1-dioxo-1λ⁶-thian-4-yl)amino]-1-(2,2,2-trifluoroethyl)-1H-indol-2-yl}prop-2-yn-1-yl)amino]-N-methylpyridine-2-carboxamide | 534.2 [(M + H)⁺] |
| 415 | 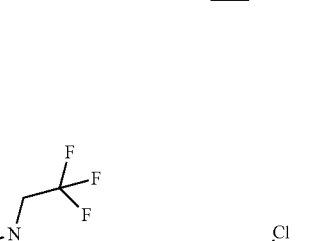 | 4-[(2-{3-[(3-chloro-4-methanesulfonylphenyl)amino]prop-1-yn-1-yl}-1-(2,2,2-trifluoroethyl)-1H-indol-4-yl)amino]-1λ⁶-thiane-1,1-dione | 588.2 [(M + H)⁺] |
| 416 | 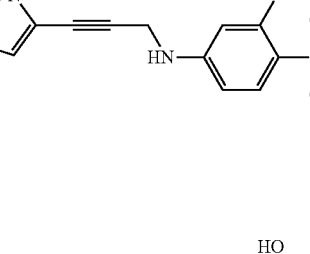 | N-(2,3-dihydroxypropyl)-5-[(3-{4-[(1,1-dioxo-1λ⁶-thian-4-yl)amino]-1-(2,2,2-trifluoroethyl)-1H-indol-2-yl}prop-2-yn-1-yl)amino]pyridine-2-carboxamide | 594.3 [(M + H)⁺] |

-continued

| Ex | Structure | Name | LC-MS (ES+, m/z) |
|---|---|---|---|
| 417 | 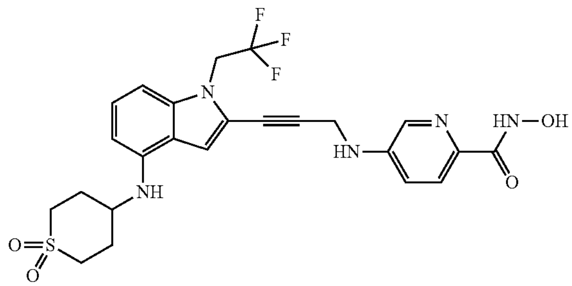 [SMILES: O=C(NO)c1ccc(NCC#Cc2cc3c(NC4CCS(=O)(=O)CC4)cccc3n2CC(F)(F)F)cn1] | 5-[(3-{4-[(1,1-dioxo-1λ6-thian-4-yl)amino]-1-(2,2,2-trifluoroethyl)-1H-indol-2-yl}prop-2-yn-1-yl)amino]-N-hydroxypyridine-2-carboxamide | 536.2 [(M + H)+] |
| 418 | 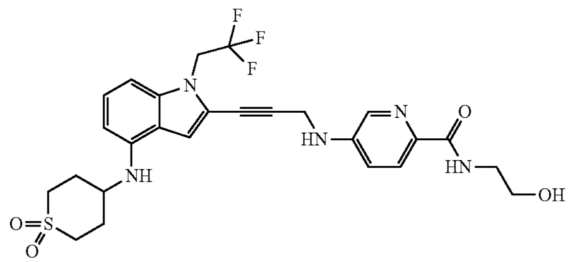 [SMILES: O=C(NCCO)c1ccc(NCC#Cc2cc3c(NC4CCS(=O)(=O)CC4)cccc3n2CC(F)(F)F)cn1] | 5-[(3-{4-[(1,1-dioxo-1λ6-thian-4-yl)amino]-1-(2,2,2-trifluoroethyl)-1H-indol-2-yl}prop-2-yn-1-yl)amino]-N-(2-hydroxyethyl)pyridine-2-carboxamide | 564.3 [(M + H)+] |
| 419 | 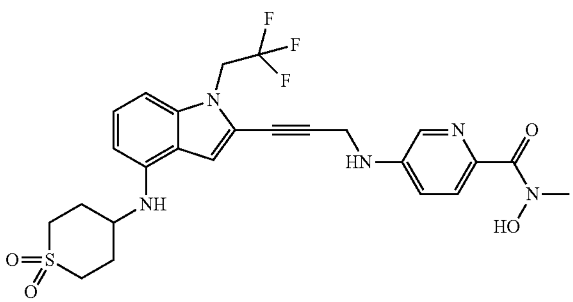 [SMILES: CN(O)C(=O)c1ccc(NCC#Cc2cc3c(NC4CCS(=O)(=O)CC4)cccc3n2CC(F)(F)F)cn1] | 5-[(3-{4-[(1,1-dioxo-1λ6-thian-4-yl)amino]-1-(2,2,2-trifluoroethyl)-1H-indol-2-yl}prop-2-yn-1-yl)amino]-N-hydroxy-N-methylpyridine-2-carboxamide | 550.2 [(M + H)+] |
| 420 | 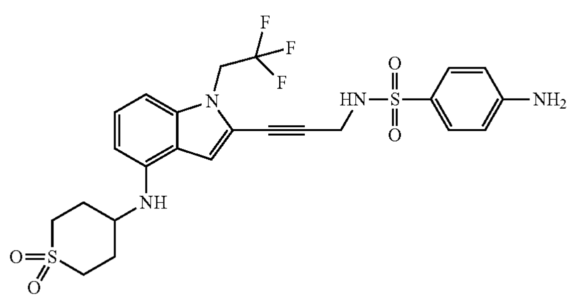 [SMILES: Nc1ccc(S(=O)(=O)NCC#Cc2cc3c(NC4CCS(=O)(=O)CC4)cccc3n2CC(F)(F)F)cc1] | 4-amino-N-(3-{4-[(1,1-dioxo-1λ6-thian-4-yl)amino]-1-(2,2,2-trifluoroethyl)-1H-indol-2-yl}prop-2-yn-1-yl)benzene-1-sulfonamide | 555.2 [(M + H)+] |
| 421 | 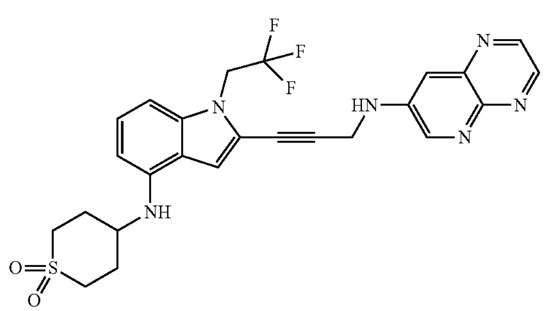 | 4-({2-[3-({pyrido[2,3-b]pyrazin-7-yl}amino)prop-1-yn-1-yl]-1-(2,2,2-trifluoroethyl)-1H-indol-4-yl}amino)-1λ6-thiane-1,1-dione | 529.2 [(M + H)+] |

| Ex | Structure | Name | LC-MS (ES+, m/z) |
|---|---|---|---|
| 422 | 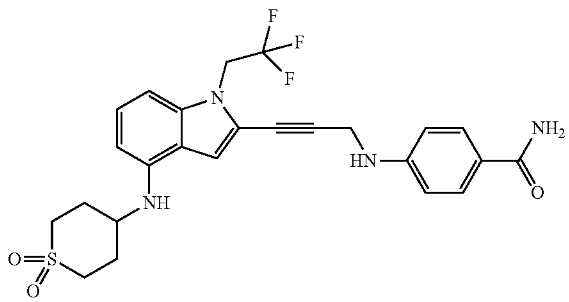 [SMILES: NC(=O)c1ccc(NCC#Cc2cc3c(NC4CCS(=O)(=O)CC4)cccc3n2CC(F)(F)F)cc1] | 4-[(3-{4-[(1,1-dioxo-1λ6-thian-4-yl)amino]-1-(2,2,2-trifluoroethyl)-1H-indol-2-yl}prop-2-yn-1-yl)amino]-benzamide | 519.2 [(M + H)+] |
| 423 | 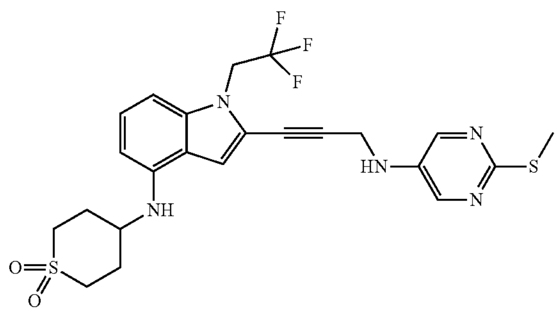 [SMILES: CSc1ncc(NCC#Cc2cc3c(NC4CCS(=O)(=O)CC4)cccc3n2CC(F)(F)F)cn1] | 4-{[2-(3-{[2-(methylsulfanyl)pyrimidin-5-yl]amino}prop-1-yn-1-yl)-1-(2,2,2-trifluoroethyl)-1H-indol-4-yl]amino}-1λ6-thiane-1,1-dione | 524.1 [(M + H)+] |
| 424 | 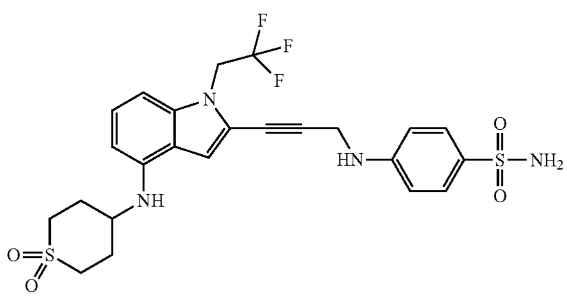 [SMILES: NS(=O)(=O)c1ccc(NCC#Cc2cc3c(NC4CCS(=O)(=O)CC4)cccc3n2CC(F)(F)F)cc1] | 4-[(3-{4-[(1,1-dioxo-1λ6-thian-4-yl)amino]-1-(2,2,2-trifluoroethyl)-1H-indol-2-yl}prop-2-yn-1-yl)amino]benzene-1-sulfonamide | 555.2 [(M + H)+] |
| 425 | 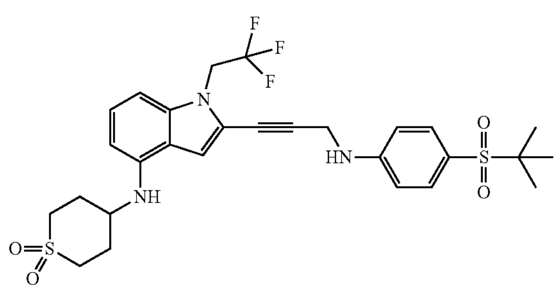 [SMILES: CC(C)(C)S(=O)(=O)c1ccc(NCC#Cc2cc3c(NC4CCS(=O)(=O)CC4)cccc3n2CC(F)(F)F)cc1] | 4-{[2-(3-{[4-(2-methylpropane-2-sulfonyl)phenyl]amino}prop-1-yn-1-yl)-1-(2,2,2-trifluoroethyl)-1H-indol-4-yl]amino}-1λ6-thiane-1,1-dione | 596.3 [(M + H)+] |
| 426 | 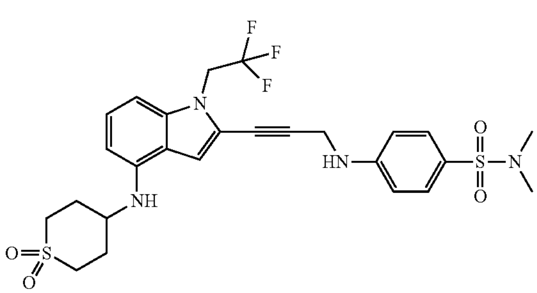 [SMILES: CN(C)S(=O)(=O)c1ccc(NCC#Cc2cc3c(NC4CCS(=O)(=O)CC4)cccc3n2CC(F)(F)F)cc1] | 4-[(3-{4-[(1,1-dioxo-1λ6-thian-4-yl)amino]-1-(2,2,2-trifluoroethyl)-1H-indol-2-yl}prop-2-yn-1-yl)amino]-N,N-dimethylbenzene-1-sulfonamide | 583.3 [(M + H)+] |

-continued

| Ex | Structure | Name | LC-MS (ES+, m/z) |
|---|---|---|---|
| 427 | 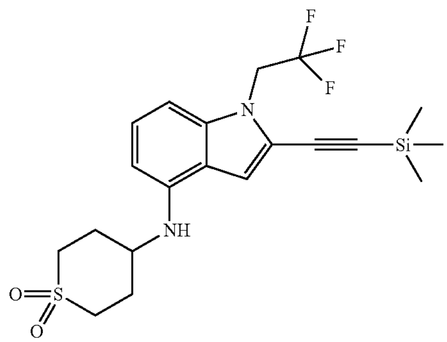 [SMILES: C[Si](C)(C)C#Cc1cc2c(NC3CCS(=O)(=O)CC3)cccc2n1CC(F)(F)F] | 4-{[1-(2,2,2-trifluoroethyl)-2-[2-(trimethylsilyl)ethynyl]-1H-indol-4-yl]amino)-1λ⁶-thiane-1,1-dione | 443.2 [(M + H)+] |
| 428 | 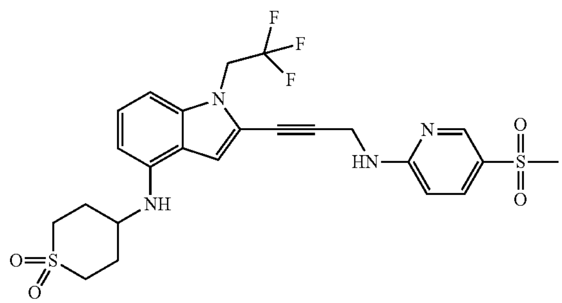 [SMILES: CS(=O)(=O)c1ccc(NCC#Cc2cc3c(NC4CCS(=O)(=O)CC4)cccc3n2CC(F)(F)F)nc1] | 4-[(2-{3-[(5-methanesulfonylpyridin-2-yl)amino]prop-1-yn-1-yl}-1-(2,2,2-trifluoroethyl)-1H-indol-4-yl)amino]-1λ⁶-thiane-1,1-dione | 555.2 [(M + H)+] |
| 429 | 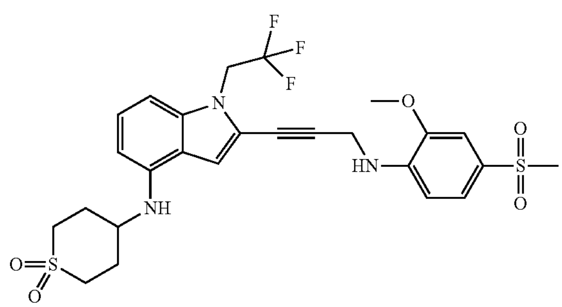 | 4-[(2-{3-[(4-methanesulfonyl-2-methoxyphenyl)amino]prop-1-yn-1-yl}-1-(2,2,2-trifluoroethyl)-1H-indol-4-yl)amino]-1λ⁶-thiane-1,1-dione | 584.2 [(M + H)+] |
| 430 | 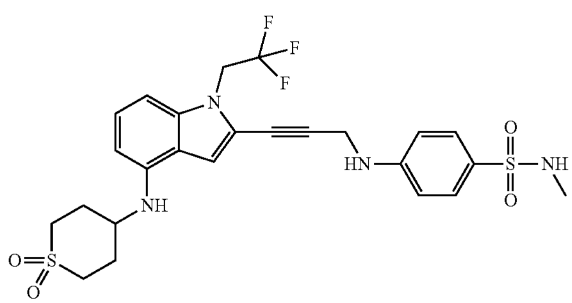 [SMILES: CNS(=O)(=O)c1ccc(NCC#Cc2cc3c(NC4CCS(=O)(=O)CC4)cccc3n2CC(F)(F)F)cc1] | 4-[(3-{4-[(1,1-dioxo-1λ⁶-thian-4-yl)amino]-1-(2,2,2-trifluoroethyl)-1H-indol-2-yl}prop-2-yn-1-yl)amino]-N-methylbenzene-1-sulfonamide | 569.3 [(M + H)+] |
| 431 | 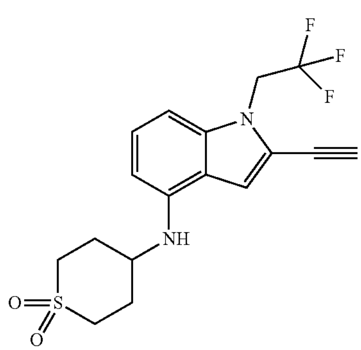 [SMILES: C#Cc1cc2c(NC3CCS(=O)(=O)CC3)cccc2n1CC(F)(F)F] | 4-{[2-ethynyl-1-(2,2,2-trifluoroethyl)-1H-indol-4-yl]amino}-1λ⁶-thiane-1,1-dione | 371.1 [(M + H)+] |

-continued

| Ex | Structure | Name | LC-MS (ES+, m/z) |
|---|---|---|---|
| 432 | 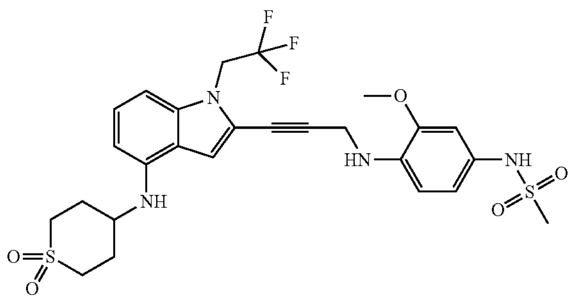 [SMILES: COc1cc(NS(C)(=O)=O)ccc1NCC#Cc1cc2c(NC3CCS(=O)(=O)CC3)cccc2n1CC(F)(F)F] | N-{4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxyphenyl}methanesulfonamide | 599.3 [(M + H)⁺] |
| 433 | 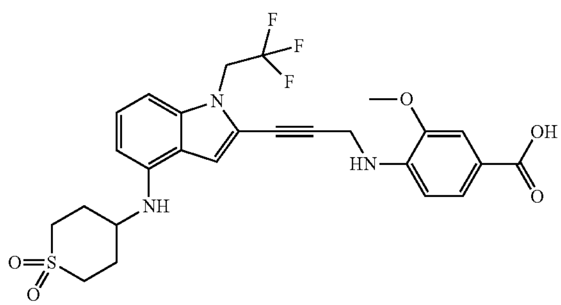 [SMILES: COc1cc(C(=O)O)ccc1NCC#Cc1cc2c(NC3CCS(=O)(=O)CC3)cccc2n1CC(F)(F)F] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzoic acid | 550.1 [(M + H)⁺] |
| 434 | 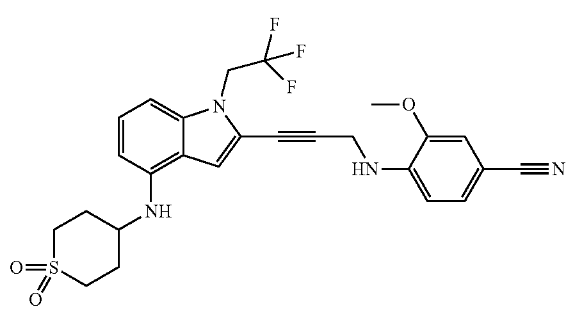 [SMILES: COc1cc(C#N)ccc1NCC#Cc1cc2c(NC3CCS(=O)(=O)CC3)cccc2n1CC(F)(F)F] | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzonitrile | 531.3 [(M + H)⁺] |
| 435 | 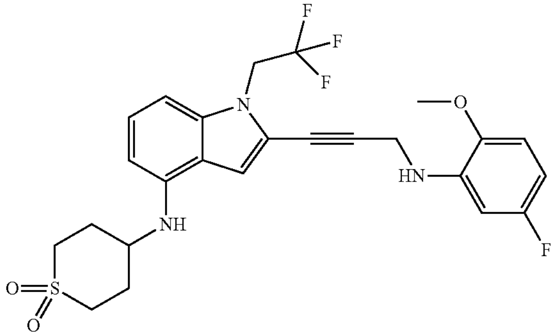 [SMILES: COc1ccc(F)cc1NCC#Cc1cc2c(NC3CCS(=O)(=O)CC3)cccc2n1CC(F)(F)F] | 4-[(2-{3-[(5-fluoro-2-methoxyphenyl)amino]prop-1-yn-1-yl}-1-(2,2,2-trifluoroethyl)-1H-indol-4-yl)amino]-1λ⁶-thiane-1,1-dione | 524.4 [(M + H)⁺] |

-continued

| Ex | Structure | Name | LC-MS (ES+, m/z) |
|---|---|---|---|
| 436 | 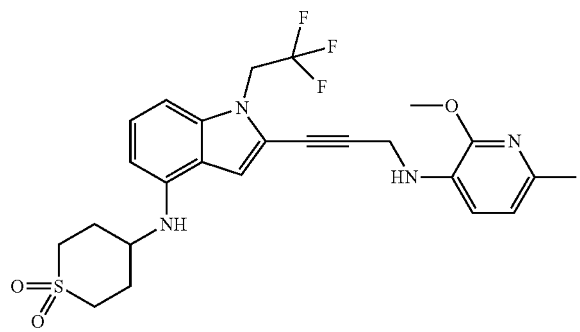 [SMILES: COc1nc(C)ccc1NCC#Cc1cc2c(NC3CCS(=O)(=O)CC3)cccc2n1CC(F)(F)F] | 4-[(2-{3-[(2-methoxy-6-methylpyridin-3-yl)amino]prop-1-yn-1-yl}-1-(2,2,2-trifluoroethyl)-1H-indol-4-yl)amino]-1λ6-thiane-1,1-dione | 521 [(M + H)+] |
| 437 | 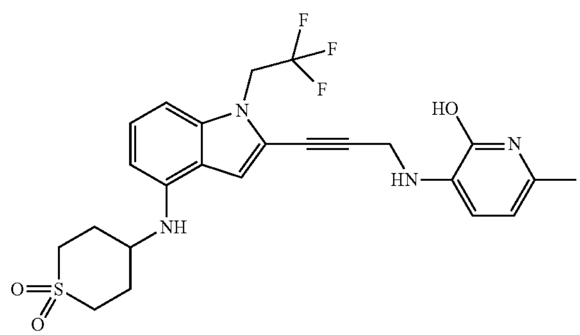 [SMILES: Cc1ccc(NCC#Cc2cc3c(NC4CCS(=O)(=O)CC4)cccc3n2CC(F)(F)F)c(O)n1] | 4-[(2-{3-[(2-hydroxy-6-methylpyridin-3-yl)amino]prop-1-yn-1-yl}-1-(2,2,2-trifluoroethyl)-1H-indol-4-yl)amino]-1λ6-thiane-1,1-dione | 507 [(M + H)+] |
| 438 | 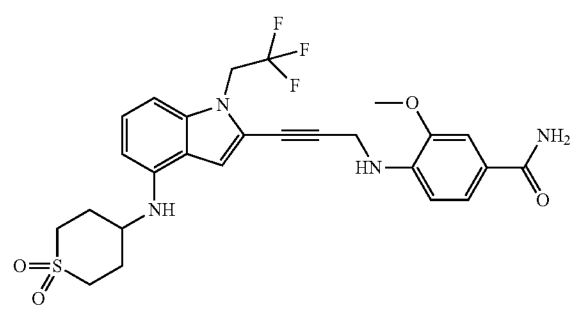 [SMILES: COc1cc(C(N)=O)ccc1NCC#Cc1cc2c(NC3CCS(=O)(=O)CC3)cccc2n1CC(F)(F)F] | 4-[(3-{4-[(1,1-dioxo-1λ6-thian-4-yl)amino]-1-(2,2,2-trifluoroethyl)-1H-indol-2-yl}prop-2-yn-1-yl)amino]-3-methoxybenzamide | 549.4 [(M + H)+] |
| 439 | 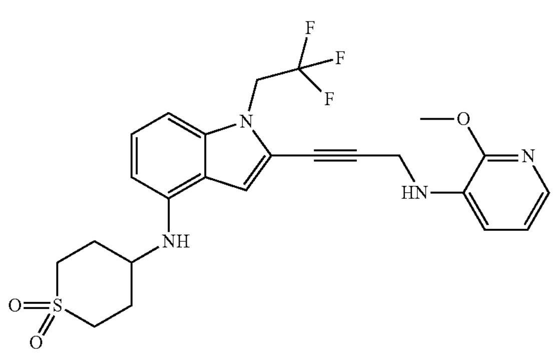 [SMILES: COc1ncccc1NCC#Cc1cc2c(NC3CCS(=O)(=O)CC3)cccc2n1CC(F)(F)F] | 4-[(2-{3-[(2-methoxypyridin-3-yl)amino]prop-1-yn-1-yl}-1-(2,2,2-trifluoroethyl)-1H-indol-4-yl)amino]-1λ6-thiane-1,1-dione | 507.2 [(M + H)+] |

| Ex | Structure | Name | LC-MS (ES+, m/z) |
|---|---|---|---|
| 440 | 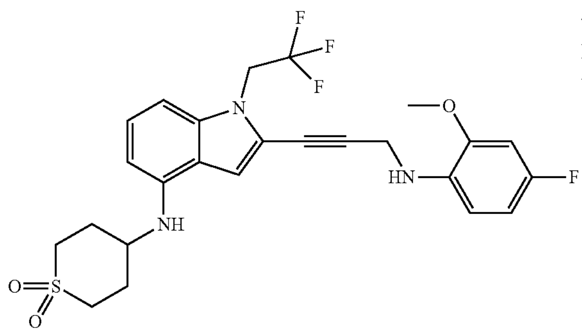 [SMILES: COc1cc(F)ccc1NCC#Cc1cc2c(NC3CCS(=O)(=O)CC3)cccc2n1CC(F)(F)F] | 4-[(2-{3-[(4-fluoro-2-methoxyphenyl)amino]prop-1-yn-1-yl}-1-(2,2,2-trifluoroethyl)-1H-indol-4-yl)amino]-1λ6-thiane-1,1-dione | 524.1 [(M + H)+] |
| 441 | 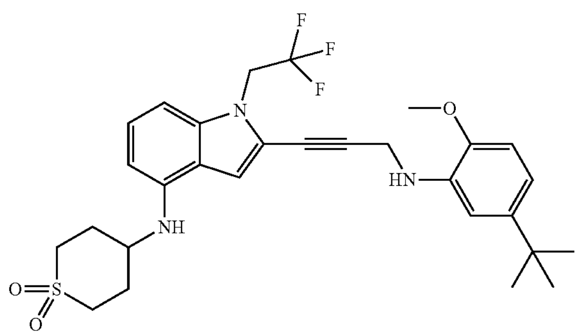 [SMILES: COc1ccc(C(C)(C)C)cc1NCC#Cc1cc2c(NC3CCS(=O)(=O)CC3)cccc2n1CC(F)(F)F] | 4-[(2-{3-[(5-tert-butyl-2-methoxyphenyl)amino]prop-1-yn-1-yl}-1-(2,2,2-trifluoroethyl)-1H-indol-4-yl)amino]-1λ6-thiane-1,1-dione | 562.2 [(M + H)+] |
| 442 | 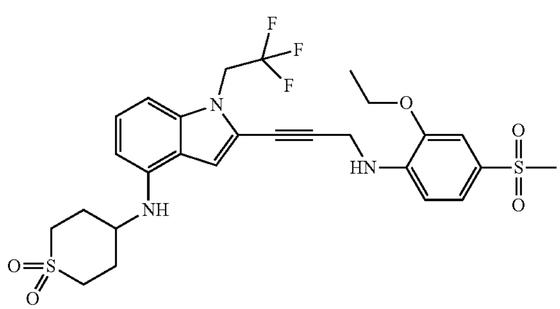 [SMILES: CCOc1cc(S(C)(=O)=O)ccc1NCC#Cc1cc2c(NC3CCS(=O)(=O)CC3)cccc2n1CC(F)(F)F] | 4-[(2-{3-[(2-ethoxy-4-methanesulfonylphenyl)amino]prop-1-yn-1-yl}-1-(2,2,2-trifluoroethyl)-1H-indol-4-yl)amino]-1λ6-thiane-1,1-dione | 598.1 [(M + H)+] |
| 443 | 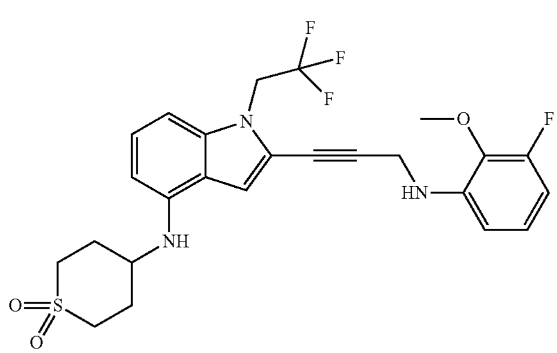 [SMILES: COc1c(F)cccc1NCC#Cc1cc2c(NC3CCS(=O)(=O)CC3)cccc2n1CC(F)(F)F] | 4-[(2-{3-[(3-fluoro-2-methoxyphenyl)amino]prop-1-yn-1-yl}-1-(2,2,2-trifluoroethyl)-1H-indol-4-yl)amino]-1λ6-thiane-1,1-dione | 524.4 [(M + H)+] |

-continued

| Ex | Name | LC-MS (ES+, m/z) |
|---|---|---|
| 444 | 4-({2-[3-(methylamino)prop-1-yn-1-yl]-1-(2,2,2-trifluoroethyl)-1H-indol-4-yl}amino)-1λ⁶-thiane-1,1-dione | 414.3 [(M + H)+] |
| 445 | 4-[(3-{4-[(1,1-dioxo-1λ⁶-thian-4-yl)amino]-1-(2,2,2-trifluoroethyl)-1H-indol-2-yl}prop-2-yn-1-yl)amino]-3-methoxybenzene-1-sulfonamide | 585 [(M + H)+] |
| 446 | 4-[(2-{3-[(2-fluoro-6-methoxyphenyl)amino]prop-1-yn-1-yl}-1-(2,2,2-trifluoroethyl)-1H-indol-4-yl)amino]-1λ⁶-thiane-1,1-dione | 524.2 [(M + H)+] |
| 447 | 3-[(3-{4-[(1,1-dioxo-1λ⁶-thian-4-yl)amino]-1-(2,2,2-trifluoroethyl)-1H-indol-2-yl}prop-2-yn-1-yl)amino]-4-methoxybenzonitrile | 531.1 [(M + H)+] |

| Ex | Structure | Name | LC-MS (ES+, m/z) |
|---|---|---|---|
| 448 | 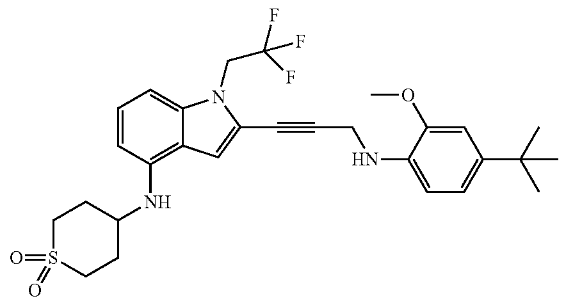 [SMILES: COc1cc(C(C)(C)C)ccc1NCC#Cc1cc2c(NC3CCS(=O)(=O)CC3)cccc2n1CC(F)(F)F] | 4-[(2-{3-[(4-tert-butyl-2-methoxy-phenyl)amino]prop-1-yn-1-yl}-1-(2,2,2-trifluoroethyl)-1H-indol-4-yl)amino]-1λ6-thiane-1,1-dione | 562.2 [(M + H)+] |
| 449 | 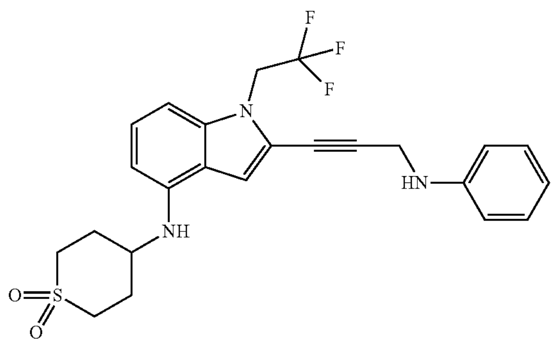 [SMILES: O=S1(=O)CCC(Nc2cccc3c2cc(C#CCNc2ccccc2)n3CC(F)(F)F)CC1] | 4-({2-[3-(phenylamino)prop-1-yn-1-yl]-1-(2,2,2-trifluoroethyl)-1H-indol-4-yl}amino)-1λ6-thiane-1,1-dione | 476.4 [(M + H)+] |
| 450 | 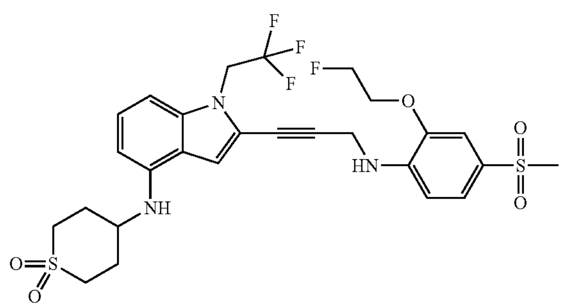 [SMILES: CS(=O)(=O)c1ccc(NCC#Cc2cc3c(NC4CCS(=O)(=O)CC4)cccc3n2CC(F)(F)F)c(OCCF)c1] | 4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}-1λ6-thiane-1,1-dione | 616.1 [(M + H)+] |
| 451 | 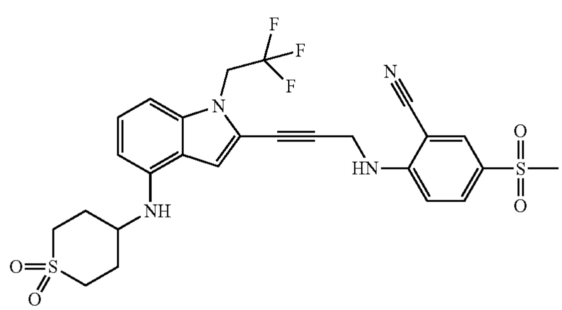 [SMILES: CS(=O)(=O)c1ccc(NCC#Cc2cc3c(NC4CCS(=O)(=O)CC4)cccc3n2CC(F)(F)F)c(C#N)c1] | 2-[(3-{4-[(1,1-dioxo-1λ6-thian-4-yl)amino]-1-(2,2,2-trifluoroethyl)-1H-indol-2-yl}prop-2-yn-1-yl)amino]-5-methanesulfonylbenzonitrile | 579.1 [(M + H)+] |
| 452 | 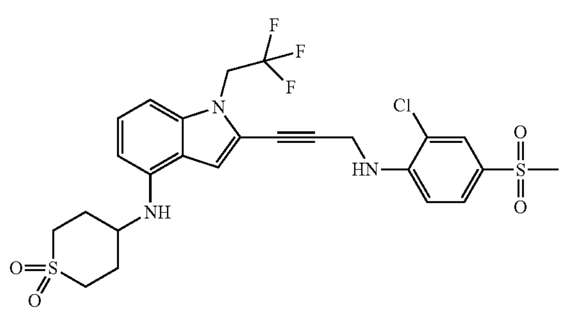 | 4-[(2-{3-[(2-chloro-4-methanesulfonyl-phenyl)amino]prop-1-yn-1-yl}-1-(2,2,2-trifluoroethyl)-1H-indol-4-yl)amino]-1λ6-thiane-1,1-dione | 588.1 [(M + H)+] |

-continued

| Ex | Structure | Name | LC-MS (ES+, m/z) |
|---|---|---|---|
| 453 | 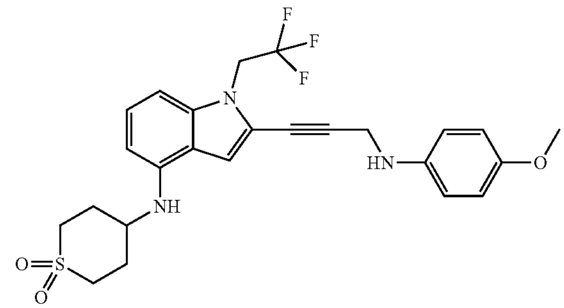 [SMILES: COc1ccc(NCC#Cc2cc3c(NC4CCS(=O)(=O)CC4)cccc3n2CC(F)(F)F)cc1] | 4-[(2-{3-[(4-methoxyphenyl)amino]prop-1-yn-1-yl}-1-(2,2,2-trifluoroethyl)-1H-indol-4-yl)amino]-1λ⁶-thiane-1,1-dione | 506.2 [(M + H)+] |
| 454 | 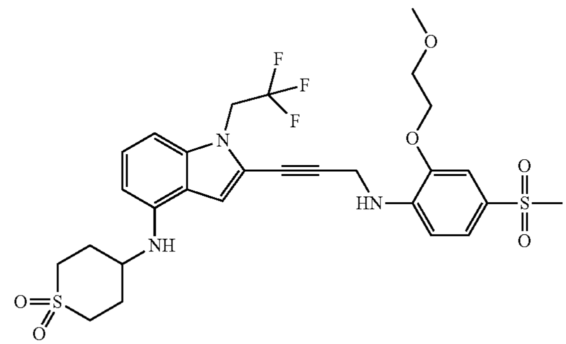 [SMILES: COCCOc1cc(S(C)(=O)=O)ccc1NCC#Cc1cc2c(NC3CCS(=O)(=O)CC3)cccc2n1CC(F)(F)F] | 4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}-1λ⁶-thiane-1,1-dione | 628.1 [(M + H)+] |

Example 455: Preparation of 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide

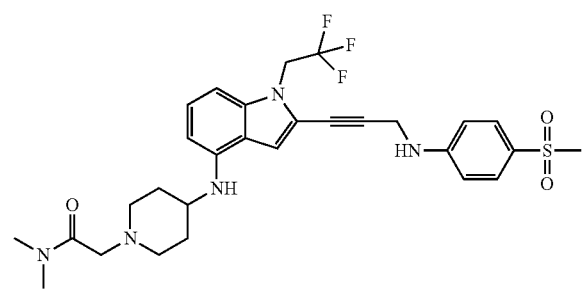

Synthetic Scheme:

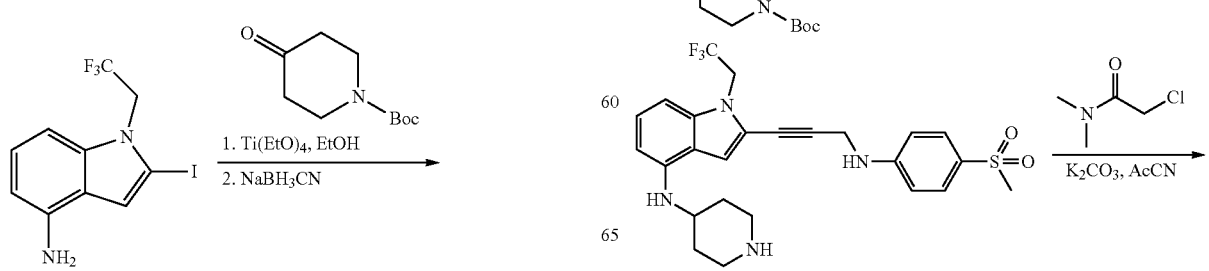

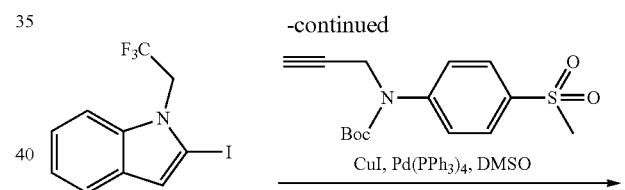

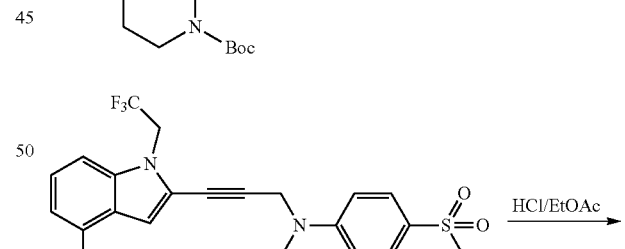

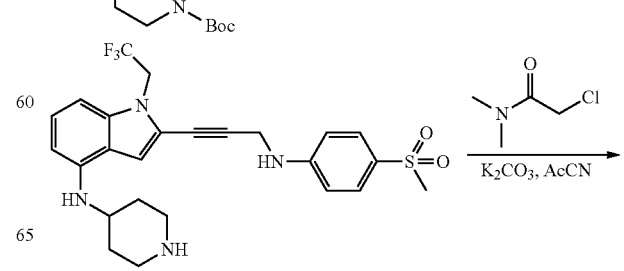

291

-continued

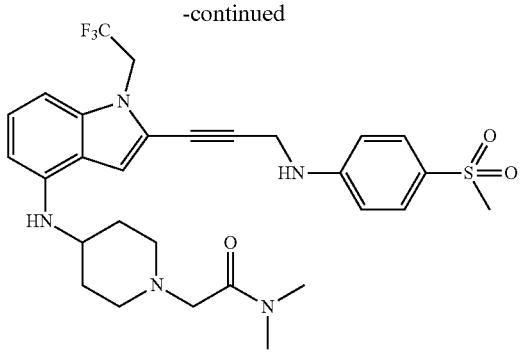

To a solution of 4-(methylsulfonyl)aniline (15 g, 87.61 mmol) in dioxane (100 mL) was added di-tert-butyl dicarbonate (57.36 g, 262.82 mmol). The mixture was stirred at 110° C. for 10 h then concentrated in vacuo to give the crude product, tert-butyl N-(4-methylsulfonylphenyl)carbamate (20 g, 73.71 mmol, 84% yield). The crude product was used without further purification.

To a solution of tert-butyl N-(4-methylsulfonylphenyl)carbamate (17 g, 62.65 mmol) in dimethylformamide (260 mL) cooled to 0° C. was added sodium hydride (7.52 g, 187.96 mmol, 60% in mineral oil). The mixture was stirred at 0° C. for 30 min, and propargyl bromide (22.36 g, 187.96 mmol, 16.2 mL) was then added to the reaction. After stirring at 0° C. for an additional 40 min, the reaction mixture was poured into water (300 mL) and extracted with ethyl acetate (2×100 mL). The combined organic layers were washed with brine (100 mL), dried over anhydrous sodium sulfate, filtered, and concentrated in vacuo. The crude product was purified by flash column chromatography (silica gel, eluting with petroleum ether/ethyl acetate: 10/1 to 1/1) to give tert-butyl (4-(methylsulfonyl)phenyl)(prop-2-yn-1-yl)carbamate as a white solid (16.8 g, 87% yield).

To a mixture of 2-iodo-1-(2,2,2-trifluoroethyl)-1H-indol-4-amine (1 equiv.) in ethanol at 25° C. was added tert-butyl 4-oxopiperidine-1-carboxylate (5 equiv.) and tetraethoxytitanium (5 equiv.). The mixture was stirred at 50° C. for 12 h, and sodium cyanoborohydride (5 equiv.) was then added to the reaction. After stirring at 25° C. for 2 h, the mixture was poured into a saturated solution of sodium bicarbonate and stirred for 30 min. The reaction mixture was then filtered through Celite and washed with ethyl acetate. The aqueous layer was extracted with ethyl acetate. The combined

292 organic layers were washed with brine, dried over anhydrous sodium sulfate, filtered, and concentrated in vacuo. The crude product was purified by flash column chromatography (silica gel, eluting with petroleum ether/ethyl acetate: 100/0 to 25/1) to give tert-butyl 4-((2-iodo-1-(2,2,2-trifluoroethyl)-1H-indol-4-yl)amino)piperidine-1-carboxylate.

To a solution of tert-butyl (4-(methylsulfonyl)phenyl)(prop-2-yn-1-yl)carbamate (2 equiv.) in dimethyl sulfoxide was added N-isopropylpropan-2-amine (30 equiv.), CuI (2 equiv.), tert-butyl 4-((2-iodo-1-(2,2,2-trifluoroethyl)-1H-indol-4-yl)amino)piperidine-1-carboxylate (1 equiv.) and Pd(Ph$_3$)$_4$ (0.25 equiv.). After stirring the reaction at 20° C. for 1 h under a nitrogen atmosphere, the mixture was poured into a saturated EDTA solution. The biphasic mixture was stirred at room temperature for 20 min and then extracted with ethyl acetate. The combined organic layers were washed with brine, dried over anhydrous sodium sulfate, filtered, and concentrated in vacuo. The crude product was purified by flash column chromatography to give tert-butyl 4-((2-(3-((tert-butoxycarbonyl)(4-(methylsulfonyl)phenyl)amino)prop-1-yn-1-yl)-1-(2,2,2-trifluoroethyl)-1H-indol-4-yl)amino)piperidine-1-carboxylate as light yellow solid.

To a solution of tert-butyl 4-((2-(3-((tert-butoxycarbonyl)(4-(methylsulfonyl)phenyl)amino)-prop-1-yn-1-yl)-1-(2,2,2-trifluoroethyl)-1H-indol-4-yl)amino)piperidine-1-carboxylate (1 equiv.) in ethyl acetate was added HCl/ethyl acetate, and the resulting mixture was stirred at 20° C. for 1 h. The mixture was then concentrated in vacuo to give 2-(3-((4-(methylsulfonyl)phenyl)amino)prop-1-yn-1-yl)-N-(piperidin-4-yl)-1-(2,2,2-trifluoroethyl)-1H-indol-4-amine as hydrochloride salt (light yellow solid).

A mixture of 2-(3-((4-(methylsulfonyl)phenyl)amino)prop-1-yn-1-yl)-N-(piperidin-4-yl)-1-(2,2,2-trifluoroethyl)-1H-indol-4-amine (1 equiv., hydrochloride salt), 2-chloro-N,N-dimethylacetamide (3 equiv.) and potassium carbonate (3 equiv.) in acetonitrile was stirred at 50° C. for 0.5 h. The solvent was removed, and the residue was diluted with water and extracted with ethyl acetate. The combined organic layers were washed with brine, dried over anhydrous sodium sulfate, filtered, and concentrated in vacuo. The crude product was purified by preparative HPLC to give 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N,N-dimethylacetamide as light yellow solid.

LC-MS (ES$^+$, m/z): 590.4 [(M+H)$^+$]

Starting with 2-iodo-1-(2,2,2-trifluoroethyl)-1H-indol-4-amine and using a method similar to that described in Example 455, the following compounds were prepared:

| Ex | Structure | Name | LC-MS (ES$^+$, m/z) |
|---|---|---|---|
| 456 | 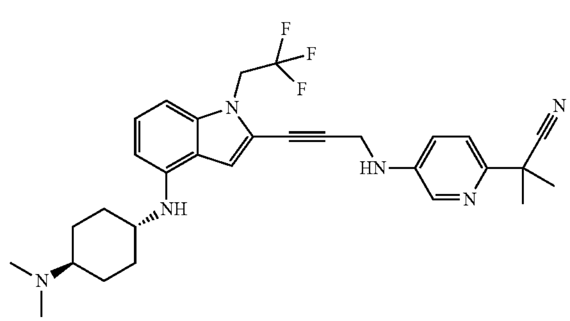 [SMILES: CN(C)[C@H]1CC[C@H](Nc2cccc3c2cc(C#CCNc2ccc(C(C)(C)C#N)nc2)n3CC(F)(F)F)CC1] | 2-methyl-2-(5-{[3-(4-{[(1r,4r)-4-(dimethylamino)cyclohexyl]amino}-1-(2,2,2-trifluoroethyl)-1H-indol-2-yl)prop-2-yn-1-yl]amino}pyridin-2-yl)propanenitrile | 537.2 [(M + H)$^+$] |

-continued

| Ex | Structure | Name | LC-MS (ES+, m/z) |
|---|---|---|---|
| 457 | 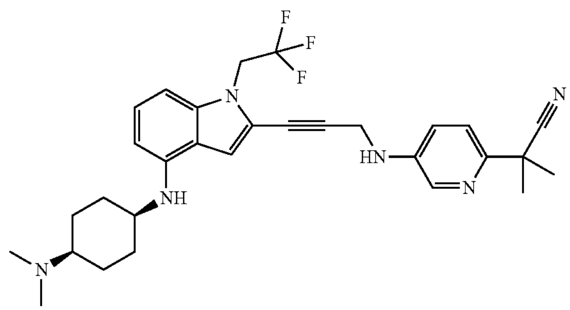 [SMILES: CN(C)[C@H]1CC[C@@H](Nc2cccc3c2cc(C#CCNc2ccc(C(C)(C)C#N)nc2)n3CC(F)(F)F)CC1] | 2-(5-((3-(4-(((1s,4s)-4-(dimethylamino)-cyclohexyl)amino)-1-(2,2,2-trifluoroethyl)-1H-indol-2-yl)prop-2-yn-1-yl)amino)pyridin-2-yl)-2-methylpropanenitrile | 537.2 [(M + H)+] |
| 458 | 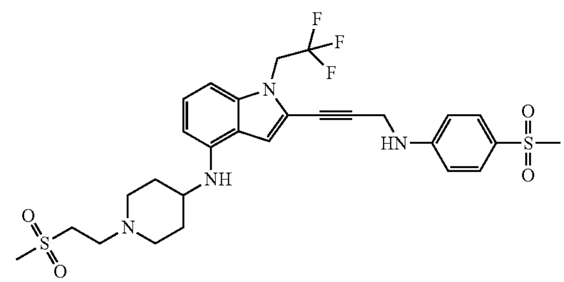 | N-[1-(2-methanesulfonylethyl)piperidin-4-yl]-2-{3-[(4-methanesulfonylphenyl)-amino]prop-1-yn-1-yl}-1-(2,2,2-trifluoroethyl)-1H-indol-4-amine | 611.3 [(M + H)+] |
| 459 | 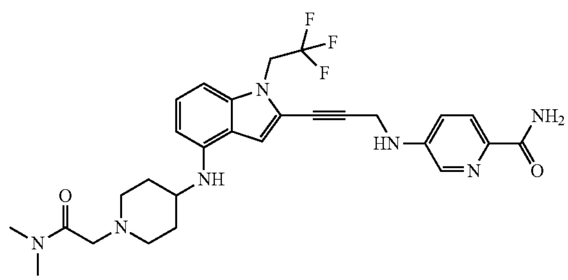 [SMILES: CN(C)C(=O)CN1CCC(Nc2cccc3c2cc(C#CCNc2ccc(C(N)=O)nc2)n3CC(F)(F)F)CC1] | 5-({3-[4-({1-[(dimethylcarbamoyl)methyl]piperidin-4-yl}amino)-1-(2,2,2-trifluoroethyl)-1H-indol-2-yl]prop-2-yn-1-yl}amino)pyridine-2-carboxamide | 556.3 [(M + H)+] |
| 460 | 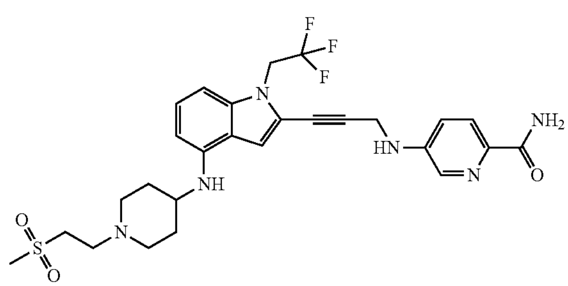 [SMILES: CS(=O)(=O)CCN1CCC(Nc2cccc3c2cc(C#CCNc2ccc(C(N)=O)nc2)n3CC(F)(F)F)CC1] | 5-{[3-(4-{[1-(2-methanesulfonylethyl)piperidin-4-yl]amino}-1-(2,2,2-trifluoroethyl)-1H-indol-2-yl)prop-2-yn-1-yl]amino}pyridine-2-carboxamide | 577.3 [(M + H)+] |
| 461 | 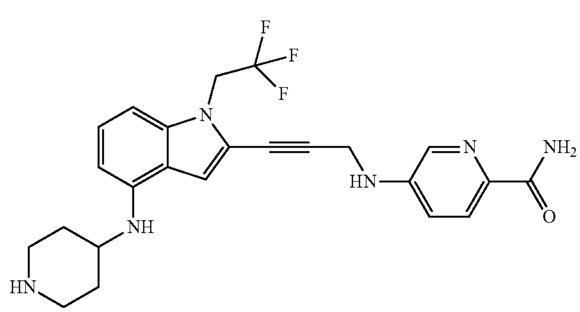 [SMILES: NC(=O)c1ccc(NCC#Cc2cc3c(NC4CCNCC4)cccc3n2CC(F)(F)F)cn1] | 5-[(3-{4-[(piperidin-4-yl)amino]-1-(2,2,2-trifluoroethyl)-1H-indol-2-yl}prop-2-yn-1-yl)amino]pyridine-2-carboxamide | 471.3 [(M + H)+] |

| Ex | Name | LC-MS (ES+, m/z) |
|---|---|---|
| 462 | 5-{[3-(4-{[1-(carbamoylmethyl)piperidin-4-yl]amino}-1-(2,2,2-trifluoroethyl)-1H-indol-2-yl)prop-2-yn-1-yl]amino}pyridine-2-carboxamide | 528.3 [(M + H)+] |
| 463 | 5-{[3-(4-{[1-(2-hydroxyethyl)piperidin-4-yl]amino}-1-(2,2,2-trifluoroethyl)-1H-indol-2-yl)prop-2-yn-1-yl]amino}pyridine-2-carboxamide | 515.2 [(M + H)+] |
| 464 | 5-{[3-(4-{[1-(oxan-4-yl)piperidin-4-yl]amino}-1-(2,2,2-trifluoroethyl)-1H-indol-2-yl)prop-2-yn-1-yl]amino}pyridine-2-carboxamide | 555.3 [(M + H)+] |
| 465 | 5-{[3-(4-{[(1r,4r)-4-(dimethylamino)-cyclohexyl]amino}-1-(2,2,2-trifluoroethyl)-1H-indol-2-yl)prop-2-yn-1-yl]amino}pyridine-2-carboxamide | 513.3 [(M + H)+] |
| 466 | 4-{[3-(4-{[1-(2-methanesulfonyl-ethyl)piperidin-4-yl]amino}-1-(2,2,2-trifluoroethyl)-1H-indol-2-yl)prop-2-yn-1-yl]amino}benzene-1-sulfonamide | 612.3 [(M + H)+] |

-continued

| Ex | Structure | Name | LC-MS (ES+, m/z) |
|---|---|---|---|
| 467 | 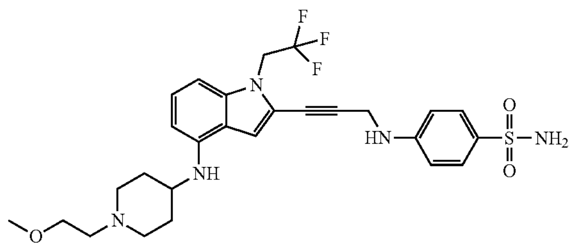 [SMILES: COCCN1CCC(Nc2cccc3c2cc(C#CCNc2ccc(S(N)(=O)=O)cc2)n3CC(F)(F)F)CC1] | 4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide | 564.0 [(M + H)+] |
| 468 | 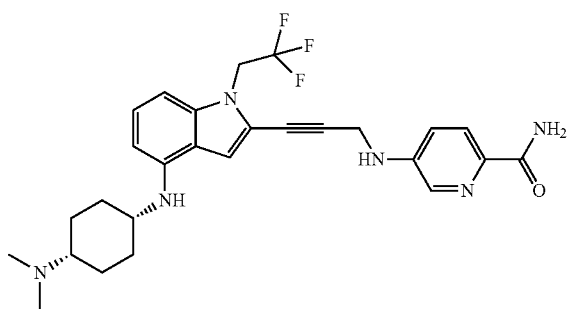 [SMILES: CN(C)[C@H]1CC[C@@H](Nc2cccc3c2cc(C#CCNc2ccc(C(N)=O)nc2)n3CC(F)(F)F)CC1] | 5-{[3-(4-{[(1s,4s)-4-(dimethylamino)-cyclohexyl]amino}-1-(2,2,2-trifluoroethyl)-1H-indol-2-yl)prop-2-yn-1-yl]amino}pyridine-2-carboxamide | 513.3 [(M + H)+] |
| 469 | 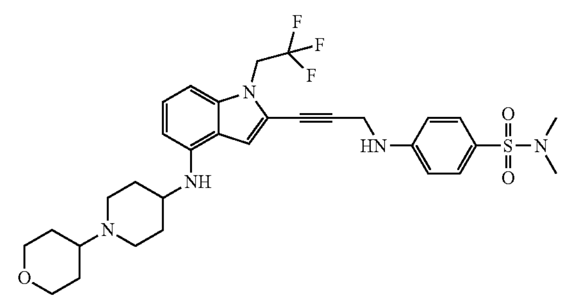 [SMILES: CN(C)S(=O)(=O)c1ccc(NCC#Cc2cc3c(NC4CCN(C5CCOCC5)CC4)cccc3n2CC(F)(F)F)cc1] | N,N-dimethyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide | 618.4 [(M + H)+] |
| 470 | 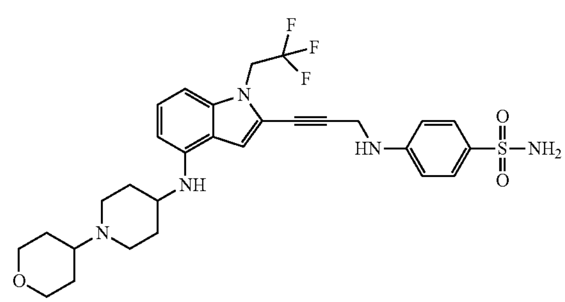 [SMILES: NS(=O)(=O)c1ccc(NCC#Cc2cc3c(NC4CCN(C5CCOCC5)CC4)cccc3n2CC(F)(F)F)cc1] | 4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide | 590.3 [(M + H)+] |
| 471 | 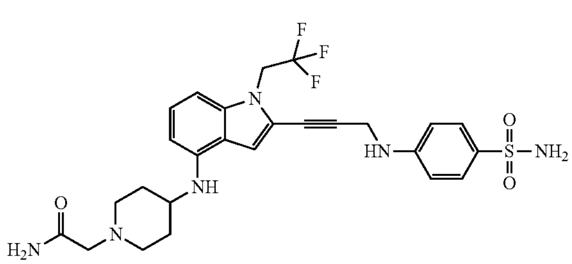 [SMILES: NC(=O)CN1CCC(Nc2cccc3c2cc(C#CCNc2ccc(S(N)(=O)=O)cc2)n3CC(F)(F)F)CC1] | 2-{4-[(2-{3-[(4-sulfamoylphenyl)-amino]prop-1-yn-1-yl}-1-(2,2,2-trifluoroethyl)-1H-indol-4-yl)amino]-piperidin-1-yl}acetamide | 563.3 [(M + H)+] |

-continued

| Ex | Structure | Name | LC-MS (ES+, m/z) |
|---|---|---|---|
| 472 | 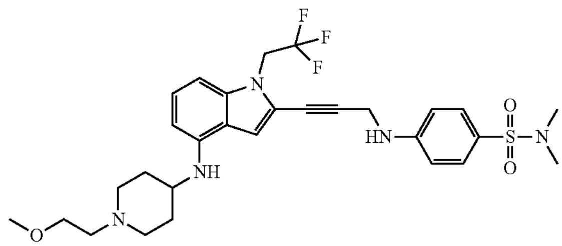 | 4-{3-(4-{[1-(2-methoxyethyl)piperidin-4-yl]amino}-1-(2,2,2-trifluoroethyl)-1H-indol-2-yl)prop-2-yn-1-yl]amino}-N,N-dimethylbenzene-1-sulfonamide | 592.3 [(M + H)+] |
| 473 | 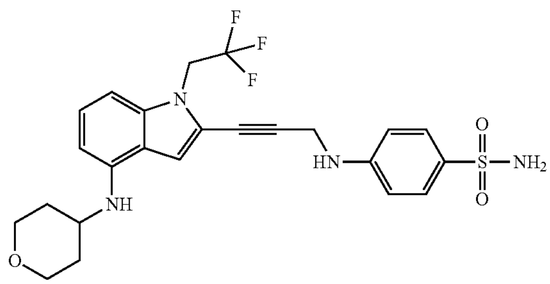 [SMILES: NS(=O)(=O)c1ccc(NCC#Cc2cc3c(NC4CCOCC4)cccc3n2CC(F)(F)F)cc1] | 4-[(3-{4-[(oxan-4-yl)amino]-1-(2,2,2-trifluoroethyl)-1H-indol-2-yl}prop-2-yn-1-yl)amino]benzene-1-sulfonamide | 507.2 [(M + H)+] |
| 474 | 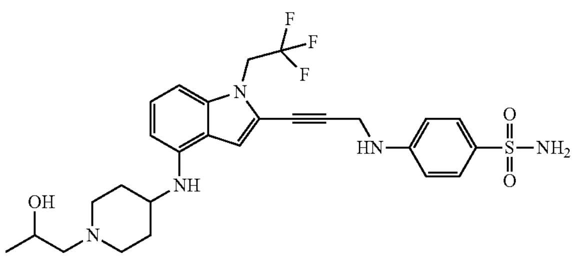 [SMILES: CC(O)CN1CCC(Nc2cccc3c2cc(C#CCNc2ccc(S(N)(=O)=O)cc2)n3CC(F)(F)F)CC1] | 4-{[3-(4-{[1-(2-hydroxypropyl)piperidin-4-yl]amino}-1-(2,2,2-trifluoroethyl)-1H-indol-2-yl)prop-2-yn-1-yl]amino}benzene-1-sulfonamide | 564.3 [(M + H)+] |
| 475 | 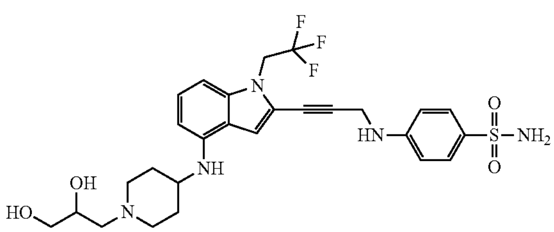 [SMILES: NS(=O)(=O)c1ccc(NCC#Cc2cc3c(NC4CCN(CC(O)CO)CC4)cccc3n2CC(F)(F)F)cc1] | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}benzene-1-sulfonamide | 580.3 [(M + H)+] |
| 476 | 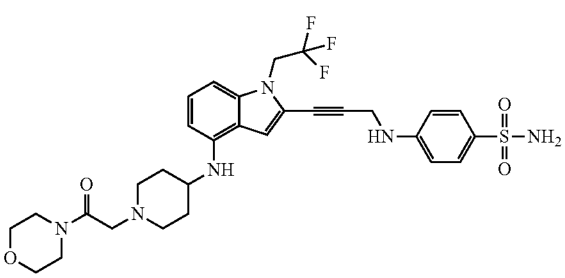 [SMILES: NS(=O)(=O)c1ccc(NCC#Cc2cc3c(NC4CCN(CC(=O)N5CCOCC5)CC4)cccc3n2CC(F)(F)F)cc1] | 4-({3-[4-({1-[2-(morpholin-4-yl)-2-oxoethyl]piperidin-4-yl}amino)-1-(2,2,2-trifluoroethyl)-1H-indol-2-yl]prop-2-yn-1-yl}amino)benzene-1-sulfonamide | 633.3 [(M + H)+] |
| 477 | 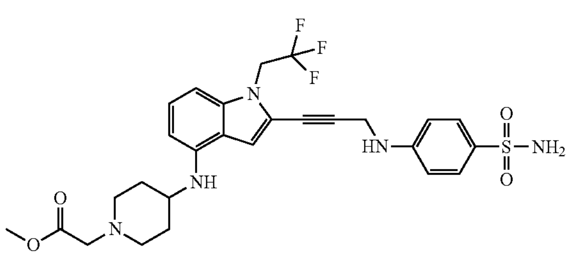 [SMILES: COC(=O)CN1CCC(Nc2cccc3c2cc(C#CCNc2ccc(S(N)(=O)=O)cc2)n3CC(F)(F)F)CC1] | methyl 2-{4-[(2-{3-[(4-sulfamoylphenyl)-amino]prop-1-yn-1-yl}-1-(2,2,2-trifluoro-ethyl)-1H-indol-4-yl)amino]piperidin-1-yl}acetate | 578.3 [(M + H)+] |

| Ex | Name | LC-MS (ES+, m/z) |
|---|---|---|
| 478 | 4-{[3-(4-{[1-(2-hydroxyethyl)piperidin-4-yl]amino}-1-(2,2,2-trifluoroethyl)-1H-indol-2-yl)prop-2-yn-1-yl]amino}benzene-1-sulfonamide | 549.9 [(M + H)+] |
| 479 | 4-({3-[4-({1-[2-(2-hydroxyethoxy)ethyl]piperidin-4-yl}amino)-1-(2,2,2-trifluoroethyl)-1H-indol-2-yl]prop-2-yn-1-yl}amino)benzene-1-sulfonamide | 594.0 [(M + H)+] |
| 480 | N,N-dimethyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide | 591.3 [(M + H)+] |
| 481 | 4-({3-[4-({1-[2-(4-hydroxypiperidin-1-yl)-2-oxoethyl]piperidin-4-yl}amino)-1-(2,2,2-trifluoroethyl)-1H-indol-2-yl]prop-2-yn-1-yl}amino)benzene-1-sulfonamide | 647.4 [(M + H)+] |
| 482 | 2-{4-[(2-{3-[(4-sulfamoylphenyl)amino]prop-1-yn-1-yl}-1-(2,2,2-trifluoroethyl)-1H-indol-4-yl)amino]piperidin-1-yl}acetic acid | 564.3 [(M + H)+] |

-continued

| Ex | Name | LC-MS (ES+, m/z) |
|---|---|---|
| 483 | 4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide | 646.4 [(M + H)+] |
| 484 | N-methyl-2-{4-[(2-{3-[(4-sulfamoylphenyl)amino]prop-1-yn-1-yl}-1-(2,2,2-trifluoroethyl)-1H-indol-4-yl)amino]piperidin-1-yl}acetamide | 577.0 [(M + H)+] |
| 485 | N-methyl-4-[(3-{4-[(oxan-4-yl)amino]-1-(2,2,2-trifluoroethyl)-1H-indol-2-yl}prop-2-yn-1-yl)amino]benzene-1-sulfonamide | 521.3 [(M + H)+] |
| 486 | 4-{[3-(4-{[1-(2-methoxyethyl)piperidin-4-yl]amino}-1-(2,2,2-trifluoroethyl)-1H-indol-2-yl)prop-2-yn-1-yl]amino}-N-methylbenzene-1-sulfonamide | 578.2 [(M + H)+] |
| 487 | N-methyl-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide | 604.0 [(M + H)+] |

| Ex | Structure | Name | LC-MS (ES+, m/z) |
|---|---|---|---|
| 488 | 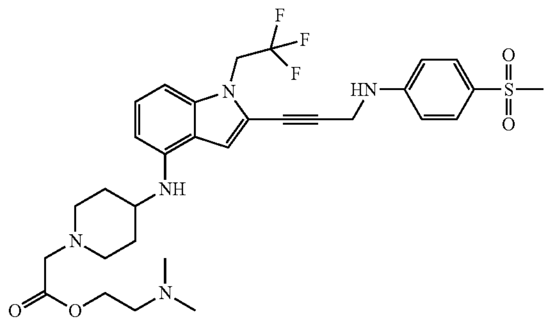 [SMILES: CN(C)CCOC(=O)CN1CCC(Nc2cccc3c2cc(C#CCNc2ccc(S(C)(=O)=O)cc2)n3CC(F)(F)F)CC1] | 2-(dimethylamino)ethyl 2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetate | 632.2 [(M + H)+] |
| 489 | 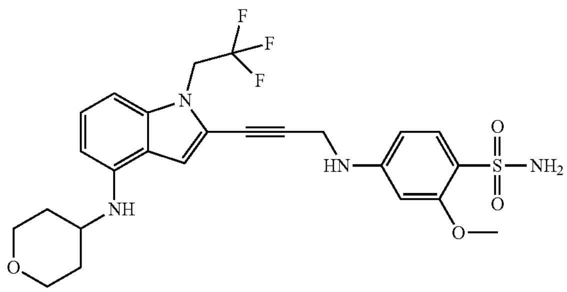 [SMILES: COc1cc(NCC#Cc2cc3c(NC4CCOCC4)cccc3n2CC(F)(F)F)ccc1S(N)(=O)=O] | 2-methoxy-4-[(3-{4-[(oxan-4-yl)amino]-1-(2,2,2-trifluoroethyl)-1H-indol-2-yl}prop-2-yn-1-yl)amino]benzene-1-sulfonamide | 537.2 [(M + H)+] |
| 490 | 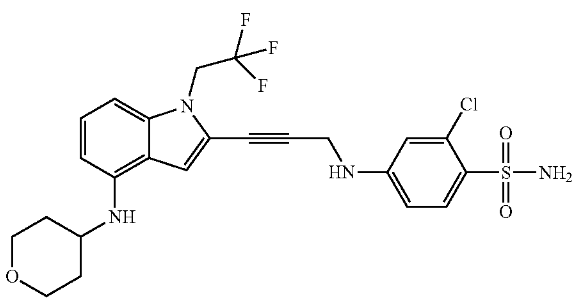 [SMILES: NS(=O)(=O)c1ccc(NCC#Cc2cc3c(NC4CCOCC4)cccc3n2CC(F)(F)F)cc1Cl] | 2-chloro-4-[(3-{4-[(oxan-4-yl)amino]-1-(2,2,2-trifluoroethyl)-1H-indol-2-yl}prop-2-yn-1-yl)amino]benzene-1-sulfonamide | 541.1 [(M + H)+] |
| 491 | 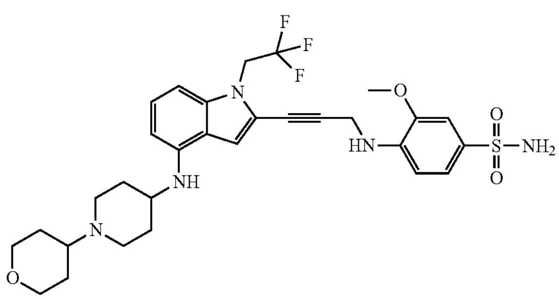 [SMILES: COc1cc(S(N)(=O)=O)ccc1NCC#Cc1cc2c(NC3CCN(C4CCOCC4)CC3)cccc2n1CC(F)(F)F] | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzene-1-sulfonamide | 620.2 [(M + H)+] |
| 492 | 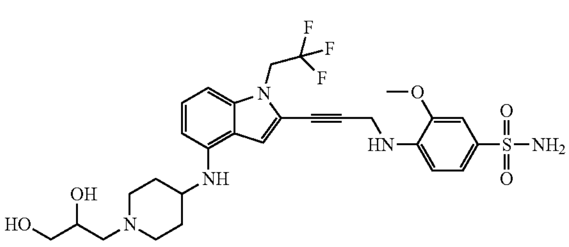 [SMILES: COc1cc(S(N)(=O)=O)ccc1NCC#Cc1cc2c(NC3CCN(CC(O)CO)CC3)cccc2n1CC(F)(F)F] | 4-{[3-(4-{[1-(2,3-dihydroxypropyl)-piperidin-4-yl]amino}-1-(2,2,2-trifluoro-ethyl)-1H-indol-2-yl)prop-2-yn-1-yl]amino}-3-methoxybenzene-1-sulfonamide | 610.2 [(M + H)+] |

-continued

| Ex | Structure | Name | LC-MS (ES+, m/z) |
|---|---|---|---|
| 493 | 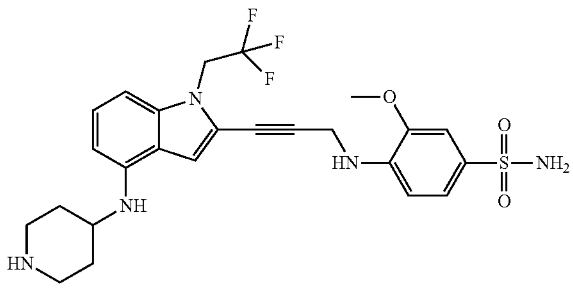 [SMILES: COc1cc(S(N)(=O)=O)ccc1NCC#Cc1cc2c(NC3CCNCC3)cccc2n1CC(F)(F)F] | 3-methoxy-4-[(3-{4-[(piperidin-4-yl)amino]-1-(2,2,2-trifluoroethyl)-1H-indol-2-yl}prop-2-yn-1-yl)amino]benzene-1-sulfonamide | 536.2 [(M + H)+] |
| 494 | 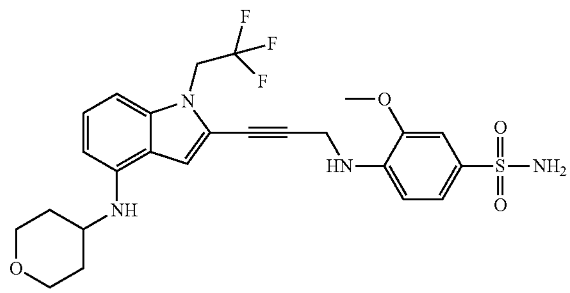 [SMILES: COc1cc(S(N)(=O)=O)ccc1NCC#Cc1cc2c(NC3CCOCC3)cccc2n1CC(F)(F)F] | 3-methoxy-4-[(3-{4-[(oxan-4-yl)amino]-1-(2,2,2-trifluoroethyl)-1H-indol-2-yl}prop-2-yn-1-yl)amino]benzene-1-sulfonamide | 537.1 [(M + H)+] |
| 495 | 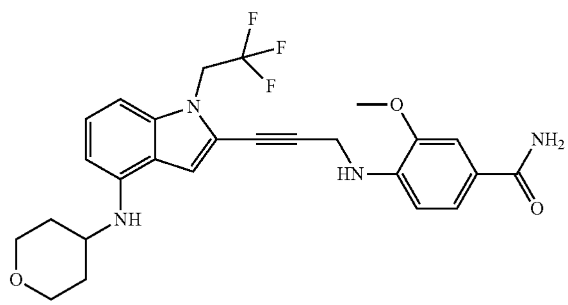 [SMILES: COc1cc(C(N)=O)ccc1NCC#Cc1cc2c(NC3CCOCC3)cccc2n1CC(F)(F)F] | 3-methoxy-4-[(3-{4-[(oxan-4-yl)amino]-1-(2,2,2-trifluoroethyl)-1H-indol-2-yl}prop-2-yn-1-yl)amino]benzamide | 501.2 [(M + H)+] |
| 496 | 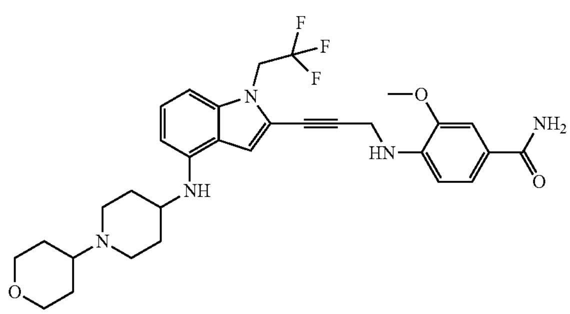 [SMILES: COc1cc(C(N)=O)ccc1NCC#Cc1cc2c(NC3CCN(C4CCOCC4)CC3)cccc2n1CC(F)(F)F] | 3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}benzamide | 584.3 [(M + H)+] |
| 497 | 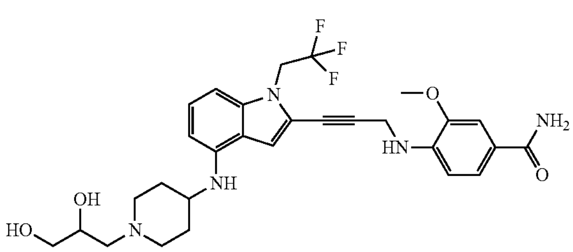 [SMILES: COc1cc(C(N)=O)ccc1NCC#Cc1cc2c(NC3CCN(CC(O)CO)CC3)cccc2n1CC(F)(F)F] | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzamide | 574.2 [(M + H)+] |

Example 498: Preparation of 2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile

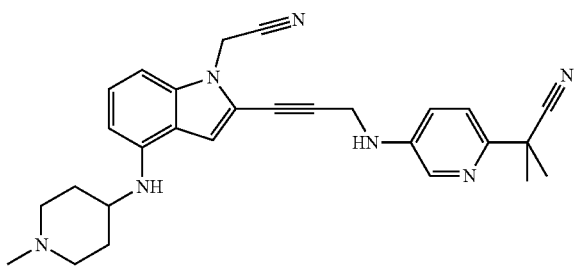 [SMILES: CN1CCC(Nc2cccc3c2cc(C#CCNc2ccc(C(C)(C)C#N)nc2)n3CC#N)CC1]

Synthetic Scheme:

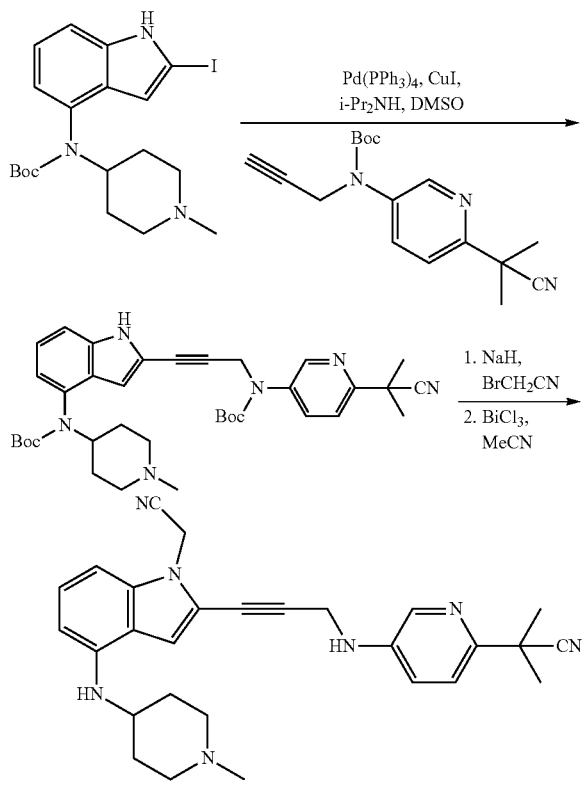

A flask was charged with CuI (89 mg, 465.6 μmol) and diisopropylamine (222 mg, 2.2 mmol, 309 μL), and a solution of tert-butyl (2-iodo-1H-indol-4-yl)(1-methylpiperidin-4-yl)carbamate (200 mg, 439.2 μmol, prepared from 2-iodo-4-nitro-1H-indole) and tert-butyl (6-(2-cyanopropan-2-yl)pyridin-3-yl)(prop-2-yn-1-yl)carbamate (197 mg, 658.9 μmol) in dimethyl sulfoxide (3 mL) was added under nitrogen, followed by the addition of tetrakis(triphenylphosphine)palladium(0) (61 mg, 52.7 μmol). After stirring the reaction at 45° C. for 1 h, the reaction was diluted with 20 mL of ethyl acetate and 50 mL of 1M EDTA and stirred at 25° C. for 1 h. The reaction was extracted with ethyl acetate (3×10 mL) and washed with saturated brine (50 mL), dried over anhydrous sodium sulfate and concentrated in vacuo. The crude residue was purified by preparative thin layer chromatography (silica gel, eluting with petroleum ether/ethyl acetate: 1/1) to give tert-butyl (2-(3-((tert-butoxycarbonyl)(6-(2-cyanopropan-2-yl)pyridin-3-yl)amino)prop-1-yn-1-yl)-1H-indol-4-yl)(1-methylpiperidin-4-yl)carbamate as yellow solid (200 mg, 319.1 μmol, 73% yield).

To a mixture of tert-butyl (2-(3-((tert-butoxycarbonyl)(6-(2-cyanopropan-2-yl)pyridin-3-yl)amino)prop-1-yn-1-yl)-1H-indol-4-yl)(1-methylpiperidin-4-yl)carbamate (200 mg, 319 μmol) in dimethylformamide (3 mL) cooled to 0° C. were added sodium hydride (38 mg, 957 μmol, 60% in mineral oil) and 2-bromoacetonitrile (147 mg, 957 μmol). The reaction was stirred at 0° C. for 2 h, and poured into ice water (50 mL, 1/1 w/w). The reaction mixture was then extracted with ethyl acetate (3×10 mL). The combined organic layers were washed with brine (3×10 mL), dried over anhydrous sodium sulfate, filtered, and concentrated in vacuo to give tert-butyl (2-(3-((tert-butoxycarbonyl)(6-(2-cyanopropan-2-yl)pyridin-3-yl)amino)prop-1-yn-1-yl)-1-(cyanomethyl)-1H-indol-4-yl)(1-methylpiperidin-4-yl)carbamate as yellow oil (200 mg, crude).

To a mixture of tert-butyl (2-(3-((tert-butoxycarbonyl)(6-(2-cyanopropan-2-yl)pyridin-3-yl)amino)prop-1-yn-1-yl)-1-(cyanomethyl)-1H-indol-4-yl)(1-methylpiperidin-4-yl)carbamate (100 mg, 1 equiv.) was added bismuth trichloride (15 equiv.) in acetonitrile (5 mL) in one portion at 50° C. under a nitrogen atmosphere. The mixture was stirred at 50° C. for 1 h, poured into a sodium bicarbonate ice water mixture (30 mL, 1/1 w/w), and an EDTA solution (2M, 50 mL) was added to the resulting mixture. The biphasic mixture was stirred at room temperature for 2 h, then separated into aqueous and organic phases. The aqueous phase was extracted with ethyl acetate (3×20 mL). The combined organic layers were washed with brine (3×20 mL), dried over anhydrous sodium sulfate, filtered, and concentrated in vacuo. The crude product was purified by preparative HPLC to give 2-[5-({3-[1-(cyanomethyl)-4-[(1-methylpiperidin-4-yl)amino]-1H-indol-2-yl]prop-2-yn-1-yl}amino)pyridin-2-yl]-2-methylpropanenitrile as yellow solid.

LC-MS (ES$^+$, m/z): 466.3 [(M+H)$^+$]

Starting with 2-iodo-4-nitro-1H-indole and using a method similar to that described in Example 498, the following compounds were prepared:

| Ex | Structure | Name | LC-MS (ES+, m/z) |
|---|---|---|---|
| 499 | 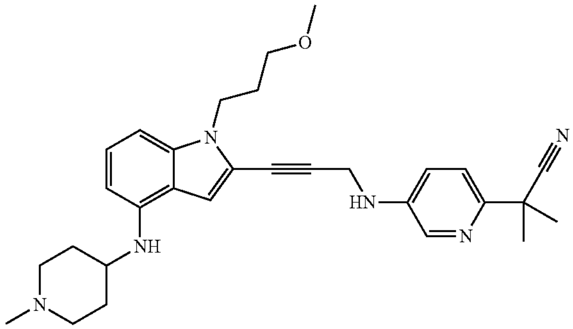 [SMILES: COCCCn1c(C#CCNc2ccc(C(C)(C)C#N)nc2)cc2c(NC3CCN(C)CC3)cccc21] | 2-[5-({3-[1-(3-methoxypropyl)-4-[(1-methylpiperidin-4-yl)amino]-1H-indol-2-yl]prop-2-yn-1-yl}amino)pyridin-2-yl]-2-methylpropanenitrile | 499.4 [(M + H)+] |
| 500 | 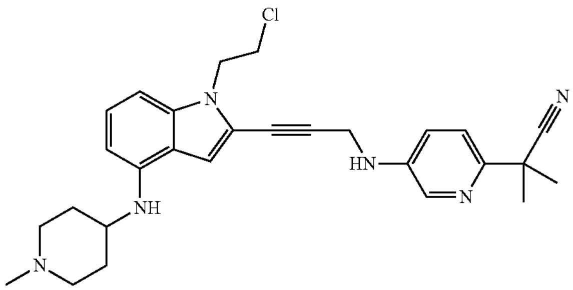 [SMILES: CN1CCC(Nc2cccc3c2cc(C#CCNc2ccc(C(C)(C)C#N)nc2)n3CCCl)CC1] | 2-[5-({3-[1-(2-chloroethyl)-4-[(1-methylpiperidin-4-yl)amino]-1H-indol-2-yl]prop-2-yn-1-yl}amino)pyridin-2-yl]-2-methylpropanenitrile | 489.3 [(M + H)+] |
| 501 | 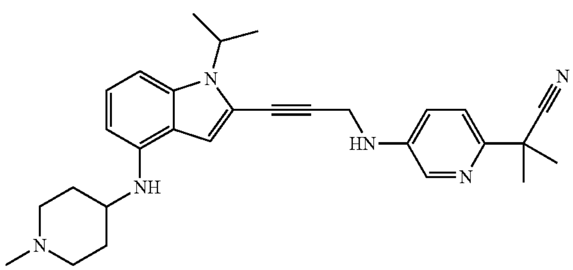 [SMILES: CC(C)n1c(C#CCNc2ccc(C(C)(C)C#N)nc2)cc2c(NC3CCN(C)CC3)cccc21] | 2-methyl-2-{5-[(3-{4-[(1-methylpiperidin-4-yl)amino]-1-(propan-2-yl)-1H-indol-2-yl}prop-2-yn-1-yl)amino]pyridin-2-yl}propanenitrile | 469.4 [(M + H)+] |
| 502 | 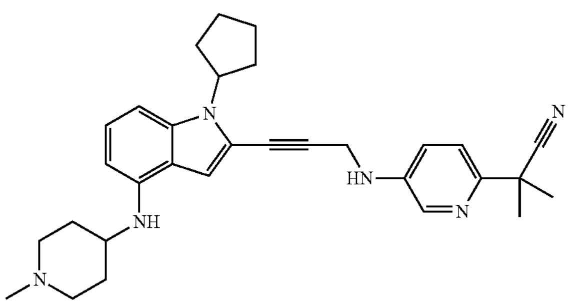 [SMILES: CN1CCC(Nc2cccc3c2cc(C#CCNc2ccc(C(C)(C)C#N)nc2)n3C2CCCC2)CC1] | 2-{5-[(3-{1-cyclopentyl-4-[(1-methylpiperidin-4-yl)amino]-1H-indol-2-yl}prop-2-yn-1-yl)amino]pyridin-2-yl}-2-methylpropanenitrile | 495.4 [(M + H)+] |
| 503 | 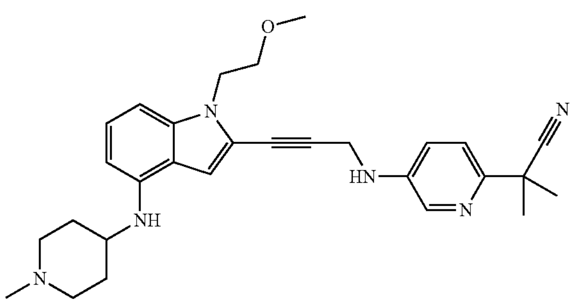 [SMILES: COCCn1c(C#CCNc2ccc(C(C)(C)C#N)nc2)cc2c(NC3CCN(C)CC3)cccc21] | 2-[5-({3-[1-(2-methoxyethyl)-4-[(1-methylpiperidin-4-yl)amino]-1H-indol-2-yl]prop-2-yn-1-yl}amino)pyridin-2-yl]-2-methylpropanenitrile | 485.4 [(M + H)+] |

-continued

| Ex | Name | LC-MS (ES+, m/z) |
|---|---|---|
| 504 | 2-methyl-2-{5-[(3-{4-[(1-methylpiperidin-4-yl)amino]-1-(3,3,3-trifluoropropyl)-1H-indol-2-yl}prop-2-yn-1-yl)amino]pyridin-2-yl}propanenitrile | 523.3 [(M + H)+] |
| 505 | 1-(2-chloroethyl)-N-(1-methylpiperidin-4-yl)-2-{3-[(6-methylpyridin-3-yl)amino]-prop-1-yn-1-yl}-1H-indol-4-amine | 436.3 [(M + H)+] |
| 506 | 1-(2-chloroethyl)-2-{3-[(4-chlorophenyl)-amino]prop-1-yn-1-yl}-N-(1-methylpiperidin-4-yl)-1H-indol-4-amine | 455.2 [(M + H)+] |
| 507 | 2-[5-({3-[1-(1-cyanoethyl)-4-[(1-methylpiperidin-4-yl)amino]-1H-indol-2-yl]prop-2-yn-1-yl}amino)pyridin-2-yl]-2-methylpropanenitrile | 480.3 [(M + H)+] |
| 508 | 2-[5-({3-[1-(cyanomethyl)-4-[(1,1-dioxo-1$\lambda^6$-thian-4-yl)amino]-1H-indol-2-yl]prop-2-yn-1-yl}amino)pyridin-2-yl]-2-methylpropanenitrile | 501.3 [(M + H)+] |

| Ex | Structure | Name | LC-MS (ES+, m/z) |
|---|---|---|---|
| 509 | 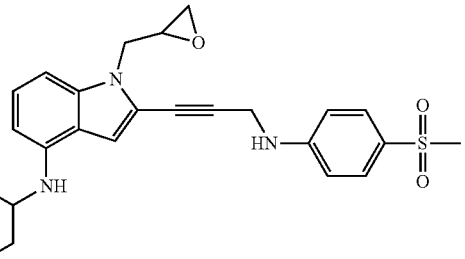 | 4-[(2-{3-[(4-methanesulfonylphenyl)amino]prop-1-yn-1-yl}-1-(oxiran-2-ylmethyl)-1H-indol-4-yl)amino]-1λ⁶-thiane-1,1-dione | 528.2 [(M + H)+] |
| 510 | 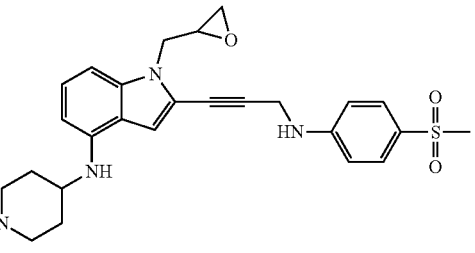 | 2-{3-[(4-methanesulfonylphenyl)-amino]prop-1-yn-1-yl}-N-[1-(oxan-4-yl)piperidin-4-yl]-1-(oxiran-2-ylmethyl)-1H-indol-4-amine | 563.2 [(M + H)+] |
| 511 | 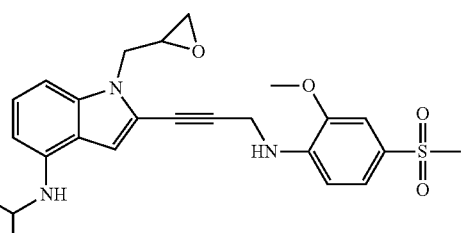 | 4-[(2-{3-[(4-methanesulfonyl-2-methoxyphenyl)amino]prop-1-yn-1-yl}-1-(oxiran-2-ylmethyl)-1H-indol-4-yl)amino]-1λ⁶-thiane-1,1-dione | 558.2 [(M + H)+] |
| 512 | 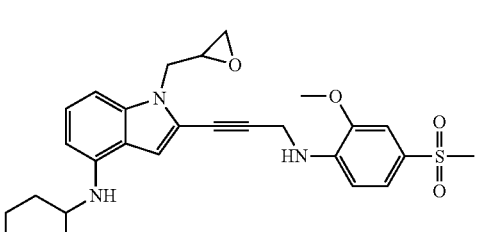 | 2-{3-[(4-methanesulfonyl-2-methoxy-phenyl)amino]prop-1-yn-1-yl}-N-[1-(oxan-4-yl)piperidin-4-yl]-1-(oxiran-2-ylmethyl)-1H-indol-4-amine | 593.2 [(M + H)+] |

Example 513: Preparation of 1-[6-(1-cyano-1-methylethyl)pyridin-3-yl]-3-(3-{4-[(1-methylpiperidin-4-yl)amino]-1-(2,2,2-trifluoroethyl)-1H-indol-2-yl}prop-2-yn-1-yl)urea

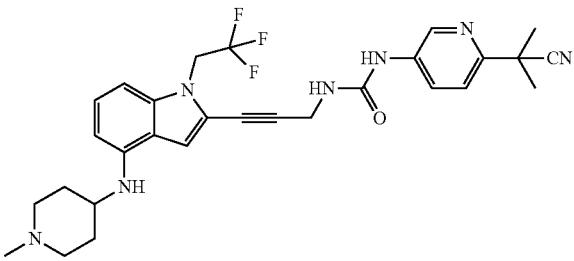 [SMILES: CN1CCC(Nc2cccc3c2cc(C#CCNC(=O)Nc2ccc(C(C)(C)C#N)nc2)n3CC(F)(F)F)CC1]

To a mixture of propargyl bromide (2.1 g, 38.1 mmol, 2.44 mL) in acetonitrile (80 mL) was added pyridine (7.54 g, 95.3 mmol, 7.69 mL) at 0° C. The mixture was stirred at 0° C. for 1 h, and phenyl carbonochloridate (6.0 g, 38.3 mmol) was added to the reaction. After stirring the reaction at 0° C. for 1 h, the reaction mixture was poured into water (100 mL), and the aqueous phase was extracted with ethyl acetate (3×50 mL). The combined organic layers were washed with brine (3×50 mL), dried over anhydrous sodium sulfate, filtered, and concentrated in vacuo. The crude product was purified by flash column chromatography (silica gel, eluting with petroleum ether/ethyl acetate: 20/1 to 5/1) to give phenyl prop-2-yn-1-ylcarbamate as white solids (5 g, 75% yield).

To a mixture of phenyl prop-2-yn-1-ylcarbamate (100 mg, 570.8 µmol) in acetonitrile (3 mL) was added triethylamine (144 mg, 1.4 mmol, 198 µL) and 2-(5-aminopyridin-2-yl)-2-methylpropanenitrile (92 mg, 570.8 µmol) at 20° C. The mixture was stirred at 50° C. for 2 h and at 100° C. for 12 h. The reaction mixture was poured into water (10 mL), and the aqueous phase was extracted with ethyl acetate (3×10 mL). The combined organic layers were washed with brine (3×10 mL), dried over anhydrous sodium sulfate, filtered, and concentrated in vacuo. The crude product was purified by preparative thin layer chromatography (silica gel, eluting with petroleum ether/ethyl acetate: 1/1) to give 1-(6-(2-cyanopropan-2-yl)pyridin-3-yl)-3-(prop-2-yn-1-yl)urea as white solid (90 mg, 46% yield).

To a mixture of 1-(6-(2-cyanopropan-2-yl)pyridin-3-yl)-3-(prop-2-yn-1-yl)urea (90 mg) in dimethyl sulfoxide (2 mL) at 25° C. were added diisopropylamine (160.5 mg, 1.59 mmol), CuI (60.4 mg, 317.3 µmol), 2-iodo-N-(1-methylpiperidin-4-yl)-1-(2,2,2-trifluoroethyl)-1H-indol-4-amine (80 mg, 158.6 µmol) and tetrakis(triphenylphosphine)palladium (0) (37 mg, 31.7 µmol). The mixture was stirred at 25° C. for 1 h and diluted with ethyl acetate (10 mL) before being poured into a 2 N EDTA solution (30 mL) and stirred for 2 h. The aqueous phase was extracted with ethyl acetate (2×30 mL). The combined organic layers were washed with brine (3×30 mL), dried over anhydrous sodium sulfate, filtered, and concentrated in vacuo. The crude product was purified by preparative HPLC to give 1-[6-(1-cyano-1-methylethyl)pyridin-3-yl]-3-(3-{4-[(1-methylpiperidin-4-yl)amino]-1-(2,2,2-trifluoroethyl)-1H-indol-2-yl}prop-2-yn-1-yl)urea as white solid (19.6 mg, 22% yield).

LC-MS (ES$^+$, m/z): 552.4 [(M+H)$^+$]

Starting with 2-iodo-4-nitro-1H-indole and using a method similar to that described in Example 513, the following compounds were prepared:

| Ex | Structure | Name | LC-MS (ES$^+$, m/z) |
|---|---|---|---|
| 514 | 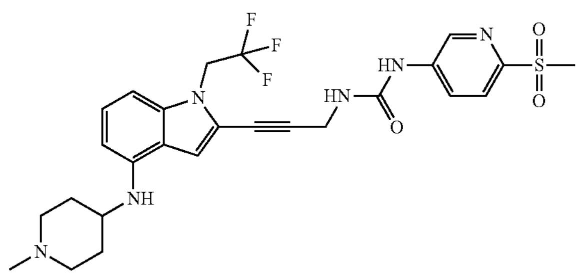 | 1-(6-methanesulfonylpyridin-3-yl)-3-(3-{4-[(1-methylpiperidin-4-yl)amino]-1-(2,2,2-trifluoroethyl)-1H-indol-2-yl}prop-2-yn-1-yl)urea | 563.3 [(M + H)$^+$] |
| 515 | 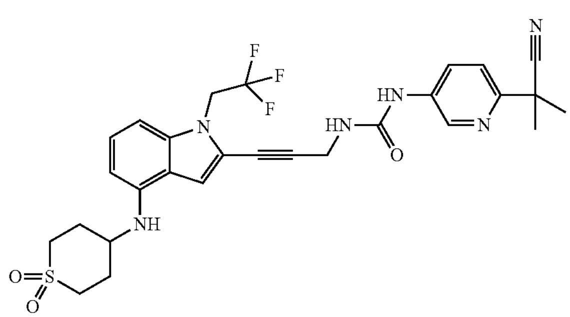 [SMILES: CC(C)(C#N)c1ccc(NC(=O)NCC#Cc2cc3c(NC4CCS(=O)(=O)CC4)cccc3n2CC(F)(F)F)cn1] | 1-[6-(1-cyano-1-methylethyl)pyridin-3-yl]-3-(3-{4-[(1,1-dioxo-1λ$^6$-thian-4-yl)amino]-1-(2,2,2-trifluoroethyl)-1H-indol-2-yl}prop-2-yn-1-yl)urea | 587.3 [(M + H)$^+$] |

| Ex | Structure | Name | LC-MS (ES+, m/z) |
|---|---|---|---|
| 516 | 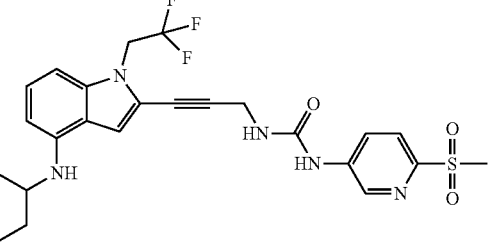 | 3-(3-{4-[(1,1-dioxo-1λ6-thian-4-yl)amino]-1-(2,2,2-trifluoroethyl)-1H-indol-2-yl}prop-2-yn-1-yl)-1-(6-methanesulfonylpyridin-3-yl)urea | 598.2 [(M + H)+] |
| 517 | 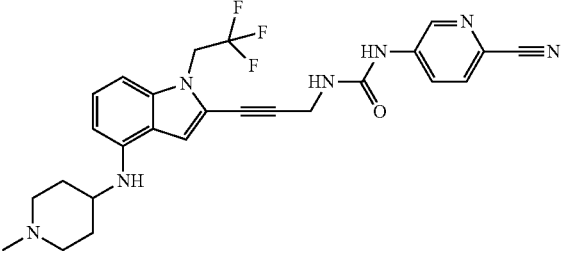 [SMILES: CN1CCC(Nc2cccc3c2cc(C#CCNC(=O)Nc2ccc(C#N)nc2)n3CC(F)(F)F)CC1] | 1-(6-cyanopyridin-3-yl)-3-(3-{4-[(1-methylpiperidin-4-yl)amino]-1-(2,2,2-trifluoroethyl)-1H-indol-2-yl}prop-2-yn-1-yl)urea | 510.2 [(M + H)+] |
| 518 | 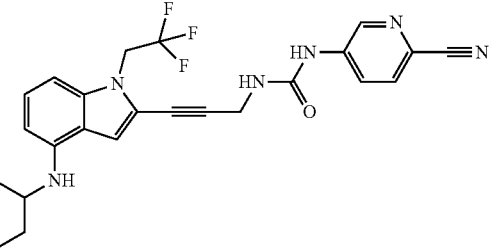 | 1-(6-cyanopyridin-3-yl)-3-(3-{4-[(1,1-dioxo-1λ6-thian-4-yl)amino]-1-(2,2,2-trifluoroethyl)-1H-indol-2-yl}prop-2-yn-1-yl)urea | 545.3 [(M + H)+] |
| 519 | 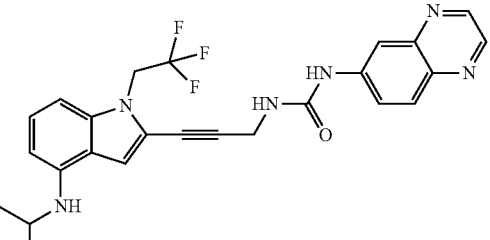 | 3-(3-{4-[(1,1-dioxo-1λ6-thian-4-yl)amino]-1-(2,2,2-trifluoroethyl)-1H-indol-2-yl}prop-2-yn-1-yl)-1-(quinoxalin-6-yl)urea | 571.1 [(M + H)+] |
| 520 | 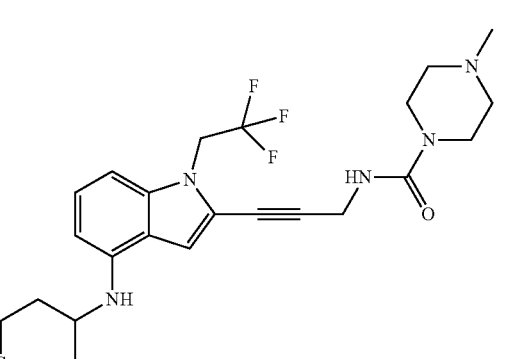 | N-(3-{4-[(1,1-dioxo-1λ6-thian-4-yl)amino]-1-(2,2,2-trifluoroethyl)-1H-indol-2-yl}prop-2-yn-1-yl)-4-methylpiperazine-1-carboxamide | 526.3 [(M + H)+] |

| Ex | Structure | Name | LC-MS (ES+, m/z) |
|---|---|---|---|
| 521 | 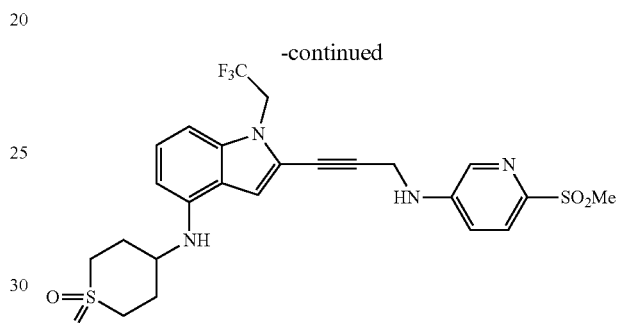 | N-(3-{4-[(1,1-dioxo-1λ⁶-thian-4-yl)amino]-1-(2,2,2-trifluoroethyl)-1H-indol-2-yl}prop-2-yn-1-yl)morpholine-4-carboxamide | 513.2 [(M + H)⁺] |

Example 522: Preparation of 4-[(2-{3-[(6-methane-sulfonylpyridin-3-yl)amino]prop-1-yn-1-yl}-1-(2,2,2-trifluoroethyl)-1H-indol-4-yl)amino]-1λ⁶-thiane-1,1-dione

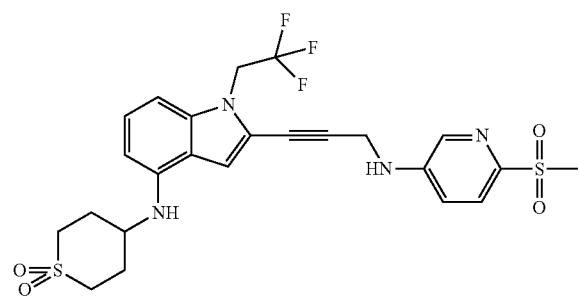 [SMILES: CS(=O)(=O)c1ccc(NCC#Cc2cc3c(NC4CCS(=O)(=O)CC4)cccc3n2CC(F)(F)F)cn1]

Synthetic Scheme:

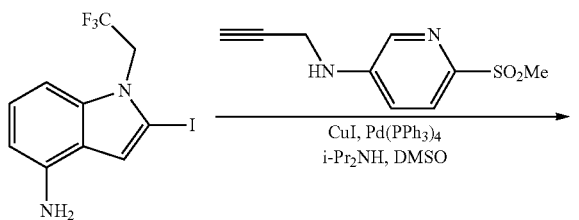

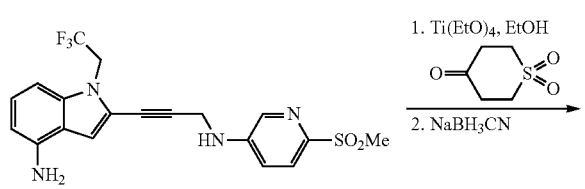

A mixture of 6-(methylsulfonyl)pyridin-3-amine (5 g, 29.04 mmol) and di-tert-butyl dicarbonate (95.07 g, 435.60 mmol) in dioxane (80 mL) was stirred at 110° C. for 72 h. The solvent was removed, and the crude product was purified by flash column chromatography (silica gel, eluting with petroleum ether/ethyl acetate: 5/1 to 1/1) to give tert-butyl (6-(methylsulfonyl)pyridin-3-yl)carbamate as yellow solid (6 g, 75.86% yield).

To a solution of tert-butyl (6-(methylsulfonyl)pyridin-3-yl)carbamate (1.7 g, 6.24 mmol) in dimethylformamide (20 mL) was added sodium hydride (624 mg, 15.60 mmol, 60% in mineral oil). After stirring the reaction at 0° C. for 30 min, propargyl bromide (1.86 g, 12.48 mmol, 1.34 mL) was added, and the mixture was stirred at 0° C. for 1 h under a nitrogen atmosphere. The mixture was quenched by adding a saturated ammonium chloride solution (20 mL), and the mixture was extracted with methylene chloride (2×20 mL). The combined organic layers were washed with water (20 mL) and brine (20 mL), dried over anhydrous sodium sulfate, filtered, and concentrated in vacuo. The crude product was purified by flash column chromatography (silica gel, eluting with petroleum ether/ethyl acetate: 1/1) to give tert-butyl (6-(methylsulfonyl)pyridin-3-yl)(prop-2-yn-1-yl)carbamate (1.8 g) as a yellow solid.

A solution of tert-butyl (6-(methylsulfonyl)pyridin-3-yl)(prop-2-yn-1-yl)carbamate (6 g, 19.33 mmol) in HCl/ethyl acetate (60 mL) was stirred at 25° C. for 12 h. The mixture was filtered and concentrated in vacuo to give 6-(methylsulfonyl)-N-(prop-2-yn-1-yl)pyridin-3-amine hydrochloride as a yellow solid (3 g, crude), which was used without further purification.

To a solution of 2-iodo-1-(2,2,2-trifluoroethyl)-1H-indol-4-amine (1.50 g, 6.08 mmol) in dimethyl sulfoxide (20 mL)

was added diisopropylamine (2.56 g, 25.33 mmol, 3.56 mL), CuI (1.02 g, 5.37 mmol), 6-(methylsulfonyl)-N-(prop-2-yn-1-yl)pyridin-3-amine hydrochloride (1.72 g, 5.07 mmol), and tetrakis(triphenylphosphine)palladium(0) (703 mg, 608 μmol). The reaction mixture was stirred at 25° C. for 1 h under a nitrogen atmosphere, then poured into an EDTA solution (20 mL) and ethyl acetate (20 mL). The biphasic mixture was stirred at room temperature for 1 h and then separated. The aqueous layer was extracted with ethyl acetate (2×20 mL). The combined organic layers were washed with brine (20 mL), dried over anhydrous sodium sulfate, filtered, and concentrated in vacuo. The crude product was purified by flash column chromatography (silica gel, eluting with petroleum ether/ethyl acetate: 1/1) to give 2-(3-((6-(methylsulfonyl)pyridin-3-yl)amino)prop-1-yn-1-yl)-1-(2,2,2-trifluoroethyl)-1H-indol-4-amine as dark brown oil (2 g, 93% yield).

To a solution of 2-(3-((6-(methylsulfonyl)pyridin-3-yl)amino)prop-1-yn-1-yl)-1-(2,2,2-trifluoroethyl)-1H-indol-4-amine (200 mg, 473.46 μmol) in ethanol (2 mL) was added Ti(EtO)$_4$ (301 mg, 2.37 mmol, 311 μL) and tetrahydro-4H-thiopyran-4-one 1,1-dioxide (351 mg, 2.37 mmol). The reaction was stirred at 50° C. for 12 h. Sodium cyanoborohydride (89 mg, 1.42 mmol) was then added to the reaction mixture, and the reaction was stirred at 50° C. for 1 h under a nitrogen atmosphere. The mixture was poured into a cold saturated sodium bicarbonate solution (5 mL). The mixture was filtered through Celite, and the filtrate was extracted with ethyl acetate (2×10 mL). The combined organic layers were washed with water (10 mL) and brine (10 mL), dried over anhydrous sodium sulfate, filtered, and concentrated in vacuo. The crude product was purified by preparative HPLC to give 4-[(2-{3-[(6-methanesulfonylpyridin-3-yl)amino]prop-1-yn-1-yl}-1-(2,2,2-trifluoroethyl)-1H-indol-4-yl)amino]-1λ$^6$-thiane-1,1-dione as yellow oil.

LC-MS (ES$^+$, m/z): 555.2 [(M+H)$^+$]

Starting with 2-(3-((6-(methylsulfonyl)pyridin-3-yl)amino)prop-1-yn-1-yl)-1-(2,2,2-trifluoroethyl)-1H-indol-4-amine and using a method similar to that described in Example 522, the following compounds were prepared:

| Ex | Structure | Name | LC-MS (ES$^+$, m/z) |
|---|---|---|---|
| 523 | 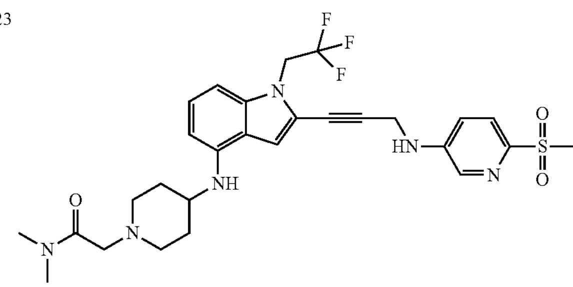 | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-N,N-dimethylacetamide | 591.3 [(M + H)$^+$] |
| 524 | 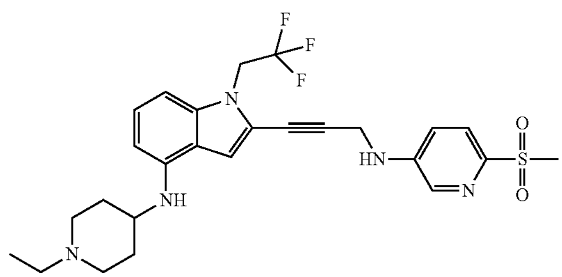 [SMILES: CCN1CCC(Nc2cccc3c2cc(C#CCNc2ccc(S(C)(=O)=O)nc2)n3CC(F)(F)F)CC1] | N-(1-ethylpiperidin-4-yl)-2-{3-[(6-methanesulfonylpyridin-3-yl)amino]prop-1-yn-1-yl}-1-(2,2,2-trifluoroethyl)-1H-indol-4-amine | 534.3 [(M + H)$^+$] |
| 525 | 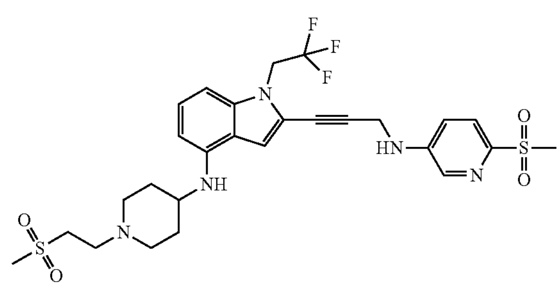 | N-[1-(2-methanesulfonylethyl)piperidin-4-yl]-2-{3-[(6-methanesulfonylpyridin-3-yl)amino]prop-1-yn-1-yl}-1-(2,2,2-trifluoroethyl)-1H-indol-4-amine | 612.3 [(M + H)$^+$] |

| Ex | Structure | Name | LC-MS (ES+, m/z) |
|---|---|---|---|
| 526 | 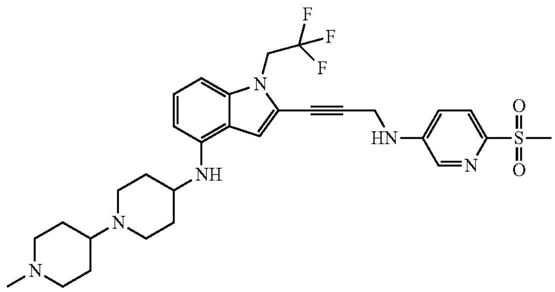 | 2-{3-[(6-methanesulfonylpyridin-3-yl)amino]prop-1-yn-1-yl}-N-[1-(1-methylpiperidin-4-yl)piperidin-4-yl]-1-(2,2,2-trifluoroethyl)-1H-indol-4-amine | 603.2 [(M + H)+] |
| 527 | 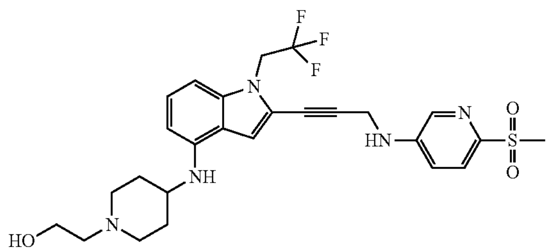 | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}ethan-1-ol | 550.3 [(M + H)+] |
| 528 | 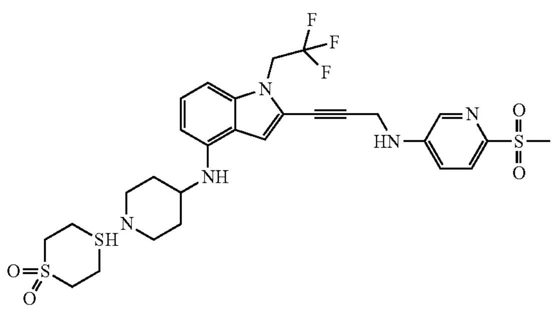 | 4-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl}-1λ⁶-thiane-1,1-dione | 638.1 [(M + H)+] |
| 529 | 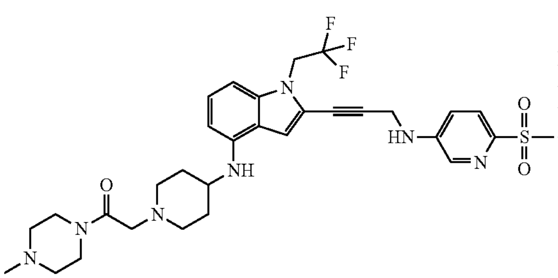 | 2-{4-[(2-{3-[(6-methanesulfonylpyridin-3-yl)amino]prop-1-yn-1-yl}-1-(2,2,2-trifluoroethyl)-1H-indol-4-yl)amino]piperidin-1-yl)-1-(4-methylpiperazin-1-yl)ethan-1-one | 646.3 [(M + H)+] |

Example 530: Preparation of 2-{3-[(4-methanesulfonylphenyl)amino]prop-1-yn-1-yl}-N-(oxan-4-yl)-1-(2,2,2-trifluoroethyl)-1H-indol-4-amine

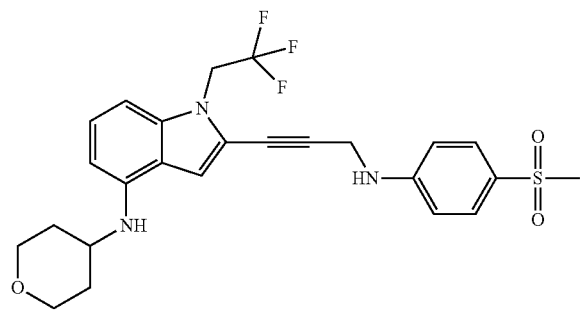 [SMILES: CS(=O)(=O)c1ccc(NCC#Cc2cc3c(NC4CCOCC4)cccc3n2CC(F)(F)F)cc1]

To a solution of 4-(methylsulfonyl)-N-(prop-2-yn-1-yl)aniline (369.2 mg, prepared from 4-(methylsulfonyl)aniline and propargyl bromide) in dimethyl sulfoxide (1 mL) was added N-isopropylpropan-2-amine (268 mg), CuI (50 mg), 2-iodo-1-(2,2,2-trifluoroethyl)-1H-indol-4-amine (300 mg), and tetrakis(triphenylphosphine)palladium(0) (102 mg). The mixture was stirred at 35° C. for 4 h, poured into a saturated sodium bicarbonate solution (30 mL), and filtered. The filtrate was extracted with ethyl acetate (2×10 mL), the combined organic layers were poured into a saturated EDTA solution (20 mL), and the resulting biphasic mixture was stirred for 1 h. Upon separating the biphasic mixture into organic and aqueous layers, the organic layer was concentrated under reduced pressure, and the crude residue was purified by preparative thin layer chromatography to give 2-(3-((4-(methylsulfonyl)phenyl)amino)prop-1-yn-1-yl)-1-(2,2,2-trifluoroethyl)-1H-indol-4-amine as yellow solid (250 mg, 68% yield).

2-(3-((4-(Methylsulfonyl)phenyl)amino)prop-1-yn-1-yl)-1-(2,2,2-trifluoroethyl)-1H-indol-4-amine was coupled with tetrahydro-4H-pyran-4-one using a method similar to that described in Example 455.

LC-MS (ES+, m/z): 506.2 [(M+H)+]

Starting with 2-iodo-1-(2,2,2-trifluoroethyl)-1H-indol-4-amine and using a method similar to that described in Example 522, the following compounds were prepared:

| Ex | Structure | Name | LC-MS (ES+, m/z) |
|---|---|---|---|
| 531 | 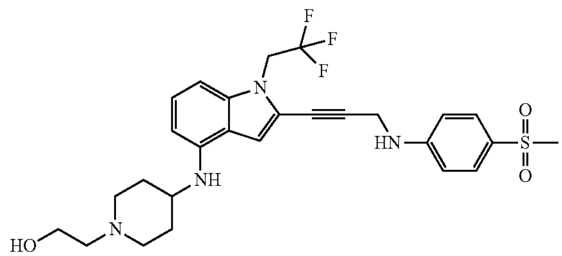 [SMILES: CS(=O)(=O)c1ccc(NCC#Cc2cc3c(NC4CCN(CCO)CC4)cccc3n2CC(F)(F)F)cc1] | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}ethan-1-ol | 549.3 [(M + H)+] |
| 532 | 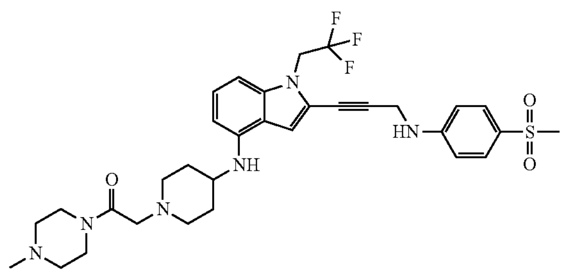 | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one | 645.4 [(M + H)+] |
| 533 | 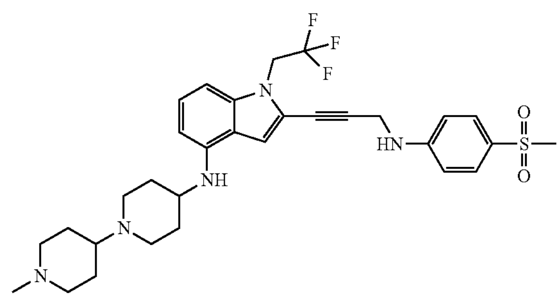 | 2-{3-[(4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine | 602.4 [(M + H)+] |
| 534 | 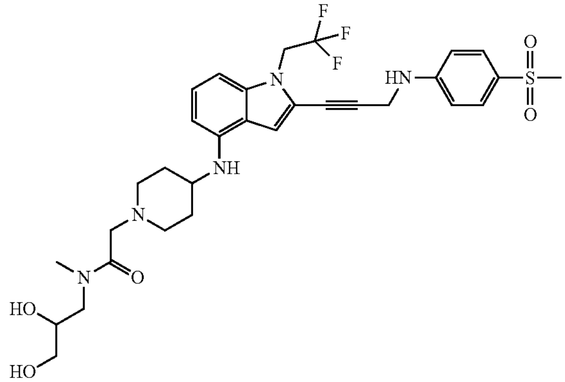 [SMILES: CN(CC(O)CO)C(=O)CN1CCC(Nc2cccc3c2cc(C#CCNc2ccc(S(C)(=O)=O)cc2)n3CC(F)(F)F)CC1] | N-(2,3-dihydroxypropyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}-N-methylacetamide | 650.2 [(M + H)+] |

-continued

| Ex | Structure | Name | LC-MS (ES+, m/z) |
|---|---|---|---|
| 535 | 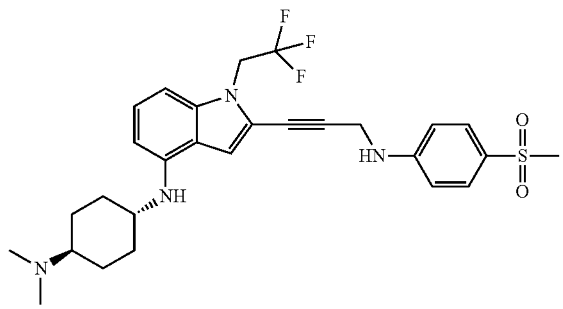 | 4-N-(2-{3-[(4-methanesulfonylphenyl)-amino]prop-1-yn-1-yl}-1-(2,2,2-trifluoroethyl)-1H-indol-4-yl)-1-N,1-N-dimethylcyclohexane-1,4-diamine | 547.3 [(M + H)+] |
| 536 | 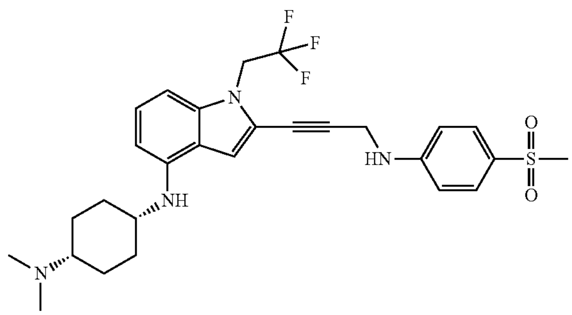 | (1s,4s)-4-N-(2-{3-[(4-methanesulfonyl-phenyl)amino]prop-1-yn-1-yl}-1-(2,2,2-trifluoroethyl)-1H-indol-4-yl)-1-N,1-N-dimethylcyclohexane-1,4-diamine | 547.3 [(M + H)+] |
| 537 | 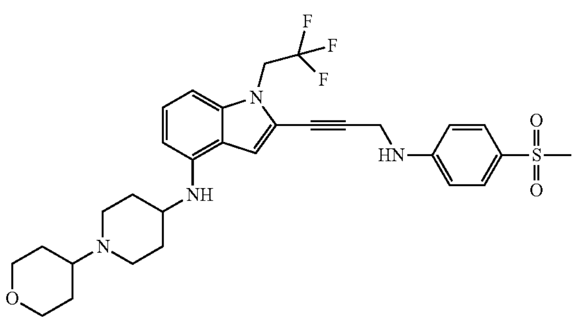 [SMILES: CS(=O)(=O)c1ccc(NCC#Cc2cc3c(NC4CCN(C5CCOCC5)CC4)cccc3n2CC(F)(F)F)cc1] | 2-{3-[(4-methanesulfonylphenyl)-amino]prop-1-yn-1-yl}-N-[1-(oxan-4-yl)piperidin-4-yl]-1-(2,2,2-trifluoroethyl)-1H-indol-4-amine | 589.3 [(M + H)+] |
| 538 | 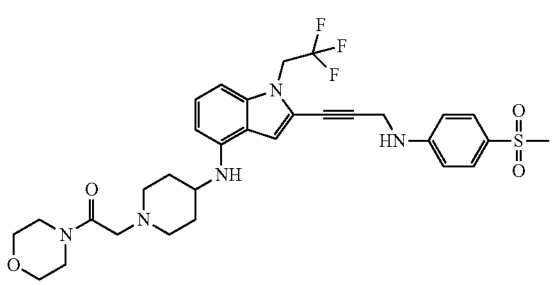 [SMILES: CS(=O)(=O)c1ccc(NCC#Cc2cc3c(NC4CCN(CC(=O)N5CCOCC5)CC4)cccc3n2CC(F)(F)F)cc1] | 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-1-(morpholin-4-yl)ethan-1-one | 632.3 [(M + H)+] |
| 539 | 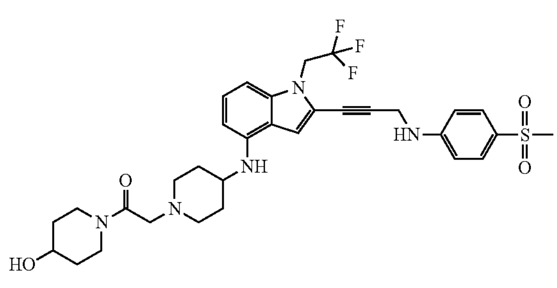 [SMILES: CS(=O)(=O)c1ccc(NCC#Cc2cc3c(NC4CCN(CC(=O)N5CCC(O)CC5)CC4)cccc3n2CC(F)(F)F)cc1] | 1-(4-hydroxypiperidin-1-yl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}ethan-1-one | 646.3 [(M + H)+] |

-continued

| Ex | Structure | Name | LC-MS (ES⁺, m/z) |
|---|---|---|---|
| 540 | 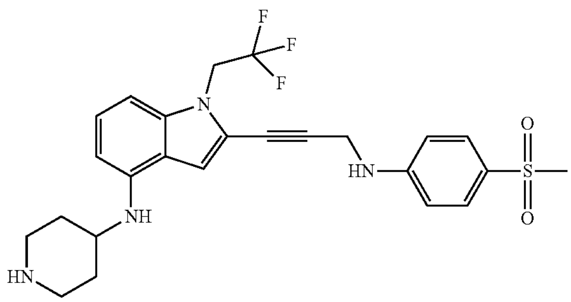 [SMILES: CS(=O)(=O)c1ccc(NCC#Cc2cc3c(NC4CCNCC4)cccc3n2CC(F)(F)F)cc1] | 2-{3-[(4-methanesulfonylphenyl)-amino]prop-1-yn-1-yl}-N-(piperidin-4-yl)-1-(2,2,2-trifluoroethyl)-1H-indol-4-amine | 505.2 [(M + H)⁺] |
| 541 | 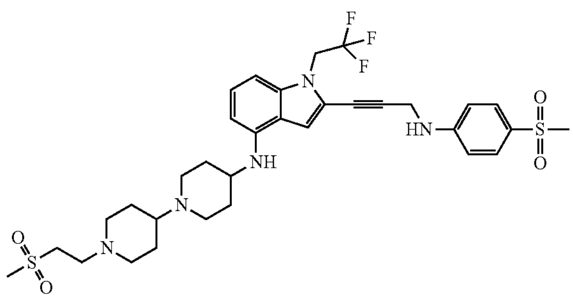 | N-{1-[1-(2-methanesulfonylethyl)piperidin-4-yl]piperidin-4-yl}-2-{3-[(4-methanesulfonylphenyl)amino]prop-1-yn-1-yl}-1-(2,2,2-trifluoroethyl)-1H-indol-4-amine | 694.3 [(M + H)⁺] |
| 542 | 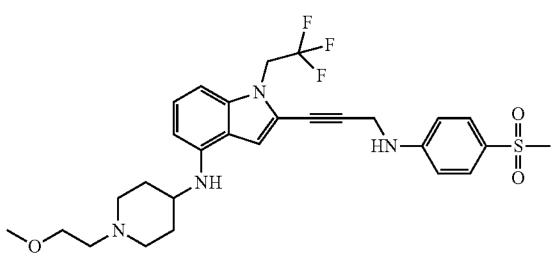 | 2-{3-[(4-methanesulfonylphenyl)-amino]prop-1-yn-1-yl}-N-[1-(2-methoxyethyl)piperidin-4-yl]-1-(2,2,2-trifluoroethyl)-1H-indol-4-amine | 563.3 [(M + H)⁺] |
| 543 | 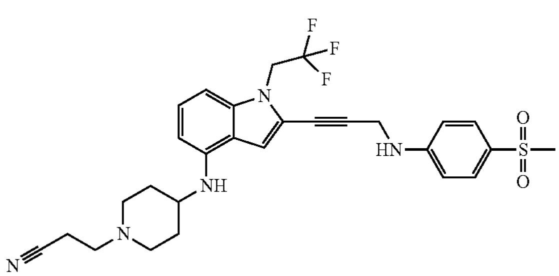 [SMILES: CS(=O)(=O)c1ccc(NCC#Cc2cc3c(NC4CCN(CCC#N)CC4)cccc3n2CC(F)(F)F)cc1] | 3-{4-[(2-{3-[(4-methane-sulfonylphenyl)-amino]prop-1-yn-1-yl}-1-(2,2,2-trifluoroethyl)-1H-indol-4-yl)amino]piperidin-1-yl}propanenitrile | 558.3 [(M + H)⁺] |
| 544 | 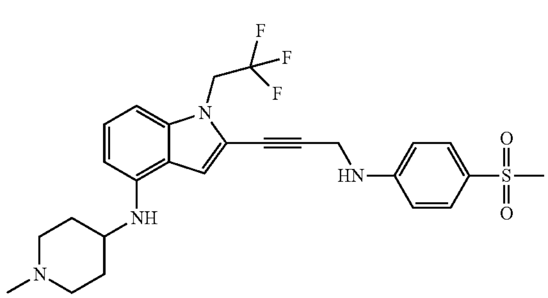 | 2-{3-[(4-methanesulfonylphenyl)-amino]prop-1-yn-1-yl}-N-(1-methylpiperidin-4-yl)-1-(2,2,2-trifluoroethyl)-1H-indol-4-amine | 519.3 [(M + H)⁺] |

| Ex | Structure | Name | LC-MS (ES+, m/z) |
|---|---|---|---|
| 545 | 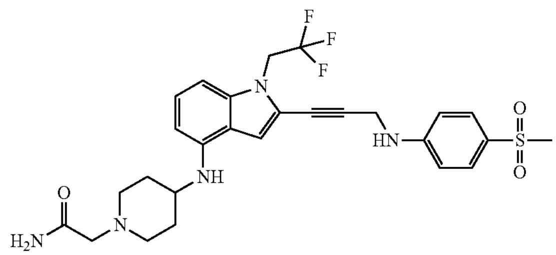 [SMILES: CS(=O)(=O)c1ccc(NCC#Cc2cc3c(NC4CCN(CC(N)=O)CC4)cccc3n2CC(F)(F)F)cc1] | 2-{4-[(2-{3-[(4-methane-sulfonylphenyl)-amino]prop-1-yn-1-yl}-1-(2,2,2-trifluoroethyl)-1H-indol-4-yl)amino]piperidin-1-yl}acetamide | 562.3 [(M + H)+] |
| 546 | 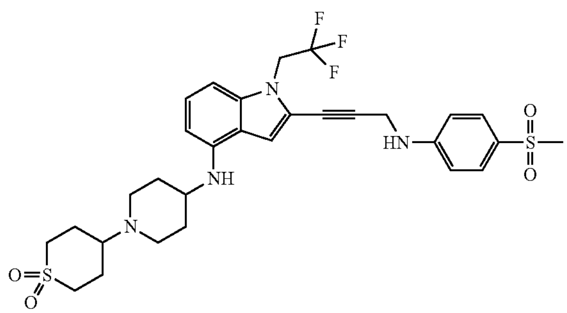 [SMILES: CS(=O)(=O)c1ccc(NCC#Cc2cc3c(NC4CCN(C5CCS(=O)(=O)CC5)CC4)cccc3n2CC(F)(F)F)cc1] | 4-{4-[(2-{3-[(4-methane-sulfonylphenyl)-amino]prop-1-yn-1-yl}-1-(2,2,2-trifluoroethyl)-1H-indol-4-yl)amino]piperidin-1-yl}-1λ⁶-thiane-1,1-dione | 637.3 [(M + H)+] |
| 547 | 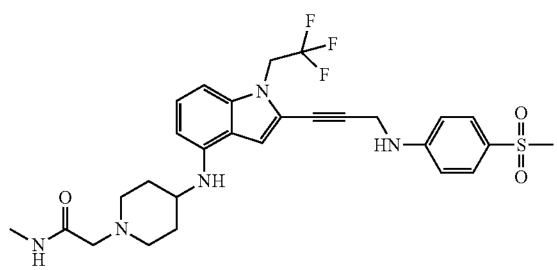 | 2-{4-[(2-{3-[(4-methane-sulfonylphenyl)amino]prop-1-yn-1-yl}-1-(2,2,2-trifluoroethyl)-1H-indol-4-yl)amino]piperidin-1-yl}-N-methylacetamide | 576.3 [(M + H)+] |
| 548 | 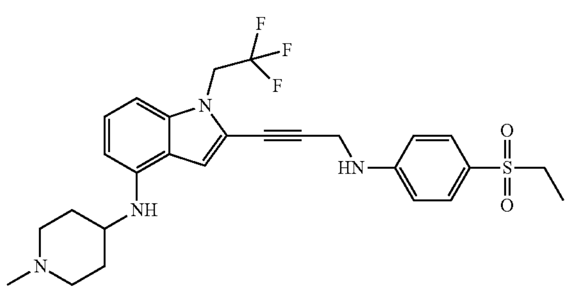 [SMILES: CCS(=O)(=O)c1ccc(NCC#Cc2cc3c(NC4CCN(C)CC4)cccc3n2CC(F)(F)F)cc1] | 2-(3-{[4-(ethanesulfonyl)phenyl]amino}prop-1-yn-1-yl)-N-(1-methylpiperidin-4-yl)-1-(2,2,2-trifluoroethyl)-1H-indol-4-amine | 533.2 [(M + H)+] |
| 549 | 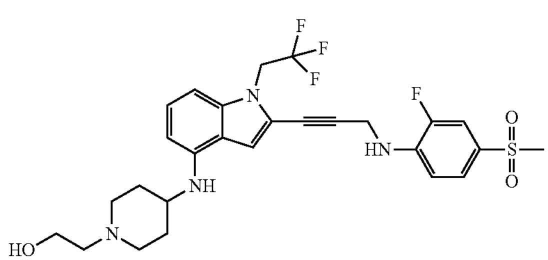 | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}ethan-1-ol | 567.3 [(M + H)+] |

| Ex | Structure | Name | LC-MS (ES+, m/z) |
|---|---|---|---|
| 550 | 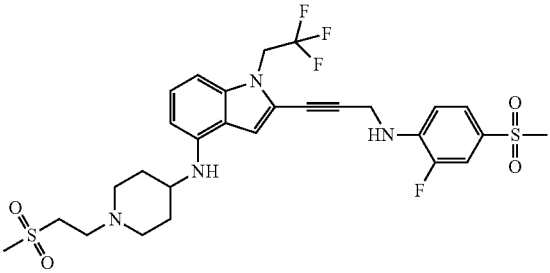 | 2-{3-[(2-fluoro-4-methane-sulfonylphenyl)-amino]prop-1-yn-1-yl}-N-[1-(2-methanesulfonylethyl)-piperidin-4-yl]-1-(2,2,2-trifluoroethyl)-1H-indol-4-amine | 629.3 [(M + H)+] |
| 551 | 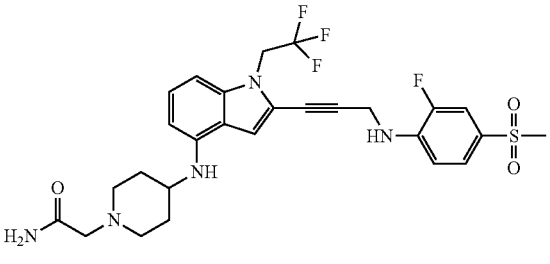 [SMILES: CS(=O)(=O)c1ccc(NCC#Cc2cc3c(NC4CCN(CC(N)=O)CC4)cccc3n2CC(F)(F)F)c(F)c1] | 2-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}acetamide | 580.3 [(M + H)+] |
| 552 | 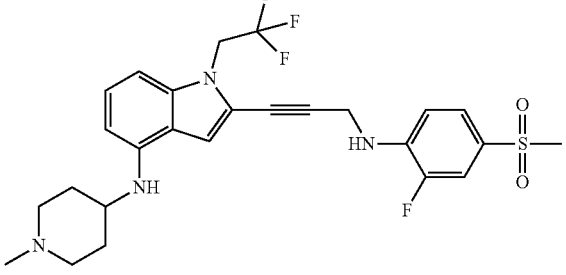 | 2-{3-[(2-fluoro-4-methane-sulfonylphenyl)-amino]prop-1-yn-1-yl}-N-(1-methylpiperidin-4-yl)-1-(2,2,2-trifluoroethyl)-1H-indol-4-amine | 537.3 [(M + H)+] |
| 553 | 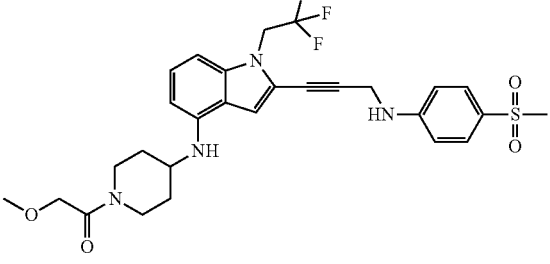 | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}-2-methoxyethan-1-one | 577.3 [(M + H)+] |
| 554 | 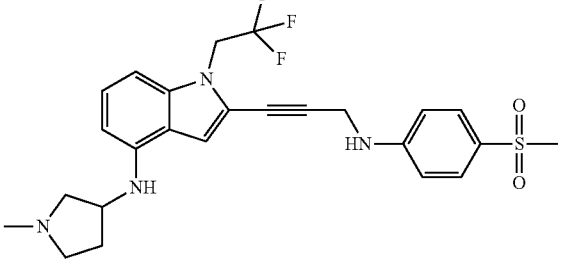 | 2-{3-[(4-methanesulfonyl-phenyl)amino]prop-1-yn-1-yl}-N-(1-methylpyrrolidin-3-yl)-1-(2,2,2-trifluoroethyl)-1H-indol-4-amine | 505.2 [(M + H)+] |

| Ex | Structure | Name | LC-MS (ES+, m/z) |
|---|---|---|---|
| 555 | 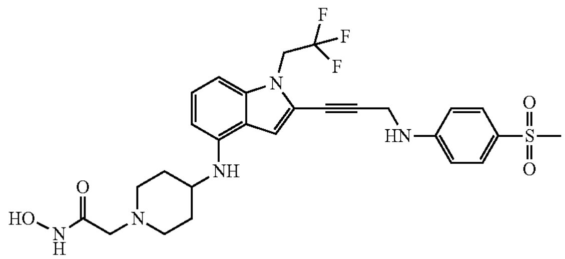 [SMILES: CS(=O)(=O)c1ccc(NCC#Cc2cc3c(NC4CCN(CC(=O)NO)CC4)cccc3n2CC(F)(F)F)cc1] | N-hydroxy-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide | 578.3 [(M + H)+] |
| 556 | 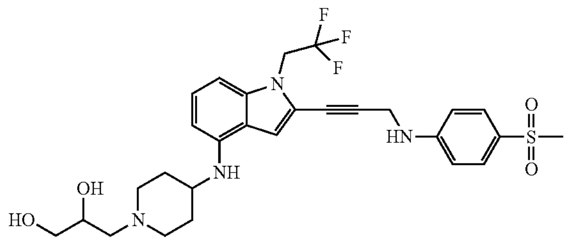 [SMILES: CS(=O)(=O)c1ccc(NCC#Cc2cc3c(NC4CCN(CC(O)CO)CC4)cccc3n2CC(F)(F)F)cc1] | 3-{4-[(2-{3-[(4-methanesulfonylphenyl)amino]prop-1-yn-1-yl}-1-(2,2,2-trifluoroethyl)-1H-indol-4-yl)amino]piperidin-1-yl}propane-1,2-diol | 579.3 [(M + H)+] |
| 557 | 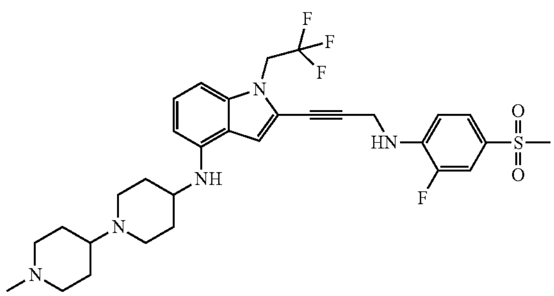 | 2-{3-[(2-fluoro-4-methanesulfonylphenyl)amino]prop-1-yn-1-yl}-N-[1-(1-methylpiperidin-4-yl)piperidin-4-yl]-1-(2,2,2-trifluoroethyl)-1H-indol-4-amine | 620.4 [(M + H)+] |
| 558 | 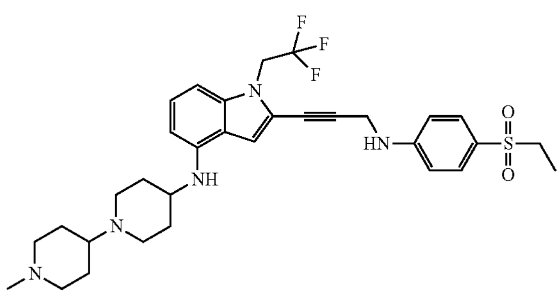 [SMILES: CCS(=O)(=O)c1ccc(NCC#Cc2cc3c(NC4CCN(C5CCN(C)CC5)CC4)cccc3n2CC(F)(F)F)cc1] | 2-(3-{[4-(ethanesulfonyl)phenyl]amino}prop-1-yn-1-yl)-N-[1-(1-methylpiperidin-4-yl)piperidin-4-yl]-1-(2,2,2-trifluoroethyl)-1H-indol-4-amine | 616.2 [(M + H)+] |
| 559 | 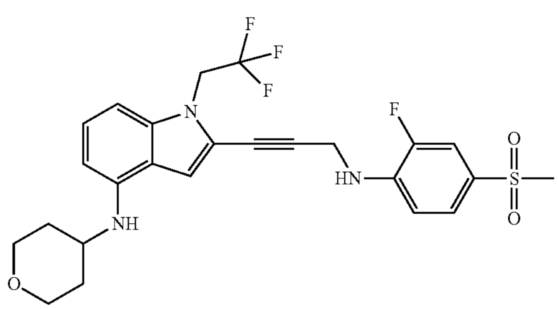 [SMILES: CS(=O)(=O)c1ccc(NCC#Cc2cc3c(NC4CCOCC4)cccc3n2CC(F)(F)F)c(F)c1] | 2-{3-[(2-fluoro-4-methanesulfonylphenyl)amino]prop-1-yn-1-yl}-N-(oxan-4-yl)-1-(2,2,2-trifluoroethyl)-1H-indol-4-amine | 524.2 [(M + H)+] |

-continued

| Ex | Structure | Name | LC-MS (ES+, m/z) |
|---|---|---|---|
| 560 | 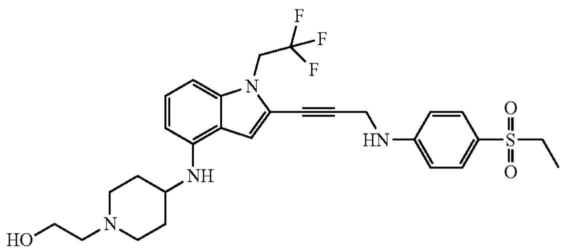 [SMILES: CCS(=O)(=O)c1ccc(NCC#Cc2cc3c(NC4CCN(CCO)CC4)cccc3n2CC(F)(F)F)cc1] | 2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethan-1-ol | 563.3 [(M + H)+] |
| 561 | 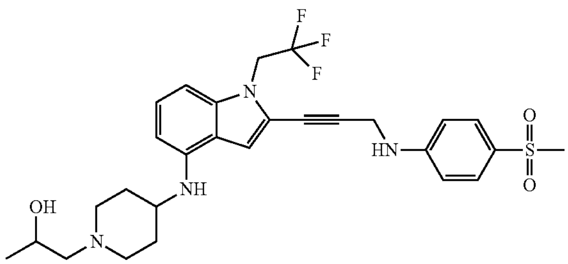 [SMILES: CC(O)CN1CCC(Nc2cccc3c2cc(C#CCNc2ccc(S(C)(=O)=O)cc2)n3CC(F)(F)F)CC1] | 1-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propan-2-ol | 563.3 [(M + H)+] |
| 562 | 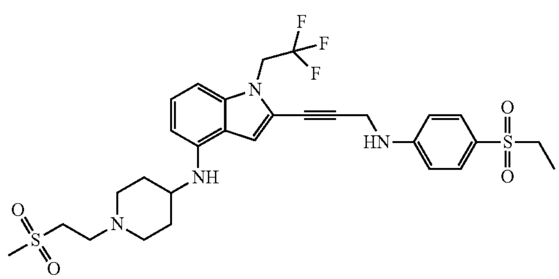 [SMILES: CCS(=O)(=O)c1ccc(NCC#Cc2cc3c(NC4CCN(CCS(C)(=O)=O)CC4)cccc3n2CC(F)(F)F)cc1] | 2-(3-{[4-(ethanesulfonyl)-phenyl]amino}prop-1-yn-1-yl)-N-[1-(2-methanesulfonylethyl)piperidin-4-yl]-1-(2,2,2-trifluoroethyl)-1H-indol-4-amine | 625.3 [(M + H)+] |
| 563 | 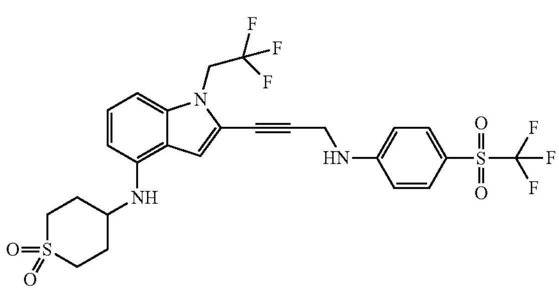 [SMILES: O=S1(=O)CCC(Nc2cccc3c2cc(C#CCNc2ccc(S(=O)(=O)C(F)(F)F)cc2)n3CC(F)(F)F)CC1] | 4-{[1-(2,2,2-trifluoroethyl)-2-{3-[(4-trifluoromethanesulfonylphenyl)amino]prop-1-yn-1-yl}-1H-indol-4-yl]amino}-1λ⁶-thiane-1,1-dione | 608.1 [(M + H)+] |
| 564 | 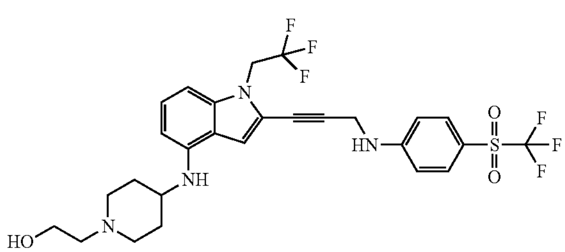 [SMILES: O=S(=O)(c1ccc(NCC#Cc2cc3c(NC4CCN(CCO)CC4)cccc3n2CC(F)(F)F)cc1)C(F)(F)F] | 2-(4-{[1-(2,2,2-trifluoroethyl)-2-{3-[(4-trifluoromethanesulfonylphenyl)amino]prop-1-yn-1-yl}-1H-indol-4-yl]amino}piperidin-1-yl)ethan-1-ol | 603.2 [(M + H)+] |

-continued

| Ex | Structure | Name | LC-MS (ES+, m/z) |
|---|---|---|---|
| 565 | 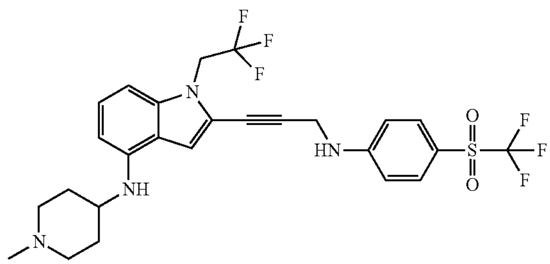 [SMILES: CN1CCC(Nc2cccc3c2cc(C#CCNc2ccc(S(=O)(=O)C(F)(F)F)cc2)n3CC(F)(F)F)CC1] | N-(1-methylpiperidin-4-yl)-1-(2,2,2-trifluoroethyl)-2-{3-[(4-trifluoromethanesulfonylphenyl)amino]prop-1-yn-1-yl}-1H-indol-4-amine | 573.3 [(M + H)+] |
| 566 | 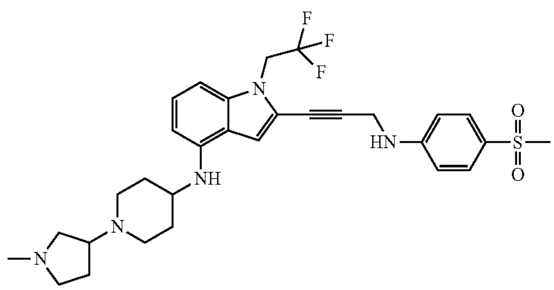 | 2-{3-[(4-methanesulfonyl-phenyl)amino]prop-1-yn-1-yl}-N-[1-(1-methylpyrrolidin-3-yl)piperidin-4-yl]-1-(2,2,2-trifluoroethyl)-1H-indol-4-amine | 588.3 [(M + H)+] |
| 567 | 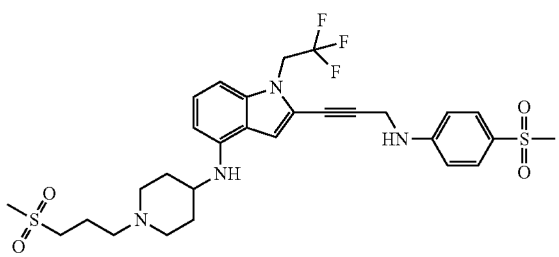 | 2-{3-[(4-methanesulfonyl-phenyl)amino]prop-1-yn-1-yl}-N-[1-(3-methanesulfonylpropyl)piperidin-4-yl]-1-(2,2,2-trifluoroethyl)-1H-indol-4-amine | 625.3 [(M + H)+] |
| 568 | 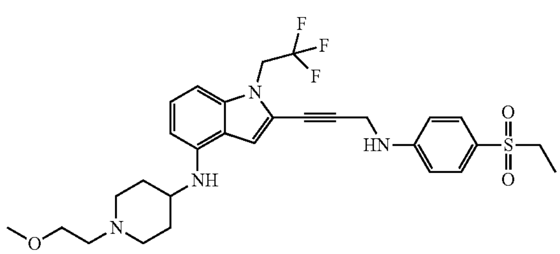 [SMILES: CCS(=O)(=O)c1ccc(NCC#Cc2cc3c(NC4CCN(CCOC)CC4)cccc3n2CC(F)(F)F)cc1] | 2-(3-{[4-(ethanesulfonyl)-phenyl]amino}prop-1-yn-1-yl)-N-[1-(2-methoxyethyl)piperidin-4-yl]-1-(2,2,2-trifluoroethyl)-1H-indol-4-amine | 577.3 [(M + H)+] |
| 569 | 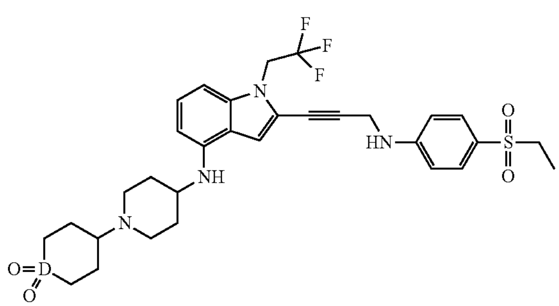 | 4-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)-1λ⁶-thiane-1,1-dione | 651.3 [(M + H)+] |

-continued

| Ex | Structure | Name | LC-MS (ES⁺, m/z) |
|---|---|---|---|
| 570 | 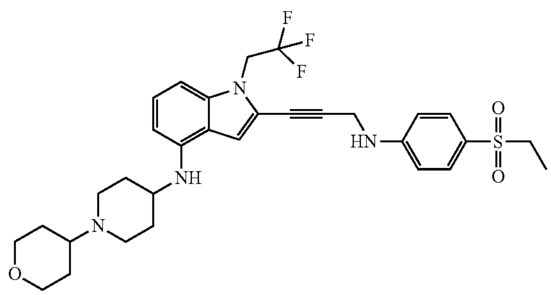 [SMILES: CCS(=O)(=O)c1ccc(NCC#Cc2cc3c(NC4CCN(C5CCOCC5)CC4)cccc3n2CC(F)(F)F)cc1] | 2-(3-{[4-(ethanesulfonyl)-phenyl]amino}prop-1-yn-1-yl)-N-[1-(oxan-4-yl)piperidin-4-yl]-1-(2,2,2-trifluoroethyl)-1H-indol-4-amine | 603.3 [(M + H)⁺] |
| 571 | 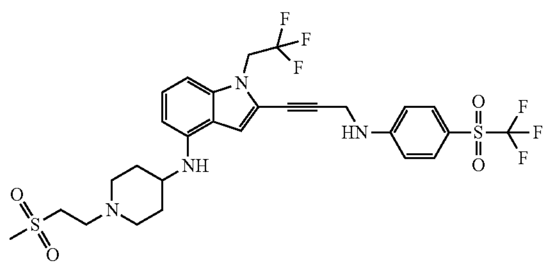 [SMILES: CS(=O)(=O)CCN1CCC(Nc2cccc3c2cc(C#CCNc2ccc(S(=O)(=O)C(F)(F)F)cc2)n3CC(F)(F)F)CC1] | N-[1-(2-methanesulfonylethyl)-piperidin-4-yl]-1-(2,2,2-trifluoroethyl)-2-{3-[(4-trifluoromethane-sulfonylphenyl)amino]prop-1-yn-1-yl}-1H-indol-4-amine | 665.3 [(M + H)⁺] |
| 572 | 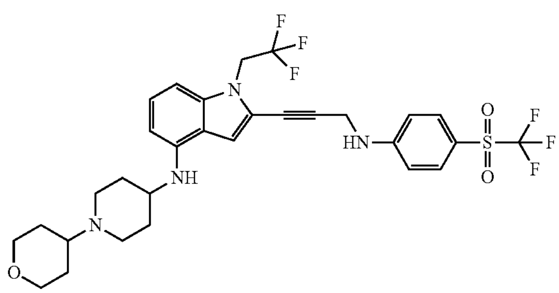 [SMILES: O=S(=O)(c1ccc(NCC#Cc2cc3c(NC4CCN(C5CCOCC5)CC4)cccc3n2CC(F)(F)F)cc1)C(F)(F)F] | N-[1-(oxan-4-yl)piperidin-4-yl]-1-(2,2,2-trifluoroethyl)-2-{3-[(4-trifluoromethanesulfonylphenyl)amino]prop-1-yn-1-yl}-1H-indol-4-amine | 643.3 [(M + H)⁺] |
| 573 | 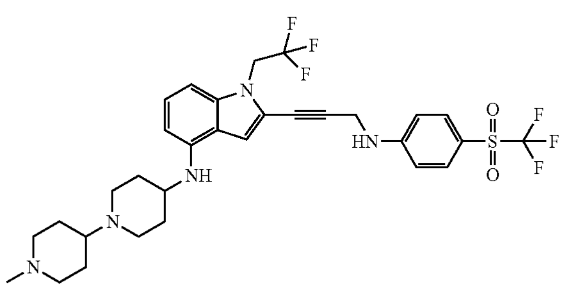 [SMILES: CN1CCC(N2CCC(Nc3cccc4c3cc(C#CCNc3ccc(S(=O)(=O)C(F)(F)F)cc3)n4CC(F)(F)F)CC2)CC1] | N-[1-(1-methylpiperidin-4-yl)piperidin-4-yl]-1-(2,2,2-trifluoroethyl)-2-{3-[(4-trifluoromethanesulfonylphenyl)amino]prop-1-yn-1-yl}-1H-indol-4-amine | 656.3 [(M + H)⁺] |
| 574 | 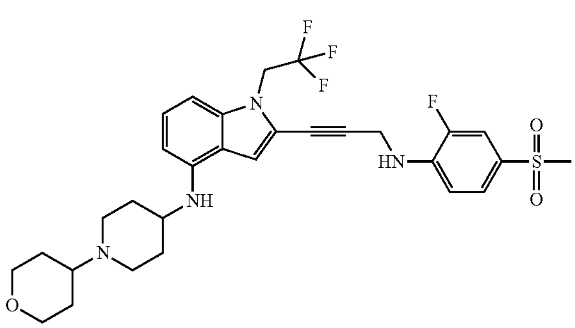 [SMILES: CS(=O)(=O)c1ccc(NCC#Cc2cc3c(NC4CCN(C5CCOCC5)CC4)cccc3n2CC(F)(F)F)c(F)c1] | 2-{3-[(2-fluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine | 607.2 [(M + H)⁺] |

-continued

| Ex | Structure | Name | LC-MS (ES+, m/z) |
|---|---|---|---|
| 575 | 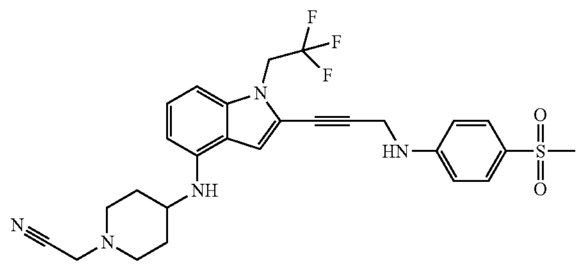 [SMILES: CS(=O)(=O)c1ccc(NCC#Cc2cc3c(NC4CCN(CC#N)CC4)cccc3n2CC(F)(F)F)cc1] | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetonitrile | 544.3 [(M + H)+] |
| 576 | 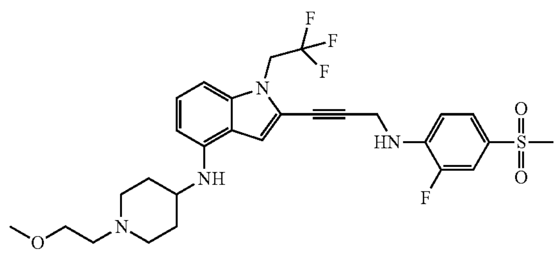 | 2-{3-[(2-fluoro-4-methanesulfonylphenyl)amino]prop-1-yn-1-yl}-N-[1-(2-methoxyethyl)piperidin-4-yl]-1-(2,2,2-trifluoroethyl)-1H-indol-4-amine | 581.0 [(M + H)+] |
| 577 | 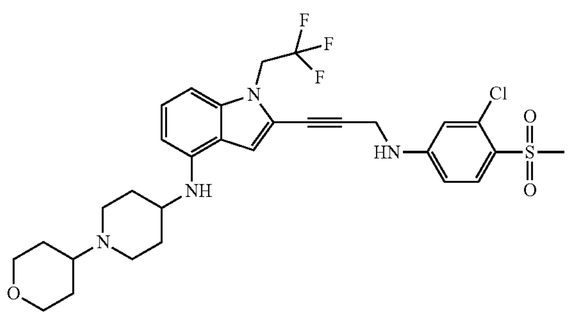 [SMILES: CS(=O)(=O)c1ccc(NCC#Cc2cc3c(NC4CCN(C5CCOCC5)CC4)cccc3n2CC(F)(F)F)cc1Cl] | 2-{3-[(3-chloro-4-methanesulfonylphenyl)amino]prop-1-yn-1-yl}-N-[1-(oxan-4-yl)piperidin-4-yl]-1-(2,2,2-trifluoroethyl)-1H-indol-4-amine | 623.3 [(M + H)+] |
| 578 | 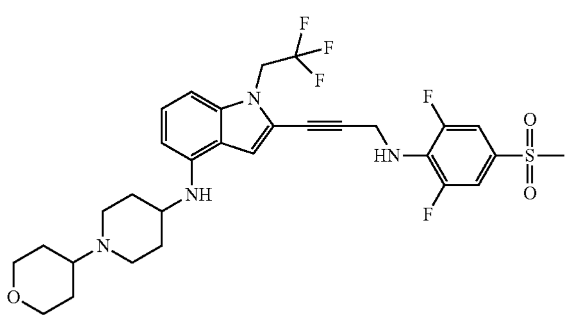 [SMILES: CS(=O)(=O)c1cc(F)c(NCC#Cc2cc3c(NC4CCN(C5CCOCC5)CC4)cccc3n2CC(F)(F)F)c(F)c1] | 2-{3-[(2,6-difluoro-4-methanesulfonyl-phenyl)amino]prop-1-yn-1-yl}-N-[1-(oxan-4-yl)piperidin-4-yl]-1-(2,2,2-trifluoroethyl)-1H-indol-4-amine | 625.3 [(M + H)+] |
| 579 | 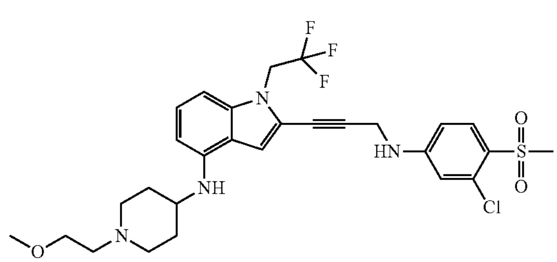 | 2-{3-[(3-chloro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine | 597.3 [(M + H)+] |

-continued

| Ex | Name | LC-MS (ES+, m/z) |
|---|---|---|
| 580 | 2-{4-[(2-{3-[(3-chloro-4-methanesulfonylphenyl)amino]prop-1-yn-1-yl}-1-(2,2,2-trifluoroethyl)-1H-indol-4-yl)amino]piperidin-1-yl}ethan-1-ol | 582.9 [(M + H)+] |
| 581 | (2S)-3-{4-[(2-{3-[(4-methanesulfonyl-phenyl)amino]prop-1-yn-1-yl}-1-(2,2,2-trifluoroethyl)-1H-indol-4-yl)amino]piperidin-1-yl}propane-1,2-diol | 579.3 [(M + H)+] |
| 582 | N-(5-aminopentyl)-2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamide | 647.3 [(M + H)+] |
| 583 | 2-{3-[(2,6-difluoro-4-methanesulfonyl-phenyl)amino]prop-1-yn-1-yl}-N-[1-(2-methoxyethyl)piperidin-4-yl]-1-(2,2,2-trifluoroethyl)-1H-indol-4-amine | 599.2 [(M + H)+] |
| 584 | 2-(3-{[4-(ethanesulfonyl)phenyl]-amino}prop-1-yn-1-yl)-N-(oxan-4-yl)-1-(2,2,2-trifluoroethyl)-1H-indol-4-amine | 520.0 [(M + H)+] |

| Ex | Structure | Name | LC-MS (ES+, m/z) |
|---|---|---|---|
| 585 | 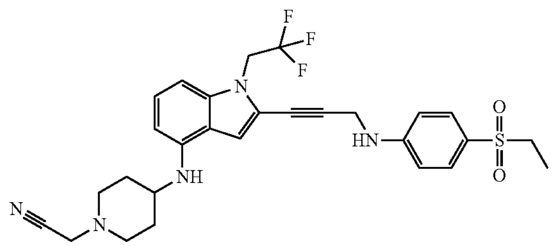 [SMILES: CCS(=O)(=O)c1ccc(NCC#Cc2cc3c(NC4CCN(CC#N)CC4)cccc3n2CC(F)(F)F)cc1] | 2-(4-{[2-(3-{[4-(ethanesulfonyl)phenyl]amino}prop-1-yn-1-yl)-1-(2,2,2-trifluoroethyl)-1H-indol-4-yl]amino}piperidin-1-yl)acetonitrile | 558.3 [(M + H)+] |
| 586 | 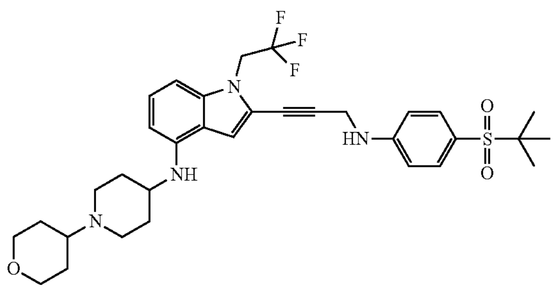 [SMILES: CC(C)(C)S(=O)(=O)c1ccc(NCC#Cc2cc3c(NC4CCN(C5CCOCC5)CC4)cccc3n2CC(F)(F)F)cc1] | 2-(3-{[4-(2-methylpropane-2-sulfonyl)phenyl]amino}prop-1-yn-1-yl)-N-[1-(oxan-4-yl)piperidin-4-yl]-1-(2,2,2-trifluoroethyl)-1H-indol-4-amine | 631.4 [(M + H)+] |
| 587 | 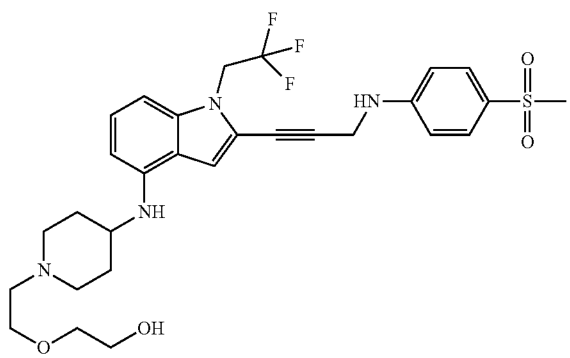 [SMILES: CS(=O)(=O)c1ccc(NCC#Cc2cc3c(NC4CCN(CCOCCO)CC4)cccc3n2CC(F)(F)F)cc1] | 2-(2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}ethoxy)ethan-1-ol | 593.3 [(M + H)+] |
| 588 | 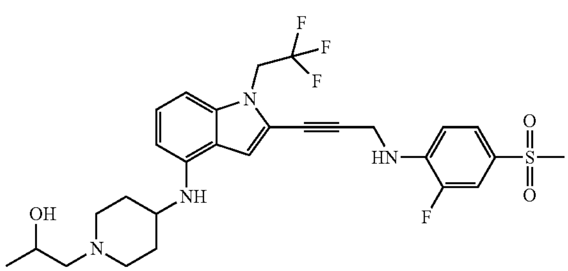 [SMILES: CC(O)CN1CCC(Nc2cccc3c2cc(C#CCNc2ccc(S(C)(=O)=O)cc2F)n3CC(F)(F)F)CC1] | 1-{4-[(2-{3-[(2-fluoro-4-methane-sulfonylphenyl)amino]prop-1-yn-1-yl}-1-(2,2,2-trifluoroethyl)-1H-indol-4-yl)amino]piperidin-1-yl}propan-2-ol | 581.3 [(M + H)+] |
| 589 | 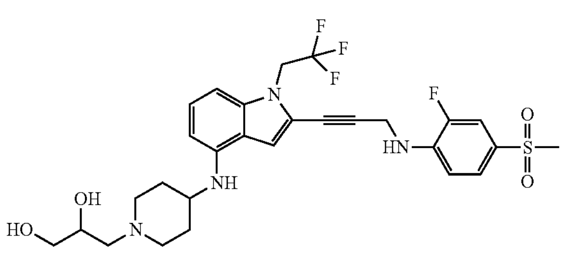 [SMILES: CS(=O)(=O)c1ccc(NCC#Cc2cc3c(NC4CCN(CC(O)CO)CC4)cccc3n2CC(F)(F)F)c(F)c1] | 3-{4-[(2-{3-[(2-fluoro-4-methanesulfonylphenyl)amino]prop-1-yn-1-yl}-1-(2,2,2-trifluoroethyl)-1H-indol-4-yl)amino]piperidin-1-yl}propane-1,2-diol | 597.2 [(M + H)+] |

-continued

| Ex | Structure | Name | LC-MS (ES+, m/z) |
|---|---|---|---|
| 590 | 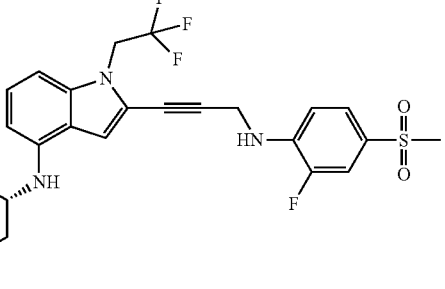 | (1s,4s)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine | 565.0 [(M + H)+] |
| 591 | 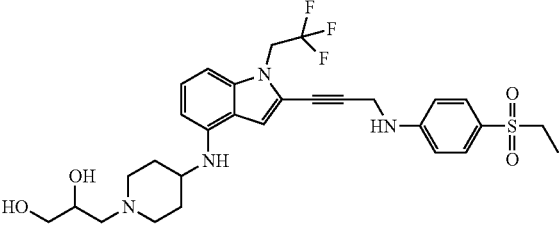 [SMILES: CCS(=O)(=O)c1ccc(NCC#Cc2cc3c(NC4CCN(CC(O)CO)CC4)cccc3n2CC(F)(F)F)cc1] | 3-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propane-1,2-diol | 593.3 [(M + H)+] |
| 592 | 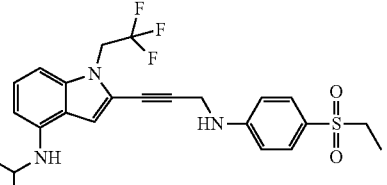 | 2-(3-{[4-(ethanesulfonyl)-phenyl]amino}prop-1-yn-1-yl)-N-[1-(3-methanesulfonylpropyl)-piperidin-4-yl]-1-(2,2,2-trifluoroethyl)-1H-indol-4-amine | 639.3 [(M + H)+] |
| 593 | 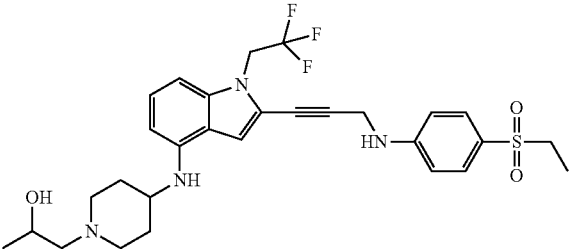 [SMILES: CCS(=O)(=O)c1ccc(NCC#Cc2cc3c(NC4CCN(CC(C)O)CC4)cccc3n2CC(F)(F)F)cc1] | 1-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)propan-2-ol | 577.3 [(M + H)+] |
| 594 | 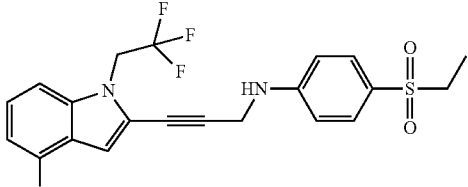 | 2-[2-(4-{[2-(3-{[4-(ethanesulfonyl)-phenyl]amino}prop-1-yn-1-yl)-1-(2,2,2-trifluoroethyl)-1H-indol-4-yl]amino}piperidin-1-yl)ethoxy]ethan-1-ol | 607.3 [(M + H)+] |

-continued

| Ex | Structure | Name | LC-MS (ES+, m/z) |
|---|---|---|---|
| 595 | 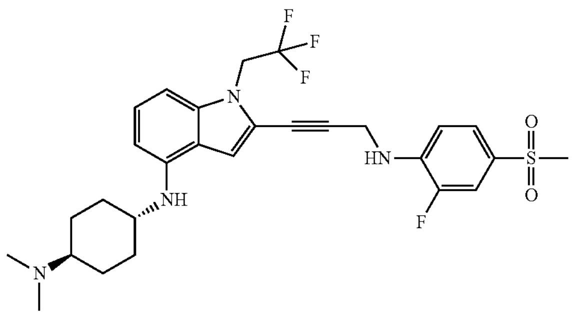 | (1r,4r)-4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethyl-cyclohexane-1,4-diamine | 565.3 [(M + H)+] |
| 596 | 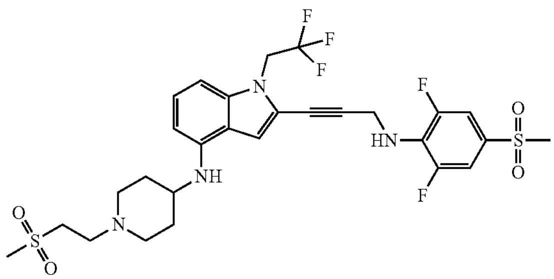 | 2-{3-[(2,6-difluoro-4-methanesulfonylphenyl)amino]prop-1-yn-1-yl}-N-[1-(2-methanesulfonylethyl)piperidin-4-yl]-1-(2,2,2-trifluoroethyl)-1H-indol-4-amine | 647.3 [(M + H)+] |
| 597 | 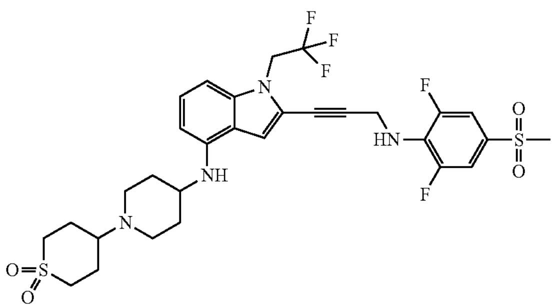 [SMILES: CS(=O)(=O)c1cc(F)c(NCC#Cc2cc3c(NC4CCN(C5CCS(=O)(=O)CC5)CC4)cccc3n2CC(F)(F)F)c(F)c1] | 4-{4-[(2-{3-[(2,6-difluoro-4-methanesulfonylphenyl)amino]prop-1-yn-1-yl}-1-(2,2,2-trifluoroethyl)-1H-indol-4-yl)amino]piperidin-1-yl}-1$\lambda^6$-thiane-1,1-dione | 673.3 [(M + H)+] |
| 598 | 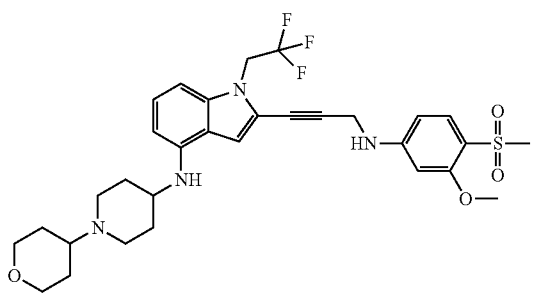 [SMILES: COc1cc(NCC#Cc2cc3c(NC4CCN(C5CCOCC5)CC4)cccc3n2CC(F)(F)F)ccc1S(C)(=O)=O] | 2-{3-[(4-methanesulfonyl-3-methoxyphenyl)amino]prop-1-yn-1-yl}-N-[1-(oxan-4-yl)piperidin-4-yl]-1-(2,2,2-trifluoroethyl)-1H-indol-4-amine | 619.3 [(M + H)+] |
| 599 | 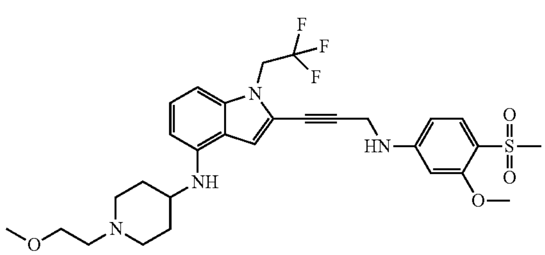 | 2-{3-[(4-methanesulfonyl-3-methoxyphenyl)amino]prop-1-yn-1-yl}-N-[1-(2-methoxyethyl)piperidin-4-yl]-1-(2,2,2-trifluoroethyl)-1H-indol-4-amine | 593.3 [(M + H)+] |

-continued

| Ex | Structure | Name | LC-MS (ES+, m/z) |
|---|---|---|---|
| 600 | 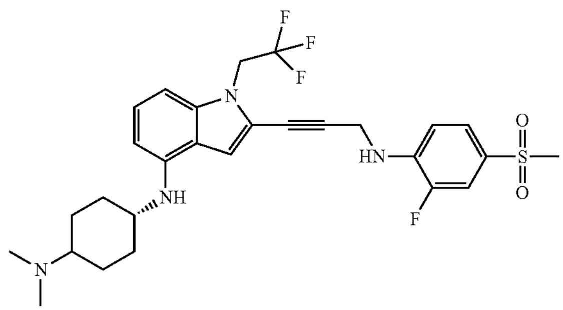 | 4-N-(2-{3-[(2-fluoro-4-methanesulfonylphenyl)amino]prop-1-yn-1-yl}-1-(2,2,2-trifluoroethyl)-1H-indol-4-yl)-1-N,1-N-dimethylcyclohexane-1,4-diamine | 565.3 [(M + H)+] |
| 601 | 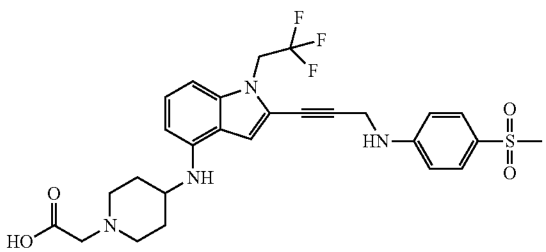 [SMILES: CS(=O)(=O)c1ccc(NCC#Cc2cc3c(NC4CCN(CC(=O)O)CC4)cccc3n2CC(F)(F)F)cc1] | 2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetic acid | 563.2 [(M + H)+] |
| 602 | 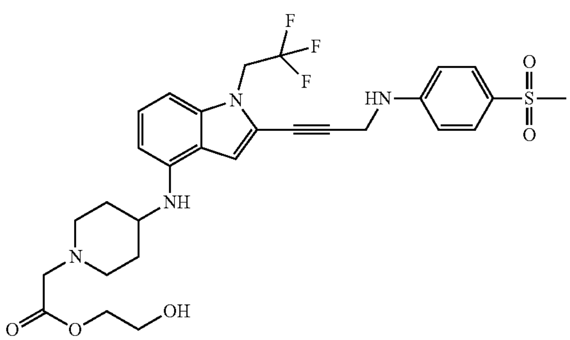 [SMILES: CS(=O)(=O)c1ccc(NCC#Cc2cc3c(NC4CCN(CC(=O)OCCO)CC4)cccc3n2CC(F)(F)F)cc1] | 2-hydroxyethyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate | 607.0 [(M + H)+] |
| 603 | 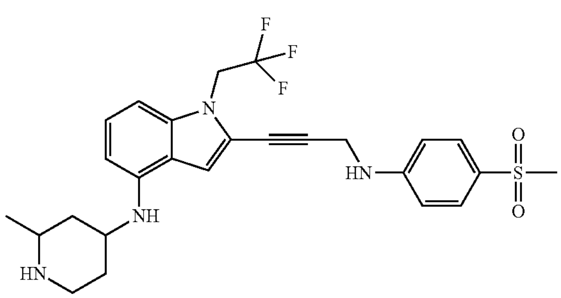 | 2-{3-[(4-methanesulfonylphenyl)-amino]prop-1-yn-1-yl}-N-(2-methylpiperidin-4-yl)-1-(2,2,2-trifluoroethyl)-1H-indol-4-amine | 519.2 [(M + H)+] |
| 604 | 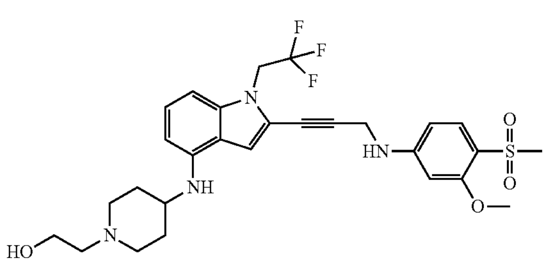 [SMILES: COc1cc(NCC#Cc2cc3c(NC4CCN(CCO)CC4)cccc3n2CC(F)(F)F)ccc1S(C)(=O)=O] | 2-{4-[(2-{3-[(4-methanesulfonyl-3-methoxyphenyl)amino]prop-1-yn-1-yl}-1-(2,2,2-trifluoroethyl)-1H-indol-4-yl)amino]piperidin-1-yl}ethan-1-ol | 579.3 [(M + H)+] |

| Ex | Structure | Name | LC-MS (ES+, m/z) |
|---|---|---|---|
| 605 | 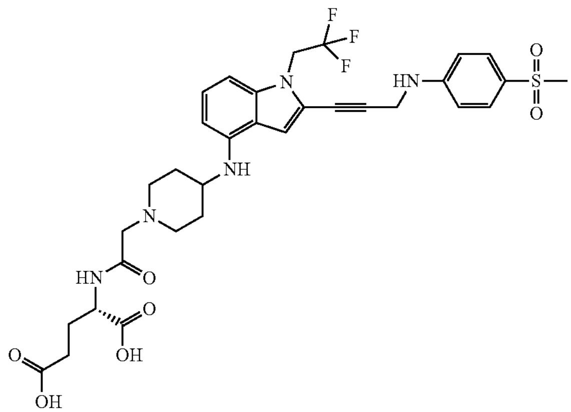 [SMILES: CS(=O)(=O)c1ccc(NCC#Cc2cc3c(NC4CCN(CC(=O)N[C@@H](CCC(=O)O)C(=O)O)CC4)cccc3n2CC(F)(F)F)cc1] | (2S)-2-(2-{4-[(2-{3-[(4-methane-sulfonylphenyl)amino]prop-1-yn-1-yl}-1-(2,2,2-trifluoroethyl)-1H-indol-4-yl)amino]piperidin-1-yl}acetamido)pentanedioic acid | 692.1 [(M + H)+] |
| 606 | 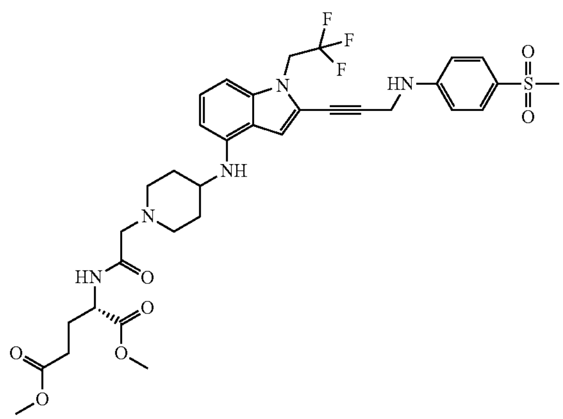 [SMILES: COC(=O)CC[C@H](NC(=O)CN1CCC(Nc2cccc3c2cc(C#CCNc2ccc(S(C)(=O)=O)cc2)n3CC(F)(F)F)CC1)C(=O)OC] | 1,5-dimethyl (2S)-2-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentanedioate | 720.3 [(M + H)+] |
| 607 | 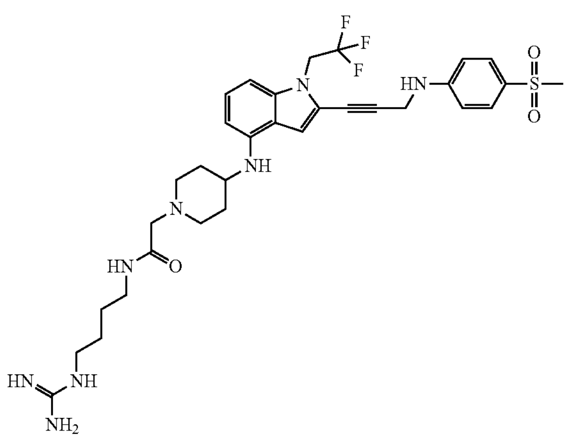 [SMILES: CS(=O)(=O)c1ccc(NCC#Cc2cc3c(NC4CCN(CC(=O)NCCCCNC(=N)N)CC4)cccc3n2CC(F)(F)F)cc1] | N-(4-carbamimidamidobutyl)-2-{4-[(2-{3-[(4-methanesulfonylphenyl)-amino]prop-1-yn-1-yl}-1-(2,2,2-trifluoroethyl)-1H-indol-4-yl)amino]piperidin-1-yl}acetamide | 675.3 [(M + H)+] |
| 608 | 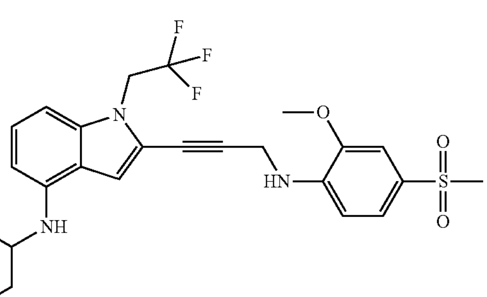 | 2-{3-[(4-methanesulfonyl-2-methoxyphenyl)amino]prop-1-yn-1-yl}-N-(oxan-4-yl)-1-(2,2,2-trifluoroethyl)-1H-indol-4-amine | 536.3 [(M + H)+] |

| Ex | Structure | Name | LC-MS (ES+, m/z) |
|---|---|---|---|
| 609 | 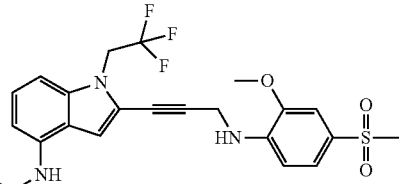 | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-ol | 579.3 [(M + H)+] |
| 610 | 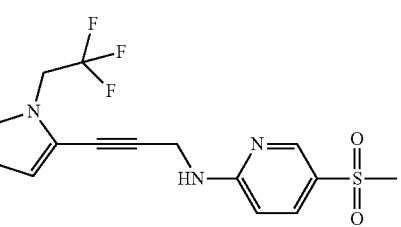 | 2-{3-[(5-methanesulfonylpyridin-2-yl)amino]prop-1-yn-1-yl}-N-(oxan-4-yl)-1-(2,2,2-trifluoroethyl)-1H-indol-4-amine | 507.2 [(M + H)+] |
| 611 | 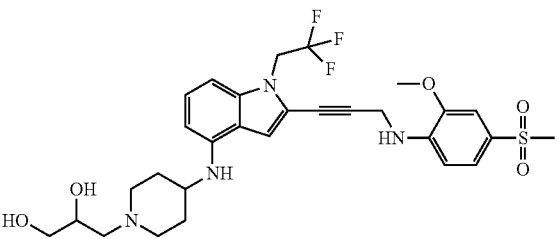 [SMILES: COc1cc(S(C)(=O)=O)ccc1NCC#Cc1cc2c(NC3CCN(CC(O)CO)CC3)cccc2n1CC(F)(F)F] | 3-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propane-1,2-diol | 609.3 [(M + H)+] |
| 612 | 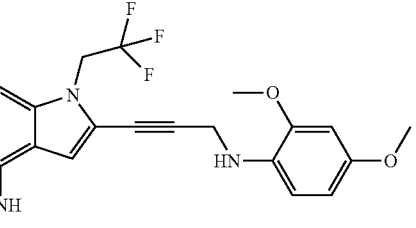 | 4-[(2-{3-[(2,4-dimethoxyphenyl)-amino]prop-1-yn-1-yl}-1-(2,2,2-trifluoroethyl)-1H-indol-4-yl)amino]-1λ☐-thiane-1,1-dione | 536.2 [(M + H)+] |
| 613 | 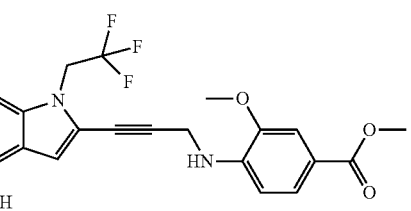 | methyl 4-[(3-{4-[(1,1-dioxo-1λ☐-thian-4-yl)amino]-1-(2,2,2-trifluoroethyl)-1H-indol-2-yl}prop-2-yn-1-yl)amino]-3-methoxybenzoate | 564.1 [(M + H)+] |

| Ex | Structure | Name | LC-MS (ES+, m/z) |
|---|---|---|---|
| 614 | 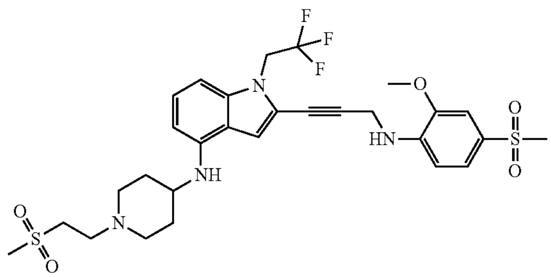 | 2-{3-[(4-methanesulfonyl-2-methoxyphenyl)amino]prop-1-yn-1-yl}-N-[1-(2-methanesulfonylethyl)-piperidin-4-yl]-1-(2,2,2-trifluoroethyl)-1H-indol-4-amine | 641.2 [(M + H)+] |
| 615 | 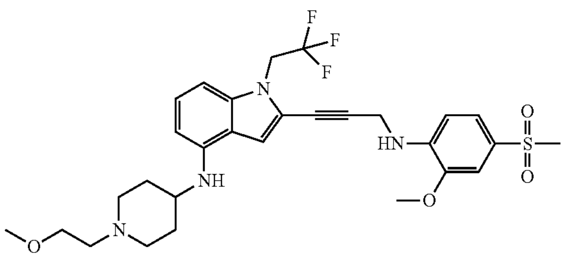 | 2-{3-[(4-methanesulfonyl-2-methoxyphenyl)amino]prop-1-yn-1-yl}-N-[1-(2-methoxyethyl)piperidin-4-yl]-1-(2,2,2-trifluoroethyl)-1H-indol-4-amine | 593.2 [(M + H)+] |
| 616 | 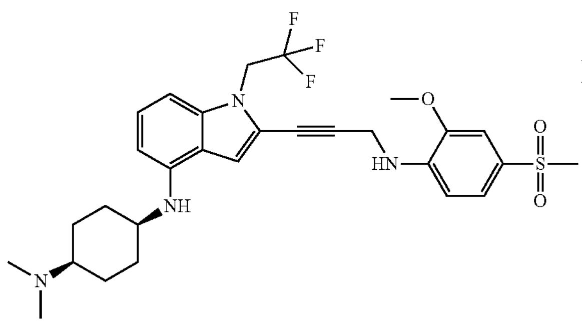 | (1s,4s)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine | 577.3 [(M + H)+] |
| 617 | 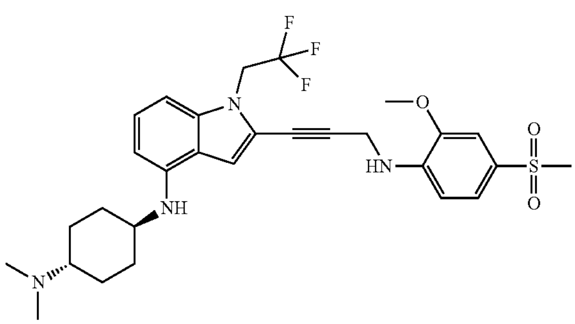 | (1r,4r)-4-N-(2-{3-[(4-methanesulfonyl-2-methoxyphenyl)amino]prop-1-yn-1-yl}-1-(2,2,2-trifluoroethyl)-1H-indol-4-yl)-1-N,1-N-dimethylcyclohexane-1,4-diamine | 577.2 [(M + H)+] |
| 618 | 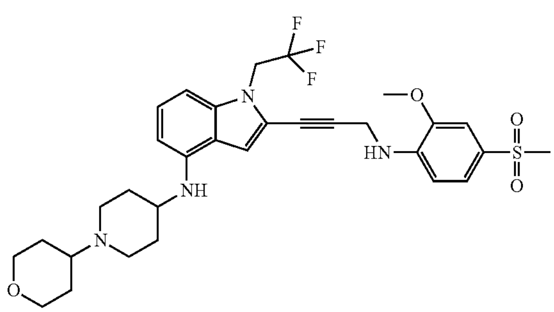 [SMILES: COc1cc(S(C)(=O)=O)ccc1NCC#Cc1cc2c(NC3CCN(C4CCOCC4)CC3)cccc2n1CC(F)(F)F] | 2-{3-[(4-methanesulfonyl-2-methoxyphenyl)amino]prop-1-yn-1-yl}-N-[1-(oxan-4-yl)piperidin-4-yl]-1-(2,2,2-trifluoroethyl)-1H-indol-4-amine | 619.5 [(M + H)+] |

-continued

| Ex | Structure | Name | LC-MS (ES+, m/z) |
|---|---|---|---|
| 619 | 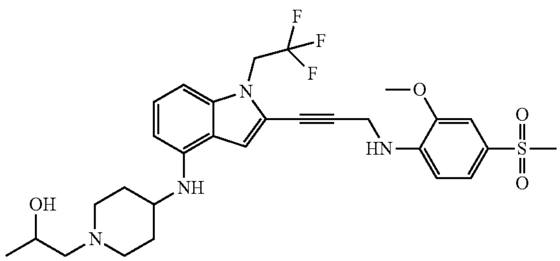 [SMILES: COc1cc(S(C)(=O)=O)ccc1NCC#Cc1cc2c(NC3CCN(CC(C)O)CC3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}propan-2-ol | 593.5 [(M + H)+] |
| 620 | 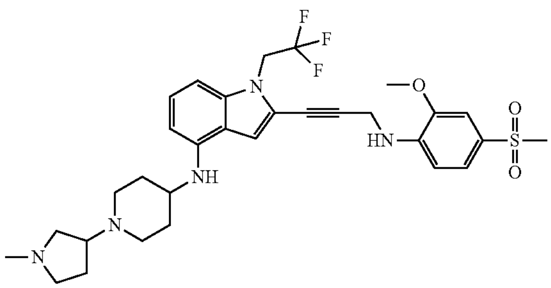 | 2-{3-[(4-methanesulfonyl-2-methoxyphenyl)amino]prop-1-yn-1-yl}-N-[1-(1-methylpyrrolidin-3-yl)piperidin-4-yl]-1-(2,2,2-trifluoroethyl)-1H-indol-4-amine | 618.2 [(M + H)+] |
| 621 | 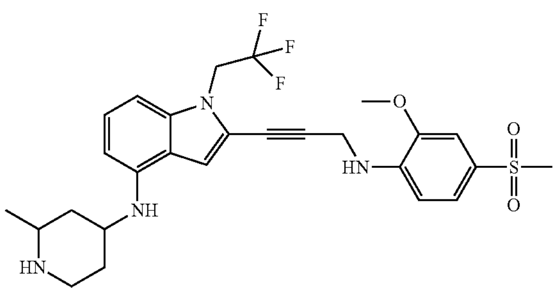 | 2-{3-[(4-methanesulfonyl-2-methoxyphenyl)amino]prop-1-yn-1-yl}-N-(2-methylpiperidin-4-yl)-1-(2,2,2-trifluoroethyl)-1H-indol-4-amine | 549.2 [(M + H)+] |
| 622 | 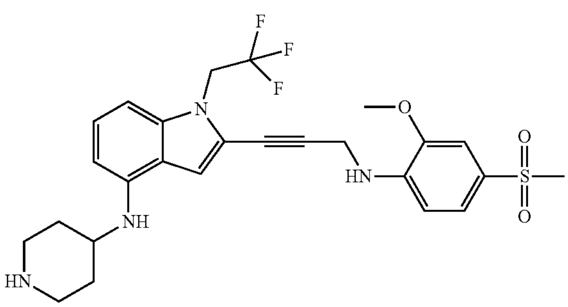 [SMILES: COc1cc(S(C)(=O)=O)ccc1NCC#Cc1cc2c(NC3CCNCC3)cccc2n1CC(F)(F)F] | 2-{3-[(4-methanesulfonyl-2-methoxyphenyl)amino]prop-1-yn-1-yl}-N-(piperidin-4-yl)-1-(2,2,2-trifluoroethyl)-1H-indol-4-amine | 535.1 [(M + H)+] |
| 623 | 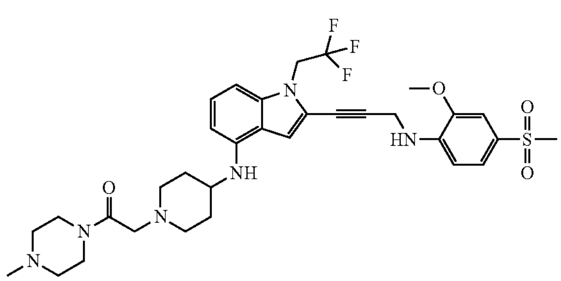 | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(4-methylpiperazin-1-yl)ethan-1-one | 675.6 [(M + H)+] |

-continued

| Ex | Structure | Name | LC-MS (ES+, m/z) |
|---|---|---|---|
| 624 | 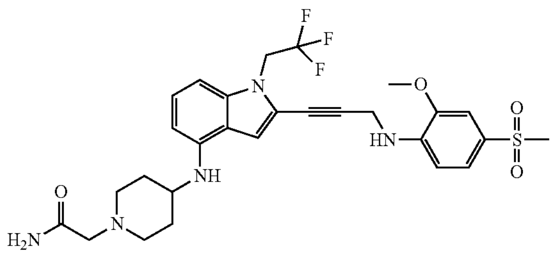 [SMILES: COc1cc(S(C)(=O)=O)ccc1NCC#Cc1cc2c(NC3CCN(CC(N)=O)CC3)cccc2n1CC(F)(F)F] | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetamide | 592.2 [(M + H)+] |
| 625 | 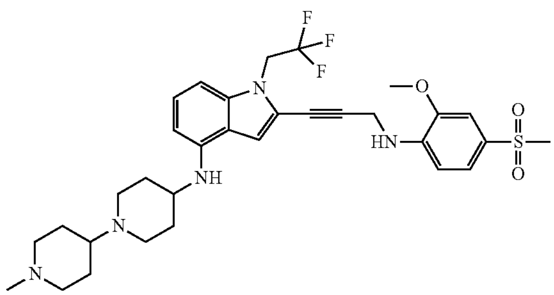 | 2-{3-[(4-methanesulfonyl-2-methoxyphenyl)amino]prop-1-yn-1-yl}-N-[1-(1-methylpiperidin-4-yl)piperidin-4-yl]-1-(2,2,2-trifluoroethyl)-1H-indol-4-amine | 632.6 [(M + H)+] |
| 626 | 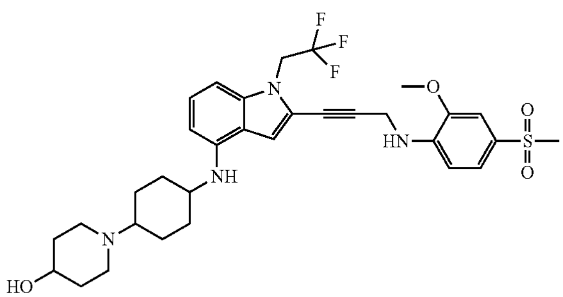 [SMILES: COc1cc(S(C)(=O)=O)ccc1NCC#Cc1cc2c(NC3CCC(N4CCC(O)CC4)CC3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}piperidin-4-ol | 633.6 [(M + H)+] |
| 627 | 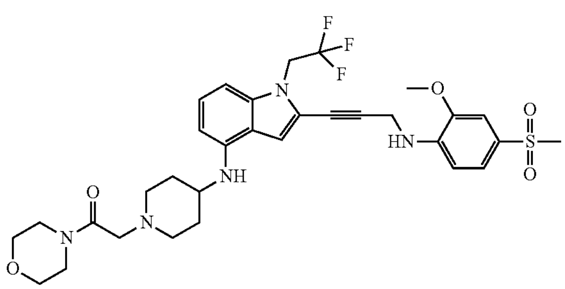 [SMILES: COc1cc(S(C)(=O)=O)ccc1NCC#Cc1cc2c(NC3CCN(CC(=O)N4CCOCC4)CC3)cccc2n1CC(F)(F)F] | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-1-(morpholin-4-yl)ethan-1-one | 662.6 [(M + H)+] |
| 628 | 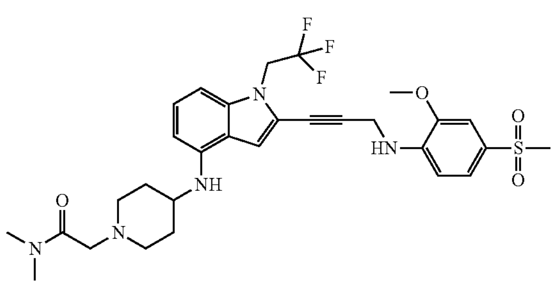 | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}-N,N-dimethylacetamide | 620.5 [(M + H)+] |

-continued

| Ex | Structure | Name | LC-MS (ES+, m/z) |
|---|---|---|---|
| 629 | 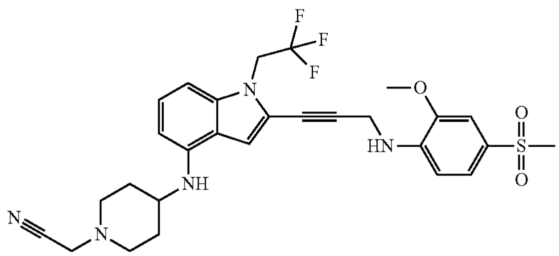 [SMILES: COc1cc(S(C)(=O)=O)ccc1NCC#Cc1cc2c(NC3CCN(CC#N)CC3)cccc2n1CC(F)(F)F] | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetonitrile | 574.5 [(M + H)+] |
| 630 | 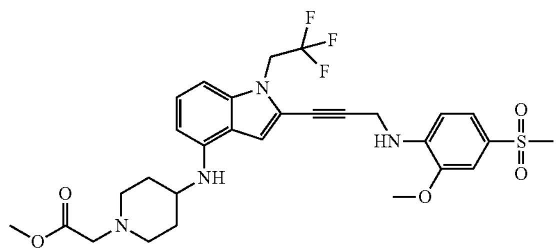 | methyl 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetate | 607.5 [(M + H)+] |
| 631 | 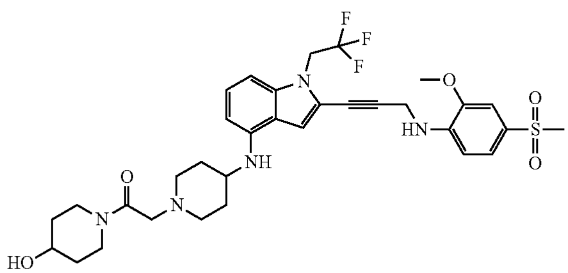 [SMILES: COc1cc(S(C)(=O)=O)ccc1NCC#Cc1cc2c(NC3CCN(CC(=O)N4CCC(O)CC4)CC3)cccc2n1CC(F)(F)F] | 1-(4-hydroxypiperidin-1-yl)-2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one | 676.6 [(M + H)+] |
| 632 | 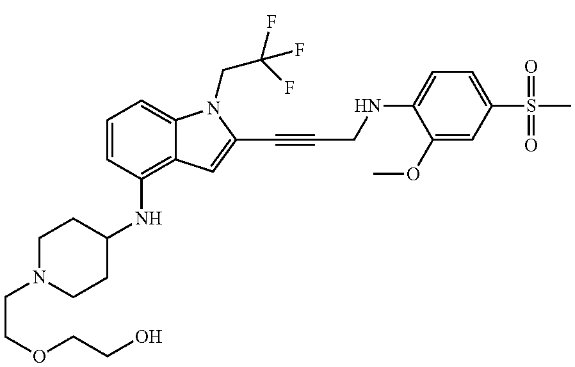 [SMILES: COc1cc(S(C)(=O)=O)ccc1NCC#Cc1cc2c(NC3CCN(CCOCCO)CC3)cccc2n1CC(F)(F)F] | 2-(2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethoxy)ethan-1-ol | 623.3 [(M + H)+] |
| 633 | 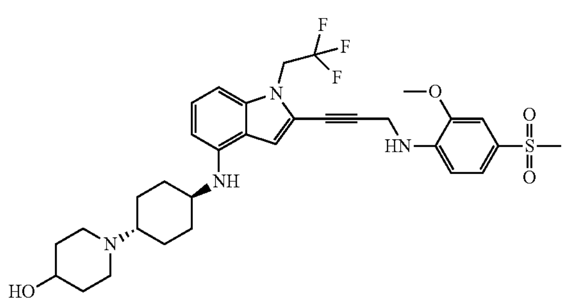 [SMILES: COc1cc(S(C)(=O)=O)ccc1NCC#Cc1cc2c(N[C@H]3CC[C@H](N4CCC(O)CC4)CC3)cccc2n1CC(F)(F)F] | 1-[(1r,4r)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]piperidin-4-ol | 633.2 [(M + H)+] |

| Ex | Structure | Name | LC-MS (ES+, m/z) |
|---|---|---|---|
| 634 | 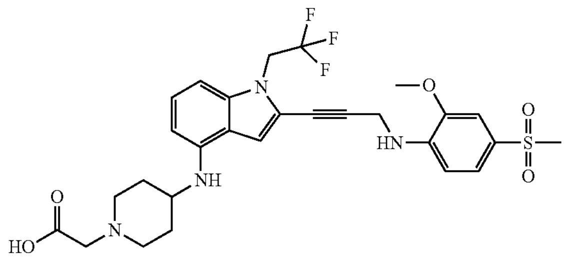 [SMILES: COc1cc(S(C)(=O)=O)ccc1NCC#Cc1cc2c(NC3CCN(CC(=O)O)CC3)cccc2n1CC(F)(F)F] | 2-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}acetic acid | 593.2 [(M + H)+] |
| 635 | 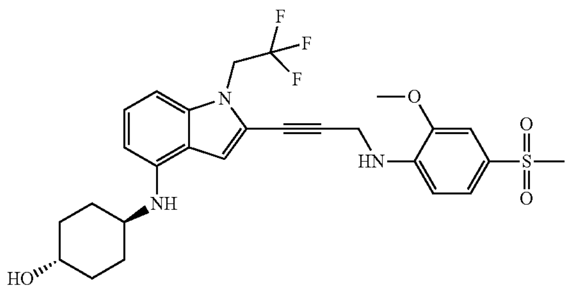 [SMILES: COc1cc(S(C)(=O)=O)ccc1NCC#Cc1cc2c(N[C@H]3CC[C@H](O)CC3)cccc2n1CC(F)(F)F] | (1r,4r)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol | 550.2 [(M + H)+] |
| 636 | 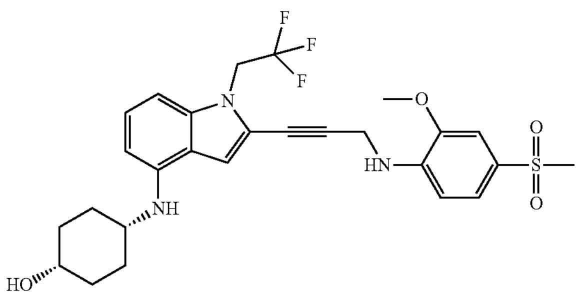 [SMILES: COc1cc(S(C)(=O)=O)ccc1NCC#Cc1cc2c(N[C@H]3CC[C@@H](O)CC3)cccc2n1CC(F)(F)F] | (1s,4s)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexan-1-ol | 550.2 [(M + H)+] |
| 637 | 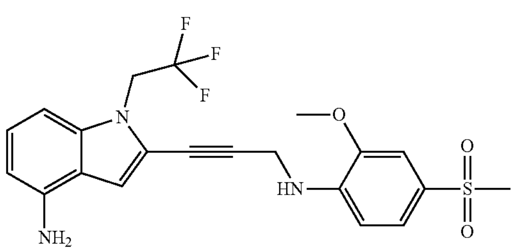 [SMILES: COc1cc(S(C)(=O)=O)ccc1NCC#Cc1cc2c(N)cccc2n1CC(F)(F)F] | 2-{3-[(4-methanesulfonyl-2-methoxyphenyl)amino]prop-1-yn-1-yl}-1-(2,2,2-trifluoroethyl)-1H-indol-4-amine | 452.1 [(M + H)+] |
| 638 | 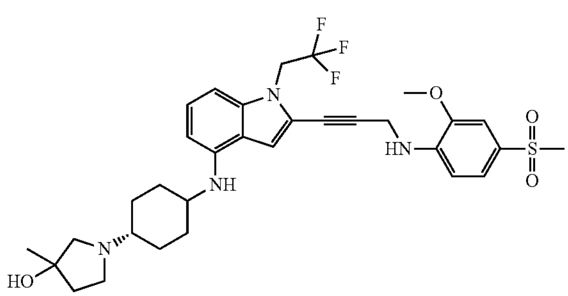 | 1-{4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl}-3-methylpyrrolidin-3-ol | 633.6 [(M + H)+] |

-continued

| Ex | Structure | Name | LC-MS (ES+, m/z) |
|---|---|---|---|
| 639 | 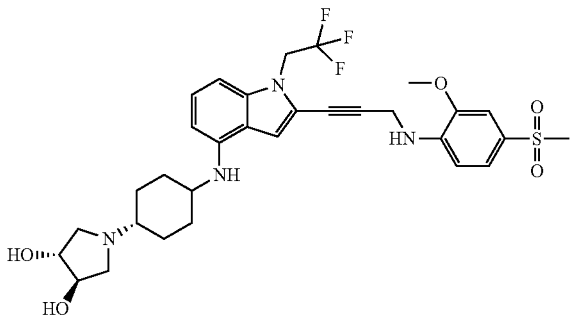 | (3R,4R)-1-{4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl}-pyrrolidine-3,4-diol | 635.3 [(M + H)+] |
| 640 | 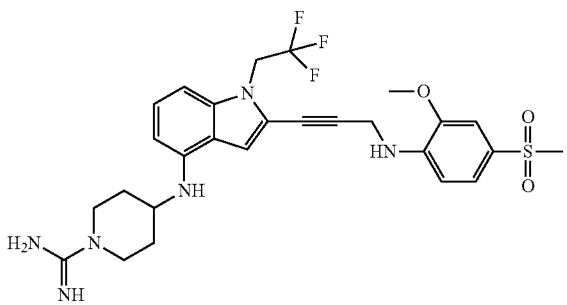 [SMILES: COc1cc(S(C)(=O)=O)ccc1NCC#Cc1cc2c(NC3CCN(C(=N)N)CC3)cccc2n1CC(F)(F)F] | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboximidamide | 577.2 [(M + H)+] |
| 641 | 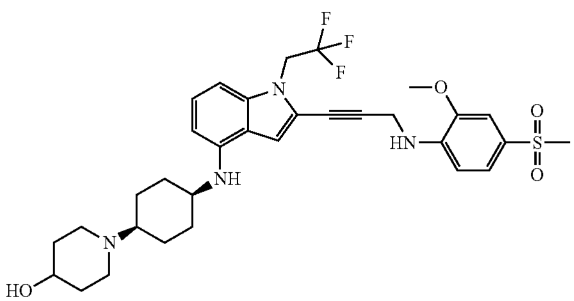 [SMILES: COc1cc(S(C)(=O)=O)ccc1NCC#Cc1cc2c(N[C@H]3CC[C@@H](N4CCC(O)CC4)CC3)cccc2n1CC(F)(F)F] | 1-[(1s,4s)-4-[(2-{3-[(4-methane-sulfonyl-2-methoxyphenyl)amino]prop-1-yn-1-yl}-1-(2,2,2-trifluoroethyl)-1H-indol-4-yl)amino]cyclohexyl]piperidin-4-ol | 633.2 [(M + H)+] |
| 642 | 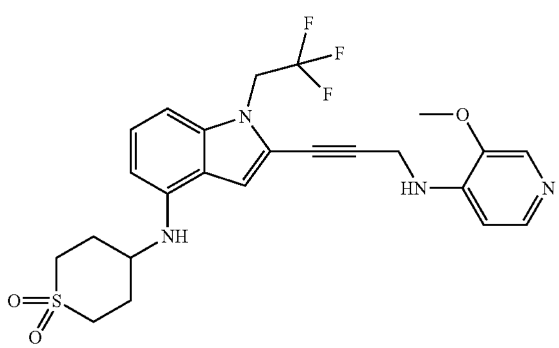 [SMILES: COc1cnccc1NCC#Cc1cc2c(NC3CCS(=O)(=O)CC3)cccc2n1CC(F)(F)F] | 4-[(2-{3-[(3-methoxypyridin-4-yl)amino]prop-1-yn-1-yl}-1-(2,2,2-trifluoroethyl)-1H-indol-4-yl)amino]-1λ⁶-thiane-1,1-dione | 507.2 [(M + H)+] |
| 643 | 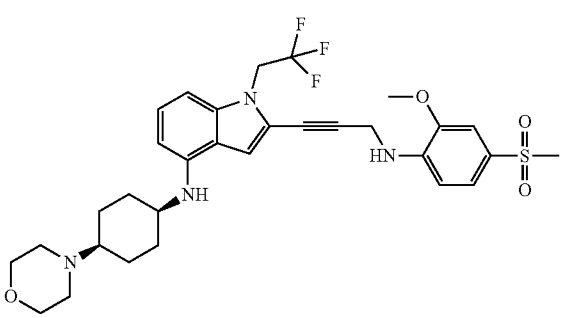 [SMILES: COc1cc(S(C)(=O)=O)ccc1NCC#Cc1cc2c(N[C@H]3CC[C@@H](N4CCOCC4)CC3)cccc2n1CC(F)(F)F] | 2-{3-[(4-methanesulfonyl-2-methoxyphenyl)amino]prop-1-yn-1-yl}-N-[(1s,4s)-4-(morpholin-4-yl)cyclohexyl]-1-(2,2,2-trifluoroethyl)-1H-indol-4-amine | 619.2 [(M + H)+] |

-continued

| Ex | Structure | Name | LC-MS (ES⁺, m/z) |
|---|---|---|---|
| 644 | 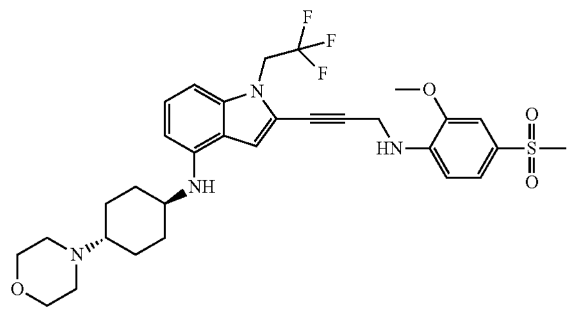 [SMILES: COc1cc(S(C)(=O)=O)ccc1NCC#Cc1cc2c(N[C@H]3CC[C@H](N4CCOCC4)CC3)cccc2n1CC(F)(F)F] | 2-{3-[(4-methanesulfonyl-2-methoxyphenyl)amino]prop-1-yn-1-yl}-N-[(1r,4r)-4-(morpholin-4-yl)cyclohexyl]-1-(2,2,2-trifluoroethyl)-1H-indol-4-amine | 619.2 [(M + H)⁺] |
| 645 | 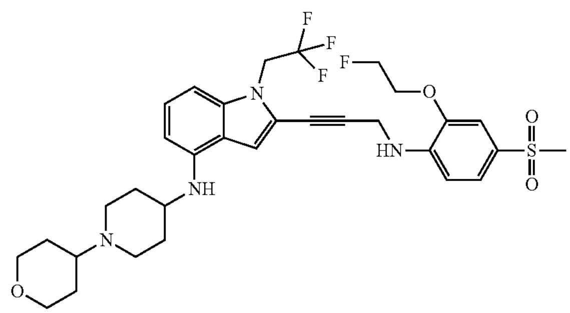 [SMILES: CS(=O)(=O)c1ccc(NCC#Cc2cc3c(NC4CCN(C5CCOCC5)CC4)cccc3n2CC(F)(F)F)c(OCCF)c1] | 2-(3-{[2-(2-fluoroethoxy)-4-methanesulfonylphenyl]amino}prop-1-yn-1-yl)-N-[1-(oxan-4-yl)piperidin-4-yl]-1-(2,2,2-trifluoroethyl)-1H-indol-4-amine | 651.3 [(M + H)⁺] |
| 646 | 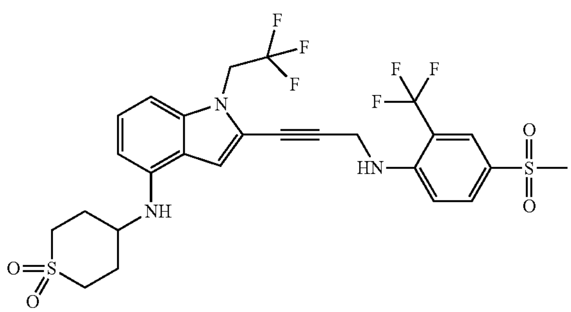 [SMILES: CS(=O)(=O)c1ccc(NCC#Cc2cc3c(NC4CCS(=O)(=O)CC4)cccc3n2CC(F)(F)F)c(C(F)(F)F)c1] | 4-{[2-(3-{[4-methanesulfonyl-2-(trifluoromethyl)phenyl]amino}prop-1-yn-1-yl)-1-(2,2,2-trifluoroethyl)-1H-indol-4-yl]amino}-1λ⁶-thiane-1,1-dione | 622.1 [(M + H)⁺] |
| 647 | 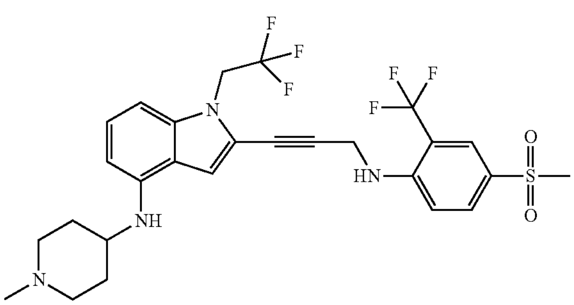 | 2-(3-{[4-methanesulfonyl-2-(trifluoromethyl)phenyl]amino}prop-1-yn-1-yl)-N-(1-methylpiperidin-4-yl)-1-(2,2,2-trifluoroethyl)-1H-indol-4-amine | 587.2 [(M + H)⁺] |
| 648 | 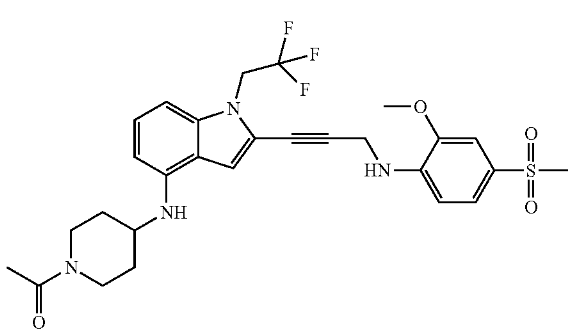 [SMILES: COc1cc(S(C)(=O)=O)ccc1NCC#Cc1cc2c(NC3CCN(C(C)=O)CC3)cccc2n1CC(F)(F)F] | 1-{4-[(2-{3-[(4-methanesulfonyl-2-methoxyphenyl)amino]prop-1-yn-1-yl}-1-(2,2,2-trifluoroethyl)-1H-indol-4-yl)amino]piperidin-1-yl}ethan-1-one | 577.2 [(M + H)⁺] |

| Ex | Structure | Name | LC-MS (ES+, m/z) |
|---|---|---|---|
| 649 | 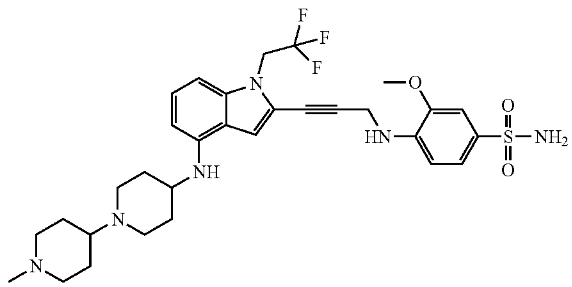 [SMILES: COc1cc(S(N)(=O)=O)ccc1NCC#Cc1cc2c(NC3CCN(C4CCN(C)CC4)CC3)cccc2n1CC(F)(F)F] | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzene-1-sulfonamide | 633.2 [(M + H)+] |
| 650 | 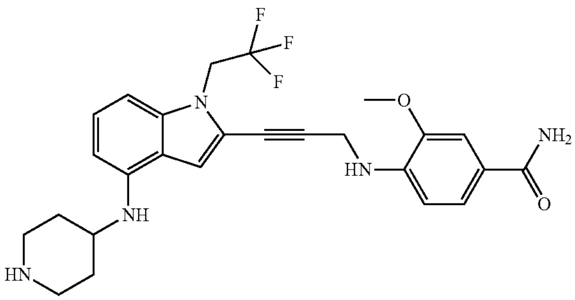 [SMILES: COc1cc(C(N)=O)ccc1NCC#Cc1cc2c(NC3CCNCC3)cccc2n1CC(F)(F)F] | 3-methoxy-4-[(3-{4-[(piperidin-4-yl)amino]-1-(2,2,2-trifluoroethyl)-1H-indol-2-yl}prop-2-yn-1-yl)amino]-benzamide | 500.3 [(M + H)+] |
| 651 | 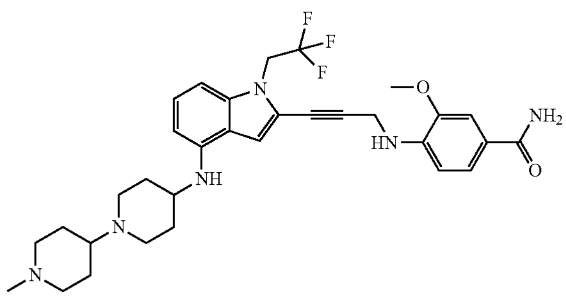 [SMILES: COc1cc(C(N)=O)ccc1NCC#Cc1cc2c(NC3CCN(C4CCN(C)CC4)CC3)cccc2n1CC(F)(F)F] | 3-methoxy-4-{[3-(4-{[1-(1-methylpiperidin-4-yl)piperidin-4-yl]amino}-1-(2,2,2-trifluoroethyl)-1H-indol-2-yl)prop-2-yn-1-yl]amino}benzamide | 597.3 [(M + H)+] |
| 652 | 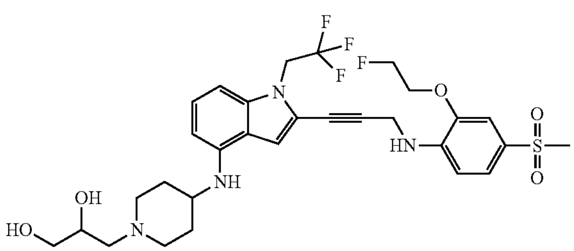 [SMILES: CS(=O)(=O)c1ccc(NCC#Cc2cc3c(NC4CCN(CC(O)CO)CC4)cccc3n2CC(F)(F)F)c(OCCF)c1] | 3-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)propane-1,2-diol | 641.3 [(M + H)+] |
| 653 | 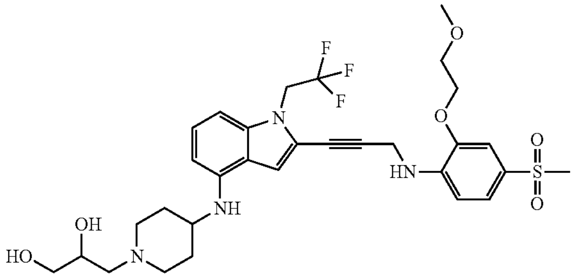 [SMILES: COCCOc1cc(S(C)(=O)=O)ccc1NCC#Cc1cc2c(NC3CCN(CC(O)CO)CC3)cccc2n1CC(F)(F)F] | 3-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)propane-1,2-diol | 653.2 [(M + H)+] |

| Ex | Structure | Name | LC-MS (ES+, m/z) |
|---|---|---|---|
| 654 | 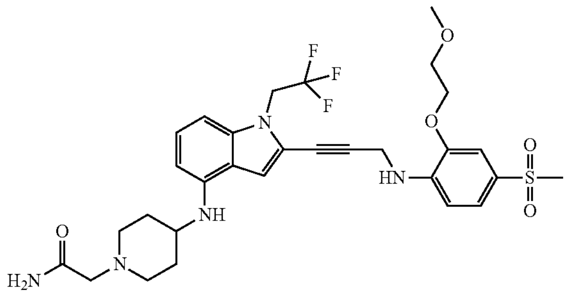 [SMILES: COCCOc1cc(S(C)(=O)=O)ccc1NCC#Cc1cc2c(NC3CCN(CC(N)=O)CC3)cccc2n1CC(F)(F)F] | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)acetamide | 636.2 [(M + H)+] |
| 655 | 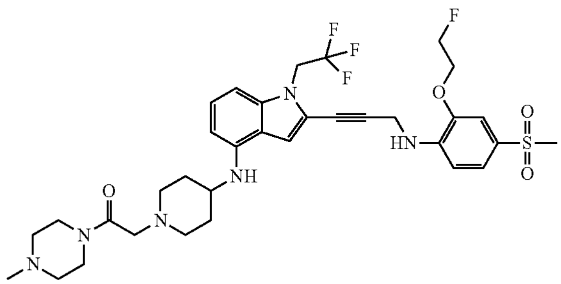 | 2-(4-{[2-(3-{[2-(2-fluoroethoxy)-4-methanesulfonylphenyl]amino}prop-1-yn-1-yl)-1-(2,2,2-trifluoroethyl)-1H-indol-4-yl]amino}piperidin-1-yl)-1-(4-methylpiperazin-1-yl)ethan-1-one | 707.2 [(M + H)+] |
| 656 | 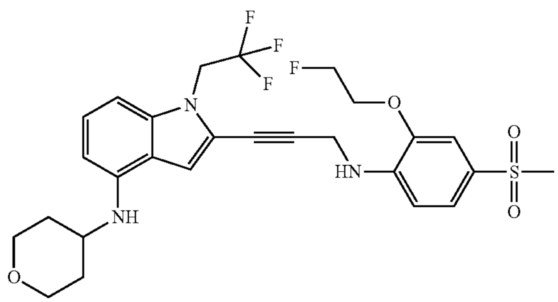 [SMILES: CS(=O)(=O)c1ccc(NCC#Cc2cc3c(NC4CCOCC4)cccc3n2CC(F)(F)F)c(OCCF)c1] | 2-(3-{[2-(2-fluoroethoxy)-4-methanesulfonylphenyl]amino}prop-1-yn-1-yl)-N-(oxan-4-yl)-1-(2,2,2-trifluoroethyl)-1H-indol-4-amine | 568.1 [(M + H)+] |
| 657 | 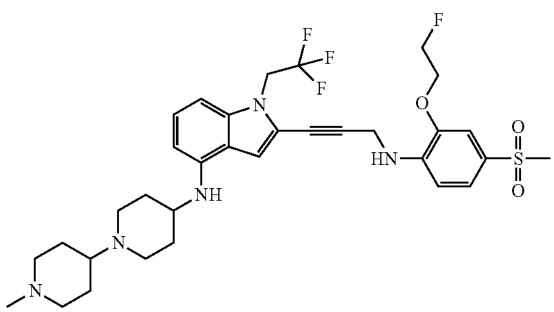 | 2-(3-{[2-(2-fluoroethoxy)-4-methanesulfonylphenyl]amino}prop-1-yn-1-yl)-N-[1-(1-methylpiperidin-4-yl)piperidin-4-yl]-1-(2,2,2-trifluoroethyl)-1H-indol-4-amine | 664.2 [(M + H)+] |
| 658 | 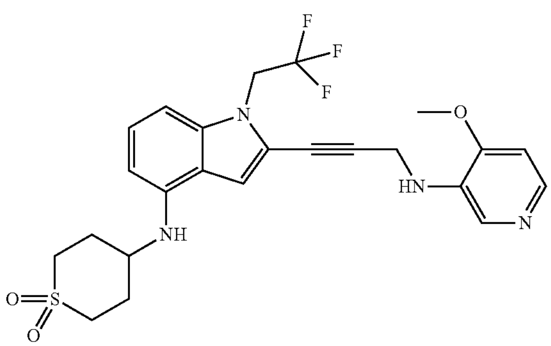 [SMILES: COc1ccncc1NCC#Cc1cc2c(NC3CCS(=O)(=O)CC3)cccc2n1CC(F)(F)F] | 4-[(2-{3-[(4-methoxypyridin-3-yl)amino]prop-1-yn-1-yl}-1-(2,2,2-trifluoroethyl)-1H-indol-4-yl)amino]-1λ⁶-thiane-1,1-dione | 507.1 [(M + H)+] |

| Ex | Structure | Name | LC-MS (ES+, m/z) |
|---|---|---|---|
| 659 | 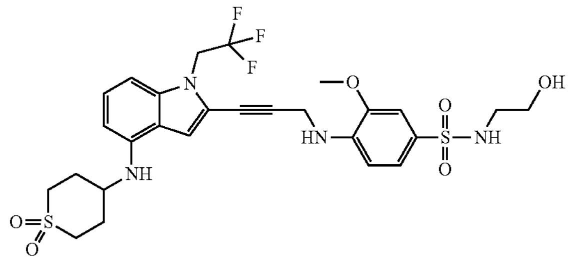 [SMILES: COc1cc(S(=O)(=O)NCCO)ccc1NCC#Cc1cc2c(NC3CCS(=O)(=O)CC3)cccc2n1CC(F)(F)F] | S-{4-[(3-{4-[(1,1-dioxo-1λ⬜-thian-4-yl)amino]-1-(2,2,2-trifluoroethyl)-1H-indol-2-yl}prop-2-yn-1-yl)amino]-3-methoxyphenyl}-2-hydroxyethane-1-sulfonamido | 629.3 [(M + H)+] |
| 660 | 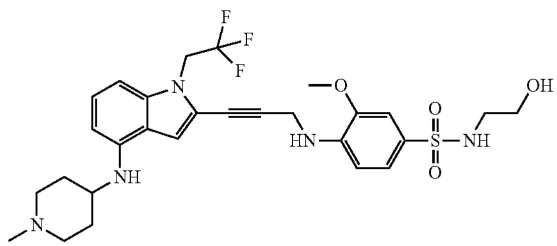 [SMILES: COc1cc(S(=O)(=O)NCCO)ccc1NCC#Cc1cc2c(NC3CCN(C)CC3)cccc2n1CC(F)(F)F] | 2-hydroxy-S-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}ethane-1-sulfonamido | 594.4 [(M + H)+] |

Example 661: Preparation of 2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile

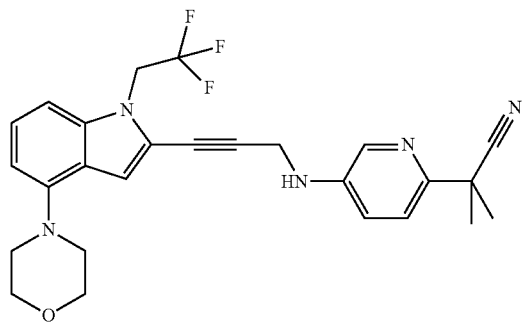 [SMILES: CC(C)(C#N)c1ccc(NCC#Cc2cc3c(N4CCOCC4)cccc3n2CC(F)(F)F)cn1]

To a solution of 2-(5-((3-(4-bromo-1-(2,2,2-trifluoroethyl)-1H-indol-2-yl)prop-2-yn-1-yl)amino)pyridin-2-yl)-2-methylpropanenitrile (50 mg, 105.20 μmol, prepared in a similar manner as described in Example 142) in toluene (3 mL) were added morpholine (28 mg, 315.6 μmol, 28 μL), NaOtBu (10 mg, 105.2 μmol), and Pd₂(dba)₃ (10 mg, 10.5 μmol). The mixture was degassed and gassed with nitrogen twice, and the resulting mixture was heated to 65° C. for 2 h. The reaction mixture was poured into an EDTA solution (~5 mL) and stirred at room temperature for 2 h. Then the aqueous layer was extracted with ethyl acetate (2×5 mL). The combined organic layers were washed with brine (2 mL), dried over anhydrous sodium sulfate, filtered, and concentrated in vacuo. The crude product was purified by preparative HPLC to give 2-methyl-2-[5-({3-[4-(morpholin-4-yl)-1-(2,2,2-trifluoroethyl)-1H-indol-2-yl]prop-2-yn-1-yl}amino)pyridin-2-yl]propanenitrile.

LC-MS (ES+, m/z): 484.3 [(M+H)+]

Example 662: Preparation of 2-{4-[(2-{3-[(4-methanesulfonylphenyl)amino]prop-1-yn-1-yl}-1-(2,2,2-trifluoroethyl)-1H-indol-4-yl)amino]piperidin-1-yl}-N-[5-(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetamido)pentyl]acetamide

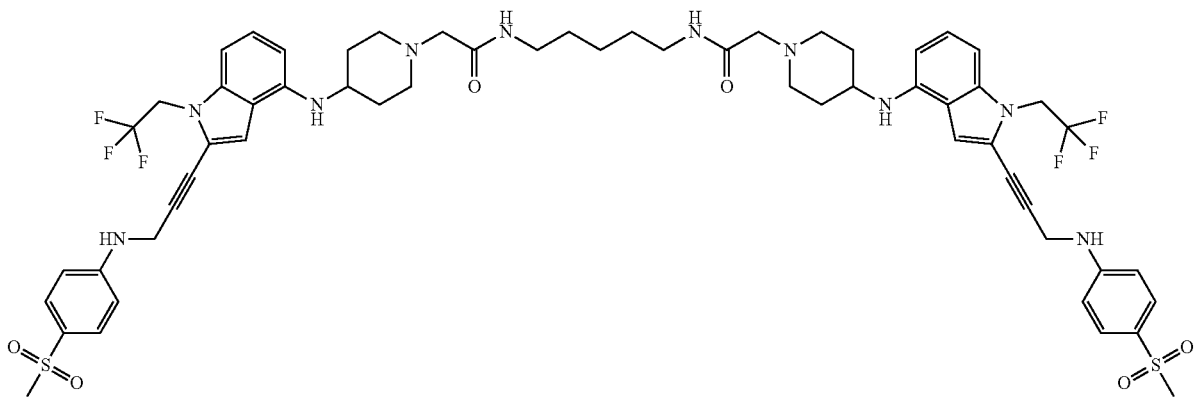 [SMILES: CS(=O)(=O)c1ccc(NCC#Cc2cc3c(NC4CCN(CC(=O)NCCCCCNC(=O)CN5CCC(Nc6cccc7c6cc(C#CCNc6ccc(S(C)(=O)=O)cc6)n7CC(F)(F)F)CC5)CC4)cccc3n2CC(F)(F)F)cc1]

N-(5-Aminopentyl)-2-{4-[(2-{3-[(4-methanesulfonyl-phenyl)amino]prop-1-yn-1-yl}-1-(2,2,2-trifluoroethyl)-1H-indol-4-yl)amino]piperidin-1-yl}acetamide (Example 582) was coupled with 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetic acid (Example 601) using HATU/triethylamine in methylene chloride.

LC-MS (ES+, m/z): 1191.0 [(M+H)+]

Example 663: Preparation of 6-[(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetyl)oxy]hexyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate

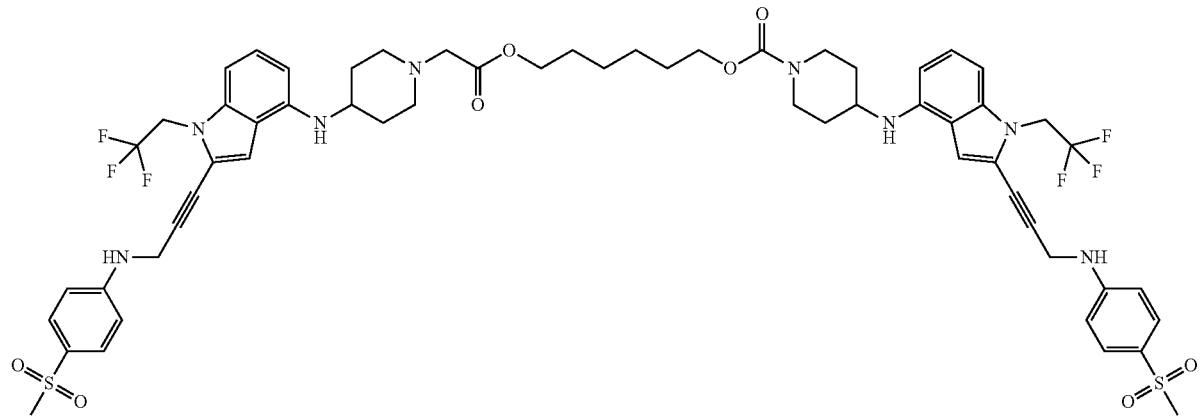 [SMILES: CS(=O)(=O)c1ccc(NCC#Cc2cc3c(NC4CCN(CC(=O)OCCCCCCOC(=O)N5CCC(Nc6cccc7c6cc(C#CCNc6ccc(S(C)(=O)=O)cc6)n7CC(F)(F)F)CC5)CC4)cccc3n2CC(F)(F)F)cc1]

6-[(2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetyl)oxy]hexyl 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetate was prepared by coupling 2-{4-[(2-{3-[(4-methanesulfonylphenyl)amino]prop-1-yn-1-yl}-1-(2,2,2-trifluoroethyl)-1H-indol-4-yl)amino]piperidin-1-yl}acetic acid (Example 601) with 1,6-dibromohexane using potassium carbonate/potassium iodide in dimethylformamide.

LC-MS (ES+, m/z): 1207.2 [(M+H)+]

Starting with 2-iodo-1-(2,2,2-trifluoroethyl)-1H-indol-4-amine and using the similar method as described in Example 522, the following compounds were prepared:

| Ex | Structure | Name | LC-MS (ES+, m/z) |
|---|---|---|---|
| 664 | 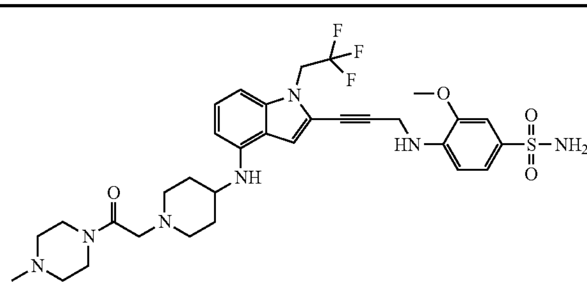 | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzene-1-sulfonamide | 676.3 [(M + H)+] |

-continued

| Ex | Name | LC-MS (ES+, m/z) |
|---|---|---|
| 665 | 2-{5-methanesulfonyl-2-[(3-{4-[(1-methylpiperidin-4-yl)amino]-1-(2,2,2-trifluoroethyl)-1H-indol-2-yl}prop-2-yn-1-yl)amino]phenoxy}acetamide | 592.2 [(M + H)+] |
| 666 | 2-(3-{[4-methanesulfonyl-2-(2-methoxyethoxy)phenyl]amino}prop-1-yn-1-yl)-N-[1-(oxan-4-yl)piperidin-4-yl]-1-(2,2,2-trifluoroethyl)-1H-indol-4-amine | 663.2 [(M + H)+] |
| 667 | 2-(4-{[2-(3-{[4-methanesulfonyl-2-(2-methoxyethoxy)phenyl]amino}prop-1-yn-1-yl)-1-(2,2,2-trifluoroethyl)-1H-indol-4-yl]amino}piperidin-1-yl)ethan-1-ol | 623.2 [(M + H)+] |
| 668 | 3-methoxy-4-[(3-{4-[(oxan-4-yl)amino]-1-(2,2,2-trifluoroethyl)-1H-indol-2-yl}prop-2-yn-1-yl)amino]benzoic acid | 502.2 [(M + H)+] |
| 669 | 2-{2-[(3-{4-[(1,1-dioxo-1λ6-thian-4-yl)amino]-1-(2,2,2-trifluoroethyl)-1H-indol-2-yl}prop-2-yn-1-yl)amino]-5-methanesulfonylphenoxy}acetamide | 627.2 [(M + H)+] |

-continued

| Ex | Structure | Name | LC-MS (ES+, m/z) |
|---|---|---|---|
| 670 | 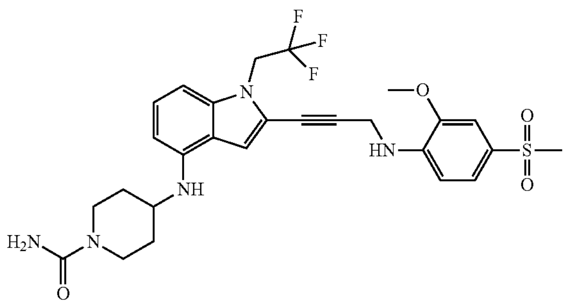 [SMILES: COc1cc(S(C)(=O)=O)ccc1NCC#Cc1cc2c(NC3CCN(C(N)=O)CC3)cccc2n1CC(F)(F)F] | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carboxamide | 578.2 [(M + H)+] |
| 671 | 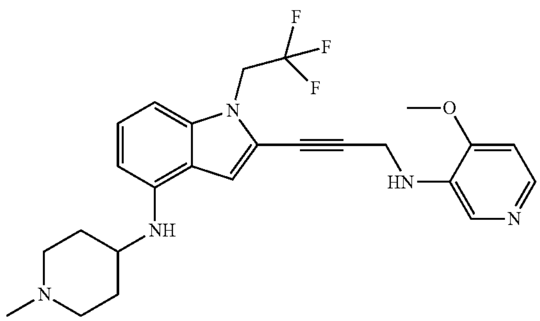 [SMILES: COc1ccncc1NCC#Cc1cc2c(NC3CCN(C)CC3)cccc2n1CC(F)(F)F] | 2-{3-[(4-methoxypyridin-3-yl)amino]prop-1-yn-1-yl}-N-(1-methylpiperidin-4-yl)-1-(2,2,2-trifluoroethyl)-1H-indol-4-amine | 472.2 [(M + H)+] |
| 672 | 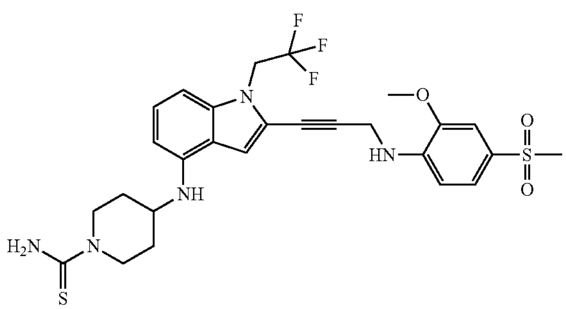 [SMILES: COc1cc(S(C)(=O)=O)ccc1NCC#Cc1cc2c(NC3CCN(C(N)=S)CC3)cccc2n1CC(F)(F)F] | 4-[(2-{3-[(4-methanesulfonyl-2-methoxyphenyl)amino]prop-1-yn-1-yl}-1-(2,2,2-trifluoroethyl)-1H-indol-4-yl)amino]piperidine-1-carbothioamide | 594.2 [(M + H)+] |
| 673 | 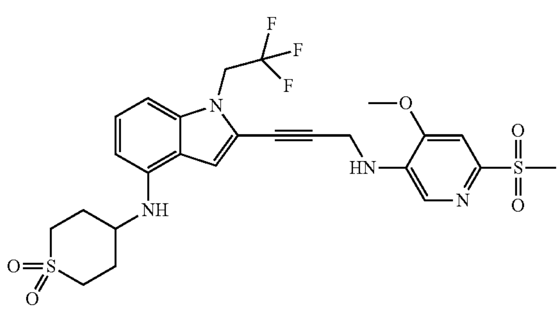 | 4-[(2-{3-[(6-methanesulfonyl-4-methoxypyridin-3-yl)amino]prop-1-yn-1-yl}-1-(2,2,2-trifluoroethyl)-1H-indol-4-yl)amino]-1$\lambda^6$-thiane-1,1-dione | 585.0 [(M + H)+] |
| 674 | 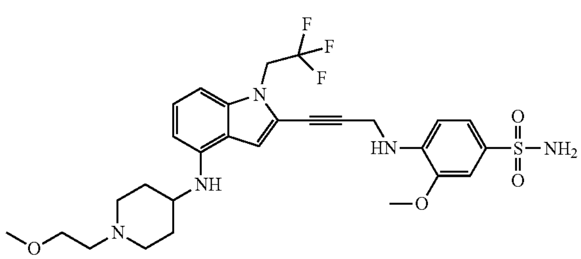 [SMILES: COCCN1CCC(Nc2cccc3c2cc(C#CCNc2ccc(S(N)(=O)=O)cc2OC)n3CC(F)(F)F)CC1] | 3-methoxy-4-{[3-(4-{[1-(2-methoxyethyl)piperidin-4-yl]amino}-1-(2,2,2-trifluoroethyl)-1H-indol-2-yl)prop-2-yn-1-yl]amino}benzene-1-sulfonamide | 594.2 [(M + H)+] |

-continued

| Ex | Structure | Name | LC-MS (ES+, m/z) |
|---|---|---|---|
| 675 | 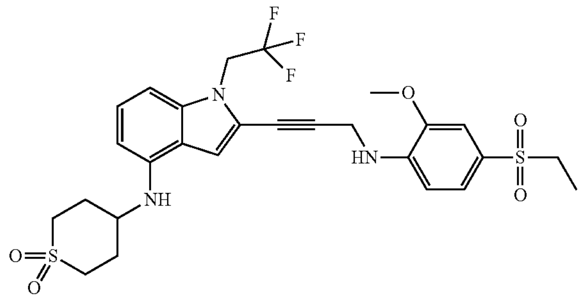 [SMILES: CCS(=O)(=O)c1ccc(NCC#Cc2cc3c(NC4CCS(=O)(=O)CC4)cccc3n2CC(F)(F)F)c(OC)c1] | 4-{[2-(3-{[4-(ethanesulfonyl)-2-methoxyphenyl]amino}prop-1-yn-1-yl)-1-(2,2,2-trifluoroethyl)-1H-indol-4-yl]amino}-1λ⁶-thiane-1,1-dione | 598.2 [(M + H)⁺] |
| 676 | 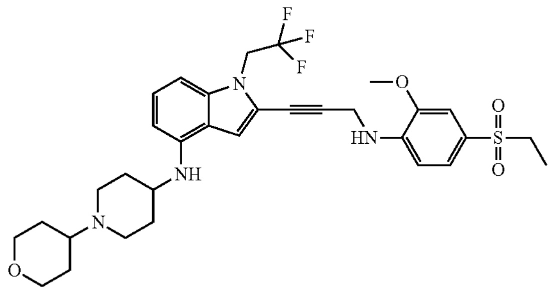 [SMILES: CCS(=O)(=O)c1ccc(NCC#Cc2cc3c(NC4CCN(C5CCOCC5)CC4)cccc3n2CC(F)(F)F)c(OC)c1] | 2-(3-{[4-(ethanesulfonyl)-2-methoxyphenyl]amino}prop-1-yn-1-yl)-N-[1-(oxan-4-yl)piperidin-4-yl]-1-(2,2,2-trifluoroethyl)-1H-indol-4-amine | 633.2 [(M + H)⁺] |
| 677 | 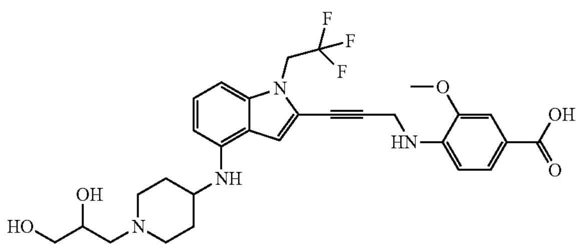 [SMILES: COc1cc(C(=O)O)ccc1NCC#Cc1cc2c(NC3CCN(CC(O)CO)CC3)cccc2n1CC(F)(F)F] | 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoic acid | 575.2 [(M + H)⁺] |
| 678 | 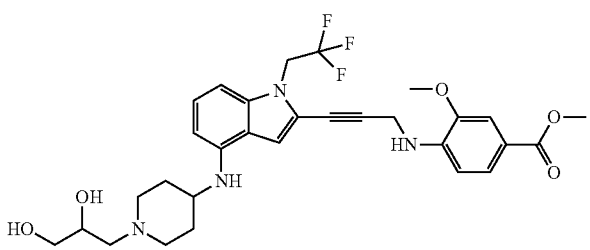 [SMILES: COC(=O)c1ccc(NCC#Cc2cc3c(NC4CCN(CC(O)CO)CC4)cccc3n2CC(F)(F)F)c(OC)c1] | methyl 4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxybenzoate | 589.2 [(M + H)⁺] |
| 679 | 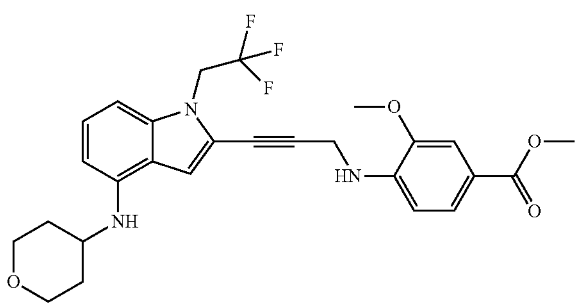 [SMILES: COC(=O)c1ccc(NCC#Cc2cc3c(NC4CCOCC4)cccc3n2CC(F)(F)F)c(OC)c1] | methyl 3-methoxy-4-[(3-{4-[(oxan-4-yl)amino]-1-(2,2,2-trifluoroethyl)-1H-indol-2-yl}prop-2-yn-1-yl)amino]benzoate | 516.2 [(M + H)⁺] |

| Ex | Structure | Name | LC-MS (ES+, m/z) |
|---|---|---|---|
| 680 | 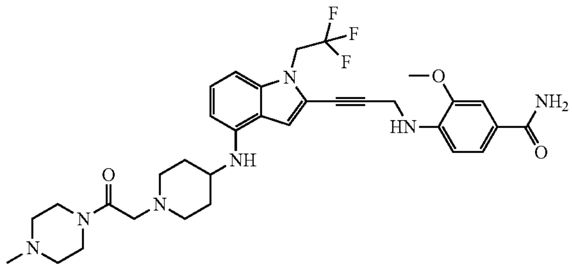 [SMILES: COc1cc(C(N)=O)ccc1NCC#Cc1cc2c(NC3CCN(CC(=O)N4CCN(C)CC4)CC3)cccc2n1CC(F)(F)F] | 3-methoxy-4-({3-[4-({1-[2-(4-methylpiperazin-1-yl)-2-oxoethyl]piperidin-4-yl}amino)-1-(2,2,2-trifluoroethyl)-1H-indol-2-yl]prop-2-yn-1-yl}amino)benzamide | 640.3 [(M + H)+] |
| 681 | 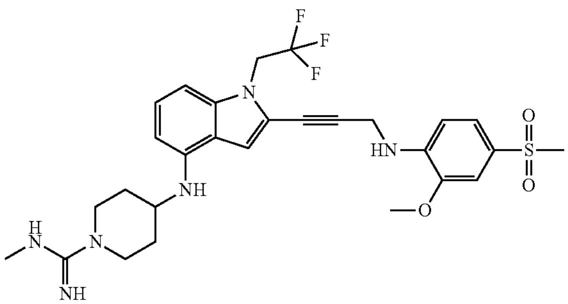 | 4-[(2-{3-[(4-methanesulfonyl-2-methoxyphenyl)amino]prop-1-yn-1-yl}-1-(2,2,2-trifluoroethyl)-1H-indol-4-yl)amino]-N-methylpiperidine-1-carboximidamide | 591.2 [(M + H)+] |
| 682 | 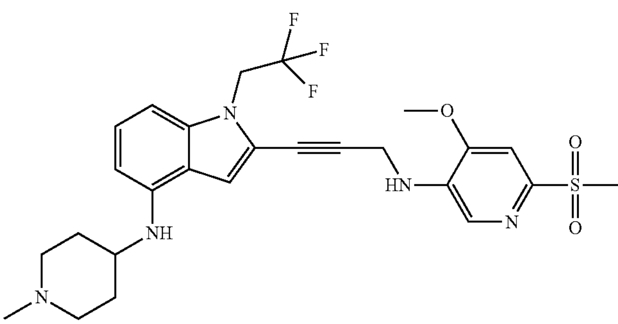 | 2-{3-[(6-methanesulfonyl-4-methoxypyridin-3-yl)amino]prop-1-yn-1-yl}-N-(1-methylpiperidin-4-yl)-1-(2,2,2-trifluoroethyl)-1H-indol-4-amine | 550.1 [(M + H)+] |
| 683 | 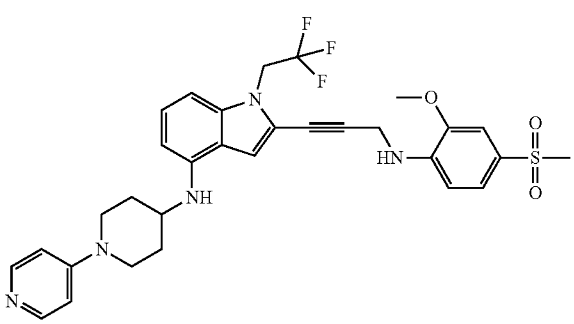 [SMILES: COc1cc(S(C)(=O)=O)ccc1NCC#Cc1cc2c(NC3CCN(c4ccncc4)CC3)cccc2n1CC(F)(F)F] | 2-{3-[(4-methanesulfonyl-2-methoxyphenyl)amino]prop-1-yn-1-yl}-N-[1-(pyridin-4-yl)piperidin-4-yl]-1-(2,2,2-trifluoroethyl)-1H-indol-4-amine | 612.2 [(M + H)+] |
| 684 | 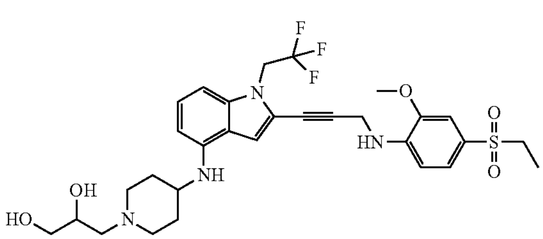 [SMILES: CCS(=O)(=O)c1ccc(NCC#Cc2cc3c(NC4CCN(CC(O)CO)CC4)cccc3n2CC(F)(F)F)c(OC)c1] | 3-(4-{[2-(3-{[4-(ethanesulfonyl)-2-methoxyphenyl]amino}prop-1-yn-1-yl)-1-(2,2,2-trifluoroethyl)-1H-indol-4-yl]amino}piperidin-1-yl)propane-1,2-diol | 623.3 [(M + H)+] |

| Ex | Structure | Name | LC-MS (ES+, m/z) |
|---|---|---|---|
| 685 | 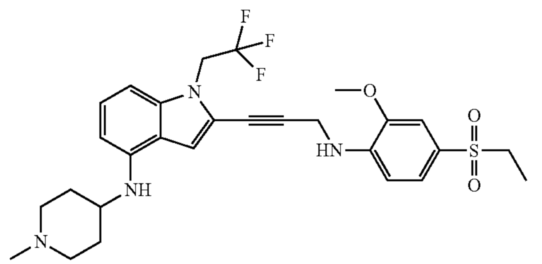 [SMILES: CCS(=O)(=O)c1ccc(NCC#Cc2cc3c(NC4CCN(C)CC4)cccc3n2CC(F)(F)F)c(OC)c1] | 2-(3-{[4-(ethanesulfonyl)-2-methoxyphenyl]amino}prop-1-yn-1-yl)-N-(1-methylpiperidin-4-yl)-1-(2,2,2-trifluoroethyl)-1H-indol-4-amine | 563.2 [(M + H)+] |
| 686 | 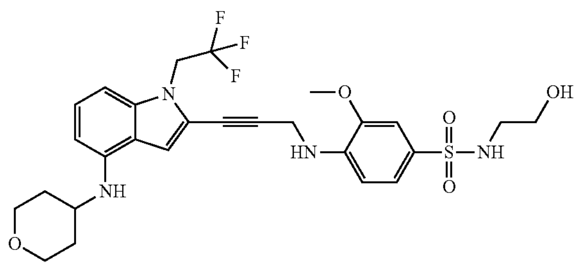 [SMILES: COc1cc(S(=O)(=O)NCCO)ccc1NCC#Cc1cc2c(NC3CCOCC3)cccc2n1CC(F)(F)F] | 2-hydroxy-S-{3-methoxy-4-[(3-{4-[(oxan-4-yl)amino]-1-(2,2,2-trifluoroethyl)-1H-indol-2-yl}prop-2-yn-1-yl)amino]phenyl}ethane-1-sulfonamido | 581.2 [(M + H)+] |
| 687 | 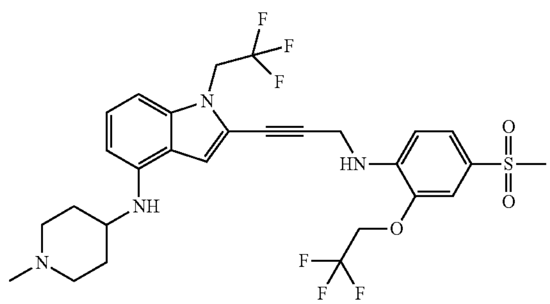 | 2-(3-{[4-methanesulfonyl-2-(2,2,2-trifluoroethoxy)phenyl]amino}prop-1-yn-1-yl)-N-(1-methylpiperidin-4-yl)-1-(2,2,2-trifluoroethyl)-1H-indol-4-amine | 617.2 [(M + H)+] |
| 688 | 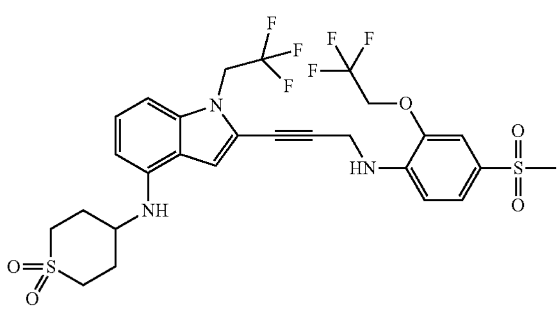 [SMILES: CS(=O)(=O)c1ccc(NCC#Cc2cc3c(NC4CCS(=O)(=O)CC4)cccc3n2CC(F)(F)F)c(OCC(F)(F)F)c1] | 4-{[2-(3-{[4-methanesulfonyl-2-(2,2,2-trifluoroethoxy)phenyl]amino}prop-1-yn-1-yl)-1-(2,2,2-trifluoroethyl)-1H-indol-4-yl]amino}-1λ6-thiane-1,1-dione | 652.1 [(M + H)+] |
| 689 | 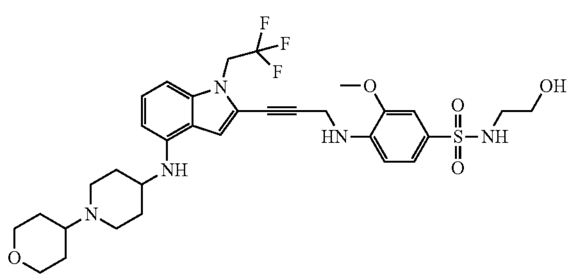 [SMILES: COc1cc(S(=O)(=O)NCCO)ccc1NCC#Cc1cc2c(NC3CCN(C4CCOCC4)CC3)cccc2n1CC(F)(F)F] | 2-hydroxy-S-(3-methoxy-4-{[3-(4-{[1-(oxan-4-yl)piperidin-4-yl]amino}-1-(2,2,2-trifluoroethyl)-1H-indol-2-yl)prop-2-yn-1-yl]amino}phenyl)ethane-1-sulfonamido | 664.3 [(M + H)+] |

-continued

| Ex | Structure | Name | LC-MS (ES+, m/z) |
|---|---|---|---|
| 690 | 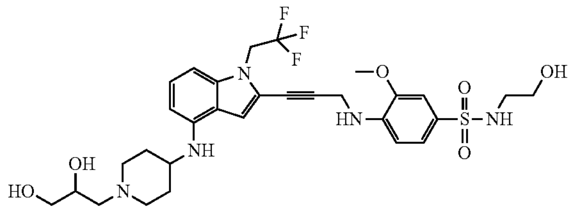 [SMILES: COc1cc(S(=O)(=O)NCCO)ccc1NCC#Cc1cc2c(NC3CCN(CC(O)CO)CC3)cccc2n1CC(F)(F)F] | S-(4-{[3-(4-{[1-(2,3-dihydroxypropyl)piperidin-4-yl]amino}-1-(2,2,2-trifluoroethyl)-1H-indol-2-yl)prop-2-yn-1-yl]amino}-3-methoxyphenyl)-2-hydroxyethane-1-sulfonamido | 654.2 [(M + H)+] |
| 691 | 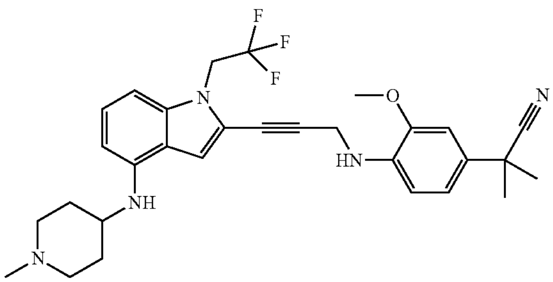 [SMILES: COc1cc(C(C)(C)C#N)ccc1NCC#Cc1cc2c(NC3CCN(C)CC3)cccc2n1CC(F)(F)F] | 2-{3-methoxy-4-[(3-{4-[(1-methylpiperidin-4-yl)amino]-1-(2,2,2-trifluoroethyl)-1H-indol-2-yl}prop-2-yn-1-yl)amino]phenyl}-2-methylpropanenitrile | 538.2 [(M + H)+] |
| 692 | 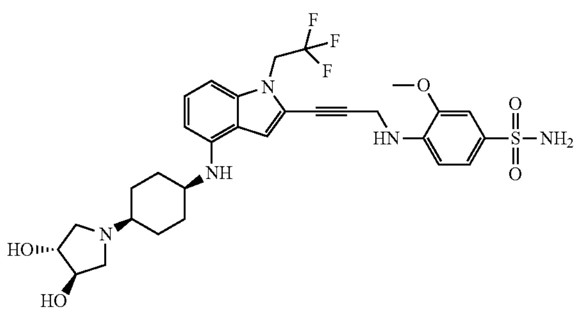 [SMILES: COc1cc(S(N)(=O)=O)ccc1NCC#Cc1cc2c(N[C@H]3CC[C@@H](N4C[C@@H](O)[C@H](O)C4)CC3)cccc2n1CC(F)(F)F] | 3-methoxy-4-{[3-(4-{[(1s,4s)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide | 636.2 [(M + H)+] |
| 693 | 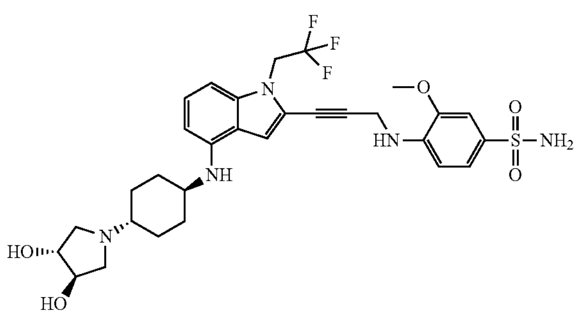 [SMILES: COc1cc(S(N)(=O)=O)ccc1NCC#Cc1cc2c(N[C@H]3CC[C@H](N4C[C@@H](O)[C@H](O)C4)CC3)cccc2n1CC(F)(F)F] | 3-methoxy-4-{[3-(4-{[(1r,4r)-4-[(3R,4R)-3,4-dihydroxypyrrolidin-1-yl]cyclohexyl]amino}-1-(2,2,2-trifluoroethyl)-1H-indol-2-yl)prop-2-yn-1-yl]amino}benzene-1-sulfonamide | 636.2 [(M + H)+] |
| 694 | 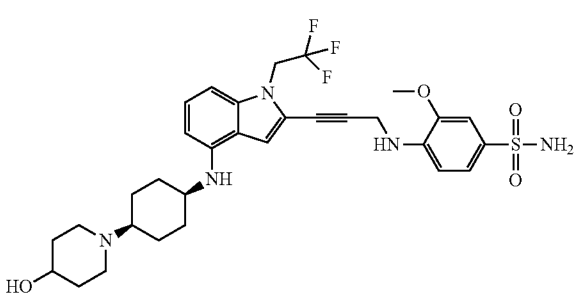 [SMILES: COc1cc(S(N)(=O)=O)ccc1NCC#Cc1cc2c(N[C@H]3CC[C@@H](N4CCC(O)CC4)CC3)cccc2n1CC(F)(F)F] | 3-methoxy-4-{[3-(4-{[(1s,4s)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide | 634.2 [(M + H)+] |

-continued

| Ex | Structure | Name | LC-MS (ES+, m/z) |
|---|---|---|---|
| 695 | 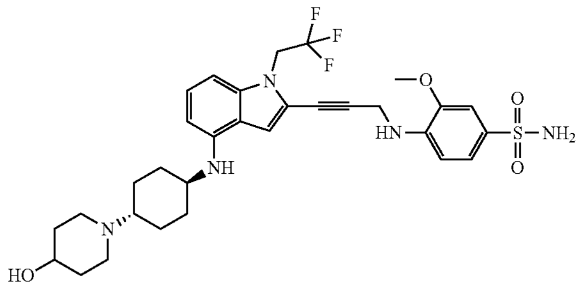 [SMILES: COc1cc(S(N)(=O)=O)ccc1NCC#Cc1cc2c(N[C@H]3CC[C@H](N4CCC(O)CC4)CC3)cccc2n1CC(F)(F)F] | 3-methoxy-4-{[3-(4-{[(1r,4r)-4-(4-hydroxypiperidin-1-yl)cyclohexyl]amino}-1-(2,2,2-trifluoroethyl)-1H-indol-2-yl)prop-2-yn-1-yl]amino}benzene-1-sulfonamide | 634.3 [(M + H)+] |
| 696 | 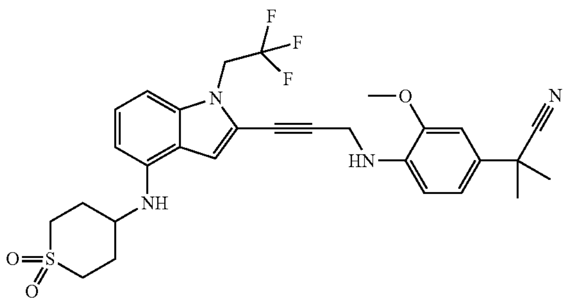 [SMILES: COc1cc(C(C)(C)C#N)ccc1NCC#Cc1cc2c(NC3CCS(=O)(=O)CC3)cccc2n1CC(F)(F)F] | 2-{4-[(3-{4-[(1,1-dioxo-1λ6-thian-4-yl)amino]-1-(2,2,2-trifluoroethyl)-1H-indol-2-yl}prop-2-yn-1-yl)amino]-3-methoxyphenyl}-2-methylpropanenitrile | 573.2 [(M + H)+] |
| 697 | 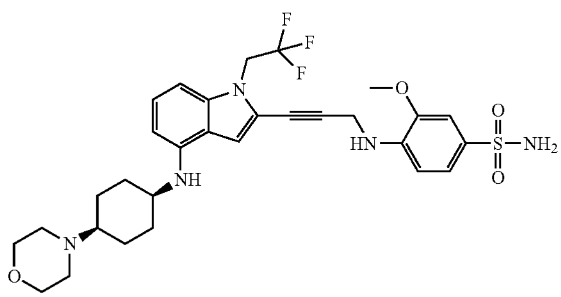 [SMILES: COc1cc(S(N)(=O)=O)ccc1NCC#Cc1cc2c(N[C@H]3CC[C@@H](N4CCOCC4)CC3)cccc2n1CC(F)(F)F] | 3-methoxy-4-{[3-(4-{[(1s,4s)-4-(morpholin-4-yl)cyclohexyl]amino}-1-(2,2,2-trifluoroethyl)-1H-indol-2-yl)prop-2-yn-1-yl]amino}benzene-1-sulfonamide | 620.3 [(M + H)+] |
| 698 | 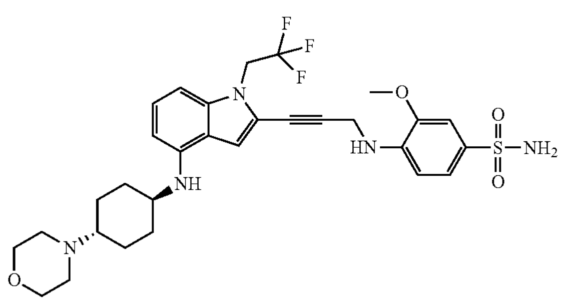 [SMILES: COc1cc(S(N)(=O)=O)ccc1NCC#Cc1cc2c(N[C@H]3CC[C@H](N4CCOCC4)CC3)cccc2n1CC(F)(F)F] | 3-methoxy-4-{[3-(4-{[(1r,4r)-4-(morpholin-4-yl)cyclohexyl]amino}-1-(2,2,2-trifluoroethyl)-1H-indol-2-yl)prop-2-yn-1-yl]amino}benzene-1-sulfonamide | 620.3 [(M + H)+] |
| 699 | 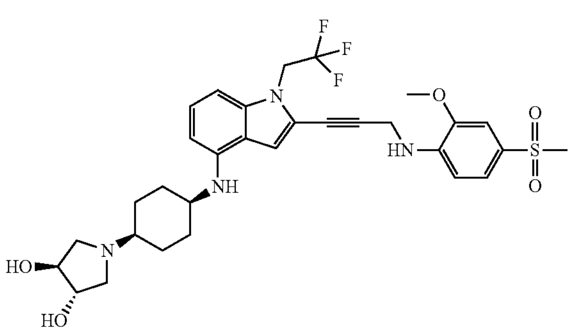 [SMILES: COc1cc(S(C)(=O)=O)ccc1NCC#Cc1cc2c(N[C@H]3CC[C@@H](N4C[C@H](O)[C@@H](O)C4)CC3)cccc2n1CC(F)(F)F] | (3S,4S)-1-[(1s,4s)-4-[(2-{3-[(4-methanesulfonyl-2-methoxyphenyl)amino]prop-1-yn-1-yl}-1-(2,2,2-trifluoroethyl)-1H-indol-4-yl)amino]cyclohexyl]pyrrolidine-3,4-diol | 635.3 [(M + H)+] |

| Ex | Structure | Name | LC-MS (ES⁺, m/z) |
|---|---|---|---|
| 700 | 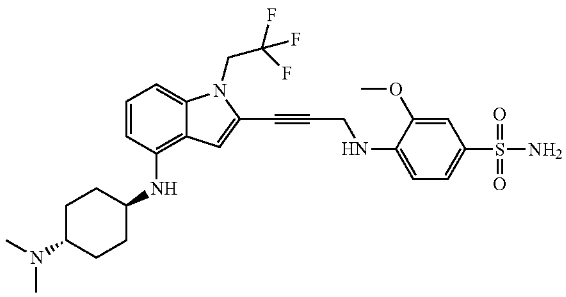 [SMILES: COc1cc(S(N)(=O)=O)ccc1NCC#Cc1cc2c(N[C@H]3CC[C@H](N(C)C)CC3)cccc2n1CC(F)(F)F] | 3-methoxy-4-{[3-(4-{[(1r,4r)-4-(dimethylamino)cyclohexyl]amino}-1-(2,2,2-trifluoroethyl)-1H-indol-2-yl)prop-2-yn-1-yl]amino}benzene-1-sulfonamide | 578.2 [(M + H)⁺] |
| 701 | 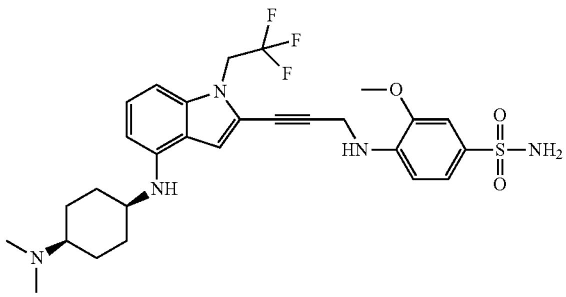 [SMILES: COc1cc(S(N)(=O)=O)ccc1NCC#Cc1cc2c(N[C@H]3CC[C@@H](N(C)C)CC3)cccc2n1CC(F)(F)F] | 3-methoxy-4-{[3-(4-{[(1s,4s)-4-(dimethylamino)cyclohexyl]amino}-1-(2,2,2-trifluoroethyl)-1H-indol-2-yl)prop-2-yn-1-yl]amino}benzene-1-sulfonamide | 578.3 [(M + H)⁺] |

Example 702: In Vitro DNA Binding Activity Assay

The ability of a compound of the invention to stabilize p53 Y220C and increase the DNA binding activity of p53 Y220C was measured by a homogeneous time-resolved fluorescence (HTRF) assay. Recombinant His-tagged p53 Y220C used in the HTRF assay was expressed in the bacterium *E. coli*. The recombinant protein was a truncation mutant containing only amino acids 94-312 of p53, which encompassed the DNA binding domain (DBD) of p53 (SEQ ID NO.: 1). The His-tagged p53 Y220C was tested for DNA binding ability with a consensus sequence of DNA (DNA duplex with a sequence of 5'-ATTAGGCATGTCTAG-GCATGTCTAGG-3'; SEQ ID NO.: 2). SEQ ID NO.: 2 was then conjugated with a biotin label and used in the activity assay.

The binding of the recombinant His-tagged p53 Y220C protein and the biotin-labeled consensus DNA was measured using fluorescence resonance energy transfer (FRET). For the FRET assay, the binding between the p53 mutant and the DNA sequence was measured by detecting the fluorescence of the interaction between an anti-His antibody conjugated to allophycocyanin (APC) and streptavidin conjugated to europium to detect the biotin-labeled DNA.

The test compounds were prepared as 4.5 mM stock solutions in dimethylsulfoxide (DMSO). The compound from Example 2 was used to test the stabilization of p53 Y220C and increase in DNA binding activity of p53 Y220C. The stock solutions were then serially diluted 3-fold in DMSO, and 1.2 µL of the diluted solutions was added to each well of a 384-well polypropylene black plate. 30 µL of a 181 nM solution of the recombinant His-tagged p53 Y220C protein and 12.1 nM of allophycocyanin (APC) conjugated anti-His tag antibody in ice-cold Assay Buffer 1 (50 mM Tris-HCl, pH 7.4; 75 mM KCl; 0.75 mM DTT; and 0.2 mg/mL bovine serum albumin (BSA)) was added to each well containing the test compounds.

As a background control, 30 µL of Assay Buffer 1 containing 12.1 nM of APC anti-His antibody was also added into a second set of serially-diluted compound plates. The test and control samples were spun at 1200 rpm for 1 minute and incubated at room temperature for 15 minutes. The samples were then further incubated at either 27° C. or 29° C. for 60 min. Five microliters of 311 nM biotin labeled consensus DNA (SEQ ID NO.: 2) and 13.03 nM europium-conjugated streptavidin in Assay Buffer 2 (50 mM Tris-HCl, pH 7.4; 75 mM KCl; and 0.2 mg/mL BSA) were added to each well for both the test and control plates. The plates were spun at 1200 rpm for 1 minute and incubated at room temperature for 20 minutes. The assay signals were monitored by reading excitation at 340 nm, and emission fluorescence at 615 nm and 665 nm on a plate reader.

Normalized time-resolved fluorescence resonance energy transfer (TR-FRET) assay signal ($R_n$) was calculated by the formula:

$$R_n = [(A - B_a - CD)/(D - B_d)](D_c - B_d)$$

where

A was the fluorescence intensity of the sample at 665 nm;
D was the fluorescence intensity of the sample at 615 nm;
$B_a$ and $B_d$ were plate background readings at 665 nm and 615 nm, respectively; and
$D_c$ was the fluorescence intensity of 1.8 nM Eu-SA in the assay buffer at 615 nm.

The cross talk factor (C) was determined by the following formula:

$$C = (A_c - B_a)/(D_c - B_d)$$

where $A_c$ was the fluorescence intensity of 1.8 nM Eu-labeled anti-FLAG antibody in the assay buffer at 665 nm.

The results of the experiment are shown in FIG. 1. The $SC_{150}$ values were calculated using either Prism™ or ActivityBase™ as shown in FIG. 1. The percentage of activation of protein DNA binding in the presence of a compound of the invention compared to the absence of the compound was denoted by a $SC_{150}$ value, which indicated the concentration of the compound required to increase the DNA binding activity by 50%. The result indicted that a compound of the invention increased the protein DNA binding activity of the p53 mutant by 50% at $SC_{150}$ values of 10.9 μM.

Figure 2:
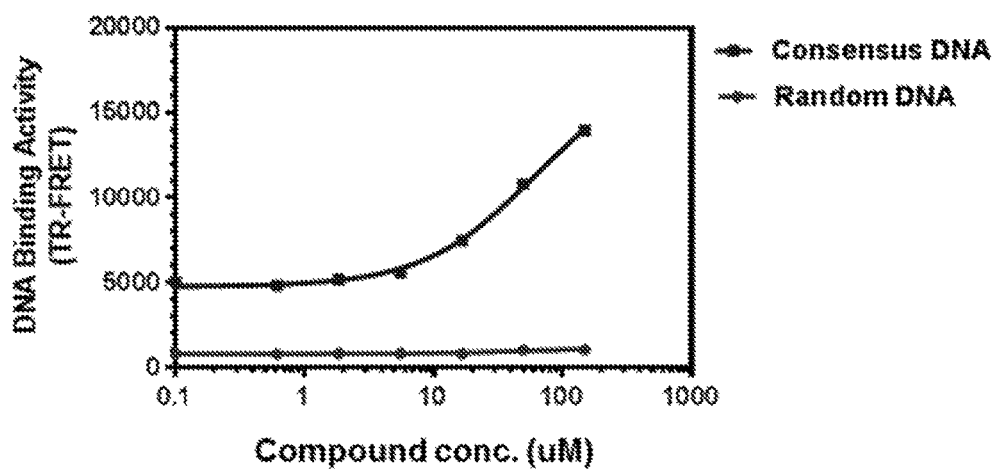
FIG. 2 shows a protein DNA binding assay of mutant p53 in the presence of a compound of the invention to demonstrate the specificity of a compound of the invention.

To test compound specificity, compound 2 was tested using a biotin DNA duplex with a random DNA sequence under identical conditions as shown in FIG. 2. The results indicate that a compound of the invention was specific to the consensus sequence of SEQ ID NO.: 2.

EMBODIMENTS

The following non-limiting embodiments provide illustrative examples of the invention, but do not limit the scope of the invention.

Embodiment 1

A compound of the formula:

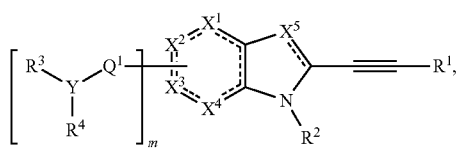

wherein:
each ═══ is independently a single bond or a double bond;
$X^1$ is $CR^5$, $CR^5R^6$, N, $NR^5$, O, S, C═O, C═S, or a carbon atom connected to $Q^1$;
$X^2$ is $CR^7$, $CR^7R^8$, N, $NR^7$, O, S, C═O, C═S, or a carbon atom connected to $Q^1$;
$X^3$ is $CR^9$, $CR^9R^{10}$, N, $NR^9$, O, S, C═O, C═S, or a carbon atom connected to $Q^1$;
$X^4$ is $CR^{11}$, $CR^{11}R^{12}$, N, $NR^{11}$, O, S, C═O, C═S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
$Q^1$ is C═O, C═S, C═$CR^{14}R^{15}$, C═$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, C═O, C═S, —CN, —Si$R^{16}R^{17}R^{18}$, alkyl, alkenyl, alkynyl, aryl, heteroaryl, or heterocyclyl, each of which is independently substituted or unsubstituted, or hydrogen;
each $R^3$ and $R^4$ is independently absent, —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

Embodiment 2

The compound of embodiment 1, wherein $X^3$ is a carbon atom connected to $Q^1$, and Y is N or O.

Embodiment 3

The compound of any one of embodiments 1-2, wherein m is 1, and Y is N.

Embodiment 4

The compound of any one of embodiments 1-3, wherein the compound is of the formula:

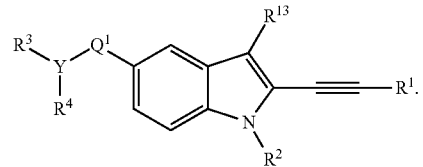

Embodiment 5

The compound of any one of embodiments 1-4, wherein $R^1$ is alkyl, alkenyl, —C(O)$R^{16}$, —C(O)O$R^{16}$, or —C(O)N$R^{16}R^{17}$.

Embodiment 6

The compound of any one of embodiments 1-5, wherein $R^1$ is alkyl substituted with N$R^{16}R^{17}$.

Embodiment 7

The compound of any one of embodiments 1-6, wherein the compound is of the formula:

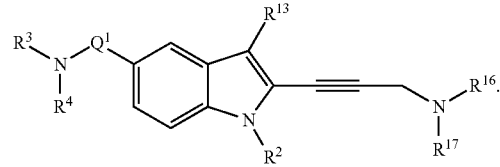

Embodiment 8

The compound of any one of embodiments 1-7, wherein each $R^{16}$ and $R^{17}$ is independently alkyl, alkenyl, aryl, heteroaryl, heterocyclyl, or hydrogen.

Embodiment 9

The compound of any one of embodiments 1-8, wherein $R^{16}$ is hydrogen or alkyl.

Embodiment 10

The compound of any one of embodiments 1-9, wherein $R^{17}$ is aryl, heteroaryl, or heterocyclyl, each of which is independently substituted or unsubstituted with halogen, alkyl, or hydroxyl.

Embodiment 11

The compound of any one of embodiments 1-10, wherein $Q^1$ is C=O, C=NR$^{14}$, a bond, alkylene, or alkenylene.

Embodiment 12

The compound of any one of embodiments 1-11, wherein $Q^1$ is $C_1$-alkylene.

Embodiment 13

The compound of any one of embodiments 1-12, wherein $R^2$ is hydrogen or alkyl.

Embodiment 14

The compound of any one of embodiments 1-13, wherein $R^2$ is alkyl.

Embodiment 15

The compound of any one of embodiments 1-14, wherein $R^2$ is cycloalkyl.

Embodiment 16

The compound of any one of embodiments 1-15, wherein $R^{13}$ is alkyl, alkenyl, hydrogen, or halogen.

Embodiment 17

The compound of any one of embodiments 1-16, wherein $R^{13}$ is hydrogen.

Embodiment 18

The compound of any one of embodiments 1-17, wherein $R^3$ and $R^4$ are each independently alkyl, alkenyl, aryl, heteroaryl, heterocyclyl, or hydrogen.

Embodiment 19

The compound of any one of embodiments 1-18, wherein $R^4$ is alkyl substituted with aryl.

Embodiment 20

The compound of any one of embodiments 1-17, wherein $R^3$ and $R^4$ together with the nitrogen atom to which $R^3$ and $R^4$ are bound form a ring, wherein the ring is substituted or unsubstituted.

Embodiment 21

The compound of any one of embodiments 1-17 and 20, wherein $R^3$ and $R^4$ together with the nitrogen atom to which $R^3$ and $R^4$ are bound form a heterocycle, wherein the heterocycle is substituted by at least one substituent.

Embodiment 22

The compound of any one of embodiments 1-21, wherein $X^1$ is a carbon atom connected to $Q^1$.

Embodiment 23

The compound of any one of embodiments 1-22, wherein m is 1.

Embodiment 24

The compound of any one of embodiments 1-3, 5, 6, 8-19 and 22-23, wherein the compound is of the formula:

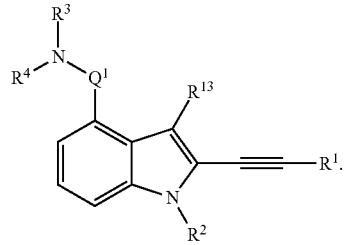

Embodiment 25

The compound of any one of embodiments 1-24, wherein $R^1$ is alkyl, alkenyl, —C(O)R$^{16}$, —C(O)OR$^{16}$, or —C(O)NR$^{16}$R$^{17}$.

Embodiment 26

The compound of any one of embodiments 1-25, wherein $R^1$ is alkyl substituted with NR$^{16}$R$^{17}$.

Embodiment 27

The compound of any one of embodiments 1-3, 5, 6, 8-19 and 22-26, wherein the compound is of the formula:

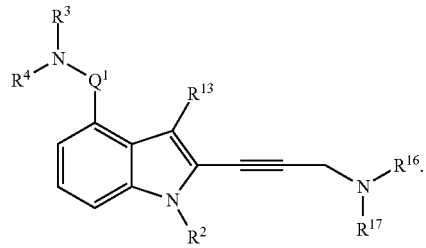

Embodiment 28

The compound of any one of embodiments 1-27, wherein each $R^{16}$ and $R^{17}$ is independently alkyl, alkenyl, aryl, heteroaryl, heterocyclyl, or hydrogen.

Embodiment 29

The compound of any one of embodiments 1-28, wherein $R^{16}$ is hydrogen or alkyl.

Embodiment 30

The compound of any one of embodiments 1-29, wherein R is aryl, heteroaryl, or heterocyclyl, each of which is independently substituted or unsubstituted with alkyl, each of which is independently substituted or unsubstituted with halogen, alkyl, or hydroxyl.

Embodiment 31

The compound of any one of embodiments 1-30, wherein $Q^1$ is C=O, C=$NR^{14}$, a bond, alkylene, or alkenylene.

Embodiment 32

The compound of any one of embodiments 1-31, wherein $Q^1$ is $C_1$-alkylene.

Embodiment 33

The compound of any one of embodiments 1-32, wherein $R^2$ is hydrogen or alkyl.

Embodiment 34

The compound of any one of embodiments 1-33, wherein $R^{13}$ is alkyl, alkenyl, hydrogen, or halogen.

Embodiment 35

The compound of any one of embodiments 1-34, wherein $R^{13}$ is hydrogen.

Embodiment 36

The compound of any one of embodiments 1-19 and 22-35, wherein $R^3$ and $R^4$ are each independently alkyl, alkenyl, aryl, heteroaryl, heterocyclyl, or hydrogen.

Embodiment 37

The compound of any one of embodiments 1-3, 5, 6, 8-23, 25, 26, and 28-36, wherein $R^3$ and $R^4$ together with the nitrogen atom to which $R^3$ and $R^4$ are bound form a ring, wherein the ring is substituted or unsubstituted.

Embodiment 38

The compound of any one of embodiments 1-3, 5, 6, 8-23, 25, 26, and 28-37, wherein $R^3$ and $R^4$ together with the nitrogen atom to which $R^3$ and $R^4$ are bound form a heterocycle, wherein the heterocycle is substituted by at least one substituent.

Embodiment 39

The compound of any one of embodiments 1-3, 5, 6, 8-23, 25, 26, and 28-38, wherein $R^3$ and $R^4$ together with the nitrogen atom to which $R^3$ and $R^4$ are bound form a heterocycle, wherein the heterocycle is optionally substituted by a substituted or unsubstituted heterocycle.

Embodiment 40

The compound of any one of embodiments 1-3, 5, 6, 8-23, 26, and 28-39, wherein the compound is of the formula:

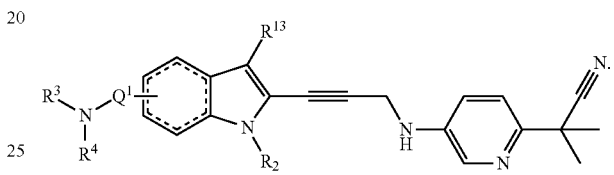

Embodiment 41

A compound of the formula:

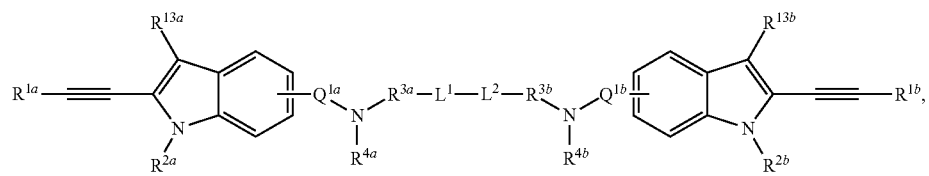

wherein:
each $Q^{1a}$ and $Q^{1b}$ is independently C=O, C=S, C=$CR^{14'}R^{15'}$, C=$NR^{14'}$, alkylene, alkenylene, or alkynylene, each of which is independently substituted or unsubstituted, or a bond;

each $R^{1a}$ and $R^{1b}$ is independently —C(O)$R^{16'}$, —C(O)O$R^{16'}$, —C(O)N$R^{16'}R^{17'}$, —O$R^{16'}$, —S$R^{16'}$, —N$R^{16'}R^{17'}$, —N$R^{16'}$C(O)$R^{16'}$, —OC(O)$R^{16'}$, C=O, C=S, —CN, —Si$R^{16'}R^{17'}R^{18'}$, alkyl, alkenyl, alkynyl, aryl, heteroaryl, or heterocyclyl, each of which is independently substituted or unsubstituted, or hydrogen;

each $R^{3a}$ and $R^{3b}$ is independently alkylene, alkenylene, alkynylene, arylene, heteroarylene, or heterocyclene, each of which is independently substituted or unsubstituted, or hydrogen;

each $R^{4a}$ and $R^{4b}$ is independently absent, —C(O)$R^{19'}$, —C(O)O$R^{19'}$, —C(O)N$R^{19'}R^{20'}$, —SO$R^{19'}$, —SO$_2R^{19'}$, alkyl, alkenyl, alkynyl, aryl, heteroaryl, or heterocyclyl, each of which is independently substituted or unsubstituted, or hydrogen;

each $R^{2a}$, $R^{2b}$, $R^{13a}$, and $R^{13b}$ is independently —C(O)$R^{21'}$, —C(O)O$R^{21'}$, —C(O)N$R^{21'}R^{22'}$, —O$R^{21'}$, —S$R^{21'}$, —N$R^{21'}R^{22'}$, —N$R^{21'}$C(O)$R^{22'}$, —OC(O)$R^{21'}$, alkyl, alkenyl, alkynyl, aryl, heteroaryl, or heterocyclyl, each of which is independently substituted or unsubstituted, or hydrogen or halogen;

each $R^{19'}$ and $R^{20'}$ is —C(O)$R^{23'}$, —C(O)O$R^{23'}$, —C(O)N$R^{23'}R^{24'}$, —O$R^{23'}$, —S$R^{23'}$, —N$R^{23'}R^{24'}$, —N$R^{23'}$C(O)$R^{24'}$, —OC(O)$R^{23'}$, alkyl, alkenyl, alkynyl, aryl, heteroaryl, or heterocyclyl, each of which is independently substituted or unsubstituted, or hydrogen or halogen;

each $R^{21'}$ and $R^{22'}$ is independently alkyl, alkenyl, alkynyl, aryl, heteroaryl, or heterocyclyl, each of which is independently substituted or unsubstituted, or hydrogen;

each $R^{23'}$ and $R^{24'}$ is independently alkyl, alkenyl, alkynyl, aryl, heteroaryl, or heterocyclyl, each of which is independently substituted or unsubstituted, or hydrogen, $L^1$ is methylene that is unsubstituted or substituted; and $L^2$ is a linker moiety, or a pharmaceutically acceptable salt thereof.

Embodiment 42

The compound of embodiment 41, wherein $L_2$ is alkylene, alkenylene, alkynylene, heteroalkylene, cycloalkylene, heterocycloalkylene, cycloarylene, heterocycloalkylene, or C(O)O$R^a$, wherein $R^a$ is alkylene.

Embodiment 43

A pharmaceutical composition comprising a compound of any one of embodiments 1-42.

Embodiment 44

The pharmaceutical composition of embodiment 43, further comprising a pharmaceutically-acceptable excipient.

Embodiment 101

A method of increasing p53 mutant activity in a cell, the method comprising contacting the cell with a therapeutically-effective amount of a compound that binds the p53 mutant, wherein the compound increases the ability of the p53 mutant to bind DNA.

Embodiment 102

The method of embodiment 101, wherein the compound is a compound of any one of embodiments 1-42.

Embodiment 103

A method of inducing apoptosis in a cell, the method comprising contacting the cell with a therapeutically-effective amount of a compound that binds a p53 mutant, wherein the compound increases the ability of the p53 mutant to bind DNA, wherein the cell expresses the p53 mutant.

Embodiment 104

The method of embodiment 103, wherein the compound is a compound of any one of embodiments 1-42.

Embodiment 105

A method of treating a condition, the method comprising administering to a subject in need thereof a therapeutically-effective amount of a compound of any one of embodiments 1-42.

Embodiment 106

The method of any one of embodiments 101-104, wherein the binding of the compound to the p53 mutant increases the ability of the p53 mutant to bind DNA by at least about 50% as compared to the ability of the p53 mutant to bind DNA in absence of the compound.

Embodiment 107

The method of any one of embodiments 101-104 and 106, wherein the p53 mutant has a mutation at amino acid 220.

Embodiment 108

The method of any one of embodiments 101-104, and 106-107, wherein the p53 mutant is p53 Y220C.

Embodiment 109

The method of any one of embodiments 101-104 and 106-108, wherein the compound induces a conformational change in the p53 mutant.

Embodiment 110

The method of any one of embodiments 101-104 and 106-109, wherein the compound preferentially binds the p53 mutant as compared to wild type p53.

Embodiment 111

The method of any one of embodiments 101-104 and 106-110, wherein the binding of the compound to the p53 mutant induces apoptosis in a cell.

Embodiment 112

The method of any one of embodiments 101-104 and 106-111, wherein the binding of the compound to the p53 mutant induces cell cycle arrest in a cell.

Embodiment 113

The method of any one of embodiments 101-113, wherein the therapeutically-effective amount is from about 20 mg to about 2000 mg.

Embodiment 114

The method of embodiment 105, wherein the condition is cancer.

Embodiment 115

The method of any one of embodiments 105 and 114, wherein the condition is ovarian cancer.

Embodiment 116

The method of any one of embodiments 105 and 114, wherein the condition is breast cancer.

Embodiment 117

The method of any one of embodiments 105 and 114, wherein the condition is lung cancer.

Embodiment 118

The method of any one of embodiments 105 and 113-117, wherein the administration is oral.

Embodiment 119

The method of any one of embodiments 105 and 113-111, wherein the administration is intravenous.

Embodiment 120

The method of any one of embodiments 105 and 113-111, wherein the administration is subcutaneous.

Embodiment 121

The method of any one of embodiments 105 and 113-111, wherein the administration is topical.

Embodiment 122

The method of any one of embodiments 105 and 113-121, wherein the subject is human.

Embodiment 123

A method of treating a condition, the method comprising administering to a subject in need thereof a therapeutically-effective amount of a compound that binds a p53 mutant in the subject, wherein the binding of the compound to the p53 mutant increases the ability of the p53 mutant to bind DNA by at least about 50% as compared to the ability of the p53 mutant to bind DNA in absence of the compound.

Embodiment 124

The method of embodiment 123, wherein the p53 mutant has a mutation at amino acid 220.

Embodiment 125

The method of any one of embodiments 123-124, wherein the p53 mutant is p53 Y220C.

Embodiment 126

The method of any one of embodiments 123-125, wherein the compound increases the stability of a biologically-active conformation of the p53 mutant relative to the stability of the biologically-active conformation of the p53 mutant in absence of the compound.

Embodiment 127

The method of any one of embodiments 123-126, wherein the compound preferentially binds the p53 mutant as compared to wild type p53.

Embodiment 128

The method of any one of embodiments 123-127, wherein the binding of the compound to the p53 mutant induces apoptosis in a cell.

Embodiment 129

The method of any one of embodiments 123-128, wherein the binding of the compound to the p53 mutant induces cell cycle arrest in a cell.

Embodiment 130

The method of any one of embodiments 123-129, wherein the therapeutically-effective amount is from about 20 to about 2000 mg.

Embodiment 131

The method of any one of embodiments 123-130, wherein the condition is cancer.

Embodiment 132

The method of any one of embodiments 123-131, wherein the condition is ovarian cancer.

Embodiment 133

The method of any one of embodiments 123-131, wherein the condition is breast cancer.

Embodiment 134

The method of any one of embodiments 123-131, wherein the condition is lung cancer.

Embodiment 135

The method of any one of embodiments 123-134, wherein the administration is oral.

Embodiment 136

The method of any one of embodiments 123-134, wherein the administration is intravenous.

Embodiment 137

The method of any one of embodiments 123-134, wherein the administration is subcutaneous.

Embodiment 138

The method of any one of embodiments 123-134, wherein the administration is topical.

Embodiment 139

The method of any one of embodiments 123-138, wherein the subject is human.

Embodiment 201

A method of determining an ability of a compound to activate mutant p53 binding to DNA comprising:

a) contacting the compound with a tagged mutant p53 moiety and an antibody conjugated to a fluorescence energy acceptor against the tag in a test chamber;
b) contacting the tagged mutant p53 moiety with a biotin-labeled DNA and streptavidin conjugated to a fluorescence energy donor in the test chamber;
c) irradiating the test chamber with light that promotes fluorescence resonance energy transfer;
d) determining an $SC_{150}$ value of the compound based on the fluorescence resonance energy transfer;
e) comparing the $SC_{150}$ value of the compound with that of a control sample, wherein the control sample does not comprise the compound; and
f) determining a level of activation of protein DNA binding in the presence of a compound.

Embodiment 202

The method of embodiment 201, wherein the tagged mutant p53 is His-tagged.

Embodiment 203

The method of any one of embodiments 201-202, wherein the tagged mutant p53 comprises a Y220C mutation.

Embodiment 204

The method of any one of embodiments 201-203, wherein the tagged mutant p53 comprises amino acids 94-312 of wild type p53.

Embodiment 205

The method of any one of embodiments 201-204, wherein the fluorescence energy acceptor is allophycocyanin (APC).

Embodiment 206

The method of any one of embodiments 201-205, wherein the DNA is a DNA duplex of SEQ ID NO.: 2.

Embodiment 207

The method of any one of embodiments 201-206, wherein the method is a homogeneous time-resolved assay.

---

What is claimed is:

1. A compound of the formula:

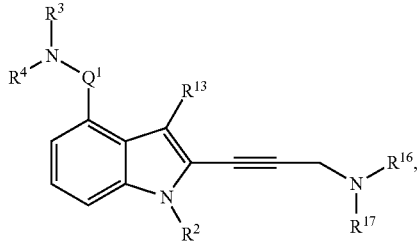

wherein:

$Q^1$ is $C_1$-alkylene; or a bond;

each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is independently substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen, or $R^3$ and $R^4$ together with the nitrogen atom to which $R^3$ and $R^4$ are bound form a ring, wherein the ring is substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^2$, $R^{13}$, $R^{14}$, and $R^{15}$, is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen;

$R^{16}$ is hydrogen;

$R^{17}$ is phenyl substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^{19}$ and $R^{20}$ is C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen; and each $R^{21}$, $R^{22}$, $R^{23}$, and $R^{24}$ is independently alkyl, alkenyl, alkynyl, aryl, heteroaryl, or heterocyclyl, each of which is independently substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen;

or a pharmaceutically-acceptable salt thereof.

2. The compound of claim 1, wherein $R^2$ is hydrogen or alkyl.

3. The compound of claim 2, wherein $R^2$ is alkyl.

4. The compound of claim 3, wherein $R^2$ is cycloalkyl.

5. The compound of claim 1, wherein $R^{13}$ is alkyl, alkenyl, hydrogen, or halogen.

6. The compound of claim 1, wherein $R^{13}$ is hydrogen.

7. The compound of claim 1, wherein $R^3$ and $R^4$ are each independently alkyl, alkenyl, aryl, heteroaryl, heterocyclyl, or hydrogen.

8. The compound of claim 1, wherein $R^4$ is alkyl substituted with aryl.

9. The compound of claim 1, wherein $R^3$ and $R^4$ together with the nitrogen atom to which $R^3$ and $R^4$ are bound form a ring, wherein the ring is substituted or unsubstituted.

10. The compound of claim 1, wherein $R^3$ and $R^4$ together with the nitrogen atom to which $R^3$ and $R^4$ are bound form a heterocycle, wherein the heterocycle is substituted by at least one substituent.

11. The compound of claim 1, wherein $R^{17}$ is phenyl substituted or unsubstituted with alkyl, wherein the alkyl is optionally substituted with halogen, alkyl, or hydroxyl.

12. The compound of claim 1, wherein $R^3$ and $R^4$ together with the nitrogen atom to which $R^3$ and $R^4$ are bound form a heterocycle, wherein the heterocycle is optionally substituted by a heterocycle.

13. A method of inducing apoptosis in a cell, the method comprising contacting the cell with a therapeutically-effective amount of a compound that binds a p53 mutant, wherein the compound increases the ability of the p53 mutant to bind DNA, wherein the cell expresses the p53 mutant, wherein the compound is a compound of the formula:

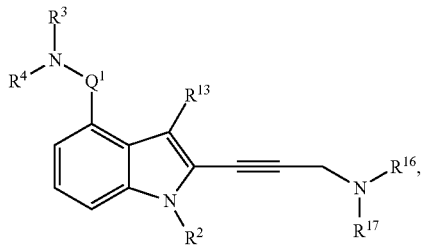

wherein:
$Q^1$ is $C_1$-alkylene; or a bond;
each $R^3$ and $R^4$ is independently, —C(O)R$^{19}$, —C(O)OR$^{19}$, —C(O)NR$^{19}$R$^{20}$, —SOR$^{19}$, —SO$_2$R$^{19}$, alkyl, alkylene, alkenyl, alkenylene, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen, or $R^3$ and $R^4$ together with the nitrogen atom to which $R^3$ and $R^4$ are bound form a ring, wherein the ring is substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^2$, $R^{13}$, $R^{14}$, and $R^{15}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen;

$R^{16}$ is hydrogen, $R^{17}$ is phenyl substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^{19}$ and $R^{20}$ is —C(O)R$^{23}$, —C(O)OR$^{23}$, —C(O)NR$^{23}$R$^{24}$, —OR$^{23}$C, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen; and each $R^{21}$, $R^{22}$, $R^{23}$, and $R^{24}$ is independently alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen;

or a pharmaceutically-acceptable salt thereof.

14. The method of claim 13, wherein the p53 mutant has a mutation at amino acid 220.

15. The method of claim 14, wherein the p53 mutant is p53 Y220C.

16. The method of claim 13, wherein the compound induces a conformational change in the p53 mutant.

17. The method of claim 13, wherein the compound selectively binds the p53 mutant as compared to wild type p53.

18. The method of claim 13, wherein the therapeutically-effective amount is from about 20 mg to about 2000 mg.

19. A method of treating cancer, the method comprising administering to a subject in need thereof a therapeutically-effective amount of a compound, wherein the compound is of the formula:

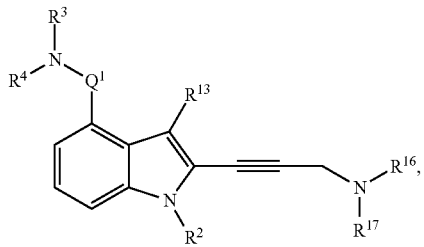

wherein:

$Q^1$ is $C_1$-alkylene; or a bond;

each $R^3$ and $R^4$ is independently, —C(O)$R^{19}$, —C(O)O$R^{19}$, —C(O)N$R^{19}R^{20}$, —SO$R^{19}$, —SO$_2R^{19}$, alkyl, alkylene, alkenyl, alkenylene, alkynyl, aryl, heteroaryl, or heterocyclyl, each of which is substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen, or $R^3$ and $R^4$ together with the nitrogen atom to which $R^3$ and $R^4$ are bound form a ring, wherein the ring is substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^2$, $R^{13}$, $R^{14}$, and $R^{15}$ is independently —C(O)$R^{21}$, —C(O)O$R^{21}$, —C(O)N$R^{21}R^{22}$, —O$R^{21}$, —S$R^{21}$,
—N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen;

$R^{16}$ is hydrogen;

$R^{17}$ is phenyl substituted or -unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, cycloalkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen or halogen; and each $R^{21}$, $R^{22}$, $R^{23}$, and $R^{24}$ is independently alkyl, alkenyl, alkynyl, aryl, heteroaryl, or heterocyclyl, each of which is independently substituted or unsubstituted with a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, or an ester group; or hydrogen;

or a pharmaceutically-acceptable salt thereof.

20. The method of claim 19, wherein the therapeutically-effective amount is from about 20 mg to about 2000 mg.

21. The method of claim 19, wherein the cancer is ovarian cancer.

22. The method of claim 19, wherein the cancer is breast cancer.

23. The method of claim 19, wherein the cancer is lung cancer.

24. The method of claim 19, wherein the administration is oral.

25. The method of claim 19, wherein the administration is intravenous.

26. The method of claim 19, wherein the administration is subcutaneous.

27. The method of claim 19, wherein the administration is topical.

28. The method of claim 19, wherein the subject is human.

29. The method of claim 19, wherein the compound increases the stability of a biologically-active conformation of the p53 mutant relative to the stability of the biologically-active conformation of the p53 mutant in absence of the compound.

30. The compound of claim 1, wherein $R^2$ is alkyl substituted with halo.

31. The compound of claim 30, wherein $R^2$ is ethyl substituted with halo.

32. The compound of claim 31, wherein $R^2$ is ethyl substituted with fluoro.

33. The method of claim 13, $R^{17}$ is phenyl substituted or unsubstituted with halogen, alkyl, or hydroxyl.

34. The method of claim 13, wherein $R^2$ is alkyl.

35. The method of claim 34, wherein $R^2$ is alkyl substituted with halo.

36. The method of claim 35 wherein $R^2$ is ethyl substituted with halo.

37. The method of claim 36, wherein $R^2$ is ethyl substituted with fluoro.

38. The method of claim 13, wherein $R^{13}$ is alkyl, alkenyl, hydrogen, or halogen.

39. The method of claim 13, wherein each $R^3$ and $R^4$ is independently alkyl, alkenyl, aryl, heteroaryl, heterocyclyl, or hydrogen.

40. The method of claim 19, $R^{17}$ is phenyl substituted or unsubstituted with halogen, alkyl, or hydroxyl.

41. The method of claim 19, wherein $R^2$ is alkyl.

42. The method of claim 41, wherein $R^2$ is alkyl substituted with halo.

43. The method of claim 42, wherein $R^2$ is ethyl substituted with halo.

44. The method of claim 43, wherein $R^2$ is ethyl substituted with fluoro.

45. The method of claim 19, wherein $R^{13}$ is alkyl, alkenyl, hydrogen, or halogen.

46. The method of claim 19, wherein $R^3$ and $R^4$ are each independently alkyl, alkenyl, aryl, heteroaryl, heterocyclyl, or hydrogen.

* * * * *

UNITED STATES PATENT AND TRADEMARK OFFICE
CERTIFICATE OF CORRECTION

PATENT NO. : 10,138,219 B2
APPLICATION NO. : 15/436333
DATED : November 27, 2018
INVENTOR(S) : Vu et al.

It is certified that error appears in the above-identified patent and that said Letters Patent is hereby corrected as shown below:

In the Claims

Column 417, Claim 33, Line 21:
Replace "The method of claim 13, $R^{17}$ is phenyl substituted or unsubstituted with halogen, alkyl, or hydroxyl," with --The method of claim 13, wherein $R^{17}$ is phenyl substituted or unsubstituted with halogen, alkyl, or hydroxyl,--

Column 418, Claim 40, Line 10:
Replace "The method of claim 19, $R^{17}$ is phenyl substituted or unsubstituted with halogen, alkyl, or hydroxyl," with --The method of claim 19, wherein $R^{17}$ is phenyl substituted or unsubstituted with halogen, alkyl, or hydroxyl,--

Signed and Sealed this
Twenty-fourth Day of March, 2020

Andrei Iancu
*Director of the United States Patent and Trademark Office*